US012655424B2

(12) United States Patent
Borrajo et al.

(10) Patent No.: US 12,655,424 B2
(45) Date of Patent: Jun. 16, 2026

(54) METHODS AND COMPOSITIONS FOR TRANS-SPLICING UTILIZING SMALL NUCLEAR RNAs AND SMALL NUCLEOLAR RNAs

(71) Applicant: Amber Bio Inc., San Francisco, CA (US)

(72) Inventors: Jacob Borrajo, San Francisco, CA (US); Sam Demario, San Francisco, CA (US); Kamyab Javanmardi, San Francisco, CA (US); David Yao, San Francisco, CA (US); Brigit Riley, San Francisco, CA (US)

(73) Assignee: Amber Bio Inc., San Francisco, CA (US)

( * ) Notice: Subject to any disclaimer, the term of this patent is extended or adjusted under 35 U.S.C. 154(b) by 0 days.

(21) Appl. No.: 18/938,180

(22) Filed: Nov. 5, 2024

(65) Prior Publication Data

US 2025/0250563 A1     Aug. 7, 2025

Related U.S. Application Data

(60) Provisional application No. 63/656,569, filed on Jun. 5, 2024, provisional application No. 63/554,139, filed on Feb. 15, 2024, provisional application No. 63/552,646, filed on Feb. 12, 2024, provisional application No. 63/550,019, filed on Feb. 5, 2024.

(51) Int. Cl.
*C12N 15/11*          (2006.01)
*C12N 15/88*          (2006.01)

(52) U.S. Cl.
CPC ............ *C12N 15/111* (2013.01); *C12N 15/88* (2013.01); *C12N 2310/12* (2013.01); *C12N 2830/50* (2013.01)

(58) Field of Classification Search
CPC .......................... C12N 15/113; C12N 15/111
See application file for complete search history.

(56) References Cited

U.S. PATENT DOCUMENTS

| | | | |
|---|---|---|---|
| 5,173,414 A | 12/1992 | Lebkowski et al. | |
| 5,658,776 A | 8/1997 | Flotte et al. | |
| 5,786,211 A | 7/1998 | Johnson | |
| 5,871,982 A | 2/1999 | Wilson et al. | |
| 5,942,395 A | 8/1999 | Fournier et al. | |
| 6,258,595 B1 | 7/2001 | Gao et al. | |
| 7,399,753 B2 | 7/2008 | Mitchell et al. | |
| 8,053,232 B2 | 11/2011 | Puttaraju et al. | |
| 8,603,457 B2 * | 12/2013 | Yu ........................ | C12N 15/113 |
| | | | 514/44 R |
| 8,735,366 B2 | 5/2014 | Bauer et al. | |
| 8,883,753 B2 | 11/2014 | Puttaraju et al. | |
| 9,040,491 B2 | 5/2015 | Dreyfuss et al. | |
| 9,074,207 B2 | 7/2015 | Pagani et al. | |
| 9,669,109 B1 | 6/2017 | Pagani et al. | |
| 10,987,433 B2 | 4/2021 | Bennett et al. | |
| 11,377,646 B2 | 7/2022 | Doudna et al. | |
| 11,530,398 B2 | 12/2022 | Doudna et al. | |
| 11,578,313 B2 | 2/2023 | Doudna et al. | |
| 11,685,909 B2 | 6/2023 | Doudna et al. | |
| 11,739,309 B2 | 8/2023 | Doudna et al. | |
| 11,767,528 B2 | 9/2023 | Borrajo | |
| 11,946,050 B2 | 4/2024 | Bruno Quinta De Souza Leal | |
| 11,993,776 B2 | 5/2024 | Johnson et al. | |
| 2004/0058344 A1 | 3/2004 | Mitchell et al. | |
| 2006/0134658 A1 | 6/2006 | Garcia-Blanco | |
| 2006/0194317 A1 | 8/2006 | Puttaraju et al. | |
| 2006/0234247 A1 | 10/2006 | Puttaraju et al. | |
| 2011/0212058 A1 | 9/2011 | Lamond et al. | |
| 2013/0059901 A1 | 3/2013 | Bauer et al. | |
| 2014/0186300 A1 | 7/2014 | Yu et al. | |
| 2015/0209448 A1 | 7/2015 | de Boer et al. | |
| 2022/0062437 A1 | 3/2022 | Bennett et al. | |
| 2022/0160898 A1 | 5/2022 | Michalakis et al. | |
| 2022/0213469 A1 | 7/2022 | Blainey et al. | |
| 2022/0243194 A1 | 8/2022 | Wei et al. | |
| 2023/0340469 A1 | 10/2023 | Nelles | |
| 2024/0011026 A1 | 1/2024 | Nelles | |
| 2024/0209366 A1 | 6/2024 | Nelles | |

FOREIGN PATENT DOCUMENTS

| | | |
|---|---|---|
| EP | 1521766 B1 | 11/2012 |
| EP | 2205739 B1 | 7/2014 |
| EP | 2627339 B1 | 5/2015 |
| EP | 2872632 A1 | 5/2015 |
| EP | 2320952 B1 | 5/2016 |
| EP | 3377116 A1 | 9/2018 |
| EP | 3781213 A1 | 2/2021 |
| EP | 3898996 A1 | 10/2021 |

(Continued)

OTHER PUBLICATIONS

Coady et al., 2007, Molecular Therapy, vol. 15, No. 8, p. 1471-1478 (Year: 2007).*
Dooley et al., 2018, Molecular Therapy: Nucleic Acids, vol. 12, p. 294-308 (Year: 2018).*
Jorjani et al., 2016, Nucleic Acids Research, vol. 44, No. 11, p. 5068-5082 (Year: 2016).*
Monjaret et al., 2014, Molecular Therapy, vol. 22, No. 6, p. 1176-1187 (Year: 2014).*
Puttaraju et al., 1999, Nature Biotechnology, vol. 17, p. 246-252 (Year: 1999).*
Wally et al., 2012, Journal of Investigative Dermatology, vol. 132, p. 1959-1966 (Year: 2012).*
*Homo sapiens* small nucleolar RBA, H/ACA box 48 (SNORA48), small nucleolar RBA NCBI Reference Sequence: NR_002918.1 (Year: 2020).*

(Continued)

*Primary Examiner* — Soren Harward
*Assistant Examiner* — Jenna L Persons
(74) *Attorney, Agent, or Firm* — Morgan, Lewis & Bockius LLP

(57) ABSTRACT

The present disclosure provides compositions and methods of use thereof for targeting trans-splicing of a pre-mRNA in a cell utilizing small nuclear RNAs (snRNAs) and small nucleolar RNAs (snoRNAs), and related methods.

32 Claims, 37 Drawing Sheets

Specification includes a Sequence Listing.

(56) References Cited

FOREIGN PATENT DOCUMENTS

| EP | 4217010 A1 | 8/2023 | |
| EP | 4323391 A1 | 2/2024 | |
| EP | 4370680 A2 | 5/2024 | |
| WO | 95/13392 A1 | 5/1995 | |
| WO | 96/17947 A1 | 10/1996 | |
| WO | 97/06243 A1 | 2/1997 | |
| WO | 97/08298 A1 | 3/1997 | |
| WO | 97/09441 A2 | 3/1997 | |
| WO | 97/21825 A1 | 6/1997 | |
| WO | 99/11764 A2 | 3/1999 | |
| WO | 2013151666 A2 | 10/2013 | |
| WO | 2020181101 A1 | 9/2020 | |
| WO | 2020181102 A1 | 9/2020 | |
| WO | 2021034717 A1 | 2/2021 | |
| WO | 2021133829 A1 | 7/2021 | |
| WO | 2021216512 A1 | 10/2021 | |
| WO | 2022055998 A1 | 3/2022 | |
| WO | 2022067228 A1 | 3/2022 | |
| WO | 2022220968 A1 | 10/2022 | |
| WO | 2023039346 A1 | 3/2023 | |
| WO | 2023039373 A2 | 3/2023 | |
| WO | 2023064895 A1 | 4/2023 | |
| WO | 2023130959 A1 | 7/2023 | |
| WO | 2023201203 A2 | 10/2023 | |
| WO | 2023215761 A1 | 11/2023 | |
| WO | 2023220566 A1 | 11/2023 | |
| WO | 2023237627 A1 | 12/2023 | |
| WO | 2023237638 A1 | 12/2023 | |
| WO | 2023250384 A2 | 12/2023 | |
| WO | 2024019801 A1 | 1/2024 | |
| WO | 2024068898 A1 | 4/2024 | |
| WO | 2024102659 A1 | 5/2024 | |
| WO | 2024112957 A1 | 5/2024 | |
| WO | 2024124237 A2 | 6/2024 | |
| WO | 2024124238 A1 | 6/2024 | |
| WO | WO-2024118946 A1 * | 6/2024 | |
| WO | WO-2024163839 A1 * | 8/2024 | ........... C12N 15/113 |
| WO | WO-2025170919 A1 * | 8/2025 | ........... C12N 15/113 |

OTHER PUBLICATIONS

Bergeron, Sep. 27, 2022, Nucleic Acids Research, vol. 51, D291-D296; https://bioinfo-scottgroup.med.usherbrooke.ca/snoDB/ (Year: 2022).*

Reichow et al., 2007, Nucleic Acids Research, vol. 35, No. 5, p. 1452-1464 (Year: 2017).*

Zeng, et al., "Predicting RNA splicing from DNA sequence using Pangolin", Genome Biology, vol. 23, No. 103 (2022).

Zuker, et al., "Mfold web server for nucleic acid folding and hybridization prediction" Mfold web server for nucleic acid folding and hybridization prediction, Nucleic Acids Research, 2003, vol. 31, No. 13, 3406-3415.

Zuker, et al., "Optimal computer folding of lare RNA sequences using thermodynamics and auxiliary Information" Nucleic Acids Research, vol. 9, No. 1 (1981).

Akiyama, et al., "A max-margin training of RNA secondary structure prediction integrated with the thermodynamic model", Journal of Bioinformatics and Computational Biology, vol. 1, No. 6, published Dec. 19, 2018.

Andronescu, et al., "Computational approaches for RNA energy parameter estimation," Bioinformatics, vol. 16, No. 12, pp. 2304-2318 (2010).

Andronescu, et al., "Efficient parameter estimation for RNA secondary structure prediction", Bioinformatics, vol. 23, pp. i19-i28, (2007).

Black, et al., "U2 as well as U1 Small Nuclear Ribonucleoproteins are Involved in Premessenger RNA Splicing", (1985) Cell 42: 737-750.

Bratkovic, et al., "Functional diversity of small nucleolar RNAs", Nucleic Acids Res. Feb. 28, 2020; 48(4): 1627-1651.

Charenton, et al., "Mechanism of 5' splice site transfer for human spliceosome activation", (2019) Science 364:362-367.

Chen, et al., "RNA Secondary Structure Prediction by Learning Unrolled Algorithms", Published as a conference paper at International Conference on Learning Representations (ICLR) (2020) (arXiv:2002.05810).

Cotten, et al., "Specific contacts between mammalian U7 snRNA and histone precursor RNA are indispensable for the in vitro 3' RNA processing reaction", (1988) The EMBO Journal 7:801-808.

Dieci, et al., "Eukaryotic snoRNAs: A paradigm for gene expression flexibility", Elsevier, Genomics 94 (2009) 83-88.

Do, et al., "ONTRAfold: RNA secondary structure prediction without physics-based models", Bioinformatics, vol. 22, No. 14, 2006.

Eddy, et al., "RNA sequence analysis using convariance models", Nucleic Acids Research, 1994, vol. 22, No. 11, 2079-2088.

Jaganathan, et al., "Predicting Splicing from Primary Sequence with Deep Learning", Cell, vol. 176, No. 3, pp. 535-548 (2019).

Kolossova, et al., "U11 snRNA interacts in vivo with the 5' splice site of U12-dependent (AU-AC) pre-mRNA introns", (1997) RNA 3: 227.

Lasda and Blumenthal, "Trans-splicing", Wiley Interdiscip Rev RNA, vol. 2, No. 3, pp. 417-434 (2011).

Laughlin, et al., "Cloning of infectious adeno-associated virus genomes in bacterial plasmids", Gene, vol. 23, No. 1, pp. 65-73 (1983).

Lebkowski, et al., "Adeno-Associated Virus: a Vector System for Efficient Introduction and Integration of DNA into a Variety of Mammalian Cell Types", Molecular and Cellular Biology. 1988, vol. 8, No. 10, p. 3988-399.

Liu, et al., "Partial correction of endogenous ΔF508 CFTR in human cystic fibrosis airway epithelia by spliceosome-mediated RNA trans-splicing", Nat Biotechnol, vol. 20, pp. 47-52 (2002).

Liu, et al., "Splicing inactivation generates hybrid mRNA-snoRNA transcripts targeted by cytoplasmic RNA decay", RNAS, Jul. 25, 2022. vol. 119, No. 31, pp. 1-9.

Lorenz, et al., "ViennaRNA Package 2.0", Algorithms for Molecular Biology 2011, 6:26.

Ma, et al., "Pol III Promoters to Express Small RNAs: Delineation of Transcription Initiation", Mol Ther Nucleic Acids, vol. 3, No. 5, e161 (2014).

Mansfield, et al., "Repair of CFTR mRNA by spliceosome-mediated RNA trans-splicing", Gene Therapy (2000) 7, 1885-1895.

Markham & Zuker, "UNAFold Software for Nucleic Acid Folding and Hybridization," Methods Mol Biol, vol. 453, pp. 3-31 (2008).

Matera, et al., "A day in the life of the spliceosome", Nat Rev Mol Cell Biol, vol. 15, pp. 108-121 (2014).

McLaughlin, et al., "Adeno-Associated Virus General Transduction Vectors: Analysis of Proviral Structures", Journal of Virology, (1988) vol. 62, No. 6, p. 1963-1973.

Miyagishi, et al., "U6 promoter-driven siRNAs with four uridine 3' overhangs efficiently suppress targeted gene expression in mammalian cells", Nature Biotechnology, vol. 19 (2022).

Mosig, et al., "To code or not to code? That is the question for RNA in timekeeping", Biochem (Lond) (2020) vol. 42, No. 2: pp. 12-15.

Muzyczka, "Use of Adeno-Associated Virus as a General Transduction Vector for Mammalian Cells", Current Topics in Microbiology and Immunology, vol. 158, 1992.

Nguyen, et al., "The architecture of the spliceosomal U4/U6. U5 tri-snRNP", (2015), Nature 523:47-52.

Ni, et al., "Small Nucleolar RNAs Direct Site-Specific Synthesis of Pseudouridine in Ribosomal RNA", Cell. May 16, 1997;89(4):565-71.

Paul, et al., "Increased Viral Titer Through Concentration of Viral Harvests from Retroviral Packaging Lines", Human Gene Therapy 4:609-615 (1993).

Reuter, et al., "RNAstructure: software for RNA secondary structure prediction and analysis", Reuter and Mathews BMC Bioinformatics 2010, 11:129.

Rindt, et al., "Replacement of huntingtin exon 1 by trans-splicing", Cell. Mol. Life Sci. (2012) 69:4191-4204.

Rivas, et al., "A range of complex probabilistic models for RNA secondary structure prediction that includes the nearest-neighbor model and more," RNA, vol. 18, No. 2: pp. 193-212 (2025).

(56)            References Cited

OTHER PUBLICATIONS

Roithova, et al., "The Sm-core mediates the retention of partially-assembled spliceosomal snRNPs in Cajal bodies until their full maturation", Nucleic Acids Research, 2018, vol. 46, No. 7, 3774-3790.

Rossi, et al., "Involvement of U1 Small Nuclear Ribonucleoproteins (snRNP) in 5* Splice Site-U1 snRNP Interaction", vol. 271, No. 39, Issue of Sep. 27, pp. 23985-23991, 1996.

Samulski, et al., "Cloning of adeno-associated virus into pBR322: Rescue of intact virus from the recombinant plasmid in human cells", Proc. Natt Acad. Sci. USA vol. 79, pp. 2077-2081, Mar. 1982, Microbiology.

Samulski, et al., "Helper-Free Stocks of Recombinant Adeno-Associated Viruses: Normal Integration Does Not Require Viral Gene Expression", Journal of Virology, (1989) pp. 3822-3828.

Schroeder, et al., "Optical Melting Measurements of Nucleic Acid Thermodynamics", Methods Enzymol. (2009) 468: 371-387.

Semple, et al., "Rational design of cationic lipids for siRNA delivery", Nature Biotechnology, vol. 28, pp. 172-176 (2010).

Senapathy, et al., "Replication of Adeno-associated virus DNA", J. Mol. Kiol. (1984) 178, 179, 1-20.

Singh, et al., "RNA secondary structure prediction using an ensemble of two-dimensional deep neural networks and transfer learning", Nature Communications, vol. 10, No. 5407 (2019).

Soldati, et al., "Structural and Functional Characterization of Mouse U7 Small Nuclear RNA Active in 3' Processing of Histone Pre-mRNA", (1988), Molecular and Cellular Biology 8:1518-1524.

Strub, et al., "The cDNA sequences of the sea urchin U7 small nuclear RNAsuggest specific contacts between histone mRNA precursor andU7 RNA during RNA processing", (1984) EMBO journal 3:2801-2807.

The RNAcentral Consortium "RNAcentral: a comprehensive database of non-coding RNA sequences," Nucleic Acids Research, vol. 45, No. D1, pp: D128-34 (2016).

Tratschin, et al., "A Human Parvovirus, Adeno-Associated Virus, as a Eucaryotic Vector: Transient Expression and Encapsidation of the Procaryotic Gene for Chloramphenicol Acetyltransferase", Molecular and Cellular Biology, Oct. 1984, p. 2072-2081.

Turner, et al., "NNDB: the nearest neighbor parameter database for predicting stability of nucleic acid secondary structure", Nucleic Acids Research, 2010, vol. 38, D280-D282.

Turunen, et al., "HnRNPH1/H2, U1 snRNP, and U11 snRNP cooperate to regulate the stability of the U11-48K pre-mRNA", (2013) RNA 4:61-76.

Wilkinson, et al., "RNA Splicing by the Spliceosome", Annual Review of Biochemistry, vol. 89, pp. 359-388 (2020).

Xia, et al., "An enhanced U6 promoter for synthesis of short hairpin RNA", Nucleic Acids Research, 2003, vol. 31, No. 17 e100.

Zakov, et al., "Rich Parameterization Improves RNA Structure Prediction", Journal of Computational Biology, vol. 18, No. 11, pp. 1525-1542 (2011).

Hirose, et al., "Splicing-Dependent and -Independent Modes of Assembly for Intron-Encoded Box C/D snoRNPs in Mammalian Cells," Molecular Cell, vol. 12, pp. 113-123, Jul. 2003.

Wang, et al. "The m6A Consensus Motif Provides a Paradigm of Epitranscriptomic Studies," Biochemistry 2021, 60, 3410-3412.

* cited by examiner cis-splicing trans-splicing

U7-based splice editor (U7-SE) examples

SEQ ID NO: 794

SEQ ID NO: 795

SEQ ID NO: 796

SEQ ID NO: 797

U7-SE schematic

U7 snRNA
(ncRNA)   binding domain trans-spliced mRNA

U7-SE / target RNA-RNA interactions trans-spliced mRNA

U1-based splice editor (U1-SE) examples

SEQ ID NO: 798

SEQ ID NO: 799

SEQ ID NO: 800 folded RNA

U1-SE schematic

U1-SE / target RNA-RNA interactions

U11-based splice editor (U11-SE)

SEQ ID NO: 801

SEQ ID NO: 802

SEQ ID NO: 803

U11-SE schematic

U11-SE / target RNA-RNA interactions

Sm-based splice editor (Sm-SE) examples
SEQ ID NO: 804
binding domain          Sm-linker          intron          exon
SEQ ID NO: 805
binding domain          Sm-linker          intron          exon
SEQ ID NO: 806
binding domain          Sm-linker          intron          exon
SEQ ID NO: 807
binding domain          Sm-linker          intron          exon
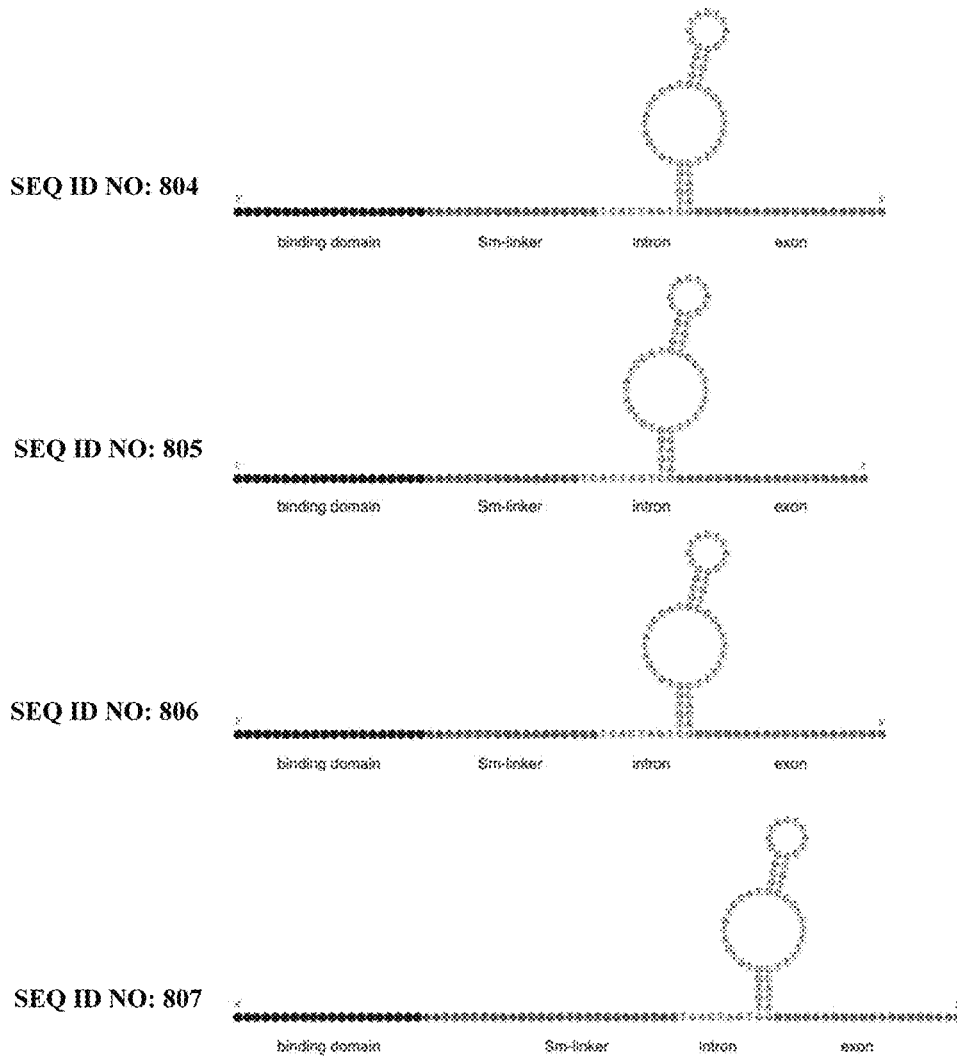
FIG. 5A
folded RNA
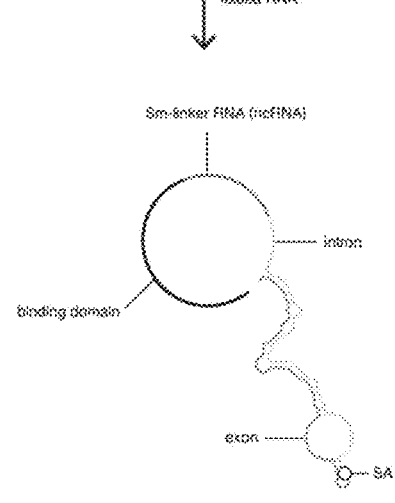
Sm-linker RNA (ncRNA)
intron
binding domain
exon
SA

FIG. 5B        Sm-SE schematic
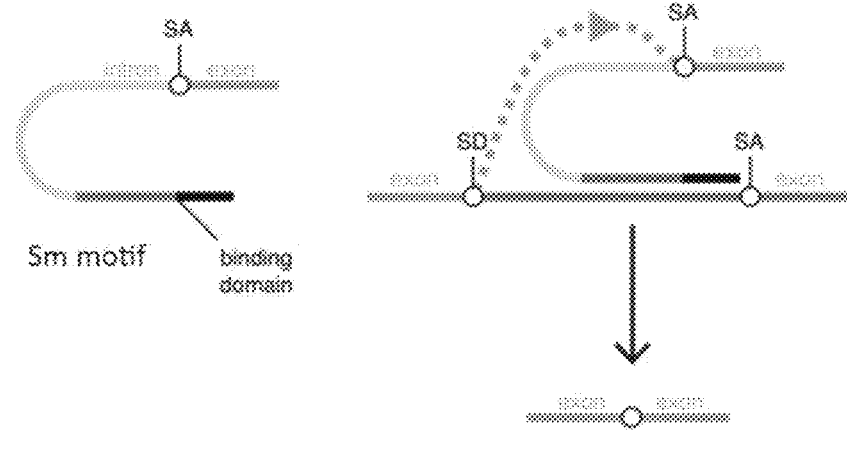
Sm-SE / target RNA-RNA interactions
FIG. 5C
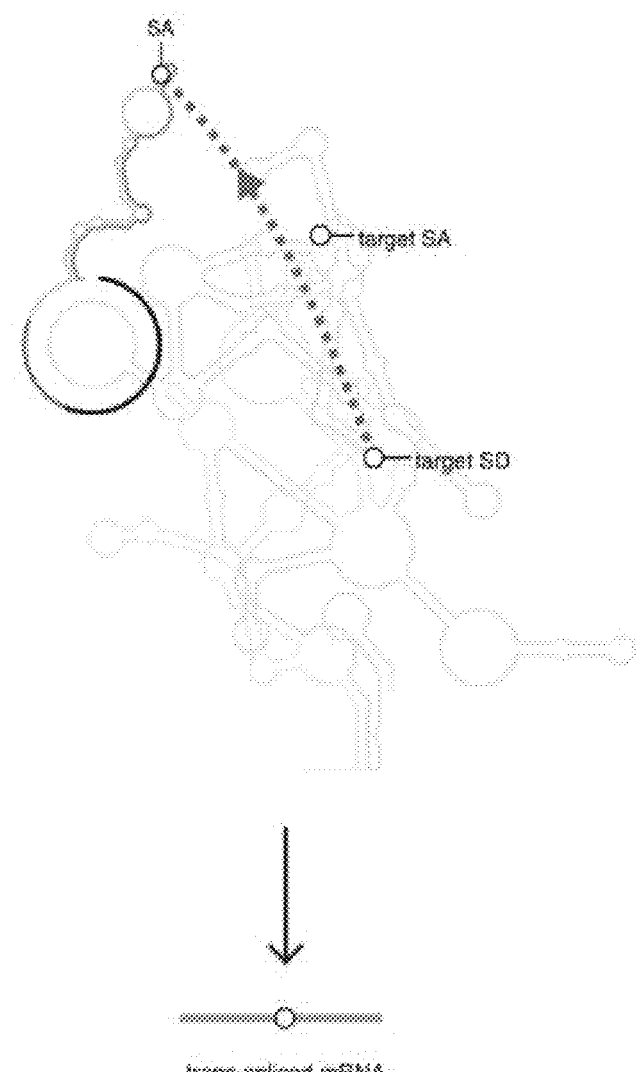

engineered snoRNA (esnoRNA)-based splice editor (esnoRNA-SE) examples

SEQ ID NO: 808

SEQ ID NO: 809

SEQ ID NO: 810

SEQ ID NO: 811 esnoRNA-SE schematic

FIG. 6C     esnoRNA-SE / target RNA-RNA interactions snoRNA

Modified
binding
domain of the
snoRNA

USH2A trans-splicing
(transient reporter)

HEK293T transfection repRNA
AAV-delivered

Human Protein components
Endogenous

5' Splice Editing

SEQUENCE LISTING

Sequence total quantity: 811
SEQ ID NO: 1        moltype =   length =
SEQUENCE: 1
000

SEQ ID NO: 2        moltype =   length =
SEQUENCE: 2
000

SEQ ID NO: 3        moltype =   length =
SEQUENCE: 3
000

SEQ ID NO: 4        moltype =   length =
SEQUENCE: 4
000

SEQ ID NO: 5        moltype =   length =
SEQUENCE: 5
000

SEQ ID NO: 6        moltype =   length =
SEQUENCE: 6
000

SEQ ID NO: 7        moltype =   length =
SEQUENCE: 7
000

SEQ ID NO: 8        moltype =   length =
SEQUENCE: 8
000

SEQ ID NO: 9        moltype = RNA   length = 154
FEATURE             Location/Qualifiers
source              1..154
                    mol_type = other RNA
                    organism = synthetic construct
SEQUENCE: 9
atacttacgt aacaggagaa aatacggcca tgaagttggt gtttctcggg ggcgatttct   60
ccattgtact cagtatgtgc tgactgactc ctgttacttc cacatgtggg gaaactggac  120
tgtaatttgt ggtggtgggg aattgcgttc gcgc                              154

SEQ ID NO: 10       moltype = RNA   length = 154
FEATURE             Location/Qualifiers
source              1..154
                    mol_type = other RNA
                    organism = synthetic construct
SEQUENCE: 10
tacttacgta acaggagaaa atacggccat gaagttggtg tttctcgggg gcgatttctc   60
cattgtactc agtatgtgct gactgactcc tgttacttcc acatgtgggg aaactggact  120
gtaatttgtg gtggtgggga attgcgttcg cgct                              154

SEQ ID NO: 11       moltype = RNA   length = 154
FEATURE             Location/Qualifiers
source              1..154
                    mol_type = other RNA
                    organism = synthetic construct
SEQUENCE: 11
acttacgtaa caggagaaaa tacggccatg aagttggtgt ttctcggggg cgatttctcc   60

-continued

```
attgtactca gtatgtgctg actgactcct gttacttcca catgtgggga aactggactg   120
taatttgtgg tggtgggggaa ttgcgttcgc gctt                             154

SEQ ID NO: 12            moltype = RNA   length = 154
FEATURE                  Location/Qualifiers
source                   1..154
                         mol_type = other RNA
                         organism = synthetic construct
SEQUENCE: 12
cttacgtaac aggagaaaat acggccatga agttggtgtt tctcgggggc gatttctcca   60
ttgtactcag tatgtgctga ctgactcctg ttacttccac atgtggggaa actggactgt   120
aatttgtggt ggtggggaat tgcgttcgcg cttt                              154

SEQ ID NO: 13            moltype = RNA   length = 154
FEATURE                  Location/Qualifiers
source                   1..154
                         mol_type = other RNA
                         organism = synthetic construct
SEQUENCE: 13
ttacgtaaca ggagaaaata cggccatgaa gttggtgttt ctcggggcg atttctccat    60
tgtactcagt atgtgctgac tgactcctgt tacttccaca tgtggggaaa ctggactgta   120
atttgtggtg tgggggaatt gcgttcgcgc tttc                              154

SEQ ID NO: 14            moltype = RNA   length = 154
FEATURE                  Location/Qualifiers
source                   1..154
                         mol_type = other RNA
                         organism = synthetic construct
SEQUENCE: 14
tacgtaacag gagaaaatac ggccatgaag ttggtgtttc tcggggcga tttctccatt    60
gtactcagta tgtgctgact gactcctgtt acttccacat gtgggaaac tggactgtaa    120
tttgtggtgg tggggaattg cgttcgcgct ttct                              154

SEQ ID NO: 15            moltype = RNA   length = 154
FEATURE                  Location/Qualifiers
source                   1..154
                         mol_type = other RNA
                         organism = synthetic construct
SEQUENCE: 15
acgtaacagg agaaatacg gccatgaagt tggtgtttct cggggcgat ttctccattg     60
tactcagtat gtgctgactg actcctgtta cttccacatg tggggaaact ggactgtaat   120
ttgtggtggt gggggaattgc gttcgcgctt tctt                             154

SEQ ID NO: 16            moltype = RNA   length = 154
FEATURE                  Location/Qualifiers
source                   1..154
                         mol_type = other RNA
                         organism = synthetic construct
SEQUENCE: 16
cgtaacagga gaaaatacgg ccatgaagtt ggtgtttctc ggggcgatt tctccattgt     60
actcagtatg tgctgactga ctcctgttac ttccacatgt ggggaaactg gactgtaatt   120
tgtggtggtg gggaattgcg ttcgcgcttt cttc                              154

SEQ ID NO: 17            moltype = RNA   length = 154
FEATURE                  Location/Qualifiers
source                   1..154
                         mol_type = other RNA
                         organism = synthetic construct
SEQUENCE: 17
gtaacaggag aaaatacggc catgaagttg gtgtttctcg ggggcgattt ctccattgta    60
ctcagtatgt gctgactgac tcctgttact ccacatgtg gggaaactgg actgtaattt    120
gtggtggtgg ggaattgcgt tcgcgctttc ttct                              154

SEQ ID NO: 18            moltype = RNA   length = 153
FEATURE                  Location/Qualifiers
source                   1..153
                         mol_type = other RNA
                         organism = synthetic construct
SEQUENCE: 18
taacaggaga aaatacggcc atgaagttgg tgtttctcgg gggcgatttc tccattgtac    60
tcagtatgtg ctgactgact cctgttactt ccacatgtgg ggaaactgga ctgtaatttg   120
tggtggtggg gaattgcgtt cgcgctttct tct                               153

SEQ ID NO: 19            moltype = RNA   length = 154
FEATURE                  Location/Qualifiers
source                   1..154
                         mol_type = other RNA
                         organism = synthetic construct
SEQUENCE: 19
```

-continued

```
atatttactt ggcagggag ataacgtgac cacgaaggtg gtttttcccag ggctgaggct   60
tattcattgt actccggatg tgctgaccc tgcgatttcc ccaaatgtgg gaaactcgac   120
tgcataattt gtggtagtgg ggggctgtgt ccgt                              154
```

SEQ ID NO: 20          moltype = RNA   length = 154
FEATURE                Location/Qualifiers
source                 1..154
                       mol_type = other RNA
                       organism = synthetic construct
SEQUENCE: 20

```
tatttacttg gcaggggaga taacgtgacc acgaaggtgg ttttcccagg gctgaggctt   60
attcattgta ctccggatgt gctgacccct gcgatttccc caaatgtggg aaactcgact   120
gcataatttg tggtagtggg gggctgtgtc cgtg                              154
```

SEQ ID NO: 21          moltype = RNA   length = 154
FEATURE                Location/Qualifiers
source                 1..154
                       mol_type = other RNA
                       organism = synthetic construct
SEQUENCE: 21

```
atttacttgg cagggagat aacgtgacca cgaaggtggt tttcccaggg ctgaggctta   60
ttcattgtac tccggatgtg ctgacccctg cgatttcccc aaatgtggga aactcgactg   120
cataatttgt ggtagtgggg ggctgtgtcc gtgc                              154
```

SEQ ID NO: 22          moltype = RNA   length = 154
FEATURE                Location/Qualifiers
source                 1..154
                       mol_type = other RNA
                       organism = synthetic construct
SEQUENCE: 22

```
tttacttggc aggggagata acgtgaccac gaaggtggtt ttcccagggc tgaggcttat   60
tcattgtact ccggatgtgc tgaccctgc gatttcccca aatgtgggaa actcgactgc   120
ataatttgtg gtagtggggg gctgtgtccg tgct                              154
```

SEQ ID NO: 23          moltype = RNA   length = 154
FEATURE                Location/Qualifiers
source                 1..154
                       mol_type = other RNA
                       organism = synthetic construct
SEQUENCE: 23

```
ttacttggca ggggagataa cgtgaccacg aaggtggttt tcccagggct gaggcttatt   60
cattgtactc cggatgtgct gaccctgcg atttccccaa atgtgggaaa ctcgactgca   120
taatttgtgg tagtggggg ctgtgtccgt gctt                              154
```

SEQ ID NO: 24          moltype = RNA   length = 154
FEATURE                Location/Qualifiers
source                 1..154
                       mol_type = other RNA
                       organism = synthetic construct
SEQUENCE: 24

```
tacttggcag gggagataac gtgaccacga aggtggtttt cccagggctg aggcttattc   60
attgtactcc ggatgtgctg accctgcga tttccccaaa tgtgggaaac tcgactgcat   120
aatttgtggt agtgggggc tgtgtccgtg cttt                              154
```

SEQ ID NO: 25          moltype = RNA   length = 154
FEATURE                Location/Qualifiers
source                 1..154
                       mol_type = other RNA
                       organism = synthetic construct
SEQUENCE: 25

```
acttggcagg ggagataacg tgaccacgaa ggtggttttc ccagggctga ggcttattca   60
ttgtactccg gatgtgctga cccctgcgat tccccaaat gtgggaaact cgactgcata   120
atttgtggta gtgggggct gtgtccgtgc tttt                              154
```

SEQ ID NO: 26          moltype = RNA   length = 154
FEATURE                Location/Qualifiers
source                 1..154
                       mol_type = other RNA
                       organism = synthetic construct
SEQUENCE: 26

```
cttggcaggg gagataacgt gaccacgaag gtggttttcc cagggctgag gcttattcat   60
tgtactccgg atgtgctgac ccctgcgatt tccccaaatg tgggaaactc gactgcataa   120
tttgtggtag tgggggctg tgtccgtgct tttc                              154
```

SEQ ID NO: 27          moltype = RNA   length = 154
FEATURE                Location/Qualifiers
source                 1..154
                       mol_type = other RNA
                       organism = synthetic construct

```
SEQUENCE: 27
ttggcagggg agataacgtg accacgaagg tggttttccc agggctgagg cttattcatt   60
gtactccgga tgtgctgacc cctgcgattt ccccaaatgt gggaaactcg actgcataat  120
ttgtggtagt gggggctgt gtccgtgctt ttcc                              154

SEQ ID NO: 28          moltype = RNA   length = 154
FEATURE                Location/Qualifiers
source                 1..154
                       mol_type = other RNA
                       organism = synthetic construct
SEQUENCE: 28
tggcagggga gataacgtga ccacgaaggt ggttttccca gggctgaggc ttattcattg   60
tactccggat gtgctgaccc ctgcgatttc cccaaatgtg ggaaactcga ctgcataatt  120
tgtggtagtg gggggctgtg tccgtgcttt tccc                             154

SEQ ID NO: 29          moltype = RNA   length = 154
FEATURE                Location/Qualifiers
source                 1..154
                       mol_type = other RNA
                       organism = synthetic construct
SEQUENCE: 29
atacttacct ggcagggcag ataccatgat cttaaaggca gttttcccag ggcaaggctt   60
atccattcca ctctggatcc attataggggg catgctgatc cctggaattg ccccaaatgt  120
gggaagctct actgcaaaat ttttggtagt gagc                             154

SEQ ID NO: 30          moltype = RNA   length = 154
FEATURE                Location/Qualifiers
source                 1..154
                       mol_type = other RNA
                       organism = synthetic construct
SEQUENCE: 30
tacttacctg gcaggcaga taccatgatc ttaaaggcag ttttcccagg gcaaggctta   60
tccattccac tctggatcca ttataggggc atgctgatcc ctggaattgc cccaaatgtg  120
ggaagctcta ctgcaaaatt tttggtagtg agcg                             154

SEQ ID NO: 31          moltype = RNA   length = 154
FEATURE                Location/Qualifiers
source                 1..154
                       mol_type = other RNA
                       organism = synthetic construct
SEQUENCE: 31
acttacctgg caggcagat accatgatct taaaggcagt tttcccaggg caaggcttat   60
ccattccact ctggatccat tataggggca tgctgatccc tggaattgcc ccaaatgtgg  120
gaagctctac tgcaaaattt ttggtagtga gcga                             154

SEQ ID NO: 32          moltype = RNA   length = 154
FEATURE                Location/Qualifiers
source                 1..154
                       mol_type = other RNA
                       organism = synthetic construct
SEQUENCE: 32
cttacctggc aggcagata ccatgatctt aaaggcagtt ttcccagggc aaggcttatc   60
cattccactc tggatccatt ataggggcat gctgatccct ggaattgccc caaatgtggg  120
aagctctact gcaaaatttt tggtagtgag cgat                             154

SEQ ID NO: 33          moltype = RNA   length = 154
FEATURE                Location/Qualifiers
source                 1..154
                       mol_type = other RNA
                       organism = synthetic construct
SEQUENCE: 33
ttacctggca gggcagatac catgatctta aaggcagttt cccagggca aggcttatcc   60
attccactct ggatccatta taggggcatg ctgatccctg gaattgcccc aaatgtggga  120
agctctactg caaaattttt ggtagtgagc gatg                             154

SEQ ID NO: 34          moltype = RNA   length = 154
FEATURE                Location/Qualifiers
source                 1..154
                       mol_type = other RNA
                       organism = synthetic construct
SEQUENCE: 34
tacctgcag gcagatacc atgatcttaa aggcagtttt cccagggcaa ggcttatcca   60
ttccactctg atccattat aggggcatgc tgatccctgg aattgcccca aatgtgggaa  120
gctctactgc aaaatttttg gtagtgagcg atgg                             154

SEQ ID NO: 35          moltype = RNA   length = 154
FEATURE                Location/Qualifiers
source                 1..154
                       mol_type = other RNA
```

-continued

```
                               organism = synthetic construct
SEQUENCE: 35
acctggcagg gcagatacca tgatcttaaa ggcagttttc ccagggcaag gcttatccat   60
tccactctgg atccattata ggggcatgct gatccctgga attgccccaa atgtgggaag   120
ctctactgca aaatttttgg tagtgagcga tggc                              154

SEQ ID NO: 36           moltype = RNA   length = 154
FEATURE                 Location/Qualifiers
source                  1..154
                        mol_type = other RNA
                        organism = synthetic construct
SEQUENCE: 36
cctggcaggg cagataccat gatcttaaag gcagttttcc cagggcaagg cttatccatt   60
ccactctgga tccattatag gggcatgctg atccctggaa ttgccccaaa tgtgggaagc   120
tctactgcaa aatttttggt agtgagcgat ggca                              154

SEQ ID NO: 37           moltype = RNA   length = 154
FEATURE                 Location/Qualifiers
source                  1..154
                        mol_type = other RNA
                        organism = synthetic construct
SEQUENCE: 37
ctggcagggc agataccatg atcttaaagg cagttttccc agggcaaggc ttatccattc   60
cactctggat ccattatagg ggcatgctga tccctggaat tgccccaaat gtgggaagct   120
ctactgcaaa attttggta gtgagcgatg gcat                               154

SEQ ID NO: 38           moltype = RNA   length = 154
FEATURE                 Location/Qualifiers
source                  1..154
                        mol_type = other RNA
                        organism = synthetic construct
SEQUENCE: 38
tggcagggca gataccatga tcttaaaggc agttttccca gggcaaggct tatccattcc   60
actctggatc cattataggg gcatgctgat ccctggaatt gccccaaatg tgggaagctc   120
tactgcaaaa tttttggtag tgagcgatgg catt                              154

SEQ ID NO: 39           moltype = RNA   length = 154
FEATURE                 Location/Qualifiers
source                  1..154
                        mol_type = other RNA
                        organism = synthetic construct
SEQUENCE: 39
atacttacct ggcaggggag ataccatgat cacgaaggtg gttttcccag ggcgaggctt   60
atccattgca ctccggatgt gctgacccct gcgatttccc caaatgtggg aaactcgact   120
gcataatttg tggtagtggg ggactgcgtt cgcg                              154

SEQ ID NO: 40           moltype = RNA   length = 154
FEATURE                 Location/Qualifiers
source                  1..154
                        mol_type = other RNA
                        organism = synthetic construct
SEQUENCE: 40
tacttacctg gcaggggaga taccatgatc acgaaggtgg ttttcccagg gcgaggctta   60
tccattgcac tccggatgtg ctgacccctg cgatttcccc aaatgtggga aactcgactg   120
cataatttgt ggtagtgggg gactgcgttc gcgc                              154

SEQ ID NO: 41           moltype = RNA   length = 154
FEATURE                 Location/Qualifiers
source                  1..154
                        mol_type = other RNA
                        organism = synthetic construct
SEQUENCE: 41
acttacctgg caggggagat accatgatca cgaaggtggt tttcccaggg cgaggcttat   60
ccattgcact ccggatgtgc tgacccctgc gatttcccca aatgtgggaa actcgactgc   120
ataatttgtg gtagtggggg actgcgttcg cgct                              154

SEQ ID NO: 42           moltype = RNA   length = 154
FEATURE                 Location/Qualifiers
source                  1..154
                        mol_type = other RNA
                        organism = synthetic construct
SEQUENCE: 42
cttacctggc aggggagata ccatgatcac gaaggtggtt tcccagggc gaggcttatc    60
cattgcactc cggatgtgct gacccctgcg atttccccaa atgtgggaaa ctcgactgca   120
taatttgtgg tagtggggga ctgcgttcgc gctt                              154

SEQ ID NO: 43           moltype = RNA   length = 154
FEATURE                 Location/Qualifiers
source                  1..154
```

-continued

```
                         mol_type = other RNA
                         organism = synthetic construct
SEQUENCE: 43
ttacctggca ggggagatac catgatcacg aaggtggttt tcccagggcg aggcttatcc   60
attgcactcc ggatgtgctg acccctgcga tttccccaaa tgtgggaaac tcgactgcat  120
aatttgtggt agtgggggac tgcgttcgcg cttt                              154

SEQ ID NO: 44           moltype = RNA   length = 154
FEATURE                 Location/Qualifiers
source                  1..154
                        mol_type = other RNA
                        organism = synthetic construct
SEQUENCE: 44
tacctggcag gggagatacc atgatcacga aggtggtttt cccagggcga ggcttatcca   60
ttgcactccg gatgtgctga cccctgcgat ttccccaaat gtgggaaact cgactgcata  120
atttgtggta gtgggggact gcgttcgcgc tttc                              154

SEQ ID NO: 45           moltype = RNA   length = 154
FEATURE                 Location/Qualifiers
source                  1..154
                        mol_type = other RNA
                        organism = synthetic construct
SEQUENCE: 45
acctggcagg ggagatacca tgatcacgaa ggtggttttc caggcgag gcttatccat    60
tgcactccg atgtgctgac ccctgcgatt tccccaaatg tgggaaactc gactgcataa  120
tttgtggtag tgggggactg cgttcgcgct ttcc                              154

SEQ ID NO: 46           moltype = RNA   length = 154
FEATURE                 Location/Qualifiers
source                  1..154
                        mol_type = other RNA
                        organism = synthetic construct
SEQUENCE: 46
cctggcaggg gagataccat gatcacgaag gtggttttcc caggcgagg cttatccatt   60
gcactccgga tgtgctgacc cctgcgattt ccccaaatgt gggaaactcg actgcataat  120
ttgtggtagt gggggactgc gttcgcgctt tccc                              154

SEQ ID NO: 47           moltype = RNA   length = 154
FEATURE                 Location/Qualifiers
source                  1..154
                        mol_type = other RNA
                        organism = synthetic construct
SEQUENCE: 47
ctggcagggg agataccatg atcacgaagg tggttttccc agggcgaggc ttatccattg   60
cactccggat gtgctgaccc ctgcgatttc cccaaatgtg ggaaactcga ctgcataatt  120
tgtggtagtg ggggactgcg ttcgcgcttt cccc                              154

SEQ ID NO: 48           moltype = RNA   length = 154
FEATURE                 Location/Qualifiers
source                  1..154
                        mol_type = other RNA
                        organism = synthetic construct
SEQUENCE: 48
tggcagggga gataccatga tcacgaaggt ggttttccca gggcgaggct tatccattgc   60
actccggatg tgctgacccc tgcgatttcc caaatgtgg gaaactcgac tgcataattt   120
gtggtagtgg gggactgcgt tcgcgctttc ccct                              154

SEQ ID NO: 49           moltype = RNA   length = 154
FEATURE                 Location/Qualifiers
source                  1..154
                        mol_type = other RNA
                        organism = synthetic construct
SEQUENCE: 49
atacttccct gacaggggag atacctagga atccaacttc ccagggcaag actgatctat   60
tgcactatgg atgtgccgac ccctgagatt tacaaaattg tgggaaactc aactgcataa  120
tttatggaaa tgaaggactg tgtttgcgct ttca                              154

SEQ ID NO: 50           moltype = RNA   length = 153
FEATURE                 Location/Qualifiers
source                  1..153
                        mol_type = other RNA
                        organism = synthetic construct
SEQUENCE: 50
tacttccctg acaggggaga tacctaggaa tccaacttcc cagggcaaga ctgatctatt   60
gcactatgga tgtgccgacc cctgagattt acaaaattgt gggaaactca actgcataat  120
ttatggaaat gaaggactgt gtttgcgctt tca                               153

SEQ ID NO: 51           moltype = RNA   length = 152
FEATURE                 Location/Qualifiers
```

```
source                   1..152
                         mol_type = other RNA
                         organism = synthetic construct
SEQUENCE: 51
acttccctga caggggagat acctaggaat ccaacttccc agggcaagac tgatctattg    60
cactatggat gtgccgaccc ctgagattta caaaattgtg ggaaactcaa ctgcataatt   120
tatggaaatg aaggactgtg tttgcgcttt ca                                 152

SEQ ID NO: 52             moltype = RNA   length = 151
FEATURE                  Location/Qualifiers
source                   1..151
                         mol_type = other RNA
                         organism = synthetic construct
SEQUENCE: 52
cttccctgac aggggagata cctaggaatc caacttccca gggcaagact gatctattgc    60
actatggatg tgccgacccc tgagatttac aaaattgtgg gaaactcaac tgcataattt   120
atggaaatga aggactgtgt ttgcgctttc a                                  151

SEQ ID NO: 53             moltype = RNA   length = 150
FEATURE                  Location/Qualifiers
source                   1..150
                         mol_type = other RNA
                         organism = synthetic construct
SEQUENCE: 53
ttccctgaca ggggagatac ctaggaatcc aacttcccag gcaagactg atctattgca     60
ctatggatgt gccgacccct gagatttaca aaattgtggg aaactcaact gcataattta   120
tggaaatgaa ggactgtgtt tgcgctttca                                    150

SEQ ID NO: 54             moltype = RNA   length = 149
FEATURE                  Location/Qualifiers
source                   1..149
                         mol_type = other RNA
                         organism = synthetic construct
SEQUENCE: 54
tccctgacag gggagatacc taggaatcca acttcccagg gcaagactga tctattgcac    60
tatggatgtg ccgacccctg agatttacaa aattgtggga aactcaactg cataatttat   120
ggaaatgaag gactgtgttt gcgctttca                                     149

SEQ ID NO: 55             moltype = RNA   length = 148
FEATURE                  Location/Qualifiers
source                   1..148
                         mol_type = other RNA
                         organism = synthetic construct
SEQUENCE: 55
ccctgacagg ggagatacct aggaatccaa cttcccaggg caagactgat ctattgcact    60
atggatgtgc cgaccctga gatttacaaa attgtgggaa actcaactgc ataatttatg    120
gaaatgaagg actgtgtttg cgctttca                                      148

SEQ ID NO: 56             moltype = RNA   length = 147
FEATURE                  Location/Qualifiers
source                   1..147
                         mol_type = other RNA
                         organism = synthetic construct
SEQUENCE: 56
cctgacaggg gagataccta ggaatccaac ttcccagggc aagactgatc tattgcacta    60
tggatgtgcc gaccctgag atttacaaaa ttgtgggaaa ctcaactgca taatttatgg    120
aaatgaagga ctgtgtttgc gctttca                                       147

SEQ ID NO: 57             moltype = RNA   length = 146
FEATURE                  Location/Qualifiers
source                   1..146
                         mol_type = other RNA
                         organism = synthetic construct
SEQUENCE: 57
ctgacagggg agatacctag gaatccaact tcccagggca agactgatct attgcactat    60
ggatgtgccg accctgaga tttacaaaat tgtgggaaac tcaactgcat aatttatgga    120
aatgaaggac tgtgtttgcg ctttca                                        146

SEQ ID NO: 58             moltype = RNA   length = 145
FEATURE                  Location/Qualifiers
source                   1..145
                         mol_type = other RNA
                         organism = synthetic construct
SEQUENCE: 58
tgacagggga gatacctagg aatccaactt cccagggcaa gactgatcta ttgcactatg    60
gatgtgccga ccctgagat ttacaaaatt gtgggaaact caactgcata atttatgaa    120
atgaaggact gtgtttgcgc tttca                                         145

SEQ ID NO: 59             moltype = RNA   length = 154
```

```
FEATURE              Location/Qualifiers
source               1..154
                     mol_type = other RNA
                     organism = synthetic construct
SEQUENCE: 59
aaacttctct gccaggggag ataccatgat cacaaaggtg gctttctcag ggaaaggctg      60
atttattgca ctccagatgt gctgacccct gagatttctc caaatgtggg aaactcagct     120
gcataaatttg tggaagcgaa ggactgtgtt tgtg                               154

SEQ ID NO: 60        moltype = RNA   length = 154
FEATURE              Location/Qualifiers
source               1..154
                     mol_type = other RNA
                     organism = synthetic construct
SEQUENCE: 60
aacttctctg ccaggggaga taccatgatc acaaaggtgg ctttctcagg gaaaggctga      60
tttattgcac tccagatgtg ctgacccctg agatttctcc aaatgtggga aactcagctg     120
cataatttgt ggaagcgaag gactgtgttt gtgc                               154

SEQ ID NO: 61        moltype = RNA   length = 154
FEATURE              Location/Qualifiers
source               1..154
                     mol_type = other RNA
                     organism = synthetic construct
SEQUENCE: 61
acttctctgc caggggagat accatgatca caaaggtggc tttctcaggg aaaggctgat      60
ttattgcact ccagatgtgc tgacccctga gatttctcca aatgtgggaa actcagctgc     120
ataatttgtg gaagcgaagg actgtgtttg tgct                               154

SEQ ID NO: 62        moltype = RNA   length = 154
FEATURE              Location/Qualifiers
source               1..154
                     mol_type = other RNA
                     organism = synthetic construct
SEQUENCE: 62
cttctctgcc aggggagata ccatgatcac aaaggtggct ttctcaggga aaggctgatt      60
tattgcactc cagatgtgct gacccctgag atttctccaa atgtgggaaa ctcagctgca     120
taatttgtgg aagcgaagga ctgtgtttgt gctt                               154

SEQ ID NO: 63        moltype = RNA   length = 154
FEATURE              Location/Qualifiers
source               1..154
                     mol_type = other RNA
                     organism = synthetic construct
SEQUENCE: 63
ttctctgcca ggggagatac catgatcaca aaggtggctt tctcagggaa aggctgattt      60
attgcactcc agatgtgctg acccctgaga tttctccaaa tgtgggaaac tcagctgcat     120
aatttgtgga agcgaaggac tgtgtttgtg cttt                               154

SEQ ID NO: 64        moltype = RNA   length = 154
FEATURE              Location/Qualifiers
source               1..154
                     mol_type = other RNA
                     organism = synthetic construct
SEQUENCE: 64
tctctgccag gggagatacc atgatcacaa aggtggcttt ctcagggaaa ggctgattta      60
ttgcactcca gatgtgctga cccctgagat tctccaaat gtgggaaact cagctgcata     120
atttgtggaa gcgaaggact gtgtttgtgc tttc                               154

SEQ ID NO: 65        moltype = RNA   length = 154
FEATURE              Location/Qualifiers
source               1..154
                     mol_type = other RNA
                     organism = synthetic construct
SEQUENCE: 65
ctctgccagg ggagatacca tgatcacaaa ggtggctttc tcagggaaag gctgatttat      60
tgcactccag atgtgctgac ccctgagatt tctccaaatg tgggaaactc agctgcataa     120
tttgtggaag cgaaggactg tgtttgtgct ttca                               154

SEQ ID NO: 66        moltype = RNA   length = 154
FEATURE              Location/Qualifiers
source               1..154
                     mol_type = other RNA
                     organism = synthetic construct
SEQUENCE: 66
tctgccaggg gagataccat gatcacaaag gtggctttct cagggaaagg ctgatttatt      60
gcactccaga tgtgctgacc cctgagattt ccaaatgt gggaaactca gctgcataat     120
ttgtggaagc gaaggactgt gtttgtgctt tcat                               154
```

```
SEQ ID NO: 67            moltype = RNA   length = 154
FEATURE                  Location/Qualifiers
source                   1..154
                         mol_type = other RNA
                         organism = synthetic construct
SEQUENCE: 67
ctgccagggg agataccatg atcacaaagg tggctttctc agggaaaggc tgatttattg   60
cactccagat gtgctgaccc ctgagatttc tccaaatgtg ggaaactcag ctgcataatt  120
tgtggaagcg aaggactgtg tttgtgcttt catg                              154

SEQ ID NO: 68            moltype = RNA   length = 154
FEATURE                  Location/Qualifiers
source                   1..154
                         mol_type = other RNA
                         organism = synthetic construct
SEQUENCE: 68
tgccagggga gataccatga tcacaaaggt ggctttctca gggaaaggct gatttattgc   60
actccagatg tgctgacccc tgagatttct ccaaatgtgg gaaactcagc tgcataattt  120
gtggaagcga aggactgtgt ttgtgctttc atgt                              154

SEQ ID NO: 69            moltype = RNA   length = 154
FEATURE                  Location/Qualifiers
source                   1..154
                         mol_type = other RNA
                         organism = synthetic construct
SEQUENCE: 69
atacttctct gccaggggag atactgtgat catgaaggtg gctttcccag ggcaaggctg   60
atctattgca ttctggatgt gctgactcct acgatttccc caagtgtggg aaactcaact  120
gcataatttg tggaagtaat gactgtgttt gcac                              154

SEQ ID NO: 70            moltype = RNA   length = 154
FEATURE                  Location/Qualifiers
source                   1..154
                         mol_type = other RNA
                         organism = synthetic construct
SEQUENCE: 70
tacttctctg ccaggggaga tactgtgatc atgaaggtgg ctttcccagg gcaaggctga   60
tctattgcat tctggatgtg ctgactccta cgatttcccc aagtgtggga aactcaactg  120
cataatttgt ggaagtaatg actgtgtttg cact                              154

SEQ ID NO: 71            moltype = RNA   length = 154
FEATURE                  Location/Qualifiers
source                   1..154
                         mol_type = other RNA
                         organism = synthetic construct
SEQUENCE: 71
acttctctgc caggggagat actgtgatca tgaaggtggc tttcccaggg caaggctgat   60
ctattgcatt ctggatgtgc tgactcctac gatttcccca agtgtgggaa actcaactgc  120
ataatttgtg gaagtaatga ctgtgtttgc actt                              154

SEQ ID NO: 72            moltype = RNA   length = 154
FEATURE                  Location/Qualifiers
source                   1..154
                         mol_type = other RNA
                         organism = synthetic construct
SEQUENCE: 72
cttctctgcc aggggagata ctgtgatcat gaaggtggct ttcccagggc aaggctgatc   60
tattgcattc tggatgtgct gactcctacg atttccccaa gtgtgggaaa ctcaactgca  120
taatttgtgg aagtaatgac tgtgtttgca cttt                              154

SEQ ID NO: 73            moltype = RNA   length = 154
FEATURE                  Location/Qualifiers
source                   1..154
                         mol_type = other RNA
                         organism = synthetic construct
SEQUENCE: 73
ttctctgcca ggggagatac tgtgatcatg aaggtggctt tcccagggca aggctgatct   60
attgcattct ggatgtgctg actcctacga tttccccaag tgtgggaaac tcaactgcat  120
aatttgtgga agtaatgact gtgtttgcac tttc                              154

SEQ ID NO: 74            moltype = RNA   length = 154
FEATURE                  Location/Qualifiers
source                   1..154
                         mol_type = other RNA
                         organism = synthetic construct
SEQUENCE: 74
tctctgccag gggagatact gtgatcatga aggtggcttt cccagggcaa ggctgatcta   60
ttgcattctg atgtgctga ctcctacgat ttccccaagt gtgggaaact caactgcata  120
atttgtggaa gtaatgactg tgtttgcact ttca                              154
```

-continued

```
SEQ ID NO: 75              moltype = RNA   length = 154
FEATURE                    Location/Qualifiers
source                     1..154
                           mol_type = other RNA
                           organism = synthetic construct
SEQUENCE: 75
ctctgccagg ggagatactg tgatcatgaa ggtggctttc ccagggcaag gctgatctat    60
tgcattctgg atgtgctgac tcctacgatt tccccaagtg tgggaaactc aactgcataa   120
tttgtggaag taatgactgt gtttgcactt tcac                                154

SEQ ID NO: 76              moltype = RNA   length = 154
FEATURE                    Location/Qualifiers
source                     1..154
                           mol_type = other RNA
                           organism = synthetic construct
SEQUENCE: 76
tctgccaggg gagatactgt gatcatgaag gtggctttcc cagggcaagg ctgatctatt    60
gcattctgga tgtgctgact cctacgattt ccccaagtgt gggaaactca actgcataat   120
ttgtggaagt aatgactgtg tttgcacttt cacg                                154

SEQ ID NO: 77              moltype = RNA   length = 154
FEATURE                    Location/Qualifiers
source                     1..154
                           mol_type = other RNA
                           organism = synthetic construct
SEQUENCE: 77
ctgccagggg agatactgtg atcatgaagg tggctttccc agggcaaggc tgatctattg    60
cattctggat gtgctgactc ctacgatttc cccaagtgtg ggaaactcaa ctgcataatt   120
tgtggaagta atgactgtgt ttgcactttc acgt                                154

SEQ ID NO: 78              moltype = RNA   length = 153
FEATURE                    Location/Qualifiers
source                     1..153
                           mol_type = other RNA
                           organism = synthetic construct
SEQUENCE: 78
tgccagggga gatactgtga tcatgaaggt ggctttccca gggcaaggct gatctattgc    60
attctggatg tgctgactcc tacgatttcc ccaagtgtgg gaaactcaac tgcataattt   120
gtggaagtaa tgactgtgtt tgcactttca cgt                                 153

SEQ ID NO: 79              moltype = RNA   length = 154
FEATURE                    Location/Qualifiers
source                     1..154
                           mol_type = other RNA
                           organism = synthetic construct
SEQUENCE: 79
atacttccct gccaggggag ataccgtgat catgaaggtg gctttcccag ggaaaggccg    60
atatgttgca ctctagatgt gctgacccgt gagatttccc caaatgtggg acactcaaat   120
gcataattgg tggaagtgaa ggactgtgtt tgtg                                154

SEQ ID NO: 80              moltype = RNA   length = 154
FEATURE                    Location/Qualifiers
source                     1..154
                           mol_type = other RNA
                           organism = synthetic construct
SEQUENCE: 80
tacttccctg ccaggggaga taccgtgatc atgaaggtgg ctttcccagg gaaaggccga    60
tatgttgcac tctagatgtg ctgacccgtg agatttcccc aaatgtggga cactcaaatg   120
cataattggt ggaagtgaag gactgtgttt gtgc                                154

SEQ ID NO: 81              moltype = RNA   length = 154
FEATURE                    Location/Qualifiers
source                     1..154
                           mol_type = other RNA
                           organism = synthetic construct
SEQUENCE: 81
acttccctgc caggggagat accgtgatca tgaaggtggc tttcccaggg aaaggccgat    60
atgttgcact ctagatgtgc tgacccgtga gatttcccca aatgtgggac actcaaatgc   120
ataattggtg gaagtgaagg actgtgtttg tgct                                154

SEQ ID NO: 82              moltype = RNA   length = 154
FEATURE                    Location/Qualifiers
source                     1..154
                           mol_type = other RNA
                           organism = synthetic construct
SEQUENCE: 82
cttccctgcc aggggagata ccgtgatcat gaaggtggct ttcccaggga aaggccgata    60
tgttgcactc tagatgtgct gacccgtgag atttccccaa atgtgggaca ctcaaatgca   120
```

-continued

```
taattggtgg aagtgaagga ctgtgtttgt gctt                                        154

SEQ ID NO: 83            moltype = RNA   length = 154
FEATURE                  Location/Qualifiers
source                   1..154
                         mol_type = other RNA
                         organism = synthetic construct
SEQUENCE: 83
ttccctgcca ggggagatac cgtgatcatg aaggtggctt tcccagggaa aggccgatat          60
gttgcactct agatgtgctg acccgtgaga tttccccaaa tgtgggacac tcaaatgcat         120
aattggtgga agtgaaggac tgtgtttgtg cttt                                       154

SEQ ID NO: 84            moltype = RNA   length = 154
FEATURE                  Location/Qualifiers
source                   1..154
                         mol_type = other RNA
                         organism = synthetic construct
SEQUENCE: 84
tccctgccag gggagatacc gtgatcatga aggtggcttt cccagggaaa ggccgatatg          60
ttgcactcta gatgtgctga cccgtgagat ttccccaaat gtgggacact caaatgcata         120
attggtggaa gtgaaggact gtgtttgtgc tttc                                       154

SEQ ID NO: 85            moltype = RNA   length = 154
FEATURE                  Location/Qualifiers
source                   1..154
                         mol_type = other RNA
                         organism = synthetic construct
SEQUENCE: 85
ccctgccagg ggagataccg tgatcatgaa ggtggctttc ccagggaaag gccgatatgt          60
tgcactctag atgtgctgac ccgtgagatt tccccaaatg tgggacactc aaatgcataa         120
ttggtggaag tgaaggactg tgtttgtgct ttca                                       154

SEQ ID NO: 86            moltype = RNA   length = 153
FEATURE                  Location/Qualifiers
source                   1..153
                         mol_type = other RNA
                         organism = synthetic construct
SEQUENCE: 86
cctgccaggg gagataccgt gatcatgaag gtggctttcc cagggaaagg ccgatatgtt          60
gcactctaga tgtgctgacc cgtgagattt ccccaaatgt gggacactca aatgcataat         120
tggtggaagt gaaggactgt gtttgtgctt tca                                        153

SEQ ID NO: 87            moltype = RNA   length = 152
FEATURE                  Location/Qualifiers
source                   1..152
                         mol_type = other RNA
                         organism = synthetic construct
SEQUENCE: 87
ctgccagggg agataccgtg atcatgaagg tggctttccc agggaaaggc cgatatgttg          60
cactctagat gtgctgaccc gtgagatttc cccaaatgtg ggacactcaa atgcataatt         120
ggtggaagtg aaggactgtg tttgtgcttt ca                                         152

SEQ ID NO: 88            moltype = RNA   length = 151
FEATURE                  Location/Qualifiers
source                   1..151
                         mol_type = other RNA
                         organism = synthetic construct
SEQUENCE: 88
tgccagggga gataccgtga tcatgaaggt ggctttccca gggaaaggcc gatatgttgc          60
actctagatg tgctgacccg tgagatttcc ccaaatgtgg gacactcaaa tgcataattg         120
gtggaagtga aggactgtgt ttgtgctttc a                                          151

SEQ ID NO: 89            moltype = RNA   length = 154
FEATURE                  Location/Qualifiers
source                   1..154
                         mol_type = other RNA
                         organism = synthetic construct
SEQUENCE: 89
ttaactacct gacagaggag atactgtgat catgaaagtg gttttcctag ggcaagactt          60
atccgttgca ctccagatgt gctgactcat gcaatttccc caaatgtggg aaactcgact         120
acataatttc tggtggtagg ggactgcgtt catg                                       154

SEQ ID NO: 90            moltype = RNA   length = 154
FEATURE                  Location/Qualifiers
source                   1..154
                         mol_type = other RNA
                         organism = synthetic construct
SEQUENCE: 90
taactacctg acagaggaga tactgtgatc atgaaagtgg ttttcctagg gcaagactta          60
```

-continued

```
tccgttgcac tccagatgtg ctgactcatg caatttcccc aaatgtggga aactcgacta   120
cataatttct ggtggtaggg gactgcgttc atgt                                154

SEQ ID NO: 91              moltype = RNA   length = 154
FEATURE                    Location/Qualifiers
source                     1..154
                           mol_type = other RNA
                           organism = synthetic construct
SEQUENCE: 91
aactacctga cagaggagat actgtgatca tgaaagtggt tttcctaggg caagacttat   60
ccgttgcact ccagatgtgc tgactcatgc aatttcccca aatgtgggaa actcgactac   120
ataatttctg gtggtagggg actgcgttca tgtt                                154

SEQ ID NO: 92              moltype = RNA   length = 154
FEATURE                    Location/Qualifiers
source                     1..154
                           mol_type = other RNA
                           organism = synthetic construct
SEQUENCE: 92
actacctgac agaggagata ctgtgatcat gaaagtggtt ttcctagggc aagacttatc   60
cgttgcactc cagatgtgct gactcatgca atttccccaa atgtgggaaa ctcgactaca   120
taatttctgg tggtagggga ctgcgttcat gttc                                154

SEQ ID NO: 93              moltype = RNA   length = 154
FEATURE                    Location/Qualifiers
source                     1..154
                           mol_type = other RNA
                           organism = synthetic construct
SEQUENCE: 93
ctacctgaca gaggagatac tgtgatcatg aaagtggttt tcctagggca agacttatcc   60
gttgcactcc agatgtgctg actcatgcaa tttccccaaa tgtgggaaac tcgactacat   120
aatttctggt ggtaggggac tgcgttcatg ttct                                154

SEQ ID NO: 94              moltype = RNA   length = 154
FEATURE                    Location/Qualifiers
source                     1..154
                           mol_type = other RNA
                           organism = synthetic construct
SEQUENCE: 94
tacctgacag aggagatact gtgatcatga aagtggtttt cctagggcaa gacttatccg   60
ttgcactcca gatgtgctga ctcatgcaat tccccaaat gtgggaaact cgactacata   120
atttctggtg gtaggggact gcgttcatgt tctc                                154

SEQ ID NO: 95              moltype = RNA   length = 154
FEATURE                    Location/Qualifiers
source                     1..154
                           mol_type = other RNA
                           organism = synthetic construct
SEQUENCE: 95
acctgacaga ggagatactg tgatcatgaa agtggttttc ctagggcaag acttatccgt   60
tgcactccag atgtgctgac tcatgcaatt ccccaaatg tgggaaactc gactacataa   120
tttctggtgg taggggactg cgttcatgtt ctcc                                154

SEQ ID NO: 96              moltype = RNA   length = 154
FEATURE                    Location/Qualifiers
source                     1..154
                           mol_type = other RNA
                           organism = synthetic construct
SEQUENCE: 96
cctgacagag gagatactgt gatcatgaaa gtggttttcc tagggcaaga cttatccgtt   60
gcactccaga tgtgctgact catgcaattt ccccaaatgt gggaaactcg actacataat   120
ttctggtggt aggggactgc gttcatgttc tccc                                154

SEQ ID NO: 97              moltype = RNA   length = 154
FEATURE                    Location/Qualifiers
source                     1..154
                           mol_type = other RNA
                           organism = synthetic construct
SEQUENCE: 97
ctgacagagg agatactgtg atcatgaaag tggttttcct agggcaagac ttatccgttg   60
cactccagat gtgctgactc atgcaatttc cccaaatgtg gaaactcga ctacataatt   120
tctggtggta ggggactgcg ttcatgttct cccc                                154

SEQ ID NO: 98              moltype = RNA   length = 154
FEATURE                    Location/Qualifiers
source                     1..154
                           mol_type = other RNA
                           organism = synthetic construct
SEQUENCE: 98
```

```
tgacagagga gatactgtga tcatgaaagt ggttttccta gggcaagact tatccgttgc   60
actccagatg tgctgactca tgcaatttcc ccaaatgtgg gaaactcgac tacataattt  120
ctggtggtag gggactgcgt tcatgttctc ccct                             154

SEQ ID NO: 99            moltype = RNA   length = 147
FEATURE                  Location/Qualifiers
source                   1..147
                         mol_type = other RNA
                         organism = synthetic construct
SEQUENCE: 99
agacttatct ggcaggggag acaccatgaa catgaggata gttttcccaa ggcaagtttc   60
aacccttgca ctctagatga tgagattact taatgggtac aatgcatgtg atttgggtaa  120
tggatactgt agaaacactg acgtcac                                     147

SEQ ID NO: 100           moltype = RNA   length = 146
FEATURE                  Location/Qualifiers
source                   1..146
                         mol_type = other RNA
                         organism = synthetic construct
SEQUENCE: 100
gacttatctg gcaggggaga caccatgaac atgaggatag ttttcccaag gcaagtttca   60
acccttgcac tctagatgat gagattactt aatgggtaca atgcatgtga tttgggtaat  120
ggatactgta gaaacactga cgtcac                                      146

SEQ ID NO: 101           moltype = RNA   length = 145
FEATURE                  Location/Qualifiers
source                   1..145
                         mol_type = other RNA
                         organism = synthetic construct
SEQUENCE: 101
acttatctgg caggggagac accatgaaca tgaggatagt tttcccaagg caagtttcaa   60
cccttgcact ctagatgatg agattactta atgggtacaa tgcatgtgat ttgggtaatg  120
gatactgtag aaacactgac gtcac                                       145

SEQ ID NO: 102           moltype = RNA   length = 144
FEATURE                  Location/Qualifiers
source                   1..144
                         mol_type = other RNA
                         organism = synthetic construct
SEQUENCE: 102
cttatctggc aggggagaca ccatgaacat gaggatagtt ttcccaaggc aagtttcaac   60
ccttgcactc tagatgatga gattacttaa tgggtacaat gcatgtgatt tgggtaatgg  120
atactgtaga aacactgacg tcac                                        144

SEQ ID NO: 103           moltype = RNA   length = 143
FEATURE                  Location/Qualifiers
source                   1..143
                         mol_type = other RNA
                         organism = synthetic construct
SEQUENCE: 103
ttatctggca ggggagacac catgaacatg aggatagttt tcccaaggca agtttcaacc   60
cttgcactct agatgatgag attacttaat gggtacaatg catgtgattt gggtaatgga  120
tactgtagaa acactgacgt cac                                         143

SEQ ID NO: 104           moltype = RNA   length = 142
FEATURE                  Location/Qualifiers
source                   1..142
                         mol_type = other RNA
                         organism = synthetic construct
SEQUENCE: 104
tatctggcag gggagacacc atgaacatga ggatagtttt cccaaggcaa gtttcaaccc   60
ttgcactcta gatgatgaga ttacttaatg ggtacaatgc atgtgatttg ggtaatggat  120
actgtagaaa cactgacgtc ac                                          142

SEQ ID NO: 105           moltype = RNA   length = 141
FEATURE                  Location/Qualifiers
source                   1..141
                         mol_type = other RNA
                         organism = synthetic construct
SEQUENCE: 105
atctggcagg ggagacacca tgaacatgag gatagttttc ccaaggcaag tttcaaccct   60
tgcactctag atgatgagat tacttaatgg gtacaatgca tgtgatttgg gtaatggata  120
ctgtagaaac actgacgtca c                                           141

SEQ ID NO: 106           moltype = RNA   length = 140
FEATURE                  Location/Qualifiers
source                   1..140
                         mol_type = other RNA
                         organism = synthetic construct
```

```
SEQUENCE: 106
tctggcaggg gagacaccat gaacatgagg atagttttcc caaggcaagt ttcaacccttt   60
gcactctaga tgatgagatt acttaatggg tacaatgcat gtgatttggg taatggatac   120
tgtagaaaca ctgacgtcac                                                140

SEQ ID NO: 107        moltype = RNA   length = 139
FEATURE               Location/Qualifiers
source                1..139
                      mol_type = other RNA
                      organism = synthetic construct
SEQUENCE: 107
ctggcagggg agacaccatg aacatgagga tagtttttcc aaggcaagtt tcaacccttg   60
cactctagat gatgagatta cttaatgggt acaatgcatg tgatttgggt aatggatact   120
gtagaaacac tgacgtcac                                                139

SEQ ID NO: 108        moltype = RNA   length = 138
FEATURE               Location/Qualifiers
source                1..138
                      mol_type = other RNA
                      organism = synthetic construct
SEQUENCE: 108
tggcagggga gacaccatga acatgaggat agtttttccca aggcaagttt caacccttgc   60
actctagatg atgagattac ttaatgggta caatgcatgt gatttgggta atggatactg   120
tagaaacact gacgtcac                                                138

SEQ ID NO: 109        moltype = RNA   length = 149
FEATURE               Location/Qualifiers
source                1..149
                      mol_type = other RNA
                      organism = synthetic construct
SEQUENCE: 109
agactcatct ggcagcggag ataccatgaa catcacggta gttttcccaa agcaagtttc   60
caccccttgca ctccggatga tgagacatta cttaatggat acaatgcatg tgatttgagt   120
gatggatact gtggaaacac cgacttcac                                     149

SEQ ID NO: 110        moltype = RNA   length = 148
FEATURE               Location/Qualifiers
source                1..148
                      mol_type = other RNA
                      organism = synthetic construct
SEQUENCE: 110
gactcatctg gcagcggaga taccatgaac atcacggtag ttttcccaaa gcaagtttcc   60
accccttgcac tccggatgat gagacattac ttaatggata caatgcatgt gatttgagtg   120
atggatactg tggaaacacc gacttcac                                      148

SEQ ID NO: 111        moltype = RNA   length = 147
FEATURE               Location/Qualifiers
source                1..147
                      mol_type = other RNA
                      organism = synthetic construct
SEQUENCE: 111
actcatctgg cagcggagat accatgaaca tcacggtagt tttcccaaag caagtttcca   60
cccttgcact ccggatgatg agacattact taatggatac aatgcatgtg atttgagtga   120
tggatactgt ggaaacaccg acttcac                                       147

SEQ ID NO: 112        moltype = RNA   length = 146
FEATURE               Location/Qualifiers
source                1..146
                      mol_type = other RNA
                      organism = synthetic construct
SEQUENCE: 112
ctcatctggc agcggagata ccatgaacat cacggtagtt ttcccaaagc aagtttccac   60
ccttgcactc cggatgatga gacattactt aatggataca atgcatgtga tttgagtgat   120
ggatactgtg gaaacaccga cttcac                                        146

SEQ ID NO: 113        moltype = RNA   length = 145
FEATURE               Location/Qualifiers
source                1..145
                      mol_type = other RNA
                      organism = synthetic construct
SEQUENCE: 113
tcatctggca gcggagatac catgaacatc acggtagttt cccaaagca agtttccacc   60
cttgcactcc ggatgatgag acattactta atggatacaa tgcatgtgat ttgagtgatg   120
gatactgtgg aaacaccgac ttcac                                         145

SEQ ID NO: 114        moltype = RNA   length = 144
FEATURE               Location/Qualifiers
source                1..144
                      mol_type = other RNA
```

-continued

```
                          organism = synthetic construct
SEQUENCE: 114
catctggcag cggagatacc atgaacatca cggtagtttt cccaaagcaa gtttccaccc   60
ttgcactccg gatgatgaga cattacttaa tggatacaat gcatgtgatt tgagtgatgg   120
atactgtgga aacaccgact tcac                                         144

SEQ ID NO: 115          moltype = RNA   length = 143
FEATURE                 Location/Qualifiers
source                  1..143
                        mol_type = other RNA
                        organism = synthetic construct
SEQUENCE: 115
atctggcagc ggagatacca tgaacatcac ggtagttttc ccaaagcaag tttccaccct   60
tgcactccgg atgatgagac attacttaat ggatacaatg catgtgattt gagtgatgga   120
tactgtggaa acaccgactt cac                                           143

SEQ ID NO: 116          moltype = RNA   length = 142
FEATURE                 Location/Qualifiers
source                  1..142
                        mol_type = other RNA
                        organism = synthetic construct
SEQUENCE: 116
tctggcagcg gagataccat gaacatcacg gtagttttcc caaagcaagt ttccaccctt   60
gcactccgga tgatgagaca ttacttaatg gatacaatgc atgtgatttg agtgatggat   120
actgtggaaa caccgacttc ac                                            142

SEQ ID NO: 117          moltype = RNA   length = 141
FEATURE                 Location/Qualifiers
source                  1..141
                        mol_type = other RNA
                        organism = synthetic construct
SEQUENCE: 117
ctggcagcgg agataccatg aacatcacgg tagttttccc aaagcaagtt ccacccttg    60
cactccggat gatgagacat tacttaatgg atacaatgca tgtgatttga gtgatggata   120
ctgtggaaac accgacttca c                                             141

SEQ ID NO: 118          moltype = RNA   length = 140
FEATURE                 Location/Qualifiers
source                  1..140
                        mol_type = other RNA
                        organism = synthetic construct
SEQUENCE: 118
tggcagcgga gataccatga acatcacggt agttttccca aagcaagttt ccacccttgc   60
actccggatg atgagacatt acttaatgga tacaatgcat gtgatttgag tgatggatac   120
tgtggaaaca ccgacttcac                                               140

SEQ ID NO: 119          moltype = RNA   length = 154
FEATURE                 Location/Qualifiers
source                  1..154
                        mol_type = other RNA
                        organism = synthetic construct
SEQUENCE: 119
agacttggca ggggagatag catgatcacg aaggtggttt tcccaaggca agatttattc   60
actgcactct ggatgtgctg acccctacga tttccgccca atggggaagc ttgactgctt   120
agtttgttgt ggcaggggac tgtgttcaca cttt                               154

SEQ ID NO: 120          moltype = RNA   length = 154
FEATURE                 Location/Qualifiers
source                  1..154
                        mol_type = other RNA
                        organism = synthetic construct
SEQUENCE: 120
gacttggcag gggagatagc atgatcacga aggtggtttt cccaaggcaa gatttattca   60
ctgcactctg gatgtgctga cccctacgat ttccgcccaa tggggaagct tgactgctta   120
gtttgttgtg gcaggggact gtgttcacac tttt                               154

SEQ ID NO: 121          moltype = RNA   length = 154
FEATURE                 Location/Qualifiers
source                  1..154
                        mol_type = other RNA
                        organism = synthetic construct
SEQUENCE: 121
acttggcagg ggagatagca tgatcacgaa ggtggttttc ccaaggcaag atttattcac   60
tgcactctgg atgtgctgac ccctacgatt tccgcccaat ggggaagctt gactgcttag   120
tttgttgtgg caggggactg tgttcacact tttc                               154

SEQ ID NO: 122          moltype = RNA   length = 154
FEATURE                 Location/Qualifiers
source                  1..154
```

```
                                mol_type = other RNA
                                organism = synthetic construct
SEQUENCE: 122
cttggcaggg gagatagcat gatcacgaag gtggttttcc caaggcaaga tttattcact    60
gcactctgga tgtgctgacc cctacgattt ccgcccaatg gggaagcttg actgcttagt   120
ttgttgtggc aggggactgt gttcacactt ttcc                               154

SEQ ID NO: 123          moltype = RNA   length = 154
FEATURE                 Location/Qualifiers
source                  1..154
                        mol_type = other RNA
                        organism = synthetic construct
SEQUENCE: 123
ttggcagggg agatagcatg atcacgaagg tggtttttcc aaggcaagat ttattcactg    60
cactctggat gtgctgaccc ctacgatttc cgcccaatgg ggaagcttga ctgcttagtt   120
tgttgtggca ggggactgtg ttcacacttt tccc                               154

SEQ ID NO: 124          moltype = RNA   length = 154
FEATURE                 Location/Qualifiers
source                  1..154
                        mol_type = other RNA
                        organism = synthetic construct
SEQUENCE: 124
tggcagggga gatagcatga tcacgaaggt ggtttttccca aggcaagatt tattcactgc    60
actctggatg tgctgacccc tacgattccc gcccaatggg gaagcttgac tgcttagttt   120
gttgtggcag gggactgtgt tcacactttt cccg                               154

SEQ ID NO: 125          moltype = RNA   length = 154
FEATURE                 Location/Qualifiers
source                  1..154
                        mol_type = other RNA
                        organism = synthetic construct
SEQUENCE: 125
ggcaggggag atagcatgat cacgaaggtg gttttcccaa ggcaagattt attcactgca    60
ctctggatgt gctgacccct acgattccg cccaatgggg aagcttgact gcttagtttg    120
ttgtggcagg ggactgtgtt cacacttttc ccgg                               154

SEQ ID NO: 126          moltype = RNA   length = 153
FEATURE                 Location/Qualifiers
source                  1..153
                        mol_type = other RNA
                        organism = synthetic construct
SEQUENCE: 126
gcaggggaga tagcatgatc acgaaggtgg tttttcccaag gcaagattta ttcactgcac    60
tctggatgtg ctgacccta cgatttccgc ccaatgggga agcttgactg cttagtttgt    120
tgtggcaggg gactgtgttc acacttttcc cgg                                153

SEQ ID NO: 127          moltype = RNA   length = 152
FEATURE                 Location/Qualifiers
source                  1..152
                        mol_type = other RNA
                        organism = synthetic construct
SEQUENCE: 127
caggggagat agcatgatca cgaaggtggt tttcccaagg caagatttat tcactgcact    60
ctggatgtgc tgacccctac gatttccgcc caatggggaa gcttgactgc ttagtttgtt   120
gtggcagggg actgtgttca cactttccc gg                                  152

SEQ ID NO: 128          moltype = RNA   length = 151
FEATURE                 Location/Qualifiers
source                  1..151
                        mol_type = other RNA
                        organism = synthetic construct
SEQUENCE: 128
aggggagata gcatgatcac gaaggtggtt ttcccaaggc aagatttatt cactgcactc    60
tggatgtgct gacccctacg atttccgccc aatggggaag cttgactgct tagtttgttg   120
tggcagggga ctgtgttcac acttttcccg g                                  151

SEQ ID NO: 129          moltype = RNA   length = 154
FEATURE                 Location/Qualifiers
source                  1..154
                        mol_type = other RNA
                        organism = synthetic construct
SEQUENCE: 129
atacttaaca tggcagagga gatatcataa tcacaaaggt agttttccca gggcaagcct    60
tatccactgc attccagatg tgctcacctc tgtggtttcc ccaaatgtgg aaaactggac   120
tgcataattt gtggtagcgg gggactgcat taat                               154

SEQ ID NO: 130          moltype = RNA   length = 154
FEATURE                 Location/Qualifiers
```

-continued

```
source                    1..154
                          mol_type = other RNA
                          organism = synthetic construct
SEQUENCE: 130
tacttaacat ggcagaggag atatcataat cacaaaggta gttttcccag ggcaagcctt   60
atccactgca ttccagatgt gctcacctct gtggtttccc caaatgtgga aaactggact   120
gcataatttg tggtagcggg ggactgcatt aata                               154

SEQ ID NO: 131           moltype = RNA   length = 154
FEATURE                  Location/Qualifiers
source                   1..154
                         mol_type = other RNA
                         organism = synthetic construct
SEQUENCE: 131
acttaacatg gcagaggaga tatcataatc acaaaggtag ttttcccagg gcaagcctta   60
tccactgcat tccagatgtg ctcacctctg tggtttcccc aaatgtggaa aactggactg   120
cataatttgt ggtagcgggg gactgcatta atac                               154

SEQ ID NO: 132           moltype = RNA   length = 154
FEATURE                  Location/Qualifiers
source                   1..154
                         mol_type = other RNA
                         organism = synthetic construct
SEQUENCE: 132
cttaacatgg cagaggagat atcataatca caaaggtagt tttcccaggg caagccttat   60
ccactgcatt ccagatgtgc tcacctctgt ggtttcccca aatgtggaaa actggactgc   120
ataatttgtg gtagcggggg actgcattaa tacc                               154

SEQ ID NO: 133           moltype = RNA   length = 154
FEATURE                  Location/Qualifiers
source                   1..154
                         mol_type = other RNA
                         organism = synthetic construct
SEQUENCE: 133
ttaacatggc agaggagata tcataatcac aaaggtagtt ttcccagggc aagccttatc   60
cactgcattc cagatgtgct cacctctgtg gtttccccaa atgtggaaaa ctggactgca   120
taatttgtgg tagcggggga ctgcattaat acct                               154

SEQ ID NO: 134           moltype = RNA   length = 154
FEATURE                  Location/Qualifiers
source                   1..154
                         mol_type = other RNA
                         organism = synthetic construct
SEQUENCE: 134
taacatggca gaggagatat cataatcaca aaggtagttt tcccagggca agccttatcc   60
actgcattcc agatgtgctc acctctgtgg tttccccaaa tgtggaaaac tggactgcat   120
aatttgtggt agcgggggac tgcattaata cctt                               154

SEQ ID NO: 135           moltype = RNA   length = 154
FEATURE                  Location/Qualifiers
source                   1..154
                         mol_type = other RNA
                         organism = synthetic construct
SEQUENCE: 135
aacatggcag aggagatatc ataatcacaa aggtagtttt cccagggcaa gccttatcca   60
ctgcattcca gatgtgctca cctctgtggt ttccccaaat gtggaaaact ggactgcata   120
atttgtggta gcgggggact gcattaatac cttc                               154

SEQ ID NO: 136           moltype = RNA   length = 154
FEATURE                  Location/Qualifiers
source                   1..154
                         mol_type = other RNA
                         organism = synthetic construct
SEQUENCE: 136
acatggcaga ggagatatca taatcacaaa ggtagttttc cagggcaag ccttatccac    60
tgcattccag atgtgctcac ctctgtggtt tccccaaatg tggaaaactg gactgcataa   120
tttgtggtag cgggggactg cattaatacc ttcc                               154

SEQ ID NO: 137           moltype = RNA   length = 154
FEATURE                  Location/Qualifiers
source                   1..154
                         mol_type = other RNA
                         organism = synthetic construct
SEQUENCE: 137
catggcagag gagatatcat aatcacaaag gtagttttcc cagggcaagc cttatccact   60
gcattccaga tgtgctcacc tctgtggttt cccaaatgt ggaaaactgg actgcataat    120
ttgtggtagc gggggactgc attaatacct cct                                154

SEQ ID NO: 138           moltype = RNA   length = 154
```

-continued

```
FEATURE               Location/Qualifiers
source                1..154
                      mol_type = other RNA
                      organism = synthetic construct
SEQUENCE: 138
atggcagagg agatatcata atcacaaagg tagtttttccc agggcaagcc ttatccactg    60
cattccagat gtgctcacct ctgtggtttc cccaaatgtg gaaaactgga ctgcataatt   120
tgtggtagcg ggggactgca ttaataccatt cctc                               154

SEQ ID NO: 139      moltype = RNA   length = 133
FEATURE               Location/Qualifiers
source                1..133
                      mol_type = other RNA
                      organism = synthetic construct
SEQUENCE: 139
aaaaagggct tctgctgtga gtggcacaca tagggcatcg tttgctcttg gtgccagaat    60
caacatcaag agatttcaga agcataattt tttggtactt gggcagctgg tgatcattgg   120
tcctgtagcc ctt                                                       133

SEQ ID NO: 140      moltype = RNA   length = 132
FEATURE               Location/Qualifiers
source                1..132
                      mol_type = other RNA
                      organism = synthetic construct
SEQUENCE: 140
aaaagggctt ctgctgtgag tggcacacat agggcatcgt ttgctcttgg tgccagaatc    60
aacatcaaga gatttcagaa gcataatttt ttggtacttg ggcagctggt gatcattggt   120
cctgtagccc tt                                                        132

SEQ ID NO: 141      moltype = RNA   length = 131
FEATURE               Location/Qualifiers
source                1..131
                      mol_type = other RNA
                      organism = synthetic construct
SEQUENCE: 141
aaagggcttc tgctgtgagt ggcacacata gggcatcgtt tgctcttggt gccagaatca    60
acatcaagag atttcagaag cataattttt tggtacttgg gcagctggtg atcattggtc   120
ctgtagccct t                                                         131

SEQ ID NO: 142      moltype = RNA   length = 130
FEATURE               Location/Qualifiers
source                1..130
                      mol_type = other RNA
                      organism = synthetic construct
SEQUENCE: 142
aagggcttct gctgtgagtg gcacacatag ggcatcgttt gctcttggtg ccagaatcaa    60
catcaagaga tttcagaagc ataatttttt ggtacttggg cagctggtga tcattggtcc   120
tgtagccctt                                                           130

SEQ ID NO: 143      moltype = RNA   length = 129
FEATURE               Location/Qualifiers
source                1..129
                      mol_type = other RNA
                      organism = synthetic construct
SEQUENCE: 143
agggcttctg ctgtgagtgg cacacatagg gcatcgtttg ctcttggtgc cagaatcaac    60
atcaagagat ttcagaagca taattttttg gtacttgggc agctggtgat cattggtcct   120
gtagccctt                                                            129

SEQ ID NO: 144      moltype = RNA   length = 128
FEATURE               Location/Qualifiers
source                1..128
                      mol_type = other RNA
                      organism = synthetic construct
SEQUENCE: 144
gggcttctgc tgtgagtggc acacataggg catcgtttgc tcttggtgcc agaatcaaca    60
tcaagagatt tcagaagcat aattttttgg tacttgggca gctggtgatc attggtcctg   120
tagccctt                                                             128

SEQ ID NO: 145      moltype = RNA   length = 127
FEATURE               Location/Qualifiers
source                1..127
                      mol_type = other RNA
                      organism = synthetic construct
SEQUENCE: 145
ggcttctgct gtgagtggca cacatagggc atcgtttgct cttggtgcca gaatcaacat    60
caagagattt cagaagcata attttttggt acttgggcag ctggtgatca ttggtcctgt   120
agccctt                                                              127
```

-continued

```
SEQ ID NO: 146          moltype = RNA   length = 126
FEATURE                 Location/Qualifiers
source                  1..126
                        mol_type = other RNA
                        organism = synthetic construct
SEQUENCE: 146
gcttctgctg tgagtggcac acatagggca tcgtttgctc ttggtgccag aatcaacatc   60
aagagatttc agaagcataa ttttttggta cttgggcagc tggtgatcat tggtcctgta  120
gcccttc                                                             126

SEQ ID NO: 147          moltype = RNA   length = 125
FEATURE                 Location/Qualifiers
source                  1..125
                        mol_type = other RNA
                        organism = synthetic construct
SEQUENCE: 147
cttctgctgt gagtggcaca catagggcat cgtttgctct tggtgccaga atcaacatca   60
agagatttca gaagcataat tttttggtac ttgggcagct ggtgatcatt ggtcctgtag  120
ccctt                                                               125

SEQ ID NO: 148          moltype = RNA   length = 124
FEATURE                 Location/Qualifiers
source                  1..124
                        mol_type = other RNA
                        organism = synthetic construct
SEQUENCE: 148
ttctgctgtg agtggcacac atagggcatc gtttgctctt ggtgccagaa tcaacatcaa   60
gagatttcag aagcataatt ttttggtact tgggcagctg gtgatcattg gtcctgtagc  120
cctt                                                                124

SEQ ID NO: 149          moltype = RNA   length = 129
FEATURE                 Location/Qualifiers
source                  1..129
                        mol_type = other RNA
                        organism = synthetic construct
SEQUENCE: 149
aaaaaaagct gctgttgtga gtgatacatg cagggcaact tgattgctct tagtgcagaa   60
ttgacatcaa ggaattttgg aagtataatt ttttggcagg tggatagctg gttgtattag  120
tccattctc                                                           129

SEQ ID NO: 150          moltype = RNA   length = 128
FEATURE                 Location/Qualifiers
source                  1..128
                        mol_type = other RNA
                        organism = synthetic construct
SEQUENCE: 150
aaaaaagctg ctgttgtgag tgatacatgc agggcaactt gattgctctt agtgcagaat   60
tgacatcaag gaattttgga agtataattt tttggcaggt ggatagctgg ttgtattagt  120
ccattctc                                                            128

SEQ ID NO: 151          moltype = RNA   length = 127
FEATURE                 Location/Qualifiers
source                  1..127
                        mol_type = other RNA
                        organism = synthetic construct
SEQUENCE: 151
aaaaagctgc tgttgtgagt gatacatgca gggcaacttg attgctctta gtgcagaatt   60
gacatcaagg aattttggaa gtataatttt tggcaggtg gatagctggt tgtattagtc  120
cattctc                                                             127

SEQ ID NO: 152          moltype = RNA   length = 126
FEATURE                 Location/Qualifiers
source                  1..126
                        mol_type = other RNA
                        organism = synthetic construct
SEQUENCE: 152
aaaagctgct gttgtgagtg atacatgcag ggcaacttga ttgctcttag tgcagaattg   60
acatcaagga attttggaag tataattttt tggcaggtgg atagctggtt gtattagtcc  120
attctc                                                              126

SEQ ID NO: 153          moltype = RNA   length = 125
FEATURE                 Location/Qualifiers
source                  1..125
                        mol_type = other RNA
                        organism = synthetic construct
SEQUENCE: 153
aaagctgctg ttgtgagtga tacatgcagg gcaacttgat tgctcttagt gcagaattga   60
catcaaggaa ttttggaagt ataatttttt ggcaggtgga tagctggttg tattagtcca  120
ttctc                                                               125
```

```
SEQ ID NO: 154          moltype = RNA  length = 124
FEATURE                 Location/Qualifiers
source                  1..124
                        mol_type = other RNA
                        organism = synthetic construct
SEQUENCE: 154
aagctgctgt tgtgagtgat acatgcaggg caacttgatt gctcttagtg cagaattgac   60
atcaaggaat tttggaagta taattttttg gcaggtggat agctggttgt attagtccat  120
tctc                                                                124

SEQ ID NO: 155          moltype = RNA  length = 123
FEATURE                 Location/Qualifiers
source                  1..123
                        mol_type = other RNA
                        organism = synthetic construct
SEQUENCE: 155
agctgctgtt gtgagtgata catgcagggc aacttgattg ctcttagtgc agaattgaca   60
tcaaggaatt ttggaagtat aattttttgg caggtggata gctggttgta ttagtccatt  120
ctc                                                                 123

SEQ ID NO: 156          moltype = RNA  length = 122
FEATURE                 Location/Qualifiers
source                  1..122
                        mol_type = other RNA
                        organism = synthetic construct
SEQUENCE: 156
gctgctgttg tgagtgatac atgcagggca acttgattgc tcttagtgca gaattgacat   60
caaggaattt tggaagtata atttttggc aggtggatag ctggttgtat tagtccattc  120
tc                                                                  122

SEQ ID NO: 157          moltype = RNA  length = 121
FEATURE                 Location/Qualifiers
source                  1..121
                        mol_type = other RNA
                        organism = synthetic construct
SEQUENCE: 157
ctgctgttgt gagtgataca tgcagggcaa cttgattgct cttagtgcag aattgacatc   60
aaggaatttt ggaagtataa tttttggca ggtggatagc tggttgtatt agtccattct  120
c                                                                   121

SEQ ID NO: 158          moltype = RNA  length = 120
FEATURE                 Location/Qualifiers
source                  1..120
                        mol_type = other RNA
                        organism = synthetic construct
SEQUENCE: 158
tgctgttgtg agtgatacat gcagggcaac ttgattgctc ttagtgcaga attgacatca   60
aggaattttg gaagtataat tttttggcag gtggatagct ggttgtatta gtccattctc  120

SEQ ID NO: 159          moltype = RNA  length = 133
FEATURE                 Location/Qualifiers
source                  1..133
                        mol_type = other RNA
                        organism = synthetic construct
SEQUENCE: 159
aaaaagggct tctgtcatga gtggcacaca taggacaact caatttctct tcatgcagaa   60
taaacatcaa gagattttgg aagcgtaatt tttggtagtt gggcagctgg tgatcactgg  120
tgccagcacc ctt                                                      133

SEQ ID NO: 160          moltype = RNA  length = 132
FEATURE                 Location/Qualifiers
source                  1..132
                        mol_type = other RNA
                        organism = synthetic construct
SEQUENCE: 160
aaaagggctt ctgtcatgag tggcacacat aggacaactc aatttctctt catgcagaat   60
aaacatcaag agattttgga agcgtaattt ttggtagttg gcagctggt gatcactggt  120
gccagcaccc tt                                                       132

SEQ ID NO: 161          moltype = RNA  length = 131
FEATURE                 Location/Qualifiers
source                  1..131
                        mol_type = other RNA
                        organism = synthetic construct
SEQUENCE: 161
aaagggcttc tgtcatgagt ggcacacata ggacaactca atttctcttc atgcagaata   60
aacatcaaga gattttggaa gcgtaatttt tggtagttgg gcagctggtg atcactggtg  120
ccagcaccct t                                                        131
```

```
SEQ ID NO: 162          moltype = RNA   length = 130
FEATURE                 Location/Qualifiers
source                  1..130
                        mol_type = other RNA
                        organism = synthetic construct
SEQUENCE: 162
aagggcttct gtcatgagtg gcacacatag gacaactcaa tttctcttca tgcagaataa    60
acatcaagag attttggaag cgtaattttt ggtagttggg cagctggtga tcactggtgc   120
cagcaccctt                                                          130

SEQ ID NO: 163          moltype = RNA   length = 129
FEATURE                 Location/Qualifiers
source                  1..129
                        mol_type = other RNA
                        organism = synthetic construct
SEQUENCE: 163
agggcttctg tcatgagtgg cacacatagg acaactcaat ttctcttcat gcagaataaa    60
catcaagaga ttttggaagc gtaatttttg gtagttgggc agctggtgat cactggtgcc   120
agcaccctt                                                           129

SEQ ID NO: 164          moltype = RNA   length = 128
FEATURE                 Location/Qualifiers
source                  1..128
                        mol_type = other RNA
                        organism = synthetic construct
SEQUENCE: 164
gggcttctgt catgagtggc acacatagga caactcaatt tctcttcatg cagaataaac    60
atcaagagat tttggaagcg taattttttg tagttgggca gctggtgatc actggtgcca   120
gcacccctt                                                           128

SEQ ID NO: 165          moltype = RNA   length = 127
FEATURE                 Location/Qualifiers
source                  1..127
                        mol_type = other RNA
                        organism = synthetic construct
SEQUENCE: 165
ggcttctgtc atgagtggca cacataggac aactcaattt ctcttcatgc agaataaaca    60
tcaagagatt ttggaagcgt aattttttgg t agttgggcag ctggtgatca ctggtgccag   120
caccctt                                                             127

SEQ ID NO: 166          moltype = RNA   length = 126
FEATURE                 Location/Qualifiers
source                  1..126
                        mol_type = other RNA
                        organism = synthetic construct
SEQUENCE: 166
gcttctgtca tgagtggcac acataggaca actcaatttc tcttcatgca gaataaacat    60
caagagattt tggaagcgta attttttggta gttgggcagc tggtgatcac tggtgccagc   120
acccctt                                                             126

SEQ ID NO: 167          moltype = RNA   length = 125
FEATURE                 Location/Qualifiers
source                  1..125
                        mol_type = other RNA
                        organism = synthetic construct
SEQUENCE: 167
cttctgtcat gagtggcaca cataggacaa ctcaatttct cttcatgcag aataaacatc    60
aagagatttg gaagcgtaa tttttggtag ttgggcagct ggtgatcact ggtgccagca   120
ccctt                                                               125

SEQ ID NO: 168          moltype = RNA   length = 124
FEATURE                 Location/Qualifiers
source                  1..124
                        mol_type = other RNA
                        organism = synthetic construct
SEQUENCE: 168
ttctgtcatg agtggcacac ataggacaac tcaatttctc ttcatgcaga ataaacatca    60
agagattttg gaagcgtaat ttttggtagt tgggcagctg tgatcactg gtgccagcac   120
cctt                                                                124

SEQ ID NO: 169          moltype = RNA   length = 133
FEATURE                 Location/Qualifiers
source                  1..133
                        mol_type = other RNA
                        organism = synthetic construct
SEQUENCE: 169
aaaaagggct tctgtcatga gtggcctatg tagggcaacc agattgctct tcatgtggaa    60
ttgacatcaa gagctttcag aagtgtattt tttggaagtt gggcagctgg taatcattgg   120
```

-continued

```
tcttggcatc ctt                                                         133

SEQ ID NO: 170          moltype = RNA   length = 132
FEATURE                 Location/Qualifiers
source                  1..132
                        mol_type = other RNA
                        organism = synthetic construct
SEQUENCE: 170
aaaagggctt ctgtcatgag tggcctatgt agggcaacca gattgctctt catgtggaat    60
tgacatcaag agctttcaga agtgtatttt ttggaagttg ggcagctggt aatcattggt    120
cttggcatcc tt                                                         132

SEQ ID NO: 171          moltype = RNA   length = 131
FEATURE                 Location/Qualifiers
source                  1..131
                        mol_type = other RNA
                        organism = synthetic construct
SEQUENCE: 171
aaagggcttc tgtcatgagt ggcctatgta gggcaaccag attgctcttc atgtggaatt    60
gacatcaaga gctttcagaa gtgtattttt tggaagttgg gcagctggta atcattggtc    120
ttggcatcct t                                                          131

SEQ ID NO: 172          moltype = RNA   length = 130
FEATURE                 Location/Qualifiers
source                  1..130
                        mol_type = other RNA
                        organism = synthetic construct
SEQUENCE: 172
aagggcttct gtcatgagtg gcctatgtag ggcaaccaga ttgctcttca tgtggaattg    60
acatcaagag ctttcagaag tgtatttttt ggaagttggg cagctggtaa tcattggtct    120
tggcatcctt                                                            130

SEQ ID NO: 173          moltype = RNA   length = 129
FEATURE                 Location/Qualifiers
source                  1..129
                        mol_type = other RNA
                        organism = synthetic construct
SEQUENCE: 173
agggcttctg tcatgagtgg cctatgtagg gcaaccagat tgctcttcat gtggaattga    60
catcaagagc tttcagaagt gtattttttg gaagttgggc agctggtaat cattggtctt    120
ggcatcctt                                                             129

SEQ ID NO: 174          moltype = RNA   length = 128
FEATURE                 Location/Qualifiers
source                  1..128
                        mol_type = other RNA
                        organism = synthetic construct
SEQUENCE: 174
gggcttctgt catgagtggc ctatgtaggg caaccagatt gctcttcatg tggaattgac    60
atcaagagct ttcagaagtg tattttttgg aagttgggca gctggtaatc attggtcttg    120
gcatcctt                                                              128

SEQ ID NO: 175          moltype = RNA   length = 127
FEATURE                 Location/Qualifiers
source                  1..127
                        mol_type = other RNA
                        organism = synthetic construct
SEQUENCE: 175
ggcttctgtc atgagtggcc tatgtagggc aaccagattg ctcttcatgt ggaattgaca    60
tcaagagctt tcagaagtgt attttttgga agttgggcag ctggtaatca ttggtcttgg    120
catcctt                                                               127

SEQ ID NO: 176          moltype = RNA   length = 126
FEATURE                 Location/Qualifiers
source                  1..126
                        mol_type = other RNA
                        organism = synthetic construct
SEQUENCE: 176
gcttctgtca tgagtggcct atgtagggca accagattgc tcttcatgtg gaattgacat    60
caagagcttt cagaagtgta ttttttggaa gttgggcagc tggtaatcat tggtcttggc    120
atcctt                                                                126

SEQ ID NO: 177          moltype = RNA   length = 125
FEATURE                 Location/Qualifiers
source                  1..125
                        mol_type = other RNA
                        organism = synthetic construct
SEQUENCE: 177
cttctgtcat gagtggccta tgtagggcaa ccagattgct cttcatgtgg aattgacatc    60
```

-continued

```
aagagctttc agaagtgtat tttttggaag ttgggcagct ggtaatcatt ggtcttggca    120
tcctt                                                                 125

SEQ ID NO: 178          moltype = RNA   length = 124
FEATURE                 Location/Qualifiers
source                  1..124
                        mol_type = other RNA
                        organism = synthetic construct
SEQUENCE: 178
ttctgtcatg agtggcctat gtagggcaac cagattgctc ttcatgtgga attgacatca     60
agagctttca gaagtgtatt ttttggaagt tgggcagctg gtaatcattg gtcttggcat    120
cctt                                                                  124

SEQ ID NO: 179          moltype = RNA   length = 142
FEATURE                 Location/Qualifiers
source                  1..142
                        mol_type = other RNA
                        organism = synthetic construct
SEQUENCE: 179
aaaggggggct tctgtcatga gtggcacaca ttgggcaact caactgctct tcatgaggaa     60
tcaacatcag gaggttttgg aagaatgatt tttttggtag ttgggcagct tgtgagaaaa    120
aaatgttttc aggcaaatcc tc                                              142

SEQ ID NO: 180          moltype = RNA   length = 141
FEATURE                 Location/Qualifiers
source                  1..141
                        mol_type = other RNA
                        organism = synthetic construct
SEQUENCE: 180
aagggggctt ctgtcatgag tggcacacat tgggcaactc aactgctctt catgaggaat     60
caacatcagg aggttttgga agaatgattt ttttggtagt tgggcagctt gtgagaaaaa    120
aatgttttca ggcaaatcct c                                               141

SEQ ID NO: 181          moltype = RNA   length = 140
FEATURE                 Location/Qualifiers
source                  1..140
                        mol_type = other RNA
                        organism = synthetic construct
SEQUENCE: 181
aggggcttc tgtcatgagt ggcacacatt gggcaactca actgctcttc atgaggaatc      60
aacatcagga ggttttggaa gaatgatttt tttggtagtt gggcagcttg tgagaaaaaa    120
atgttttcag gcaaatcctc                                                 140

SEQ ID NO: 182          moltype = RNA   length = 139
FEATURE                 Location/Qualifiers
source                  1..139
                        mol_type = other RNA
                        organism = synthetic construct
SEQUENCE: 182
ggggcttct gtcatgagtg gcacacattg ggcaactcaa ctgctcttca tgaggaatca      60
acatcaggag gttttggaag aatgattttt ttggtagttg ggcagcttgt gagaaaaaaa    120
tgttttcagg caaatcctc                                                  139

SEQ ID NO: 183          moltype = RNA   length = 138
FEATURE                 Location/Qualifiers
source                  1..138
                        mol_type = other RNA
                        organism = synthetic construct
SEQUENCE: 183
ggggcttctg tcatgagtgg cacacattgg gcaactcaac tgctcttcat gaggaatcaa      60
catcaggagg ttttggaaga atgattttt tggtagttgg gcagcttgtg agaaaaaaat    120
gttttcaggc aaatcctc                                                   138

SEQ ID NO: 184          moltype = RNA   length = 137
FEATURE                 Location/Qualifiers
source                  1..137
                        mol_type = other RNA
                        organism = synthetic construct
SEQUENCE: 184
gggcttctgt catgagtggc acacattggg caactcaact gctcttcatg aggaatcaac      60
atcaggaggt tttggaagaa tgattttttt ggtagttggg cagcttgtga gaaaaaaatg    120
ttttcaggca atcctc                                                     137

SEQ ID NO: 185          moltype = RNA   length = 136
FEATURE                 Location/Qualifiers
source                  1..136
                        mol_type = other RNA
                        organism = synthetic construct
SEQUENCE: 185
```

-continued

```
ggcttctgtc atgagtggca cacattgggc aactcaactg ctcttcatga ggaatcaaca    60
tcaggaggtt ttggaagaat gattttttg gtagttgggc agcttgtgag aaaaaaatgt    120
tttcaggcaa atcctc                                                     136

SEQ ID NO: 186          moltype = RNA   length = 135
FEATURE                 Location/Qualifiers
source                  1..135
                        mol_type = other RNA
                        organism = synthetic construct
SEQUENCE: 186
gcttctgtca tgagtggcac acattgggca actcaactgc tcttcatgag gaatcaacat    60
caggaggttt tggaagaatg attttttgg tagttgggca gcttgtgaga aaaaatgtt    120
ttcaggcaaa tcctc                                                      135

SEQ ID NO: 187          moltype = RNA   length = 134
FEATURE                 Location/Qualifiers
source                  1..134
                        mol_type = other RNA
                        organism = synthetic construct
SEQUENCE: 187
cttctgtcat gagtggcaca cattgggcaa ctcaactgct cttcatgagg aatcaacatc    60
aggaggtttt ggaagaatga tttttttggt agttgggcag cttgtgagaa aaaatgtttt    120
tcaggcaaat cctc                                                       134

SEQ ID NO: 188          moltype = RNA   length = 133
FEATURE                 Location/Qualifiers
source                  1..133
                        mol_type = other RNA
                        organism = synthetic construct
SEQUENCE: 188
ttctgtcatg agtggcacac attgggcaac tcaactgctc ttcatgagga atcaacatca    60
ggaggttttg gaagaatgat tttttggta gttgggcagc ttgtgagaaa aaatgtttt    120
caggcaaatc ctc                                                        133

SEQ ID NO: 189          moltype = RNA   length = 134
FEATURE                 Location/Qualifiers
source                  1..134
                        mol_type = other RNA
                        organism = synthetic construct
SEQUENCE: 189
aaaaagggct tctgtcgtga gtggcacacg tagggcaact cgattgctct gcgtgcggaa    60
tcgacatcaa gagatttcgg aagcataatt ttttggtatt tgggcagctg gtgatcgttg    120
gtcccggcgc cctt                                                       134

SEQ ID NO: 190          moltype = RNA   length = 133
FEATURE                 Location/Qualifiers
source                  1..133
                        mol_type = other RNA
                        organism = synthetic construct
SEQUENCE: 190
aaaagggctt ctgtcgtgag tggcacacgt agggcaactc gattgctctg cgtgcggaat    60
cgacatcaag agatttcgga agcataattt tttggtattt gggcagctgg tgatcgttgg    120
tcccggcgcc ctt                                                        133

SEQ ID NO: 191          moltype = RNA   length = 132
FEATURE                 Location/Qualifiers
source                  1..132
                        mol_type = other RNA
                        organism = synthetic construct
SEQUENCE: 191
aaagggcttc tgtcgtgagt ggcacacgta gggcaactcg attgctctgc gtgcggaatc    60
gacatcaaga gatttcggaa gcataatttt ttggtatttg gcagctggt gatcgttggt    120
cccggcgccc tt                                                         132

SEQ ID NO: 192          moltype = RNA   length = 131
FEATURE                 Location/Qualifiers
source                  1..131
                        mol_type = other RNA
                        organism = synthetic construct
SEQUENCE: 192
aagggcttct gtcgtgagtg gcacacgtag ggcaactcga ttgctctgcg tgcggaatcg    60
acatcaagag atttcggaag cataattttt tggtatttgg gcagctggtg atcgttggtc    120
ccggcgccct t                                                          131

SEQ ID NO: 193          moltype = RNA   length = 130
FEATURE                 Location/Qualifiers
source                  1..130
                        mol_type = other RNA
                        organism = synthetic construct
```

```
SEQUENCE: 193
agggcttctg tcgtgagtgg cacacgtagg gcaactcgat tgctctgcgt gcggaatcga    60
catcaagaga tttcggaagc ataatttttt ggtatttggg cagctggtga tcgttggtcc   120
cggcgccctt                                                          130

SEQ ID NO: 194          moltype = RNA   length = 129
FEATURE                 Location/Qualifiers
source                  1..129
                        mol_type = other RNA
                        organism = synthetic construct
SEQUENCE: 194
gggcttctgt cgtgagtggc acacgtaggg caactcgatt gctctgcgtg cggaatcgac    60
atcaagagat ttcggaagca taatttttg gtatttgggc agctggtgat cgttggtccc    120
ggcgccctt                                                           129

SEQ ID NO: 195          moltype = RNA   length = 128
FEATURE                 Location/Qualifiers
source                  1..128
                        mol_type = other RNA
                        organism = synthetic construct
SEQUENCE: 195
ggcttctgtc gtgagtggca cacgtagggc aactcgattg ctctgcgtgc ggaatcgaca    60
tcaagagatt tcggaagcat aatttttgg tatttgggca gctggtgatc gttggtcccg    120
gcgccctt                                                            128

SEQ ID NO: 196          moltype = RNA   length = 127
FEATURE                 Location/Qualifiers
source                  1..127
                        mol_type = other RNA
                        organism = synthetic construct
SEQUENCE: 196
gcttctgtcg tgagtggcac acgtagggca actcgattgc tctgcgtgcg gaatcgacat    60
caagagattt cggaagcata attttttggt atttgggcag ctggtgatcg ttggtcccgg    120
cgccctt                                                             127

SEQ ID NO: 197          moltype = RNA   length = 126
FEATURE                 Location/Qualifiers
source                  1..126
                        mol_type = other RNA
                        organism = synthetic construct
SEQUENCE: 197
cttctgtcgt gagtggcaca cgtagggcaa ctcgattgct ctgcgtgcgg aatcgacatc    60
aagagatttc ggaagcataa ttttttggta tttgggcagc tggtgatcgt tggtcccggc    120
gccctt                                                              126

SEQ ID NO: 198          moltype = RNA   length = 125
FEATURE                 Location/Qualifiers
source                  1..125
                        mol_type = other RNA
                        organism = synthetic construct
SEQUENCE: 198
ttctgtcgtg agtggcacac gtagggcaac tcgattgctc tgcgtgcgga atcgacatca    60
agagatttcg gaagcataat tttttggtat ttgggcagct ggtgatcgtt ggtcccggcg    120
ccctt                                                               125

SEQ ID NO: 199          moltype = RNA   length = 131
FEATURE                 Location/Qualifiers
source                  1..131
                        mol_type = other RNA
                        organism = synthetic construct
SEQUENCE: 199
aaaaagggct tctgtcgtga gtggcacacg taggcaact cgattgctct gcgtgcggaa     60
tcgacatcaa gagatttcgg aagcataatt ttttggtatt tgggcagctg gtgatcgttg    120
gtcccggcgc c                                                        131

SEQ ID NO: 200          moltype = RNA   length = 130
FEATURE                 Location/Qualifiers
source                  1..130
                        mol_type = other RNA
                        organism = synthetic construct
SEQUENCE: 200
aaaagggctt ctgtcgtgag tggcacacgt agggcaactc gattgctctg cgtgcggaat    60
cgacatcaag agatttcgga agcataattt tttggtattt gggcagctgg tgatcgttgg    120
tcccggcgcc                                                          130

SEQ ID NO: 201          moltype = RNA   length = 129
FEATURE                 Location/Qualifiers
source                  1..129
                        mol_type = other RNA
```

```
                        organism = synthetic construct
SEQUENCE: 201
aaagggcttc tgtcgtgagt ggcacacgta gggcaactcg attgctctgc gtgcggaatc    60
gacatcaaga gatttcggaa gcataatttt ttggtatttg ggcagctggt gatcgttggt   120
cccggcgcc                                                            129

SEQ ID NO: 202         moltype = RNA   length = 128
FEATURE                Location/Qualifiers
source                 1..128
                       mol_type = other RNA
                       organism = synthetic construct
SEQUENCE: 202
aagggcttct gtcgtgagtg gcacacgtag ggcaactcga ttgctctgcg tgcggaatcg    60
acatcaagag atttcggaag cataattttt tggtatttg gcagctggtg atcgttggtc    120
ccggcgcc                                                             128

SEQ ID NO: 203         moltype = RNA   length = 127
FEATURE                Location/Qualifiers
source                 1..127
                       mol_type = other RNA
                       organism = synthetic construct
SEQUENCE: 203
agggcttctg tcgtgagtgg cacacgtagg gcaactcgat tgctctgcgt gcggaatcga    60
catcaagaga tttcggaagc ataatttttt ggtatttggg cagctggtga tcgttggtcc   120
cggcgcc                                                              127

SEQ ID NO: 204         moltype = RNA   length = 126
FEATURE                Location/Qualifiers
source                 1..126
                       mol_type = other RNA
                       organism = synthetic construct
SEQUENCE: 204
gggcttctgt cgtgagtggc acacgtaggg caactcgatt gctctgcgtg cggaatcgac    60
atcaagagat ttcggaagca taatttttg gtatttgggc agctggtgat cgttggtccc    120
ggcgcc                                                               126

SEQ ID NO: 205         moltype = RNA   length = 125
FEATURE                Location/Qualifiers
source                 1..125
                       mol_type = other RNA
                       organism = synthetic construct
SEQUENCE: 205
ggcttctgtc gtgagtggca cacgtagggc aactcgattg ctctgcgtgc ggaatcgaca    60
tcaagagatt tcggaagcat aattttttgg tatttgggca gctggtgatc gttggtcccg    120
gcgcc                                                                125

SEQ ID NO: 206         moltype = RNA   length = 124
FEATURE                Location/Qualifiers
source                 1..124
                       mol_type = other RNA
                       organism = synthetic construct
SEQUENCE: 206
gcttctgtcg tgagtggcac acgtagggca actcgattgc tctgcgtgcg gaatcgacat    60
caagagattt cggaagcata attttttggt atttgggcag ctggtgatcg ttggtcccgg   120
cgcc                                                                 124

SEQ ID NO: 207         moltype = RNA   length = 123
FEATURE                Location/Qualifiers
source                 1..123
                       mol_type = other RNA
                       organism = synthetic construct
SEQUENCE: 207
cttctgtcgt gagtggcaca cgtagggcaa ctcgattgct ctgcgtgcgg aatcgacatc    60
aagagatttc ggaagcataa ttttttggta tttgggcagc tggtgatcgt tggtcccggc   120
gcc                                                                  123

SEQ ID NO: 208         moltype = RNA   length = 122
FEATURE                Location/Qualifiers
source                 1..122
                       mol_type = other RNA
                       organism = synthetic construct
SEQUENCE: 208
ttctgtcgtg agtggcacac gtagggcaac tcgattgctc tgcgtgcgga atcgacatca    60
agagatttcg gaagcataat ttttggtat ttgggcagct ggtgatcgtt ggtcccggcg    120
cc                                                                   122

SEQ ID NO: 209         moltype = RNA   length = 11
FEATURE                Location/Qualifiers
source                 1..11
```

-continued

```
                              mol_type = other RNA
                              organism = synthetic construct
SEQUENCE: 209
aatttttgga g                                                           11

SEQ ID NO: 210      moltype =   length =
SEQUENCE: 210
000

SEQ ID NO: 211      moltype = RNA  length = 11
FEATURE             Location/Qualifiers
source              1..11
                    mol_type = other RNA
                    organism = synthetic construct
SEQUENCE: 211
tatttttgga g                                                           11

SEQ ID NO: 212      moltype = RNA  length = 11
FEATURE             Location/Qualifiers
source              1..11
                    mol_type = other RNA
                    organism = synthetic construct
SEQUENCE: 212
gatttttgga g                                                           11

SEQ ID NO: 213      moltype = RNA  length = 11
FEATURE             Location/Qualifiers
source              1..11
                    mol_type = other RNA
                    organism = synthetic construct
SEQUENCE: 213
catttttgga g                                                           11

SEQ ID NO: 214      moltype = RNA  length = 11
FEATURE             Location/Qualifiers
source              1..11
                    mol_type = other RNA
                    organism = synthetic construct
SEQUENCE: 214
atttttgga g                                                            11

SEQ ID NO: 215      moltype = RNA  length = 11
FEATURE             Location/Qualifiers
source              1..11
                    mol_type = other RNA
                    organism = synthetic construct
SEQUENCE: 215
agtttttgga g                                                           11

SEQ ID NO: 216      moltype = RNA  length = 11
FEATURE             Location/Qualifiers
source              1..11
                    mol_type = other RNA
                    organism = synthetic construct
SEQUENCE: 216
acttttgga g                                                            11

SEQ ID NO: 217      moltype = RNA  length = 11
FEATURE             Location/Qualifiers
source              1..11
                    mol_type = other RNA
                    organism = synthetic construct
SEQUENCE: 217
aaatttgga g                                                            11

SEQ ID NO: 218      moltype = RNA  length = 11
FEATURE             Location/Qualifiers
source              1..11
                    mol_type = other RNA
                    organism = synthetic construct
SEQUENCE: 218
aagtttgga g                                                            11

SEQ ID NO: 219      moltype = RNA  length = 11
FEATURE             Location/Qualifiers
source              1..11
                    mol_type = other RNA
                    organism = synthetic construct
SEQUENCE: 219
```

-continued

```
aactttttgga g                                                      11

SEQ ID NO: 220        moltype = RNA   length = 11
FEATURE               Location/Qualifiers
source                1..11
                      mol_type = other RNA
                      organism = synthetic construct SEQUENCE: 220
aatatttgga g                                                       11

SEQ ID NO: 221        moltype = RNA   length = 11
FEATURE               Location/Qualifiers
source                1..11
                      mol_type = other RNA
                      organism = synthetic construct SEQUENCE: 221
aatgtttgga g                                                       11

SEQ ID NO: 222        moltype = RNA   length = 11
FEATURE               Location/Qualifiers
source                1..11
                      mol_type = other RNA
                      organism = synthetic construct SEQUENCE: 222
aatctttgga g                                                       11

SEQ ID NO: 223        moltype = RNA   length = 11
FEATURE               Location/Qualifiers
source                1..11
                      mol_type = other RNA
                      organism = synthetic construct SEQUENCE: 223
aattattgga g                                                       11

SEQ ID NO: 224        moltype = RNA   length = 11
FEATURE               Location/Qualifiers
source                1..11
                      mol_type = other RNA
                      organism = synthetic construct SEQUENCE: 224
aattgttgga g                                                       11

SEQ ID NO: 225        moltype = RNA   length = 11
FEATURE               Location/Qualifiers
source                1..11
                      mol_type = other RNA
                      organism = synthetic construct SEQUENCE: 225
aattcttgga g                                                       11

SEQ ID NO: 226        moltype = RNA   length = 11
FEATURE               Location/Qualifiers
source                1..11
                      mol_type = other RNA
                      organism = synthetic construct SEQUENCE: 226
aatttatgga g                                                       11

SEQ ID NO: 227        moltype = RNA   length = 11
FEATURE               Location/Qualifiers
source                1..11
                      mol_type = other RNA
                      organism = synthetic construct SEQUENCE: 227
aatttgtgga g                                                       11

SEQ ID NO: 228        moltype = RNA   length = 11
FEATURE               Location/Qualifiers
source                1..11
                      mol_type = other RNA
                      organism = synthetic construct SEQUENCE: 228
aatttctgga g                                                       11

SEQ ID NO: 229        moltype = RNA   length = 11
FEATURE               Location/Qualifiers
source                1..11
                      mol_type = other RNA
                      organism = synthetic construct
```

-continued

```
SEQUENCE: 229
aatttttagga g                                                                      11

SEQ ID NO: 230            moltype = RNA   length = 11
FEATURE                   Location/Qualifiers
source                    1..11
                          mol_type = other RNA
                          organism = synthetic construct SEQUENCE: 230
aattttggga g                                                                       11

SEQ ID NO: 231            moltype = RNA   length = 11
FEATURE                   Location/Qualifiers
source                    1..11
                          mol_type = other RNA
                          organism = synthetic construct SEQUENCE: 231
aattttcgga g                                                                       11

SEQ ID NO: 232            moltype = RNA   length = 11
FEATURE                   Location/Qualifiers
source                    1..11
                          mol_type = other RNA
                          organism = synthetic construct SEQUENCE: 232
aatttttaga g                                                                       11

SEQ ID NO: 233            moltype = RNA   length = 11
FEATURE                   Location/Qualifiers
source                    1..11
                          mol_type = other RNA
                          organism = synthetic construct SEQUENCE: 233
aatttttga g                                                                        11

SEQ ID NO: 234            moltype = RNA   length = 11
FEATURE                   Location/Qualifiers
source                    1..11
                          mol_type = other RNA
                          organism = synthetic construct SEQUENCE: 234
aatttttcga g                                                                       11

SEQ ID NO: 235            moltype = RNA   length = 11
FEATURE                   Location/Qualifiers
source                    1..11
                          mol_type = other RNA
                          organism = synthetic construct SEQUENCE: 235
aatttttgaa g                                                                       11

SEQ ID NO: 236            moltype = RNA   length = 11
FEATURE                   Location/Qualifiers
source                    1..11
                          mol_type = other RNA
                          organism = synthetic construct SEQUENCE: 236
aatttttgta g                                                                       11

SEQ ID NO: 237            moltype = RNA   length = 11
FEATURE                   Location/Qualifiers
source                    1..11
                          mol_type = other RNA
                          organism = synthetic construct SEQUENCE: 237
aatttttgca g                                                                       11

SEQ ID NO: 238            moltype = RNA   length = 11
FEATURE                   Location/Qualifiers
source                    1..11
                          mol_type = other RNA
                          organism = synthetic construct SEQUENCE: 238
aatttttggt g                                                                       11

SEQ ID NO: 239            moltype = RNA   length = 11
FEATURE                   Location/Qualifiers
source                    1..11
                          mol_type = other RNA
```

```
                          organism = synthetic construct
SEQUENCE: 239
aatttttggg g                                                          11

SEQ ID NO: 240           moltype = RNA   length = 11
FEATURE                  Location/Qualifiers
source                   1..11
                         mol_type = other RNA
                         organism = synthetic construct
SEQUENCE: 240
aatttttggc g                                                          11

SEQ ID NO: 241           moltype = RNA   length = 11
FEATURE                  Location/Qualifiers
source                   1..11
                         mol_type = other RNA
                         organism = synthetic construct
SEQUENCE: 241
aatttttgga a                                                          11

SEQ ID NO: 242           moltype = RNA   length = 11
FEATURE                  Location/Qualifiers
source                   1..11
                         mol_type = other RNA
                         organism = synthetic construct
SEQUENCE: 242
aatttttgga t                                                          11

SEQ ID NO: 243           moltype = RNA   length = 11
FEATURE                  Location/Qualifiers
source                   1..11
                         mol_type = other RNA
                         organism = synthetic construct
SEQUENCE: 243
aatttttgga c                                                          11

SEQ ID NO: 244           moltype = RNA   length = 11
FEATURE                  Location/Qualifiers
source                   1..11
                         mol_type = other RNA
                         organism = synthetic construct
SEQUENCE: 244
aatgttttga g                                                          11

SEQ ID NO: 245           moltype = RNA   length = 11
FEATURE                  Location/Qualifiers
source                   1..11
                         mol_type = other RNA
                         organism = synthetic construct
SEQUENCE: 245
aatttgtgta g                                                          11

SEQ ID NO: 246           moltype = RNA   length = 11
FEATURE                  Location/Qualifiers
source                   1..11
                         mol_type = other RNA
                         organism = synthetic construct
SEQUENCE: 246
agtttttgga a                                                          11

SEQ ID NO: 247           moltype = RNA   length = 11
FEATURE                  Location/Qualifiers
source                   1..11
                         mol_type = other RNA
                         organism = synthetic construct
SEQUENCE: 247
attttgtgga g                                                          11

SEQ ID NO: 248           moltype = RNA   length = 11
FEATURE                  Location/Qualifiers
source                   1..11
                         mol_type = other RNA
                         organism = synthetic construct
SEQUENCE: 248
aatgtttgca g                                                          11

SEQ ID NO: 249           moltype = RNA   length = 11
FEATURE                  Location/Qualifiers
source                   1..11
```

-continued

```
                        mol_type = other RNA
                        organism = synthetic construct
SEQUENCE: 249
aatgttggga g                                                    11

SEQ ID NO: 250          moltype = RNA   length = 11
FEATURE                 Location/Qualifiers
source                  1..11
                        mol_type = other RNA
                        organism = synthetic construct
SEQUENCE: 250
aattgctgga g                                                    11

SEQ ID NO: 251          moltype = RNA   length = 11
FEATURE                 Location/Qualifiers
source                  1..11
                        mol_type = other RNA
                        organism = synthetic construct
SEQUENCE: 251
aattttagca g                                                    11

SEQ ID NO: 252          moltype = RNA   length = 11
FEATURE                 Location/Qualifiers
source                  1..11
                        mol_type = other RNA
                        organism = synthetic construct
SEQUENCE: 252
aaggtttgga g                                                    11

SEQ ID NO: 253          moltype = RNA   length = 11
FEATURE                 Location/Qualifiers
source                  1..11
                        mol_type = other RNA
                        organism = synthetic construct
SEQUENCE: 253
gatttgtgga g                                                    11

SEQ ID NO: 254          moltype = RNA   length = 11
FEATURE                 Location/Qualifiers
source                  1..11
                        mol_type = other RNA
                        organism = synthetic construct
SEQUENCE: 254
acttttgga a                                                     11

SEQ ID NO: 255          moltype = RNA   length = 11
FEATURE                 Location/Qualifiers
source                  1..11
                        mol_type = other RNA
                        organism = synthetic construct
SEQUENCE: 255
aaattatgga g                                                    11

SEQ ID NO: 256          moltype = RNA   length = 11
FEATURE                 Location/Qualifiers
source                  1..11
                        mol_type = other RNA
                        organism = synthetic construct
SEQUENCE: 256
aattttgcga g                                                    11

SEQ ID NO: 257          moltype = RNA   length = 11
FEATURE                 Location/Qualifiers
source                  1..11
                        mol_type = other RNA
                        organism = synthetic construct
SEQUENCE: 257
aatttctgga a                                                    11

SEQ ID NO: 258          moltype = RNA   length = 11
FEATURE                 Location/Qualifiers
source                  1..11
                        mol_type = other RNA
                        organism = synthetic construct
SEQUENCE: 258
tatttttggt g                                                    11

SEQ ID NO: 259          moltype = RNA   length = 11
FEATURE                 Location/Qualifiers
```

-continued

```
source                    1..11
                          mol_type = other RNA
                          organism = synthetic construct SEQUENCE: 259
gattttagga g                                                          11

SEQ ID NO: 260           moltype = RNA  length = 11
FEATURE                  Location/Qualifiers
source                   1..11
                         mol_type = other RNA
                         organism = synthetic construct SEQUENCE: 260
aatctgtgga g                                                          11

SEQ ID NO: 261           moltype = RNA  length = 11
FEATURE                  Location/Qualifiers
source                   1..11
                         mol_type = other RNA
                         organism = synthetic construct SEQUENCE: 261
aaattttaga g                                                          11

SEQ ID NO: 262           moltype = RNA  length = 11
FEATURE                  Location/Qualifiers
source                   1..11
                         mol_type = other RNA
                         organism = synthetic construct SEQUENCE: 262
aattttcga c                                                           11

SEQ ID NO: 263           moltype = RNA  length = 11
FEATURE                  Location/Qualifiers
source                   1..11
                         mol_type = other RNA
                         organism = synthetic construct SEQUENCE: 263
aattttggg t                                                           11

SEQ ID NO: 264           moltype = RNA  length = 11
FEATURE                  Location/Qualifiers
source                   1..11
                         mol_type = other RNA
                         organism = synthetic construct SEQUENCE: 264
aatctttgga a                                                          11

SEQ ID NO: 265           moltype = RNA  length = 11
FEATURE                  Location/Qualifiers
source                   1..11
                         mol_type = other RNA
                         organism = synthetic construct SEQUENCE: 265
aattattggt g                                                          11

SEQ ID NO: 266           moltype = RNA  length = 11
FEATURE                  Location/Qualifiers
source                   1..11
                         mol_type = other RNA
                         organism = synthetic construct SEQUENCE: 266
aattttaaga g                                                          11

SEQ ID NO: 267           moltype = RNA  length = 11
FEATURE                  Location/Qualifiers
source                   1..11
                         mol_type = other RNA
                         organism = synthetic construct SEQUENCE: 267
aatgttagga g                                                          11

SEQ ID NO: 268           moltype = RNA  length = 11
FEATURE                  Location/Qualifiers
source                   1..11
                         mol_type = other RNA
                         organism = synthetic construct SEQUENCE: 268
aattttagaa g                                                          11

SEQ ID NO: 269           moltype = RNA  length = 11
```

-continued

```
FEATURE                Location/Qualifiers
source                 1..11
                       mol_type = other RNA
                       organism = synthetic construct
SEQUENCE: 269
atttttggc g                                                      11

SEQ ID NO: 270         moltype = RNA   length = 11
FEATURE                Location/Qualifiers
source                 1..11
                       mol_type = other RNA
                       organism = synthetic construct
SEQUENCE: 270
aacttttggt g                                                     11

SEQ ID NO: 271         moltype = RNA   length = 11
FEATURE                Location/Qualifiers
source                 1..11
                       mol_type = other RNA
                       organism = synthetic construct
SEQUENCE: 271
aatgtttgga t                                                     11

SEQ ID NO: 272         moltype = RNA   length = 11
FEATURE                Location/Qualifiers
source                 1..11
                       mol_type = other RNA
                       organism = synthetic construct
SEQUENCE: 272
aattttagga t                                                     11

SEQ ID NO: 273         moltype = RNA   length = 11
FEATURE                Location/Qualifiers
source                 1..11
                       mol_type = other RNA
                       organism = synthetic construct
SEQUENCE: 273
aattttgat g                                                      11

SEQ ID NO: 274         moltype = RNA   length = 11
FEATURE                Location/Qualifiers
source                 1..11
                       mol_type = other RNA
                       organism = synthetic construct
SEQUENCE: 274
aattcttggt g                                                     11

SEQ ID NO: 275         moltype = RNA   length = 11
FEATURE                Location/Qualifiers
source                 1..11
                       mol_type = other RNA
                       organism = synthetic construct
SEQUENCE: 275
aatccttgga g                                                     11

SEQ ID NO: 276         moltype = RNA   length = 11
FEATURE                Location/Qualifiers
source                 1..11
                       mol_type = other RNA
                       organism = synthetic construct
SEQUENCE: 276
aattttcaa g                                                      11

SEQ ID NO: 277         moltype = RNA   length = 11
FEATURE                Location/Qualifiers
source                 1..11
                       mol_type = other RNA
                       organism = synthetic construct
SEQUENCE: 277
catttttgca g                                                     11

SEQ ID NO: 278         moltype = RNA   length = 11
FEATURE                Location/Qualifiers
source                 1..11
                       mol_type = other RNA
                       organism = synthetic construct
SEQUENCE: 278
catttttcga g                                                     11
```

-continued

```
SEQ ID NO: 279        moltype = RNA   length = 11
FEATURE               Location/Qualifiers
source                1..11
                      mol_type = other RNA
                      organism = synthetic construct SEQUENCE: 279
aattttgggc g                                                      11

SEQ ID NO: 280        moltype = RNA   length = 11
FEATURE               Location/Qualifiers
source                1..11
                      mol_type = other RNA
                      organism = synthetic construct SEQUENCE: 280
agtttttgca g                                                      11

SEQ ID NO: 281        moltype = RNA   length = 11
FEATURE               Location/Qualifiers
source                1..11
                      mol_type = other RNA
                      organism = synthetic construct SEQUENCE: 281
aaaatttgga g                                                      11

SEQ ID NO: 282        moltype = RNA   length = 11
FEATURE               Location/Qualifiers
source                1..11
                      mol_type = other RNA
                      organism = synthetic construct SEQUENCE: 282
aactcttgga g                                                      11

SEQ ID NO: 283        moltype = RNA   length = 11
FEATURE               Location/Qualifiers
source                1..11
                      mol_type = other RNA
                      organism = synthetic construct SEQUENCE: 283
aatttgtgga c                                                      11

SEQ ID NO: 284        moltype = RNA   length = 11
FEATURE               Location/Qualifiers
source                1..11
                      mol_type = other RNA
                      organism = synthetic construct SEQUENCE: 284
acttttggt g                                                       11

SEQ ID NO: 285        moltype = RNA   length = 11
FEATURE               Location/Qualifiers
source                1..11
                      mol_type = other RNA
                      organism = synthetic construct SEQUENCE: 285
attttttgaa g                                                      11

SEQ ID NO: 286        moltype = RNA   length = 11
FEATURE               Location/Qualifiers
source                1..11
                      mol_type = other RNA
                      organism = synthetic construct SEQUENCE: 286
attttttgga a                                                      11

SEQ ID NO: 287        moltype = RNA   length = 11
FEATURE               Location/Qualifiers
source                1..11
                      mol_type = other RNA
                      organism = synthetic construct SEQUENCE: 287
aagttatgga g                                                      11

SEQ ID NO: 288        moltype = RNA   length = 11
FEATURE               Location/Qualifiers
source                1..11
                      mol_type = other RNA
                      organism = synthetic construct SEQUENCE: 288
catttctgga g                                                      11
```

-continued

```
SEQ ID NO: 289           moltype = RNA  length = 11
FEATURE                  Location/Qualifiers
source                   1..11
                         mol_type = other RNA
                         organism = synthetic construct
SEQUENCE: 289
agttcttgga g                                                          11

SEQ ID NO: 290           moltype = RNA  length = 11
FEATURE                  Location/Qualifiers
source                   1..11
                         mol_type = other RNA
                         organism = synthetic construct
SEQUENCE: 290
aattttggaa g                                                          11

SEQ ID NO: 291           moltype = RNA  length = 11
FEATURE                  Location/Qualifiers
source                   1..11
                         mol_type = other RNA
                         organism = synthetic construct
SEQUENCE: 291
agtatttgga g                                                          11

SEQ ID NO: 292           moltype = RNA  length = 11
FEATURE                  Location/Qualifiers
source                   1..11
                         mol_type = other RNA
                         organism = synthetic construct
SEQUENCE: 292
aattttgggc c                                                          11

SEQ ID NO: 293           moltype = RNA  length = 11
FEATURE                  Location/Qualifiers
source                   1..11
                         mol_type = other RNA
                         organism = synthetic construct
SEQUENCE: 293
aattcttgta g                                                          11

SEQ ID NO: 294           moltype = RNA  length = 11
FEATURE                  Location/Qualifiers
source                   1..11
                         mol_type = other RNA
                         organism = synthetic construct
SEQUENCE: 294
aattttggga a                                                          11

SEQ ID NO: 295           moltype = RNA  length = 11
FEATURE                  Location/Qualifiers
source                   1..11
                         mol_type = other RNA
                         organism = synthetic construct
SEQUENCE: 295
tattttttga g                                                          11

SEQ ID NO: 296           moltype = RNA  length = 11
FEATURE                  Location/Qualifiers
source                   1..11
                         mol_type = other RNA
                         organism = synthetic construct
SEQUENCE: 296
aacttttgta g                                                          11

SEQ ID NO: 297           moltype = RNA  length = 11
FEATURE                  Location/Qualifiers
source                   1..11
                         mol_type = other RNA
                         organism = synthetic construct
SEQUENCE: 297
aattattgca g                                                          11

SEQ ID NO: 298           moltype = RNA  length = 11
FEATURE                  Location/Qualifiers
source                   1..11
                         mol_type = other RNA
                         organism = synthetic construct
SEQUENCE: 298
```

-continued

```
aatttttggt a                                                           11

SEQ ID NO: 299           moltype = RNA   length = 11
FEATURE                  Location/Qualifiers
source                   1..11
                         mol_type = other RNA
                         organism = synthetic construct SEQUENCE: 299
aattttcgaa g                                                           11

SEQ ID NO: 300           moltype = RNA   length = 11
FEATURE                  Location/Qualifiers
source                   1..11
                         mol_type = other RNA
                         organism = synthetic construct SEQUENCE: 300
tatctttgga g                                                           11

SEQ ID NO: 301           moltype = RNA   length = 11
FEATURE                  Location/Qualifiers
source                   1..11
                         mol_type = other RNA
                         organism = synthetic construct SEQUENCE: 301
aatttttcgt g                                                           11

SEQ ID NO: 302           moltype = RNA   length = 11
FEATURE                  Location/Qualifiers
source                   1..11
                         mol_type = other RNA
                         organism = synthetic construct SEQUENCE: 302
aatctttggc g                                                           11

SEQ ID NO: 303           moltype = RNA   length = 11
FEATURE                  Location/Qualifiers
source                   1..11
                         mol_type = other RNA
                         organism = synthetic construct SEQUENCE: 303
gatttatgga g                                                           11

SEQ ID NO: 304           moltype = RNA   length = 11
FEATURE                  Location/Qualifiers
source                   1..11
                         mol_type = other RNA
                         organism = synthetic construct SEQUENCE: 304
aatttttcga a                                                           11

SEQ ID NO: 305           moltype = RNA   length = 11
FEATURE                  Location/Qualifiers
source                   1..11
                         mol_type = other RNA
                         organism = synthetic construct SEQUENCE: 305
cctttttgga g                                                           11

SEQ ID NO: 306           moltype = RNA   length = 11
FEATURE                  Location/Qualifiers
source                   1..11
                         mol_type = other RNA
                         organism = synthetic construct SEQUENCE: 306
tatttttgaa g                                                           11

SEQ ID NO: 307           moltype = RNA   length = 11
FEATURE                  Location/Qualifiers
source                   1..11
                         mol_type = other RNA
                         organism = synthetic construct SEQUENCE: 307
aattttttgta a                                                          11

SEQ ID NO: 308           moltype = RNA   length = 11
FEATURE                  Location/Qualifiers
source                   1..11
                         mol_type = other RNA
                         organism = synthetic construct
```

-continued

```
SEQUENCE: 308
aattttgaga g                                                      11

SEQ ID NO: 309          moltype = RNA   length = 11
FEATURE                 Location/Qualifiers
source                  1..11
                        mol_type = other RNA
                        organism = synthetic construct
SEQUENCE: 309
aagtattgga g                                                      11

SEQ ID NO: 310          moltype = RNA   length = 11
FEATURE                 Location/Qualifiers
source                  1..11
                        mol_type = other RNA
                        organism = synthetic construct
SEQUENCE: 310
aattttagga c                                                      11

SEQ ID NO: 311          moltype = RNA   length = 11
FEATURE                 Location/Qualifiers
source                  1..11
                        mol_type = other RNA
                        organism = synthetic construct
SEQUENCE: 311
aatttttaaa g                                                      11

SEQ ID NO: 312          moltype = RNA   length = 11
FEATURE                 Location/Qualifiers
source                  1..11
                        mol_type = other RNA
                        organism = synthetic construct
SEQUENCE: 312
aattcttgga t                                                      11

SEQ ID NO: 313          moltype = RNA   length = 11
FEATURE                 Location/Qualifiers
source                  1..11
                        mol_type = other RNA
                        organism = synthetic construct
SEQUENCE: 313
aatttgtggt g                                                      11

SEQ ID NO: 314          moltype = RNA   length = 11
FEATURE                 Location/Qualifiers
source                  1..11
                        mol_type = other RNA
                        organism = synthetic construct
SEQUENCE: 314
aattttcggg g                                                      11

SEQ ID NO: 315          moltype = RNA   length = 11
FEATURE                 Location/Qualifiers
source                  1..11
                        mol_type = other RNA
                        organism = synthetic construct
SEQUENCE: 315
actttttga g                                                       11

SEQ ID NO: 316          moltype = RNA   length = 11
FEATURE                 Location/Qualifiers
source                  1..11
                        mol_type = other RNA
                        organism = synthetic construct
SEQUENCE: 316
aagtttcgga g                                                      11

SEQ ID NO: 317          moltype = RNA   length = 11
FEATURE                 Location/Qualifiers
source                  1..11
                        mol_type = other RNA
                        organism = synthetic construct
SEQUENCE: 317
acttttggga g                                                      11

SEQ ID NO: 318          moltype = RNA   length = 11
FEATURE                 Location/Qualifiers
source                  1..11
                        mol_type = other RNA
```

```
                          organism = synthetic construct
SEQUENCE: 318
gactttttgga g                                                                 11

SEQ ID NO: 319            moltype = RNA   length = 11
FEATURE                   Location/Qualifiers
source                    1..11
                          mol_type = other RNA
                          organism = synthetic construct
SEQUENCE: 319
cttttttgga g                                                                  11

SEQ ID NO: 320            moltype = RNA   length = 11
FEATURE                   Location/Qualifiers
source                    1..11
                          mol_type = other RNA
                          organism = synthetic construct
SEQUENCE: 320
cattgttgga g                                                                  11

SEQ ID NO: 321            moltype = RNA   length = 11
FEATURE                   Location/Qualifiers
source                    1..11
                          mol_type = other RNA
                          organism = synthetic construct
SEQUENCE: 321
aatattttga g                                                                  11

SEQ ID NO: 322            moltype = RNA   length = 11
FEATURE                   Location/Qualifiers
source                    1..11
                          mol_type = other RNA
                          organism = synthetic construct
SEQUENCE: 322
aagttttggc g                                                                  11

SEQ ID NO: 323            moltype = RNA   length = 11
FEATURE                   Location/Qualifiers
source                    1..11
                          mol_type = other RNA
                          organism = synthetic construct
SEQUENCE: 323
aattttagga a                                                                  11

SEQ ID NO: 324            moltype = RNA   length = 11
FEATURE                   Location/Qualifiers
source                    1..11
                          mol_type = other RNA
                          organism = synthetic construct
SEQUENCE: 324
aacttgtgga g                                                                  11

SEQ ID NO: 325            moltype = RNA   length = 11
FEATURE                   Location/Qualifiers
source                    1..11
                          mol_type = other RNA
                          organism = synthetic construct
SEQUENCE: 325
atttttgggg g                                                                  11

SEQ ID NO: 326            moltype = RNA   length = 11
FEATURE                   Location/Qualifiers
source                    1..11
                          mol_type = other RNA
                          organism = synthetic construct
SEQUENCE: 326
aattttaga t                                                                   11

SEQ ID NO: 327            moltype = RNA   length = 11
FEATURE                   Location/Qualifiers
source                    1..11
                          mol_type = other RNA
                          organism = synthetic construct
SEQUENCE: 327
tattttggga g                                                                  11

SEQ ID NO: 328            moltype = RNA   length = 11
FEATURE                   Location/Qualifiers
source                    1..11
```

-continued

```
                              mol_type = other RNA
                              organism = synthetic construct
SEQUENCE: 328
aatttgtggg g                                                    11

SEQ ID NO: 329           moltype = RNA   length = 11
FEATURE                  Location/Qualifiers
source                   1..11
                         mol_type = other RNA
                         organism = synthetic construct
SEQUENCE: 329
aattttagg g                                                     11

SEQ ID NO: 330           moltype = RNA   length = 11
FEATURE                  Location/Qualifiers
source                   1..11
                         mol_type = other RNA
                         organism = synthetic construct
SEQUENCE: 330
aattttcgta g                                                    11

SEQ ID NO: 331           moltype = RNA   length = 11
FEATURE                  Location/Qualifiers
source                   1..11
                         mol_type = other RNA
                         organism = synthetic construct
SEQUENCE: 331
aattttctga g                                                    11

SEQ ID NO: 332           moltype = RNA   length = 11
FEATURE                  Location/Qualifiers
source                   1..11
                         mol_type = other RNA
                         organism = synthetic construct
SEQUENCE: 332
gattcttgga g                                                    11

SEQ ID NO: 333           moltype = RNA   length = 11
FEATURE                  Location/Qualifiers
source                   1..11
                         mol_type = other RNA
                         organism = synthetic construct
SEQUENCE: 333
aatctttgga t                                                    11

SEQ ID NO: 334           moltype = RNA   length = 11
FEATURE                  Location/Qualifiers
source                   1..11
                         mol_type = other RNA
                         organism = synthetic construct
SEQUENCE: 334
aaattttggc g                                                    11

SEQ ID NO: 335           moltype = RNA   length = 11
FEATURE                  Location/Qualifiers
source                   1..11
                         mol_type = other RNA
                         organism = synthetic construct
SEQUENCE: 335
aatcattgga g                                                    11

SEQ ID NO: 336           moltype = RNA   length = 11
FEATURE                  Location/Qualifiers
source                   1..11
                         mol_type = other RNA
                         organism = synthetic construct
SEQUENCE: 336
aacttttggc g                                                    11

SEQ ID NO: 337           moltype = RNA   length = 11
FEATURE                  Location/Qualifiers
source                   1..11
                         mol_type = other RNA
                         organism = synthetic construct
SEQUENCE: 337
aatttttggg a                                                    11

SEQ ID NO: 338           moltype = RNA   length = 11
FEATURE                  Location/Qualifiers
```

-continued

```
source                    1..11
                          mol_type = other RNA
                          organism = synthetic construct SEQUENCE: 338
aatgtttggt g                                                          11

SEQ ID NO: 339            moltype = RNA   length = 11
FEATURE                   Location/Qualifiers
source                    1..11
                          mol_type = other RNA
                          organism = synthetic construct SEQUENCE: 339
aatttatgca g                                                          11

SEQ ID NO: 340            moltype = RNA   length = 11
FEATURE                   Location/Qualifiers
source                    1..11
                          mol_type = other RNA
                          organism = synthetic construct SEQUENCE: 340
aatctctgga g                                                          11

SEQ ID NO: 341            moltype = RNA   length = 11
FEATURE                   Location/Qualifiers
source                    1..11
                          mol_type = other RNA
                          organism = synthetic construct SEQUENCE: 341
agtttgtgga g                                                          11

SEQ ID NO: 342            moltype = RNA   length = 11
FEATURE                   Location/Qualifiers
source                    1..11
                          mol_type = other RNA
                          organism = synthetic construct SEQUENCE: 342
aagttttgga t                                                          11

SEQ ID NO: 343            moltype = RNA   length = 11
FEATURE                   Location/Qualifiers
source                    1..11
                          mol_type = other RNA
                          organism = synthetic construct SEQUENCE: 343
tatttttggc g                                                          11

SEQ ID NO: 344            moltype = RNA   length = 11
FEATURE                   Location/Qualifiers
source                    1..11
                          mol_type = other RNA
                          organism = synthetic construct SEQUENCE: 344
aatttctgaa g                                                          11

SEQ ID NO: 345            moltype = RNA   length = 11
FEATURE                   Location/Qualifiers
source                    1..11
                          mol_type = other RNA
                          organism = synthetic construct SEQUENCE: 345
tatttctgga g                                                          11

SEQ ID NO: 346            moltype = RNA   length = 11
FEATURE                   Location/Qualifiers
source                    1..11
                          mol_type = other RNA
                          organism = synthetic construct SEQUENCE: 346
aattttttgct g                                                         11

SEQ ID NO: 347            moltype = RNA   length = 11
FEATURE                   Location/Qualifiers
source                    1..11
                          mol_type = other RNA
                          organism = synthetic construct SEQUENCE: 347
aaatcttgga g                                                          11

SEQ ID NO: 348            moltype = RNA   length = 11
```

-continued

| FEATURE | Location/Qualifiers |
|---|---|
| source | 1..11 |
| | mol_type = other RNA |
| | organism = synthetic construct |

SEQUENCE: 348
aaatttttga g                                                               11

| SEQ ID NO: 349 | moltype = RNA length = 11 |
|---|---|
| FEATURE | Location/Qualifiers |
| source | 1..11 |
| | mol_type = other RNA |
| | organism = synthetic construct |

SEQUENCE: 349
tatttttgta g                                                               11

| SEQ ID NO: 350 | moltype = RNA length = 11 |
|---|---|
| FEATURE | Location/Qualifiers |
| source | 1..11 |
| | mol_type = other RNA |
| | organism = synthetic construct |

SEQUENCE: 350
gattattgga g                                                               11

| SEQ ID NO: 351 | moltype = RNA length = 11 |
|---|---|
| FEATURE | Location/Qualifiers |
| source | 1..11 |
| | mol_type = other RNA |
| | organism = synthetic construct |

SEQUENCE: 351
aagttctgga g                                                               11

| SEQ ID NO: 352 | moltype = RNA length = 11 |
|---|---|
| FEATURE | Location/Qualifiers |
| source | 1..11 |
| | mol_type = other RNA |
| | organism = synthetic construct |

SEQUENCE: 352
aatctttgaa g                                                               11

| SEQ ID NO: 353 | moltype = RNA length = 11 |
|---|---|
| FEATURE | Location/Qualifiers |
| source | 1..11 |
| | mol_type = other RNA |
| | organism = synthetic construct |

SEQUENCE: 353
aaatattgga g                                                               11

| SEQ ID NO: 354 | moltype = RNA length = 11 |
|---|---|
| FEATURE | Location/Qualifiers |
| source | 1..11 |
| | mol_type = other RNA |
| | organism = synthetic construct |

SEQUENCE: 354
aactattgga g                                                               11

| SEQ ID NO: 355 | moltype = RNA length = 11 |
|---|---|
| FEATURE | Location/Qualifiers |
| source | 1..11 |
| | mol_type = other RNA |
| | organism = synthetic construct |

SEQUENCE: 355
aatatatgga g                                                               11

| SEQ ID NO: 356 | moltype = RNA length = 11 |
|---|---|
| FEATURE | Location/Qualifiers |
| source | 1..11 |
| | mol_type = other RNA |
| | organism = synthetic construct |

SEQUENCE: 356
attctttgga g                                                               11

| SEQ ID NO: 357 | moltype = RNA length = 11 |
|---|---|
| FEATURE | Location/Qualifiers |
| source | 1..11 |
| | mol_type = other RNA |
| | organism = synthetic construct |

SEQUENCE: 357
gatttttgaa g                                                               11

-continued

```
SEQ ID NO: 358          moltype = RNA   length = 11
FEATURE                 Location/Qualifiers
source                  1..11
                        mol_type = other RNA
                        organism = synthetic construct SEQUENCE: 358
aagttttggt g                                                    11

SEQ ID NO: 359          moltype = RNA   length = 11
FEATURE                 Location/Qualifiers
source                  1..11
                        mol_type = other RNA
                        organism = synthetic construct SEQUENCE: 359
aatctttgca g                                                    11

SEQ ID NO: 360          moltype = RNA   length = 11
FEATURE                 Location/Qualifiers
source                  1..11
                        mol_type = other RNA
                        organism = synthetic construct SEQUENCE: 360
actttttggc g                                                    11

SEQ ID NO: 361          moltype = RNA   length = 11
FEATURE                 Location/Qualifiers
source                  1..11
                        mol_type = other RNA
                        organism = synthetic construct SEQUENCE: 361
gattttggga g                                                    11

SEQ ID NO: 362          moltype = RNA   length = 11
FEATURE                 Location/Qualifiers
source                  1..11
                        mol_type = other RNA
                        organism = synthetic construct SEQUENCE: 362
catttttgga a                                                    11

SEQ ID NO: 363          moltype = RNA   length = 11
FEATURE                 Location/Qualifiers
source                  1..11
                        mol_type = other RNA
                        organism = synthetic construct SEQUENCE: 363
aattttttga c                                                    11

SEQ ID NO: 364          moltype = RNA   length = 11
FEATURE                 Location/Qualifiers
source                  1..11
                        mol_type = other RNA
                        organism = synthetic construct SEQUENCE: 364
aaattttgca g                                                    11

SEQ ID NO: 365          moltype = RNA   length = 11
FEATURE                 Location/Qualifiers
source                  1..11
                        mol_type = other RNA
                        organism = synthetic construct SEQUENCE: 365
acttttgaa g                                                     11

SEQ ID NO: 366          moltype = RNA   length = 11
FEATURE                 Location/Qualifiers
source                  1..11
                        mol_type = other RNA
                        organism = synthetic construct SEQUENCE: 366
agtctttgga g                                                    11

SEQ ID NO: 367          moltype = RNA   length = 11
FEATURE                 Location/Qualifiers
source                  1..11
                        mol_type = other RNA
                        organism = synthetic construct SEQUENCE: 367
agtttatgga g                                                    11
```

-continued

```
SEQ ID NO: 368          moltype = RNA  length = 11
FEATURE                 Location/Qualifiers
source                  1..11
                        mol_type = other RNA
                        organism = synthetic construct
SEQUENCE: 368
acttcttgga g                                                   11

SEQ ID NO: 369          moltype = RNA  length = 11
FEATURE                 Location/Qualifiers
source                  1..11
                        mol_type = other RNA
                        organism = synthetic construct
SEQUENCE: 369
aattttttca g                                                   11

SEQ ID NO: 370          moltype = RNA  length = 11
FEATURE                 Location/Qualifiers
source                  1..11
                        mol_type = other RNA
                        organism = synthetic construct
SEQUENCE: 370
aattttcgga t                                                   11

SEQ ID NO: 371          moltype = RNA  length = 11
FEATURE                 Location/Qualifiers
source                  1..11
                        mol_type = other RNA
                        organism = synthetic construct
SEQUENCE: 371
aatttttgta t                                                   11

SEQ ID NO: 372          moltype = RNA  length = 11
FEATURE                 Location/Qualifiers
source                  1..11
                        mol_type = other RNA
                        organism = synthetic construct
SEQUENCE: 372
aatgtctgga g                                                   11

SEQ ID NO: 373          moltype = RNA  length = 11
FEATURE                 Location/Qualifiers
source                  1..11
                        mol_type = other RNA
                        organism = synthetic construct
SEQUENCE: 373
aattgttggg g                                                   11

SEQ ID NO: 374          moltype = RNA  length = 11
FEATURE                 Location/Qualifiers
source                  1..11
                        mol_type = other RNA
                        organism = synthetic construct
SEQUENCE: 374
aatttatgga c                                                   11

SEQ ID NO: 375          moltype = RNA  length = 11
FEATURE                 Location/Qualifiers
source                  1..11
                        mol_type = other RNA
                        organism = synthetic construct
SEQUENCE: 375
aatttatgaa g                                                   11

SEQ ID NO: 376          moltype = RNA  length = 11
FEATURE                 Location/Qualifiers
source                  1..11
                        mol_type = other RNA
                        organism = synthetic construct
SEQUENCE: 376
aatttatggg g                                                   11

SEQ ID NO: 377          moltype = RNA  length = 11
FEATURE                 Location/Qualifiers
source                  1..11
                        mol_type = other RNA
                        organism = synthetic construct
SEQUENCE: 377
```

-continued

```
aatttgtcga g                                                    11

SEQ ID NO: 378          moltype = RNA   length = 11
FEATURE                 Location/Qualifiers
source                  1..11
                        mol_type = other RNA
                        organism = synthetic construct SEQUENCE: 378
aattgttgga a                                                    11

SEQ ID NO: 379          moltype = RNA   length = 11
FEATURE                 Location/Qualifiers
source                  1..11
                        mol_type = other RNA
                        organism = synthetic construct SEQUENCE: 379
tgtttttgga g                                                    11

SEQ ID NO: 380          moltype = RNA   length = 11
FEATURE                 Location/Qualifiers
source                  1..11
                        mol_type = other RNA
                        organism = synthetic construct SEQUENCE: 380
aaatttagga g                                                    11

SEQ ID NO: 381          moltype = RNA   length = 11
FEATURE                 Location/Qualifiers
source                  1..11
                        mol_type = other RNA
                        organism = synthetic construct SEQUENCE: 381
aatttttgt g                                                     11

SEQ ID NO: 382          moltype = RNA   length = 11
FEATURE                 Location/Qualifiers
source                  1..11
                        mol_type = other RNA
                        organism = synthetic construct SEQUENCE: 382
cattcttgga g                                                    11

SEQ ID NO: 383          moltype = RNA   length = 11
FEATURE                 Location/Qualifiers
source                  1..11
                        mol_type = other RNA
                        organism = synthetic construct SEQUENCE: 383
aattctcgga g                                                    11

SEQ ID NO: 384          moltype = RNA   length = 11
FEATURE                 Location/Qualifiers
source                  1..11
                        mol_type = other RNA
                        organism = synthetic construct SEQUENCE: 384
aatttttata g                                                    11

SEQ ID NO: 385          moltype = RNA   length = 11
FEATURE                 Location/Qualifiers
source                  1..11
                        mol_type = other RNA
                        organism = synthetic construct SEQUENCE: 385
actttttaga g                                                    11

SEQ ID NO: 386          moltype = RNA   length = 11
FEATURE                 Location/Qualifiers
source                  1..11
                        mol_type = other RNA
                        organism = synthetic construct SEQUENCE: 386
aattgttaga g                                                    11

SEQ ID NO: 387          moltype = RNA   length = 11
FEATURE                 Location/Qualifiers
source                  1..11
                        mol_type = other RNA
                        organism = synthetic construct
```

-continued

```
SEQUENCE: 387
cgtttttgga g                                                                    11

SEQ ID NO: 388           moltype = RNA   length = 11
FEATURE                  Location/Qualifiers
source                   1..11
                         mol_type = other RNA
                         organism = synthetic construct SEQUENCE: 388
aatttttgcg g                                                                    11

SEQ ID NO: 389           moltype = RNA   length = 11
FEATURE                  Location/Qualifiers
source                   1..11
                         mol_type = other RNA
                         organism = synthetic construct SEQUENCE: 389
aagtttttgaa g                                                                   11

SEQ ID NO: 390           moltype = RNA   length = 11
FEATURE                  Location/Qualifiers
source                   1..11
                         mol_type = other RNA
                         organism = synthetic construct SEQUENCE: 390
aattttcgga a                                                                    11

SEQ ID NO: 391           moltype = RNA   length = 11
FEATURE                  Location/Qualifiers
source                   1..11
                         mol_type = other RNA
                         organism = synthetic construct SEQUENCE: 391
aatttttcca g                                                                    11

SEQ ID NO: 392           moltype = RNA   length = 11
FEATURE                  Location/Qualifiers
source                   1..11
                         mol_type = other RNA
                         organism = synthetic construct SEQUENCE: 392
attttttgta g                                                                    11

SEQ ID NO: 393           moltype = RNA   length = 11
FEATURE                  Location/Qualifiers
source                   1..11
                         mol_type = other RNA
                         organism = synthetic construct SEQUENCE: 393
aatctttaga g                                                                    11

SEQ ID NO: 394           moltype = RNA   length = 11
FEATURE                  Location/Qualifiers
source                   1..11
                         mol_type = other RNA
                         organism = synthetic construct SEQUENCE: 394
aattttacga g                                                                    11

SEQ ID NO: 395           moltype = RNA   length = 11
FEATURE                  Location/Qualifiers
source                   1..11
                         mol_type = other RNA
                         organism = synthetic construct SEQUENCE: 395
catttttggc g                                                                    11

SEQ ID NO: 396           moltype = RNA   length = 11
FEATURE                  Location/Qualifiers
source                   1..11
                         mol_type = other RNA
                         organism = synthetic construct SEQUENCE: 396
aatttgcgga g                                                                    11

SEQ ID NO: 397           moltype = RNA   length = 11
FEATURE                  Location/Qualifiers
source                   1..11
                         mol_type = other RNA
```

```
                        organism = synthetic construct
SEQUENCE: 397
catctttgga g                                                    11

SEQ ID NO: 398          moltype = RNA   length = 11
FEATURE                 Location/Qualifiers
source                  1..11
                        mol_type = other RNA
                        organism = synthetic construct
SEQUENCE: 398
aacttttgaa g                                                    11

SEQ ID NO: 399          moltype = RNA   length = 11
FEATURE                 Location/Qualifiers
source                  1..11
                        mol_type = other RNA
                        organism = synthetic construct
SEQUENCE: 399
aatttttcta g                                                    11

SEQ ID NO: 400          moltype = RNA   length = 33
FEATURE                 Location/Qualifiers
source                  1..33
                        mol_type = other RNA
                        organism = synthetic construct
SEQUENCE: 400
caggtttttcc agtgttcact gaaatttgtc tct                           33

SEQ ID NO: 401          moltype = RNA   length = 31
FEATURE                 Location/Qualifiers
source                  1..31
                        mol_type = other RNA
                        organism = synthetic construct
SEQUENCE: 401
aaggtttttct ggtctttatc agaaagcctc c                             31

SEQ ID NO: 402          moltype = RNA   length = 31
FEATURE                 Location/Qualifiers
source                  1..31
                        mol_type = other RNA
                        organism = synthetic construct
SEQUENCE: 402
caggtttttct ggttttcact gcaaaacccc a                             31

SEQ ID NO: 403          moltype = RNA   length = 31
FEATURE                 Location/Qualifiers
source                  1..31
                        mol_type = other RNA
                        organism = synthetic construct
SEQUENCE: 403
cagactttac ggtgcttacc agaaagctcc c                              31

SEQ ID NO: 404          moltype = RNA   length = 45
FEATURE                 Location/Qualifiers
source                  1..45
                        mol_type = other RNA
                        organism = synthetic construct
SEQUENCE: 404
cacgttttcc ggttgtcact cccaggtagg ctggggaaga ggcat               45

SEQ ID NO: 405          moltype = RNA   length = 31
FEATURE                 Location/Qualifiers
source                  1..31
                        mol_type = other RNA
                        organism = synthetic construct
SEQUENCE: 405
cagtctttcc agtttttgcc ggaaagcccc t                              31

SEQ ID NO: 406          moltype = RNA   length = 31
FEATURE                 Location/Qualifiers
source                  1..31
                        mol_type = other RNA
                        organism = synthetic construct
SEQUENCE: 406
caggctttct ggtttttgcc agaaagcccc c                              31

SEQ ID NO: 407          moltype = RNA   length = 31
FEATURE                 Location/Qualifiers
source                  1..31
```

-continued

```
                          mol_type = other RNA
                          organism = synthetic construct
SEQUENCE: 407
caggttttc agttttcacc agaatgccca c                              31

SEQ ID NO: 408          moltype = RNA   length = 31
FEATURE                 Location/Qualifiers
source                  1..31
                        mol_type = other RNA
                        organism = synthetic construct
SEQUENCE: 408
caggtttct ggtctttact ggaaagccca a                              31

SEQ ID NO: 409          moltype = RNA   length = 31
FEATURE                 Location/Qualifiers
source                  1..31
                        mol_type = other RNA
                        organism = synthetic construct
SEQUENCE: 409
caggctttcc ggttttacc agaaagcccc c                              31

SEQ ID NO: 410          moltype = RNA   length = 31
FEATURE                 Location/Qualifiers
source                  1..31
                        mol_type = other RNA
                        organism = synthetic construct
SEQUENCE: 410
caggttttc ggttttact ggaaagcccc a                               31

SEQ ID NO: 411          moltype = RNA   length = 31
FEATURE                 Location/Qualifiers
source                  1..31
                        mol_type = other RNA
                        organism = synthetic construct
SEQUENCE: 411
caggctttcc agtaaataca ggaaagccct c                             31

SEQ ID NO: 412          moltype = RNA   length = 31
FEATURE                 Location/Qualifiers
source                  1..31
                        mol_type = other RNA
                        organism = synthetic construct
SEQUENCE: 412
caggctttcc ggtttttgct ggaaagactc c                             31

SEQ ID NO: 413          moltype = RNA   length = 31
FEATURE                 Location/Qualifiers
source                  1..31
                        mol_type = other RNA
                        organism = synthetic construct
SEQUENCE: 413
aaggtttct ggtctttact gaaaagcccc a                              31

SEQ ID NO: 414          moltype = RNA   length = 31
FEATURE                 Location/Qualifiers
source                  1..31
                        mol_type = other RNA
                        organism = synthetic construct
SEQUENCE: 414
tgggctttct gttttttacg agaaagtcct c                             31

SEQ ID NO: 415          moltype = RNA   length = 30
FEATURE                 Location/Qualifiers
source                  1..30
                        mol_type = other RNA
                        organism = synthetic construct
SEQUENCE: 415
cagatttctc agttttcact ggaaaccctt                               30

SEQ ID NO: 416          moltype = RNA   length = 31
FEATURE                 Location/Qualifiers
source                  1..31
                        mol_type = other RNA
                        organism = synthetic construct
SEQUENCE: 416
caggttttcc tgtcttcacc ggaactcccc a                             31

SEQ ID NO: 417          moltype = RNA   length = 32
FEATURE                 Location/Qualifiers
```

-continued

```
source                   1..32
                         mol_type = other RNA
                         organism = synthetic construct
SEQUENCE: 417
caggttttct ggtttgcact agaaaaacca ta                                        32

SEQ ID NO: 418           moltype = RNA  length = 31
FEATURE                  Location/Qualifiers
source                   1..31
                         mol_type = other RNA
                         organism = synthetic construct
SEQUENCE: 418
cagatttttct ggttttttacc agaaaattta a                                       31

SEQ ID NO: 419           moltype = RNA  length = 31
FEATURE                  Location/Qualifiers
source                   1..31
                         mol_type = other RNA
                         organism = synthetic construct
SEQUENCE: 419
caggtcttct tgttttttact ggaaaatcct c                                        31

SEQ ID NO: 420           moltype = RNA  length = 31
FEATURE                  Location/Qualifiers
source                   1..31
                         mol_type = other RNA
                         organism = synthetic construct
SEQUENCE: 420
caggtttttcc ggtcttcacc agaaaacccc t                                        31

SEQ ID NO: 421           moltype = RNA  length = 31
FEATURE                  Location/Qualifiers
source                   1..31
                         mol_type = other RNA
                         organism = synthetic construct
SEQUENCE: 421
caggtttttcc gatttttact ggaaagccct t                                        31

SEQ ID NO: 422           moltype = RNA  length = 29
FEATURE                  Location/Qualifiers
source                   1..29
                         mol_type = other RNA
                         organism = synthetic construct
SEQUENCE: 422
caggtttttct ggttttccag aaaacctcc                                           29

SEQ ID NO: 423           moltype = RNA  length = 29
FEATURE                  Location/Qualifiers
source                   1..29
                         mol_type = other RNA
                         organism = synthetic construct
SEQUENCE: 423
caggtttttcc agttttcact ggaacctct                                           29

SEQ ID NO: 424           moltype = RNA  length = 30
FEATURE                  Location/Qualifiers
source                   1..30
                         mol_type = other RNA
                         organism = synthetic construct
SEQUENCE: 424
ccggcttttcc agttttgccg gaaagccccc                                          30

SEQ ID NO: 425           moltype = RNA  length = 29
FEATURE                  Location/Qualifiers
source                   1..29
                         mol_type = other RNA
                         organism = synthetic construct
SEQUENCE: 425
caggtttttct ggttttttacc agaacttaa                                          29

SEQ ID NO: 426           moltype = RNA  length = 45
FEATURE                  Location/Qualifiers
source                   1..45
                         mol_type = other RNA
                         organism = synthetic construct
SEQUENCE: 426
cacgtttttcc ggttgtcact cccaggtggg ctcgggaaga ggcat                         45

SEQ ID NO: 427           moltype = RNA  length = 31
```

-continued

```
FEATURE               Location/Qualifiers
source                1..31
                      mol_type = other RNA
                      organism = synthetic construct
SEQUENCE: 427
caggctttcc ggtctttacc ggaaagccta t                             31

SEQ ID NO: 428        moltype = RNA   length = 31
FEATURE               Location/Qualifiers
source                1..31
                      mol_type = other RNA
                      organism = synthetic construct
SEQUENCE: 428
caggctttct ggtttttgcc ggaaagccct c                             31

SEQ ID NO: 429        moltype = RNA   length = 31
FEATURE               Location/Qualifiers
source                1..31
                      mol_type = other RNA
                      organism = synthetic construct
SEQUENCE: 429
caggctttca ggtctttgcc agaaagcccc a                             31

SEQ ID NO: 430        moltype = RNA   length = 30
FEATURE               Location/Qualifiers
source                1..30
                      mol_type = other RNA
                      organism = synthetic construct
SEQUENCE: 430
caggctttct tgttttcact ggaagcctcc                               30

SEQ ID NO: 431        moltype = RNA   length = 31
FEATURE               Location/Qualifiers
source                1..31
                      mol_type = other RNA
                      organism = synthetic construct
SEQUENCE: 431
caggtttttc agtcttcacc ggaaagctcc c                             31

SEQ ID NO: 432        moltype = RNA   length = 37
FEATURE               Location/Qualifiers
source                1..37
                      mol_type = other RNA
                      organism = synthetic construct
SEQUENCE: 432
cagattttct ggtttttcacc acgaaagaaa tgtcatt                      37

SEQ ID NO: 433        moltype = RNA   length = 30
FEATURE               Location/Qualifiers
source                1..30
                      mol_type = other RNA
                      organism = synthetic construct
SEQUENCE: 433
cagttctcct ggattttaca ggaaaacccc                               30

SEQ ID NO: 434        moltype = RNA   length = 31
FEATURE               Location/Qualifiers
source                1..31
                      mol_type = other RNA
                      organism = synthetic construct
SEQUENCE: 434
caggctttct ggcatttgcc agaaagccct g                             31

SEQ ID NO: 435        moltype = RNA   length = 31
FEATURE               Location/Qualifiers
source                1..31
                      mol_type = other RNA
                      organism = synthetic construct
SEQUENCE: 435
cagactttcc tgtttttaac agaaagcccc c                             31

SEQ ID NO: 436        moltype = RNA   length = 31
FEATURE               Location/Qualifiers
source                1..31
                      mol_type = other RNA
                      organism = synthetic construct
SEQUENCE: 436
caggctttcc ggtttttgct ggaaagctcc c                             31
```

```
SEQ ID NO: 437          moltype = RNA   length = 28
FEATURE                 Location/Qualifiers
source                  1..28
                        mol_type = other RNA
                        organism = synthetic construct
SEQUENCE: 437
cagcttttcc agttttcact gaggtaaa                                      28

SEQ ID NO: 438          moltype = RNA   length = 31
FEATURE                 Location/Qualifiers
source                  1..31
                        mol_type = other RNA
                        organism = synthetic construct
SEQUENCE: 438
taggttttct ggtttttatt gggaaatcac a                                  31

SEQ ID NO: 439          moltype = RNA   length = 32
FEATURE                 Location/Qualifiers
source                  1..32
                        mol_type = other RNA
                        organism = synthetic construct
SEQUENCE: 439
cagggtttct ggtggtacca gcagactcca ca                                 32

SEQ ID NO: 440          moltype = RNA   length = 30
FEATURE                 Location/Qualifiers
source                  1..30
                        mol_type = other RNA
                        organism = synthetic construct
SEQUENCE: 440
caagtttccc agttttcact ggaacctccg                                    30

SEQ ID NO: 441          moltype = RNA   length = 31
FEATURE                 Location/Qualifiers
source                  1..31
                        mol_type = other RNA
                        organism = synthetic construct
SEQUENCE: 441
cagattttcc agtttttact agaaaccccc c                                  31

SEQ ID NO: 442          moltype = RNA   length = 31
FEATURE                 Location/Qualifiers
source                  1..31
                        mol_type = other RNA
                        organism = synthetic construct
SEQUENCE: 442
cagggtttcc agttttcact gtataccatc c                                  31

SEQ ID NO: 443          moltype = RNA   length = 31
FEATURE                 Location/Qualifiers
source                  1..31
                        mol_type = other RNA
                        organism = synthetic construct
SEQUENCE: 443
caagttctct ggtcttcact ggaaaaccca t                                  31

SEQ ID NO: 444          moltype = RNA   length = 31
FEATURE                 Location/Qualifiers
source                  1..31
                        mol_type = other RNA
                        organism = synthetic construct
SEQUENCE: 444
tagattttct ggtctttacc agaaagactc c                                  31

SEQ ID NO: 445          moltype = RNA   length = 32
FEATURE                 Location/Qualifiers
source                  1..32
                        mol_type = other RNA
                        organism = synthetic construct
SEQUENCE: 445
gcaggttttc tggtttttat tggaaaacct tc                                 32

SEQ ID NO: 446          moltype = RNA   length = 33
FEATURE                 Location/Qualifiers
source                  1..33
                        mol_type = other RNA
                        organism = synthetic construct
SEQUENCE: 446
caggtttttc acttttcacc agaaactgcc tct                                33
```

-continued

```
SEQ ID NO: 447          moltype = RNA   length = 31
FEATURE                 Location/Qualifiers
source                  1..31
                        mol_type = other RNA
                        organism = synthetic construct
SEQUENCE: 447
taggctttcc ggtttttgca ggaaagcccc c                                 31

SEQ ID NO: 448          moltype = RNA   length = 31
FEATURE                 Location/Qualifiers
source                  1..31
                        mol_type = other RNA
                        organism = synthetic construct
SEQUENCE: 448
caggtttttcc agtctttacc agaaagccac t                                31

SEQ ID NO: 449          moltype = RNA   length = 33
FEATURE                 Location/Qualifiers
source                  1..33
                        mol_type = other RNA
                        organism = synthetic construct
SEQUENCE: 449
caggtttttt ggtcttcaca ggaaacttcc cct                               33

SEQ ID NO: 450          moltype = RNA   length = 31
FEATURE                 Location/Qualifiers
source                  1..31
                        mol_type = other RNA
                        organism = synthetic construct
SEQUENCE: 450
caggtttttct gcttttcact ggaagactcc c                                31

SEQ ID NO: 451          moltype = RNA   length = 31
FEATURE                 Location/Qualifiers
source                  1..31
                        mol_type = other RNA
                        organism = synthetic construct
SEQUENCE: 451
cagactttcc agtttttgcc agaaagcccca c                                31

SEQ ID NO: 452          moltype = RNA   length = 31
FEATURE                 Location/Qualifiers
source                  1..31
                        mol_type = other RNA
                        organism = synthetic construct
SEQUENCE: 452
caggctttct ggtttttgcc caaaagcctc t                                 31

SEQ ID NO: 453          moltype = RNA   length = 31
FEATURE                 Location/Qualifiers
source                  1..31
                        mol_type = other RNA
                        organism = synthetic construct
SEQUENCE: 453
caggtttttcc aatcttcact gaaaagcttt a                                31

SEQ ID NO: 454          moltype = RNA   length = 31
FEATURE                 Location/Qualifiers
source                  1..31
                        mol_type = other RNA
                        organism = synthetic construct
SEQUENCE: 454
ctggttccta gtcttcactg gaagcaccct c                                 31

SEQ ID NO: 455          moltype = RNA   length = 29
FEATURE                 Location/Qualifiers
source                  1..29
                        mol_type = other RNA
                        organism = synthetic construct
SEQUENCE: 455
ggctttccgc tcttcattgg aaagcccat                                    29

SEQ ID NO: 456          moltype = RNA   length = 31
FEATURE                 Location/Qualifiers
source                  1..31
                        mol_type = other RNA
                        organism = synthetic construct
SEQUENCE: 456
```

-continued

```
caggtttttc agtttttagc agaaaacctc c                              31

SEQ ID NO: 457            moltype = RNA   length = 29
FEATURE                   Location/Qualifiers
source                    1..29
                          mol_type = other RNA
                          organism = synthetic construct
SEQUENCE: 457
caggttctct ggtttttact gaaaccaaa                                 29

SEQ ID NO: 458            moltype = RNA   length = 31
FEATURE                   Location/Qualifiers
source                    1..31
                          mol_type = other RNA
                          organism = synthetic construct
SEQUENCE: 458
caggtttttcc agtcttcact ggaaagccct t                             31

SEQ ID NO: 459            moltype = RNA   length = 31
FEATURE                   Location/Qualifiers
source                    1..31
                          mol_type = other RNA
                          organism = synthetic construct
SEQUENCE: 459
caggctttct ggtttttgcc ggaaggcctc c                              31

SEQ ID NO: 460            moltype = RNA   length = 32
FEATURE                   Location/Qualifiers
source                    1..32
                          mol_type = other RNA
                          organism = synthetic construct
SEQUENCE: 460
caggtttttct gttttttaac tagaaaactc cc                            32

SEQ ID NO: 461            moltype = RNA   length = 31
FEATURE                   Location/Qualifiers
source                    1..31
                          mol_type = other RNA
                          organism = synthetic construct
SEQUENCE: 461
taggctttct ggtttttgct ggaaagcccc c                              31

SEQ ID NO: 462            moltype = RNA   length = 32
FEATURE                   Location/Qualifiers
source                    1..32
                          mol_type = other RNA
                          organism = synthetic construct
SEQUENCE: 462
caggtttccc ggtttttacc agaaaaatct aa                             32

SEQ ID NO: 463            moltype = RNA   length = 32
FEATURE                   Location/Qualifiers
source                    1..32
                          mol_type = other RNA
                          organism = synthetic construct
SEQUENCE: 463
caggtttttcc agtctttacc agaaatgccc cc                            32

SEQ ID NO: 464            moltype = RNA   length = 30
FEATURE                   Location/Qualifiers
source                    1..30
                          mol_type = other RNA
                          organism = synthetic construct
SEQUENCE: 464
ggtttttctgg tcatcgctgg aaacaccctc                               30

SEQ ID NO: 465            moltype = RNA   length = 31
FEATURE                   Location/Qualifiers
source                    1..31
                          mol_type = other RNA
                          organism = synthetic construct
SEQUENCE: 465
caacctttct ggtttttgct agaaagttct c                              31

SEQ ID NO: 466            moltype = RNA   length = 31
FEATURE                   Location/Qualifiers
source                    1..31
                          mol_type = other RNA
                          organism = synthetic construct
```

-continued

```
SEQUENCE: 466
caggcctttg ggtctttact ggaaaacccc t                                         31

SEQ ID NO: 467        moltype = RNA   length = 35
FEATURE               Location/Qualifiers
source                1..35
                      mol_type = other RNA
                      organism = synthetic construct
SEQUENCE: 467
tatgttttcc ggttttcact cccaggtagg ctcgg                                     35

SEQ ID NO: 468        moltype = RNA   length = 31
FEATURE               Location/Qualifiers
source                1..31
                      mol_type = other RNA
                      organism = synthetic construct
SEQUENCE: 468
caaattttct ggcttttcca ggaaaatccc c                                         31

SEQ ID NO: 469        moltype = RNA   length = 28
FEATURE               Location/Qualifiers
source                1..28
                      mol_type = other RNA
                      organism = synthetic construct
SEQUENCE: 469
taggttttcc agtgaccaga aaatcctc                                             28

SEQ ID NO: 470        moltype = RNA   length = 31
FEATURE               Location/Qualifiers
source                1..31
                      mol_type = other RNA
                      organism = synthetic construct
SEQUENCE: 470
caggtcttcg ggtttttaac tggaaacctt c                                         31

SEQ ID NO: 471        moltype = RNA   length = 32
FEATURE               Location/Qualifiers
source                1..32
                      mol_type = other RNA
                      organism = synthetic construct
SEQUENCE: 471
gcaggctttc cagttttttc tggaaagcct ca                                        32

SEQ ID NO: 472        moltype = RNA   length = 29
FEATURE               Location/Qualifiers
source                1..29
                      mol_type = other RNA
                      organism = synthetic construct
SEQUENCE: 472
ggctttctgg tttttactgg aaagccccc                                            29

SEQ ID NO: 473        moltype = RNA   length = 31
FEATURE               Location/Qualifiers
source                1..31
                      mol_type = other RNA
                      organism = synthetic construct
SEQUENCE: 473
caggtttccc agtattcacc ggaaagctcc a                                         31

SEQ ID NO: 474        moltype = RNA   length = 43
FEATURE               Location/Qualifiers
source                1..43
                      mol_type = other RNA
                      organism = synthetic construct
SEQUENCE: 474
caggctttct agttttccca cactaagaaa caaaaaaacc tgt                            43

SEQ ID NO: 475        moltype = RNA   length = 32
FEATURE               Location/Qualifiers
source                1..32
                      mol_type = other RNA
                      organism = synthetic construct
SEQUENCE: 475
gcaagctttc tggttttggc caaaaagcca cc                                        32

SEQ ID NO: 476        moltype = RNA   length = 24
FEATURE               Location/Qualifiers
source                1..24
                      mol_type = other RNA
```

-continued

```
                              organism = synthetic construct
SEQUENCE: 476
ttctggtttt caccagaaac cact                                              24

SEQ ID NO: 477           moltype = RNA   length = 32
FEATURE                  Location/Qualifiers
source                   1..32
                         mol_type = other RNA
                         organism = synthetic construct
SEQUENCE: 477
gcaagttttc tagcctgtac ctgaaagcct ca                                     32

SEQ ID NO: 478           moltype = RNA   length = 30
FEATURE                  Location/Qualifiers
source                   1..30
                         mol_type = other RNA
                         organism = synthetic construct
SEQUENCE: 478
aagttttctt gtttttacca gaaaactcct                                        30

SEQ ID NO: 479           moltype = RNA   length = 29
FEATURE                  Location/Qualifiers
source                   1..29
                         mol_type = other RNA
                         organism = synthetic construct
SEQUENCE: 479
ggctttccaa tttttgccag aaagccccc                                         29

SEQ ID NO: 480           moltype = RNA   length = 33
FEATURE                  Location/Qualifiers
source                   1..33
                         mol_type = other RNA
                         organism = synthetic construct
SEQUENCE: 480
agctggtttt ctggttttca ccggaagacc cat                                    33

SEQ ID NO: 481           moltype = RNA   length = 32
FEATURE                  Location/Qualifiers
source                   1..32
                         mol_type = other RNA
                         organism = synthetic construct
SEQUENCE: 481
caggccttct ggtttttgct gggaagtccc ca                                     32

SEQ ID NO: 482           moltype = RNA   length = 31
FEATURE                  Location/Qualifiers
source                   1..31
                         mol_type = other RNA
                         organism = synthetic construct
SEQUENCE: 482
caggttttcc agtttgtacc agaaaacccc t                                      31

SEQ ID NO: 483           moltype = RNA   length = 22
FEATURE                  Location/Qualifiers
source                   1..22
                         mol_type = other RNA
                         organism = synthetic construct
SEQUENCE: 483
caggtttcac ccaaaaaccc ac                                                22

SEQ ID NO: 484           moltype = RNA   length = 32
FEATURE                  Location/Qualifiers
source                   1..32
                         mol_type = other RNA
                         organism = synthetic construct
SEQUENCE: 484
taggctttct ggcttttta cggaaagccc ct                                      32

SEQ ID NO: 485           moltype = RNA   length = 31
FEATURE                  Location/Qualifiers
source                   1..31
                         mol_type = other RNA
                         organism = synthetic construct
SEQUENCE: 485
cagggtttct ggttttcacc aggaaacaaa a                                      31

SEQ ID NO: 486           moltype = RNA   length = 31
FEATURE                  Location/Qualifiers
source                   1..31
```

-continued

```
                                  mol_type = other RNA
                                  organism = synthetic construct
SEQUENCE: 486
caggtttttcc tgtctttact agaaacccct c                                               31

SEQ ID NO: 487          moltype = RNA   length = 31
FEATURE                 Location/Qualifiers
source                  1..31
                        mol_type = other RNA
                        organism = synthetic construct
SEQUENCE: 487
caggtttttat aggtttttacc agaaaacttc c                                              31

SEQ ID NO: 488          moltype = RNA   length = 31
FEATURE                 Location/Qualifiers
source                  1..31
                        mol_type = other RNA
                        organism = synthetic construct
SEQUENCE: 488
caggcttccc aattttttgct ggaaagcccc t                                               31

SEQ ID NO: 489          moltype = RNA   length = 31
FEATURE                 Location/Qualifiers
source                  1..31
                        mol_type = other RNA
                        organism = synthetic construct
SEQUENCE: 489
caggcttttt gggttaggtc agaaagtccc c                                                31

SEQ ID NO: 490          moltype = RNA   length = 29
FEATURE                 Location/Qualifiers
source                  1..29
                        mol_type = other RNA
                        organism = synthetic construct
SEQUENCE: 490
caggtttttg gttttttagc gaaaccctc                                                   29

SEQ ID NO: 491          moltype = RNA   length = 33
FEATURE                 Location/Qualifiers
source                  1..33
                        mol_type = other RNA
                        organism = synthetic construct
SEQUENCE: 491
caggcttttct ggttttcacc ataaaatgcc cca                                             33

SEQ ID NO: 492          moltype = RNA   length = 43
FEATURE                 Location/Qualifiers
source                  1..43
                        mol_type = other RNA
                        organism = synthetic construct
SEQUENCE: 492
caggtcttcg gggtttttaca aaaagaagaa gaaatccacc ccc                                  43

SEQ ID NO: 493          moltype = RNA   length = 32
FEATURE                 Location/Qualifiers
source                  1..32
                        mol_type = other RNA
                        organism = synthetic construct
SEQUENCE: 493
caagttctct ggtctcccaa caagaaaccc cc                                               32

SEQ ID NO: 494          moltype = RNA   length = 33
FEATURE                 Location/Qualifiers
source                  1..33
                        mol_type = other RNA
                        organism = synthetic construct
SEQUENCE: 494
caggatttct ggtttctggt ggaaagctcc cat                                              33

SEQ ID NO: 495          moltype = RNA   length = 30
FEATURE                 Location/Qualifiers
source                  1..30
                        mol_type = other RNA
                        organism = synthetic construct
SEQUENCE: 495
aggctttcca gttttttgctg gaaagcccct                                                 30

SEQ ID NO: 496          moltype = RNA   length = 30
FEATURE                 Location/Qualifiers
```

-continued

```
source                    1..30
                          mol_type = other RNA
                          organism = synthetic construct
SEQUENCE: 496
caggttttcc agtctttgtc aaatgccttc                                          30

SEQ ID NO: 497            moltype = RNA   length = 34
FEATURE                   Location/Qualifiers
source                    1..34
                          mol_type = other RNA
                          organism = synthetic construct
SEQUENCE: 497
caggctttcc agtttttgcc agtgtgaacc caaa                                     34

SEQ ID NO: 498            moltype = RNA   length = 31
FEATURE                   Location/Qualifiers
source                    1..31
                          mol_type = other RNA
                          organism = synthetic construct
SEQUENCE: 498
caggctttct ggtttttatc agaaagcctc c                                        31

SEQ ID NO: 499            moltype = RNA   length = 33
FEATURE                   Location/Qualifiers
source                    1..33
                          mol_type = other RNA
                          organism = synthetic construct
SEQUENCE: 499
gaggttttct ggttttcacc agaaccaacc ctt                                      33

SEQ ID NO: 500            moltype = RNA   length = 31
FEATURE                   Location/Qualifiers
source                    1..31
                          mol_type = other RNA
                          organism = synthetic construct
SEQUENCE: 500
cagattttcc agcttttact ggaagccccc t                                        31

SEQ ID NO: 501            moltype = RNA   length = 33
FEATURE                   Location/Qualifiers
source                    1..33
                          mol_type = other RNA
                          organism = synthetic construct
SEQUENCE: 501
caggttttct ggttttcact ggaaaatacc tca                                      33

SEQ ID NO: 502            moltype = RNA   length = 33
FEATURE                   Location/Qualifiers
source                    1..33
                          mol_type = other RNA
                          organism = synthetic construct
SEQUENCE: 502
catgtttttt ggtgttaata aaaacccgca cac                                      33

SEQ ID NO: 503            moltype = RNA   length = 31
FEATURE                   Location/Qualifiers
source                    1..31
                          mol_type = other RNA
                          organism = synthetic construct
SEQUENCE: 503
aaggctttcc ggtttttgca ggaaagcaac c                                        31

SEQ ID NO: 504            moltype = RNA   length = 30
FEATURE                   Location/Qualifiers
source                    1..30
                          mol_type = other RNA
                          organism = synthetic construct
SEQUENCE: 504
agtctttccg ggttttgtca gaaaggccct                                          30

SEQ ID NO: 505            moltype = RNA   length = 31
FEATURE                   Location/Qualifiers
source                    1..31
                          mol_type = other RNA
                          organism = synthetic construct
SEQUENCE: 505
gcaggttttc tggtttctac tggaagcttc t                                        31

SEQ ID NO: 506            moltype = RNA   length = 31
```

-continued

```
FEATURE             Location/Qualifiers
source              1..31
                    mol_type = other RNA
                    organism = synthetic construct
SEQUENCE: 506
caggctttct ggttttttact ggaaagcccc t                                   31

SEQ ID NO: 507      moltype = RNA   length = 31
FEATURE             Location/Qualifiers
source              1..31
                    mol_type = other RNA
                    organism = synthetic construct
SEQUENCE: 507
caggctttcc aatttttgcc agaaagctcc c                                    31

SEQ ID NO: 508      moltype = RNA   length = 31
FEATURE             Location/Qualifiers
source              1..31
                    mol_type = other RNA
                    organism = synthetic construct
SEQUENCE: 508
caggtttttct ggttctcacc agaaaacgcc a                                   31

SEQ ID NO: 509      moltype = RNA   length = 31
FEATURE             Location/Qualifiers
source              1..31
                    mol_type = other RNA
                    organism = synthetic construct
SEQUENCE: 509
caggtttttct ggtcttcact ggaagaccac t                                   31

SEQ ID NO: 510      moltype = RNA   length = 34
FEATURE             Location/Qualifiers
source              1..34
                    mol_type = other RNA
                    organism = synthetic construct
SEQUENCE: 510
caggtggttt tccggtcttt accagtaagc cccc                                 34

SEQ ID NO: 511      moltype = RNA   length = 31
FEATURE             Location/Qualifiers
source              1..31
                    mol_type = other RNA
                    organism = synthetic construct
SEQUENCE: 511
caggtttttcc agtttctacc agaaacccct a                                   31

SEQ ID NO: 512      moltype = RNA   length = 32
FEATURE             Location/Qualifiers
source              1..32
                    mol_type = other RNA
                    organism = synthetic construct
SEQUENCE: 512
caggtttttct ggtctttacc agaaaagtct cc                                  32

SEQ ID NO: 513      moltype = RNA   length = 32
FEATURE             Location/Qualifiers
source              1..32
                    mol_type = other RNA
                    organism = synthetic construct
SEQUENCE: 513
ccaggctttc tggttttttac cggaaagccc cg                                  32

SEQ ID NO: 514      moltype = RNA   length = 32
FEATURE             Location/Qualifiers
source              1..32
                    mol_type = other RNA
                    organism = synthetic construct
SEQUENCE: 514
caggtttttc actttttact agaaaaacca gt                                   32

SEQ ID NO: 515      moltype = RNA   length = 35
FEATURE             Location/Qualifiers
source              1..35
                    mol_type = other RNA
                    organism = synthetic construct
SEQUENCE: 515
taggctttct gggaggtctt taccagaaag cctcc                                35
```

-continued

```
SEQ ID NO: 516            moltype = RNA   length = 32
FEATURE                   Location/Qualifiers
source                    1..32
                          mol_type = other RNA
                          organism = synthetic construct
SEQUENCE: 516
tacattttcc agttttcacc aggaatctgc ct                              32

SEQ ID NO: 517            moltype = RNA   length = 31
FEATURE                   Location/Qualifiers
source                    1..31
                          mol_type = other RNA
                          organism = synthetic construct
SEQUENCE: 517
taggttttcc agttttcacc agaaaatccc g                               31

SEQ ID NO: 518            moltype = RNA   length = 31
FEATURE                   Location/Qualifiers
source                    1..31
                          mol_type = other RNA
                          organism = synthetic construct
SEQUENCE: 518
caggttttct ggttttacg agactccccc a                                31

SEQ ID NO: 519            moltype = RNA   length = 30
FEATURE                   Location/Qualifiers
source                    1..30
                          mol_type = other RNA
                          organism = synthetic construct
SEQUENCE: 519
caggctttct gttttttgct aaaatcctcc                                 30

SEQ ID NO: 520            moltype = RNA   length = 32
FEATURE                   Location/Qualifiers
source                    1..32
                          mol_type = other RNA
                          organism = synthetic construct
SEQUENCE: 520
ctgggcgtac tggctcacgc ctataatccc aa                              32

SEQ ID NO: 521            moltype = RNA   length = 29
FEATURE                   Location/Qualifiers
source                    1..29
                          mol_type = other RNA
                          organism = synthetic construct
SEQUENCE: 521
ggctctccgg tttttgccag aatgcccac                                  29

SEQ ID NO: 522            moltype = RNA   length = 31
FEATURE                   Location/Qualifiers
source                    1..31
                          mol_type = other RNA
                          organism = synthetic construct
SEQUENCE: 522
tgggtttct ggtgaaaact agactgcccc c                                31

SEQ ID NO: 523            moltype = RNA   length = 31
FEATURE                   Location/Qualifiers
source                    1..31
                          mol_type = other RNA
                          organism = synthetic construct
SEQUENCE: 523
caggctttct ggttttaca ggaaggcccc t                                31

SEQ ID NO: 524            moltype = RNA   length = 29
FEATURE                   Location/Qualifiers
source                    1..29
                          mol_type = other RNA
                          organism = synthetic construct
SEQUENCE: 524
ggttttctgg ttctcactgg aaaacccc                                   29

SEQ ID NO: 525            moltype = RNA   length = 31
FEATURE                   Location/Qualifiers
source                    1..31
                          mol_type = other RNA
                          organism = synthetic construct
SEQUENCE: 525
caggctttcc ggtaaagact ggaaagcccc t                               31
```

```
SEQ ID NO: 526            moltype = RNA  length = 31
FEATURE                   Location/Qualifiers
source                    1..31
                          mol_type = other RNA
                          organism = synthetic construct
SEQUENCE: 526
caggttttcc agtttttacc agaaaactct c                                      31

SEQ ID NO: 527            moltype = RNA  length = 31
FEATURE                   Location/Qualifiers
source                    1..31
                          mol_type = other RNA
                          organism = synthetic construct
SEQUENCE: 527
aaggttttct ggtcttcact ggaagaccac t                                      31

SEQ ID NO: 528            moltype = RNA  length = 31
FEATURE                   Location/Qualifiers
source                    1..31
                          mol_type = other RNA
                          organism = synthetic construct
SEQUENCE: 528
gaggttttct ggtcttcact ggaagaccac t                                      31

SEQ ID NO: 529            moltype = RNA  length = 31
FEATURE                   Location/Qualifiers
source                    1..31
                          mol_type = other RNA
                          organism = synthetic construct
SEQUENCE: 529
taggttttct ggtcttcact ggaagaccac t                                      31

SEQ ID NO: 530            moltype = RNA  length = 31
FEATURE                   Location/Qualifiers
source                    1..31
                          mol_type = other RNA
                          organism = synthetic construct
SEQUENCE: 530
ccggttttct ggtcttcact ggaagaccac t                                      31

SEQ ID NO: 531            moltype = RNA  length = 31
FEATURE                   Location/Qualifiers
source                    1..31
                          mol_type = other RNA
                          organism = synthetic construct
SEQUENCE: 531
cgggttttct ggtcttcact ggaagaccac t                                      31

SEQ ID NO: 532            moltype = RNA  length = 31
FEATURE                   Location/Qualifiers
source                    1..31
                          mol_type = other RNA
                          organism = synthetic construct
SEQUENCE: 532
ctggttttct ggtcttcact ggaagaccac t                                      31

SEQ ID NO: 533            moltype = RNA  length = 31
FEATURE                   Location/Qualifiers
source                    1..31
                          mol_type = other RNA
                          organism = synthetic construct
SEQUENCE: 533
catgttttct ggtcttcact ggaagacaac t                                      31

SEQ ID NO: 534            moltype = RNA  length = 31
FEATURE                   Location/Qualifiers
source                    1..31
                          mol_type = other RNA
                          organism = synthetic construct
SEQUENCE: 534
cacgttttct ggtcttcact ggaagacgac t                                      31

SEQ ID NO: 535            moltype = RNA  length = 31
FEATURE                   Location/Qualifiers
source                    1..31
                          mol_type = other RNA
                          organism = synthetic construct
SEQUENCE: 535
```

-continued

```
caagttttct ggtcttcact ggaagactac t                              31

SEQ ID NO: 536         moltype = RNA   length = 31
FEATURE                Location/Qualifiers
source                 1..31
                       mol_type = other RNA
                       organism = synthetic construct
SEQUENCE: 536
cagcttttct ggtcttcact ggaagagcac t                              31

SEQ ID NO: 537         moltype = RNA   length = 31
FEATURE                Location/Qualifiers
source                 1..31
                       mol_type = other RNA
                       organism = synthetic construct
SEQUENCE: 537
cagatttct ggtcttcact ggaagatcac t                               31

SEQ ID NO: 538         moltype = RNA   length = 31
FEATURE                Location/Qualifiers
source                 1..31
                       mol_type = other RNA
                       organism = synthetic construct
SEQUENCE: 538
cagttttct ggtcttcact ggaagaacac t                               31

SEQ ID NO: 539         moltype = RNA   length = 31
FEATURE                Location/Qualifiers
source                 1..31
                       mol_type = other RNA
                       organism = synthetic construct
SEQUENCE: 539
cagggtttct ggtcttcact ggaagcccac t                              31

SEQ ID NO: 540         moltype = RNA   length = 31
FEATURE                Location/Qualifiers
source                 1..31
                       mol_type = other RNA
                       organism = synthetic construct
SEQUENCE: 540
caggatttct ggtcttcact ggaagtccac t                              31

SEQ ID NO: 541         moltype = RNA   length = 31
FEATURE                Location/Qualifiers
source                 1..31
                       mol_type = other RNA
                       organism = synthetic construct
SEQUENCE: 541
caggctttct ggtcttcact ggaaggccac t                              31

SEQ ID NO: 542         moltype = RNA   length = 31
FEATURE                Location/Qualifiers
source                 1..31
                       mol_type = other RNA
                       organism = synthetic construct
SEQUENCE: 542
caggtgttct ggtcttcact ggaacaccac t                              31

SEQ ID NO: 543         moltype = RNA   length = 31
FEATURE                Location/Qualifiers
source                 1..31
                       mol_type = other RNA
                       organism = synthetic construct
SEQUENCE: 543
caggtattct ggtcttcact ggaataccac t                              31

SEQ ID NO: 544         moltype = RNA   length = 31
FEATURE                Location/Qualifiers
source                 1..31
                       mol_type = other RNA
                       organism = synthetic construct
SEQUENCE: 544
caggtcttct ggtcttcact ggaagaccac t                              31

SEQ ID NO: 545         moltype = RNA   length = 31
FEATURE                Location/Qualifiers
source                 1..31
                       mol_type = other RNA
                       organism = synthetic construct
```

-continued

```
SEQUENCE: 545
caggttttct ggtcttcact ggaaaaccac t                                     31

SEQ ID NO: 546          moltype = RNA   length = 31
FEATURE                 Location/Qualifiers
source                  1..31
                        mol_type = other RNA
                        organism = synthetic construct
SEQUENCE: 546
caggttctct ggtcttcact ggaggaccac t                                     31

SEQ ID NO: 547          moltype = RNA   length = 31
FEATURE                 Location/Qualifiers
source                  1..31
                        mol_type = other RNA
                        organism = synthetic construct
SEQUENCE: 547
caggttgtct ggtcttcact ggacgaccac t                                     31

SEQ ID NO: 548          moltype = RNA   length = 31
FEATURE                 Location/Qualifiers
source                  1..31
                        mol_type = other RNA
                        organism = synthetic construct
SEQUENCE: 548
caggttatct ggtcttcact ggatgaccac t                                     31

SEQ ID NO: 549          moltype = RNA   length = 31
FEATURE                 Location/Qualifiers
source                  1..31
                        mol_type = other RNA
                        organism = synthetic construct
SEQUENCE: 549
caggtttact ggtcttcact ggtagaccac t                                     31

SEQ ID NO: 550          moltype = RNA   length = 31
FEATURE                 Location/Qualifiers
source                  1..31
                        mol_type = other RNA
                        organism = synthetic construct
SEQUENCE: 550
caggtttgct ggtcttcact ggcagaccac t                                     31

SEQ ID NO: 551          moltype = RNA   length = 31
FEATURE                 Location/Qualifiers
source                  1..31
                        mol_type = other RNA
                        organism = synthetic construct
SEQUENCE: 551
caggtttcct ggtcttcact gggagaccac t                                     31

SEQ ID NO: 552          moltype = RNA   length = 31
FEATURE                 Location/Qualifiers
source                  1..31
                        mol_type = other RNA
                        organism = synthetic construct
SEQUENCE: 552
caggtttttt ggtcttcact gaaagaccac t                                     31

SEQ ID NO: 553          moltype = RNA   length = 31
FEATURE                 Location/Qualifiers
source                  1..31
                        mol_type = other RNA
                        organism = synthetic construct
SEQUENCE: 553
caggttttgt ggtcttcact gcaagaccac t                                     31

SEQ ID NO: 554          moltype = RNA   length = 31
FEATURE                 Location/Qualifiers
source                  1..31
                        mol_type = other RNA
                        organism = synthetic construct
SEQUENCE: 554
caggttttat ggtcttcact gtaagaccac t                                     31

SEQ ID NO: 555          moltype = RNA   length = 31
FEATURE                 Location/Qualifiers
source                  1..31
                        mol_type = other RNA
```

```
                        organism = synthetic construct
SEQUENCE: 555
caggttttcc ggtcttcact ggaagaccac t                                       31

SEQ ID NO: 556          moltype = RNA   length = 31
FEATURE                 Location/Qualifiers
source                  1..31
                        mol_type = other RNA
                        organism = synthetic construct
SEQUENCE: 556
caggttttca ggtcttcact tgaagaccac t                                       31

SEQ ID NO: 557          moltype = RNA   length = 31
FEATURE                 Location/Qualifiers
source                  1..31
                        mol_type = other RNA
                        organism = synthetic construct
SEQUENCE: 557
caggttttct ggtcttcact agaagaccac t                                       31

SEQ ID NO: 558          moltype = RNA   length = 31
FEATURE                 Location/Qualifiers
source                  1..31
                        mol_type = other RNA
                        organism = synthetic construct
SEQUENCE: 558
caggttttcg ggtcttcact cgaagaccac t                                       31

SEQ ID NO: 559          moltype = RNA   length = 31
FEATURE                 Location/Qualifiers
source                  1..31
                        mol_type = other RNA
                        organism = synthetic construct
SEQUENCE: 559
caggttttct tgtcttcaca ggaagaccac t                                       31

SEQ ID NO: 560          moltype = RNA   length = 31
FEATURE                 Location/Qualifiers
source                  1..31
                        mol_type = other RNA
                        organism = synthetic construct
SEQUENCE: 560
caggttttct agtcttcact ggaagaccac t                                       31

SEQ ID NO: 561          moltype = RNA   length = 31
FEATURE                 Location/Qualifiers
source                  1..31
                        mol_type = other RNA
                        organism = synthetic construct
SEQUENCE: 561
caggttttct ggtcttcacc ggaagaccac t                                       31

SEQ ID NO: 562          moltype = RNA   length = 31
FEATURE                 Location/Qualifiers
source                  1..31
                        mol_type = other RNA
                        organism = synthetic construct
SEQUENCE: 562
caggttttct cgtcttcacg ggaagaccac t                                       31

SEQ ID NO: 563          moltype = RNA   length = 31
FEATURE                 Location/Qualifiers
source                  1..31
                        mol_type = other RNA
                        organism = synthetic construct
SEQUENCE: 563
caggttttct gttcttcaat ggaagaccac t                                       31

SEQ ID NO: 564          moltype = RNA   length = 31
FEATURE                 Location/Qualifiers
source                  1..31
                        mol_type = other RNA
                        organism = synthetic construct
SEQUENCE: 564
caggttttct gatcttcatt ggaagaccac t                                       31

SEQ ID NO: 565          moltype = RNA   length = 31
FEATURE                 Location/Qualifiers
source                  1..31
```

```
                                mol_type = other RNA
                                organism = synthetic construct
SEQUENCE: 565
caggtttttct gctcttcagt ggaagaccac t                                           31

SEQ ID NO: 566          moltype = RNA   length = 31
FEATURE                 Location/Qualifiers
source                  1..31
                        mol_type = other RNA
                        organism = synthetic construct
SEQUENCE: 566
caggtttttct ggccttcgct ggaagaccac t                                           31

SEQ ID NO: 567          moltype = RNA   length = 31
FEATURE                 Location/Qualifiers
source                  1..31
                        mol_type = other RNA
                        organism = synthetic construct
SEQUENCE: 567
caggtttttct gggcttccct ggaagaccac t                                           31

SEQ ID NO: 568          moltype = RNA   length = 31
FEATURE                 Location/Qualifiers
source                  1..31
                        mol_type = other RNA
                        organism = synthetic construct
SEQUENCE: 568
caggtttttct ggacttctct ggaagaccac t                                           31

SEQ ID NO: 569          moltype = RNA   length = 31
FEATURE                 Location/Qualifiers
source                  1..31
                        mol_type = other RNA
                        organism = synthetic construct
SEQUENCE: 569
caggtttttct ggttttcact ggaagaccac t                                           31

SEQ ID NO: 570          moltype = RNA   length = 31
FEATURE                 Location/Qualifiers
source                  1..31
                        mol_type = other RNA
                        organism = synthetic construct
SEQUENCE: 570
caggtttttct ggtattcact ggaagaccac t                                           31

SEQ ID NO: 571          moltype = RNA   length = 31
FEATURE                 Location/Qualifiers
source                  1..31
                        mol_type = other RNA
                        organism = synthetic construct
SEQUENCE: 571
caggtttttct ggtgttcact ggaagaccac t                                           31

SEQ ID NO: 572          moltype = RNA   length = 31
FEATURE                 Location/Qualifiers
source                  1..31
                        mol_type = other RNA
                        organism = synthetic construct
SEQUENCE: 572
caggtttttct ggtcatcact ggaagaccac t                                           31

SEQ ID NO: 573          moltype = RNA   length = 31
FEATURE                 Location/Qualifiers
source                  1..31
                        mol_type = other RNA
                        organism = synthetic construct
SEQUENCE: 573
caggtttttct ggtcgtcact ggaagaccac t                                           31

SEQ ID NO: 574          moltype = RNA   length = 31
FEATURE                 Location/Qualifiers
source                  1..31
                        mol_type = other RNA
                        organism = synthetic construct
SEQUENCE: 574
caggtttttct ggtcctcact ggaagaccac t                                           31

SEQ ID NO: 575          moltype = RNA   length = 31
FEATURE                 Location/Qualifiers
```

-continued

```
source                   1..31
                         mol_type = other RNA
                         organism = synthetic construct
SEQUENCE: 575
caggtttct ggtctacact ggaagaccac t                                  31

SEQ ID NO: 576           moltype = RNA   length = 31
FEATURE                  Location/Qualifiers
source                   1..31
                         mol_type = other RNA
                         organism = synthetic construct
SEQUENCE: 576
caggtttttct ggtctgcact ggaagaccac t                                31

SEQ ID NO: 577           moltype = RNA   length = 31
FEATURE                  Location/Qualifiers
source                   1..31
                         mol_type = other RNA
                         organism = synthetic construct
SEQUENCE: 577
caggtttttct ggtctccact ggaagaccac t                                31

SEQ ID NO: 578           moltype = RNA   length = 31
FEATURE                  Location/Qualifiers
source                   1..31
                         mol_type = other RNA
                         organism = synthetic construct
SEQUENCE: 578
caggtttttct ggtcttaact ggaagaccac t                                31

SEQ ID NO: 579           moltype = RNA   length = 31
FEATURE                  Location/Qualifiers
source                   1..31
                         mol_type = other RNA
                         organism = synthetic construct
SEQUENCE: 579
caggtttttct ggtcttgact ggaagaccac t                                31

SEQ ID NO: 580           moltype = RNA   length = 31
FEATURE                  Location/Qualifiers
source                   1..31
                         mol_type = other RNA
                         organism = synthetic construct
SEQUENCE: 580
caggtttttct ggtctttact ggaagaccac t                                31

SEQ ID NO: 581           moltype = RNA   length = 31
FEATURE                  Location/Qualifiers
source                   1..31
                         mol_type = other RNA
                         organism = synthetic construct
SEQUENCE: 581
caggtttttct ggtcttcact ggaagaccgc t                                31

SEQ ID NO: 582           moltype = RNA   length = 31
FEATURE                  Location/Qualifiers
source                   1..31
                         mol_type = other RNA
                         organism = synthetic construct
SEQUENCE: 582
caggtttttct ggtcttcact ggaagacccc t                                31

SEQ ID NO: 583           moltype = RNA   length = 31
FEATURE                  Location/Qualifiers
source                   1..31
                         mol_type = other RNA
                         organism = synthetic construct
SEQUENCE: 583
caggtttttct ggtcttcact ggaagacctc t                                31

SEQ ID NO: 584           moltype = RNA   length = 31
FEATURE                  Location/Qualifiers
source                   1..31
                         mol_type = other RNA
                         organism = synthetic construct
SEQUENCE: 584
caggtttttct ggtcttcact ggaagaccag t                                31

SEQ ID NO: 585           moltype = RNA   length = 31
```

-continued

```
FEATURE                 Location/Qualifiers
source                  1..31
                        mol_type = other RNA
                        organism = synthetic construct
SEQUENCE: 585
caggttttct ggtcttcact ggaagaccat t                                       31

SEQ ID NO: 586          moltype = RNA   length = 31
FEATURE                 Location/Qualifiers
source                  1..31
                        mol_type = other RNA
                        organism = synthetic construct
SEQUENCE: 586
caggttttct ggtcttcact ggaagaccaa t                                       31

SEQ ID NO: 587          moltype = RNA   length = 31
FEATURE                 Location/Qualifiers
source                  1..31
                        mol_type = other RNA
                        organism = synthetic construct
SEQUENCE: 587
caggttttct ggtcttcact ggaagaccac a                                       31

SEQ ID NO: 588          moltype = RNA   length = 31
FEATURE                 Location/Qualifiers
source                  1..31
                        mol_type = other RNA
                        organism = synthetic construct
SEQUENCE: 588
caggttttct ggtcttcact ggaagaccac g                                       31

SEQ ID NO: 589          moltype = RNA   length = 31
FEATURE                 Location/Qualifiers
source                  1..31
                        mol_type = other RNA
                        organism = synthetic construct
SEQUENCE: 589
caggttttct ggtcttcact ggaagaccac c                                       31

SEQ ID NO: 590          moltype = RNA   length = 132
FEATURE                 Location/Qualifiers
source                  1..132
                        mol_type = other RNA
                        organism = synthetic construct
SEQUENCE: 590
tcctcctaca aaggcgtgtc tgtggttccc tgtctttgga cacgtaagaa ttggaggaaa    60
ataaatgtgg atttgggaaa ctttgaggcc agcttgcttc ttgcaggctc atgatcaacc   120
aatctcacat aa                                                            132

SEQ ID NO: 591          moltype = RNA   length = 131
FEATURE                 Location/Qualifiers
source                  1..131
                        mol_type = other RNA
                        organism = synthetic construct
SEQUENCE: 591
ctccatgtat ctttgggacc tgtcagccgt ggcagtctcc cttcctagcc atggaagagc    60
atatccttgt ttattggcaa agctgtcacc atttaattgg tatcagattc tgacttgcac   120
aagtaacatt c                                                             131

SEQ ID NO: 592          moltype = RNA   length = 132
FEATURE                 Location/Qualifiers
source                  1..132
                        mol_type = other RNA
                        organism = synthetic construct
SEQUENCE: 592
ctgcgaatat tctcgctgtt ctgatttgt aatagtcagg acaggctaaa cattcgctat      60
attaagacca tgcatgtgtc cccaaaccta gttctttccc taggtctggt ttcataaatg   120
ctggtgataa ac                                                            132

SEQ ID NO: 593          moltype = RNA   length = 133
FEATURE                 Location/Qualifiers
source                  1..133
                        mol_type = other RNA
                        organism = synthetic construct
SEQUENCE: 593
gcatggccga atactgtgtt tttatcagta gtttacacag ccagacacca tgcaaaagca    60
gtcttccctt tagaatgact gatggtatgc taaggttttt catagcatat cattattaaa   120
ggtgaataca aat                                                          133
```

-continued

```
SEQ ID NO: 594         moltype = RNA   length = 139
FEATURE                Location/Qualifiers
source                 1..139
                       mol_type = other RNA
                       organism = synthetic construct
SEQUENCE: 594
tgcactgcat ggtatctgca ctcagcagtt tacacctgct agggtgttca aaggtcagtg    60
ctatagaaat tcagtatctg gcatcgttgg ttttcttggc tttgtgcttg ttaaacctgg   120
tatttctact gatacagta                                                139

SEQ ID NO: 595         moltype = RNA   length = 134
FEATURE                Location/Qualifiers
source                 1..134
                       mol_type = other RNA
                       organism = synthetic construct
SEQUENCE: 595
tggtccatcc taatccctgc cggtccatct gtggcctgcc aggtttcgct tgtggaccag    60
agcaccctag aagcctcacc cgaggagtga gcagggctcc agtgggctca cgtcatgggc   120
acttctagac actc                                                     134

SEQ ID NO: 596         moltype = RNA   length = 136
FEATURE                Location/Qualifiers
source                 1..136
                       mol_type = other RNA
                       organism = synthetic construct
SEQUENCE: 596
cacctgcatt caaaaatgat cacgggctgc ctgtgctctg gtcatcaata acgcagggag    60
aggaattgct gaaagccgtt tcccgtgttt ggagggttca cacctgtccc tttcaaatgc   120
tggcgctttc acacac                                                   136

SEQ ID NO: 597         moltype = RNA   length = 134
FEATURE                Location/Qualifiers
source                 1..134
                       mol_type = other RNA
                       organism = synthetic construct
SEQUENCE: 597
tgcattctta aaccctcttg gtggcttccc tgtaaatgct tccaagatat gagcgaatgc    60
tatagaaatt gcaggaaagt ccaaagggct gcgcgtctcc tgtggctcag tcttatttca   120
tacctgcaac atct                                                     134

SEQ ID NO: 598         moltype = RNA   length = 133
FEATURE                Location/Qualifiers
source                 1..133
                       mol_type = other RNA
                       organism = synthetic construct
SEQUENCE: 598
attgcaccta aacccaagaa tcactgtttc ttatagcggt ggtttaaaca gaggtgcaaa    60
cagcaagcgg atcttgtcgc ctttgggggg ctgtggccgt gcccctcaaa gtgaatttgg   120
aggttccaca act                                                      133

SEQ ID NO: 599         moltype = RNA   length = 132
FEATURE                Location/Qualifiers
source                 1..132
                       mol_type = other RNA
                       organism = synthetic construct
SEQUENCE: 599
cttcccattt atttgctgct tgtagtctca cagtgatacg agcagttata cgcatgggat    60
aaaataacat tgggccactg taaattgaga tgaagtaacc attttcatct cttctgcagg   120
gactagacat tg                                                       132

SEQ ID NO: 600         moltype = RNA   length = 135
FEATURE                Location/Qualifiers
source                 1..135
                       mol_type = other RNA
                       organism = synthetic construct
SEQUENCE: 600
ctgcattctt aaaccctctt ggtagcttcg ttctaagtgc ttccaagata tgagtgaatg    60
ctatagaaat tgcaggggag tccaaagggc tgcgcttctc ccgtggctca gtcttatttc   120
atacctgcga catct                                                    135

SEQ ID NO: 601         moltype = RNA   length = 131
FEATURE                Location/Qualifiers
source                 1..131
                       mol_type = other RNA
                       organism = synthetic construct
SEQUENCE: 601
aggcaggatc tagttacatt gtagctgtga agtgctgcat tgtctttgcc ccctgctcaa    60
aataaaactg ttacctttca agccctgtct gccatggtgc tgtagcagca gggatgtttg   120
gtctcataca t                                                        131
```

```
SEQ ID NO: 602              moltype = RNA   length = 123
FEATURE                    Location/Qualifiers
source                     1..123
                           mol_type = other RNA
                           organism = synthetic construct
SEQUENCE: 602
actggaggac taaggaggct gggtctgatg aggcaagatt ttgctgatac attgctccta   60
gaaaaaaggg ttggcaagag cagccctgga gactcacacg gctgactgtt ctacccaaca   120
ctc                                                                 123

SEQ ID NO: 603              moltype = RNA   length = 129
FEATURE                    Location/Qualifiers
source                     1..129
                           mol_type = other RNA
                           organism = synthetic construct
SEQUENCE: 603
aagcaggatt cagactacaa tatagctgtt aagtgctgta ttgtcattcc ccctgctcaa   60
attaaagttg tttcttaact atacccatct gctattctgt agcagccagg gatgcttggt   120
cacatacat                                                           129

SEQ ID NO: 604              moltype = RNA   length = 132
FEATURE                    Location/Qualifiers
source                     1..132
                           mol_type = other RNA
                           organism = synthetic construct
SEQUENCE: 604
ggcttcctag tacttaccat ggtctgtgtt cttacgctga ctgtatagaa acaggaggca   60
gagtaaaccg accccacata tacctcagcc caggccctgt gctgcgtctg tattgtgaat   120
caggagacat gg                                                       132

SEQ ID NO: 605              moltype = RNA   length = 139
FEATURE                    Location/Qualifiers
source                     1..139
                           mol_type = other RNA
                           organism = synthetic construct
SEQUENCE: 605
tggctcgatt tcctgggggg tggtctcagc ccactccacc tcccctcagc cgagcctaga   60
gtagaggggc caggcatcct ccccagggga ggggcgttga agcaaggagc ctctcctggg   120
ctgtcctagc ctcacattt                                                139

SEQ ID NO: 606              moltype = RNA   length = 132
FEATURE                    Location/Qualifiers
source                     1..132
                           mol_type = other RNA
                           organism = synthetic construct
SEQUENCE: 606
gttgaggtct atcccgatag gtcttttcct gtagcctgca cgttgttgga aatgcctcat   60
agagtaactc tgtgatttta ctttacttac aggactattg ttacatctgt gggaaggaac   120
cacaagacag tt                                                       132

SEQ ID NO: 607              moltype = RNA   length = 133
FEATURE                    Location/Qualifiers
source                     1..133
                           mol_type = other RNA
                           organism = synthetic construct
SEQUENCE: 607
ttctcaccta aacccaagaa tcactgtttc ttatagcggt ggtttaaaca gaggtgcaaa   60
cagcaagtga atctcgtcgc ctttgcgggg ctgtggccat gccctcaaa ggaaatttgg    120
aggtctaca gcc                                                       133

SEQ ID NO: 608              moltype = RNA   length = 128
FEATURE                    Location/Qualifiers
source                     1..128
                           mol_type = other RNA
                           organism = synthetic construct
SEQUENCE: 608
aggtcatttc aaagaggtct tgtgaggctg tgaaaccaag agctcttaac actgcgacca   60
aagatggaag ttctctatag gatgccatgg catttgatgg tgctatgttt tcttgaggag   120
atataaga                                                            128

SEQ ID NO: 609              moltype = RNA   length = 131
FEATURE                    Location/Qualifiers
source                     1..131
                           mol_type = other RNA
                           organism = synthetic construct
SEQUENCE: 609
ccctcctaca aaggcatgtc tatagttcct tgtctttgga catgtaagaa ttggaggcaa   60
agaaatgtgg acttggagaa atctgggggcc agcttgctct ccgcaggctc aagatcaacc   120
```

```
atcccacata g                                                              131

SEQ ID NO: 610          moltype = RNA  length = 125
FEATURE                 Location/Qualifiers
source                  1..125
                        mol_type = other RNA
                        organism = synthetic construct
SEQUENCE: 610
gcagactcac tatgcacctg actgtacttc caggcaggtg ctttttctgt ctgccagaga    60
aacattccag ggtgctgtgg ctgcctcacc tatccagggc gatgcagctc cctggggaca    120
caggt                                                                125

SEQ ID NO: 611          moltype = RNA  length = 125
FEATURE                 Location/Qualifiers
source                  1..125
                        mol_type = other RNA
                        organism = synthetic construct
SEQUENCE: 611
gcagactcac tctgcatctg actatacttc caggcgggtg ctttttctgt ctgccagata    60
aacattccag ggtgctgtgg ccgcctcacg tatccagagt gatgcagctc cctggggaca    120
caggt                                                                125

SEQ ID NO: 612          moltype = RNA  length = 148
FEATURE                 Location/Qualifiers
source                  1..148
                        mol_type = other RNA
                        organism = synthetic construct
SEQUENCE: 612
tgatggctgt tcctctcact gcttgaagcc ttaggcagtg ggattttgat ccatcatata    60
tcaaaaatgg cttatcttca ctcagggcac catgaggatg ggctggctgt ccgttagtgc    120
cttctgattt ttgcggagtc aaacaatt                                       148

SEQ ID NO: 613          moltype = RNA  length = 127
FEATURE                 Location/Qualifiers
source                  1..127
                        mol_type = other RNA
                        organism = synthetic construct
SEQUENCE: 613
ctggggaatt caaacttgtg ttaagaaaat gtgtcccagt gtgcaatggc tgcaaacagc    60
agcttccttg gtagtgtatg cagcctgttt gttgtacggg ttgctctaaa gggccttgga    120
gacagtc                                                              127

SEQ ID NO: 614          moltype = RNA  length = 126
FEATURE                 Location/Qualifiers
source                  1..126
                        mol_type = other RNA
                        organism = synthetic construct
SEQUENCE: 614
aggtcacttc aaagagggct tgtggggctg tgaaaccaag aggtcttaac agtatgacca    60
aaaactgaag ttctctatag gatgctgtag cactcaatgg tgctatgttt tcctcaggag    120
atatga                                                               126

SEQ ID NO: 615          moltype = RNA  length = 139
FEATURE                 Location/Qualifiers
source                  1..139
                        mol_type = other RNA
                        organism = synthetic construct
SEQUENCE: 615
ctgtccgttg ctggcttcac aagtactagt ataattttta aaatgtttta ttattttgaa    60
aataatgttg taattcatgc cagggactga caaaagactt gagacaggat ggttattctt    120
gtcagctaag gtcacattg                                                 139

SEQ ID NO: 616          moltype = RNA  length = 113
FEATURE                 Location/Qualifiers
source                  1..113
                        mol_type = other RNA
                        organism = synthetic construct
SEQUENCE: 616
tccaaacaga cactgatggc accttctgcc atttaggaat ttgtttttaaa acagacattt   60
gtctagatat ttcctttgtg gcctcctccc catcaaaagt caatcaaaca tcg           113

SEQ ID NO: 617          moltype = RNA  length = 143
FEATURE                 Location/Qualifiers
source                  1..143
                        mol_type = other RNA
                        organism = synthetic construct
SEQUENCE: 617
gccctatgtt aaaattttaa ttctgcactt actaactatc ttgggaacct tgggcaagta    60
accaacctct tgtgctttgg tttcctcatt ggtaaaatgg ggataacagt acttacctca    120
```

```
cagagttgtt gagaggaaca aat                                             143

SEQ ID NO: 618            moltype = RNA   length = 125
FEATURE                   Location/Qualifiers
source                    1..125
                          mol_type = other RNA
                          organism = synthetic construct
SEQUENCE: 618
atgcaggtac tgttacaata caactgatgt gttttgttgt cgttccccct gcttaaagca    60
cttgatgcat aactctgtct accttcattc cgtagtaaga cagagacgct tggcttcaga    120
cattt                                                                 125

SEQ ID NO: 619            moltype = RNA   length = 147
FEATURE                   Location/Qualifiers
source                    1..147
                          mol_type = other RNA
                          organism = synthetic construct
SEQUENCE: 619
tcactgccct gctcaccctt cctgagtccg gcggcaaggg taactctggg agcatcgtag    60
agggcagaga agaagaaacc ctgaggtccc attatgtcag cccttctat cacacgggag     120
gagactgagg acagaaaggg aacagag                                         147

SEQ ID NO: 620            moltype = RNA   length = 147
FEATURE                   Location/Qualifiers
source                    1..147
                          mol_type = other RNA
                          organism = synthetic construct
SEQUENCE: 620
cttttctcag tggtgcaaga agattaagcc acattctggc tttagagagg catttctgag    60
agagatgaag gacacttcgt tccccagccc caacctaagc atgtgactgt actcaccttg    120
tcagatgctg ttggaacctg ctgaca                                          147

SEQ ID NO: 621            moltype = RNA   length = 122
FEATURE                   Location/Qualifiers
source                    1..122
                          mol_type = other RNA
                          organism = synthetic construct
SEQUENCE: 621
ctggaggact aaggaggctg ggtctgatga ggcaagattt tgctgataca ttgctcctag    60
aaaaaagggt tggcaagagc agccctggag actcacacgg ctgactgttc tacccaacac    120
tc                                                                    122

SEQ ID NO: 622            moltype = RNA   length = 118
FEATURE                   Location/Qualifiers
source                    1..118
                          mol_type = other RNA
                          organism = synthetic construct
SEQUENCE: 622
tagtgtggaa ctgtctactc ctcattcctg tggaagcagg aatacattca taacatgctc    60
cattaaaaaa ggagttctag gccaggcagc gtgcctcatg cctggaatcc cagcactt       118

SEQ ID NO: 623            moltype = RNA   length = 126
FEATURE                   Location/Qualifiers
source                    1..126
                          mol_type = other RNA
                          organism = synthetic construct
SEQUENCE: 623
atacctaaac ccaagaatca ctttcttata gtgatgattt aaacagatgc aaacagcgag    60
cacatcttgt cacctttgcg ggactgtggc tgtgccccctc gcagtaaatt tggaggttct    120
acatcc                                                                126

SEQ ID NO: 624            moltype = RNA   length = 133
FEATURE                   Location/Qualifiers
source                    1..133
                          mol_type = other RNA
                          organism = synthetic construct
SEQUENCE: 624
aggcaggatc tagttacatt gtagctgtga agtgctgcat tgtctttgcc ccctgctcaa    60
aataaaactg ttacctttca agccctgtct gccatggtgc tgtagcagca gggatgtttg    120
gtctcataca tgt                                                        133

SEQ ID NO: 625            moltype = RNA   length = 81
FEATURE                   Location/Qualifiers
source                    1..81
                          mol_type = other RNA
                          organism = synthetic construct
SEQUENCE: 625
cactagaaga cagaattcac agaagtagca tttcaccttt tgcctttaca gaagtatatt    60
tggctgtttt gtgagacatt c                                               81
```

```
SEQ ID NO: 626          moltype = RNA   length = 112
FEATURE                 Location/Qualifiers
source                  1..112
                        mol_type = other RNA
                        organism = synthetic construct
SEQUENCE: 626
acttttacag gtagaatagt aaagcacagt gttgattgcc caagatttat tttactttga    60
aaaaattaga aatttattac tatagcaaat gtctagaact ttggaaacaa gt            112

SEQ ID NO: 627          moltype = RNA   length = 134
FEATURE                 Location/Qualifiers
source                  1..134
                        mol_type = other RNA
                        organism = synthetic construct
SEQUENCE: 627
atgcatctat ttgacagacc tggagcagtt gctatctgct gctatggttt ccaccacaga    60
tgcaagaaga acatgtcctt gcgctttccg tctgtctaat tgtggcagct gagattgaat   120
agaggaatac agga                                                     134

SEQ ID NO: 628          moltype = RNA   length = 136
FEATURE                 Location/Qualifiers
source                  1..136
                        mol_type = other RNA
                        organism = synthetic construct
SEQUENCE: 628
aagcactgcc tttgaacctg atgtgtcttg tttgtagctt cacgggccaa gcaacagtgc    60
tagagcataa cgacttgtta taactggggc tcttcagctc tcaactgaac tgctctttta   120
aaaacaaggt acattt                                                   136

SEQ ID NO: 629          moltype =   length =
SEQUENCE: 629
000

SEQ ID NO: 630          moltype = RNA   length = 133
FEATURE                 Location/Qualifiers
source                  1..133
                        mol_type = other RNA
                        organism = synthetic construct
SEQUENCE: 630
agcctttgtg ttgcccattc actttggaaa ctagtgaatg tggtgtcaaa aaaggcgtaa    60
attaaacgct ttgcagcctt ttcctgccct taaatttgat acctttggtg taggagctgc   120
ataagtaaca gtt                                                      133

SEQ ID NO: 631          moltype = RNA   length = 132
FEATURE                 Location/Qualifiers
source                  1..132
                        mol_type = other RNA
                        organism = synthetic construct
SEQUENCE: 631
ttccaaagtg ttgagttcag tccagggcag cttccctgtt ctgttaatta aactttggga    60
cattaaaatg ggctaaggga gatgattggg tagaaagtat tattctattc atttgcctcc   120
cagcctacaa aa                                                       132

SEQ ID NO: 632          moltype = RNA   length = 126
FEATURE                 Location/Qualifiers
source                  1..126
                        mol_type = other RNA
                        organism = synthetic construct
SEQUENCE: 632
aagcaacact ctgtggcaga tgatcaaaac tgtctgacac aatttgagct tgctatagca    60
agaaagtcta acctattccg gtgttctctc tcccatgaga caagccgtta tatagactta   120
aacagt                                                              126

SEQ ID NO: 633          moltype =   length =
SEQUENCE: 633
000

SEQ ID NO: 634          moltype = RNA   length = 132
FEATURE                 Location/Qualifiers
source                  1..132
                        mol_type = other RNA
                        organism = synthetic construct
SEQUENCE: 634
ttccacagct actggtctgc agctgttctt atggtagcag ttgtggcatt cctctgtggg    60
aaagaaactg ttaacacaaa cacctctttc ttagcaaaac agaaagtggg tatatatgtg   120
tgacagacac aa                                                       132

SEQ ID NO: 635          moltype = RNA   length = 134
```

```
FEATURE              Location/Qualifiers
source               1..134
                     mol_type = other RNA
                     organism = synthetic construct
SEQUENCE: 635
tgcagccgtg tcaaattcag tacctgtcct atgcatggta ggcactggcc cagaaggctg   60
ccacagaaac actgtgactc atgggccctg ttcctgtgtc ccaggctcag ggataaattt   120
ggttacagac atca                                                      134

SEQ ID NO: 636       moltype =    length =
SEQUENCE: 636
000

SEQ ID NO: 637       moltype =    length =
SEQUENCE: 637
000

SEQ ID NO: 638       moltype = RNA   length = 133
FEATURE              Location/Qualifiers
source               1..133
                     mol_type = other RNA
                     organism = synthetic construct
SEQUENCE: 638
tgcagccgtg tcaattcagt acctgtccta tgcatggtag gcactggccc agaaggctgc   60
cacagaaaca ctgtgactca tgggccctgt tcctgtgtcc caggctcagg gataaatttg   120
gttacagaca tca                                                       133

SEQ ID NO: 639       moltype =    length =
SEQUENCE: 639
000

SEQ ID NO: 640       moltype = RNA   length = 134
FEATURE              Location/Qualifiers
source               1..134
                     mol_type = other RNA
                     organism = synthetic construct
SEQUENCE: 640
tggtaatgga tttatggtgg gtccttctct gtgggcctct catagtgtac ccatgccata   60
gcaaatggca gcctcgaacc attgcccagt ccccttacct gtgggctgtg agcactgaag   120
ggggttgcac agtg                                                      134

SEQ ID NO: 641       moltype =    length =
SEQUENCE: 641
000

SEQ ID NO: 642       moltype = RNA   length = 132
FEATURE              Location/Qualifiers
source               1..132
                     mol_type = other RNA
                     organism = synthetic construct
SEQUENCE: 642
cagcatgttt ccaagggctg tggctggtca tagccatggg atctccaact gcatgcaaga   60
gcaacctgga aagactttga cagcgcaggt cagtacaata cctgcaagct gccactcagc   120
tttcctataa tg                                                        132

SEQ ID NO: 643       moltype =    length =
SEQUENCE: 643
000

SEQ ID NO: 644       moltype = RNA   length = 133
FEATURE              Location/Qualifiers
source               1..133
                     mol_type = other RNA
                     organism = synthetic construct
SEQUENCE: 644
ggtctctcag ctccgcttaa ccacacgggt ccagtgtgtg cttggcgtgt tttcagggag   60
gcagagaaag gctctcctaa tgcacgacag acccgcccag aatggcctct ctgttcctag   120
gagtgcgaca att                                                       133

SEQ ID NO: 645       moltype = RNA   length = 135
FEATURE              Location/Qualifiers
source               1..135
                     mol_type = other RNA
                     organism = synthetic construct
SEQUENCE: 645
agcactatat ttaaacctgt ggatgggaat attccccatt cttggttacg ctgtagtgca   60
aaagaattcc tggctctctg ttgcacagct gacttgtgcc attctgctgt tgctgtatag   120
agttaaggaa catgg                                                     135
```

-continued

```
SEQ ID NO: 646          moltype =    length =
SEQUENCE: 646
000

SEQ ID NO: 647          moltype = RNA   length = 130
FEATURE                 Location/Qualifiers
source                  1..130
                        mol_type = other RNA
                        organism = synthetic construct
SEQUENCE: 647
tgcctcattc tagagaatgg gcactgttga tcatggtgtc caaaaatagt taatgtggct    60
aaattgagac aggttatgct tccatcacag tatgcatatt gcagtggtga caatgagacc   120
tgtaacattt                                                          130

SEQ ID NO: 648          moltype = RNA   length = 135
FEATURE                 Location/Qualifiers
source                  1..135
                        mol_type = other RNA
                        organism = synthetic construct
SEQUENCE: 648
taggccctga atcaagacca atggtttgct gtagctgttg gtttcaaaca ggagctaaga    60
gtgatgtctt ccttgtggtc tgttggctat tcagtattcc agtgcgaatt gccaattcag   120
ttggaagaaa catag                                                    135

SEQ ID NO: 649          moltype =    length =
SEQUENCE: 649
000

SEQ ID NO: 650          moltype = RNA   length = 130
FEATURE                 Location/Qualifiers
source                  1..130
                        mol_type = other RNA
                        organism = synthetic construct
SEQUENCE: 650
atcgaggcta gagtcacgct tgggtatcgg ctattgcctg agtgtgctag agtcctcgaa    60
gagtaactgc tgaccttatt cactggctgt gggccttatg gcacagtcag tcaccaggtt   120
agagacatgc                                                          130

SEQ ID NO: 651          moltype =    length =
SEQUENCE: 651
000

SEQ ID NO: 652          moltype = RNA   length = 149
FEATURE                 Location/Qualifiers
source                  1..149
                        mol_type = other RNA
                        organism = synthetic construct
SEQUENCE: 652
tgcacactat taaagctcag ggtggaggcc agtcttggct catgaacttc tgagtgtcgg    60
aagtgtgcta tatcaatggc aggattttcg ctaacaccag tagagcttgc ctctatgact   120
ggagtttggt agtactcgct gccacatag                                     149

SEQ ID NO: 653          moltype = RNA   length = 139
FEATURE                 Location/Qualifiers
source                  1..139
                        mol_type = other RNA
                        organism = synthetic construct
SEQUENCE: 653
gacctcctgg gatcgcatct ggagagtgcc tagtattctg ccagcttcgg aaagggaggg    60
aaagcaagcc tggcagaggc acccattcca ttcccagctt gctccgtagc tggcgattgg   120
aagacactct gcgacagtg                                                139

SEQ ID NO: 654          moltype =    length =
SEQUENCE: 654
000

SEQ ID NO: 655          moltype = RNA   length = 133
FEATURE                 Location/Qualifiers
source                  1..133
                        mol_type = other RNA
                        organism = synthetic construct
SEQUENCE: 655
tagcaagcct ccagcgtgct tgggtctgcg gtgaccctat gcattccttc agtgcttgct    60
agaacagttt tgaaacggtt tgaggccttg ccctgctcca tccagagcaa ggttatagaa   120
atttcagaca atg                                                      133

SEQ ID NO: 656          moltype =    length =
SEQUENCE: 656
000
```

-continued

```
SEQ ID NO: 657          moltype = RNA   length = 134
FEATURE                 Location/Qualifiers
source                  1..134
                        mol_type = other RNA
                        organism = synthetic construct
SEQUENCE: 657
ttggccctta tcgaagctgc agctgcttcc gcatagctgc tgtggtcaaa aaggagccca   60
gagtgacagt tttccttgac ggtcgccgtt ctgtttgttg taactgatct gcaacatttt  120
gggaaaatac agtt                                                     134

SEQ ID NO: 658          moltype = DNA   length = 31
FEATURE                 Location/Qualifiers
source                  1..31
                        mol_type = other DNA
                        organism = synthetic construct
SEQUENCE: 658
acacaggcac tggccactga aatttttgga g                                   31

SEQ ID NO: 659          moltype = DNA   length = 47
FEATURE                 Location/Qualifiers
source                  1..47
                        mol_type = other DNA
                        organism = synthetic construct
SEQUENCE: 659
taggctttct ggcttttcac cggaaagccc ctaaatgatt aaattaa                  47

SEQ ID NO: 660          moltype = DNA   length = 31
FEATURE                 Location/Qualifiers
source                  1..31
                        mol_type = other DNA
                        organism = synthetic construct
SEQUENCE: 660
gattaggcac acacaggcac aatttttgga g                                   31

SEQ ID NO: 661          moltype =   length =
SEQUENCE: 661
000

SEQ ID NO: 662          moltype = DNA   length = 31
FEATURE                 Location/Qualifiers
source                  1..31
                        mol_type = other DNA
                        organism = synthetic construct
SEQUENCE: 662
cttccttgac gattaggcac aatttttgga g                                   31

SEQ ID NO: 663          moltype =   length =
SEQUENCE: 663
000

SEQ ID NO: 664          moltype = DNA   length = 31
FEATURE                 Location/Qualifiers
source                  1..31
                        mol_type = other DNA
                        organism = synthetic construct
SEQUENCE: 664
accttcttcc ttgacgatta aatttttgga g                                   31

SEQ ID NO: 665          moltype =   length =
SEQUENCE: 665
000

SEQ ID NO: 666          moltype = DNA   length = 31
FEATURE                 Location/Qualifiers
source                  1..31
                        mol_type = other DNA
                        organism = synthetic construct
SEQUENCE: 666
acacaggcac tggccactga tgcgtgtcat t                                   31

SEQ ID NO: 667          moltype =   length =
SEQUENCE: 667
000

SEQ ID NO: 668          moltype = DNA   length = 31
FEATURE                 Location/Qualifiers
source                  1..31
                        mol_type = other DNA
```

```
                         organism = synthetic construct
SEQUENCE: 668
ggcacacaca ggcactggcc tgcgtgtcat t                                          31

SEQ ID NO: 669        moltype =    length =
SEQUENCE: 669
000

SEQ ID NO: 670        moltype = DNA   length = 31
FEATURE               Location/Qualifiers
source                1..31
                      mol_type = other DNA
                      organism = synthetic construct
SEQUENCE: 670
acgagctcag cctatgcgag aatttttgga g                                          31

SEQ ID NO: 671        moltype =    length =
SEQUENCE: 671
000

SEQ ID NO: 672        moltype = DNA   length = 31
FEATURE               Location/Qualifiers
source                1..31
                      mol_type = other DNA
                      organism = synthetic construct
SEQUENCE: 672
ccacctaccc tatcgtgcgg aatttttgga g                                          31

SEQ ID NO: 673        moltype =    length =
SEQUENCE: 673
000

SEQ ID NO: 674        moltype = DNA   length = 83
FEATURE               Location/Qualifiers
source                1..83
                      mol_type = other DNA
                      organism = synthetic construct
SEQUENCE: 674
ggtcaatgat gtgttggcat gtatcaggta ttcctgtggc tgatgtgtaa taacactgga          60
tgaagggaca cacactgaga cct                                                   83

SEQ ID NO: 675        moltype = DNA   length = 103
FEATURE               Location/Qualifiers
source                1..103
                      mol_type = other DNA
                      organism = synthetic construct
SEQUENCE: 675
tatgataggg acttagggtg ggtcaatgat gtgttggcat gtatcaggta ttcctgtggc          60
tgatgtgtaa taacactgga tgaagggaca cacactgaga cct                            103

SEQ ID NO: 676        moltype = DNA   length = 103
FEATURE               Location/Qualifiers
source                1..103
                      mol_type = other DNA
                      organism = synthetic construct
SEQUENCE: 676
ggtcaatgat gtgttggcat gtatcaggta ttcctgtggc tgatgtgtaa taacactgga          60
tgaagggaca cacactgaga ccttatgata gggacttagg gtg                            103

SEQ ID NO: 677        moltype = DNA   length = 83
FEATURE               Location/Qualifiers
source                1..83
                      mol_type = other DNA
                      organism = synthetic construct
SEQUENCE: 677
ggtcaatgat gtgttggcat gtatggtaca ggtattcctc tgatgtgtaa taacactctg          60
tggatgaagg gacactgaga cct                                                   83

SEQ ID NO: 678        moltype = DNA   length = 103
FEATURE               Location/Qualifiers
source                1..103
                      mol_type = other DNA
                      organism = synthetic construct
SEQUENCE: 678
tatgataggg acttagggtg ggtcaatgat gtgttggcat gtatggtaca ggtattcctc          60
tgatgtgtaa taacactctg tggatgaagg gacactgaga cct                            103

SEQ ID NO: 679        moltype = DNA   length = 103
FEATURE               Location/Qualifiers
```

```
source                    1..103
                          mol_type = other DNA
                          organism = synthetic construct
SEQUENCE: 679
ggtcaatgat gtgttggcat gtatggtaca ggtattcctc tgatgtgtaa taacactctg   60
tggatgaagg gacactgaga ccttatgata gggacttagg gtg                     103

SEQ ID NO: 680            moltype = DNA   length = 135
FEATURE                   Location/Qualifiers
source                    1..135
                          mol_type = other DNA
                          organism = synthetic construct
SEQUENCE: 680
agcactataa agggacctgt ggatgggaat attccccatt cttggtacac acatagtgca   60
aaagaattcc tggctctctg ttgcacagct gacttgtgcc attctgctgt tgctgtatag  120
agttaaggaa catgg                                                    135

SEQ ID NO: 681            moltype = DNA   length = 155
FEATURE                   Location/Qualifiers
source                    1..155
                          mol_type = other DNA
                          organism = synthetic construct
SEQUENCE: 681
tatgataggg acttagggtg agcactataa agggacctgt ggatgggaat attccccatt   60
cttggtacac acatagtgca aaagaattcc tggctctctg ttgcacagct gacttgtgcc  120
attctgctgt tgctgtatag agttaaggaa catgg                              155

SEQ ID NO: 682            moltype = DNA   length = 155
FEATURE                   Location/Qualifiers
source                    1..155
                          mol_type = other DNA
                          organism = synthetic construct
SEQUENCE: 682
agcactataa agggacctgt ggatgggaat attccccatt cttggtacac acatagtgca   60
aaagaattcc tggctctctg ttgcacagct gacttgtgcc attctgctgt tgctgtatag  120
agttaaggaa catggtatga tagggactta gggtg                              155

SEQ ID NO: 683            moltype = DNA   length = 132
FEATURE                   Location/Qualifiers
source                    1..132
                          mol_type = other DNA
                          organism = synthetic construct
SEQUENCE: 683
cagcatgttt ccaagggctg tggctggtca tagccatggg atctccaact gcatgcaaga   60
gcaacctgga aagacacaca cagcgcaggt cagtacaata cctgcaagct gcatgccagc  120
tttcctataa tg                                                       132

SEQ ID NO: 684            moltype = DNA   length = 152
FEATURE                   Location/Qualifiers
source                    1..152
                          mol_type = other DNA
                          organism = synthetic construct
SEQUENCE: 684
tatgataggg acttagggtg cagcatgttt ccaagggctg tggctggtca tagccatggg   60
atctccaact gcatgcaaga gcaacctgga aagacacaca cagcgcaggt cagtacaata  120
cctgcaagct gcatgccagc tttcctataa tg                                 152

SEQ ID NO: 685            moltype = DNA   length = 152
FEATURE                   Location/Qualifiers
source                    1..152
                          mol_type = other DNA
                          organism = synthetic construct
SEQUENCE: 685
cagcatgttt ccaagggctg tggctggtca tagccatggg atctccaact gcatgcaaga   60
gcaacctgga aagacacaca cagcgcaggt cagtacaata cctgcaagct gcatgccagc  120
tttcctataa tgtatgatag ggacttaggg tg                                 152

SEQ ID NO: 686            moltype =    length =
SEQUENCE: 686
000

SEQ ID NO: 687            moltype =    length =
SEQUENCE: 687
000

SEQ ID NO: 688            moltype =    length =
SEQUENCE: 688
000
```

-continued

```
SEQ ID NO: 689          moltype =    length =
SEQUENCE: 689
000

SEQ ID NO: 690          moltype =    length =
SEQUENCE: 690
000

SEQ ID NO: 691          moltype =    length =
SEQUENCE: 691
000

SEQ ID NO: 692          moltype =    length =
SEQUENCE: 692
000

SEQ ID NO: 693          moltype =    length =
SEQUENCE: 693
000

SEQ ID NO: 694          moltype =    length =
SEQUENCE: 694
000

SEQ ID NO: 695          moltype =    length =
SEQUENCE: 695
000

SEQ ID NO: 696          moltype =    length =
SEQUENCE: 696
000

SEQ ID NO: 697          moltype =    length =
SEQUENCE: 697
000

SEQ ID NO: 698          moltype =    length =
SEQUENCE: 698
000

SEQ ID NO: 699          moltype =    length =
SEQUENCE: 699
000

SEQ ID NO: 700          moltype =    length =
SEQUENCE: 700
000

SEQ ID NO: 701          moltype = DNA  length = 11
FEATURE                 Location/Qualifiers
source                  1..11
                        mol_type = other DNA
                        organism = synthetic construct
SEQUENCE: 701
aatttttgga g                                                      11

SEQ ID NO: 702          moltype = DNA  length = 20
FEATURE                 Location/Qualifiers
source                  1..20
                        mol_type = other DNA
                        organism = synthetic construct
SEQUENCE: 702
taaaatatat ttaaaaggtg                                             20

SEQ ID NO: 703          moltype = DNA  length = 11
FEATURE                 Location/Qualifiers
source                  1..11
                        mol_type = other DNA
                        organism = synthetic construct
SEQUENCE: 703
aacgcgtcat g                                                      11

SEQ ID NO: 704          moltype =    length =
SEQUENCE: 704
000

SEQ ID NO: 705          moltype =    length =
SEQUENCE: 705
000
```

-continued

SEQ ID NO: 706          moltype = DNA   length = 20
FEATURE                 Location/Qualifiers
source                  1..20
                        mol_type = other DNA
                        organism = synthetic construct
SEQUENCE: 706
tcacacctaa gccctaaaga                                              20

SEQ ID NO: 707          moltype = DNA   length = 20
FEATURE                 Location/Qualifiers
source                  1..20
                        mol_type = other DNA
                        organism = synthetic construct
SEQUENCE: 707
gttccgcgtt acataactta                                             20

SEQ ID NO: 708          moltype = DNA   length = 579
FEATURE                 Location/Qualifiers
source                  1..579
                        mol_type = other DNA
                        organism = synthetic construct
SEQUENCE: 708
tcacacctaa gccctaaaga gcctgtactt gttaacaccg aatgtgatgc cctgtaggcc   60
ttcctgacta tggcggccta cttatcctgt cccttttttt tccacaggag cgcaccatct  120
tcttcaagga cgacggcaac tacaagaccc gcgccgaggt gaagttcgag ggcgacaccc  180
tggtgaaccg catcgagctg aagggcatcg acttcaagga ggacggcaac atcctggggc  240
acaagctgga gtacaactac aacagccaca acgtctatat catggccgac aagcagaaga  300
acggcatcaa ggtgaacttc aagatccgcc acaacatcga ggacggcagc gtgcagctcg  360
ccgaccacta ccagcagaac acccccatcg gcgacggccc cgtgctgctg cccgacaacc  420
actacctgag cacccagtcc gccctgagca aagaccccaa cgagaagcgc gatcacatgg  480
tcctgctgga gttcgtgacc gccgccggga tcactctcgg catggacgag ctgtacaagt  540
aatggcttgt ttattgcagc ttataatggt tacaaataa                        579

SEQ ID NO: 709          moltype = DNA   length = 622
FEATURE                 Location/Qualifiers
source                  1..622
                        mol_type = other DNA
                        organism = synthetic construct
SEQUENCE: 709
tcacacctaa gccctaaaga aattttggga taggctttct ggcttttttac cggaaagccc   60
ctgcctgtac ttgttaacac cgaatgtgat gccctgtagg ccttcctgac tatggcggcc  120
tacttatcct gtcccttttt tttccacagg agcgcaccat cttcttcaag gacgacggca  180
actacaagac ccgcgccgag gtgaagttcg agggcgacac cctggtgaac cgcatcgagc  240
tgaagggcat cgacttcaag gaggacggca acatcctggg gcacaagctg gagtacaact  300
acaacagcca caacgtctat atcatggccg acaagcagaa gaacggcatc aaggtgaact  360
tcaagatccg ccacaacatc gaggacggca gcgtgcagct cgccgaccac taccagcaga  420
acaccccat cggcgacggc cccgtgctgc tgcccgacaa ccactacctg agcacccagt  480
ccgccctgag caaagacccc aacgagaagc gcgatcacat ggtcctgctg gagttcgtga  540
ccgccgccgg gatcactctc ggcatggacg agctgtacaa gtaatggctt gtttattgca  600
gcttataatg gttacaaata aa                                           622

SEQ ID NO: 710          moltype = DNA   length = 621
FEATURE                 Location/Qualifiers
source                  1..621
                        mol_type = other DNA
                        organism = synthetic construct
SEQUENCE: 710
gttccgcgtt acataactta aattttggga taggctttct ggcttttttac cggaaagccc   60
ctgcctgtac ttgttaacac cgaatgtgat gccctgtagg ccttcctgac tatggcggcc  120
tacttatcct gtcccttttt tttccacagg agcgcaccat cttcttcaag gacgacggca  180
actacaagac ccgcgccgag gtgaagttcg agggcgacac cctggtgaac cgcatcgagc  240
tgaagggcat cgacttcaag gaggacggca acatcctggg gcacaagctg gagtacaact  300
acaacagcca caacgtctat atcatggccg acaagcagaa gaacggcatc aaggtgaact  360
tcaagatccg ccacaacatc gaggacggca gcgtgcagct cgccgaccac taccagcaga  420
acaccccat cggcgacggc cccgtgctgc tgcccgacaa ccactacctg agcacccagt  480
ccgccctgag caaagacccc aacgagaagc gcgatcacat ggtcctgctg gagttcgtga  540
ccgccgccgg gatcactctc ggcatggacg agctgtacaa gtaatggctt gtttattgca  600
gcttataatg gttacaaata a                                            621

SEQ ID NO: 711          moltype = DNA   length = 610
FEATURE                 Location/Qualifiers
source                  1..610
                        mol_type = other DNA
                        organism = synthetic construct
SEQUENCE: 711
gtcggtctcg gatctcacac ctaagcccta aagaaacgcg tcatgtaggc tttctggctt   60
tttaccggaa agccctgcc tgtacttgtt aacaccgaat gtgatgccct gtaggccttc  120
ctgactatgg cggcctactt atcctgtccc ttttttttcc acaggagcgc accatcttct  180

-continued

```
tcaaggacga cggcaactac aagaccgcg ccgaggtgaa gttcgagggc gacaccctgg   240
tgaaccgcat cgagctgaag ggcatcgact tcaaggagga cggcaacatc ctggggcaca   300
agctggagta caactacaac agccacaacg tctatatcat ggccgacaag cagaagaacg   360
gcatcaaggt gaacttcaag atccgccaca acatcgagga cggcagcgtg cagctcgccg   420
accactacca gcagaacacc cccatcggcg acggccccgt gctgctgccc gacaaccact   480
acctgagcac ccagtccgcc ctgagcaaag accccaacga gaagcgcgat cacatggtcc   540
tgctggagtt cgtgaccgcc gccgggatca ctctcggcat ggacgagctg tacaagtaat   600
ggccgagacc                                                         610

SEQ ID NO: 712          moltype = DNA  length = 250
FEATURE                 Location/Qualifiers
source                  1..250
                        mol_type = other DNA
                        organism = synthetic construct
SEQUENCE: 712
tccaatgctc ttcagtaggg tcatgaaggt ttttcttttc ctgagaaaac aacacgtatt    60
gttttctcag gttttgcttt ttggcctttt tctagcttaa aaaaaaaaaa agcaaaagat   120
gctggtggtt ggcactcctg gtttccagga cggggttcaa atccctgcgg cgtctttgct   180
ttgactacta atctgtcttc aggactcttt ctgtatttct ccttttctct gcaggtgcta   240
gttcttggag                                                         250

SEQ ID NO: 713          moltype = DNA  length = 4216
FEATURE                 Location/Qualifiers
source                  1..4216
                        mol_type = other DNA
                        organism = synthetic construct
SEQUENCE: 713
ccctgaattc gcatctagac cagacagcac gtaattgacc gccagaacgc gcaatttgac    60
gaccagcgga tatgagattc tgtgcactca cgagaacgtt accgacgatt cccagtatt    120
tggcgctgcc ataatccaaa tatcaagcga atcccatgtg accgtctcag cgggcgacga   180
tctcagaaca gttaaacgta gttattaata gtaatcaatt acggggtcat tagttcatag   240
cccatatatg gagttccgcg ttacataact tacggtaaat ggcccgcctg gctgaccgcc   300
caacgacccc cgcccattga cgtcaataat gacgtatgtt cccatagtaa cgccaatagg   360
gactttccat tgacgtcaat gggtggagta tttacggtaa atggcccact tggcagtaca   420
tcaagtgtat catatgccaa gtacgccccc tattggcgtc aatgacggta aatggcccgc   480
ctggcattat gcccagtaca tgaccttatg gactttcct acttggcagt acatctacgt   540
attagtcatc gctattacca tggtgatgcg gttttggcag tacatcaatg ggcgtggata   600
gcggtttgac tcacggggat ttccaagtct ccaccccatt gacgtcaatg ggagtttgtt   660
ttggcaccaa aatcaacggg actttccaaa atgtcgtaac aactccgccc cattgacgca   720
aatgggcggt aggcgtgtac ggtgggaggt ctatataagc agagctggtt tagtgaaccg   780
tcagatccgc tagcgctacc ggtcgccact atggtgagca aggcgagga gctgttcacc   840
ggggtggtgc ccatcctggt cgagctggac ggcgacgtaa acggccacaa gttcagcgtg   900
tccggcgagg gcgagggcga tgccacctac ggcaagctga ccctgaagtt catctgcacc   960
accggcaagc tgcccgtgcc ctggcccacc ctcgtgacca ccctgaccta cggcgtgcag  1020
tgcttcagcc gctaccccga ccacatgaag cagcacgact tcttcaagtc cgccatgccc  1080
gaaggctacg tccaggagcg caccatcttc ttcaaggacg acggcaacta caagacccgc  1140
gccgaggtga agttcgaggg cgacaccctg gtgaaccgca tcgagctgaa gggcatcgac  1200
ttcaaggagg acggcaacat cctggggcac aagctggagt acaactacaa cagccacaac  1260
gtctatatca tggccgacaa gcagaagaac ggcatcaagg taagtgtaac gcaaaagttt  1320
acagtcacat ctctattacc atctggaata aaattctcta tttgatttct taactgaaga  1380
gtaaagcaaa tttcttttgtc acggacagcc cgggagcaca tgaggatcac ccatgtcgca  1440
cgagcgacat gaggatcacc catgtcgctt tcactagtct gtggtgtgat atccatggga  1500
gcacatgagg atcacccatg tgccacgagc gacatgagga tcacccatgt ccaatttgga  1560
tgaaattaac tgtttaggag aagttaccta agttaacaaa aggaatgtca ttgtgcactg  1620
aaaatgtaat acatttaaat gattaaatta aggccggcat ggtcccagcc tcctcgctgg  1680
cgccggctgg gcaacatgct tcggcatggc gaatgggact ggcgatccag acatgataag  1740
atacattgat gagtttggac aaaccacaac tagaatgcag tgaaaaaaat gctttatttg  1800
tgaaatttgt gatgctattg ctttatttgt aaccattata agctgcaata aacgctgttt  1860
atgagacggg aatgtacgga acctcgatgc cattgcatct gaacgcctgg cgatcagacg  1920
acactagagt cacgacgata ccaggtctgt catatgagcg gaacccatgc cagattgacc  1980
caactccatg aaaactacgat gcagagactg gactagtgca ctgcagtaca aatctgctcg  2040
tcagtggtgc tcacactgac gaatcatgta cagatcatac cgatgactgc ctggcgactc  2100
acaactaagc aagacagccg gaaccagcgc cggcgaacga cactgcatat atggcatatc  2160
acaacagtcc aactagtgca ctgcagtaca gcggccgca ttatcaaaaa ggatcttcac  2220
ctagatcctt ttaaattaaa aatgaagttt taaatcaatc taaagtatat atgagtaaac  2280
ttggtctgac agttaccaat gcttaatcag tgaggcacct atctcagcga tctgtctatt  2340
tcgttcatcc atagttgcct gactccccgt cgtgtagata actacgatac gggagggctt  2400
accatctggc cccagtgctg caatgatacc gcgggaccca cgctcaccgg ctccagattt  2460
atcagcaata aaccagccag ccggaagggc cgagccgaga gtggtcctg caactttatc  2520
cgcctccatc cagtctatta attgttgccg ggaagctaga gtaagtagtt cgccagttaa  2580
tagtttgcgc aacgttgttg ccattgctac aggcatcgtg gtgtcacgct cgtcgtttgg  2640
tatggcttca ttcagctccg gttcccaacg atcaaggcga gttacatgat cccccatgtt  2700
gtgcaaaaaa gcggttagct ccttcggtcc tccgatcgtt gtcagaagta agttggccgc  2760
agtgttatca ctcatggtta tggcagcact gcataattct cttactgtca tgccatccgt  2820
aagatgcttt tctgtgactg gtgagtactc aaccaagtca ttctgagaat agtgtatgcg  2880
gcgaccgagt tgctcttgcc cggcgtcaat acgggataat accgcgccac atagcagaac  2940
tttaaaagtg ctcatcattg gaaaacgttc ttcggggcga aaactctcaa ggatcttacc  3000
gctgttgaga tccagttcga tgtaacccac tcgtgcaccc aactgatctt cagcatcttt  3060
tactttcacc agcgtttctg ggtgagcaaa aacaggaagg caaaatgccg caaaaaaggg  3120
```

```
aataagggcg acacggaaat gttgaatact catactcttc cttttttcaat attattgaag    3180
catttatcag ggttattgtc tcatgagcgg atacatattt gaatgtattt agaaaaataa    3240
acaaataggg gttccgcgca catttccccg aaaagtgcca cctgtcatga ccaaaatccc    3300
ttaacgtgag ttttcgttcc actgagcgtc agaccccgta gaaaagatca aaggatcttc    3360
ttgagatcct ttttttctgc gcgtaatctg ctgcttgcaa acaaaaaaac caccgctacc    3420
agcggtggtt tgtttgccgg atcaagagct accaactctt tttccgaagg taactggctt    3480
cagcagagcg cagataccaa atactgttct tctagtgtag ccgtagttag gccaccactt    3540
caagaactct gtagcaccgc ctacatacct cgctctgcta atcctgttac cagtggctgc    3600
tgccagtggc gataagtcgt gtcttaccgg gttggactca agacgatagt taccggataa    3660
ggcgcagcgg tcgggctgaa cggggggttc gtgcacacag cccagcttgg agcgaacgac    3720
ctacaccgaa ctgagatacc tacagcgtga gctatgagaa agcgccacgc ttcccgaagg    3780
gagaaaggcg gacaggtatc cggtaagcgg cagggtcgga acaggagagc gcacgaggga    3840
gcttccaggg ggaaacgcct ggtatcttta tagtcctgtc gggtttcgcc acctctgact    3900
tgagcgtcga ttttgtgat gctcgtcagg ggggcggagc ctatggaaaa acgccagcaa    3960
cgcggccttt ttacggttcc tggccttttg ctggcctttt gctcacatgt tctttcctgc    4020
gttatcccct gattctgtgg ataaccgtgc ggccgcccct gaattcgcat ctagaggaat    4080
gtacggaacc tcgatgccat tgcatctgaa cgcctggcga tcagacgaca ctagagtcac    4140
gacgatacca ggtctgtcat atgagcggaa cccatgccaa attgacccaa ctccatgaaa    4200
ctacgatgca gagact                                                    4216
```

```
SEQ ID NO: 714          moltype = DNA  length = 4381
FEATURE                 Location/Qualifiers
source                  1..4381
                        mol_type = other DNA
                        organism = synthetic construct
SEQUENCE: 714
gcggccgcga ttatcaaaaa ggatcttcac ctagatcctt ttaaattaaa aatgaagttt    60
taaatcaatc taaagtatat atgagtaaac ttggtctgac agttaccaat gcttaatcag    120
tgaggcacct atctcagcga tctgtctatt tcgttcatcc atagttgcct gactccccgt    180
cgtgtagata actacgatac gggagggctt accatctggc cccagtgctg caatgatacc    240
gcgggaccca cgctcaccgg ctccagattt atcagcaata aaccagccag ccggaagggc    300
cgagcgcaga agtggtcctg caactttatc cgcctccatc cagtctatta attgttgccg    360
ggaagctaga gtaagtagtt cgccagttaa tagtttgcgc aacgttgttg ccattgctac    420
aggcatcgtg gtgtcacgct cgtcgtttgg tatggcttca ttcagctccg gttcccaacg    480
atcaaggcga gttacatgat cccccatgtt gtgcaaaaaa gcggttagct ccttcggtcc    540
tccgatcgtt gtcagaagta agttggccgc agtgttatca ctcatggtta tggcagcact    600
gcataattct cttactgtca tgccatccgt aagatgcttt tctgtgactg gtgagtactc    660
aaccaagtca ttctgagaat agtgtatgcg gcgaccgagt tgctcttgcc cggcgtcaat    720
acgggataat accgcgccac atagcagaac tttaaaagtg ctcatcattg gaaaacgttc    780
ttcggggcga aaactctcaa ggatcttacc gctgttgaga tccagttcga tgtaacccac    840
tcgtgcaccc aactgatctt cagcatcttt tactttcacc agcgtttctg ggtgagcaaa    900
aacaggaagg caaaatgccg caaaaaaggg aataagggcg acacggaaat gttgaatact    960
catactcttc cttttttcaat attattgaag catttatcag ggttattgtc tcatgagcgg    1020
atacatattt gaatgtattt agaaaaataa acaaataggg gttccgcgca catttccccg    1080
aaaagtgcca cctgtcatga ccaaaatccc ttaacgtgag ttttcgttcc actgagcgtc    1140
agacccgta gaaaagatca aaggatcttc ttgagatcct tttttttctgc gcgtaatctg    1200
ctgcttgcaa acaaaaaaac caccgctacc agcggtggtt tgtttgccgg atcaagagct    1260
accaactctt tttccgaagg taactggctt cagcagagcg cagataccaa atactgttct    1320
tctagtgtag ccgtagttag gccaccactt caagaactct gtagcaccgc ctacatacct    1380
cgctctgcta atcctgttac cagtggctgc tgccagtggc gataagtcgt gtcttaccgg    1440
gttggactca agacgatagt taccggataa ggcgcagcgg tcgggctgaa cggggggttc    1500
gtgcacacag cccagcttgg agcgaacgac ctacaccgaa ctgagatacc tacagcgtga    1560
gctatgagaa agcgccacgc ttcccgaagg gagaaaggcg gacaggtatc cggtaagcgg    1620
cagggtcgga acaggagagc gcacgaggga gcttccaggg ggaaacgcct ggtatcttta    1680
tagtcctgtc gggtttcgcc acctctgact tgagcgtcga ttttgtgat gctcgtcagg    1740
ggggcggagc ctatggaaaa acgccagcaa cgcggccttt ttacggttcc tggccttttg    1800
ctggcctttt gctcacatgt tctttcctgc gttatcccct gattctgtgg ataaccgtgc    1860
ggccgcccct gaattcgcat ctagaggaat gtacggaacc tcgatgccat tgcatctgaa    1920
cgcctggcga tcagacgaca ggtctgtcat atgagcggaa    1980
cccatgccag attgacccaa ctccatgaaa ctacgatgca gaccctgaat tcgcatctag    2040
accagacagc acgtaattga ccgccagaac gcgcaatttg acgaccagcg gatatgagat    2100
tctgtgcact cacgagaacg ttaccgacga tttcccagta tttggcgctg ccataatcca    2160
aatatcaagc gaatcccatg tgaccgtctc agcgggcgac gatctcagaa cagttaaacg    2220
tacttctgcc tgcctagaga tccagtttat cgattagtta ttaatagtaa tcaattacgg    2280
ggtcattagt tcatagccca tatatggagt tccgcgttac ataacttacg gtaaatggcc    2340
cgcctggctg accgcccaac gacccccgcc cattgacgtc aataatgacg tatgttccca    2400
tagtaacgcc aataggggact ttccattgac gtcaatgggt ggagtattta cggtaaactg    2460
cccacttggc agtacatcaa gtgtatcata tgccaagtac gccccctatt gacgtcaatg    2520
acggtaaatg gcccgcctgg cattatgccc agtacatgac cttatgggac tttcctactt    2580
ggcagtacat ctacgtatta gtcatcgcta ttaccatggt gatgcggttt tggcagtaca    2640
tcaatgggcg tggatagcgg tttgactcac ggggatttcc aagtctccac cccattgacg    2700
tcaatgggag tttgttttgg caccaaaatc aacgggactt tccaaaatgt cgtaacaact    2760
ccgccccatt gacgcaaatg ggcggtaggc gtgtacggtg ggaggtctat ataagcagag    2820
ctggtttagt gaaccgtcgg atcttccatt tcgggtgtca tatggtgacg    2880
aagggcgagg agctgttcac cggggtggtg cccatcctgg tcgagctgga cggcgacgta    2940
aacggccaca agttcagcgt gtccggcgag ggcgagggcg atgccaccta cggcaagctg    3000
accctgaagt tcatctgcac caccggcaag ctgcccgtgc cctggcccac cctcgtgacc    3060
accctgacct acggcgtgca gtgcttcagc cgctaccccg accacatgaa gcagcacgac    3120
ttcttcaagt ccgccatgcc cgaaggctac gtccaggagc gcaccatctt cttcaaggac    3180
```

```
gacggcaact acaagacccg cgccgaggtg aagttcgagg gcgacaccct ggtgaaccgc   3240
atcgagctga agggcatcga cttcaaggag gacggcaaca tcctggggca caagctggag   3300
tacaactaca acagccacaa cgtctatatc atggccgaca agcagaagaa cggcatcaag   3360
gtaagtgtaa cgcaaaagtt tacagtcaca tctctattac catctggaat aaaattctct   3420
atttgatttc ttaactgaag agtaaagcaa atttctttgt cacggacagc ccgggagcac   3480
atgaggatca cccatgtgcc acgagcgaca tgaggatcac ccatgtcgct ttcactagtc   3540
tgtggtgtga tatccatggg agcacatgag gatcacccat gtgccacgag cgacatgagg   3600
atcacccatg tccaatttgg atgaaattaa ctgtttagga gaagttacct aagttaacaa   3660
aaggaatgtc attgtgcact gaaaatgtaa tacatttaaa tgattaaatt aagcaggtgt   3720
ccctgacctg ggtagagtgg catctggttg gtgatgccca tctcatatca gccagggact   3780
gggcaactcc ttgttctctc cagcttggct tttgatccgt gcccatgcct ggcctggttc   3840
ttgggcgcgt ggggccggca tggtcccagc ctcctcgctg cgccggctg ggcaacatgc    3900
ttcggcatgg cgaatgggac tggcttgtt attgcagctt ataatggtta caaataaagc    3960
aatagcatca caaatttcac aaataaagca ttttttcac tgcattctag ttgtggtttg    4020
tccaaactca tcaatgtatc ttatgctgtt tatgagacgg gaatgtacgg aacctcgatg    4080
ccattgcatc tgaacgcctg gcgatcgac gacactagg tcacgacgat accaggtctg     4140
tcatatgagc ggaacccatg ccagattgac ccaactccat gaaactacga tgcagagact   4200
ggactagtgc actgcagtac aaatctgctc gtcagtggtg ctcacactga cgaatcatgt   4260
acagatcata ccgatgactg cctggcgact cacaactaag caagacagcc ggaaccagcg    4320
ccggcgaaca ccactgcata tatggcatat cacaacagtc caactagtgc actgcagtac   4380
a                                                                    4381
```

```
SEQ ID NO: 715          moltype = DNA   length = 4381
FEATURE                 Location/Qualifiers
source                  1..4381
                        mol_type = other DNA
                        organism = synthetic construct
SEQUENCE: 715
gcggccgcga ttatcaaaaa ggatcttcac ctagatcctt ttaaattaaa aatgaagttt   60
taaatcaatc taaagtatat atgagtaaac ttggtctgac agttaccaat gcttaatcag   120
tgaggcacct atctcagcga tctgtctatt tcgttcatcc atagttgcct gactccccgt   180
cgtgtagata actacgatac gggagggctt accatctggc cccagtgctg caatgatacc   240
gcgggaccca cgctcaccgg ctccagattt atcagcaata aaccagccag ccggaagggc   300
cgagcgcaga agtggtcctg caactttatc cgcctccatc cagtctatta attgttgccg   360
ggaagctaga gtaagtagtt cgccagttaa tagtttgcgc aacgttgttg ccattgctac   420
aggcatcgtg gtgtcacgct cgtcgtttgg tatggcttca ttcagctccg gttcccaacg   480
atcaaggcga gttacatgat cccccatgtt gtgcaaaaaa gcggttagct ccttcggtcc   540
tccgatcgtt gtcagaagta agttggccgc agtgttatca ctcatggtta tggcagcact   600
gcataattct cttactgtca tgccatccgt aagatgcttt tctgtgactg gtgagtactc   660
aaccaagtca ttctgagaat agtgtatgcg gcgaccgagt tgctcttgcc cggcgtcaat   720
acgggataat accgcgccac atagcagaac tttaaaagtg ctcatcattg gaaaacgttc   780
ttcggggcga aaactctcaa ggatcttacc gctgttgaga tccagttcga tgtaacccac   840
tcgtgcaccc aactgatctt cagcatcttt tactttcacc agcgtttctg ggtgagcaaa   900
aacaggaagg caaaatgccg caaaaaaggg aataagggcg acacggaaat gttgaatact   960
catactcttc ctttttcaat attattgaag catttatcag ggttattgtc tcatgagcgg   1020
atacatattt gaatgtattt agaaaaataa acaaataggg gttccgcgca catttccccg   1080
aaaagtgcca cctgtcatga ccaaaatccc ttaacgtgag ttttcgttcc actgagcgtc   1140
agaccccgta gaaaagatca aaggatcttc ttgagatcct ttttttctgc gcgtaatctg   1200
ctgcttgcaa acaaaaaaac caccgctacc agcggtggtt tgtttgccgg atcaagagct   1260
accaactctt tttccgaagg taactggctt cagcagagcg cagataccaa atactgttct   1320
tctagtgtag ccgtagttag gccaccactt caagaactct gtagcaccgc ctacatacct   1380
cgctctgcta atcctgttac cagtggctgc tgccagtggc gataagtcgt gtcttaccgg   1440
gttggactca agacgatagt taccggataa ggcgcagcgg tcgggctgaa cggggggttc   1500
gtgcacacag cccagcttgg agcgaacgac ctacaccgaa ctgagatacc tacagcgtga   1560
gctatgagaa agcgccacgc ttcccgaagg gagaaaggcg gacaggtatc cggtaagcgg   1620
cagggtcgga acaggagagc gcacgaggga gcttccaggg ggaaacgcct ggtatcttta   1680
tagtcctgtc gggtttcgcc acctctgact tgagcgtcga ttttttgtgat gctcgtcagg   1740
ggggcggagc ctatggaaaa acgccagcaa cgcggccttt ttacggttcc tggccttttg   1800
ctggcctttt gctcacatgt tctttcctgc gttatcccct gattctgtgg ataaccgtgc   1860
ggccgcccct gaattcgcat ctagaggaat gtacggaacc tcgatgccat ctgcatctgaa  1920
cgcctggcga tcagacgaca ctagagtcac gacgatacca ggtctgtcat atgagcggaa   1980
cccatgccag attgacccaa ctccatgaaa ctacgatgca gacctgaat tcgcatctag    2040
accagacagc acgtaattga ccgccagaac gcgcaatttg acgaccagcg gatatgagat   2100
tctgtgcact cacgagaacg ttaccgacga tttcccagta tttggcgctg ccataatcca   2160
aatatcaagc gaatcccatg tgaccgtctc agcgggcgac gatctcagaa cagttaaacg   2220
tacttctgcc tgcctagaga tccagtttat cgattagtta ttaatagtaa tcaattacgg   2280
ggtcattagt tcatagccca tatatggagt tccgcgttac ataacttacg gtaaatggcc   2340
cgcctggctg accgcccaac gacccccgcc cattgacgtc aataatgacg tatgttccca   2400
tagtaacgcc aatagggact ttccattgac gtcaatgggt ggagtattta cggtaaactg   2460
cccacttggc agtacatcaa gtgtatcata tgccaagtac gccccctatt gacgtcaatg   2520
acggtaaatg gcccgcctgg cattatgccc agtacatgac cttatgggac tttcctactt   2580
ggcagtacat ctacgtatta gtcatcgcta ttaccatggt gatgcggttt tggcagtaca   2640
tcaatgggcg tggatagcgg tttgactcac ggggatttcc aagtctccac cccattgacg   2700
tcaatgggag tttgttttgg caccaaaatc aacgggactt tccaaaatgt cgtaacaact   2760
ccgccccatt gacgcaaatg ggcggtaggc gtgtacggtg ggaggtctat ataagcagag   2820
ctggtttagt gaaccgtcgg atcttccatt tcgggtgtcg tgacggccac tatggtgagc   2880
aagggcgagg agctgttcac cggggtggtg cccatcctgg tcgagctgga cggcgacgta   2940
aacgccacac agttcagcgt gtccggcgag ggcgagggcg atgccaccta cggcaagctg   3000
accctgaagt tcatctgcac caccggcaag ctgcccgtgc cctggcccac cctcgtgacc   3060
```

```
accctgacct acggcgtgca gtgcttcagc cgctaccccg accacatgaa gcagcacgac   3120
ttcttcaagt ccgccatgcc cgaaggctac gtccaggagc gcaccatctt cttcaaggac   3180
gacggcaact acaagacccg cgccgaggtg aagttcgagg gcgacaccct ggtgaaccgc   3240
atcgagctga agggcatcga cttcaaggag gacggcaaca tcctggggca caagctggag   3300
tacaactaca acagccacaa cgtctatatc atggccgaca agcagaagaa cggcatcaag   3360
gtaagtgtaa cgcaaaagtt tacagtcaca tctctattac catctggaat aaaattctct   3420
atttgatttc ttaactgaag agtaaagcaa atttctttgt cacggacagc ccgggagcac   3480
atgaggatca cccatgtgcc acgagcgaca tgaggatcac ccatgtcgct ttcactagtc   3540
tgtggtgtga tatccatggg agcacatgag gatcacccat gtgccacgag cgacatgagg   3600
atcacccatg tccaatttgg atgaaattaa ctgtttagga gaagttacct aagttaacaa   3660
aaggaatgtc attgtgcact gaaaatgtaa tacatttaaa tgattaaatt aagcaggtgt   3720
ccctgacctg ggtagagtgg catctggttg gtgatgccca tctcatatca gccagggaca   3780
aagcaactcc ttgttctctc cagcttggct tttgatccgt gcccatgcct ggcctggttc   3840
ttggacacat agggccggca tggtcccagc ctcctcgctg gcgccgggctg ggcaacatgc   3900
ttcggcatgg cgaatgggac tggcttgttt attgcagctt ataatggtta caaataaagc   3960
aatagcatca caaatttcac aaataaagca ttttttttcac tgcattctag ttgtggtttg   4020
tccaaactca tcaatgtatc ttatgctgtt tatgagacgg gaatgtacgg aacctcgatg   4080
ccattgcatc tgaacgcctg gcgatcagac gacactagag tcacgacgat accaggtctg   4140
tcatatgagc ggaacccatg ccagattgac ccaactccat gaaactacga tgcagagact   4200
ggactagtgc actgcagtac aaatctgctc gtcagtggtg ctcacactga cgaatcatgt   4260
acagatcata ccgatgactg cctggcgact cacaactaag caagacagcc ggaaccagcg   4320
ccggcgaaca ccactgcata tatggcatat cacaacagtc caactagtgc actgcagtac   4380
a                                                                   4381
```

```
SEQ ID NO: 716          moltype = DNA  length = 4531
FEATURE                 Location/Qualifiers
source                  1..4531
                        mol_type = other DNA
                        organism = synthetic construct
SEQUENCE: 716
gcggccgcga ttatcaaaaa ggatcttcac ctagatcctt ttaaattaaa aatgaagttt   60
taaatcaatc taaagtatat atgagtaaac ttggtctgac agttaccaat gcttaatcag   120
tgaggcacct atctcagcga tctgtctatt tcgttcatcc atagttgcct gactccccgt   180
cgtgtagata actacgatac gggagggctt accatctggc cccagtgctg caatgatacc   240
gcgggaccca cgctcaccgg ctccagattt atcagcaata aaccagccag ccggaagggc   300
cgagcgcaga agtggtcctg caactttatc cgcctccatc cagtctatta attgttgccg   360
ggaagctaga gtaagtagtt cgccagttaa tagtttcgc aacgttgttg ccattgctac   420
aggcatcgtg gtgtcacgct cgtcgtttgg tatggcttca ttcagctccg gttcccaacg   480
atcaaggcga gttacatgat cccccatgtt gtgcaaaaa gcggttagct ccttcggtcc   540
tccgatcgtt gtcagaagta agttggccgc agtgttatca ctcatggtta tggcagcact   600
gcataattct cttactgtca tgccatccgt aagatgcttt tctgtgactg gtgagtactc   660
aaccaagtca ttctgagaat agtgtatgcg cgaccgagt tgctcttgcc cggcgtcaat   720
acgggataat accgcgccac atagcagaac tttaaaagtg ctcatcattg gaaaacgttc   780
ttcggggcga aaactctcaa ggatcttacc gctgttgaga tccagttcga tgtaacccac   840
tcgtgcaccc aactgatctt cagcatcttt tactttcacc agcgtttctg ggtgagcaaa   900
aacaggaagg caaaatgccg caaaaaaggg aataagggcg acacggaaat gttgaatact   960
catactcttc cttttttcaat attattgaag catttatcag ggttattgtc tcatgagcgg   1020
atacatattt gaatgtattt agaaaaataa acaaataggg gttccgcgca catttccccg   1080
aaaagtgcca cctgtcatga ccaaaatccc ttaacgtgag ttttcgttcc actgagcgtc   1140
agaccccgta gaaaagatca aaggatcttc ttgagatcct ttttttctgc gcgtaatctg   1200
ctgcttgcaa acaaaaaaac caccgctacc agcggtggtt tgtttgccgg atcaagagct   1260
accaactctt tttccgaagg taactggctt cagcagagc cagataccaa atactgttct   1320
tctagtgtag ccgtagttag gccaccactt caagaactct gtagcaccgc ctacatacct   1380
cgctctgcta atcctgttac cagtggctgc tgccagtggc gataagtcgt gtcttaccgg   1440
gttggactca agacgatagt taccggataa ggcgcagcgg tcgggctgaa cggggggttc   1500
gtgcacacag cccagcttgg agcgaacgac ctacaccgaa ctgagatacc tacagcgtga   1560
gctatgagaa agcgccacgc ttcccgaagg gagaaaggcg gacaggtatc cggtaagcgg   1620
cagggtcgga acaggagagc gcacgaggga gcttccaggg ggaaacgcct ggtatcttta   1680
tagtcctgtc gggtttcgcc acctctgact tgagcgtcga tttttgtgat gctcgtcagg   1740
ggggcggagc ctatggaaaa acgccagcaa cgcggccttt ttacggttcc tggccttttg   1800
ctggcctttt gctcacatgt tctttcctgc gttatcccct gattctgtgg ataaccgtgc   1860
ggccgcccct gaattcgcat ctagaggaat gtacggaacc tcgatgccat tgcatctgaa   1920
cgcctggcga tcagacgaca ctagagtcac gacgatacca ggtctgtcat atgagcggaa   1980
cccatgcag attgacccaa ctccatgaaa ctacgatctag gacccta act ccatgaaa   2040
accagacagc acgtaattga ccgccagaac gcgcaatttg acgaccagcg gatatgagat   2100
tctgtgcact cacgagaacg ttaccgacga tttcccagta tttggcgctg ccataatcca   2160
aatatcaagc gaatcccatg tgaccgtctc agcgggcgac gatctcagaa cagttaaacg   2220
tacttctgcc tgcctagaga tccagtttat cgattagtta ttaatagtaa tcaattacgg   2280
ggtcattagt tcatagccca tatatggagt tccgcgttac ataacttacg gtaaatggcc   2340
cgcctggctg accgcccaac gacccccgcc cattgacgtc aataatgacg tatgttccca   2400
tagtaacgcc aatagggact ttccattgac gtcaatgggt ggagtattta cggtaaactg   2460
cccacttggc agtacatcaa gtgtatcata tgccaagtac gccccctatt gacgtcaatg   2520
acggtaaatg gcccgcctgg cattatgccc agtacatgac cttatgggac tttcctactt   2580
ggcagtacat ctacgtatta gtcatcgcta ttaccatggt gatgcggttt tggcagtaca   2640
tcaatgggcg tggatagcgg tttgactcac ggggatttcc aagtctccac cccattgacg   2700
tcaatgggag tttgttttgg caccaaaatc aacgggactt ccaaaatgt cgtaacaact   2760
ccgccccatt gacgcaaatg ggcggtaggc gtgtacggtg ggaggtctat ataagcagag   2820
ctggtttagt gaaccgtcgg atcttccatt tcgggtgtcg tgacgccac tatggtgagc   2880
aagggcgagg agctgttcac cggggtggtg cccatcctgg tcgagctgga cggcgacgta   2940
```

-continued

```
aacggccaca agttcagcgt gtccggcgag ggcgagggcg atgccaccta cggcaagctg   3000
accctgaagt tcatctgcac caccggcaag ctgcccgtgc cctggcccac cctcgtgacc   3060
accctgacct acggcgtgca gtgcttcagc cgctaccccg accacatgaa gcagcacgac   3120
ttcttcaagt ccgccatgcc cgaaggctac gtccaggagc gcaccatctt cttcaaggac   3180
gacggcaact acaagacccg cgccgaggtg aagttcgagg gcgacaccct ggtgaaccgc   3240
atcgagctga agggcatcga cttcaaggag gacggcaaca tcctggggca caagctggag   3300
tacaactaca acagccacaa cgtctatatc atggccgaca agcagaagaa cggcatcaag   3360
gtaagtgtaa cgcaaaagtt tacagtcaca tctctattac catctggaat aaaattctct   3420
atttgatttc ttaactgaag agtaaagcaa atttctttgt cacggacagc ccgggagcac   3480
atgaggatca cccatgtgcc acgagcgaca tgaggatcac ccatgtcgct ttcactagtc   3540
tgtggtgtga tatccatggg agcacatgag gatcacccat gtgccacgag cgacatgagg   3600
atcacccatg tccaatttgg atgaaaattaa ctgtttagga gaagttacct aagttaacaa   3660
aaggaatgtc attgtgcact gaaaatgtaa tacatttaaa tgattaaatt aagcaggtgt   3720
ccctgacctg ggtagagtgg catctggttg gtgatgccca tctcatatca gccagggact   3780
gggcaactcc ttgttcatcc cagcttggct tttgatccgt gcccatgcct ggttcatgcc   3840
ttgggcgcgt gggtttcctt taaagaggtg gtattgtagc cagcttatat ttgcatctac   3900
agccatgttt ctagtccagc ttggtgtgca atactagatg agttaataac tggtccttgt   3960
ttctgatctg gttcccattg tgtaactgtg ttgattggga ggggccggca tggtcccagc   4020
ctcctcgctg gcgccggctg ggcaacatgc ttcggcatgg cgaatgggac tggcttgttt   4080
attgcagctt ataatggtta caaataaagc aatagcatca caaatttcac aaataaagca   4140
ttttttttcac tgcattctag ttgtggtttg tccaaactca tcaatgtatc ttatgctgtt   4200
tatgagacgg gaatgtacgg aacctcgatg ccattgcatc gtaacgcctg ggatcagac   4260
gacactagag tcacgacgat accaggtctg tcatatgagc ggaacccatg ccagattgac   4320
ccaactccat gaaactacga tgcagagact ggactagtgc actgcagtac aaatctgctc   4380
gtcagtggtg ctcacactga cgaatcatgt acagatcata ccgatgactg cctggcgact   4440
cacaactaag caagacagcc ggaaccagcg ccggcgaaca ccactgcata tatggcatat   4500
cacaacagtc caactagtgc actgcagtac a                                  4531
```

```
SEQ ID NO: 717              moltype = DNA   length = 4381
FEATURE                     Location/Qualifiers
source                      1..4381
                            mol_type = other DNA
                            organism = synthetic construct
SEQUENCE: 717
gcggccgcga ttatcaaaaa ggatcttcac ctagatcctt ttaaattaaa aatgaagttt   60
taaatcaatc taaagtatat atgagtaaac ttggtctgac agttaccaat gcttaatcag   120
tgaggcacct atctcagcga tctgtctatt tcgttcatcc atagttgcct gactccccgt   180
cgtgtagata actacgatac gggagggctt accatctggc cccagtgctg caatgatacc   240
gcgggaccca cgctcaccgg ctccagattt atcagcaata aaccagccag ccggaagggc   300
cgagcgcaga agtggtcctg caactttatc cgcctccatc cagtctatta attgttgccg   360
ggaagctaga gtaagtagtt cgccagttaa tagtttgcgc aacgttgttg ccattgctac   420
aggcatcgtg gtgtcacgct cgtcgtttgg tatggcttca ttcagctccg gttcccaacg   480
atcaaggcga gttacatgat cccccatgtt gtgcaaaaaa gcggttagct ccttcggtcc   540
tccgatcgtt gtcagaagta agttggccgc agtgttatca ctcatggtta tggcagcact   600
gcataattct cttactgtca tgccatccgt aagatgcttt tctgtgactg gtgagtactc   660
aaccaagtca ttctgagaat agtgtatgcg gcgaccgagt tgctcttgcc cggcgtcaat   720
acgggataat accgcgccac atagcagaac tttaaaagtg ctcatcattg gaaaacgttc   780
ttcggggcga aaactctcaa ggatcttacc gctgttgaga tccagttcga tgtaacccac   840
tcgtgcaccc aactgatctt cagcatcttt tactttcacc agcgtttctg ggtgagcaaa   900
aacaggaagg caaaatgccg caaaaaaggg aataagggcg acacgaaat gttgaatact   960
catactcttc cttttttcaat attattgaag catttatcag ggttattgtc tcatgagcgg   1020
atacatattt gaatgtattt agaaaaataa acaaataggg gttccgcgca catttccccg   1080
aaaagtgcca cctgtcatga ccaaaatccc ttaacgtgag ttttcgttcc actgagcgtc   1140
agacccccgta gaaaagatca aaggatcttc ttgagatcct ttttttctgc gcgtaatctg   1200
ctgcttgcaa acaaaaaaac caccgctacc agcggtggtt tgtttgccgg atcaagagct   1260
accaactctt tttccgaagg taactggctt cagcagagcg cagataccaa atactgttct   1320
tctagtgtag ccgtagttag gccaccactt caagaactct gtagcaccgc ctacatacct   1380
cgctctgcta atcctgttac cagtggctgc tgccagtggc gataagtcgt gtcttaccgg   1440
gttggactca agacgatagt taccggataa ggcgcagcgg tcgggctgaa cggggggttc   1500
gtgcacacag cccagcttgg agcgaacgac ctacaccgaa ctgagatacc tacagcgtga   1560
gctatgagaa agcgccacgc ttcccgaagg agaaaggcg gacaggtatc cggtaagcgg   1620
cagggtcgga acaggagagc gcacgaggga gcttccaggg ggaaacgcct ggtatcttta   1680
tagtcctgtc gggtttcgcc acctctgact tgagcgtcga ttttttgtgat gctcgtcagg   1740
ggggcggagc ctatggaaaa acgccagcaa cgcggccttt ttacggttcc tggccttttg   1800
ctggcctttt gctcacatgt tctttcctgc gttatcccct gattctgtgg ataaccgtgc   1860
ggccgcccct gaattcgcat ctagaggaat gtacggaacc tcgatgccat tgcatctgaa   1920
cgcctggcga tcagacgaca ctagagtcac gacgatacca ggtctgtcat atgagcggaa   1980
cccatgcag attgacccaa ctccatgaaa ctacgatgca gacctgaat tcgcatctag   2040
accagacagc acgtaattga ccgccagaac gcgcaatttg acgaccagcg gatatgagat   2100
tctgtgcact cacagagacg ttaccgacga tttcccagta tttggcgctg ccataatcca   2160
aatatcaagc gaatcccatg tgaccgtctc agcgggcgac gatctcagaa cagttaaacg   2220
tacttctgcc tgcctagaga tccagtttat cgattagtta ttaatagtaa tcaattacgg   2280
ggtcattagt tcatagccca tatatggagt tccgcgttac ataacttacg gtaaatggcc   2340
cgcctggctg accgcccaac gacccccgcc cattgacgtc aataatgacg tatgttccca   2400
tagtaacgcc aatagggact ttccattgac gtcaatgggt ggagtattta cggtaaactg   2460
cccacttggc agtacatcaa gtgtatcata tgccaagtac gccccctatt gacgtcaatg   2520
acggtaaatg gcccgcctgg cattatgccc agtacatgac cttatgggac tttcctactt   2580
ggcagtacat ctacgtatta gtcatcgcta ttaccatggt gatgcggttt tggcagtaca   2640
tcaatgggcg tggatagcgg tttgactcac ggggatttcc aagtctccac cccattgacg   2700
```

-continued

```
tcaatgggag tttgtttttgg caccaaaatc aacgggactt tccaaaatgt cgtaacaact  2760
ccgcccccatt gacgcaaatg ggcggtaggc gtgtacggtg ggaggtctat ataagcagag  2820
ctggtttagt gaaccgtcgg atcttccatt tcgggtgtcg tgacggccac tatggtgagc  2880
aagggcgagg agctgttcac cggggtggtg cccatcctgg tcgagctgga cggcgacgta  2940
aacggccaca agttcagcgt gtccggcgag ggcgagggcg atgccaccta cggcaagctg  3000
accctgaagt tcatctgcac caccggcaag ctgcccgtgc cctggcccac cctcgtgacc  3060
accctgacct acggcgtgca gtgcttcagc cgctaccccg accacatgaa gcagcacgac  3120
ttcttcaagt ccgccatgcc cgaaggctac gtccaggagc gcaccatctt cttcaaggac  3180
gacggcaact acaagacccg cgccgaggtg aagttcgagg gcgacaccct ggtgaaccgc  3240
atcgagctga agggcatcga cttcaaggag gacggcaaca tcctgggca caagctggag  3300
tacaactaca acagccacaa cgtctatatc atggccgaca agcagaagaa cggcatcaag  3360
gtaagtgtaa cgcaaaagtt tacagtcaca tctctattac catctggaat aaaattctct  3420
atttgatttc ttaactgaag agtaaagcaa atttctttgt cacggacagc ccgggagcac  3480
atgaggaatc cccatgtgcc acgagcgaca tgaggatcac ccatgtcgct ttcactagtc  3540
tgtggtgtga tatccatggg agcacatgag gatcacccat gtgccacgag cgacatgagg  3600
atcacccatg tccaatttgg atgaaattaa ctgtttagga gaagttacct aagttaacaa  3660
aaggaatgtc attgtgcact gaaaatgtaa tacatttaaa tgattaaatt aagcaggtgt  3720
ccctgacctg ggtagagtgg catctggttg gtgatgccca tctcatatca gccagggact  3780
gggcaactcc ttgttcatcc cagcttggct tttgatccgt gcccatgcct ggttcatgcc  3840
ttgggcgcgt ggggccggca tggtcccagc ctcctcgctg gcgccggctg ggcaacatgc  3900
ttcggcatgg cgaatgggac tggcttgttt attgcagctt ataatggtta caaataaagc  3960
aatagcatca caaatttcac aaataaagca tttttttcac tgcattctag ttgtggtttg  4020
tccaaactca tcaatgtatc ttatgctgtt tatgagacgg gaatgtacgg aacctcgatg  4080
ccattgcatc tgaacgcctg gcgatcagac gacactagg tcacgacgat accaggtctg  4140
tcatatgagc ggaacccatg ccagattgac ccaactccat gaaactacga tgcagagact  4200
ggactagtgc actgcagtac aaatctgctc gtcagtggtg ctcacactga cgaatcatgt  4260
acagatcata ccgatgactg cctggcgact cacaactaag caagacagcc ggaaccagcg  4320
ccggcgaaca ccactgcata tatggcatat cacaacagtc caactagtgc actgcagtac  4380
a                                                                     4381
```

SEQ ID NO: 718        moltype = DNA   length = 4531
FEATURE               Location/Qualifiers
source                1..4531
                      mol_type = other DNA
                      organism = synthetic construct
SEQUENCE: 718

```
gcggccgcga ttatcaaaaa ggatcttcac ctagatcctt ttaaattaaa aatgaagttt  60
taaatcaatc taaagtatat atgagtaaac ttggtctgac agttaccaat gcttaatcag  120
tgaggcacct atctgcctatt tcgttcatcc atagttgcct gactcccgt  180
cgtgtagata actacgatac gggagggctt accatctggc cccagtgctg caatgatacc  240
gcgggaccca cgctcaccgg ctccagattt atcagcaata aaccagccag ccggaagggc  300
cgagcgcaga agtggtcctg caactttatc cgcctccatc cagtctatta attgttgccg  360
ggaagctaga gtaagtagtt cgccagttaa tagtttgcgc aacgttgttg ccattgctac  420
aggcatcgtg gtgtcacgct cgtcgtttgg tatggcttca ttcagctccg gttcccaacg  480
atcaaggcga gttacatgat cccccatgtt gtgcaaaaaa gcggttagct ccttcggtcc  540
tccgatcgtt gtcagaagta agttggccgc agtgttatca ctcatggtta tggcagcact  600
gcataattct cttactgtca tgccatccgt aagatgcttt tctgtgactg gtgagtactc  660
aaccaagtca ttctgagaat agtgtatgcg gcgaccgagt tgctcttgcc cggcgtcaat  720
acgggataat accgcgccac atagcagaac tttaaaagtg ctcatcattg gaaaacgttc  780
ttcggggcga aaactctcaa ggatcttacc gctgttgaga tccagttcga tgtaacccac  840
tcgtgcaccc aactgatctt cagcatcttt tactttcacc agcgtttctg ggtgagcaaa  900
aacaggaagg caaaatgccg caaaaaaggg aataagggcg acacggaaat gttgaatact  960
catactcttc ctttttcaat attattgaag catttatcag ggttattgtc tcatgagcgg  1020
atacatattt gaatgtattt agaaaaataa acaaataggg gttccgcgca catttccccg  1080
aaaagtgcca cctgtcatga ccaaaatccc ttaacgtgag ttttcgttcc actgagcgtc  1140
agacccgta gaaaagatca aaggatcttc ttgagatcct ttttttctgc gcgtaatctg  1200
ctgcttgcaa acaaaaaaac caccgctacc agcggtggt tgtttgccgg atcaagagct  1260
accaactctt tttccgaagg taactggctt cagcagagcg cagataccaa atactgttct  1320
tctagtgtag ccgtagttag gccaccactt caagaactct gtagcaccgc ctacatacct  1380
cgctctgcta atcctgttac cagtggctgc tgccagtggc gataagtcgt gtcttaccgg  1440
gttggactca agacgatagt taccggataa ggcgcagcgg tcgggctgaa cggggggttc  1500
gtgcacacag cccagcttgg agcgaacgac ctacaccgaa ctgagatacc tacagcgtga  1560
gctatgagaa agcgccacgc ttcccgaagg agaaaggcg gacaggtatc cggtaagcgg  1620
cagggtcgga acaggagagc gcacgaggga gcttccaggg ggaaacgcct ggtatcttta  1680
tagtcctgtc gggtttcgcc acctctgact tgagcgtcga tttttgtgat gctcgtcagg  1740
ggggcggagc ctatggaaaa acgccagcaa cgcggccttt ttacggttcc tggccttttg  1800
ctggcctttt gctcacatgt tctttcctgc gttatcccct gattctgtgg ataaccgtgc  1860
ggccgcccct gaattcgcat ctagaggaat gtacggaacc tcgatgccat tgcatctgaa  1920
cgcctggctg tcagacgaca ctagagtcac gacgatacca ggtctgtcat atgagcggaa  1980
cccatgccag attgacccaa ctccatgaaa ctacgatgac ccctgaat cgcatctag  2040
accagacagc acgtaattga ccgccagaac gcgcaatttg acgaccagcg gatatgagat  2100
tctgtgcact cacgagaacg ttaccgacga tttcccagta tttggcgctg ccataatcca  2160
aatatcaagc gaatcccatg tgaccgtctc agcgggcgac gatctcagaa cagttaaacg  2220
tacttctgcc tgcctagaga tccagtttat cgattagtta ttaatagtaa tcaattacgg  2280
ggtcattagt tcatagccca tatatggagt tccgcgttac ataacttacg gtaaatggcc  2340
cgcctggctg accgcccaac gacccccgcc cattgacgtc aataatgacg tatgttccca  2400
tagtaacgcc aatagggact ttccattgac gtcaatgggt ggagtattta cggtaaactg  2460
cccacttggc agtacatcaa gtgtatcata tgccaagtac gccccctatt gacgtcaatg  2520
acggtaaatg gcccgcctgg cattatgccc agtacatgac cttatgggac tttcctactt  2580
```

```
ggcagtacat ctacgtatta gtcatcgcta ttaccatggt gatgcggttt tggcagtaca   2640
tcaatgggcg tggatagcgg tttgactcac ggggatttcc aagtctccac cccattgacg   2700
tcaatgggag tttgtttlgg caccaaaatc aacgggactt tccaaaatgt cgtaacaact   2760
ccgcccatt gacgcaaatg ggcggtaggc gtgtacggtg gaggtctat ataagcagag   2820
ctggtttagt gaaccgtcgg atcttccatt tcgggtgtcg tgacggccac tatggtgagc   2880
aagggcgagg agctgttcac cggggtggtg cccatcctgg tcgagctgga cggcgacgta   2940
aacggccaca agttcagcgt gtccggcgag ggcgagggcg atgccaccta cggcaagctg   3000
accctgaagt tcatctgcac caccggcaag ctgcccgtgc cctggcccac cctcgtgacc   3060
accctgacct acggcgtgca gtgcttcagc cgctacccg accacatgaa gcagcacgac   3120
ttcttcaagt ccgccatgcc cgaaggctac gtccaggagc gcaccatctt cttcaaggac   3180
gacggcaact acaagacccg cgccgaggtg aagttcgagg gcgacaccct ggtgaaccgc   3240
atcgagctga agggcatcga cttcaaggag gacggcaaca tcctggggca caagctggag   3300
tacaactaca acagccacaa cgtctatatc atggccgaca agcagaagaa cggcatcaag   3360
gtaagtgtaa cgcaaaagtt tacagtcaca tctctattac catctggaat aaaattctct   3420
atttgatttc ttaactgaag agtaaagcaa atttctttgt cacggacagc ccgggagcac   3480
atgaggatca cccatgtgcc acgagcgaca tgaggatcac ccatgtcgct ttcactagtc   3540
tgtggtgtga tatccatggg agcacatgag gatcacccat gtgccacgag cgacatgagg   3600
atcacccatg tccaatttgg atgaaattaa ctgtttagga gaagttacct aagttaacaa   3660
aaggaatgtc attgtgcact gaaaatgtaa tacatttaaa tgattaaatt aagcaggtgt   3720
ccctgacctg ggtagagtgg catctggttg gtgatgccca tctcatatca gccagggaca   3780
aagcaactcc ttgttcatcc cagcttggct tttgatccgt gcccatgcct ggttcatgcc   3840
ttggacacat aggtttcctt taaagaggtg gtattgtagc cagcttatat ttgcatctac   3900
agccatgttt ctagtccagc ttggtgtgca atactagatg agttaataac tggtccttgt   3960
ttctgatctg gttcccattg tgtaactgtg ttgattggga agggccggca tggtcccagc   4020
ctcctcgctg gcgccggctg ggcaacatgc ttcggcatgg cgaatgggac tggcttgttt   4080
attgcagctt ataatggtta caaataaagc aatagcatca caaatttcac aaataaagca   4140
ttttttttcac tgcattctag ttgtggtttg tccaaactca tcaatgtatc ttatgctgtt   4200
tatgagacgg gaatgtacgg aacctcgatg ccattgcatc tgaacgcctg gcgatcagac   4260
gacactagag tcacgacgat accaggtctg tcatatgagc ggaacccatg ccagattgac   4320
ccaactccat gaaactacga tgcagagact ggactagtgc actgcagtac aaatctgctc   4380
gtcagtggtg ctcacactga cgaatcatgt acagatcata ccgatgactg cctggcgact   4440
cacaactaag caagacagcc ggaaccagcg ccggcgaaca ccactgcata tatggcatat   4500
cacaacagtc caactagtgc actgcagtac a                                    4531
```

```
SEQ ID NO: 719           moltype = DNA  length = 4381
FEATURE                  Location/Qualifiers
source                   1..4381
                         mol_type = other DNA
                         organism = synthetic construct
SEQUENCE: 719
gcggccgcga ttatcaaaaa ggatcttcac ctagatcctt ttaaattaaa aatgaagttt   60
taaatcaatc taaagtatat atgagtaaac ttggtctgac agttaccaat gcttaatcag   120
tgaggcacct atctcagcga tctgtctatt tcgttcatcc atagttgcct gactccccgt   180
cgtgtagata actacgatac gggagggctt accatctggc cccagtgctg caatgatacc   240
gcgggaccca cgctcaccgg ctccagattt atcagcaata aaccagccag ccggaagggc   300
cgagcgcaga agtggtcctg caactttatc cgcctccatc cagtctatta attgttgccg   360
ggaagctaga gtaagtagtt cgccagttaa tagtttgcgc aacgttgttg ccattgctac   420
aggcatcgtg gtgtcacgct cgtcgtttgg tatggcttca ttcagctccg gttcccaacg   480
atcaaggcga gttacatgat cccccatgtt gtgcaaaaaa gcggttagct ccttcggtcc   540
tccgatcgtt gtcagaagta agttggccgc agtgttatca ctcatggtta tggcagcact   600
gcataattct cttactgtca tgccatccgt aagatgcttt tctgtgactg gtgagtactc   660
aaccaagtca ttctgagaat agtgtatgcg gcgaccgagt tgctcttgcc cggcgtcaat   720
acgggataat accgcgccac atagcagaac tttaaaagtg ctcatcattg gaaaacgttc   780
ttcggggcga aaactctcaa ggatcttacc gctgttgaga tccagttcga tgtaacccac   840
tcgtgcaccc aactgatctt cagcatcttt tactttcacc agcgtttctg ggtgagcaaa   900
aacaggaagg caaaatgccg caaaaaaggg aataagggcg acacggaaat gttgaatact   960
catactcttc cttttlcaat attattgaag catttatcag ggttattgtc tcatgagcgg   1020
atacatattt gaatgtattt agaaaaataa acaaataggg gttccgcgca catttccccg   1080
aaaagtgcca cctgtcatga ccaaaatccc ttaacgtgag ttttcgttcc actgagcgtc   1140
agaccccgta gaaaagatca aaggatcttc ttgagatcct tttttctgc gcgtaatctg   1200
ctgcttgcaa acaaaaaaac caccgctacc agcggtggtt tgtttgccgg atcaagagct   1260
accaactctt tttccgaagg taactggctt cagcagagcg cagataccaa atactgttct   1320
tctagtgtag ccgtagttag gccaccactt caagaactct gtagcaccgc ctacatacct   1380
cgctctgcta atcctgttac cagtggctgc tgccagtgga gataagtcgt gtcttaccgg   1440
gttggactca agacgatagt taccggataa ggcgcagcgg tcgggctgaa cggggggttc   1500
gtgcacacag cccagcttgg agcgaacgac ctacaccgaa ctgagatacc tacagcgtga   1560
gctatgagaa agcgccacgc ttcccgaagg agaaaggcg gacaggtatc cggtaagcgg   1620
cagggtcgga acaggagagc gcacgaggga gcttccaggg ggaaacgcct ggtatcttta   1680
tagtcctgtc gggtttcgcc acctctgact tgagtcgtga ttttttgtgat gctcgtcagg   1740
ggggcggagc ctatggaaaa acgccagcaa cgcggccttt ttacggttcc tggccttttg   1800
ctggcctttt gctcacatgt tctttcctgc gttatcccct gattctgtgg ataaccgtgc   1860
ggccgcccct gaattcgcat ctagaggaat gtacggaacc tcgatgccat tgcatctgaa   1920
cgcctggcga tcagacgaca ctagagtcac gacgatacca ggtctgtcat atgagcggaa   1980
cccatgccat tgaccaa ctccatgacga ctacgatcga gaccctgaat tcgtcatctag   2040
accagacagc acgtaattga ccgccagaac gcgcaatttg acgaccagcg gatatgagat   2100
tctgtgcact cacgagaacg ttaccgacga tttcccagta tttggcgctg ccataatcca   2160
aatatcaagc gaatcccatg tgaccgtctc agcgggcgac gatctcagaa cagttaaacg   2220
tacttctgcc tgcctagaga tccagtttat cgattagtta ttaatagtaa tcaattacgg   2280
ggtcattagt tcatagccca tatatggagt tccgcgttac ataacttacg gtaaatggcc   2340
```

-continued

```
cgcctggctg accgcccaac gaccccgcc cattgacgtc aataatgacg tatgttccca    2400
tagtaacgcc aatagggact ttccattgac gtcaatgggt ggagtattta cggtaaactg    2460
cccacttggc agtacatcaa gtgtatcata tgccaagtac gccccctatt gacgtcaatg    2520
acggtaaatg gcccgcctgg cattatgccc agtacatgac cttatgggac tttcctactt    2580
ggcagtacat ctacgtatta gtcatcgcta ttaccatggt gatgcggttt tggcagtaca    2640
tcaatgggcg tggatagcgg tttgactcac ggggatttcc aagtctccac cccattgacg    2700
tcaatgggag tttgttttgg caccaaaatc aacgggactt tccaaaatgt cgtaacaact    2760
ccgccccatt gacgcaaatg ggcggtaggc gtgtacggtg ggaggtctat ataagcagag    2820
ctggtttagt gaaccgtcgg atcttccatt tcgggtgtcg tgacggccac tatggtgagc    2880
aagggcgagg agctgttcac cggggtggtg cccatcctgg tcgagctgga cggcgacgta    2940
aacggccaca agttcagcgt gtccggcgag ggcgagggcg atgccaccta cggcaagctg    3000
accctgaagt tcatctgcac caccggcaag ctgcccgtgc cctggcccac cctcgtgacc    3060
accctgacct acggcgtgca gtgcttcagc cgctaccccg accacatgaa gcagcacgac    3120
ttcttcaagt ccgccatgcc cgaaggctac gtccaggagc gcaccatctt cttcaaggac    3180
gacggcaact acaagacccg cgccgaggtg aagttcgagg gcgacaccct ggtgaaccgc    3240
atcgagctga agggcatcga cttcaaggag gacggcaaca tcctggggca caagctggag    3300
tacaactaca acagccacaa cgtctatatc atggccgaca gcagaagaa cggcatcaag    3360
gtaagtgtaa cgcaaaagtt tacagtcaca tctctattac catctggaat aaaattctct    3420
atttgatttc ttaactgaag agtaaagcaa atttctttgt cacggacagc ccgggagcac    3480
atgaggatca cccatgtgcc acgagcgaca tgaggatcac ccatgtcgct ttcactagtc    3540
tgtggtgtga tatccatggg agcacatgag gatcacccat gtgccacgag cgacatgagg    3600
atcacccatg tccaatttgg atgaaattaa ctgtttagga gaagttacct aagttaacaa    3660
aaggaatgtc attgtgcact gaaaatgtaa tacatttaaa tgattaaatt aagcaggtgt    3720
ccctgacctg ggtagagtgg catctggttg gtgatgccca tctcatatca gccagggaca    3780
aagcaactcc ttgttcatcc cagcttggct tttgatccgt gcccatgcct ggttcatgcc    3840
ttggacacat agggccggca tggtcccagc ctcctcgctg gcgccggctg ggcaacatgc    3900
ttcggcatgg cgaatgggac tggcttgttt attgcagctt ataatggtta caaataaagc    3960
aatagcatca caaatttcac aaataaaagc attttttttcac tgcattctag ttgtggtttg    4020
tccaaactca tcaatgtatc ttatgctgtt tatgagacgg gaatgtacgg aacctcgatg    4080
ccattgcatc tgaacgcctg gcgatcagac gacactagag tcacgacgat accaggtctg    4140
tcatatgagc ggaacccatg ccagattgac ccaactccat gaaactacga tgcagagact    4200
ggactagtgc actgcagtac aaatctgctc gtcagtggtg ctcacactga cgaatcatgt    4260
acagatcata ccgatgactg cctggcgact cacaactaag caagacagcc ggaaccagcg    4320
ccggcgaaca ccactgcata tatggcatat cacaacagtc caactagtgc actgcagtac    4380
a                                                                    4381

SEQ ID NO: 720             moltype = DNA  length = 5312
FEATURE                    Location/Qualifiers
source                     1..5312
                           mol_type = other DNA
                           organism = synthetic construct
SEQUENCE: 720
actggtctct gcaggctcct tgttctctcc agcttggctt ttgatccgtg cccatgcctg    60
gcctggttct tggggccggc atggtcccag cctcctcgct ggcgccggct gggcaacatg    120
cttcggcatg gcgaatggga ctggcttgtt tattgcagct tataatggtt acaaataaag    180
caatagcatc acaaatttca caaataaagc attttttttca ctgcattcta gttgtggttt    240
gtccaaactc atcaatgtat cttatgctgt ttatgagacg ggaatgtacg gaacctcgat    300
gccattgcat ctgaacgcct ggcgatcaga cgacactaga gtcacgacga taccaggtct    360
gtcatatgag cggaacccat gccagattga cccaactcca tgaaactacg atgcagagac    420
tggactagtg cactgcagta caagagaccg tcgcggccgc gattatcaaa aaggatcttc    480
acctagatcc ttttaaatta aaaatgaagt tttaaatcaa tctaaagtat atatgagtaa    540
acttggtctg acagttacca atgcttaatc agtgaggcac ctatctcagc gatctgtcta    600
tttcgttcat ccatagttgc ctgactcccc gtcgtgtaga taactacgat acgggagggc    660
ttaccatctg gccccagtgc tgcaatgata ccgcgggacc cacgctcacc ggctccagat    720
ttatcagcaa taaaccagcc agccggaagg gccgagcgca gaagtggtcc tgcaacttta    780
tccgcctcca tccagtctat taattgttgc cgggaagcta gagtaagtag ttcgccagtt    840
aatagtttgc gcaacgttgt tgccattgct acaggcatcg tggtgtcacg ctcgtcgttt    900
ggtatggctt cattcagctc cggttcccaa cgatcaaggc gagttacatg atcccccatg    960
ttgtgcaaaa aagcggttag ctccttcggt cctccgatcg ttgtcagaag taagttggcc    1020
gcagtgttat cactcatggt tatggcagca ctgcataatt ctcttactgt catgccatcc    1080
gtaagatgct tttctgtgac tggtgagtac tcaaccaagt cattctgaga atagtgtatg    1140
cggcgaccga gttgctcttg cccggcgtca atacgggata ataccgcgcc acatagcaga    1200
actttaaaag tgctcatcat tggaaaacgt tcttcggggc gaaaactctc aaggatctta    1260
ccgctgttga tccagttcga tgtaaccc actcgtgcac ccaactgatc ttcagcatct    1320
tttactttca ccagcgtttc tgggtgagca aaaacaggaa ggcaaaatgc cgcaaaaaag    1380
ggaataaggg cgacacggaa atgttgaata ctcatactct tcctttttca atattattga    1440
agcatttatc agggttattg tctcatgagc ggatacatat ttgaatgtat ttagaaaaat    1500
aaacaaatag gggttccgcg cacatttccc cgaaaagtgc cacctgtcat gaccaaaatc    1560
ccttaacgtg agttttcgtt ccactgagcg tcagaccccg tagaaaagat caaaggatct    1620
tcttgagatc ctttttttct gcgcgtaatc tgctgcttgc aaacaaaaaa accaccgcta    1680
ccagcggtgg tttgtttgcc ggatcaagag ctaccaactc tttttccgaa ggtaactggc    1740
ttcagcagag cgcagatacc aaatactgtt cttctagtgt agccgtagtt aggccaccac    1800
ttcaagaact ctgtagcacc gcctacatac ctcgctctgc taatcctgtt accagtggct    1860
gctgccagtg gcgataagtc gtgtcttacc gggttggact caagacgata gttaccggat    1920
aaggcgcagc ggtcgggctg aacggggggt tcgtgcacac agcccagctt ggagcgaacg    1980
acctacaccg aactgagata cctacagcgt gagctatgag aaagcgccac gcttcccgaa    2040
gggagaaagg cggacaggta tccggtaagc ggcagggtcg aacaggagag cgcacgagg    2100
gagcttccag ggggaaacgc ctggtatctt tatagtcctg tcgggtttcg ccacctctga    2160
cttgagcgtc gatttttgtg atgctcgtca ggggggcgga gcctatggaa aaacgccagc    2220
```

```
aacgcggcct ttttacggtt cctggccttt tgctggcctt ttgctcacat gttctttcct  2280
gcgttatccc ctgattctgt ggataaccgt gcggccgccc ctgaattcgc atctagagga  2340
atgtacggaa cctcgatgcc attgcatctg aacgcctggc gatcagacga cactagagtc  2400
acgacgatac caggtctgtc atatgagcgg aacccatgcc agattgaccc aactccatga  2460
aactacgatg cagaccctgg agaccgagtc gaccgacagc cttccaaatg ttcttcgggt  2520
gatgctgcca acttagtcga ccgacagcct tccaaatgtt cttctcaaac ggaatcgtcg  2580
tatccagcct actcgctatt gtcctcaatg ccgtattaaa tcataaaaag aaataagaaa  2640
aagaggtgcg agcctctttt ttgtgtgaca aaataaaaac atctacctat tcatatacgc  2700
tagtgtcata gtcctgaaaa tcatctgcat caagaacaat ttcacaactc ttatactttt  2760
ctcttacaag tcgttcggct tcatctggat tttcagcctc tatacttact aaacgtgata  2820
aagtttctgt aatttctact gtatcgacct gcagactggc tgtgtataag ggagcctgac  2880
atttatattc cccagaacat caggttaatg gcgtttttga tgtcattttc gcggtggctg  2940
agatcagcca cttcttcccc gataacggaa accggcacac tggccatatc ggtggtcatc  3000
atgcgccagc tttcatcccc gatatgcacc accgggtaaa gttcacggga gactttatct  3060
gacagcagac gtgcactggc caggggggatc accatccgtc gcccgggcgt gtcaataata  3120
tcactctgta catccacaaa cagacgataa cggctctctc ttttataggt gtaaacctta  3180
aactgcattt caccagtccc tgttctcgtc agcaaaagag ccgttcattt caataaaccg  3240
ggcgacctca gccatccctt cctgattttc cgctttccag cgttcggcac gcagacgacg  3300
ggcttcattc tgcatggttg tgcttaccag accggagata ttgacatcat atatgccttg  3360
agcaactgat agctgtcgct gtcaactgtc actgtaatac gctgcttcat agcacacctc  3420
tttttgaggt ctcatacaaa tctgctcgtc agtggtgctc acactgacga atcatgtaca  3480
gatcataccg atgactgcct ggcgactcac aactaagcaa gacagccgga accagcgcgg  3540
gcgaacacca ctgcatatat ggcatatcac aacagtccaa ctagtgcact gcagtacaac  3600
tggtctctcc ctgaattcgc atctagacca gacagcacgt aattgaccgc cagaacgcgc  3660
aatttgacga ccagcggata tgagattctg tgcactcacg agaacgttac cgacgatttc  3720
ccagtatttg gcgctgccat aatccaaata tcaagcgaat cccatgtgac cgtctcagcg  3780
ggcgacgatc tcagaacagt taaacgtact tctgcctgcc tagagatcca gtttatcgat  3840
tagttattaa tagtaatcaa ttacgggggtc attagttcat agcccatata tggagttccg  3900
cgttacataa cttacggtaa atggcccgcc tggctgaccg cccaacgacc cccgcccatt  3960
gacgtcaata atgacgtatg ttcccatagt aacgccaata gggactttcc attgacgtca  4020
atgggtggag tatttacggt aaaactgccca cttggcagta catcaagtgt atcatatgcc  4080
aagtacgccc cctattgacg tcaatgacgg taaatggccc gcctggcatt atgcccagta  4140
catgacctta tgggactttc ctacttggca gtacatctac gtattagtca tcgctattac  4200
catggtgatg cggtttttggc agtacatcaa tgggcgtgga tagcggtttg actcacgggg  4260
atttccaagt ctccacccca ttgacgtcaa tgggagtttg ttttggcacc aaaatcaacg  4320
ggactttcca aaatgtcgta acaactccgc cccattgacg caaatgggcg gtaggcgtgt  4380
acggtgggag gtctatataa gcagagctgg tttagtgaac cgtcggatct tccatttcgg  4440
gtgtcgtgac ggccactatg gtgagcaagg gcgaggagct gttcaccggg gtggtcccca  4500
tcctggtcga gctggacggc gacgtaaacg gccacaagtt cagcgtgtcc ggcgagggcg  4560
agggcgatgc cacctacggc aagctgaccc tgaagttcat ctgcaccacc ggcaagctgc  4620
ccgtgccctg gcccaccctc gtgaccaccc tgacctacgg cgtgcagtgc ttcagccgct  4680
accccgacca catgaagcag cacgacttct tcaagtccgc catgcccgaa ggctacgtcc  4740
aggagcgcac catcttcttc aaggacgacg gcaactacaa gacccgcgcc gaggtgaagt  4800
tcgagggcga caccctggtg aaccgcatcg agctgaaggg catcgacttc aaggaggacg  4860
gcaacatcct ggggcacaag ctggagtaca actacaacag ccacaacgtc tatatcatgg  4920
ccgacaagca gaagaacggc atcaaggtaa gtgtaacgca aaagtttaca gtcacatctc  4980
tattaccatc tggaataaaa ttctctattt gatttcttaa ctgaagagta aagcaaattt  5040
ctttgtcacg gacagcccgg gagcacatga ggatcaccca tgtgccacga gcgacatgag  5100
gatcacccat gtcgctttca ctagtctgtg gtgtgatatc catgggagca catgaggatc  5160
acccatgtgc cacgagcgac atgaggatca cccatgtcca atttggatga aattaactgt  5220
ttaggagaag ttacctaagt taacaaaagg aatgtcattg tgcactgaaa atgtaataca  5280
tttaaatgat taaattaagc agtgagacca gt                                 5312
```

```
SEQ ID NO: 721          moltype = DNA  length = 5280
FEATURE                 Location/Qualifiers
source                  1..5280
                        mol_type = other DNA
                        organism = synthetic construct
SEQUENCE: 721
actggtctct gcaggctcct tgttctctac ctggttcttg gggccggcat ggtcccagcc  60
tcctcgctgg cgccggctgg gcaacatgct tcggcatggc gaatgggact ggcttgttta  120
ttgcagctta taatggttac aaataaagca atagcatcac aaatttcaca aataaagcat  180
tttttttcact gcattctagt tgtggtttgt ccaaactcat caatgtatct tatgctgttt  240
atgagacggg aatgtacgga acctcgatgc cattgcatct gaacgcctgg cgatcagacg  300
acactagagt cacgacgata ccaggtctgt catatgagcg gaacccatgc cagattgacc  360
caactccatg aaactacgat gcagagactg gactagtgca ctgcagtaca agagaccgtc  420
gcggccgcga ttatcaaaaa ggatcttcac ctagatcctt ttaaattaaa aatgaagttt  480
taaatcaatc taaagtatat atgagtaaac ttggtctgac agttaccaat gcttaatcag  540
tgaggcacct atctctcagcga tctgtctatt tcgttcatcc atagttgcct gactccccgt  600
cgtgtagata actacgatac gggagggcct accatctggc cccagtgctg caatgatacc  660
gcgggaccca cgctcaccgg ctccagattt atcagcaata aaccagccag ccggaagggc  720
cgagcgcaga agtggtcctg caactttatc cgcctccatc cagtctatta attgttgccg  780
ggaagctaga gtaagtagtt cgccagttaa tagtttcgc aacgttgttg ccattgctac  840
aggcatcgtg gtgtcacgct cgtcgtttgg tatggcttca ttcagctccg gttcccaacg  900
atcaaggcga gttacatgat cccccatgtt gtgcaaaaaa gcggttagct ccttcggtcc  960
tccgatcgtt gtcagaagta agttggccgc agtgttatca ctcatggtta tggcagcact  1020
gcataattct cttactgtca tgccatccgt aagatgcttt tctgtgactg gtgagtactc  1080
aaccaagtca ttctgagaat agtgtatgcg gcgaccgagt tgctcttgcc cggcgtcaat  1140
acgggataat accgcgccac atagcagaac tttaaaagtg ctcatcattg gaaaacgttc  1200
```

```
ttcggggcga aaactctcaa ggatcttacc gctgttgaga tccagttcga tgtaacccac   1260
tcgtgcaccc aactgatctt cagcatcttt tacttttcacc agcgtttctg ggtgagcaaa   1320
aacaggaagg caaaatgccg caaaaaaggg aataagggcg acacggaaat gttgaatact   1380
catactcttc cttttttcaat attattgaag catttatcag ggttattgtc tcatgagcgg   1440
atacatattt gaatgtattt agaaaaataa acaaatgggg gttccgcgca catttccccg   1500
aaaagtgcca cctgtcatga ccaaaatccc ttaacgtgag ttttcgttcc actgagcgtc   1560
agaccccgta gaaaagatca aaggatcttc ttgagatcct ttttttctgc gcgtaatctg   1620
ctgcttgcaa acaaaaaaac caccgctacc agcggtggtt tgtttgccgg atcaagagct   1680
accaactctt tttccgaagg taactggctt cagcagagcg cagataccaa atactgttct   1740
tctagtgtag ccgtagttag gccaccactt caagaactct gtagcaccgc ctacatacct   1800
cgctctgcta atcctgttac cagtggctgc tgccagtggc gataagtcgt gtcttaccgg   1860
gttggactca agacgatagt taccggataa ggcgcagcgg tcgggctgaa cggggggttc   1920
gtgcacacag cccagcttgg agcgaacgac ctacaccgaa ctgagatacc tacagcgtga   1980
gctatgagaa agcgccacgc ttcccgaagg gagaaaggcg gacaggtatc cggtaagcgg   2040
cagggtcgga acaggagagc gcacgaggga gcttccaggg ggaaacgcct ggtatcttta   2100
tagtcctgtc gggtttcgcc acctctgact tgagcgtcga ttttttgtgat gctcgtcagg   2160
ggggcggagc ctatggaaaa acgccagcaa cgcggccttt ttacggttcc tggccttttg   2220
ctggcctttt gctcacatgt tctttcctgc gttatcccct gattctgtgg ataaccgtgc   2280
ggccgcccct gaattcgcat ctagaggaat gtacggaacc tcgatgccat tgcatctgaa   2340
cgcctggcga tcagacgaca ctagagtcac gacgatacca ggtctgtcat atgagcggaa   2400
cccatgccag attgacccaa ctccatgaaa ctacgatgca gaccctggag accgagtcga   2460
ccgacagcct tccaaatgtt cttcgggtga tgctgccaac ttagtcgacc gacagccttc   2520
caaatgttct tctcaaacgg aatcgtcgta tccagcctac tcgctattgt cctcaatgcc   2580
gtattaaatc ataaaaagaa ataagaaaaa gaggtgcgag cctctttttt gtgtgacaaa   2640
ataaaaacat ctacctattc atatacgcta gtgtcatagt cctgaaaatc atctgcatca   2700
agaacaattt cacaactctt atactttttct cttacaagtc gttcggcttc atctggatttt   2760
tcagcctcta tacttactaa acgtgataaa gtttctgtaa tttctactgt atcgacctgc   2820
agactggctg tgtataaggg agcctgacat ttatattccc cagaacatca ggttaatggc   2880
gtttttgatg tcattttcgc ggtggctgag atcagccact tcttcccga taacggaaac   2940
cggcacactg gccatatcgg tggtcatcat gcgccagctt tcatcccga tatgcaccac   3000
cgggtaaagt tcacgggaga ctttatctga cagcagacgt gcactggcca gggggatcac   3060
catccgtcgc ccgggcgtgt caataatatc actctgtaca tccacaaaca gacgataacg   3120
gctctctctt ttataggtgt aaaccttaaa ctgcatttca ccagtccctg ttctcgtcag   3180
caaaagagcc gttcatttca ataaacgggg cgacctcagc catcccttcc tgattttccg   3240
ctttccagcg ttcggcacgc agacgacggg cttcattctg catggttgtg cttaccagac   3300
cggagatatt gacatcatat atgccttgag caactgatag ctgtcgctgt caactgtcac   3360
tgtaatacgc tgcttcatag cacacctctt tttgaggtct catacaaatc tgctcgtcag   3420
tggtgctcac actgacgaat catgtacaga tcataccgat gactgcctgg cgactcacaa   3480
ctaagcaaga cagccggaac cagcgccggc gaacaccact gcatatatgg catatcacaa   3540
cagtccaact agtgcactgc agtacaactg gtctctccct gaattcgcat ctagaccaga   3600
cagcacgtaa ttgaccgcca gaacgcgcaa tttgacgacc agcggatatg agattctgtg   3660
cactcacgag aacgttaccg acgatttccc agtatttggc gctgccataa tccaaatatc   3720
aagcgaatcc catgtgaccg tctcagcggg cgacgatctc agaacagtta aacgtacttc   3780
tgcctgccta gagatccagt ttatcgatta gttattaata gtaatcaatt acggggtcat   3840
tagttcatag cccatatatg gagttccgcg ttacataact tacggtaaat ggcccgcctg   3900
gctgaccgc caacgacccc cgcccattga cgtcaataat gacgtatgtt cccatagtaa   3960
cgccaatagg gactttccat tgacgtcaat gggtggagta tttacggtaa actgcccact   4020
tggcagtaca tcaagtgtat catatgccaa gtacgccccc tattgacgtc aatgacggta   4080
aatggcccgc ctggcattat gcccagtaca tgaccttatg ggactttcct acttggcagt   4140
acatctacgt attagtcatc gctattacca tggtgatgcg gttttggcag tacatcaatg   4200
ggcgtggata gcggtttgac tcacggggat ttccaagtct ccacccatt gacgtcaatg   4260
ggagtttgtt ttggcaccaa aatcaacggg actttccaaa atgtcgtaac aactccgccc   4320
cattgacgca aatgggcggt aggcgtgtac ggtgggaggt ctatataagc agagctggtt   4380
tagtgaaccg tcgatcttc catttcgggt gtcgtgacgg ccactatggt gagcaagggc   4440
gaggagctgt tcaccggggt ggtgcccatc ctggtcgagc tggacggcga cgtaaacggc   4500
cacaagttca gcgtgtccgg cgagggcgag ggcgatgcca cctacggcaa gctgaccctg   4560
aagttcatct gcaccaccgg caagctgccc gtgccctggc ccaccctcgt gaccaccctg   4620
acctacggcg tgcagtgctt cagccgctac cccgaccaca tgaagcagca cgacttcttc   4680
aagtccgcca tgcccgaagg ctacgtccag gagcgcacca tcttcttcaa ggacgacggc   4740
aactacaaga cccgcgccga ggtgaagttc gagggcgaca ccctggtgaa ccgcatcgag   4800
ctgaagggca tcgacttcaa ggaggacggc aacatcctgg ggcacaagct ggagtacaac   4860
tacaacagcc acaacgtcta tatcatggcc gacaagcaga gaacggcat caaggtaagt   4920
gtaacgcaaa agtttacagt cacatctcta ttaccatctg gaataaaatt ctctatttga   4980
tttcttaact gaagagtaaa gcaaatttct ttgtcacgga cagcccggga gcacatgagg   5040
atcacccatg tgccacgagc gacatgagga tcacccatg cgctttcact agtctgtggt   5100
gtgatatcca tgggagcaca tgaggatcac ccatgtgcca cgagcgacat gaggatcacc   5160
catgtccaat ttggatgaaa ttaactgttt aggagaagtt acctaagtta acaaaaggaa   5220
tgtcattgtg cactgaaaat gtaatacatt taaatgatta aattaagcag tgagaccagt   5280
```

```
SEQ ID NO: 722         moltype = RNA  length = 11
FEATURE                Location/Qualifiers
source                 1..11
                       mol_type = other RNA
                       organism = synthetic construct
SEQUENCE: 722
gaagtagtga t                                                             11

SEQ ID NO: 723         moltype = RNA  length = 11
FEATURE                Location/Qualifiers
```

-continued

```
source                  1..11
                        mol_type = other RNA
                        organism = synthetic construct
SEQUENCE: 723
tttacagcaa g                                                        11

SEQ ID NO: 724          moltype = RNA   length = 11
FEATURE                 Location/Qualifiers
source                  1..11
                        mol_type = other RNA
                        organism = synthetic construct
SEQUENCE: 724
aattcactac t                                                        11

SEQ ID NO: 725          moltype = RNA   length = 11
FEATURE                 Location/Qualifiers
source                  1..11
                        mol_type = other RNA
                        organism = synthetic construct
SEQUENCE: 725
tgaacagaac c                                                        11

SEQ ID NO: 726          moltype = RNA   length = 11
FEATURE                 Location/Qualifiers
source                  1..11
                        mol_type = other RNA
                        organism = synthetic construct
SEQUENCE: 726
gaataggttt g                                                        11

SEQ ID NO: 727          moltype = RNA   length = 11
FEATURE                 Location/Qualifiers
source                  1..11
                        mol_type = other RNA
                        organism = synthetic construct
SEQUENCE: 727
atgaaagttc a                                                        11

SEQ ID NO: 728          moltype = RNA   length = 11
FEATURE                 Location/Qualifiers
source                  1..11
                        mol_type = other RNA
                        organism = synthetic construct
SEQUENCE: 728
gagtctgcgt g                                                        11

SEQ ID NO: 729          moltype = RNA   length = 11
FEATURE                 Location/Qualifiers
source                  1..11
                        mol_type = other RNA
                        organism = synthetic construct
SEQUENCE: 729
tccgagttcc a                                                        11

SEQ ID NO: 730          moltype = RNA   length = 11
FEATURE                 Location/Qualifiers
source                  1..11
                        mol_type = other RNA
                        organism = synthetic construct
SEQUENCE: 730
tagccggtac t                                                        11

SEQ ID NO: 731          moltype = RNA   length = 11
FEATURE                 Location/Qualifiers
source                  1..11
                        mol_type = other RNA
                        organism = synthetic construct
SEQUENCE: 731
tcatgaatgt g                                                        11

SEQ ID NO: 732          moltype = RNA   length = 137
FEATURE                 Location/Qualifiers
source                  1..137
                        mol_type = other RNA
                        organism = synthetic construct
SEQUENCE: 732
atccaaggtg attccctctc caaggggaca tcagtgcctc tcaggaaagt agcagcttgg    60
aatagaatct ggcatgccta aggcctttgg ggaactggga tgcttatttc ctctgccttc   120
cttggctgcc cacatgg                                                  137
```

-continued

```
SEQ ID NO: 733          moltype = RNA   length = 134
FEATURE                 Location/Qualifiers
source                  1..134
                        mol_type = other RNA
                        organism = synthetic construct
SEQUENCE: 733
ttgcacagtg aacacccaag tgtgctttat agttcccttg ctttgaccc tgtgctagag   60
cattgcctgc tcttctcctc tgcattaaaa ggaatattta tccttttaaa tgtattcaga  120
aagccagcac atta                                                    134

SEQ ID NO: 734          moltype = RNA   length = 139
FEATURE                 Location/Qualifiers
source                  1..139
                        mol_type = other RNA
                        organism = synthetic construct
SEQUENCE: 734
tacctcccag gatggcatct ggaagtggat agtattctgc cagctttgga aactggatga   60
aaagcaaatc tggcagaggt acccatttca ttcccagctt gctcagtagc tggtgattgg  120
aagaaactct gcaacagtg                                               139

SEQ ID NO: 735          moltype = RNA   length = 134
FEATURE                 Location/Qualifiers
source                  1..134
                        mol_type = other RNA
                        organism = synthetic construct
SEQUENCE: 735
gggtcatttc aaagagggct tatgaggctg tgaaacccag agctcttaac gctgtgacca   60
aagatggaag ttctctatag gaagccatag cactcctaat gtttggtgct atgttttcct  120
gaggagatat aaaa                                                    134

SEQ ID NO: 736          moltype = RNA   length = 135
FEATURE                 Location/Qualifiers
source                  1..135
                        mol_type = other RNA
                        organism = synthetic construct
SEQUENCE: 736
ctgcagccaa ttaagccgac tgagttcctt tcctcatggg ggcccagtgt gcaatggctg   60
taaatagcag cttccttggt agtgtatgca gcctgtttgt tgtatgggtt gctctaaggg  120
accttggaga cagtc                                                  135

SEQ ID NO: 737          moltype = RNA   length = 131
FEATURE                 Location/Qualifiers
source                  1..131
                        mol_type = other RNA
                        organism = synthetic construct
SEQUENCE: 737
ctccatgtat ctttgggacc tgtcaagtgt ggcagtctcc cttccttgcc atggaagagc   60
atattcttgt ttaccagcaa agctgtcacc atttaattgg tatcagattc tgacttgcac  120
aagtaacatt c                                                      131

SEQ ID NO: 738          moltype =    length =
SEQUENCE: 738
000

SEQ ID NO: 739          moltype =    length =
SEQUENCE: 739
000

SEQ ID NO: 740          moltype =    length =
SEQUENCE: 740
000

SEQ ID NO: 741          moltype = RNA   length = 132
FEATURE                 Location/Qualifiers
source                  1..132
                        mol_type = other RNA
                        organism = synthetic construct
SEQUENCE: 741
gcctgcattc gtaagtgatc acgggctgcc cgtgtcctgg tcattggtag tgcaggcaga   60
ggaaatgcgg gaaaggttgc tgtgtttgga gggtccacat cttcaccctc ctgtcccagg  120
agctttccta ca                                                     132

SEQ ID NO: 742          moltype = RNA   length = 133
FEATURE                 Location/Qualifiers
source                  1..133
                        mol_type = other RNA
                        organism = synthetic construct
SEQUENCE: 742
```

-continued

```
gtgcaaactc gatcactagc tctgcgtgat gtggcagaag cgaagggaac caggtttgca    60
aaagtaactg tggtgatgga aatgtgttag cctcagacac tactgaggtg gttctttcta    120
tcctagtaca gtc                                                       133

SEQ ID NO: 743          moltype = RNA   length = 132
FEATURE                 Location/Qualifiers
source                  1..132
                        mol_type = other RNA
                        organism = synthetic construct
SEQUENCE: 743
ttccaaagtg ttgagttcag tccagggcag cttccctgtt ctgttaatta aactttggga    60
cattgaaatg ggctagggga gatgattggg tagaaagcat tattttattc atttgcctcc    120
cagcctacaa aa                                                        132

SEQ ID NO: 744          moltype = RNA   length = 137
FEATURE                 Location/Qualifiers
source                  1..137
                        mol_type = other RNA
                        organism = synthetic construct
SEQUENCE: 744
cccttggccc ttatcgaagc tgcagctgct tccgcatagc tgctgtggtc aaaaaggagc    60
ccagagtgac agtttttcctt gacggtcgcc gttctgtttg ttgtaactga tctgcaacat    120
tttgggaaaa tacagtt                                                   137

SEQ ID NO: 745          moltype = RNA   length = 138
FEATURE                 Location/Qualifiers
source                  1..138
                        mol_type = other RNA
                        organism = synthetic construct
SEQUENCE: 745
tggaggactg agaaggtgag gcagttttgc cccgtgctgc cttccaccgg ttaagacctc    60
caaaatcgaa gggctgccca ggcagaggat gtccccttgc cacccttgga ggggcagcgc    120
tgtgctggcc gacatttg                                                  138

SEQ ID NO: 746          moltype = RNA   length = 132
FEATURE                 Location/Qualifiers
source                  1..132
                        mol_type = other RNA
                        organism = synthetic construct
SEQUENCE: 746
gttgaggtct atcccgatgg ggctttttcct gtagcctgca catcgttgga aacgcctcat    60
agagtaactc tgtggtttta ctttactcac aggactattg ttagatctgt gggaaggaat    120
tacaagacag tt                                                        132

SEQ ID NO: 747          moltype =   length =
SEQUENCE: 747
000

SEQ ID NO: 748          moltype = RNA   length = 141
FEATURE                 Location/Qualifiers
source                  1..141
                        mol_type = other RNA
                        organism = synthetic construct
SEQUENCE: 748
tccagctgta ggcagctgcc taggttgtct tgtacctagg caagtgttac actgctggga    60
gaacagcagc caatagctgg ttggcattct ggccctggtt catgccaact cttgtgttga    120
ctaccccagg atgccagcat a                                              141

SEQ ID NO: 749          moltype = RNA   length = 136
FEATURE                 Location/Qualifiers
source                  1..136
                        mol_type = other RNA
                        organism = synthetic construct
SEQUENCE: 749
cttcctcagc cttactccag ggactttttg ttgcctgtaa agtgctctgg cattgcctga    60
ggatagatga gaaagcacat atccctcccc agtaagacgc tgttttcttt tggggcctac    120
aagttgagct gacagt                                                    136

SEQ ID NO: 750          moltype =   length =
SEQUENCE: 750
000

SEQ ID NO: 751          moltype = RNA   length = 137
FEATURE                 Location/Qualifiers
source                  1..137
                        mol_type = other RNA
                        organism = synthetic construct
SEQUENCE: 751
gcatggtaat ggatttatgg tgggtccttc tctgtgggcc tctcatagtg tacccatgcc    60
```

-continued

```
atagcaaatg gcagcctcga accattgccc agtcccctta cctgtgggct gtgagcactg    120
aaggggttg cacagtg                                                    137

SEQ ID NO: 752          moltype = RNA   length = 133
FEATURE                 Location/Qualifiers
source                  1..133
                        mol_type = other RNA
                        organism = synthetic construct
SEQUENCE: 752
gcgctgtctt tgagcccccg ccgagcttcc tcgtggcgcc gggggtcaat ctgcagcgct    60
agagcatgtg cttgcgcata actggggccg cctggcctcc cgcgggcggc ctttttaacc    120
gcgagcgaca aga                                                       133

SEQ ID NO: 753          moltype = RNA   length = 135
FEATURE                 Location/Qualifiers
source                  1..135
                        mol_type = other RNA
                        organism = synthetic construct
SEQUENCE: 753
gcatgggttt ggatttatga tgggctggat tccctaggcc tctcatagta ccccatgcca    60
gagcaaactg tagccccaac cattgccggg cctctatgcc tgtaggctgc tggcactgaa    120
gtgggttgca cagta                                                     135

SEQ ID NO: 754          moltype = RNA   length = 138
FEATURE                 Location/Qualifiers
source                  1..138
                        mol_type = other RNA
                        organism = synthetic construct
SEQUENCE: 754
tgcactgcat ggtatctgca ctcagcagtt tatacctgct agggtgttca aaggtcagtg    60
ctatagaaat tcagtatctg gcatcgttgg ttttcttggc tttgtgcttg ttaaacctgg    120
tatttctact gatacagt                                                  138

SEQ ID NO: 755          moltype = RNA   length = 133
FEATURE                 Location/Qualifiers
source                  1..133
                        mol_type = other RNA
                        organism = synthetic construct
SEQUENCE: 755
gccctgtggt tgctggatgc tgttgtgcat ggacagctct ccagtggatt cgatgggcca    60
tagcaatcct gtgatttatg catggaggct gcttctcctc agcagctgcc atagcccggt    120
cgctggtaca tga                                                       133

SEQ ID NO: 756          moltype = RNA   length = 134
FEATURE                 Location/Qualifiers
source                  1..134
                        mol_type = other RNA
                        organism = synthetic construct
SEQUENCE: 756
acctgcattc aaaaatgatc acgggctgcc tgtgctctgg tcatcaataa cgcagggaga    60
ggaattgctg aaagccgttt cccgtgtttg gagggttcac acctgtccct ttcaaatgct    120
ggcgctttca caca                                                      134

SEQ ID NO: 757          moltype = RNA   length = 131
FEATURE                 Location/Qualifiers
source                  1..131
                        mol_type = other RNA
                        organism = synthetic construct
SEQUENCE: 757
gccgagacta gagtcacatc ctgacacaac tcttgtcctg gtgtgctaga gtactcgaag    60
agaatctact ggtcttgatt cactggtggg ggcagtcggt gcccccgtta gtgcccagat    120
cagaaacata c                                                         131

SEQ ID NO: 758          moltype = RNA   length = 135
FEATURE                 Location/Qualifiers
source                  1..135
                        mol_type = other RNA
                        organism = synthetic construct
SEQUENCE: 758
gcatgggttt ggattatgac aggcccatcc ccctggacct ctcatagtgc cccatgccag    60
agcaaactgt ggccccgaac cattgcctgg cttctgtacc cgtgggccac tggcactgaa    120
gagggttaca cagtg                                                     135

SEQ ID NO: 759          moltype =    length =
SEQUENCE: 759
000

SEQ ID NO: 760          moltype = RNA   length = 135
FEATURE                 Location/Qualifiers
```

-continued

```
source                  1..135
                        mol_type = other RNA
                        organism = synthetic construct
SEQUENCE: 760
ctgcagccaa ttaagccgac tgagttcctt tcctcatggg ggcccagtgt gcaatcgctg    60
caaacagcag cttccttggt agtatatgca gcctgtttat tgtacgggtt gctctacggg   120
accttggaga caggc                                                     135

SEQ ID NO: 761          moltype = RNA   length = 132
FEATURE                 Location/Qualifiers
source                  1..132
                        mol_type = other RNA
                        organism = synthetic construct
SEQUENCE: 761
aagcaggatt cagactacaa tatagctgct aagtgctgtg ttgtcgttcc ccctgcttaa    60
aataaagttg tttcttaact atacctgtct gctattctcc tgtagcagcc agggacgctt   120
ggtctcatac at                                                        132

SEQ ID NO: 762          moltype =    length =
SEQUENCE: 762
000

SEQ ID NO: 763          moltype = RNA   length = 123
FEATURE                 Location/Qualifiers
source                  1..123
                        mol_type = other RNA
                        organism = synthetic construct
SEQUENCE: 763
gagcactgtt cgtaacccgt tagcctggct gtagctaatg ggttccattc cggtgcaata    60
gcatttccag cgacacatga ctgactgact ggtggctttc agtttcaggt cttggagaca   120
aat                                                                  123

SEQ ID NO: 764          moltype = RNA   length = 135
FEATURE                 Location/Qualifiers
source                  1..135
                        mol_type = other RNA
                        organism = synthetic construct
SEQUENCE: 764
tttccctgac ctgggtagag tggcatccag ttggtggtgc ccatctcata tcagccaggg    60
acaaagcaac cccttgttcc tcccagcttg gcttttcatc tgtgcctatg cctggttcat   120
gccttggaca cattt                                                     135

SEQ ID NO: 765          moltype = RNA   length = 137
FEATURE                 Location/Qualifiers
source                  1..137
                        mol_type = other RNA
                        organism = synthetic construct
SEQUENCE: 765
ttggccctga atcaaggcca gcagtttgct gaagctgttg gtttcaagca ggagcctaaa    60
gaattgtctt tctatggtct gttggccatt cataactttt ggaaatgtaa tggtcaattc   120
attagaaaga aacatga                                                   137

SEQ ID NO: 766          moltype =    length =
SEQUENCE: 766
000

SEQ ID NO: 767          moltype = RNA   length = 136
FEATURE                 Location/Qualifiers
source                  1..136
                        mol_type = other RNA
                        organism = synthetic construct
SEQUENCE: 767
gcatgggttt ggatttatga tgggcccgtc cccctggacc tctcatagta ccccatgcca    60
gagcaaactg tagccctgaa ccattgcctg gcctctgttc ccgtaggctg ctggcactga   120
agtgggttgc acaata                                                    136

SEQ ID NO: 768          moltype =    length =
SEQUENCE: 768
000

SEQ ID NO: 769          moltype =    length =
SEQUENCE: 769
000

SEQ ID NO: 770          moltype =    length =
SEQUENCE: 770
000

SEQ ID NO: 771          moltype = RNA   length = 132
```

-continued

```
FEATURE                  Location/Qualifiers
source                   1..132
                         mol_type = other RNA
                         organism = synthetic construct
SEQUENCE: 771
aaagcaggtt gcaattacag tgcttcattt tgtggaagta ctgccattat cctgctgaaa    60
gaaaagccgt gttaatcatt tttgattttg cctttatgag ggtaaaatca tgacagattg   120
acatggacaa tt                                                        132

SEQ ID NO: 772           moltype = RNA   length = 135
FEATURE                  Location/Qualifiers
source                   1..135
                         mol_type = other RNA
                         organism = synthetic construct
SEQUENCE: 772
gcactgcttt agagcctctg cgtgtctggc tgtggcctca gggtctagc agcagtgcta    60
gagcagaccc agcttgtcag atccggggct gcttagaggc cacctaagtg attcctttgg   120
cagcaagcaa cattc                                                     135

SEQ ID NO: 773           moltype = RNA   length = 136
FEATURE                  Location/Qualifiers
source                   1..136
                         mol_type = other RNA
                         organism = synthetic construct
SEQUENCE: 773
gctgtcctgg acctgttggc accacagaca gttgctctgc tgtgcctgtg gcctcggggc    60
aaagagaaag tggcgatttc tacactcagt gctcgggaac cagtgggcac tgagaatggt   120
ttatggcctg acatta                                                    136

SEQ ID NO: 774           moltype = RNA   length = 131
FEATURE                  Location/Qualifiers
source                   1..131
                         mol_type = other RNA
                         organism = synthetic construct
SEQUENCE: 774
ttccaaagtg ttaagttcag ttcagggtag cttccctgct ctgttaatta aactttggaa    60
cattgaaact ggctagggaa aatgattgga tagaaactat tattctattc atttatcccc   120
agcctacaaa a                                                         131

SEQ ID NO: 775           moltype =    length =
SEQUENCE: 775
000

SEQ ID NO: 776           moltype = RNA   length = 137
FEATURE                  Location/Qualifiers
source                   1..137
                         mol_type = other RNA
                         organism = synthetic construct
SEQUENCE: 776
tgcagtcaag tcaaattcag tgcccgtttc tgtcatagcg ggggctggcc cagatggctg    60
ccacagcaag ctccacagct catgggccct gggtcaccta ccctgggacc tggggataag   120
tttggctgtg gacagtg                                                   137

SEQ ID NO: 777           moltype = RNA   length = 135
FEATURE                  Location/Qualifiers
source                   1..135
                         mol_type = other RNA
                         organism = synthetic construct
SEQUENCE: 777
tgtccctgac ctgggtagag tggcatctgg ttggtgatgc ccatctcata tcagccaggg    60
acaaagcaac tccttgttca tcccagcttg gcttttgatc cgtgcccatg cctggttcat   120
gccttggaca catag                                                     135

SEQ ID NO: 778           moltype = RNA   length = 135
FEATURE                  Location/Qualifiers
source                   1..135
                         mol_type = other RNA
                         organism = synthetic construct
SEQUENCE: 778
ccgcagccaa ttaagccgac tgagttcctt tcctcatggg gacccagtgt gcgatggctg    60
cacacagcag cttccttggt agtgtacgca gcctgttggt tgtatgggtt gctctaaggg   120
accttggaga caggc                                                     135

SEQ ID NO: 779           moltype =    length =
SEQUENCE: 779
000

SEQ ID NO: 780           moltype = RNA   length = 136
FEATURE                  Location/Qualifiers
```

-continued

```
source                  1..136
                        mol_type = other RNA
                        organism = synthetic construct
SEQUENCE: 780
gggcataccc gtagaccttg tctgactgtg ctcatggcca ggcagggggg acagtgtatg   60
caagagtaat gtggagtttg tgctaactct agccagctta attagtgact ggataaattg   120
cacaactctc acattc                                                   136

SEQ ID NO: 781         moltype = RNA  length = 133
FEATURE                Location/Qualifiers
source                 1..133
                       mol_type = other RNA
                       organism = synthetic construct
SEQUENCE: 781
actgcccta gaggcgttgc agctgtggct gccgtgtcac atctgtgtca ttaggtggca    60
gagattagag aggctatgtc tacgctcagc gttctgcccc gtgaacgttt gaatgtttga    120
tagtctcaca ctc                                                      133

SEQ ID NO: 782         moltype = RNA  length = 135
FEATURE                Location/Qualifiers
source                 1..135
                       mol_type = other RNA
                       organism = synthetic construct
SEQUENCE: 782
gcacctgaat ctttcccatt ccttgctgcc tcgtgccggt gtggggacag atggtgctac    60
agaatgagca gaggaaatcc agacaggttg ttttccattt gtcttggggc ctgtctctac    120
agctctgcca cattt                                                    135

SEQ ID NO: 783         moltype = RNA  length = 138
FEATURE                Location/Qualifiers
source                 1..138
                       mol_type = other RNA
                       organism = synthetic construct
SEQUENCE: 783
ctaccaaaag ttagcttttt gggggggcagg tttttaagta acctttgcca acttgggcta    60
tttggaagag taaaagacca cactccacag tgggctatac cacttagtat agttcgctac    120
tattttgtgg cctacatg                                                 138

SEQ ID NO: 784         moltype = RNA  length = 136
FEATURE                Location/Qualifiers
source                 1..136
                       mol_type = other RNA
                       organism = synthetic construct
SEQUENCE: 784
gcatgggttt ggatttatga caggcccgtc accctgggcc tgtcatagta ccccatgcca    60
gagcaaactg tgtccccgaa ccattgcctg gcctctgtgc ccgtaggctg ctggcactga    120
agtgggttgc acagtg                                                   136

SEQ ID NO: 785         moltype = RNA  length = 134
FEATURE                Location/Qualifiers
source                 1..134
                       mol_type = other RNA
                       organism = synthetic construct
SEQUENCE: 785
actctctcgg ctctgcatag ttgcacttgg cttcacccgt gtgactttcg taacggggag    60
agagagaaaa gatctcctca ggacctcgga tgggccttac tgtggcctct ctttccttga    120
ggggtgcaac aggc                                                     134

SEQ ID NO: 786         moltype = RNA  length = 132
FEATURE                Location/Qualifiers
source                 1..132
                       mol_type = other RNA
                       organism = synthetic construct
SEQUENCE: 786
ccccttttaa aagcactcaa tgggcctgtg gctaatgacc tattgagccg tcaagaaagg    60
ggagagtgaa aacatcgctt ttgggtgaag tggcaacatg tgttgtttgc ttcaatcggt    120
ggtgtgacaa gg                                                       132

SEQ ID NO: 787         moltype = RNA  length = 132
FEATURE                Location/Qualifiers
source                 1..132
                       mol_type = other RNA
                       organism = synthetic construct
SEQUENCE: 787
ggcctcctgg tgcttaccac aggctgtgtt cttacactga ctgtatagaa agaggaggta    60
gagtaaacct accccatata cacctcagct caggccctgt gcctggtctg tattgtgaat    120
gggggaacat ag                                                       132

SEQ ID NO: 788         moltype = RNA  length = 137
```

-continued

```
FEATURE              Location/Qualifiers
source               1..137
                     mol_type = other RNA
                     organism = synthetic construct
SEQUENCE: 788
gggcatactc gtagaccttg cctgactgtg ctcatgtcca ggcagggggg acagtgtatg    60
caagaataat ttggagttcc tgccagctct aaccagcttc atcagtggct ggataaattg   120
caggactcta aacattt                                                  137

SEQ ID NO: 789        moltype = RNA  length = 132
FEATURE              Location/Qualifiers
source               1..132
                     mol_type = other RNA
                     organism = synthetic construct
SEQUENCE: 789
ctgcgaatat tctcgctgtt ctgattttgt aatagtcagg acaggctaaa cattcgctat    60
attaagacca tgcatgtgtc cccaaaccta gttctttccc taggtctggt tttataaatg   120
ctggtgataa ac                                                       132

SEQ ID NO: 790        moltype =   length =
SEQUENCE: 790
000

SEQ ID NO: 791        moltype =   length =
SEQUENCE: 791
000

SEQ ID NO: 792        moltype =   length =
SEQUENCE: 792
000

SEQ ID NO: 793        moltype =   length =
SEQUENCE: 793
000

SEQ ID NO: 794        moltype = DNA  length = 247
FEATURE              Location/Qualifiers
source               1..247
                     mol_type = other DNA
                     organism = synthetic construct
SEQUENCE: 794
tacttacctg gcaggggaga taccatgatc acgaaggtgg ttttttcccag ggcgaggctt    60
atccattgca ctccggatgt gctgacccct gcgatttccc caaatgtggg aaactcgact   120
gcataaatttg tggtagtggg ggactgcgtt cgcgctttcc cctgtcacta gtctgtggtg   180
tgatatccat ggcggcctac ttatcctgtc ccttttttttt ccacagnnnn nnnnnnnnnn   240
nnnnnnn                                                             247

SEQ ID NO: 795        moltype = DNA  length = 242
FEATURE              Location/Qualifiers
source               1..242
                     mol_type = other DNA
                     organism = synthetic construct
SEQUENCE: 795
acctggcagg ggagatacca tgatcacgaa ggtggttttc ccagggcgag gcttatccat    60
tgcactccgg atgtgctgac ccctgcgatt tccccaaatg tgggaaactc gactgcataa   120
ttttgtggta gtgggggact gcgttcgcgc tttcccctgt cactagtctg tggtgtgata   180
tccatggcgg cctacttatc ctgtcccttt ttttccaca gnnnnnnnnn nnnnnnnnnnn   240
nn                                                                  242

SEQ ID NO: 796        moltype = DNA  length = 237
FEATURE              Location/Qualifiers
source               1..237
                     mol_type = other DNA
                     organism = synthetic construct
SEQUENCE: 796
ggcaggggag ataccatgat cacgaaggtg gtttttcccag ggcgaggctt atccattgca    60
ctccggatgt gctgacccct gcgatttccc caaatgtggg aaactcgact gcataaatttg   120
tggtagtggg ggactgcgtt cgcgctttcc cctgtcacta gtctgtggtg tgatatccat   180
ggcggcctac ttatcctgtc ccttttttttt ccacagnnnn nnnnnnnnnn nnnnnnn      237

SEQ ID NO: 797        moltype = DNA  length = 216
FEATURE              Location/Qualifiers
source               1..216
                     mol_type = other DNA
                     organism = synthetic construct
SEQUENCE: 797
aaaaagggct tctgtcgtga gtggcacacg taggcaact cgattgctct gcgtgcggaa      60
tcgacatcaa gagatttcgg aagcataatt ttttggtatt tgggcagctg gtgatcgttc   120
gtcccggcgc cctttcacta gtctgtggtg tgctatccat ggcggcctac ttatcctgtc   180
```

-continued

```
ccttttttttt ccacagnnnn nnnnnnnnnn nnnnnn                                        216

SEQ ID NO: 798          moltype = DNA   length = 213
FEATURE                 Location/Qualifiers
source                  1..213
                        mol_type = other DNA
                        organism = synthetic construct
SEQUENCE: 798
agggcttctg tcgtgagtgg cacacgtagg gcaactcgat tgctctgcgt gcggaatcga            60
catcaagaga tttcggaagc ataatttttt ggtatttggg cagctggtga tcgttcgtcc          120
cggcgccctt tcactagtct gtggtgtgac tatccatggc ggcctactta tcctgtccct          180
ttttttttcca cagnnnnnnn nnnnnnnnnn nnn                                       213

SEQ ID NO: 799          moltype = DNA   length = 208
FEATURE                 Location/Qualifiers
source                  1..208
                        mol_type = other DNA
                        organism = synthetic construct
SEQUENCE: 799
gcttctgtcg tgagtggcac acgtagggca actgattgct ctgcgtgcgg aatcgacatc            60
aagagatttc ggaagcataa ttttttggta tttgggcagc tggtgatcgt tcgtcccggc          120
gccctttcac tagtctgtgg tgtgatatcc atggcgggcct acttatcctg tccctttttt          180
ttccacagnn nnnnnnnnnn nnnnnnnn                                              208

SEQ ID NO: 800          moltype = DNA   length = 127
FEATURE                 Location/Qualifiers
source                  1..127
                        mol_type = other DNA
                        organism = synthetic construct
SEQUENCE: 800
aattttttgga gcaggttttc cagtgttcac tgaaatttgt ctcttcacta gtctgtggtg            60
tgatatccca tggcggccta cttatcctgt ccctttttttt tccacagnnn nnnnnnnnn          120
nnnnnnn                                                                     127

SEQ ID NO: 801          moltype = AA   length = 124
FEATURE                 Location/Qualifiers
source                  1..124
                        mol_type = protein
                        organism = synthetic construct
SEQUENCE: 801
AATTTTTGGA GAAGGTTTTC TGGTCTTTAT CAGAAAGCCT CCTCACTAGT CTGTGGTGTG            60
ATATCCATGG CGGCCTACTT ATCCTGTCCC TTTTTTTTCC ACAGNNNNNN NNNNNNNNNN          120
NNNN                                                                        124

SEQ ID NO: 802          moltype = DNA   length = 125
FEATURE                 Location/Qualifiers
source                  1..125
                        mol_type = other DNA
                        organism = synthetic construct
SEQUENCE: 802
aattttttgga gcaggttttc tggtttcact gcaaaacccc atcactagtc tgtggtgtga            60
tatccatggc ggcctactgg atcctgtccc tttttttttc cacagnnnnn nnnnnnnnnn          120
nnnnn                                                                       125

SEQ ID NO: 803          moltype = DNA   length = 138
FEATURE                 Location/Qualifiers
source                  1..138
                        mol_type = other DNA
                        organism = synthetic construct
SEQUENCE: 803
aattttttgga gcacgttttc cggttgtcac tcccaggtag gctggggaag aggcattcac            60
tagtctgtgg tgtgatatcc atggcggcct acttatcctg tcccttttttt ttccacagnn         120
nnnnnnnnnn nnnnnnnn                                                         138

SEQ ID NO: 804          moltype = DNA   length = 101
FEATURE                 Location/Qualifiers
source                  1..101
                        mol_type = other DNA
                        organism = synthetic construct
SEQUENCE: 804
aattttttgg agcgtctctt cactagtctg tggtgtgata tccatggcgg cctacttatc            60
ctgtcccttt tttttccaca gnnnnnnnnn nnnnnnnnnn n                              101

SEQ ID NO: 805          moltype = DNA   length = 98
FEATURE                 Location/Qualifiers
source                  1..98
                        mol_type = other DNA
                        organism = synthetic construct
SEQUENCE: 805
```

-continued

```
aatttttgga gaatcctcac tagtctgtgg tgtgatatcc atggcggcct acttatcctg   60
tcccttttt ttccacagnn nnnnnnnnn nnnnnnnn                               98

SEQ ID NO: 806          moltype = DNA   length = 102
FEATURE                 Location/Qualifiers
source                  1..102
                        mol_type = other DNA
                        organism = synthetic construct
SEQUENCE: 806
aatttttgga gcagcccatc actagtctgt ggtgtgatat ccatggcgtg cctacttatc   60
ctgtcccttt tttttttccac agnnnnnnnn nnnnnnnnnn nn                      102

SEQ ID NO: 807          moltype = DNA   length = 109
FEATURE                 Location/Qualifiers
source                  1..109
                        mol_type = other DNA
                        organism = synthetic construct
SEQUENCE: 807
aatttttgga gcacgttttc cggttattca ctagtctgtg gtgtgatatc catggcggcc   60
tacttatcct gtcccttttt tttccacagn nnnnnnnnnn nnnnnnnnn                109

SEQ ID NO: 808          moltype = DNA   length = 195
FEATURE                 Location/Qualifiers
source                  1..195
                        mol_type = other DNA
                        organism = synthetic construct
SEQUENCE: 808
aggtcagagg gcttgtgggg ctgtgaaacc aagaggtctt tgaccaaaaa ctgaagttct   60
ctataggatg ctgtagcact caatggtgct atgttttcct caggagatat gatcactagt  120
ctgtggtgtg atatccatgg cggcctactt atcctgtccc tttttttttc cacagnnnnn  180
nnnnnnnnnn nnnnn                                                     195

SEQ ID NO: 809          moltype = DNA   length = 186
FEATURE                 Location/Qualifiers
source                  1..186
                        mol_type = other DNA
                        organism = synthetic construct
SEQUENCE: 809
ctggagggct gggtctgatg aggcaagatt ttgctctcct agaaaaaagg gttggcaaga   60
gcagccctgg agactcacac ggctgactgt tctacccaac actctcacta gtctgtggtg  120
tgatatccat ggcggcctac ttatcctgtc ccttttttttt ccacagnnnn nnnnnnnnnn  180
nnnnnn                                                               186

SEQ ID NO: 810          moltype = DNA   length = 209
FEATURE                 Location/Qualifiers
source                  1..209
                        mol_type = other DNA
                        organism = synthetic construct
SEQUENCE: 810
tggctcgggg gggtggtctc agcccactcc acctccccga gcctagagta gaggggccag   60
gcatcctccc caggggaggg gcgttgaagc aaggagcctc tcctgggctg tcctagcctc  120
acattttcac tagtctgtgg tgtgatatcc atggcggcct acttatcctg tccctttttt  180
tttccacagn nnnnnnnnnn nnnnnnnnn                                      209

SEQ ID NO: 811          moltype = DNA   length = 214
FEATURE                 Location/Qualifiers
source                  1..214
                        mol_type = other DNA
                        organism = synthetic construct
SEQUENCE: 811
tcactgccct cttcctgagt ccggcggcaa gggtaactct gggagagggc agagaagaag   60
aaaccctgag gtcccattat gtcagcccct tctatcacac gggaggagac tgaggacaga  120
aagggaacag agtcactagt ctgtggtgtg atatccatgg cggcctactt atcctgtccc  180
tttttttttcc acagnnnnnn nnnnnnnnnn nnnn                               214
```

METHODS AND COMPOSITIONS FOR TRANS-SPLICING UTILIZING SMALL NUCLEAR RNAs AND SMALL NUCLEOLAR RNAs

CROSS-REFERENCE TO RELATED APPLICATIONS

This application claims the benefit of and priority to U.S. Provisional Application No. 63/656,569, filed on Jun. 5, 2024, U.S. Provisional Application No. 63/554,139, filed on Feb. 15, 2024, U.S. Provisional Application No. 63/552,646, filed on Feb. 12, 2024, and U.S. Provisional Application No. 63/550,019, filed on Feb. 5, 2024, the entire contents of each of which are incorporated herein.

FIELD

The disclosure relates to a nucleic acid composition for targeting trans-splicing of a pre-mRNA in a cell utilizing small nuclear RNAs (snRNAs) and small nucleolar RNAs (snoRNAs), and related methods.

SEQUENCE LISTING

The instant application contains a sequence listing, which has been submitted in XML format via PatentCenter. The contents of the XML copy named "134241-5016_Sequence-_Listing.xml," which was created on Dec. 23, 2025, and is approximately 759,007 bytes in size, the contents of which are incorporated herein by reference in their entirety.

BACKGROUND

Trans-splicing techniques for gene editing have been used to target a wide range of diseases in both in vitro and in vivo models, resulting in RNA, protein and functional correction. Trans-splicing occurs between two splice sites located on two different pre-mRNAs. While trans-splicing has been shown to demonstrate in vitro and in vivo activity, it is a relatively inefficient process that has not yet progressed to the clinic. Thus, there is a need to develop novel compositions and methods that enable specific and efficient trans-splicing to introduce desired genetic information to a cell.

SUMMARY OF THE DISCLOSURE

Therefore, the present disclosure provides, in aspects, a composition or system suitable for targeting trans-splicing of a pre-mRNA in a cell comprising one or more nucleic acids comprising one or more nucleotide sequences comprising at least one intronic sequence comprising a small nuclear RNA (snRNA), or a small nucleolar RNA (snoRNA) sequence, a splice acceptor and/or splice donor sequence.

In embodiments, the intronic sequence comprises a snRNA. In embodiments, the snRNA is selected from a U7 snRNA, a U1 snRNA, a U2 snRNA, a U4 snRNA, a U4atac snRNA, a U5 snRNA, a U6 snRNA, a U6atac snRNA, a U11 snRNA, and a U12 snRNA. In embodiments, the snRNA is a U7 snRNA. In embodiments, the composition or system comprises a snoRNA.

In embodiments, the snoRNA comprises an H/ACA box or C/D box. In embodiments, the snRNA or snoRNA sequence assembles into an RNP. In embodiments, the snRNA or snoRNA sequence comprises a sequence motif that assembles into an RNP. In embodiments, the snRNA or snoRNA sequence comprises a secondary structure that assembles into an RNP. In embodiments, the snRNA or snoRNA sequence comprises a sequence motif and a secondary structure that assembles into an RNP. In embodiments, the secondary structure comprises one or more stem loops. In embodiments, the secondary structure is or comprises a stem, internal loop, multibranch loop, or a pseudoknot. In embodiments, the RNP is selected from a small nuclear RNP (snRNP), a small nucleolar RNP (snoRNP), a small cajal body RNP (scaRNP), and a combination thereof. In embodiments, the RNP is selected from U1, U2, U4, U4atac, U5, U6, U6atac, U7, U11, and U12. In embodiments, the RNP is selected from a C/D box snoRNP and a H/ACA box snoRNP.

In embodiments, the snRNA or snoRNA target one or more exonic splicing enhancers (ESEs), one or more intronic splicing enhancers (ISEs), one or more exonic splicing silencers (ESSs), and/or one or more intronic splicing silencers (ISSs). In embodiments, the snRNA or snoRNA comprise a modification to include at least one or more exonic splicing enhancers (ESEs), at least one or more intronic splicing enhancers (ISEs), at least one or more exonic splicing silencers (ESSs), and/or at least one or more intronic splicing silencers (ISSs).

In embodiments, the composition or system comprises a repair RNA (repRNA) and a small RNA that induces cleavage in an RNA. In embodiments, the small RNA that induces cleavage in an RNA is one or more of an siRNA, small hairpin RNA (shRNA), U7 snRNA, a U1 snRNA, a U2 snRNA, a U4 snRNA, a U4atac snRNA, a U5 snRNA, a U6 snRNA, a U6atac snRNA, a U11 snRNA, a U12 snRNA, and an antisense oligonucleotide (ASO). In embodiments, the composition or system comprises a repair repRNA and the small RNA comprises a modification or mutation that attenuates, weakens, reduces, decreases, or ablates activity. In embodiments, the composition or system comprises a repair repRNA and the small RNA comprises a modification or mutation that increases, stimulates, or enhances activity as compared to an unmodified form. In embodiments, the composition or system comprises a repair repRNA and a small RNA that induces cleavage in an RNA when the present methods are undertaken in cis or trans, as described herein. In embodiments, the snRNA or snoRNA comprises a $N^6$-Methyladenosine (M6A) modification. In embodiments, the snRNA or snoRNA comprises a M6A modification when the present methods are undertaken in cis or trans, as described herein. In embodiments, the snRNA or snoRNA is modified to comprise at least one or more M6A sites. In embodiments, the snRNA or snoRNA is modified to comprise at least 1, 2, 3 4, 5, 6, 7, 8, 9, 10, 11, 12, 13, 14, 15, 16, 17, 18, 19, 20, 21, 22, 23, 24, 25, 26, 27, 28, 29, 30 or more M6A sites than the number of M6A sites in (i) an unmodified state of the snRNA or snoRNA or (ii) an exonic sequence. In embodiments, the snRNA or snoRNA is modified to not comprise M6A sites. In embodiments, the repRNA comprises at least one or more M6A sites. In embodiments, the repRNA is modified to comprise at least 1, 2, 3 4, 5, 6, 7, 8, 9, 10, 11, 12, 13, 14, 15, 16, 17, 18, 19, 20, 21, 22, 23, 24, 25, 26, 27, 28, 29, 30 or more M6A sites than the number of M6A sites in (i) an unmodified state of the repRNA or (ii) an exonic sequence. In embodiments, the repRNA comprises no M6A sites.

In embodiments, the repRNA comprises at least one intronic spacer sequence comprising at least one ISE and ESS sequences. In embodiments, the at least one intronic spacer sequence comprising at least one ISE and ESS sequences increases trans-splicing efficiency of a target RNA as compared to an unmodified form. In embodiments, the repRNA comprises at least one intronic spacer sequence comprising at least one ISE and ESS sequences. In embodiments, the at least one intronic spacer sequence comprising at least one ISE and ESS sequences decreases trans-splicing efficiency of a target RNA as compared to an unmodified form. In embodiments, the repRNA comprises at least one intronic spacer sequence comprising at least one ISE and ESS sequences. In embodiments, the at least one intronic spacer sequence comprising at least one ISE and ESS sequences increases trans-splicing efficiency of a off-target RNA as compared to an unmodified form. In embodiments, the repRNA comprises at least one intronic spacer sequence comprising at least one ISE and ESS sequences. In embodiments, the at least one intronic spacer sequence comprising at least one ISE and ESS sequences decreases trans-splicing efficiency of a off-target RNA as compared to an unmodified form.

In embodiments, the repRNA comprises a ESS, ESE, ISS, and/or ISE sequence. In embodiments, the repRNA targets one or more of ESS, ESE, ISS, and/or ISE. In embodiments, an interaction, modulation and/or binding to one or more of ESS, ESE, ISS, and/or ISE reduces or ablates interaction, modulation and/or binding of the one or more of the ESS, ESE, ISS, and/or ISE with a target. In embodiments, the repRNA comprises exon sequences with ESE and ESS sequences. In embodiments, the exon sequences with ESE and ESS sequences increase or decrease trans-splicing efficiency to an RNA target as compared to an unmodified form. In embodiments, the repRNA comprises exon sequences with ESE and ESS sequences. In embodiments, the repRNA comprises exon sequences with ESE and ESS sequences increase or decrease trans-splicing efficiency to an RNA off-target as compared to an unmodified form. In embodiments, the repRNA comprises at least one or more G4 structures. In embodiments, the repRNA comprises at least one or more G4 structures sequester SD/SA motifs. In embodiments, the G4 structure is unwound, such as by DHX36 or CNBP, and remains trapped in the unwound state in the presence of a complementary sequence (e.g., endogenous target or exogenously delivered trigger RNA). In embodiments, the G4 structure decreases off-targets as compared to an unmodified form.

In embodiments, the repRNA comprises a modification comprising at least one or more scaffolding sequences. In embodiments, the at least one or more scaffolding sequences mediates (e.g., recruits) phase condensate-like formation and/or improves local concentrations of repRNAs and other targeted proteins and/or RNA. In embodiments, the repRNA comprises a modification comprising at least one or more sequences to target the repRNA to the promoter of the target gene of interest, or to proximal condensates that may contain the promoter. In embodiments, the one or more sequences comprises an enhancer RNA, snRNA and/or snoRNA sequences.

In embodiments, the repRNA comprises a modification. In embodiments, the repRNA modification improves interaction and localization to a DNA sequence of the non-template strand of the target gene. In embodiments, the DNA sequence of the non-template strand of the target gene is the promoter, intron, exon, or enhancer. In embodiments, the modification improves interaction and localization to the DNA sequence of the non-template strand of the target gene through protein-directed (e.g. transcription factor, dCas, ZNF, or other RBP) or nucleotide-directed (e.g., R-loop) methods.

In embodiments, the repRNA comprises a modification comprising additional RNA elements. In embodiments, the repRNA modification comprising additional RNA elements improves subnuclear localization to nuclear speckles for enhanced trans-splicing efficiency. In embodiments, the additional RNA element comprise NEAT1 and/or MALAT1, or a fragment thereof. In embodiments, the additional RNA element comprises a nucleotide sequence of SEQ ID NO: 712, or a fragment or variant thereof, optionally having at least about 90%, or at least about 95%, or at least about 97%, or at least about 98%, or at least about 99% identity thereto and/or or having about 1 to about 20 (e.g. about 1, or about 2, or about 3, or about 4, or about 5) nucleic acid modifications, optionally selected from substitutions, additions, or deletions. In embodiments, the repRNA modification enables targeting to site of transcription of target RNAs. In embodiments, the repRNA comprises a modification comprising 5' UTR or 3' UTR modifications. In embodiments, the modification alters intracellular or intranuclear localization based on interactions with endogenous or exogenously supplied molecules (e.g., RNA G4 interactions with transcription factors or other proteins that are localized to specific cellular compartments).

In embodiments, the repRNA comprises a modification in the 5' UTR of the repRNA. In embodiments, the modification in the 5' UTR of the repRNA increases stability as compared to an unmodified form. In embodiments, the modification in the 5' UTR of the repRNA decreases stability as compared to an unmodified form. In embodiments, the modification in the 5' UTR of the repRNA increases or decreases translation efficiency as compared to an unmodified form. In embodiments, the repRNA comprises a modification in the 3' UTR of the repRNA. In embodiments, the modification in the 3' UTR of the repRNA increases stability as compared to an unmodified form. In embodiments, the modification in the 3' UTR of the repRNA decreases stability as compared to an unmodified form. In embodiments, the modification in the 3' UTR of the repRNA increases or decreases translation efficiency as compared to an unmodified form.

In embodiments, the repRNA comprises a modification comprising modifying the repRNA to comprise a G4 structure that mediates recruitment of splicing-associated RNA binding protein (RBPs).

In embodiments, the repRNA comprises a modification comprising at least one or more toehold switches in the repRNA. In embodiments, the at least one or more toehold switches in the repRNA conditionally activate or deactivate (e.g., SD/SA occlusion, binding motif occlusion, or RBP occlusion) upon detection of an endogenous or exogenously supplied target RNA.

In embodiments, the repRNA comprises a modification comprising at least one or more complementary riboregulators in repRNAs (in cis). In embodiments, the at least one or more complementary riboregulators in repRNAs (in cis) occlude splice donor (SD) site and reduce off-target trans-splicing.

In embodiments, the repRNA comprises a modification comprising at least one or more self-complementary riboregulators in repRNAs (in cis). In embodiments, the at least one or more self-complementary riboregulators in repRNAs (in cis) occlude splice acceptor (SA) site and reduce off-target trans-splicing.

In embodiments, the repRNA comprises a modification comprising at least one or more self-complementary riboregulators in repRNAs (in trans). In embodiments, the at least one or more self-complementary riboregulators in repRNAs (in trans) occlude splice donor (SD) site and reduce off-target trans-splicing.

In embodiments, the repRNA comprises a modification comprising at least one or more self-complementary riboregulators in repRNAs (in trans). In embodiments, the at least one or more self-complementary riboregulators in repRNAs (in trans) occlude splice acceptor (SA) site and reduce off-target trans-splicing.

In embodiments, the repRNA comprises a modification comprising at least one or more binding motifs. In embodiments, the at least one or more binding motifs increase trans-splicing efficiency, target specificity, and target site occlusion (SA, SD, ISS, ISE, ESE, and ESS) as compared to an unmodified form.

In embodiments, the repRNA comprises a modification. In embodiments, the repRNA modification enables induction of trans-splicing in response to a stimulus as compared to an unmodified form. In embodiments, the repRNA comprises a modification to turn off or decrease trans-splicing in response to a stimulus as compared to an unmodified form.

In embodiments, the repRNA comprises a modification. In embodiments, the repRNA modification enables small molecule induction of trans-splicing as compared to an unmodified form. In embodiments, the repRNA comprises a modification. In embodiments, the repRNA modification represses small molecule induction of trans-splicing as compared to an unmodified form.

In embodiments, the repRNA comprises a modification. In embodiments, the repRNA modification enables light induction of trans-splicing.

In embodiments, the repRNA comprises a modification comprising at least one or more motifs that are bound and regulated by light-sensitive proteins.

In embodiments, the snRNA or snoRNA comprises a sequence at the 3' untranslated region (3'UTR). In embodiments, the sequence at the 3' untranslated region (3'UTR) of the snRNA or snoRNA increases trans-splicing efficiency as compared to an unmodified form. In embodiments, the sequence is from the MALAT1 gene. In embodiments, the sequence is a nucleotide sequence of SEQ ID NO: 712, or a fragment or variant thereof, optionally having at least about 90%, or at least about 95%, or at least about 97%, or at least about 98%, or at least about 99% identity thereto and/or or having about 1 to about 20 (e.g. about 1, or about 2, or about 3, or about 4, or about 5) nucleic acid modifications, optionally selected from substitutions, additions, or deletions.

In embodiments, the RNP assembles on the repRNA and/or the target. In embodiments, the RNP assembles on the repRNA. In embodiments, the RNP assembles on the target. In embodiments, the RNP sterically occludes and inhibits cis-splicing.

In embodiments, the repRNA comprises a minimal intron. In embodiments, the minimal intron is less than about 50 nucleotides, less than about 60 nucleotides, less than about 70 nucleotides, less than about 80 nucleotides, less than about 90 nucleotides, less than about 100 nucleotides, less than about 110 nucleotides, less than about 120 nucleotides, less than about 130 nucleotides, less than about 140 nucleotides, or less than about 150 nucleotides, or about 50 to about 150 nucleotides, or about 50 to about 100 nucleotides, or about 50 to about 75 nucleotides, or about 75 to about 150 nucleotides, or about 100 to about 150 nucleotides, or about 120 to about 150 nucleotides.

In embodiments, the repRNA further comprises a ribozyme site. In embodiments, the ribozyme site is a hairpin, hammerhead, hepatitis delta virus (HDV), Varkud satellite (VS), or glmS ribozyme site, or a variant thereof. In embodiments, the ribozyme site is a HDV ribozyme site. In embodiments, the ribozyme site is a twister ribozyme site. In embodiments, the ribozyme site is upstream of the one or more exons and/or introns of the repRNA. In embodiments, the ribozyme cleaves the target. In embodiments, the ribozyme is a trans-cleaving ribozyme. In embodiments, the repRNA comprises a M6A modification. In embodiments, the repRNA comprises a ribozyme site that cleaves at the 5' end of the repRNA. In embodiments, the repRNA comprises a ribozyme site that cleaves at the 3' end of the repRNA. In embodiments, the repRNA comprises a ribozyme site that cleaves the snRNA or snoRNA at the 5' end of the repRNA. In embodiments, the repRNA comprises a ribozyme site that cleaves the snRNA or snoRNA at the 3' end of the repRNA.

In embodiments, the repRNA comprises a M6A modification when the present methods are undertaken in cis or trans, as described herein. In embodiments, the snRNA or snoRNA is modified to comprise at least one or more M6A sites. In embodiments, the snRNA or snoRNA is modified to comprise at least 1, 2, 3 4, 5, 6, 7, 8, 9, 10, 11, 12, 13, 14, 15, 16, 17, 18, 19, 20, 21, 22, 23, 24, 25, 26, 27, 28, 29, 30 or more M6A sites than the number of M6A sites in (i) an unmodified state of the snRNA or snoRNA or (ii) an exonic sequence. In embodiments, the snRNA or snoRNA is modified to not comprise M6A sites. In embodiments, the repRNA comprises at least one or more M6A sites. In embodiments, the repRNA is modified to comprise at least 1, 2, 3 4, 5, 6, 7, 8, 9, 10, 11, 12, 13, 14, 15, 16, 17, 18, 19, 20, 21, 22, 23, 24, 25, 26, 27, 28, 29, 30 or more M6A sites than the number of M6A sites in (i) an unmodified state of the repRNA or (ii) an exonic sequence. In embodiments, the repRNA comprises no M6A sites.

In embodiments, the composition or system further comprises at least one pre-rRNA stemloop. In embodiments, the at least one pre-rRNA stemloop removes either the 5'cap or 3' polyA tail.

In embodiments, the repRNA comprises at least one or more snRNA or snoRNA sequences. In embodiments, the at least one or more snRNA or snoRNA sequences stabilize the repRNA. In embodiments, the repRNA comprises an artificial smU7 system. In embodiments, the artificial smU7 system stabilizes the repRNA. In embodiments, the least one or more snRNA or snoRNA sequences comprise a pseudoknot at the 5' end of the snRNA or snoRNA. In embodiments, the pseudoknot at the 5' end of the snRNA or snoRNA stabilizes the repRNA. In embodiments, the least one or more snRNA or snoRNA sequences comprise a pseudoknot at the 3' end of the snRNA or snoRNA. In embodiments, the pseudoknot at the 3' end of the snRNA or snoRNA stabilizes the repRNA.

In embodiments, there are a plurality of repRNAs under the control of the same, different, or a plurality of promoters. In embodiments, the repRNA and one or more other components of the present system are under the control of the same or different promoters.

In embodiments, the repRNA comprises alternative promoters. In embodiments, the repRNA comprises at least one or more alternative Pol II promoters. In embodiments, the one or more alternative Pol II promoters cap the 5' end of the repRNA with 7 mG (7-methylguanosine) or TMG (tri-methylguanosine). In embodiments, the one or more alternative Pol II promoters cap the 5' end of the repRNA with 7 mG (7-methylguanosine) or TMG (tri-methylguanosine) stabilize the repRNA.

In embodiments, the repRNA comprises at least one or more circularized 5' replacement splice donor (SD) repRNAs. In embodiments, the one or more circularized 5' replacement splice donor (SD) repRNAs stabilize the repRNA. In embodiments, the repRNA comprising one or more circularized 5' replacement (SD) repRNAs improves stability as compared to an unmodified form and is resistant to exonucleases. In embodiments, the repRNA comprises at least one or more circularized 3' replacement splice acceptor (SA) repRNAs. In embodiments, the repRNA comprises at least one or more circularized 3' replacement splice acceptor (SA) repRNAs stabilize the repRNA. In embodiments, the repRNA comprising one or more circularized 3' replacement (SA) repRNAs. In embodiments, the repRNA comprising one or more circularized 3' replacement (SA) repRNAs improves stability as compared to an unmodified form and is resistant to exonucleases. In embodiments, the repRNA comprises at least one or more circularized internal replacement (SD+SA) repRNAs. In embodiments, the repRNA comprises at least one or more circularized internal replacement (SD+SA) repRNAs stabilize the repRNA. In embodiments, the repRNA comprising one or more circularized internal replacement (SD+SA) repRNAs improves stability as compared to an unmodified form and is resistant to exonucleases.

In embodiments, the composition or system further comprises a repair RNA (repRNA), a small RNA that induces cleavage in an RNA, and a CRISPR/Cas system. In embodiments, the CRISPR/Cas system comprises a guide RNA (gRNA) and a repRNA in cis or trans capable of Cas protein binding and trans-splicing. In embodiments, the CRISPR/Cas system is active, e.g., catalytically active. In embodiments, the CRISPR/Cas system is inactive, e.g., catalytically inactive, e.g., "dead". In embodiments, the CRISPR/Cas system is a Type III CRISPR/Cas system. In embodiments, the Type III CRISPR/Cas system is or comprises a Type IIIA, Type IIIB, Type IIIC, Type IIID, Type IIIE, or Type IIIF CRISPR/Cas system. In embodiments, the, optionally wherein the Type IIIA, Type IIIB, Type IIIC, Type IIID, Type IIIE, or Type IIIF CRISPR/Cas system is active, catalytically inactive or has reduced activity relative to wild type. In embodiments, the Type III CRISPR/Cas system is or comprises a Cas10 (Csm1), Csm2, Cas7 (Csm3), Csm4, Csm5, Cas 6, and, Cas7-11, or a fragment or variant thereof, optionally wherein the Type III CRISPR/Cas system is or comprises a Cas10 (Csm1), Csm2, Cas7 (Csm3), Csm4, Csm5, Cas 6, and, Cas7-11 is active, catalytically inactive or has reduced activity relative to wild type. In embodiments, the Type III CRISPR/Cas system comprises a domain from a different endonuclease, optionally wherein the different endonuclease is a Cas endonuclease, optionally wherein the domain is one or more of a PAM-interacting domain, optionally wherein the domain is derived from one or more of Cas9, Cas12a (Cpf1), Cas12e (CasX), Cas12d (CasY), Cas12b (C2c1), Cas13a (C2c2), Cas13b, Cas13c, Cas13d, Cas13X/Cas13bt, Cas13Y, Cas12c (C2c3), GeoCas9, CjCas9, NmeCas9, Cas12J (CasPhi), Cas12L (CasLambda), Cas12f (Cas14), Cas12g, Cas12h, Cas12i, Cas12k, NmeCas9, Nme2Cas9, CjCas9, GeoCas9, BlatCas9, PpCas9, and Cas14. In embodiments, the composition or system comprises an intronic sequence comprising a sequence which interacts with or is suitable for interacting with the CRISPR/Cas system. In embodiments, the composition or system further comprises a repair RNA (repRNA), a small RNA that induces cleavage in an RNA, and a CRISPR/Cas system when the present methods are undertaken in cis or trans, as described herein.

In embodiments, the Cas is a type I. In embodiments, the Cas is a type I-A, e.g., without limitation Cas8a or Cas5. In embodiments, the Cas is a type I. In embodiments, the Cas is a type I-B, e.g., without limitation Cas8b. In embodiments, the Cas is a type I. In embodiments, the Cas is a type I-C, e.g., without limitation Cas8c. In embodiments, the Cas is a type I. In embodiments, the Cas is a type I-D, e.g., without limitation Cas10d. In embodiments, the Cas is a type I. In embodiments, the Cas is a type I-E, e.g., without limitation Cse1 or Cse2. In embodiments, the Cas is a type I. In embodiments, the Cas is a type I-F, e.g., without limitation Csy1, Csy2, or Csy3. In embodiments, the Cas is a type I. In embodiments, the Cas is a type I-G, e.g., without limitation GSU0054. In embodiments, the Cas is a type I. In embodiments, the Cas type I is without limitation, Cas3. In embodiments, the Cas is a type II. In embodiments, the Cas is a type II-A, e.g., without limitation Csn2. In embodiments, the Cas is a type II. In embodiments, the Cas is a type II-B, e.g., without limitation Cas4. In embodiments, the Cas is a type II. In embodiments, the Cas is a type II-C. In embodiments, the Cas is a type II. In embodiments, the Cas type II is without limitation Cas 9. In embodiments, the Cas is a type III. In embodiments, the Cas is a type III-A, e.g., without limitation Csm2. In embodiments, the Cas is a type III. In embodiments, the Cas is a type III-B, e.g., without limitation Cmr5. In embodiments, the Cas is a type III. In embodiments, the Cas is a type III-C, e.g., without limitation Cas10 or Csx11. In embodiments, the Cas is a type III. In embodiments, the Cas is a type III-D, e.g., without limitation Csx10. In embodiments, the Cas is a type III. In embodiments, the Cas is a type III-E. In embodiments, the Cas is a type III. In embodiments, the Cas is a type III-F. In embodiments, the Cas is a type III. In embodiments, the Cas type III is without limitation Cas 10.

In embodiments, the Cas is a type IV. In embodiments, the Cas is a type IV-A. In embodiments, the Cas is a type IV. In embodiments, the Cas is a type IV-B. In embodiments, the Cas is a type IV. In embodiments, the Cas is a type IV-C.

In embodiments, the Cas is a type V. In embodiments, the Cas is a type V-A, e.g., without limitation Cas12a (Cpf1). In embodiments, the Cas is a type V. In embodiments, the Cas is a type V-B, e.g., without limitation Cas12b (C2c1). In embodiments, the Cas is a type V. In embodiments, the Cas is a type V-C, e.g., without limitation Cas12c (C2c3). In embodiments, the Cas is a type V. In embodiments, the Cas is a type V-D, e.g., without limitation Cas12d (CasY). In embodiments, the Cas is a type V. In embodiments, the Cas is a type V-E, e.g., without limitation Cas12e (CasX). In embodiments, the Cas is a type V. In embodiments, the Cas is a type V-F, e.g., without limitation Cas12f (Cas14, or C2c10). In embodiments, the Cas is a type V. In embodiments, the Cas is a type V-G, e.g., without limitation Cas12g. In embodiments, the Cas is a type V. In embodiments, the Cas is a type V-H, e.g., without limitation Cas12h. In embodiments, the Cas is a type V. In embodiments, the Cas is a type V-I, e.g., without limitation Cas12i. In embodiments, the Cas is a type V. In embodiments, the Cas is a type V-K, e.g., without limitation Cas12k (C2c5). In embodiments, the Cas is a type V. In embodiments, the Cas is a type V-U, e.g., without limitation C2c4, C2c8, or C2c9. In embodiments, the Cas is a type V. In embodiments, the Cas type V is without limitation Cas 12. In embodiments, the Cas is a type VI.

In embodiments, the Cas is a type VI-A, e.g., without limitation Cas13a (C2c2). In embodiments, the Cas is a type VI. In embodiments, the Cas is a type VI-B, e.g., without limitation Cas13b. In embodiments, the Cas is a type VI. In embodiments, the Cas is a type VI-C, e.g., without limitation Cas13c. In embodiments, the Cas is a type VI. In embodiments, the Cas is a type VI-D, e.g., without limitation Cas13d. In embodiments, the Cas is a type VI. In embodiments, the Cas is a type VI-X, e.g., without limitation Cas13x.1. In embodiments, the Cas is a type VI. In embodiments, the Cas is a type VI-Y. In embodiments, the Cas is a type VI. In embodiments, the Cas type VI is without limitation Cas 13.

In embodiments the Cas is Cas3, Cas8a, Cas5, Cas8b, Cas8c, Cas10d, Cse1, Cse2, Csy1, Csy2, Csy3, GSU0054, Cas10, Csm2, Cmr5, Cas10 or Csx11, Csx10, Csf1, Cas9, Csn2, Cas4, Cas12, Cas12a (Cpf1), Cas12b (C2c1), Cas12c (C2c3), Cas12d (CasY), Cas12e (CasX), Cas12f (Cas14, C2c10), Cas12g, Cas12h, Cas12i, Cas12k (C2c5), C2c4, C2c8, C2c9, Cas13, Cas13a (C2c2), Cas13b, Cas13c, Cas13d, or Cas13x.1.

In embodiments, the composition or system further comprises a protein that forms an RNP or is within an RNP, with the snRNA or snoRNA, or a nucleic acid encoding the protein that forms, or is within, the RNP. In embodiments, the snRNA, snoRNA, protein that forms or is within an RNP, a protein within the RNP, and/or a nucleic acid encoding the protein that forms or is within the RNP comprises a modification or mutation that attenuates, weakens, reduces, decreases, or ablates RNP activity, and/or leads to attenuation of RNA modifying activity as compared to an unmodified form, the RNP activity optionally being selected from cleavage, nucleic acid processing, pseudouridylation, and/or methylation. In embodiments, the snRNA, snoRNA, protein that forms or is within an RNP, and/or a nucleic acid encoding the protein that forms or is within the RNP comprises a modification or mutation that increases, stimulates, or enhances RNP activity, or enhances RNA modifying activity, the RNP activity optionally being selected from cleavage, nucleic acid processing, pseudouridylation, and/or methylation as compared to an unmodified form. In embodiments, the snRNA, snoRNA, protein that forms or is within an RNP, and/or a nucleic acid encoding the protein that forms or is within the RNP comprises at least one or more pseudouridylation sites. In embodiments, the snRNA, snoRNA, protein that forms or is within an RNP, and/or a nucleic acid encoding the protein that forms or is within the RNP comprises no pseudouridylation sites. In embodiments, the repRNA comprises at least one or more pseudouridylation sites. In embodiments, the repRNA comprises no pseudouridylation sites. In embodiments, the repRNA is modified to comprise at least 1, 2, 3 4, 5, 6, 7, 8, 9, 10, 11, 12, 13, 14, 15, 16, 17, 18, 19, 20, 21, 22, 23, 24, 25, 26, 27, 28, 29, 30 or more pseudouridylation sites than the number of pseudouridylation sites in (i) an unmodified state of the snRNA or snoRNA or (ii) an exonic sequence.

In embodiments, the composition or system comprises a repair RNA (repRNA) and/or a protein that forms or is within an RNP, with the snRNA or snoRNA, or a nucleic acid encoding the protein that forms, or is within, the RNP and/or a small RNA that induces cleavage in an RNA and/or a CRISPR/Cas system. In embodiments, the composition or system comprises a repair RNA (repRNA) and/or a protein that forms or is within an RNP, with the snRNA or snoRNA, or a nucleic acid encoding the protein that forms, or is within, the RNP and/or a small RNA that induces cleavage in an RNA and/or a CRISPR/Cas system when the present methods are undertaken in cis or trans, as described herein. In embodiments, cleavage is initiated from RNPs that are formed on the repRNA, or from RNPs that are formed in cis or trans.

In embodiments, the composition or system comprises a chimeric CRISPR-Cas gRNA and a repRNA in cis or trans capable of Cas protein binding and trans-splicing.

In embodiments, the snRNA or snoRNA comprises an Sm sequence motif, and/or wherein the snRNA or snoRNA comprises an antisense region sequence (ASR). In embodiments, the Sm sequence motif assembles with an Sm or Lsm protein into an RNP. In embodiments, the Sm or Lsm proteins are selected from a B/B', D3, D2, D1, E, F, G, LSm5, LSm7, LSm4, LSm8, LSm2, LSm3, LSm6 and LSm10 proteins.

In embodiments, the snRNA or snoRNA is at least about 10 to about 80 nucleotides, about 10 to about 70 nucleotides, about 10 to about 60 nucleotides, about 10 to about 50 nucleotides, about 10 to about 40 nucleotides, about 10 to about 30 nucleotides, about 10 to about 20 nucleotides, or about 80, 70, 60, 50, 40, 30, 20, or 10 nucleotides in length. In embodiments, wherein the snRNA or snoRNA comprises an antisense region sequence (ASR) selected from SEQ ID NOs: 700-707. In embodiments, the Sm sequence motif comprises a nucleotide sequence selected from SEQ ID NOs: 1-8.

In embodiments, the snRNA or snoRNA comprises a guide repair RNA (grepRNA) sequence. In embodiments, wherein the grepRNA sequence is selected from SEQ ID NOs: 708-711.

In embodiments, composition or system comprises a splice acceptor. In embodiments, composition or system comprises a splice donor.

In embodiments, the (a) at least one intronic sequence, (b) splice acceptor and/or splice donor sequence, and (c) at least one exonic sequence are provided in cis or trans, or are suitable for being provided in cis or trans. In embodiments, the (a) at least one intronic sequence, (b) splice acceptor and/or splice donor sequence, and (c) at least one exonic sequence are provided in trans, or are suitable for being provided in trans. In embodiments, these elements are under the control of one or more promoters. In embodiments, these elements are under the control of different promoters. In embodiments, these elements are operably linked, but separated by a cleavable sequence (e.g., a self-cleaving ribozyme). In embodiments, (i) multiple populations of repRNA are under the control of different promoters or (ii) the repRNA and another system member under control of different promoters.

In embodiments, the at least one intronic sequence comprises one or more splicing signals. In embodiments, the one or more splicing signals are selected from an exonic splicing enhancer (ESE), an intronic splicing enhancer (ISE), an exonic splicing silencer (ESS), intronic splicing silencer (ISS), a U1 binding motif (e.g., among other snRNA binding motifs), a polypyrimidine tract, a branch point, and a combination thereof.

In embodiments, the at least one intronic sequence comprises a branch point and a polypyrimidine tract.

In embodiments, the composition or system comprises 1, 2, 3, 4, 5, 6, 7, 8, 9, or 10 exons.

In embodiments, the one or more binding domain sequences is at least about 5 to about 10, about 5 to about 15, about 5 to about 20, about 10 to about 15, about 10 to about 20, about 15 to about 20, or about 20, or about 19, or about 18, or about 17, or about 16, or about 15, or about 14, or about 13, or about 12, or about 11, or about 10, or about 9, or about 8, or about 7, or about 6, or about or 5 nucleotides in length.

In embodiments, wherein the one or more binding domain sequences is less than about 250 to about 300, about 200 to about 300, about 150 to about 300, about 100 to about 300, about 50 to about 300, about 100 to about 250, about 100 to about 200, about 100 to about 150, about 50 to about 250, about 50 to about 200, about 50 to about 150, about 50 to about 100, or about 300, or about 250, or about 200, or about 150, or about 100, or about 50 nucleotides in length.

In embodiments, the one or more binding domain sequences is about 5 to about 20, about 5 to about 30, about 5 to about 40, about 5 to about 50, about 10 to about 50, about 10 to about 100, about 20 to about 100, about 30 to about 100, about 40 to about 100, about 50 to about 100, about 50 to about 150, about 50 to about 200, about 50 to about 250, about 100 to about 150, about 100 to about 200, about 100 to about 250, or about 100 to about 300 nucleotides in length.

In embodiments, the composition or system comprises one binding domain sequence. In embodiments, the composition or system comprises at least two binding domain sequences. In embodiments, the composition or system comprises 3, 4, 5, 6, 7, 8, 9, or 10 binding domain sequences.

In embodiments, when the composition or system is introduced to the cell an exon in the pre-mRNA is targeted for trans-splicing. In embodiments, the target sequence is positioned in a region of the pre-mRNA comprising the exon targeted for trans-splicing. In embodiments, the target sequence is positioned proximal to a splice site. In embodiments, the target sequence is positioned proximal to a splice donor or a splice acceptor.

In embodiments, further comprising one or more binding domain sequences of about 4 to about 300 nucleotides each with complementarity to a pre-mRNA target sequence. In embodiments the one or more binding domain sequences is at least about 5 to about 10, about 5 to about 15, about 5 to about 20, about 10 to about 15, about 10 to about 20, about 15 to about 20, or about 20, or about 19, or about 18, or about 17, or about 16, or about 15, or about 14, or about 13, or about 12, or about 11, or about 10, or about 9, or about 8, or about 7, or about 6, or about or 5 nucleotides in length. In embodiments the one or more binding domain sequences is less than about 250 to about 300, about 200 to about 300, about 150 to about 300, about 100 to about 300, about 50 to about 300, about 100 to about 250, about 100 to about 200, about 100 to about 150, about 50 to about 250, about 50 to about 200, about 50 to about 150, about 50 to about 100, or about 300, or about 250, or about 200, or about 150, or about 100, or about 50 nucleotides in length. In embodiments the one or more binding domain sequences is about 5 to about 20, about 5 to about 30, about 5 to about 40, about 5 to about 50, about 10 to about 50, about 10 to about 100, about 20 to about 100, about 30 to about 100, about 40 to about 100, about 50 to about 100, about 50 to about 150, about 50 to about 200, about 50 to about 250, about 100 to about 150, about 100 to about 200, about 100 to about 250, or about 100 to about 300 nucleotides in length.

In embodiments, the composition or system comprises one binding domain sequence. In embodiments, the composition or system comprises at least two binding domain sequences. In embodiments, the composition or system comprises 3, 4, 5, 6, 7, 8, 9, or 10 binding domain sequences. In embodiments, the small nuclear RNA (snRNA) or a small nucleolar RNA (snoRNA) sequence is greater than about 5 nucleotides in length which forms a secondary structure, and optionally comprises a sequence motif to direct the one or more binding domains to the pre-mRNA target sequence. In embodiments, small nuclear RNA (snRNA) or a small nucleolar RNA (snoRNA) sequence is about 5 to about 500, or 5 to about 400, or 5 to about 300, or 5 to about 200, or 5 to about 100, or 5 to about 90, or 5 to about 80, or 5 to about 70, or 5 to about 60, or 5 to about 50, or 5 to about 40, or 5 to about 30, or 5 to about 20, or 5 to about 10, or 7 to about 500, or 7 to about 400, or 7 to about 300, or 7 to about 200, or 7 to about 100, or 7 to about 90, or 7 to about 80, or 7 to about 70, or 7 to about 60, or 7 to about 50, or 7 to about 40, or 7 to about 30, or 7 to about 20, or 7 to about 10 nucleotides in length.

In embodiments, the composition comprises at least one exonic sequence.

In embodiments, the composition or system comprises a CRISPR/Cas system, e.g., a protein and/or nucleic acid thereof. In embodiments, the composition or system further comprises a repair RNA (repRNA) and a CRISPR/Cas system. In embodiments, the CRISPR/Cas system is active, e.g., catalytically active. In embodiments, the CRISPR/Cas system is inactive, e.g., catalytically inactive, e.g., "dead". In embodiments, the CRISPR/Cas system is a Type III CRISPR/Cas system. In embodiments, the Type III CRISPR/Cas system is or comprises a Type IIIA, Type IIIB, Type IIIC, Type IIID, Type IIIE, or Type IIIF CRISPR/Cas system, optionally wherein the Type IIIA, Type IIIB, Type IIIC, Type IIID, Type IIIE, or Type IIIF CRISPR/Cas system is active, catalytically inactive or has reduced activity relative to wild type. In embodiments, the Type III CRISPR/Cas system is or comprises a Cas10 (Csm1), Csm2, Cas7 (Csm3), Csm4, Csm5, Cas 6, and, Cas7-11, or a fragment or variant thereof, optionally wherein the Type III CRISPR/Cas system is or comprises a Cas10 (Csm1), Csm2, Cas7 (Csm3), Csm4, Csm5, Cas 6, and, Cas7-11 is active, catalytically inactive or has reduced activity relative to wild type. In embodiments, the Type III CRISPR/Cas system comprises a domain from a different endonuclease, optionally wherein the different endonuclease is a Cas endonuclease, optionally wherein the domain is one or more of a PAM-interacting domain, optionally wherein the domain is derived from one or more of Cas9, Cas12a (Cpf1), Cas12e (CasX), Cas12d (CasY), Cas12b (C2c1), Cas13a (C2c2), Cas13b, Cas13c, Cas13d, Cas13X/Cas13bt, Cas13Y, Cas12c (C2c3), GeoCas9, CjCas9, NmeCas9, Cas12J (Cas-Phi), Cas12L (CasLambda), Cas12f (Cas14), Cas12g, Cas12h, Cas12i, Cas12k, NmeCas9, Nme2Cas9, CjCas9, GeoCas9, BlatCas9, PpCas9, and Cas14. In embodiments, the composition or system comprises an intronic sequence comprising a sequence which interacts with or is suitable for interacting with the CRISPR/Cas system. In embodiments, the composition or system further comprises a repair RNA (repRNA) and a CRISPR/Cas system when the present methods are undertaken in cis or trans, as described herein.

In embodiments, the Cas is a type I. In embodiments, the Cas is a type I-A, e.g., without limitation Cas8a or Cas5. In embodiments, the Cas is a type I. In embodiments, the Cas is a type I-B, e.g., without limitation Cas8b. In embodiments, the Cas is a type I. In embodiments, the Cas is a type I-C, e.g., without limitation Cas8c. In embodiments, the Cas is a type I. In embodiments, the Cas is a type I-D, e.g., without limitation Cas10d. In embodiments, the Cas is a type I. In embodiments, the Cas is a type I-E, e.g., without limitation Cse1 or Cse2. In embodiments, the Cas is a type I. In embodiments, the Cas is a type I-F, e.g., without limitation Csy1, Csy2, or Csy3. In embodiments, the Cas is a type I. In embodiments, the Cas is a type I-G, e.g., without limitation GSU0054. In embodiments, the Cas is a type I. In embodiments, the Cas type I is without limitation, Cas3.

In embodiments, the Cas is a type II. In embodiments, the Cas is a type II-A, e.g., without limitation Csn2. In embodiments, the Cas is a type II. In embodiments, the Cas is a type II-B, e.g., without limitation Cas4. In embodiments, the Cas is a type II. In embodiments, the Cas is a type II-C. In embodiments, the Cas is a type II. In embodiments, the Cas type II is without limitation Cas 9.

In embodiments, the Cas is a type III. In embodiments, the Cas is a type III-A, e.g., without limitation Csm2. In embodiments, the Cas is a type III. In embodiments, the Cas is a type III-B, e.g., without limitation Cmr5. In embodiments, the Cas is a type III. In embodiments, the Cas is a type III-C, e.g., without limitation Cas10 or Csx11. In embodiments, the Cas is a type III. In embodiments, the Cas is a type III-D, e.g., without limitation Csx10. In embodiments, the Cas is a type III. In embodiments, the Cas is a type III-E. In embodiments, the Cas is a type III. In embodiments, the Cas is a type III-F. In embodiments, the Cas is a type III. In embodiments, the Cas type III is without limitation Cas 10.

In embodiments, the Cas is a type IV. In embodiments, the Cas is a type IV-A. In embodiments, the Cas is a type IV. In embodiments, the Cas is a type IV-B. In embodiments, the Cas is a type IV. In embodiments, the Cas is a type IV-C.

In embodiments, the Cas is a type V. In embodiments, the Cas is a type V-A, e.g., without limitation Cas12a (Cpf1). In embodiments, the Cas is a type V. In embodiments, the Cas is a type V-B, e.g., without limitation Cas12b (C2c1). In embodiments, the Cas is a type V. In embodiments, the Cas is a type V-C, e.g., without limitation Cas12c (C2c3). In embodiments, the Cas is a type V. In embodiments, the Cas is a type V-D, e.g., without limitation Cas12d (CasY). In embodiments, the Cas is a type V. In embodiments, the Cas is a type V-E, e.g., without limitation Cas12e (CasX). In embodiments, the Cas is a type V. In embodiments, the Cas is a type V-F, e.g., without limitation Cas12f (Cas14, or C2c10). In embodiments, the Cas is a type V. In embodiments, the Cas is a type V-G, e.g., without limitation Cas12g. In embodiments, the Cas is a type V. In embodiments, the Cas is a type V-H, e.g., without limitation Cas12h. In embodiments, the Cas is a type V. In embodiments, the Cas is a type V-I, e.g., without limitation Cas12i. In embodiments, the Cas is a type V. In embodiments, the Cas is a type V-K, e.g., without limitation Cas12k (C2c5). In embodiments, the Cas is a type V. In embodiments, the Cas is a type V-U, e.g., without limitation C2c4, C2c8, or C2c9. In embodiments, the Cas is a type V. In embodiments, the Cas type V is without limitation Cas 12. In embodiments, the Cas is a type VI.

In embodiments, the Cas is a type VI-A, e.g., without limitation Cas13a (C2c2). In embodiments, the Cas is a type VI. In embodiments, the Cas is a type VI-B, e.g., without limitation Cas13b. In embodiments, the Cas is a type VI. In embodiments, the Cas is a type VI-C, e.g., without limitation Cas13c. In embodiments, the Cas is a type VI. In embodiments, the Cas is a type VI-D, e.g., without limitation Cas13d. In embodiments, the Cas is a type VI. In embodiments, the Cas is a type VI-X, e.g., without limitation Cas13x.1. In embodiments, the Cas is a type VI. In embodiments, the Cas is a type VI-Y. In embodiments, the Cas is a type VI. In embodiments, the Cas type VI is without limitation Cas 13.

In embodiments the Cas is Cas3, Cas8a, Cas5, Cas8b, Cas8c, Cas10d, Cse1, Cse2, Csy1, Csy2, Csy3, GSU0054, Cas10, Csm2, Cmr5, Cas10 or Csx11, Csx10, Csf1, Cas9, Csn2, Cas4, Cas12, Cas12a (Cpf1), Cas12b (C2c1), Cas12c (C2c3), Cas12d (CasY), Cas12e (CasX), Cas12f (Cas14, C2c10), Cas12g, Cas12h, Cas12i, Cas12k (C2c5), C2c4, C2c8, C2c9, Cas13, Cas13a (C2c2), Cas13b, Cas13c, Cas13d, or Cas13x.1.

In aspects, the present disclosure provides a composition or system for targeting trans-splicing of a pre-mRNA in a cell, comprising one or more nucleic acids comprising one or more nucleotide sequences comprising from 5' to 3' at least one intronic sequence comprising a small nuclear RNA (snRNA), or a small nucleolar RNA (snoRNA) sequence, a splice acceptor and/or splice donor sequence.

In embodiments, when the composition or system is introduced to the cell an exon in the pre-mRNA is targeted for trans-splicing. In embodiments, the target sequence is positioned upstream the exon in the pre-mRNA targeted for trans-splicing. In embodiments, the target sequence is positioned proximal to a splice site. In embodiments, the target sequence is positioned proximal to a splice acceptor or a splice donor. In embodiments, trans-splicing occurs between a splice donor upstream the exon in the pre-mRNA and the splice acceptor of the composition or system. In embodiments, trans-splicing results in ligation of the 3' end of an exon upstream the splice donor in the pre-mRNA with the 5' end of the at least one exonic sequence of the composition or system. In embodiments, the one or more splicing signals comprises a branch point and a polypyrimidine tract.

In embodiments, the intronic sequence comprises a snRNA. In embodiments, the snRNA is selected from a U7 snRNA, a U1 snRNA, a U2 snRNA, a U4 snRNA, a U4atac snRNA, a U5 snRNA, a U6 snRNA, a U6atac snRNA, a U11 snRNA, and a U12 snRNA. In embodiments, the snRNA is a U7 snRNA. In embodiments, the composition or system comprises a snoRNA. In embodiments, the snoRNA comprises an H/ACA box or C/D box. In embodiments, the snRNA or snoRNA sequence assembles into an RNP. In embodiments, the snRNA or snoRNA sequence comprises a sequence motif that assembles into an RNP. In embodiments, the composition or system further comprises a protein that forms or is within an RNP, with the snRNA or snoRNA, or a nucleic acid encoding the protein that forms, or is within, the RNP. In embodiments, the snRNA, snoRNA, protein that forms or is within an RNP, and/or a nucleic acid encoding the protein that forms or is within the RNP comprises a modification or mutation that attenuates, weakens, reduces, decreases, or ablates RNP activity, and/or leads to attenuation of RNA modifying activity as compared to an unmodified form, the RNP activity optionally being selected from cleavage, nucleic acid processing, pseudouridylation, and/or methylation. In embodiments, the snRNA, snoRNA, protein that forms or is within an RNP, and/or a nucleic acid encoding the protein that forms or is within the RNP comprises a modification or mutation that increases, stimulates, or enhances RNP activity, or enhances RNA modifying activity, the RNP activity optionally being selected from cleavage, nucleic acid processing, pseudouridylation, and/or methylation. In embodiments, the snRNA, snoRNA, protein that forms or is within an RNP, and/or a nucleic acid encoding the protein that forms or is within the RNP comprises at least one or more pseudouridylation sites. In embodiments, the snRNA, snoRNA, protein that forms or is within an RNP, and/or a nucleic acid encoding the protein that forms or is within the RNP comprises no pseudouridylation sites. In embodiments, the repRNA comprises at least one or more pseudouridylation sites. In embodiments, the repRNA comprises no pseudouridylation sites. In embodiments, the repRNA is modified to comprise at least 1, 2, 3 4, 5, 6, 7, 8, 9, 10, 11, 12, 13, 14, 15, 16, 17, 18, 19, 20, 21, 22, 23, 24, 25, 26, 27, 28, 29, 30 or more pseudouridylation sites than the number of pseudouridylation sites in (i) an unmodified state of the snRNA or snoRNA or (ii) an exonic sequence.

In embodiments, the (a) at least one intronic sequence, (b) splice acceptor and/or splice donor sequence, and (c) at least one exonic sequence are provided in cis or trans, or are suitable for being provided in cis or trans. In embodiments, the (a) at least one intronic sequence, (b) splice acceptor and/or splice donor sequence, and (c) at least one exonic sequence are provided in trans, or are suitable for being provided in trans.

In embodiments, further comprising one or more binding domain sequences of about 4 to about 300 nucleotides each with complementarity to a pre-mRNA target sequence. In embodiments the one or more binding domain sequences is at least about 5 to about 10, about 5 to about 15, about 5 to about 20, about 10 to about 15, about 10 to about 20, about 15 to about 20, or about 20, or about 19, or about 18, or about 17, or about 16, or about 15, or about 14, or about 13, or about 12, or about 11, or about 10, or about 9, or about 8, or about 7, or about 6, or about or 5 nucleotides in length. In embodiments the one or more binding domain sequences is less than about 250 to about 300, about 200 to about 300, about 150 to about 300, about 100 to about 300, about 50 to about 300, about 100 to about 250, about 100 to about 200, about 100 to about 150, about 50 to about 250, about 50 to about 200, about 50 to about 150, about 50 to about 100, or about 300, or about 250, or about 200, or about 150, or about 100, or about 50 nucleotides in length. In embodiments the one or more binding domain sequences is about 5 to about 20, about 5 to about 30, about 5 to about 40, about 5 to about 50, about 10 to about 50, about 10 to about 100, about 20 to about 100, about 30 to about 100, about 40 to about 100, about 50 to about 100, about 50 to about 150, about 50 to about 200, about 50 to about 250, about 100 to about 150, about 100 to about 200, about 100 to about 250, or about 100 to about 300 nucleotides in length.

In embodiments, the composition or system comprises one binding domain sequence. In embodiments, the composition or system comprises at least two binding domain sequences. In embodiments, the composition or system comprises 3, 4, 5, 6, 7, 8, 9, or 10 binding domain sequences. In embodiments, the small nuclear RNA (snRNA) or a small nucleolar RNA (snoRNA) sequence is greater than about 5 nucleotides in length which forms a secondary structure, and optionally comprises a sequence motif to direct the one or more binding domains to the pre-mRNA target sequence. In embodiments, small nuclear RNA (snRNA) or a small nucleolar RNA (snoRNA) sequence is about 5 to about 500, or 5 to about 400, or 5 to about 300, or 5 to about 200, or 5 to about 100, or 5 to about 90, or 5 to about 80, or 5 to about 70, or 5 to about 60, or 5 to about 50, or 5 to about 40, or 5 to about 30, or 5 to about 20, or 5 to about 10, or 7 to about 500, or 7 to about 400, or 7 to about 300, or 7 to about 200, or 7 to about 100, or 7 to about 90, or 7 to about 80, or 7 to about 70, or 7 to about 60, or 7 to about 50, or 7 to about 40, or 7 to about 30, or 7 to about 20, or 7 to about 10 nucleotides in length.

In embodiments, the composition comprises at least one exonic sequence.

In embodiments, the composition or system comprises a CRISPR/Cas system, e.g., a protein and/or nucleic acid thereof. In embodiments, the composition or system further comprises a repair RNA (repRNA) and a CRISPR/Cas system. In embodiments, the CRISPR/Cas system is active, e.g., catalytically active. In embodiments, the CRISPR/Cas system is inactive, e.g., catalytically inactive, e.g., "dead". In embodiments, the CRISPR/Cas system is a Type III CRISPR/Cas system. In embodiments, the Type III CRISPR/Cas system is or comprises a Type IIIA, Type IIIB, Type IIIC, Type IIID, Type IIIE, or Type IIIF CRISPR/Cas system, optionally wherein the Type IIIA, Type IIIB, Type IIIC, Type IIID, Type IIIE, or Type IIIF CRISPR/Cas system is active, catalytically inactive or has reduced activity relative to wild type. In embodiments, the Type III CRISPR/Cas system is or comprises a Cas10 (Csm1), Csm2, Cas7 (Csm3), Csm4, Csm5, Cas 6, and, Cas7-11, or a fragment or variant thereof, optionally wherein the Type III CRISPR/Cas system is or comprises a Cas10 (Csm1), Csm2, Cas7 (Csm3), Csm4, Csm5, Cas 6, and, Cas7-11 is active, catalytically inactive or has reduced activity relative to wild type. In embodiments, the Type III CRISPR/Cas system comprises a domain from a different endonuclease, optionally wherein the different endonuclease is a Cas endonuclease, optionally wherein the domain is one or more of a PAM-interacting domain, optionally wherein the domain is derived from one or more of Cas9, Cas12a (Cpf1), Cas12e (CasX), Cas12d (CasY), Cas12b (C2c1), Cas13a (C2c2), Cas13b, Cas13c, Cas13d, Cas13X/Cas13bt, Cas13Y, Cas12c (C2c3), GeoCas9, CjCas9, NmeCas9, Cas12J (Cas-Phi), Cas12L (CasLambda), Cas12f (Cas14), Cas12g, Cas12h, Cas12i, Cas12k, NmeCas9, Nme2Cas9, CjCas9, GeoCas9, BlatCas9, PpCas9, and Cas14. In embodiments, the composition or system comprises an intronic sequence comprising a sequence which interacts with or is suitable for interacting with the CRISPR/Cas system. In embodiments, the composition or system further comprises a repair RNA (repRNA) and a CRISPR/Cas system when the present methods are undertaken in cis or trans, as described herein.

In embodiments, the Cas is a type I. In embodiments, the Cas is a type I-A, e.g., without limitation Cas8a or Cas5. In embodiments, the Cas is a type I. In embodiments, the Cas is a type I-B, e.g., without limitation Cas8b. In embodiments, the Cas is a type I. In embodiments, the Cas is a type I-C, e.g., without limitation Cas8c. In embodiments, the Cas is a type I. In embodiments, the Cas is a type I-D, e.g., without limitation Cas10d. In embodiments, the Cas is a type I. In embodiments, the Cas is a type I-E, e.g., without limitation Cse1 or Cse2. In embodiments, the Cas is a type I. In embodiments, the Cas is a type I-F, e.g., without limitation Csy1, Csy2, or Csy3. In embodiments, the Cas is a type I. In embodiments, the Cas is a type I-G, e.g., without limitation GSU0054. In embodiments, the Cas is a type I. In embodiments, the Cas type I is without limitation, Cas3.

In embodiments, the Cas is a type II. In embodiments, the Cas is a type II-A, e.g., without limitation Csn2. In embodiments, the Cas is a type II. In embodiments, the Cas is a type II-B, e.g., without limitation Cas4. In embodiments, the Cas is a type II. In embodiments, the Cas is a type II-C. In embodiments, the Cas is a type II. In embodiments, the Cas type II is without limitation Cas 9.

In embodiments, the Cas is a type III. In embodiments, the Cas is a type III-A, e.g., without limitation Csm2. In embodiments, the Cas is a type III. In embodiments, the Cas is a type III-B, e.g., without limitation Cmr5. In embodiments, the Cas is a type III. In embodiments, the Cas is a type III-C, e.g., without limitation Cas10 or Csx11. In embodiments, the Cas is a type III. In embodiments, the Cas is a type III-D, e.g., without limitation Csx10. In embodiments, the Cas is a type III. In embodiments, the Cas is a type III-E. In embodiments, the Cas is a type III. In embodiments, the Cas is a type III-F. In embodiments, the Cas is a type III. In embodiments, the Cas type III is without limitation Cas 10.

In embodiments, the Cas is a type IV. In embodiments, the Cas is a type IV-A. In embodiments, the Cas is a type IV. In embodiments, the Cas is a type IV-B. In embodiments, the Cas is a type IV. In embodiments, the Cas is a type IV-C.

In embodiments, the Cas is a type V. In embodiments, the Cas is a type V-A, e.g., without limitation Cas12a (Cpf1). In embodiments, the Cas is a type V. In embodiments, the Cas is a type V-B, e.g., without limitation Cas12b (C2c1). In embodiments, the Cas is a type V. In embodiments, the Cas is a type V-C, e.g., without limitation Cas12c (C2c3). In embodiments, the Cas is a type V. In embodiments, the Cas is a type V-D, e.g., without limitation Cas12d (CasY). In embodiments, the Cas is a type V. In embodiments, the Cas is a type V-E, e.g., without limitation Cas12e (CasX). In embodiments, the Cas is a type V. In embodiments, the Cas is a type V-F, e.g., without limitation Cas12f (Cas14, or C2c10). In embodiments, the Cas is a type V. In embodiments, the Cas is a type V-G, e.g., without limitation Cas12g. In embodiments, the Cas is a type V. In embodiments, the Cas is a type V-H, e.g., without limitation Cas12h. In embodiments, the Cas is a type V. In embodiments, the Cas is a type V-I, e.g., without limitation Cas12i. In embodiments, the Cas is a type V. In embodiments, the Cas is a type V-K, e.g., without limitation Cas12k (C2c5). In embodiments, the Cas is a type V. In embodiments, the Cas is a type V-U, e.g., without limitation C2c4, C2c8, or C2c9. In embodiments, the Cas is a type V. In embodiments, the Cas type V is without limitation Cas 12. In embodiments, the Cas is a type VI.

In embodiments, the Cas is a type VI-A, e.g., without limitation Cas13a (C2c2). In embodiments, the Cas is a type VI. In embodiments, the Cas is a type VI-B, e.g., without limitation Cas13b. In embodiments, the Cas is a type VI. In embodiments, the Cas is a type VI-C, e.g., without limitation Cas13c. In embodiments, the Cas is a type VI. In embodiments, the Cas is a type VI-D, e.g., without limitation Cas13d. In embodiments, the Cas is a type VI. In embodiments, the Cas is a type VI-X, e.g., without limitation Cas13x.1. In embodiments, the Cas is a type VI. In embodiments, the Cas is a type VI-Y. In embodiments, the Cas is a type VI. In embodiments, the Cas type VI is without limitation Cas 13.

In embodiments the Cas is Cas3, Cas8a, Cas5, Cas8b, Cas8c, Cas10d, Cse1, Cse2, Csy1, Csy2, Csy3, GSU0054, Cas10, Csm2, Cmr5, Cas10 or Csx11, Csx10, Csf1, Cas9, Csn2, Cas4, Cas12, Cas12a (Cpf1), Cas12b (C2c1), Cas12c (C2c3), Cas12d (CasY), Cas12e (CasX), Cas12f (Cas14, C2c10), Cas12g, Cas12h, Cas12i, Cas12k (C2c5), C2c4, C2c8, C2c9, Cas13, Cas13a (C2c2), Cas13b, Cas13c, Cas13d, or Cas13x.1.

In aspects, the present disclosure provides a composition or system for targeting trans-splicing of a pre-mRNA in a cell, comprising one or more nucleic acids comprising one or more nucleotide sequences comprising from 5' to 3' comprising at least one intronic sequence comprising a small nuclear RNA (snRNA), or a small nucleolar RNA (snoRNA) sequence, and/or splice donor sequence, wherein the snRNA or snoRNA forms a secondary structure and/or comprises a sequence motif to direct the one or more binding domains to the pre-mRNA target sequence.

In embodiments, when the composition or system is introduced to the cell an exon in the pre-mRNA is targeted for trans-splicing. In embodiments, the target sequence is positioned downstream the exon in the pre-mRNA. In embodiments, the target sequence is positioned proximal to a splice site. In embodiments, the target sequence is positioned proximal to a splice donor or a splice acceptor.

In embodiments, trans-splicing occurs between the splice donor of the nucleic acid and a splice acceptor downstream the exon in the pre-mRNA.

In embodiments, trans-splicing results in ligation of the 3' end of the at least one exonic sequence of the nucleic acid with the 5' end of an exon downstream the splice acceptor in the pre-mRNA. In embodiments, the intronic sequence is an snRNA. In embodiments, the snRNA is selected from a U7 snRNA, a U1 snRNA, a U2 snRNA, a U4 snRNA, a U4atac snRNA, a U5 snRNA, a U6 snRNA, a U6atac snRNA, a U11 snRNA, and a U12 snRNA. In embodiments, the snRNA assembles into an snRNP. In embodiments, the snRNA is a U7 snRNA. In embodiments, the U7 snRNA assembles into a U7 RNP. In embodiments, the snRNA is a U1 snRNA. In embodiments, the U1 snRNA assembles into a U1 RNP. In embodiments, the snRNA is a U11 snRNA. In embodiments, the U11 snRNA assembles into a U11 RNP. The composition or system of any one of the embodiments described herein, wherein the snRNA or snoRNA sequence comprises an Sm sequence motif, and/or the snRNA or snoRNA comprises an antisense region sequence (ASR).

In embodiments, the snRNA or snoRNA is at least about 10 to about 80 nucleotides, about 10 to about 70 nucleotides, about 10 to about 60 nucleotides, about 10 to about 50 nucleotides, about 10 to about 40 nucleotides, about 10 to about 30 nucleotides, about 10 to about 20 nucleotides, or about 80, 70, 60, 50, 40, 30, 20, or 10 nucleotides in length.

In embodiments, the composition or system further comprises In embodiments, the composition or system further comprises a protein that forms an RNP or is within an RNP, with the snRNA or snoRNA, or a nucleic acid encoding the protein that forms, or is within, the RNP. In embodiments, the snRNA, snoRNA, protein that forms an RNP, a protein within the RNP, and/or a nucleic acid encoding the protein that forms or is within the RNP comprises a modification or mutation that attenuates, weakens, reduces, decreases, or ablates RNP activity as compared to an unmodified form, and/or leads to attenuation of RNA modifying activity, the RNP activity optionally being selected from cleavage, nucleic acid processing, pseudouridylation, and/or methylation. In embodiments, the snRNA, snoRNA, protein that forms an RNP, and/or a nucleic acid encoding the protein that forms the RNP or is within RNP comprises a modification or mutation that increases, stimulates, or enhances RNP activity, or enhances RNA modifying activity, the RNP activity optionally being selected from cleavage, nucleic acid processing, pseudouridylation, and/or methylation as compared to an unmodified form. In embodiments, the snRNA, snoRNA, protein that forms or is within an RNP, and/or a nucleic acid encoding the protein that forms or is within the RNP comprises at least one or more pseudouridylation sites. In embodiments, the snRNA, snoRNA, protein that forms or is within an RNP, and/or a nucleic acid encoding the protein that forms or is within the RNP comprises no pseudouridylation sites. In embodiments, the repRNA comprises at least one or more pseudouridylation sites. In embodiments, the repRNA comprises no pseudouridylation sites. In embodiments, the repRNA is modified to comprise at least 1, 2, 3 4, 5, 6, 7, 8, 9, 10, 11, 12, 13, 14, 15, 16, 17, 18, 19, 20, 21, 22, 23, 24, 25, 26, 27, 28, 29, 30 or more pseudouridylation sites than the number of pseudouridylation sites in (i) an unmodified state of the snRNA or snoRNA or (ii) an exonic sequence.

In embodiments, the snRNA or snoRNA comprises an antisense region sequence (ASR) selected from SEQ ID NOs: 700-707. In embodiments, the Sm sequence motif comprises a nucleotide sequence selected from SEQ ID NOs: 1-8.

In embodiments, the snRNA or snoRNA comprises a grepRNA sequence. In embodiments, the grepRNA sequence is selected from SEQ ID NOs: 708-711.

In embodiments, the snRNA or snoRNA sequence comprises an Sm sequence motif, and/or the snRNA or snoRNA comprises an antisense region sequence (ASR), and a U7 snRNA. In embodiments, the Sm sequence motif comprises a sequence set forth in SEQ ID NOs: 3 and 4.

In embodiments, the Sm sequence motif assembles with an Sm protein into an RNP. In embodiments, the Sm protein is selected from a B/B', D3, D2, D1, E, F, and G Sm protein.

In embodiments, the snRNA or snoRNA sequence comprises a sequence having at least 80% sequence identity to a sequence selected from SEQ ID NOs: 9-210 and 212-589 or a portion thereof. In embodiments, the snRNA or snoRNA sequence comprises a region of about 7 to about 40 nucleotides in length, wherein the region comprises an Sm sequence motif, and/or wherein the snRNA or snoRNA comprises an antisense region sequence (ASR).

In embodiments, the snRNA or snoRNA comprises an antisense region sequence (ASR) selected from SEQ ID NOs: 700-707. In embodiments, the snRNA or snoRNA is at least about 10 to about 80 nucleotides, about 10 to about 70 nucleotides, about 10 to about 60 nucleotides, about 10 to about 50 nucleotides, about 10 to about 40 nucleotides, about 10 to about 30 nucleotides, about 10 to about 20 nucleotides, or about 80, 70, 60, 50, 40, 30, 20, or 10 nucleotides in length. In embodiments, the snRNA or snoRNA sequence comprises a region of about 40 to about 300 nucleotides in length, wherein the region comprises a secondary structure and/or an Sm sequence motif. In embodiments, the composition or system comprises one binding domain sequence. In embodiments, the composition or system comprises more than one binding domain sequence. In embodiments, the one or more binding domain sequences is about 5 to about 20, about 5 to about 30, about 5 to about 40, about 5 to about 50, about 10 to about 50, about 10 to about 100, about 20 to about 100, about 30 to about 100, about 40 to about 100, about 50 to about 100, about 50 to about 150, about 50 to about 200, about 50 to about 250, about 100 to about 150, about 100 to about 200, about 100 to about 250, or about 100 to about 300 nucleotides in length.

In embodiments, the (a) at least one intronic sequence, (b) splice acceptor and/or splice donor sequence, and (c) at least one exonic sequence are provided in cis or trans, or are suitable for being provided in cis or trans. In embodiments, the (a) at least one intronic sequence, (b) splice acceptor and/or splice donor sequence, and (c) at least one exonic sequence are provided in trans, or are suitable for being provided in trans.

In embodiments, further comprising one or more binding domain sequences of about 4 to about 300 nucleotides each with complementarity to a pre-mRNA target sequence. In embodiments the one or more binding domain sequences is at least about 5 to about 10, about 5 to about 15, about 5 to about 20, about 10 to about 15, about 10 to about 20, about 15 to about 20, or about 20, or about 19, or about 18, or about 17, or about 16, or about 15, or about 14, or about 13, or about 12, or about 11, or about 10, or about 9, or about 8, or about 7, or about 6, or about or 5 nucleotides in length. In embodiments the one or more binding domain sequences is less than about 250 to about 300, about 200 to about 300, about 150 to about 300, about 100 to about 300, about 50 to about 300, about 100 to about 250, about 100 to about 200, about 100 to about 150, about 50 to about 250, about 50 to about 200, about 50 to about 150, about 50 to about 100, or about 300, or about 250, or about 200, or about 150, or about 100, or about 50 nucleotides in length. In embodiments the one or more binding domain sequences is about 5 to about 20, about 5 to about 30, about 5 to about 40, about 5 to about 50, about 10 to about 50, about 10 to about 100, about 20 to about 100, about 30 to about 100, about 40 to about 100, about 50 to about 100, about 50 to about 150, about 50 to about 200, about 50 to about 250, about 100 to about 150, about 100 to about 200, about 100 to about 250, or about 100 to about 300 nucleotides in length.

In embodiments, the composition or system comprises one binding domain sequence. In embodiments, the composition or system comprises at least two binding domain sequences. In embodiments, the composition or system comprises 3, 4, 5, 6, 7, 8, 9, or 10 binding domain sequences. In embodiments, the small nuclear RNA (snRNA) or a small nucleolar RNA (snoRNA) sequence is greater than about 5 nucleotides in length which forms a secondary structure, and optionally comprises a sequence motif to direct the one or more binding domains to the pre-mRNA target sequence. In embodiments, small nuclear RNA (snRNA) or a small nucleolar RNA (snoRNA) sequence is about 5 to about 500, or 5 to about 400, or 5 to about 300, or 5 to about 200, or 5 to about 100, or 5 to about 90, or 5 to about 80, or 5 to about 70, or 5 to about 60, or 5 to about 50, or 5 to about 40, or 5 to about 30, or 5 to about 20, or 5 to about 10, or 7 to about 500, or 7 to about 400, or 7 to about 300, or 7 to about 200, or 7 to about 100, or 7 to about 90, or 7 to about 80, or 7 to about 70, or 7 to about 60, or 7 to about 50, or 7 to about 40, or 7 to about 30, or 7 to about 20, or 7 to about 10 nucleotides in length.

In embodiments, the composition comprises at least one exonic sequence.

In embodiments, the composition or system comprises a CRISPR/Cas system, e.g., a protein and/or nucleic acid thereof. In embodiments, the composition or system further comprises a repair RNA (repRNA) and a CRISPR/Cas system. In embodiments, the CRISPR/Cas system is active, e.g., catalytically active. In embodiments, the CRISPR/Cas system is inactive, e.g., catalytically inactive, e.g., "dead". In embodiments, the CRISPR/Cas system is a Type III CRISPR/Cas system. In embodiments, the Type III CRISPR/Cas system is or comprises a Type IIIA, Type IIIB, Type IIIC, Type IIID, Type IIIE, or Type IIIF CRISPR/Cas system, optionally wherein the Type IIIA, Type IIIB, Type IIIC, Type IIID, Type IIIE, or Type IIIF CRISPR/Cas system is active, catalytically inactive or has reduced activity relative to wild type. In embodiments, the Type III CRISPR/Cas system is or comprises a Cas10 (Csm1), Csm2, Cas7 (Csm3), Csm4, Csm5, Cas 6, and, Cas7-11, or a fragment or variant thereof, optionally wherein the Type III CRISPR/Cas system is or comprises a Cas10 (Csm1), Csm2, Cas7 (Csm3), Csm4, Csm5, Cas 6, and, Cas7-11 is active, catalytically inactive or has reduced activity relative to wild type. In embodiments, the Type III CRISPR/Cas system comprises a domain from a different endonuclease, optionally wherein the different endonuclease is a Cas endonuclease, optionally wherein the domain is one or more of a PAM-interacting domain, optionally wherein the domain is derived from one or more of Cas9, Cas12a (Cpf1), Cas12e (CasX), Cas12d (CasY), Cas12b (C2c1), Cas13a (C2c2), Cas13b, Cas13c, Cas13d, Cas13X/Cas13bt, Cas13Y, Cas12c (C2c3), GeoCas9, CjCas9, NmeCas9, Cas12J (Cas-Phi), Cas12L (CasLambda), Cas12f (Cas14), Cas12g, Cas12h, Cas12i, Cas12k, NmeCas9, Nme2Cas9, CjCas9, GeoCas9, BlatCas9, PpCas9, and Cas14. In embodiments, the composition or system comprises an intronic sequence comprising a sequence which interacts with or is suitable for interacting with the CRISPR/Cas system. In embodiments, the composition or system further comprises a repair RNA (repRNA) and a CRISPR/Cas system when the present methods are undertaken in cis or trans, as described herein.

In embodiments, the Cas is a type I. In embodiments, the Cas is a type I-A, e.g., without limitation Cas8a or Cas5. In embodiments, the Cas is a type I. In embodiments, the Cas is a type I-B, e.g., without limitation Cas8b. In embodiments, the Cas is a type I. In embodiments, the Cas is a type I-C, e.g., without limitation Cas8c. In embodiments, the Cas is a type I. In embodiments, the Cas is a type I-D, e.g., without limitation Cas10d. In embodiments, the Cas is a type I. In embodiments, the Cas is a type I-E, e.g., without limitation Cse1 or Cse2. In embodiments, the Cas is a type I. In embodiments, the Cas is a type I-F, e.g., without limitation Csy1, Csy2, or Csy3. In embodiments, the Cas is a type I. In embodiments, the Cas is a type I-G, e.g., without limitation GSU0054. In embodiments, the Cas is a type I. In embodiments, the Cas type I is without limitation, Cas3. In embodiments, the Cas is a type II. In embodiments, the Cas is a type II-A, e.g., without limitation Csn2. In embodiments, the Cas is a type II. In embodiments, the Cas is a type II-B, e.g., without limitation Cas4. In embodiments, the Cas is a type II. In embodiments, the Cas is a type II-C. In embodiments, the Cas is a type II. In embodiments, the Cas type II is without limitation Cas 9.

In embodiments, the Cas is a type III. In embodiments, the Cas is a type III-A, e.g., without limitation Csm2. In embodiments, the Cas is a type III. In embodiments, the Cas is a type III-B, e.g., without limitation Cmr5. In embodiments, the Cas is a type III. In embodiments, the Cas is a type III-C, e.g., without limitation Cas10 or Csx11. In embodiments, the Cas is a type III. In embodiments, the Cas is a type III-D, e.g., without limitation Csx10. In embodiments, the Cas is a type III. In embodiments, the Cas is a type III-E. In embodiments, the Cas is a type III. In embodiments, the Cas is a type III-F. In embodiments, the Cas is a type III. In embodiments, the Cas type III is without limitation Cas 10.

In embodiments, the Cas is a type IV. In embodiments, the Cas is a type IV-A. In embodiments, the Cas is a type IV. In embodiments, the Cas is a type IV-B. In embodiments, the Cas is a type IV. In embodiments, the Cas is a type IV-C.

In embodiments, the Cas is a type V. In embodiments, the Cas is a type V-A, e.g., without limitation Cas12a (Cpf1). In embodiments, the Cas is a type V. In embodiments, the Cas is a type V-B, e.g., without limitation Cas12b (C2c1). In embodiments, the Cas is a type V. In embodiments, the Cas is a type V-C, e.g., without limitation Cas12c (C2c3). In embodiments, the Cas is a type V. In embodiments, the Cas is a type V-D, e.g., without limitation Cas12d (CasY). In embodiments, the Cas is a type V. In embodiments, the Cas is a type V-E, e.g., without limitation Cas12e (CasX). In embodiments, the Cas is a type V. In embodiments, the Cas is a type V-F, e.g., without limitation Cas12f (Cas14, or C2c10). In embodiments, the Cas is a type V. In embodiments, the Cas is a type V-G, e.g., without limitation Cas12g. In embodiments, the Cas is a type V. In embodiments, the Cas is a type V-H, e.g., without limitation Cas12h. In embodiments, the Cas is a type V. In embodiments, the Cas is a type V-I, e.g., without limitation Cas12i. In embodiments, the Cas is a type V. In embodiments, the Cas is a type V-K, e.g., without limitation Cas12k (C2c5). In embodiments, the Cas is a type V. In embodiments, the Cas is a type V-U, e.g., without limitation C2c4, C2c8, or C2c9. In embodiments, the Cas is a type V. In embodiments, the Cas type V is without limitation Cas 12. In embodiments, the Cas is a type VI.

In embodiments, the Cas is a type VI-A, e.g., without limitation Cas13a (C2c2). In embodiments, the Cas is a type VI. In embodiments, the Cas is a type VI-B, e.g., without limitation Cas13b. In embodiments, the Cas is a type VI. In embodiments, the Cas is a type VI-C, e.g., without limitation Cas13c. In embodiments, the Cas is a type VI. In embodiments, the Cas is a type VI-D, e.g., without limitation Cas13d. In embodiments, the Cas is a type VI. In embodiments, the Cas is a type VI-X, e.g., without limitation Cas13x.1. In embodiments, the Cas is a type VI. In embodiments, the Cas is a type VI-Y. In embodiments, the Cas is a type VI. In embodiments, the Cas type VI is without limitation Cas 13.

In embodiments the Cas is Cas3, Cas8a, Cas5, Cas8b, Cas8c, Cas10d, Cse1, Cse2, Csy1, Csy2, Csy3, GSU0054, Cas10, Csm2, Cmr5, Cas10 or Csx11, Csx10, Csf1, Cas9, Csn2, Cas4, Cas12, Cas12a (Cpf1), Cas12b (C2c1), Cas12c (C2c3), Cas12d (CasY), Cas12e (CasX), Cas12f (Cas14, C2c10), Cas12g, Cas12h, Cas12i, Cas12k (C2c5), C2c4, C2c8, C2c9, Cas13, Cas13a (C2c2), Cas13b, Cas13c, Cas13d, or Cas13x.1.

In aspects, the present disclosure provides a composition or system for targeting trans-splicing of a pre-mRNA in a cell, comprising one or more nucleic acids comprising one or more nucleotide sequences comprising from 5' to 3' at least one intronic sequence comprising a small nuclear RNA (snRNA), or a small nucleolar RNA (snoRNA) sequence, and/or a splice acceptor. In embodiments, described herein is a composition or system for targeting trans-splicing of a pre-mRNA in a cell, comprising one or more nucleic acids comprising one or more nucleotide sequences comprising from 5' to 3': at least one intronic sequence comprising: (i) a snRNA or snoRNA sequence comprising an H/ACA box or a C/D box and one or more binding domain sequences of about 4 to about 30 nucleotides each with complementarity to a pre-mRNA target sequence; and (ii) one or more splicing signals; a splice acceptor; and at least one exonic sequence.

In embodiments, when the composition or system is introduced to the cell an exon in the pre-mRNA is targeted for trans-splicing. In embodiments, the target sequence is positioned upstream the exon in the pre-mRNA. In embodiments, the target sequence is positioned proximal to a splice site. In embodiments, the target sequence is positioned proximal to a splice donor or splice acceptor. In embodiments, trans-splicing occurs between a splice donor upstream the exon in the pre-mRNA and the splice acceptor of the composition or system. In embodiments, trans-splicing results in ligation of the 3' end of an exon upstream the splice donor in the pre-mRNA with the 5' end of the at least one exonic sequence of the composition or system.

In embodiments, the one or more splicing signals comprises a branch point and a polypyrimidine tract.

In embodiments, the intronic sequence comprises a snRNA. In embodiments, the snRNA is selected from a U7 snRNA, a U1 snRNA, a U2 snRNA, a U4 snRNA, a U4atac snRNA, a U5 snRNA, a U6 snRNA, a U6atac snRNA, a U11 snRNA, and a U12 snRNA. In embodiments, the snRNA is a U7 snRNA. In embodiments, the composition or system comprises a snoRNA. In embodiments, the snoRNA comprises an H/ACA box or C/D box. In embodiments, the snRNA or snoRNA sequence assembles into an RNP. In embodiments, the snRNA or snoRNA sequence comprises a sequence motif that assembles into an RNP. In embodiments, the composition or system further comprises In embodiments, the composition or system further comprises a protein that forms an RNP or is within an RNP, with the snRNA or snoRNA, or a nucleic acid encoding the protein that forms, or is within, the RNP. In embodiments, the snRNA, snoRNA, protein that forms an RNP, a protein within the RNP, and/or a nucleic acid encoding the protein that forms or is within the RNP comprises a modification or mutation that attenuates, weakens, reduces, decreases, or ablates RNP activity as compared to an unmodified form, and/or leads to attenuation of RNA modifying activity, the RNP activity optionally being selected from cleavage, nucleic acid processing, pseudouridylation, and/or methylation. In embodiments, the snRNA, snoRNA, protein that forms an RNP, and/or a nucleic acid encoding the protein that forms the RNP or is within RNP comprises a modification or mutation that increases, stimulates, or enhances RNP activity, or enhances RNA modifying activity, the RNP activity optionally being selected from cleavage, nucleic acid processing, pseudouridylation, and/or methylation as compared to an unmodified form.

In embodiments, the (a) at least one intronic sequence, (b) splice acceptor and/or splice donor sequence, and (c) at least one exonic sequence are provided in cis or trans, or are suitable for being provided in cis or trans. In embodiments, the (a) at least one intronic sequence, (b) splice acceptor and/or splice donor sequence, and (c) at least one exonic sequence are provided in trans, or are suitable for being provided in trans.

In embodiments, further comprising one or more binding domain sequences of about 4 to about 300 nucleotides each with complementarity to a pre-mRNA target sequence. In embodiments the one or more binding domain sequences is at least about 5 to about 10, about 5 to about 15, about 5 to about 20, about 10 to about 15, about 10 to about 20, about 15 to about 20, or about 20, or about 19, or about 18, or about 17, or about 16, or about 15, or about 14, or about 13, or about 12, or about 11, or about 10, or about 9, or about 8, or about 7, or about 6, or about or 5 nucleotides in length. In embodiments the one or more binding domain sequences is less than about 250 to about 300, about 200 to about 300, about 150 to about 300, about 100 to about 300, about 50 to about 300, about 100 to about 250, about 100 to about 200, about 100 to about 150, about 50 to about 250, about 50 to about 200, about 50 to about 150, about 50 to about 100, or about 300, or about 250, or about 200, or about 150, or about 100, or about 50 nucleotides in length. In embodiments the one or more binding domain sequences is about 5 to about 20, about 5 to about 30, about 5 to about 40, about 5 to about 50, about 10 to about 50, about 10 to about 100, about 20 to about 100, about 30 to about 100, about 40 to about 100, about 50 to about 100, about 50 to about 150, about 50 to about 200, about 50 to about 250, about 100 to about 150, about 100 to about 200, about 100 to about 250, or about 100 to about 300 nucleotides in length.

In embodiments, the composition or system comprises one binding domain sequence. In embodiments, the composition or system comprises at least two binding domain sequences. In embodiments, the composition or system comprises 3, 4, 5, 6, 7, 8, 9, or 10 binding domain sequences. In embodiments, the small nuclear RNA (snRNA) or a small nucleolar RNA (snoRNA) sequence is greater than about 5 nucleotides in length which forms a secondary structure, and optionally comprises a sequence motif to direct the one or more binding domains to the pre-mRNA target sequence. In embodiments, small nuclear RNA (snRNA) or a small nucleolar RNA (snoRNA) sequence is about 5 to about 500, or 5 to about 400, or 5 to about 300, or 5 to about 200, or 5 to about 100, or 5 to about 90, or 5 to about 80, or 5 to about 70, or 5 to about 60, or 5 to about 50, or 5 to about 40, or 5 to about 30, or 5 to about 20, or 5 to about 10, or 7 to about 500, or 7 to about 400, or 7 to about 300, or 7 to about 200, or 7 to about 100, or 7 to about 90, or 7 to about 80, or 7 to about 70, or 7 to about 60, or 7 to about 50, or 7 to about 40, or 7 to about 30, or 7 to about 20, or 7 to about 10 nucleotides in length.

In embodiments, the composition comprises at least one exonic sequence.

In embodiments, the composition or system comprises a CRISPR/Cas system, e.g., a protein and/or nucleic acid thereof. In embodiments, the composition or system further comprises a repair RNA (repRNA) and a CRISPR/Cas system. In embodiments, the CRISPR/Cas system is active, e.g., catalytically active. In embodiments, the CRISPR/Cas system is inactive, e.g., catalytically inactive, e.g., "dead". In embodiments, the CRISPR/Cas system is a Type III CRISPR/Cas system. In embodiments, the Type III CRISPR/Cas system is or comprises a Type IIIA, Type IIIB, Type IIIC, Type IIID, Type IIIE, or Type IIIF CRISPR/Cas system, optionally wherein the Type IIIA, Type IIIB, Type IIIC, Type IIID, Type IIIE, or Type IIIF CRISPR/Cas system is active, catalytically inactive or has reduced activity relative to wild type. In embodiments, the Type III CRISPR/Cas system is or comprises a Cas10 (Csm1), Csm2, Cas7 (Csm3), Csm4, Csm5, Cas 6, and, Cas7-11, or a fragment or variant thereof, optionally wherein the Type III CRISPR/Cas system is or comprises a Cas10 (Csm1), Csm2, Cas7 (Csm3), Csm4, Csm5, Cas 6, and, Cas7-11 is active, catalytically inactive or has reduced activity relative to wild type. In embodiments, the Type III CRISPR/Cas system comprises a domain from a different endonuclease, optionally wherein the different endonuclease is a Cas endonuclease, optionally wherein the domain is one or more of a PAM-interacting domain, optionally wherein the domain is derived from one or more of Cas9, Cas12a (Cpf1), Cas12e (CasX), Cas12d (CasY), Cas12b (C2c1), Cas13a (C2c2), Cas13b, Cas13c, Cas13d, Cas13X/Cas13bt, Cas13Y, Cas12c (C2c3), GeoCas9, CjCas9, NmeCas9, Cas12J (CasPhi), Cas12L (CasLambda), Cas12f (Cas14), Cas12g, Cas12h, Cas12i, Cas12k, NmeCas9, Nme2Cas9, CjCas9, GeoCas9, BlatCas9, PpCas9, and Cas14. In embodiments, the composition or system comprises an intronic sequence comprising a sequence which interacts with or is suitable for interacting with the CRISPR/Cas system. In embodiments, the composition or system further comprises a repair RNA (repRNA) and a CRISPR/Cas system when the present methods are undertaken in cis or trans, as described herein.

In embodiments, the Cas is a type I. In embodiments, the Cas is a type I-A, e.g., without limitation Cas8a or Cas5. In embodiments, the Cas is a type I. In embodiments, the Cas is a type I-B, e.g., without limitation Cas8b. In embodiments, the Cas is a type I. In embodiments, the Cas is a type I-C, e.g., without limitation Cas8c. In embodiments, the Cas is a type I. In embodiments, the Cas is a type I-D, e.g., without limitation Cas10d. In embodiments, the Cas is a type I. In embodiments, the Cas is a type I-E, e.g., without limitation Cse1 or Cse2. In embodiments, the Cas is a type I. In embodiments, the Cas is a type I-F, e.g., without limitation Csy1, Csy2, or Csy3. In embodiments, the Cas is a type I. In embodiments, the Cas is a type I-G, e.g., without limitation GSU0054. In embodiments, the Cas is a type I. In embodiments, the Cas type I is without limitation, Cas3. In embodiments, the Cas is a type II. In embodiments, the Cas is a type II-A, e.g., without limitation Csn2. In embodiments, the Cas is a type II. In embodiments, the Cas is a type II-B, e.g., without limitation Cas4. In embodiments, the Cas is a type II. In embodiments, the Cas is a type II-C. In embodiments, the Cas is a type II. In embodiments, the Cas type II is without limitation Cas 9.

In embodiments, the Cas is a type III. In embodiments, the Cas is a type III-A, e.g., without limitation Csm2. In embodiments, the Cas is a type III. In embodiments, the Cas is a type III-B, e.g., without limitation Cmr5. In embodiments, the Cas is a type III. In embodiments, the Cas is a type III-C, e.g., without limitation Cas10 or Csx11. In embodiments, the Cas is a type III. In embodiments, the Cas is a type III-D, e.g., without limitation Csx10. In embodiments, the Cas is a type III. In embodiments, the Cas is a type III-E. In embodiments, the Cas is a type III. In embodiments, the Cas is a type III-F. In embodiments, the Cas is a type III. In embodiments, the Cas type III is without limitation Cas 10.

In embodiments, the Cas is a type IV. In embodiments, the Cas is a type IV-A. In embodiments, the Cas is a type IV. In embodiments, the Cas is a type IV-B. In embodiments, the Cas is a type IV. In embodiments, the Cas is a type IV-C.

In embodiments, the Cas is a type V. In embodiments, the Cas is a type V-A, e.g., without limitation Cas12a (Cpf1). In embodiments, the Cas is a type V. In embodiments, the Cas is a type V-B, e.g., without limitation Cas12b (C2c1). In embodiments, the Cas is a type V. In embodiments, the Cas is a type V-C, e.g., without limitation Cas12c (C2c3). In embodiments, the Cas is a type V. In embodiments, the Cas is a type V-D, e.g., without limitation Cas12d (CasY). In embodiments, the Cas is a type V. In embodiments, the Cas is a type V-E, e.g., without limitation Cas12e (CasX). In embodiments, the Cas is a type V. In embodiments, the Cas is a type V-F, e.g., without limitation Cas12f (Cas14, or C2c10). In embodiments, the Cas is a type V. In embodiments, the Cas is a type V-G, e.g., without limitation Cas12g. In embodiments, the Cas is a type V. In embodiments, the Cas is a type V-H, e.g., without limitation Cas12h. In embodiments, the Cas is a type V. In embodiments, the Cas is a type V-I, e.g., without limitation Cas12i. In embodiments, the Cas is a type V. In embodiments, the Cas is a type V-K, e.g., without limitation Cas12k (C2c5). In embodiments, the Cas is a type V. In embodiments, the Cas is a type V-U, e.g., without limitation C2c4, C2c8, or C2c9. In embodiments, the Cas is a type V. In embodiments, the Cas type V is without limitation Cas 12. In embodiments, the Cas is a type VI.

In embodiments, the Cas is a type VI-A, e.g., without limitation Cas13a (C2c2). In embodiments, the Cas is a type VI. In embodiments, the Cas is a type VI-B, e.g., without limitation Cas13b. In embodiments, the Cas is a type VI. In embodiments, the Cas is a type VI-C, e.g., without limitation Cas13c. In embodiments, the Cas is a type VI. In embodiments, the Cas is a type VI-D, e.g., without limitation Cas13d. In embodiments, the Cas is a type VI. In embodiments, the Cas is a type VI-X, e.g., without limitation Cas13x.1. In embodiments, the Cas is a type VI. In embodiments, the Cas is a type VI-Y. In embodiments, the Cas is a type VI. In embodiments, the Cas type VI is without limitation Cas 13.

In embodiments the Cas is Cas3, Cas8a, Cas5, Cas8b, Cas8c, Cas10d, Cse1, Cse2, Csy1, Csy2, Csy3, GSU0054, Cas10, Csm2, Cmr5, Cas10 or Csx11, Csx10, Csf1, Cas9, Csn2, Cas4, Cas12, Cas12a (Cpf1), Cas12b (C2c1), Cas12c (C2c3), Cas12d (CasY), Cas12e (CasX), Cas12f (Cas14, C2c10), Cas12g, Cas12h, Cas12i, Cas12k (C2c5), C2c4, C2c8, C2c9, Cas13, Cas13a (C2c2), Cas13b, Cas13c, Cas13d, or Cas13x.1.

In aspects, the present disclosure provides a composition or system for targeting trans-splicing of a pre-mRNA in a cell, comprising one or more nucleic acids comprising one or more nucleotide sequences comprising from 5' to 3': (a) at least one exonic sequence; (b) a splice donor; and (c) at least one intronic sequence comprising a snRNA or snoRNA sequence comprising an H/ACA box or a C/D box and one or more binding domain sequences of about 4 to about 30 nucleotides each with complementarity to a pre-mRNA target sequence.

In embodiments, when the composition or system is introduced to the cell an exon in the pre-mRNA is targeted for trans-splicing. In embodiments, the target sequence is positioned downstream the exon in the pre-mRNA. In embodiments, the target sequence is positioned proximal to a splice site. In embodiments, the target sequence is positioned proximal to a splice donor or a splice acceptor.

In embodiments, trans-splicing occurs between the splice donor of the composition or system and a splice acceptor downstream the exon in the pre-mRNA. In embodiments, trans-splicing results in ligation of the 3' end of the at least one exonic sequence of the composition or system with the 5' end of an exon downstream the splice acceptor in the pre-mRNA.

In embodiments, the snRNA or snoRNA sequence comprises an H/ACA box comprising 5' to 3' an H consensus sequence and an ACA consensus sequence. In embodiments, the composition or system comprises at least one binding domain sequence positioned: (i) upstream the H consensus sequence; (ii) downstream the ACA consensus sequence; (iii) between the H consensus sequence and the ACA consensus sequence; or (iv) a combination of (i)-(iii).

In embodiments, the snRNA or snoRNA sequence comprises C/D box comprising 5' to 3' a C consensus sequence, a D' consensus sequence, a C' consensus sequence, and a D consensus sequence.

In embodiments, the composition or system comprises at least one binding domain positioned (i) upstream the C consensus sequence; (ii) between the C consensus sequence and the D' consensus sequence; (iii) between the D' consensus sequence and the C' consensus sequence; (iv) between the C' consensus sequence and the D consensus sequence; (v) downstream the D consensus sequence; or (vi) a combination of (i)-(v).

In embodiments, the snRNA or snoRNA sequence comprises a sequence having at least 80% sequence identity to a sequence selected from SEQ ID NOs: 590-628, 630-632, 634-635, 638, 640, 642, 644-645, 647-648, 650, 652-653, 655, 657, 732-737, 741-746, 748-749, 751-758, 760-761, 763-765, 767, 771-774, 776-778, and 780-789, or a portion thereof. In embodiments, the snRNA or snoRNA sequence comprises a region of about 40 to about 300 nucleotides in length and comprising an H consensus sequence and an ACA consensus sequence.

In embodiments, the snRNA or snoRNA sequence comprises one binding domain sequence. In embodiments, the snRNA or snoRNA sequence comprises more than one binding domain sequence. In embodiments, the composition or system comprises at least one binding domain sequence with full complementarity to the pre-mRNA target sequence. In embodiments, the composition or system comprises at least one binding domain sequence with partial complementarity to the pre-mRNA target sequence. In embodiments, the at least one binding domain sequence comprises one or more mismatches relative to the pre-mRNA target sequence. In embodiments, the at least one binding domain sequence has at least 95% complementarity to the pre-mRNA target sequence.

In embodiments, the (a) at least one intronic sequence, (b) splice acceptor and/or splice donor sequence, and (c) at least one exonic sequence are provided in cis or trans, or are suitable for being provided in cis or trans. In embodiments, the (a) at least one intronic sequence, (b) splice acceptor and/or splice donor sequence, and (c) at least one exonic sequence are provided in trans, or are suitable for being provided in trans.

In embodiments, the composition or system comprises a sequence up to about 20,000 nucleotides in length.

In embodiments, the composition or system comprises a sequence of about 50 to about 500, about 50 to about 1000, about 100 to about 500, about 100 to about 1000, about 500 to about 1000, about 500 to about 2000, about 500 to about 3,000, about 500 to about 4,000, about 500 to about 5,000, about 1,000 to about 5,000, about 1,000 to about 10,000, about 5,000 to about 15,000, or about 5,000 to about 20,000 nucleotides in length.

In embodiments, the composition or system is introduced to the cell as an RNA. In embodiments, the composition or system is introduced to the cell as a DNA.

In embodiments, the composition or system is introduced to the cell by a single viral vector. In embodiments, the viral vector is an AAV.

In embodiments, the composition or system is introduced to the cell by a non-viral vector.

In embodiments, the introduction of the composition or system to the cell results in an efficiency of trans-splicing that is greater than a composition or system lacking the snRNA or snoRNA sequence. In embodiments, the efficiency of trans-splicing is greater than about 10%, about 20%, about 30%, about 40%, about 50%, about 60%, about 70%, about 80%, about 90%, or about 99%.

In embodiments, introduction of the composition or system to the cell is without any additional protein to guide activity.

In embodiments, introduction of the composition or system to the cell results in an immunogenicity that is less than a composition or system lacking the snRNA or snoRNA sequence.

In embodiments, the composition or system is formulated as a lipid nanoparticle.

In aspects, the present disclosure provides a viral vector comprising the composition or system of any one of the embodiments described herein.

In aspects, the present disclosure provides a lipid nanoparticle comprising the composition or system of any one of the embodiments described herein.

In aspects, the present disclosure provides a cell comprising the composition or system of any one of the embodiments described herein, the viral vector of any one of the embodiments described herein, or the lipid nanoparticle of any one of the embodiments described herein.

In aspects, the present disclosure provides a pharmaceutical composition comprising the composition or system of any one of the embodiments described herein, the viral vector of any one of the embodiments described herein, or the lipid nanoparticle of any one of the embodiments described herein, and a pharmaceutically acceptable carrier.

In aspects, the present disclosure provides a pharmaceutical composition comprising the cell of any one of the embodiments described herein, and a pharmaceutically acceptable carrier.

In aspects, the present disclosure provides a method of targeting trans-splicing of a pre-mRNA in a cell, the method comprising contacting the cell with the composition or system of any one of the embodiments described herein, the viral vector of any one of the embodiments described herein, or the lipid nanoparticle of any one of the embodiments described herein, or the pharmaceutical composition of any one of the embodiments described herein, wherein when the composition or system, the viral vector, the lipid nanoparticle, or the pharmaceutical composition contacts the cell, the one or more binding domain sequences bind to the pre-mRNA, thereby targeting the pre-mRNA for trans-splicing.

In aspects, the present disclosure provides a method of correcting a mutation in a pre-mRNA in a cell, the method comprising contacting the cell with the composition or system of any one of the embodiments described herein, the viral vector of any one of the embodiments described herein, or the lipid nanoparticle of any one of the embodiments described herein, or the pharmaceutical composition of any one of the embodiments described herein, wherein when the composition or system, the viral vector, the lipid nanoparticle, or the pharmaceutical composition contacts the cell, the one or more binding domain sequences bind to the pre-mRNA at a location proximal to the mutation, and wherein trans-splicing replaces one or more exons in the pre-mRNA comprising the mutation, thereby correcting the mutation.

In aspects, the present disclosure provides a method of treating a patient with a disease or disorder associated with a mutation in a pre-mRNA, the method comprising administering to the patient an effective amount of the composition or system of any one of the embodiments described herein, the viral vector of any one of the embodiments described herein, or the lipid nanoparticle of any one of the embodiments described herein, or the pharmaceutical composition of any one of the embodiments described herein, wherein when the composition or system, the viral vector, the lipid nanoparticle, or the pharmaceutical composition is administered, the one or more binding domain sequences bind to the pre-mRNA at a location proximal to the mutation, and wherein trans-splicing replaces one or more exons in the pre-mRNA comprising the mutation, thereby correcting the mutation.

In embodiments, the present methods are conducted as essentially in FIG. 7A, FIG. 8A, and FIG. 10.

In embodiments, trans-splicing results in an mRNA that alleviates the disease or does not cause or contribute to the disease.

In embodiments, the composition or system of any one of the embodiments described herein, the viral vector of any one of the embodiments described herein, or the lipid nanoparticle of any one of the embodiments described herein, or the pharmaceutical composition of any one of the embodiments described herein for use in treating a patient with a disease or disorder associated with a mutation in a pre-mRNA, the treatment comprising administering to the patient the composition or system, the viral vector, the lipid nanoparticle, or the pharmaceutical composition, wherein when the composition or system, the viral vector, the lipid nanoparticle, or the pharmaceutical composition is administered, the one or more binding domain sequences bind to the pre-mRNA at a location proximal to the mutation, and wherein trans-splicing replaces one or more exons in the pre-mRNA comprising the mutation, thereby correcting the mutation.

In embodiments, the composition or system of any one of the embodiments described herein, the viral vector of any one of the embodiments described herein, or the lipid nanoparticle of any one of the embodiments described herein, or the pharmaceutical composition of any one of the embodiments described herein for the manufacture of a medicament for use in treating a patient with a disease or disorder associated with a mutation in a pre-mRNA, the treatment comprising administering to the patient the medicament, wherein when the medicament is administered, the one or more binding domain sequences of the composition or system binds to the pre-mRNA at a location proximal to the mutation, and wherein trans-splicing replaces one or more exons in the pre-mRNA comprising the mutation, thereby correcting the mutation.

In embodiments, the present methods are conducted as essentially in FIG. 7A, FIG. 8A, and FIG. 10.

In aspects, the present disclosure provides a kit comprising a container comprising the composition or system of any one of the embodiments described herein, the viral vector of any one of the embodiments described herein, or the lipid nanoparticle of any one of the embodiments described herein, or the pharmaceutical composition of any one of the embodiments described herein, with instructions for use in correcting a mutation in a pre-mRNA.

In embodiment, the present disclosure provides a composition or system of any one of the embodiments described herein, the viral vector of any one of the embodiments described herein, the lipid nanoparticle of any one of the embodiments described herein, the pharmaceutical composition of any one of the embodiments described herein, the method of any one of any one of the embodiments described herein, or the kit of any one of the embodiments described herein, wherein the trans-splicing system comprises an active cas nuclease. In embodiments, wherein the active cas nuclease is a Type III CRISPR/Cas system, or comprises a Type IIIA, Type IIIB, Type IIIC, Type IIID, Type IIIE, or Type IIIF CRISPR/Cas system, optionally wherein the Type IIIA, Type IIIB, Type IIIC, Type IIID, Type IIIE, Type IIIF CRISPR/Cas system, optionally wherein the Type III CRISPR/Cas system is or comprises a Cas10 (Csm1), Csm2, Cas7 (Csm3), Csm4, Csm5, Cas 6, and, Cas7-11, or a fragment or variant thereof, optionally wherein the Type III CRISPR/Cas system is or comprises a Cas10 (Csm1), Csm2, Cas7 (Csm3), Csm4, Csm5, Cas 6.

In aspects, the present disclosure provides a method of slowing, reducing, or ablating transcription of a target gene, and/or stimulating, enhancing, or increasing the Pol II stalling/release. In embodiments, this method increases trans-splicing, without wishing to be bound by theory, by forcing G4 or similarly bulky RNA-RNA motif formation downstream of the repRNA's binding motif as compared to an unmodified form.

In aspects, the present disclosure provides compositions, systems, and/or methods for separate delivery of at least one repRNA capable of trans-splicing at least one other repRNA (e.g., daisychain) and/or an endogenous RNA target, e.g., for multi-kilobase edits larger than the cargo capacity of a single AAV. In embodiments, this permits single AAV delivery, e.g., by effectively reducing the need for a cargo size that is greater than AAV loading capacity.

In aspects, the present disclosure provides a method for modifying and converting an endogenous RNA, such as and without limitation a pre-mRNA, mRNA, lncRNA, into a repRNA for trans-splicing.

In aspects, disclosed herein is a composition or system for targeting trans-splicing of a pre-mRNA in a cell, comprising one or more nucleic acids comprising one or more nucleotide sequences comprising from 5' to 3': (a) a splice donor and/or a splice acceptor; and (b) at least one intronic sequence comprising a snRNA or snoRNA sequence comprising an H/ACA box or a C/D box and one or more binding domain sequences of about 4 to about 300 nucleotides each with complementarity to a pre-mRNA target sequence.

In the embodiments, disclosed herein is a composition or system of any one of the embodiments disclosed herein, the viral vector of any one of the embodiments disclosed herein, or the lipid nanoparticle of any one of the embodiments disclosed herein, or the pharmaceutical composition of any one of the embodiments disclosed herein, or the method of any one of the embodiments disclosed herein, or the kit of any one of the embodiments disclosed herein, wherein the binding domain sequence is between about 1 nucleotide, or about 5 nucleotides, or about 10 nucleotides, or about 50 nucleotides, or about 100 nucleotides, or about 1000 nucleotides near a H/ACA box or C/D box sequence.

In the embodiments, disclosed herein is a composition or system of any one of the embodiments disclosed herein, the viral vector of any one of the embodiments disclosed herein, or the lipid nanoparticle of any one of the embodiments disclosed herein, or the pharmaceutical composition of any one of the embodiments disclosed herein, or the method of any one of the embodiments disclosed herein, or the kit of any one of the embodiments disclosed herein, wherein the snoRNA is a H/ACA snoRNA (SNORA), C/D snoRNA (SNORD), or a small cajal RNA (scaRNA).

In the embodiments, disclosed herein is a composition or system of any one of the embodiments disclosed herein, the viral vector of any one of the embodiments disclosed herein, or the lipid nanoparticle of any one of the embodiments disclosed herein, or the pharmaceutical composition of any one of the embodiments disclosed herein, or the method of any one of the embodiments disclosed herein, or the kit of any one of the embodiments disclosed herein, wherein the snoRNA is SNORA101B, SNORA48, SNORA54, SNORA66, SNORA73A, or SNORA8, or the snoRNA is SNORA101B, SNORA48, SNORA54, SNORA66, SNORA73A, or SNORA8 with at least one or more mutations.

In the embodiments, disclosed herein is a composition or system of any one of the embodiments disclosed herein, the viral vector of any one of the embodiments disclosed herein, or the lipid nanoparticle of any one of the embodiments disclosed herein, or the pharmaceutical composition of any one of the embodiments disclosed herein, or the method of any one of the embodiments disclosed herein, or the kit of any one of the embodiments disclosed herein, wherein the snoRNA is in cis with respect to the repRNA.

In the embodiments, disclosed herein is a composition or system of any one of the embodiments disclosed herein, the viral vector of any one of the embodiments disclosed herein, or the lipid nanoparticle of any one of the embodiments disclosed herein, or the pharmaceutical composition of any one of the embodiments disclosed herein, or the method of any one of the embodiments disclosed herein, or the kit of any one of the embodiments disclosed herein, wherein the snoRNA is in trans with respect to the repRNA.

In the embodiments, disclosed herein is a composition or system of any one of the embodiments disclosed herein, the viral vector of any one of the embodiments disclosed herein, or the lipid nanoparticle of any one of the embodiments disclosed herein, or the pharmaceutical composition of any one of the embodiments disclosed herein, or the method of any one of the embodiments disclosed herein, or the kit of any one of the embodiments disclosed herein, wherein the repRNA comprises a splice donor and/or a splice acceptor.

In the embodiments, disclosed herein is a composition or system of any one of the embodiments disclosed herein, the viral vector of any one of the embodiments disclosed herein, or the lipid nanoparticle of any one of the embodiments disclosed herein, or the pharmaceutical composition of any one of the embodiments disclosed herein, or the method of any one of the embodiments disclosed herein, or the kit of any one of the embodiments disclosed herein, wherein the repRNA comprises a splice donor and/or a splice acceptor, and wherein the snoRNA and snRNA are in trans with respect to the repRNA.

In the embodiments, disclosed herein is a composition or system of any one of the embodiments disclosed herein, the viral vector of any one of the embodiments disclosed herein, or the lipid nanoparticle of any one of the embodiments disclosed herein, or the pharmaceutical composition of any one of the embodiments disclosed herein, or the method of any one of the embodiments disclosed herein, or the kit of any one of the embodiments disclosed herein, wherein a mutation in H and/or ACA motifs substantially decreases the trans-splicing efficiency.

In the embodiments, disclosed herein is a composition or system of any one of the embodiments disclosed herein, the viral vector of any one of the embodiments disclosed herein, or the lipid nanoparticle of any one of the embodiments disclosed herein, or the pharmaceutical composition of any one of the embodiments disclosed herein, or the method of any one of the embodiments disclosed herein, or the kit of any one of the embodiments disclosed herein, wherein the snoRNA is added to the 3' end of a 5' repRNA.

In the embodiments, disclosed herein is a composition or system of any one of the embodiments disclosed herein, the viral vector of any one of the embodiments disclosed herein, or the lipid nanoparticle of any one of the embodiments disclosed herein, or the pharmaceutical composition of any one of the embodiments disclosed herein, or the method of any one of the embodiments disclosed herein, or the kit of any one of the embodiments disclosed herein, wherein the addition of a SNORA modification on a transcript stabilizes the 3' end of the transcript after ribozyme cleavage and polyA removal.

In the embodiments, disclosed herein is a composition or system of any one of the embodiments disclosed herein, the viral vector of any one of the embodiments disclosed herein, or the lipid nanoparticle of any one of the embodiments disclosed herein, or the pharmaceutical composition of any one of the embodiments disclosed herein, or the method of any one of the embodiments disclosed herein, or the kit of any one of the embodiments disclosed herein, wherein the snoRNA is added to the 5' end of a 3' repRNA.

In the embodiments, disclosed herein is a composition or system of any one of the embodiments disclosed herein, the viral vector of any one of the embodiments disclosed herein, or the lipid nanoparticle of any one of the embodiments disclosed herein, or the pharmaceutical composition of any one of the embodiments disclosed herein, or the method of any one of the embodiments disclosed herein, or the kit of any one of the embodiments disclosed herein, wherein the snoRNA is added to the 3' end of a 3' repRNA.

In the embodiments, disclosed herein is a composition or system of any one of the embodiments disclosed herein, the viral vector of any one of the embodiments disclosed herein, or the lipid nanoparticle of any one of the embodiments disclosed herein, or the pharmaceutical composition of any one of the embodiments disclosed herein, or the method of any one of the embodiments disclosed herein, or the kit of any one of the embodiments disclosed herein, wherein the snoRNA is added to the 5' end of a 5' repRNA.

In the embodiments, disclosed herein is a composition or system of any one of the embodiments disclosed herein, the viral vector of any one of the embodiments disclosed herein, or the lipid nanoparticle of any one of the embodiments disclosed herein, or the pharmaceutical composition of any one of the embodiments disclosed herein, or the method of any one of the embodiments disclosed herein, or the kit of any one of the embodiments disclosed herein, wherein the SNORA sequence has at least about 80%, or at least about 85%, or at least about 90%, or at least about 95%, or at least about 96%, or at least about 97%, or at least about 98%, or at least about 99% identity to any one of SEQ ID NOs: 590-628, 630-632, 634-635, 638, 640, 642, 644-645, 647-648, 650, 652-653, 655, 657, 732-737, 741-746, 748-749, 751-758, 760-761, 763-765, 767, 771-774, 776-778, and 780-789.

The details of one or more examples of the disclosure are set forth in the description below. Other features or advantages of the present disclosure will be apparent from the following drawings, detailed description of several examples, and also from the appended claims. The details of the disclosure are set forth in the accompanying description below. Although methods and materials similar or equivalent to those described herein can be used in the practice or testing of the present disclosure, illustrative methods and materials are now described. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs.

BRIEF DESCRIPTION OF THE FIGURES

FIG. 5A, FIG. 5B, and FIG. 5C provides a schematic, without wishing to be bound by theory, depicting the extended and folded secondary structure of an exemplary composition, system, and/or the one or more nucleic acids comprising one or more nucleotide sequences described herein having 5' to 3' an RNA binding domain, an ncRNA having an Sm sequence motif, intron, SA, and exon (SEQ ID NO: 804, SEQ ID NO: 805, SEQ ID NO: 806, and SEQ ID NO: 807) (FIG. 5A) and the interaction of the exemplary composition, system, and/or the one or more nucleic acids comprising one or more nucleotide sequences described herein with a target pre-mRNA that initiates a trans-splicing event between the SD of the pre-mRNA and the SA of the exemplary composition, system, and/or the one or more nucleic acids comprising one or more nucleotide sequences described herein (FIG. 5B, and FIG. 5C).

FIG. 6A, FIG. 6B, and FIG. 6C provides a schematic, without wishing to be bound by theory, depicting the extended and folded secondary structure of an exemplary composition, system, and/or the one or more nucleic acids comprising one or more nucleotide sequences described herein having 5' to 3' a snoRNA having an insertion of two RNA binding domains, intron, SA, and exon (SEQ ID NO: 808, SEQ ID NO: 809, SEQ ID NO: 810, and SEQ ID NO: 811) (FIG. 6A) and the interaction of the exemplary composition, system, and/or the one or more nucleic acids comprising one or more nucleotide sequences described herein with a target pre-mRNA that initiates a trans-splicing event between the SD of the pre-mRNA and the SA of the exemplary composition, system, and/or the one or more nucleic acids comprising one or more nucleotide sequences described herein (FIG. 6B, and FIG. 6C).

FIG. 7A provides a schematic, without wishing to be bound by theory, depicting a U7 gRNA enhancing Cas13-based trans-splicing. FIG. 7B is a graph showing data of the USH2A trans-splicing system and the combination U7 gRNAs with an RNA-targeting CRISPR-Cas (protein and CRISPR gRNA) and a repair RNA enables, compared to conditions where the U7 gRNA are not provided (RNA-targeting CRISPR-Cas system and repair RNA alone), or conditions where the U7 gRNA sequence is mutated, or conditions where the U7 gRNA is targeting a different sequence (non-targeting guide).

FIG. 8A provides a schematic, without wishing to be bound by theory, depicting a U7 gRNA enhancing Cas13-based trans-splicing. FIG. 8B is a graph showing data of the USH2A trans-splicing system and the combination U7 gRNAs with a repair RNA in trans, which enables exon replacement, compared to conditions where the U7 gRNA is not provided (repRNA alone), or conditions where the gRNA sequence is mutated, or conditions where the U7 gRNA is targeting a different sequence (non-targeting guide).

FIG. 10A provides a schematic, without wishing to be bound by theory, depicting an experimental design to test 3' trans-splicing and exon replacement using a U7 grepRNA, compared to a non-targeting ASR or a grepRNA lacking the U7 hairpin. FIG. 10B is a graph showing U7-guided trans-splicing on an USH2A target (3' RNA replacement) with transient transfection leading to 45% trans-splicing efficiency.

FIG. 11 shows pATK0388 (SEQ ID NO: 713), pATK0945 (SEQ ID NO: 714), pATK0946 (SEQ ID NO: 715), pATK0947 (SEQ ID NO: 716), pATK0948 (SEQ ID NO: 717), pATK0949 (SEQ ID NO: 718), pATK0950 (SEQ ID NO: 719), pATK0973 (SEQ ID NO: 720), and pATK0974 (SEQ ID NO: 721).

DETAILED DESCRIPTION

Figure 1A:
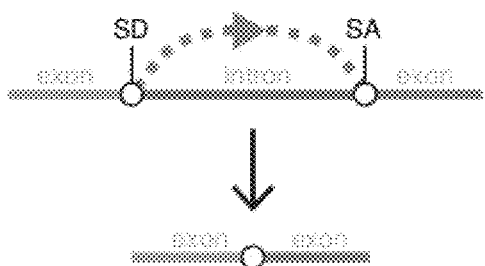
FIG. 1A and FIG. 1B provide schematics, without wishing to be bound by theory, depicting cis-splicing of a pre-mRNA (FIG. 1A) and trans-splicing between two pre-mRNA molecules (FIG. 1B). "SD" refers to a splice donor. "SA" refers to a splice acceptor.

The present disclosure provides a composition or system suitable for targeting trans-splicing of a pre-mRNA in a cell comprising one or more nucleic acids comprising one or more nucleotide sequences comprising at least one intronic sequence comprising a small nuclear RNA (snRNA), or a small nucleolar RNA (snoRNA) sequence, a splice acceptor and/or splice donor sequence. Without being bound by theory, the binding event brings the composition, system, and/or the one or more nucleic acids comprising one or more nucleotide sequences described herein into proximity of a region of the target RNA (e.g., pre-mRNA) selected for trans-splicing and recruits the spliceosome to the target RNA (e.g., pre-mRNA) such that efficient trans-splicing occurs. In some embodiments, the target RNA is a pre-mRNA. In some embodiments, the pre-mRNA comprises a nucleotide sequence comprising a disease-causing mutation. In some embodiments, the trans-splicing generates a mRNA comprising a desired alteration compared to an mRNA generated by cis-splicing of the pre-mRNA. For example, in some embodiments, the desired alteration is correction of a disease-causing mutation in the pre-mRNA.

Small nucleolar RNAs (snoRNAs) are small non-coding RNAs widely present in the nucleoli of eukaryotic cells and typically have a length of about 60-300 nucleotides. snoRNAs are mainly encoded by intronic regions of both protein coding and non-protein coding genes. Normally, snoRNAs can be mainly classified into three groups: H/ACA box snoRNAs, C/D box snoRNAs, and small cajal RNAs (scaRNAs).

Small nuclear RNAs (snRNAs) are recognized as key components of the spliceosome and are involved in the splicing of pre-mRNA. snRNAs can be complexed with many proteins to form RNA-protein complexes, which are known as small nuclear ribonucleoproteins (snRNPs), in the cell nucleus.

In embodiments, the intronic sequence comprises a snRNA. In embodiments, the snRNA is selected from a U7 snRNA, a U1 snRNA, a U2 snRNA, a U4 snRNA, a U4atac snRNA, a U5 snRNA, a U6 snRNA, a U6atac snRNA, a U11 snRNA, and a U12 snRNA. In embodiments, the snRNA is a U7 snRNA. In embodiments, the composition or system comprises a snoRNA.

In embodiments, the disclosure provides methods of targeting trans-splicing of a target RNA (e.g., pre-mRNA) in a cell, comprising introducing to the cell a composition, system, and/or the one or more nucleic acids comprising one or more nucleotide sequences described herein. In embodiments, the disclosure provides methods of correcting a mutation in at target RNA (e.g., a pre-mRNA) in a cell, comprising introducing to the cell a composition, system, and/or the one or more nucleic acids comprising one or more nucleotide sequences described herein. In some aspects, the introducing is performed in vivo. In some embodiments, the introducing is performed ex vivo. In some embodiments, the methods described herein are used to introduce a desired edit to a target nucleic acid edit in a manner that avoids certain disadvantages of gene-editing, e.g., gene-editing performed using a CRISPR/Cas system. Whereas gene-editing is associated with a risk of introducing a permanent and disease-causing off-target edit to the genome, the present disclosure provides methods of trans-splicing that avoid altering genomic DNA and enable transient editing. Thus, and without being bound by theory, the methods of the disclosure are used to introduce edits to nucleic acids in a cell in a manner that is safer than gene-editing. Additionally, in some embodiments, the methods of the disclosure are used to inactivate an undesirable off-target gene edit introduced to the genome, thereby preventing or ameliorating deleterious phenotypes associated with gene editing approaches.

In embodiments, introduction of the composition or system to the cell results in an immunogenicity that is less than a composition or system lacking the snRNA or snoRNA sequence. In embodiments, the composition or system is introduced to a cell by a single viral vector (e.g., AAV). In embodiments, introduction of the composition or system to the cell is without any additional protein to guide activity.

In embodiments, the disclosure provides methods for treating a disease or disorder in a subject in need thereof, the disease or disorder associated with (i) one or more genetic mutations, and/or (ii) an aberrant expression level and/or activity of a gene, or a transcriptional or translational product thereof, comprising administering to a subject composition, system, and/or the one or more nucleic acids comprising one or more nucleotide sequences described herein.

In embodiments, the disclosure provides methods and compositions for delivery of the composition, system, and/or the one or more nucleic acids comprising one or more nucleotide sequences described herein to a cell or a subject. In some embodiments, the composition, system, and/or the one or more nucleic acids comprising one or more nucleotide sequences described herein is delivered as a DNA. In some embodiments, the composition, system, and/or the one or more nucleic acids comprising one or more nucleotide sequences described herein is delivered as an RNA. In some aspects, the delivery comprises administering a recombinant expression vector (e.g., a viral vector, e.g., an AAV) comprising the splice editor nucleic acid molecule. In some aspects, the delivery comprises administering a non-viral vector (e.g., a lipid particle) comprising the splice editor nucleic acid molecule.

In embodiments, further comprising one or more binding domain sequences of about 4 to about 300 nucleotides each with complementarity to a pre-mRNA target sequence. In embodiments the one or more binding domain sequences is at least about 5 to about 10, about 5 to about 15, about 5 to about 20, about 10 to about 15, about 10 to about 20, about 15 to about 20, or about 20, or about 19, or about 18, or about 17, or about 16, or about 15, or about 14, or about 13, or about 12, or about 11, or about 10, or about 9, or about 8, or about 7, or about 6, or about or 5 nucleotides in length. In embodiments the one or more binding domain sequences is less than about 250 to about 300, about 200 to about 300, about 150 to about 300, about 100 to about 300, about 50 to about 300, about 100 to about 250, about 100 to about 200, about 100 to about 150, about 50 to about 250, about 50 to about 200, about 50 to about 150, about 50 to about 100, or about 300, or about 250, or about 200, or about 150, or about 100, or about 50 nucleotides in length. In embodiments the one or more binding domain sequences is about 5 to about 20, about 5 to about 30, about 5 to about 40, about 5 to about 50, about 10 to about 50, about 10 to about 100, about 20 to about 100, about 30 to about 100, about 40 to about 100, about 50 to about 100, about 50 to about 150, about 50 to about 200, about 50 to about 250, about 100 to about 150, about 100 to about 200, about 100 to about 250, or about 100 to about 300 nucleotides in length.

In embodiments, the composition or system comprises one binding domain sequence. In embodiments, the composition or system comprises at least two binding domain sequences. In embodiments, the composition or system comprises 3, 4, 5, 6, 7, 8, 9, or 10 binding domain sequences. In embodiments, the small nuclear RNA (snRNA) or a small nucleolar RNA (snoRNA) sequence is greater than about 5 nucleotides in length which forms a secondary structure, and optionally comprises a sequence motif to direct the one or more binding domains to the pre-mRNA target sequence. In embodiments, small nuclear RNA (snRNA) or a small nucleolar RNA (snoRNA) sequence is about 5 to about 500, or 5 to about 400, or 5 to about 300, or 5 to about 200, or 5 to about 100, or 5 to about 90, or 5 to about 80, or 5 to about 70, or 5 to about 60, or 5 to about 50, or 5 to about 40, or 5 to about 30, or 5 to about 20, or 5 to about 10, or 7 to about 500, or 7 to about 400, or 7 to about 300, or 7 to about 200, or 7 to about 100, or 7 to about 90, or 7 to about 80, or 7 to about 70, or 7 to about 60, or 7 to about 50, or 7 to about 40, or 7 to about 30, or 7 to about 20, or 7 to about 10 nucleotides in length.

In embodiments, the composition comprises at least one exonic sequence.

In embodiments, the composition or system comprises a CRISPR/Cas system, e.g., a protein and/or nucleic acid thereof. In embodiments, the composition or system further comprises a repair RNA (repRNA) that induces cleavage in a CRISPR/Cas system. In embodiments, the CRISPR/Cas system is active, e.g., catalytically active. In embodiments, the CRISPR/Cas system is inactive, e.g., catalytically inactive, e.g., "dead". In embodiments, the CRISPR/Cas system is a Type III CRISPR/Cas system. In embodiments, the Type III CRISPR/Cas system is or comprises a Type IIIA, Type IIIB, Type IIIC, Type IIID, Type IIIE, or Type IIIF CRISPR/Cas system, optionally wherein the Type IIIA, Type IIIB, Type IIIC, Type IIID, Type IIIE, or Type IIIF CRISPR/Cas system is active, catalytically inactive or has reduced activity relative to wild type. In embodiments, the Type III CRISPR/Cas system is or comprises a Cas10 (Csm1), Csm2, Cas7 (Csm3), Csm4, Csm5, Cas 6, and, Cas7-11, or a fragment or variant thereof, optionally wherein the Type III CRISPR/Cas system is or comprises a Cas10 (Csm1), Csm2, Cas7 (Csm3), Csm4, Csm5, Cas 6, and, Cas7-11 is active, catalytically inactive or has reduced activity relative to wild type. In embodiments, the Type III CRISPR/Cas system comprises a domain from a different endonuclease, optionally wherein the different endonuclease is a Cas endonuclease, optionally wherein the domain is one or more of a PAM-interacting domain, optionally wherein the domain is derived from one or more of Cas9, Cas12a (Cpf1), Cas12e (CasX), Cas12d (CasY), Cas12b (C2c1), Cas13a (C2c2), Cas13b, Cas13c, Cas13d, Cas13X/Cas13bt, Cas13Y, Cas12c (C2c3), GeoCas9, CjCas9, NmeCas9, Cas12J (Cas-Phi), Cas12L (CasLambda), Cas12f (Cas14), Cas12g, Cas12h, Cas12i, Cas12k, NmeCas9, Nme2Cas9, CjCas9, GeoCas9, BlatCas9, PpCas9, and Cas14. In embodiments, the composition or system comprises an intronic sequence comprising a sequence which interacts with or is suitable for interacting with the CRISPR/Cas system. In embodiments, the composition or system further comprises a repair RNA (repRNA) and a CRISPR/Cas system when the present methods are undertaken in cis or trans, as described herein.

In embodiments, the Cas is a type I. In embodiments, the Cas is a type I-A, e.g., without limitation Cas8a or Cas5. In embodiments, the Cas is a type I. In embodiments, the Cas is a type I-B, e.g., without limitation Cas8b. In embodiments, the Cas is a type I. In embodiments, the Cas is a type I-C, e.g., without limitation Cas8c. In embodiments, the Cas is a type I. In embodiments, the Cas is a type I-D, e.g., without limitation Cas10d. In embodiments, the Cas is a type I. In embodiments, the Cas is a type I-E, e.g., without limitation Cse1 or Cse2. In embodiments, the Cas is a type I. In embodiments, the Cas is a type I-F, e.g., without limitation Csy1, Csy2, or Csy3. In embodiments, the Cas is a type I. In embodiments, the Cas is a type I-G, e.g., without limitation GSU0054. In embodiments, the Cas is a type I. In embodiments, the Cas type I is without limitation, Cas3.

In embodiments, the Cas is a type II. In embodiments, the Cas is a type II-A, e.g., without limitation Csn2. In embodiments, the Cas is a type II. In embodiments, the Cas is a type II-B, e.g., without limitation Cas4. In embodiments, the Cas is a type II. In embodiments, the Cas is a type II-C. In embodiments, the Cas is a type II. In embodiments, the Cas type II is without limitation Cas 9. In embodiments, the Cas is a type III. In embodiments, the Cas is a type III-A, e.g., without limitation Csm2. In embodiments, the Cas is a type III. In embodiments, the Cas is a type III-B, e.g., without limitation Cmr5. In embodiments, the Cas is a type III. In embodiments, the Cas is a type III-C, e.g., without limitation Cas10 or Csx11. In embodiments, the Cas is a type III. In embodiments, the Cas is a type III-D, e.g., without limitation Csx10. In embodiments, the Cas is a type III. In embodiments, the Cas is a type III-E. In embodiments, the Cas is a type III. In embodiments, the Cas is a type III-F. In embodiments, the Cas is a type III. In embodiments, the Cas type III is without limitation Cas 10.

In embodiments, the Cas is a type IV. In embodiments, the Cas is a type IV-A. In embodiments, the Cas is a type IV. In embodiments, the Cas is a type IV-B. In embodiments, the Cas is a type IV. In embodiments, the Cas is a type IV-C.

In embodiments, the Cas is a type V. In embodiments, the Cas is a type V-A, e.g., without limitation Cas12a (Cpf1). In embodiments, the Cas is a type V. In embodiments, the Cas is a type V-B, e.g., without limitation Cas12b (C2c1). In embodiments, the Cas is a type V. In embodiments, the Cas is a type V-C, e.g., without limitation Cas12c (C2c3). In embodiments, the Cas is a type V. In embodiments, the Cas is a type V-D, e.g., without limitation Cas12d (CasY).

In embodiments, the Cas is a type V. In embodiments, the Cas is a type V-E, e.g., without limitation Cas12e (CasX). In embodiments, the Cas is a type V. In embodiments, the Cas is a type V-F, e.g., without limitation Cas12f (Cas14, or C2c10). In embodiments, the Cas is a type V. In embodiments, the Cas is a type V-G, e.g., without limitation Cas12g. In embodiments, the Cas is a type V. In embodiments, the Cas is a type V-H, e.g., without limitation Cas12h. In embodiments, the Cas is a type V. In embodiments, the Cas is a type V-I, e.g., without limitation Cas12i. In embodiments, the Cas is a type V. In embodiments, the Cas is a type V-K, e.g., without limitation Cas12k (C2c5). In embodiments, the Cas is a type V. In embodiments, the Cas is a type V-U, e.g., without limitation C2c4, C2c8, or C2c9. In embodiments, the Cas is a type V. In embodiments, the Cas type V is without limitation Cas 12. In embodiments, the Cas is a type VI.

In embodiments, the Cas is a type VI-A, e.g., without limitation Cas13a (C2c2). In embodiments, the Cas is a type VI. In embodiments, the Cas is a type VI-B, e.g., without limitation Cas13b. In embodiments, the Cas is a type VI. In embodiments, the Cas is a type VI-C, e.g., without limitation Cas13c. In embodiments, the Cas is a type VI. In embodiments, the Cas is a type VI-D, e.g., without limitation Cas13d. In embodiments, the Cas is a type VI. In embodiments, the Cas is a type VI-X, e.g., without limitation Cas13x.1. In embodiments, the Cas is a type VI. In embodiments, the Cas is a type VI-Y. In embodiments, the Cas is a type VI. In embodiments, the Cas type VI is without limitation Cas 13.

In embodiments the Cas is Cas3, Cas8a, Cas5, Cas8b, Cas8c, Cas10d, Cse1, Cse2, Csy1, Csy2, Csy3, GSU0054, Cas10, Csm2, Cmr5, Cas10 or Csx11, Csx10, Csf1, Cas9, Csn2, Cas4, Cas12, Cas12a (Cpf1), Cas12b (C2c1), Cas12c (C2c3), Cas12d (CasY), Cas12e (CasX), Cas12f (Cas14, C2c10), Cas12g, Cas12h, Cas12i, Cas12k (C2c5), C2c4, C2c8, C2c9, Cas13, Cas13a (C2c2), Cas13b, Cas13c, Cas13d, or Cas13x.1.

Exemplary Compositions, System, and/or Nucleic Acids

In embodiments, the disclosure provides a composition or system suitable for targeting trans-splicing of a pre-mRNA in a cell comprising one or more nucleic acids comprising one or more nucleotide sequences comprising at least one intronic sequence comprising a small nuclear RNA (snRNA), or a small nucleolar RNA (snoRNA) sequence, a splice acceptor and/or splice donor sequence.

In embodiments, the intronic sequence comprises a snRNA. In embodiments, the snRNA is selected from a U7 snRNA, a U1 snRNA, a U2 snRNA, a U4 snRNA, a U4atac snRNA, a U5 snRNA, a U6 snRNA, a U6atac snRNA, a U11 snRNA, and a U12 snRNA. In embodiments, the snRNA is a U7 snRNA. In embodiments, the composition or system comprises a snoRNA.

In embodiments, the snoRNA comprises an H/ACA box or C/D box. In embodiments, the snRNA or snoRNA sequence assembles into an RNP. In embodiments, the snRNA or snoRNA sequence comprises a sequence motif that assembles into an RNP. In embodiments, the snRNA or snoRNA sequence comprises a secondary structure that assembles into an RNP. In embodiments, the snRNA or snoRNA sequence comprises a sequence motif and a secondary structure that assembles into an RNP. In embodiments, the secondary structure comprises one or more stem loops. In embodiments, the secondary structure is or comprises a stem, internal loop, multibranch loop, or a pseudoknot. In embodiments, the RNP is selected from a small nuclear RNP (snRNP), a small nucleolar RNP (snoRNP), a small cajal body RNP (scaRNP), and a combination thereof. In embodiments, the RNP is selected from U1, U2, U4, U4atac, U5, U6, U6atac, U7, U11, and U12. In embodiments, the RNP is selected from a C/D box snoRNP and a H/ACA box snoRNP.

In embodiments, the snRNA or snoRNA target one or more exonic splicing enhancers (ESEs), one or more intronic splicing enhancers (ISEs), one or more exonic splicing silencers (ESSs), and/or one or more intronic splicing silencers (ISSs). In embodiments, the snRNA or snoRNA comprise a modification to include at least one or more exonic splicing enhancers (ESEs), at least one or more intronic splicing enhancers (ISEs), at least one or more exonic splicing silencers (ESSs), and/or at least one or more intronic splicing silencers (ISSs).

In embodiments, the composition or system comprises a repair RNA (repRNA) and a small RNA that induces cleavage in an RNA. In embodiments, the small RNA that induces cleavage in an RNA is one or more of an siRNA, small hairpin RNA (shRNA), U7 snRNA, a U1 snRNA, a U2 snRNA, a U4 snRNA, a U4atac snRNA, a U5 snRNA, a U6 snRNA, a U6atac snRNA, a U11 snRNA, a U12 snRNA, and an antisense oligonucleotide (ASO). In embodiments, the composition or system comprises a repair RNA (repRNA) and the small RNA comprises a modification or mutation that attenuates, weakens, reduces, decreases, or ablates activity as compared to an unmodified form. In embodiments, the composition or system comprises a repair RNA (repRNA) and the small RNA comprises a modification or mutation that increases, stimulates, or enhances activity as compared to an unmodified form. In embodiments, the composition or system comprises a repair RNA (repRNA) and a small RNA that induces cleavage in an RNA when the present methods are undertaken in cis or trans, as described herein.

In embodiments, the snRNA comprises a M6A modification. In embodiments, the snRNA comprises a M6A modification when the present methods are undertaken in cis or trans, as described herein. In embodiments, the snRNA or snoRNA is modified to comprise at least one or more M6A sites. In embodiments, the snRNA or snoRNA is modified to comprise at least 1, 2, 3 4, 5, 6, 7, 8, 9, 10, 11, 12, 13, 14, 15, 16, 17, 18, 19, 20, 21, 22, 23, 24, 25, 26, 27, 28, 29, 30 or more M6A sites than the number of M6A sites in (i) an unmodified state of the snRNA or snoRNA or (ii) an exonic sequence. In embodiments, the snRNA or snoRNA is modified to not comprise M6A sites. In embodiments, the repRNA comprises at least one or more M6A sites. In embodiments, the repRNA is modified to comprise at least 1, 2, 3 4, 5, 6, 7, 8, 9, 10, 11, 12, 13, 14, 15, 16, 17, 18, 19, 20, 21, 22, 23, 24, 25, 26, 27, 28, 29, 30 or more M6A sites than the number of M6A sites in (i) an unmodified state of the repRNA or (ii) an exonic sequence. In embodiments, the repRNA comprises no M6A sites.

In embodiments, the repRNA comprises at least one intronic spacer sequence comprising at least one ISE and ESS sequences. In embodiments, the at least one intronic spacer sequence comprising at least one ISE and ESS sequences increases trans-splicing efficiency of a target RNA as compared to an unmodified form. In embodiments, the repRNA comprises at least one intronic spacer sequence comprising at least one ISE and ESS sequences. In embodiments, the at least one intronic spacer sequence comprising at least one ISE and ESS sequences decreases trans-splicing efficiency of a target RNA as compared to an unmodified form. In embodiments, the repRNA comprises at least one intronic spacer sequence comprising at least one ISE and ESS sequences. In embodiments, the at least one intronic spacer sequence comprising at least one ISE and ESS sequences increases trans-splicing efficiency of a off-target RNA as compared to an unmodified form. In embodiments, the repRNA comprises at least one intronic spacer sequence comprising at least one ISE and ESS sequences. In embodiments, the at least one intronic spacer sequence comprising at least one ISE and ESS sequences decreases trans-splicing efficiency of a off-target RNA as compared to an unmodified form.

In embodiments, the repRNA comprises a ESS, ESE, ISS, and/or ISE sequence. In embodiments, the repRNA targets one or more of ESS, ESE, ISS, and/or ISE. In embodiments, an interaction, modulation and/or binding to one or more of ESS, ESE, ISS, and/or ISE reduces or ablates interaction, modulation and/or binding of the one or more of the ESS, ESE, ISS, and/or ISE with a target. In embodiments, the repRNA comprises exon sequences with ESE and ESS sequences. In embodiments, the exon sequences with ESE and ESS sequences increase or decrease trans-splicing efficiency to an RNA target as compared to an unmodified form. In embodiments, the repRNA comprises exon sequences with ESE and ESS sequences. In embodiments, the repRNA comprises exon sequences with ESE and ESS sequences increase or decrease trans-splicing efficiency to an RNA off-target as compared to an unmodified form. In embodiments, the repRNA comprises at least one or more G4 structures. In embodiments, the repRNA comprises at least one or more G4 structures sequester SD/SA motifs. In embodiments, the G4 structure is unwound, such as by DHX36 or CNBP, and remains trapped in the unwound state in the presence of a complementary sequence (e.g., endogenous target or exogenously delivered trigger RNA). In embodiments, the G4 structure decreases off-targets as compared to an unmodified form.

In embodiments, the repRNA comprises a modification comprising at least one or more scaffolding sequences. In embodiments, the at least one or more scaffolding sequences mediates (e.g., recruits) phase condensate-like formation and/or improves local concentrations of repRNAs compared to an unmodified form, and other targeted proteins and/or RNA. In embodiments, the repRNA comprises a modification comprising at least one or more sequences to target the repRNA to the promoter of the target gene of interest, or to proximal condensates that may contain the promoter. In embodiments, the one or more sequences comprises an enhancer RNA, snRNA and/or snoRNA sequences.

In embodiments, the repRNA comprises a modification. In embodiments, the repRNA modification improves interaction and localization to a DNA sequence of the non-template strand of the target gene as compared to an unmodified form. In embodiments, the DNA sequence of the non-template strand of the target gene is the promoter, intron, exon, or enhancer. In embodiments, the modification improves interaction and localization to the DNA sequence of the non-template strand of the target gene through protein-directed (e.g. transcription factor, dCas, ZNF, or other RBP) or nucleotide-directed (e.g., R-loop) methods as compared to an unmodified form.

In embodiments, the repRNA comprises a modification comprising additional RNA elements. In embodiments, the repRNA modification comprising additional RNA elements improves subnuclear localization to nuclear speckles for enhanced trans-splicing efficiency as compared to an unmodified form. In embodiments, the additional RNA element comprise NEAT1 and/or MALAT1, or a fragment thereof. In embodiments, the additional RNA element comprises a nucleotide sequence of SEQ ID NO: 712, or a fragment or variant thereof, optionally having at least about 90%, or at least about 95%, or at least about 97%, or at least about 98%, or at least about 99% identity thereto and/or or having about 1 to about 20 (e.g. about 1, or about 2, or about 3, or about 4, or about 5) nucleic acid modifications, optionally selected from substitutions, additions, or deletions. In embodiments, the repRNA comprises a modification. In embodiments, the repRNA modification enables targeting to site of transcription of target RNAs. In embodiments, the repRNA comprises a modification comprising 5' UTR or 3' UTR modifications. In embodiments, the modification alters intracellular or intranuclear localization based on interactions with endogenous or exogenously supplied molecules (e.g., RNA G4 interactions with transcription factors or other proteins that are localized to specific cellular compartments).

In embodiments, the repRNA comprises a modification in the 5' UTR of the repRNA. In embodiments, the modification in the 5' UTR of the repRNA increases stability as compared to an unmodified form. In embodiments, the modification in the 5' UTR of the repRNA decreases stability as compared to an unmodified form. In embodiments, the modification in the 5' UTR of the repRNA increases or decreases translation efficiency as compared to an unmodified form. In embodiments, the repRNA comprises a modification in the 3' UTR of the repRNA. In embodiments, the modification in the 3' UTR of the repRNA increases stability as compared to an unmodified form. In embodiments, the modification in the 3' UTR of the repRNA decreases stability as compared to an unmodified form. In embodiments, the modification in the 3' UTR of the repRNA increases or decreases translation efficiency as compared to an unmodified form.

In embodiments, the repRNA comprises a modification comprising modifying the repRNA to comprise a G4 structure that mediates recruitment of splicing-associated RBPs.

In embodiments, the repRNA comprises a modification comprising at least one or more toehold switches in the repRNA. In embodiments, the at least one or more toehold switches in the repRNA conditionally activate or deactivate (e.g., SD/SA occlusion, binding motif occlusion, or RBP occlusion) upon detection of an endogenous or exogenously supplied target RNA.

In embodiments, the repRNA comprises a modification comprising at least one or more complementary riboregulators in repRNAs (in cis). In embodiments, the at least one or more complementary riboregulators in repRNAs (in cis) occlude splice donor (SD) site and reduce off-target trans-splicing.

In embodiments, the repRNA comprises a modification comprising at least one or more self-complementary riboregulators in repRNAs (in cis). In embodiments, the at least one or more self-complementary riboregulators in repRNAs (in cis) occlude splice acceptor (SA) site and reduce off-target trans-splicing.

In embodiments, the repRNA comprises a modification comprising at least one or more self-complementary riboregulators in repRNAs (in trans). In embodiments, the at least one or more self-complementary riboregulators in repRNAs (in trans) occlude splice donor (SD) site and reduce off-target trans-splicing.

In embodiments, the repRNA comprises a modification comprising at least one or more self-complementary ribo-regulators in repRNAs (in trans). In embodiments, the at least one or more self-complementary riboregulators in repRNAs (in trans) occlude splice acceptor (SA) site and reduce off-target trans-splicing.

In embodiments, the repRNA comprises a modification comprising at least one or more binding motifs. In embodiments, the at least one or more binding motifs increase trans-splicing efficiency, target specificity, and target site occlusion (SA, SD, ISS, ISE, ESE, and ESS) as compared to an unmodified form.

In embodiments, the repRNA comprises a modification. In embodiments, the repRNA modification enables induction of trans-splicing in response to a stimulus as compared to an unmodified form. In embodiments, the repRNA comprises a modification to turn off or decrease trans-splicing in response to a stimulus as compared to an unmodified form.

In embodiments, the repRNA comprises a modification. In embodiments, the repRNA modification enables small molecule induction of trans-splicing as compared to an unmodified form. In embodiments, the repRNA comprises a modification. In embodiments, the repRNA modification represses small molecule induction of trans-splicing as compared to an unmodified form.

In embodiments, the repRNA comprises a modification. In embodiments, the repRNA modification enables light induction of trans-splicing.

In embodiments, the repRNA comprises a modification comprising at least one or more motifs that are bound and regulated by light-sensitive proteins.

In embodiments, the snRNA or snoRNA comprises a sequence at the 3' untranslated region (3'UTR). In embodiments, the sequence at the 3' untranslated region (3'UTR) of the snRNA or snoRNA increases trans-splicing efficiency as compared to an unmodified form. In embodiments, the sequence is from the MALAT1 gene. In embodiments, the sequence is a nucleotide sequence of SEQ ID NO: 712, or a fragment or variant thereof, optionally having at least about 90%, or at least about 95%, or at least about 97%, or at least about 98%, or at least about 99% identity thereto and/or or having about 1 to about 20 (e.g. about 1, or about 2, or about 3, or about 4, or about 5) nucleic acid modifications, optionally selected from substitutions, additions, or deletions.

In embodiments, the RNP assembles on the repRNA and/or the target. In embodiments, the RNP assembles on the repRNA. In embodiments, the RNP assembles on the target. In embodiments, the RNP sterically occludes and inhibits cis-splicing.

In embodiments, the repRNA comprises a minimal intron. In embodiments, the minimal intron is less than about 50 nucleotides, less than about 60 nucleotides, less than about 70 nucleotides, less than about 80 nucleotides, less than about 90 nucleotides, less than about 100 nucleotides, less than about 110 nucleotides, less than about 120 nucleotides, less than about 130 nucleotides, less than about 140 nucleotides, or less than about 150 nucleotides, or about 50 to about 150 nucleotides, or about 50 to about 100 nucleotides, or about 50 to about 75 nucleotides, or about 75 to about 150 nucleotides, or about 100 to about 150 nucleotides, or about 120 to about 150 nucleotides.

In embodiments, the repRNA further comprises a ribozyme site. In embodiments, the ribozyme site is a hairpin, hammerhead, hepatitis delta virus (HDV), Varkud satellite (VS), or glmS ribozyme site, or a variant thereof. In embodiments, the ribozyme site is a HDV ribozyme site. In embodiments, the ribozyme site is a twister ribozyme site. In embodiments, the ribozyme site is upstream of the one or more exons and/or introns of the repRNA. In embodiments, the ribozyme cleaves the target. In embodiments, the ribozyme is a trans-cleaving ribozyme.

In embodiments, the repRNA comprises a ribozyme site that cleaves at the 5' end of the repRNA.

In embodiments, the repRNA comprises a ribozyme site that cleaves at the 3' end of the repRNA.

In embodiments, the repRNA comprises a ribozyme site that cleaves the snRNA or snoRNA at the 5' end of the repRNA. In embodiments, the repRNA comprises a ribozyme site that cleaves the snRNA or snoRNA at the 3' end of the repRNA.

In embodiments, the repRNA comprises a M6A modification. In embodiments, the repRNA comprises a M6A modification when the present methods are undertaken in cis or trans, as described herein. In embodiments, the snRNA or snoRNA is modified to comprise at least one or more M6A sites. In embodiments, the snRNA or snoRNA is modified to comprise at least 1, 2, 3 4, 5, 6, 7, 8, 9, 10, 11, 12, 13, 14, 15, 16, 17, 18, 19, 20, 21, 22, 23, 24, 25, 26, 27, 28, 29, 30 or more M6A sites than the number of M6A modifications in (i) an unmodified state of the snRNA or snoRNA or (ii) an exonic sequence. In embodiments, the snRNA or snoRNA is modified to not comprise M6A sites. In embodiments, the repRNA comprises at least one or more M6A sites. In embodiments, the repRNA is modified to comprise at least 1, 2, 3 4, 5, 6, 7, 8, 9, 10, 11, 12, 13, 14, 15, 16, 17, 18, 19, 20, 21, 22, 23, 24, 25, 26, 27, 28, 29, 30 or more M6A sites than the number of M6A modifications in (i) an unmodified state of the repRNA or (ii) an exonic sequence. In embodiments, the repRNA comprises no M6A sites.

In embodiments, the composition or system further comprises at least one pre-rRNA stemloop to remove either the 5'cap or 3' polyA tail. In embodiments, stemloop intramolecular base pairing is a pattern in single-stranded RNA.

In embodiments, there are a plurality of repRNAs under the control of the same, different, or a plurality of promoters. In embodiments, the repRNA and one or more other components of the present system are under the control of the same or different promoters.

In embodiments, the repRNA comprises alternative promoters. In embodiments, the repRNA comprises at least one or more alternative Pol II promoters. In embodiments, the one or more alternative Pol II promoters cap the 5' end of the repRNA with 7 mG (7-methylguanosine) or TMG (tri-methylguanosine). In embodiments, the one or more alternative Pol II promoters cap the 5' end of the repRNA with 7 mG (7-methylguanosine) or TMG (tri-methylguanosine) stabilize the repRNA.

In embodiments, the repRNA comprises at least one or more circularized repRNAs. In embodiments, the repRNA comprises at least one or more circularized repRNAs stabilize the repRNA. In embodiments, the circular RNA (or circRNA, or circularized RNA) is a type of single-stranded RNA which, unlike linear RNA, forms a covalently closed continuous loop. Circularized RNAs can be categorized into several types, e.g., depending on processing: exonic circRNAs, intronic circRNAs, exon-intron circRNAs, read-through circRNAs, fusion circRNAs, and tRNA-derived circRNAs. In embodiments, the 3' and 5' ends of the circular RNA are joined together. In embodiments, the repRNA comprises at least one or more circularized 5' replacement (SD) repRNAs. In embodiments, the repRNA comprises at least one or more circularized 5' replacement (SD) repRNAs stabilize the repRNA. In embodiments, the repRNA comprising one or more circularized 5' replacement (SD) repRNAs improves stability and is resistant to exonucleases as compared to an unmodified form. In embodiments, the repRNA comprises at least one or more circularized 3' replacement (SA) repRNAs. In embodiments, the repRNA comprises at least one or more circularized 3' replacement (SA) repRNAs stabilize the repRNA. In embodiments, the repRNA comprising one or more circularized 3' replacement (SA) repRNAs improves stability and is resistant to exonucleases as compared to an unmodified form. In embodiments, the repRNA comprises at least one or more circularized internal replacement (SD+SA) repRNAs. In embodiments, the repRNA comprises at least one or more circularized internal replacement (SD+SA) repRNAs stabilize the repRNA. In embodiments, the repRNA comprising one or more circularized internal replacement (SD+SA) repRNAs improves stability and is resistant to exonucleases as compared to an unmodified form.

In embodiments, the composition or system further comprises a repair RNA (repRNA), a small RNA that induces cleavage in an RNA, and a CRISPR/Cas system. In embodiments, the CRISPR/Cas system is active, e.g., catalytically active. In embodiments, the CRISPR/Cas system is inactive, e.g., catalytically inactive, e.g., "dead". In embodiments, the CRISPR/Cas system is a Type III CRISPR/Cas system. In embodiments, the Type III CRISPR/Cas system is or comprises a Type IIIA, Type IIIB, Type IIIC, Type IIID, Type IIIE, or Type IIIF CRISPR/Cas system. In embodiments, the, optionally wherein the Type IIIA, Type IIIB, Type IIIC, Type IIID, Type IIIE, or Type IIIF CRISPR/Cas system is active, catalytically inactive or has reduced activity relative to wild type. In embodiments, the Type III CRISPR/Cas system is or comprises a Cas10 (Csm1), Csm2, Cas7 (Csm3), Csm4, Csm5, Cas 6, and, Cas7-11, or a fragment or variant thereof, optionally wherein the Type III CRISPR/Cas system is or comprises a Cas10 (Csm1), Csm2, Cas7 (Csm3), Csm4, Csm5, Cas 6, and, Cas7-11 is active, catalytically inactive or has reduced activity relative to wild type. In embodiments, the Type III CRISPR/Cas system comprises a domain from a different endonuclease, optionally wherein the different endonuclease is a Cas endonuclease, optionally wherein the domain is one or more of a PAM-interacting domain, optionally wherein the domain is derived from one or more of Cas9, Cas12a (Cpf1), Cas12e (CasX), Cas12d (CasY), Cas12b (C2c1), Cas13a (C2c2), Cas13b, Cas13c, Cas13d, Cas13X/Cas13bt, Cas13Y, Cas12c (C2c3), GeoCas9, CjCas9, NmeCas9, Cas12J (Cas-Phi), Cas12L (CasLambda), Cas12f (Cas14), Cas12g, Cas12h, Cas12i, Cas12k, NmeCas9, Nme2Cas9, CjCas9, GeoCas9, BlatCas9, PpCas9, and Cas14. In embodiments, the composition or system comprises an intronic sequence comprising a sequence which interacts with or is suitable for interacting with the CRISPR/Cas system. In embodiments, the composition or system further comprises a repair RNA (repRNA), a small RNA that induces cleavage in an RNA, and a CRISPR/Cas system when the present methods are undertaken in cis or trans, as described herein.

In embodiments, the Cas is a type I. In embodiments, the Cas is a type I-A, e.g., without limitation Cas8a or Cas5. In embodiments, the Cas is a type I. In embodiments, the Cas is a type I-B, e.g., without limitation Cas8b. In embodiments, the Cas is a type I. In embodiments, the Cas is a type I-C, e.g., without limitation Cas8c. In embodiments, the Cas is a type I. In embodiments, the Cas is a type I-D, e.g., without limitation Cas10d. In embodiments, the Cas is a type I. In embodiments, the Cas is a type C-E, e.g., without limitation Cse1 or Cse2. In embodiments, the Cas is a type I. In embodiments, the Cas is a type I-F, e.g., without limitation Csy1, Csy2, or Csy3. In embodiments, the Cas is a type I. In embodiments, the Cas is a type I-G, e.g., without limitation GSU0054. In embodiments, the Cas is a type I. In embodiments, the Cas type I is without limitation, Cas3.

In embodiments, the Cas is a type II. In embodiments, the Cas is a type II-A, e.g., without limitation Csn2. In embodiments, the Cas is a type II. In embodiments, the Cas is a type II-B, e.g., without limitation Cas4. In embodiments, the Cas is a type II. In embodiments, the Cas is a type II-C. In embodiments, the Cas is a type II. In embodiments, the Cas type II is without limitation Cas 9.

In embodiments, the Cas is a type III. In embodiments, the Cas is a type III-A, e.g., without limitation Csm2. In embodiments, the Cas is a type III. In embodiments, the Cas is a type III-B, e.g., without limitation Cmr5. In embodiments, the Cas is a type III. In embodiments, the Cas is a type III-C, e.g., without limitation Cas10 or Csx11. In embodiments, the Cas is a type III. In embodiments, the Cas is a type III-D, e.g., without limitation Csx10. In embodiments, the Cas is a type III. In embodiments, the Cas is a type III-E. In embodiments, the Cas is a type III-F. In embodiments, the Cas is a type III. In embodiments, the Cas type III is without limitation Cas 10.

In embodiments, the Cas is a type IV. In embodiments, the Cas is a type IV-A. In embodiments, the Cas is a type IV. In embodiments, the Cas is a type IV-B. In embodiments, the Cas is a type IV. In embodiments, the Cas is a type IV-C.

In embodiments, the Cas is a type V. In embodiments, the Cas is a type V-A, e.g., without limitation Cas12a (Cpf1). In embodiments, the Cas is a type V. In embodiments, the Cas is a type V-B, e.g., without limitation Cas12b (C2c1). In embodiments, the Cas is a type V. In embodiments, the Cas is a type V-C, e.g., without limitation Cas12c (C2c3). In embodiments, the Cas is a type V. In embodiments, the Cas is a type V-D, e.g., without limitation Cas12d (CasY). In embodiments, the Cas is a type V. In embodiments, the Cas is a type V-E, e.g., without limitation Cas12e (CasX). In embodiments, the Cas is a type V. In embodiments, the Cas is a type V-F, e.g., without limitation Cas12f (Cas14, or C2c10). In embodiments, the Cas is a type V. In embodiments, the Cas is a type V-G, e.g., without limitation Cas12g. In embodiments, the Cas is a type V. In embodiments, the Cas is a type V-H, e.g., without limitation Cas12h. In embodiments, the Cas is a type V. In embodiments, the Cas is a type V-I, e.g., without limitation Cas12i. In embodiments, the Cas is a type V. In embodiments, the Cas is a type V-K, e.g., without limitation Cas12k (C2c5). In embodiments, the Cas is a type V. In embodiments, the Cas is a type V-U, e.g., without limitation C2c4, C2c8, or C2c9. In embodiments, the Cas is a type V. In embodiments, the Cas type V is without limitation Cas 12. In embodiments, the Cas is a type VI.

In embodiments, the Cas is a type VI-A, e.g., without limitation Cas13a (C2c2). In embodiments, the Cas is a type VI. In embodiments, the Cas is a type VI-B, e.g., without limitation Cas13b. In embodiments, the Cas is a type VI. In embodiments, the Cas is a type VI-C, e.g., without limitation Cas13c. In embodiments, the Cas is a type VI. In embodiments, the Cas is a type VI-D, e.g., without limitation Cas13d. In embodiments, the Cas is a type VI. In embodiments, the Cas is a type VI-X, e.g., without limitation Cas13x.1. In embodiments, the Cas is a type VI. In embodiments, the Cas is a type VI-Y. In embodiments, the Cas is a type VI. In embodiments, the Cas type VI is without limitation Cas 13.

In embodiments the Cas is Cas3, Cas8a, Cas5, Cas8b, Cas8c, Cas10d, Cse1, Cse2, Csy1, Csy2, Csy3, GSU0054, Cas10, Csm2, Cmr5, Cas10 or Csx11, Csx10, Csf1, Cas9, Csn2, Cas4, Cas12, Cas12a (Cpf1), Cas12b (C2c1), Cas12c (C2c3), Cas12d (CasY), Cas12e (CasX), Cas12f (Cas14, C2c10), Cas12g, Cas12h, Cas12i, Cas12k (C2c5), C2c4, C2c8, C2c9, Cas13, Cas13a (C2c2), Cas13b, Cas13c, Cas13d, or Cas13x.1.

In embodiments, the composition or system further comprises In embodiments, the composition or system further comprises a protein that forms an RNP or is within an RNP, with the snRNA or snoRNA, or a nucleic acid encoding the protein that forms, or is within, the RNP. In embodiments, the snRNA, snoRNA, protein that forms an RNP, a protein within the RNP, and/or a nucleic acid encoding the protein that forms or is within the RNP comprises a modification or mutation that attenuates, weakens, reduces, decreases, or ablates RNP activity as compared to an unmodified form, and/or leads to attenuation of RNA modifying activity, the RNP activity optionally being selected from cleavage, nucleic acid processing, pseudouridylation, and/or methylation. In embodiments, the snRNA, snoRNA, protein that forms an RNP, and/or a nucleic acid encoding the protein that forms the RNP or is within RNP comprises a modification or mutation that increases, stimulates, or enhances RNP activity, or enhances RNA modifying activity, the RNP activity optionally being selected from cleavage, nucleic acid processing, pseudouridylation, and/or methylation as compared to an unmodified form. In embodiments, the repRNA comprises at least one or more pseudouridylation sites. In embodiments, the repRNA comprises no pseudouridylation sites. In embodiments, the repRNA is modified to comprise at least 1, 2, 3 4, 5, 6, 7, 8, 9, 10, 11, 12, 13, 14, 15, 16, 17, 18, 19, 20, 21, 22, 23, 24, 25, 26, 27, 28, 29, 30 or more pseudouridylation sites than the number of pseudouridylation sites in (i) an unmodified state of the snRNA or snoRNA or (ii) an exonic sequence.

In embodiments, the composition or system comprises a repair RNA (repRNA) and/or a protein that forms an RNP or is within an RNP, with the snRNA or snoRNA, or a nucleic acid encoding the protein that forms, or is within, the RNP and/or a small RNA that induces cleavage in an RNA and/or a CRISPR/Cas system. In embodiments, the composition or system comprises a repair RNA (repRNA) and/or a protein that forms an RNP or is within an RNP, with the snRNA or snoRNA, or a nucleic acid encoding the protein that forms, or is within, the RNP and/or a small RNA that induces cleavage in an RNA and/or a CRISPR/Cas system when the present methods are undertaken in cis or trans, as described herein. In embodiments, cleavage is initiated from RNPs that are formed on the repRNA, or from RNPs that are formed in cis or trans.

In embodiments, the snRNA or snoRNA comprises an Sm sequence motif, and/or wherein the snRNA or snoRNA comprises an antisense region sequence (ASR). In embodiments, the Sm sequence motif assembles with an Sm or Lsm protein into an RNP. In embodiments, the Sm or Lsm proteins are selected from a B/B', D3, D2, D1, E, F, G, LSm5, LSm7, LSm4, LSm8, LSm2, LSm3, LSm6 and LSm10 proteins.

In embodiments, the snRNA or snoRNA is at least about 10 to about 80 nucleotides, about 10 to about 70 nucleotides, about 10 to about 60 nucleotides, about 10 to about 50 nucleotides, about 10 to about 40 nucleotides, about 10 to about 30 nucleotides, about 10 to about 20 nucleotides, or about 80, 70, 60, 50, 40, 30, 20, or 10 nucleotides in length. In embodiments, wherein the snRNA or snoRNA comprises an antisense region sequence (ASR) selected from SEQ ID NOs: 700-707.

In embodiments, the Sm sequence motif comprises a nucleotide sequence selected from SEQ ID NOs: 1-8.

In embodiments, the snRNA or snoRNA comprises a guide repair RNA (grepRNA) sequence. In embodiments, wherein the grepRNA sequence is selected from SEQ ID NOs: 708-711.

In embodiments, composition or system comprises a splice acceptor. In embodiments, composition or system comprises a splice donor.

In embodiments, the (a) at least one intronic sequence, (b) splice acceptor and/or splice donor sequence, and (c) at least one exonic sequence are provided in cis or trans, or are suitable for being provided in cis or trans. In embodiments, the (a) at least one intronic sequence, (b) splice acceptor and/or splice donor sequence, and (c) at least one exonic sequence are provided in trans, or are suitable for being provided in trans.

In embodiments, the at least one intronic sequence comprises one or more splicing signals. In embodiments, the one or more splicing signals are selected from an exonic splicing enhancer (ESE), an intronic splicing enhancer (ISE), an exonic splicing silencer (ESS), intronic splicing silencer (ISS), a U1 binding motif (e.g., among other snRNA binding motifs), a polypyrimidine tract, a branch point, and a combination thereof.

In embodiments, the at least one intronic sequence comprises a branch point and a polypyrimidine tract.

In embodiments, the composition or system comprises 1, 2, 3, 4, 5, 6, 7, 8, 9, or 10 exons.

In embodiments, the one or more binding domain sequences is at least about 5 to about 10, about 5 to about 15, about 5 to about 20, about 10 to about 15, about 10 to about 20, about 15 to about 20, or about 20, or about 19, or about 18, or about 17, or about 16, or about 15, or about 14, or about 13, or about 12, or about 11, or about 10, or about 9, or about 8, or about 7, or about 6, or about or 5 nucleotides in length.

In embodiments, wherein the one or more binding domain sequences is less than about 250 to about 300, about 200 to about 300, about 150 to about 300, about 100 to about 300, about 50 to about 300, about 100 to about 250, about 100 to about 200, about 100 to about 150, about 50 to about 250, about 50 to about 200, about 50 to about 150, about 50 to about 100, or about 300, or about 250, or about 200, or about 150, or about 100, or about 50 nucleotides in length.

In embodiments, the one or more binding domain sequences is about 5 to about 20, about 5 to about 30, about 5 to about 40, about 5 to about 50, about 10 to about 50, about 10 to about 100, about 20 to about 100, about 30 to about 100, about 40 to about 100, about 50 to about 100, about 50 to about 150, about 50 to about 200, about 50 to about 250, about 100 to about 150, about 100 to about 200, about 100 to about 250, or about 100 to about 300 nucleotides in length.

In embodiments, the composition or system comprises one binding domain sequence. In embodiments, the composition or system comprises at least two binding domain sequences. In embodiments, the composition or system comprises 3, 4, 5, 6, 7, 8, 9, or 10 binding domain sequences.

In embodiments, when the composition or system is introduced to the cell an exon in the pre-mRNA is targeted for trans-splicing. In embodiments, the target sequence is positioned in a region of the pre-mRNA comprising the exon targeted for trans-splicing. In embodiments, the target sequence is positioned proximal to a splice site. In embodiments, the target sequence is positioned proximal to a splice donor or a splice acceptor.

In aspects, the present disclosure provides a composition or system for targeting trans-splicing of a pre-mRNA in a cell, comprising one or more nucleic acids comprising one or more nucleotide sequences comprising from 5' to 3': (a) at least one intronic sequence comprising: (i) one or more binding domain sequences of about 4 to about 300 nucleotides each with complementarity to a pre-mRNA target sequence; (ii) a small nuclear RNA (snRNA) or a small nucleolar RNA (snoRNA) sequence of about 7 to about 300 nucleotides in length which forms a secondary structure and/or comprises a sequence motif to direct the one or more binding domains to the pre-mRNA target sequence; and (iii) one or more splicing signals; (b) a splice acceptor; and (c) at least one exonic sequences.

In embodiments, when the composition or system is introduced to the cell an exon in the pre-mRNA is targeted for trans-splicing. In embodiments, the target sequence is positioned upstream the exon in the pre-mRNA targeted for trans-splicing. In embodiments, the target sequence is positioned proximal to a splice site. In embodiments, the target sequence is positioned proximal to a splice acceptor or a splice donor. In embodiments, trans-splicing occurs between a splice donor upstream the exon in the pre-mRNA and the splice acceptor of the composition or system. In embodiments, trans-splicing results in ligation of the 3' end of an exon upstream the splice donor in the pre-mRNA with the 5' end of the at least one exonic sequence of the composition or system. In embodiments, the one or more splicing signals comprises a branch point and a polypyrimidine tract.

In embodiments, the intronic sequence comprises a snRNA. In embodiments, the snRNA is selected from a U7 snRNA, a U1 snRNA, a U2 snRNA, a U4 snRNA, a U4atac snRNA, a U5 snRNA, a U6 snRNA, a U6atac snRNA, a U11 snRNA, and a U12 snRNA. In embodiments, the snRNA is a U7 snRNA. In embodiments, the composition or system comprises a snoRNA. In embodiments, the snoRNA comprises an H/ACA box or C/D box. In embodiments, the snRNA or snoRNA sequence assembles into an RNP. In embodiments, the snRNA or snoRNA sequence comprises a sequence motif that assembles into an RNP.

In embodiments, the composition or system further comprises In embodiments, the composition or system further comprises a protein that forms an RNP or is within an RNP, with the snRNA or snoRNA, or a nucleic acid encoding the protein that forms, or is within, the RNP. In embodiments, the snRNA, snoRNA, protein that forms an RNP, a protein within the RNP, and/or a nucleic acid encoding the protein that forms or is within the RNP comprises a modification or mutation that attenuates, weakens, reduces, decreases, or ablates RNP activity as compared to an unmodified form, and/or leads to attenuation of RNA modifying activity, the RNP activity optionally being selected from cleavage, nucleic acid processing, pseudouridylation, and/or methylation. In embodiments, the snRNA, snoRNA, protein that forms an RNP, and/or a nucleic acid encoding the protein that forms the RNP or is within RNP comprises a modification or mutation that increases, stimulates, or enhances RNP activity, or enhances RNA modifying activity, the RNP activity optionally being selected from cleavage, nucleic acid processing, pseudouridylation, and/or methylation as compared to an unmodified form. In embodiments, the repRNA comprises at least one or more pseudouridylation sites. In embodiments, the repRNA comprises no pseudouridylation sites. In embodiments, the repRNA is modified to comprise at least 1, 2, 3 4, 5, 6, 7, 8, 9, 10, 11, 12, 13, 14, 15, 16, 17, 18, 19, 20, 21, 22, 23, 24, 25, 26, 27, 28, 29, 30 or more pseudouridylation sites than the number of pseudouridylation sites in (i) an unmodified state of the snRNA or snoRNA or (ii) an exonic sequence.

In embodiments, the (a) at least one intronic sequence, (b) splice acceptor and/or splice donor sequence, and (c) at least one exonic sequence are provided in cis or trans, or are suitable for being provided in cis or trans. In embodiments, the (a) at least one intronic sequence, (b) splice acceptor and/or splice donor sequence, and (c) at least one exonic sequence are provided in trans, or are suitable for being provided in trans.

In aspects, the present disclosure provides a composition or system for targeting trans-splicing of a pre-mRNA in a cell, comprising one or more nucleic acids comprising one or more nucleotide sequences comprising from 5' to 3': at least one exonic sequence; a splice donor; at least one intronic sequence comprising: a small nuclear RNA (snRNA) or a small nucleolar RNA (snoRNA) sequence of about 7 to about 300 nucleotides in length, and (ii) one or more binding domain sequences of about 4 to about 300 nucleotides each with complementarity to a pre-mRNA target sequence, wherein the snRNA or snoRNA forms a secondary structure and/or comprises a sequence motif to direct the one or more binding domains to the pre-mRNA target sequence.

In embodiments, when the composition or system is introduced to the cell an exon in the pre-mRNA is targeted for trans-splicing. In embodiments, the target sequence is positioned downstream the exon in the pre-mRNA. In embodiments, the target sequence is positioned proximal to a splice site. In embodiments, the target sequence is positioned proximal to a splice donor or a splice acceptor.

In embodiments, trans-splicing occurs between the splice donor of the nucleic acid and a splice acceptor downstream the exon in the pre-mRNA.

In embodiments, trans-splicing results in ligation of the 3' end of the at least one exonic sequence of the nucleic acid with the 5' end of an exon downstream the splice acceptor in the pre-mRNA.

In embodiments, the intronic sequence is an snRNA. In embodiments, the snRNA is selected from a U7 snRNA, a U1 snRNA, a U2 snRNA, a U4 snRNA, a U4atac snRNA, a U5 snRNA, a U6 snRNA, a U6atac snRNA, a U11 snRNA, and a U12 snRNA. In embodiments, the snRNA assembles into an snRNP. In embodiments, the snRNA is a U7 snRNA. In embodiments, the U7 snRNA assembles into a U7 RNP. In embodiments, the snRNA is a U1 snRNA. In embodiments, the U1 snRNA assembles into a U1 RNP. In embodiments, the snRNA is a U11 snRNA. In embodiments, the U11 snRNA assembles into a U11 RNP. The composition or system of any one of the embodiments described herein, wherein the snRNA or snoRNA sequence comprises an Sm sequence motif, and/or the snRNA or snoRNA comprises an antisense region sequence (ASR).

In embodiments, the composition or system further comprises In embodiments, the composition or system further comprises a protein that forms an RNP or is within an RNP, with the snRNA or snoRNA, or a nucleic acid encoding the protein that forms, or is within, the RNP. In embodiments, the snRNA, snoRNA, protein that forms an RNP, a protein within the RNP, and/or a nucleic acid encoding the protein that forms or is within the RNP comprises a modification or mutation that attenuates, weakens, reduces, decreases, or ablates RNP activity as compared to an unmodified form, and/or leads to attenuation of RNA modifying activity, the RNP activity optionally being selected from cleavage, nucleic acid processing, pseudouridylation, and/or methylation. In embodiments, the snRNA, snoRNA, protein that forms an RNP, and/or a nucleic acid encoding the protein that forms the RNP or is within RNP comprises a modification or mutation that increases, stimulates, or enhances RNP activity, or enhances RNA modifying activity, the RNP activity optionally being selected from cleavage, nucleic acid processing, pseudouridylation, and/or methylation as compared to an unmodified form. In embodiments, the repRNA comprises at least one or more pseudouridylation sites. In embodiments, the repRNA comprises no pseudouridylation sites. In embodiments, the repRNA is modified to comprise at least 1, 2, 3 4, 5, 6, 7, 8, 9, 10, 11, 12, 13, 14, 15, 16, 17, 18, 19, 20, 21, 22, 23, 24, 25, 26, 27, 28, 29, 30 or more pseudouridylation sites than the number of pseudouridylation sites in (i) an unmodified state of the snRNA or snoRNA or (ii) an exonic sequence.

In embodiments, the snRNA or snoRNA is at least about 10 to about 80 nucleotides, about 10 to about 70 nucleotides, about 10 to about 60 nucleotides, about 10 to about 50 nucleotides, about 10 to about 40 nucleotides, about 10 to about 30 nucleotides, about 10 to about 20 nucleotides, or about 80, 70, 60, 50, 40, 30, 20, or 10 nucleotides in length.

In embodiments, the snRNA or snoRNA comprises an antisense region sequence (ASR) selected from SEQ ID NOs: 700-707. In embodiments, the Sm sequence motif comprises a nucleotide sequence selected from SEQ ID NOs: 1-8.

In embodiments, the snRNA or snoRNA comprises a grepRNA sequence. In embodiments, the grepRNA sequence is selected from SEQ ID NOs: 708-711.

In embodiments, the snRNA or snoRNA sequence comprises an Sm sequence motif, and/or the snRNA or snoRNA comprises an antisense region sequence (ASR), and a U7 snRNA. In embodiments, the Sm sequence motif comprises a sequence set forth in SEQ ID NOs: 3 and 4. In embodiments, the Sm sequence motif assembles with an Sm protein into an RNP. In embodiments, the Sm protein is selected from a B/B', D3, D2, D1, E, F, and G Sm protein.

In embodiments, the snRNA or snoRNA sequence comprises a sequence having at least 80% sequence identity to a sequence selected from SEQ ID NOs: 9-210 and 212-589 or a portion thereof. In embodiments, the snRNA or snoRNA sequence comprises a region of about 7 to about 40 nucleotides in length, wherein the region comprises an Sm sequence motif, and/or the snRNA or snoRNA comprises an antisense region sequence (ASR).

In embodiments, the snRNA or snoRNA comprises an antisense region sequence (ASR) selected from SEQ ID NOs: 700-707. In embodiments, the snRNA or snoRNA is at least about 10 to about 80 nucleotides, about 10 to about 70 nucleotides, about 10 to about 60 nucleotides, about 10 to about 50 nucleotides, about 10 to about 40 nucleotides, about 10 to about 30 nucleotides, about 10 to about 20 nucleotides, or about 80, 70, 60, 50, 40, 30, 20, or 10 nucleotides in length. In embodiments, the snRNA or snoRNA sequence comprises a region of about 40 to about 300 nucleotides in length, wherein the region comprises a secondary structure and/or an Sm sequence motif. In embodiments, the composition or system comprises one binding domain sequence. In embodiments, the composition or system comprises more than one binding domain sequence. In embodiments, the one or more binding domain sequences is about 5 to about 20, about 5 to about 30, about 5 to about 40, about 5 to about 50, about 10 to about 50, about 10 to about 100, about 20 to about 100, about 30 to about 100, about 40 to about 100, about 50 to about 100, about 50 to about 150, about 50 to about 200, about 50 to about 250, about 100 to about 150, about 100 to about 200, about 100 to about 250, or about 100 to about 300 nucleotides in length.

In embodiments, the (a) at least one intronic sequence, (b) splice acceptor and/or splice donor sequence, and (c) at least one exonic sequence are provided in cis or trans, or are suitable for being provided in cis or trans. In embodiments, the (a) at least one intronic sequence, (b) splice acceptor and/or splice donor sequence, and (c) at least one exonic sequence are provided in trans, or are suitable for being provided in trans.

In aspects, the present disclosure provides a composition or system for targeting trans-splicing of a pre-mRNA in a cell, comprising one or more nucleic acids comprising one or more nucleotide sequences comprising from 5' to 3': at least one intronic sequence comprising: (i) a snRNA or snoRNA sequence comprising an H/ACA box or a C/D box and one or more binding domain sequences of about 4 to about 30 nucleotides each with complementarity to a pre-mRNA target sequence; and (ii) one or more splicing signals; a splice acceptor; and at least one exonic sequence.

In embodiments, the composition or system comprises a CRISPR/Cas system, e.g., a protein and/or nucleic acid thereof. In embodiments, the composition or system further comprises a repair RNA (repRNA) and a CRISPR/Cas system. In embodiments, the CRISPR/Cas system is active, e.g., catalytically active. In embodiments, the CRISPR/Cas system is inactive, e.g., catalytically inactive, e.g., "dead". In embodiments, the CRISPR/Cas system is a Type III CRISPR/Cas system. In embodiments, the Type III CRISPR/Cas system is or comprises a Type IIIA, Type IIIB, Type IIIC, Type IIID, Type IIIE, or Type IIIF CRISPR/Cas system, optionally wherein the Type IIIA, Type IIIB, Type IIIC, Type IIID, Type IIIE, or Type IIIF CRISPR/Cas system is active, catalytically inactive or has reduced activity relative to wild type. In embodiments, the Type III CRISPR/Cas system is or comprises a Cas10 (Csm1), Csm2, Cas7 (Csm3), Csm4, Csm5, Cas 6, and, Cas7-11, or a fragment or variant thereof, optionally wherein the Type III CRISPR/Cas system is or comprises a Cas10 (Csm1), Csm2, Cas7 (Csm3), Csm4, Csm5, Cas 6, and, Cas7-11 is active, catalytically inactive or has reduced activity relative to wild type. In embodiments, the Type III CRISPR/Cas system comprises a domain from a different endonuclease, optionally wherein the different endonuclease is a Cas endonuclease, optionally wherein the domain is one or more of a PAM-interacting domain, optionally wherein the domain is derived from one or more of Cas9, Cas12a (Cpf1), Cas12e (CasX), Cas12d (CasY), Cas12b (C2c1), Cas13a (C2c2), Cas13b, Cas13c, Cas13d, Cas13X/Cas13bt, Cas13Y, Cas12c (C2c3), GeoCas9, CjCas9, NmeCas9, Cas12J (CasPhi), Cas12L (CasLambda), Cas12f (Cas14), Cas12g, Cas12h, Cas12i, Cas12k, NmeCas9, Nme2Cas9, CjCas9, GeoCas9, BlatCas9, PpCas9, and Cas14. In embodiments, the composition or system comprises an intronic sequence comprising a sequence which interacts with or is suitable for interacting with the CRISPR/Cas system. In embodiments, the composition or system further comprises a repair RNA (repRNA) and a CRISPR/Cas system when the present methods are undertaken in cis or trans, as described herein.

In embodiments, the Cas is a type I. In embodiments, the Cas is a type I-A, e.g., without limitation Cas8a or Cas5. In embodiments, the Cas is a type I. In embodiments, the Cas is a type I-B, e.g., without limitation Cas8b. In embodiments, the Cas is a type I. In embodiments, the Cas is a type I-C, e.g., without limitation Cas8c. In embodiments, the Cas is a type I-D, e.g., without limitation Cas10d. In embodiments, the Cas is a type I. In embodiments, the Cas is a type I-E, e.g., without limitation Cse1 or Cse2. In embodiments, the Cas is a type I. In embodiments, the Cas is a type I-F, e.g., without limitation Csy1, Csy2, or Csy3. In embodiments, the Cas is a type I. In embodiments, the Cas is a type I-G, e.g., without limitation GSU0054. In embodiments, the Cas is a type I. In embodiments, the Cas type I is without limitation, Cas3.

In embodiments, the Cas is a type II. In embodiments, the Cas is a type II-A, e.g., without limitation Csn2. In embodiments, the Cas is a type II. In embodiments, the Cas is a type II-B, e.g., without limitation Cas4. In embodiments, the Cas is a type II. In embodiments, the Cas is a type II-C. In embodiments, the Cas is a type II. In embodiments, the Cas type II is without limitation Cas 9.

In embodiments, the Cas is a type III. In embodiments, the Cas is a type III-A, e.g., without limitation Csm2. In embodiments, the Cas is a type III. In embodiments, the Cas is a type III-B, e.g., without limitation Cmr5. In embodiments, the Cas is a type III. In embodiments, the Cas is a type III-C, e.g., without limitation Cas10 or Csx11. In embodiments, the Cas is a type III. In embodiments, the Cas is a type III-D, e.g., without limitation Csx10. In embodiments, the Cas is a type III. In embodiments, the Cas is a type III-E. In embodiments, the Cas is a type III. In embodiments, the Cas is a type III-F. In embodiments, the Cas is a type III. In embodiments, the Cas type III is without limitation Cas 10.

In embodiments, the Cas is a type IV. In embodiments, the Cas is a type IV-A. In embodiments, the Cas is a type IV. In embodiments, the Cas is a type IV-B. In embodiments, the Cas is a type IV. In embodiments, the Cas is a type IV-C.

In embodiments, the Cas is a type V. In embodiments, the Cas is a type V-A, e.g., without limitation Cas12a (Cpf1). In embodiments, the Cas is a type V. In embodiments, the Cas is a type V-B, e.g., without limitation Cas12b (C2c1). In embodiments, the Cas is a type V. In embodiments, the Cas is a type V-C, e.g., without limitation Cas12c (C2c3). In embodiments, the Cas is a type V. In embodiments, the Cas is a type V-D, e.g., without limitation Cas12d (CasY). In embodiments, the Cas is a type V. In embodiments, the Cas is a type V-E, e.g., without limitation Cas12e (CasX). In embodiments, the Cas is a type V. In embodiments, the Cas is a type V-F, e.g., without limitation Cas12f (Cas14, or C2c10). In embodiments, the Cas is a type V. In embodiments, the Cas is a type V-G, e.g., without limitation Cas12g. In embodiments, the Cas is a type V. In embodiments, the Cas is a type V-H, e.g., without limitation Cas12h. In embodiments, the Cas is a type V. In embodiments, the Cas is a type V-I, e.g., without limitation Cas12i. In embodiments, the Cas is a type V. In embodiments, the Cas is a type V-K, e.g., without limitation Cas12k (C2c5). In embodiments, the Cas is a type V. In embodiments, the Cas is a type V-U, e.g., without limitation C2c4, C2c8, or C2c9. In embodiments, the Cas is a type V. In embodiments, the Cas type V is without limitation Cas 12. In embodiments, the Cas is a type VI.

In embodiments, the Cas is a type VI-A, e.g., without limitation Cas13a (C2c2). In embodiments, the Cas is a type VI. In embodiments, the Cas is a type VI-B, e.g., without limitation Cas13b. In embodiments, the Cas is a type VI. In embodiments, the Cas is a type VI-C, e.g., without limitation Cas13c. In embodiments, the Cas is a type VI. In embodiments, the Cas is a type VI-D, e.g., without limitation Cas13d. In embodiments, the Cas is a type VI. In embodiments, the Cas is a type VI-X, e.g., without limitation Cas13x.1. In embodiments, the Cas is a type VI. In embodiments, the Cas is a type VI-Y. In embodiments, the Cas is a type VI. In embodiments, the Cas type VI is without limitation Cas 13.

In embodiments the Cas is Cas3, Cas8a, Cas5, Cas8b, Cas8c, Cas10d, Cse1, Cse2, Csy1, Csy2, Csy3, GSU0054, Cas10, Csm2, Cmr5, Cas10 or Csx11, Csx10, Csf1, Cas9, Csn2, Cas4, Cas12, Cas12a (Cpf1), Cas12b (C2c1), Cas12c (C2c3), Cas12d (CasY), Cas12e (CasX), Cas12f (Cas14, C2c10), Cas12g, Cas12h, Cas12i, Cas12k (C2c5), C2c4, C2c8, C2c9, Cas13, Cas13a (C2c2), Cas13b, Cas13c, Cas13d, or Cas13x.1.

In embodiments, when the composition or system is introduced to the cell an exon in the pre-mRNA is targeted for trans-splicing. In embodiments, the target sequence is positioned upstream the exon in the pre-mRNA. In embodiments, the target sequence is positioned proximal to a splice site. In embodiments, the target sequence is positioned proximal to a splice donor or splice acceptor. In embodiments, trans-splicing occurs between a splice donor upstream the exon in the pre-mRNA and the splice acceptor of the composition or system. In embodiments, trans-splicing results in ligation of the 3' end of an exon upstream the splice donor in the pre-mRNA with the 5' end of the at least one exonic sequence of the composition or system.

In embodiments, the one or more splicing signals comprises a branch point and a polypyrimidine tract.

In embodiments, the intronic sequence comprises a snRNA. In embodiments, the snRNA is selected from a U7 snRNA, a U1 snRNA, a U2 snRNA, a U4 snRNA, a U4atac snRNA, a U5 snRNA, a U6 snRNA, a U6atac snRNA, a U11 snRNA, and a U12 snRNA. In embodiments, the snRNA is a U7 snRNA. In embodiments, the composition or system comprises a snoRNA. In embodiments, the snoRNA comprises an H/ACA box or C/D box. In embodiments, the snRNA or snoRNA sequence assembles into an RNP. In embodiments, the snRNA or snoRNA sequence comprises a sequence motif that assembles into an RNP. In embodiments, the composition or system further comprises In embodiments, the composition or system further comprises a protein that forms an RNP or is within an RNP, with the snRNA or snoRNA, or a nucleic acid encoding the protein that forms, or is within, the RNP. In embodiments, the snRNA, snoRNA, protein that forms an RNP, a protein within the RNP, and/or a nucleic acid encoding the protein that forms or is within the RNP comprises a modification or mutation that attenuates, weakens, reduces, decreases, or ablates RNP activity, and/or leads to attenuation of RNA modifying activity as compared to an unmodified form, the RNP activity optionally being selected from cleavage, nucleic acid processing, pseudouridylation, and/or methylation. In embodiments, the snRNA, snoRNA, protein that forms an RNP, and/or a nucleic acid encoding the protein that forms the RNP or is within RNP comprises a modification or mutation that increases, stimulates, or enhances RNP activity, or enhances RNA modifying activity, the RNP activity optionally being selected from cleavage, nucleic acid processing, pseudouridylation, and/or methylation as compared to an unmodified form. In embodiments, the repRNA comprises at least one or more pseudouridylation sites. In embodiments, the repRNA comprises no pseudouridylation sites. In embodiments, the repRNA is modified to comprise at least 1, 2, 3 4, 5, 6, 7, 8, 9, 10, 11, 12, 13, 14, 15, 16, 17, 18, 19, 20, 21, 22, 23, 24, 25, 26, 27, 28, 29, 30 or more pseudouridylation sites than the number of pseudou-ridylation sites in (i) an unmodified state of the snRNA or snoRNA or (ii) an exonic sequence. In embodiments, the (a) at least one intronic sequence, (b) splice acceptor and/or splice donor sequence, and (c) at least one exonic sequence are provided in cis or trans, or are suitable for being provided in cis or trans. In embodiments, the (a) at least one intronic sequence, (b) splice acceptor and/or splice donor sequence, and (c) at least one exonic sequence are provided in trans, or are suitable for being provided in trans.

In aspects, the present disclosure provides a composition or system for targeting trans-splicing of a pre-mRNA in a cell, comprising one or more nucleic acids comprising one or more nucleotide sequences comprising from 5' to 3': (a) at least one exonic sequence; (b) a splice donor; and (c) at least one intronic sequence comprising a snRNA or snoRNA sequence comprising an H/ACA box or a C/D box and one or more binding domain sequences of about 4 to about 30 nucleotides each with complementarity to a pre-mRNA target sequence.

In embodiments, when the composition or system is introduced to the cell an exon in the pre-mRNA is targeted for trans-splicing. In embodiments, the target sequence is positioned downstream the exon in the pre-mRNA. In embodiments, the target sequence is positioned proximal to a splice site. In embodiments, the target sequence is posi-tioned proximal to a splice donor or a splice acceptor.

In embodiments, trans-splicing occurs between the splice donor of the composition or system and a splice acceptor downstream the exon in the pre-mRNA. In embodiments, trans-splicing results in ligation of the 3' end of the at least one exonic sequence of the composition or system with the 5' end of an exon downstream the splice acceptor in the pre-mRNA.

In embodiments, the snRNA or snoRNA sequence com-prises an H/ACA box comprising 5' to 3' an H consensus sequence and an ACA consensus sequence. In embodiments, the composition or system comprises at least one binding domain sequence positioned: (i) upstream the H consensus sequence; (ii) downstream the ACA consensus sequence; (iii) between the H consensus sequence and the ACA consensus sequence; or (iv) a combination of (i)-(iii).

In embodiments, the snRNA or snoRNA sequence com-prises C/D box comprising 5' to 3' a C consensus sequence, a D' consensus sequence, a C' consensus sequence, and a D consensus sequence.

In embodiments, the composition or system comprises at least one binding domain positioned (i) upstream the C consensus sequence; (ii) between the C consensus sequence and the D' consensus sequence; (iii) between the D' consen-sus sequence and the C' consensus sequence; (iv) between the C' consensus sequence and the D consensus sequence; (v) downstream the D consensus sequence; or (vi) a com-bination of (i)-(v).

In embodiments, the snRNA or snoRNA sequence com-prises a sequence having at least 80% sequence identity to a sequence selected from any one of SEQ ID NOs: 590-628, 630-632, 634-635, 638, 640, 642, 644-645, 647-648, 650, 652-653, 655, 657, 732-737, 741-746, 748-749, 751-758, 760-761, 763-765, 767, 771-774, 776-778, and 780-789, or a portion thereof. In embodiments, the snRNA or snoRNA sequence comprises a region of about 40 to about 300 nucleotides in length and comprising an H consensus sequence and an ACA consensus sequence.

In embodiments, the snRNA or snoRNA sequence com-prises one binding domain sequence. In embodiments, the snRNA or snoRNA sequence comprises more than one binding domain sequence. In embodiments, the composition or system comprises at least one binding domain sequence with full complementarity to the pre-mRNA target sequence. In embodiments, the composition or system comprises at least one binding domain sequence with partial complemen-tarity to the pre-mRNA target sequence. In embodiments, the at least one binding domain sequence comprises one or more mismatches relative to the pre-mRNA target sequence. In embodiments, the at least one binding domain sequence has at least 95% complementarity to the pre-mRNA target sequence.

In embodiments, the (a) at least one intronic sequence, (b) splice acceptor and/or splice donor sequence, and (c) at least one exonic sequence are provided in cis or trans, or are suitable for being provided in cis or trans.

In embodiments, the (a) at least one intronic sequence, (b) splice acceptor and/or splice donor sequence, and (c) at least one exonic sequence are provided in trans, or are suitable for being provided in trans. In embodiments, these elements are under the control of one or more promoters. In embodi-ments, these elements are under the control of different promoters. In embodiments, these elements are operably linked, but separated by a cleavable sequence (e.g., a self-cleaving ribozyme). In embodiments, (i) multiple popula-tions of repRNA are under the control of different promoters or (ii) the repRNA and another system member under control of different promoters.

In some embodiments, a nucleic acid of the disclosure comprises at least one binding domain sequence with full complementarity to the target sequence. In some embodi-ments, the nucleic acid comprises at least one binding domain sequence with partial complementarity to the target sequence (e.g., comprising at least 95% complementarity to the target sequence). In some embodiments, the nucleic acid comprises at least one binding domain sequence with full complementarity to the target sequence and at least one binding domain sequence with partial complementarity to the target sequence (e.g., comprising at least 95% comple-mentarity to the target sequence).

In embodiments, the composition or system comprises a sequence up to about 20,000 nucleotides in length.

In embodiments, the composition or system comprises a sequence of about 50 to about 500, about 50 to about 1000, about 100 to about 500, about 100 to about 1000, about 500 to about 1000, about 500 to about 2000, about 500 to about 3,000, about 500 to about 4,000, about 500 to about 5,000, about 1,000 to about 5,000, about 1,000 to about 10,000, about 5,000 to about 15,000, or about 5,000 to about 20,000 nucleotides in length.

In embodiments, the nucleic acid of the disclosure a sequence of up to about 20,000 nucleotides in length. In some embodiments, the sequence is up to about 10,000 nucleotides in length. In some embodiments, the sequence is up to about 9,000 nucleotides in length. In some embodi-ments, the sequence is up to about 8,000 nucleotides in length. In some embodiments, the sequence is up to about 7,000 nucleotides in length. In some embodiments, the sequence is up to about 6,000 nucleotides in length. In some embodiments, the sequence is up to about 5,000 nucleotides in length. In some embodiments, the sequence is about 50 to about 500 nucleotides in length. In some embodiments, the sequence about 50 to about 1000 nucleotides in length. In some embodiments, the sequence about 100 to about 500 nucleotides in length. In some embodiments, the sequence about 100 to about 1000 nucleotides in length. In some embodiments, the sequence about 500 to about 1000 nucleo-tides in length. In some embodiments, the sequence about 500 to about 2000 nucleotides in length. In some embodiments, the sequence about 500 to about 3,000 nucleotides in length. In some embodiments, the sequence about 500 to about 4,000 nucleotides in length. In some embodiments, the sequence about 500 to about 5,000 nucleotides in length. In some embodiments, the sequence about 1,000 to about 5,000 nucleotides in length. In some embodiments, the sequence about 1,000 to about 10,000 nucleotides in length. In some embodiments, the sequence about 5,000 to about 15,000 nucleotides in length. In some embodiments, the sequence about 5,000 to about 20,000 nucleotides in length.

In embodiments, a composition, system, and/or the one or more nucleic acids comprising one or more nucleotide sequences described herein comprises a sequence selected from Table 6 or a portion thereof. Table 6 provides exemplary nucleotide sequences of composition, system, and/or the one or more nucleic acids comprising one or more nucleotide sequences described herein. As presented in Table 6, the regions of the sequence are demarcated by hyphens (-) and identification of the regions from 5' to 3' are provided as Region 1, Region 2, Region 3, and optionally Region 4. In some embodiments, a composition, system, and/or the one or more nucleic acids comprising one or more nucleotide sequences described herein comprises a sequence having the formula 5'-[A]-[B]-3', wherein [A] is a nucleotide sequence selected from Table 6 and [B] is a sequence comprising from 5' to 3' a splice acceptor and one or more exonic sequences. In some embodiments, [A] comprises a nucleotide sequence selected from Table 6, wherein the RNA-binding domain is exchanged with an RNA-binding domain described herein.

In embodiments, a composition, system, and/or the one or more nucleic acids comprising one or more nucleotide sequences described herein comprises from 5' to 3' one or more RNA binding domains described herein, a snRNA and/or snoRNA, an intronic sequence, a splice acceptor, and one or more exonic sequences, wherein the snRNA and/or snoRNA sequence has about 90%, 95%, 98%, 99%, or 100% to a snRNA and/or snoRNA sequence identified in Table 6. In some embodiments, a composition, system, and/or the one or more nucleic acids comprising one or more nucleotide sequences described herein comprises from 5' to 3' one or more exonic sequences, a splice donor, an intronic sequence, a snRNA and/or snoRNA sequence, and one or more RNA binding domains described herein, wherein the snRNA and/or snoRNA sequence has about 90%, 95%, 98%, 99%, or 100% to a snRNA and/or snoRNA sequence identified in Table 6. In some embodiments, the intronic sequence has about 90%, 95%, 98%, 99%, or 100% to an intronic sequence identified in Table 6.

Compositions, Systems, and/or Nucleic Acids for Targeted Trans-Splicing

Accurate pre-mRNA splicing is critical for proper protein expression. Nuclear pre-mRNA splicing is catalyzed by the spliceosome. Vertebrate gene architecture often consists of relatively long introns and short internal exons. The exon-intron boundaries are defined by a splice donor (the 5' splice site or splice site at the 3'end of an exon) and a splice acceptor (the 3' splice site or splice site at the 5' end of an exon). In addition to recognizing splice sites, the spliceosome relies on various splicing signals to mediate a splicing event, including a branch point sequence and a polypyrimidine tract. Typically, the branch point sequence comprises an adenosine situated within a consensus sequence and is situated about 18-40 nucleotides upstream of the 3' splice site. The polypyrimidine tract comprises a repetitive sequence of uracils and is proximal the 3' splice site. Alternative signals can enhance or decrease splicing activity, including exonic splicing enhancers (ESEs), exonic splicing silencers (ESSs), intronic splicing enhancers (ISEs), and intronic splicing silencers (ISSs). Splicing in cis ("cis-splicing") occurs when the 2' OH group of the branch adenosine of the intron carries out a nucleophilic attack on the 5' splice site (splice donor). This results in cleavage at this site and ligation of the 5' end of the intron to the branch adenosine, forming a lariat structure. The 3' splice site (splice acceptor) is attacked by the 3' OH of the 5' exon, resulting in ligation of the 5' and 3' exons to form the mRNA and release of the intron lariat (see, e.g., FIG. 1A).

Figure 1B:
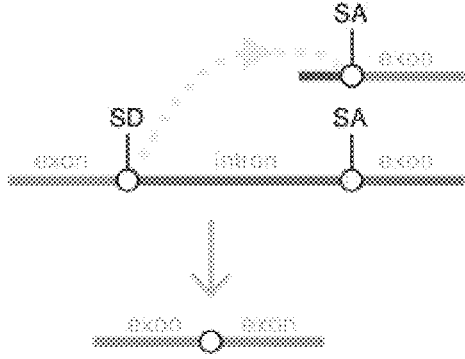
Figure 1C:
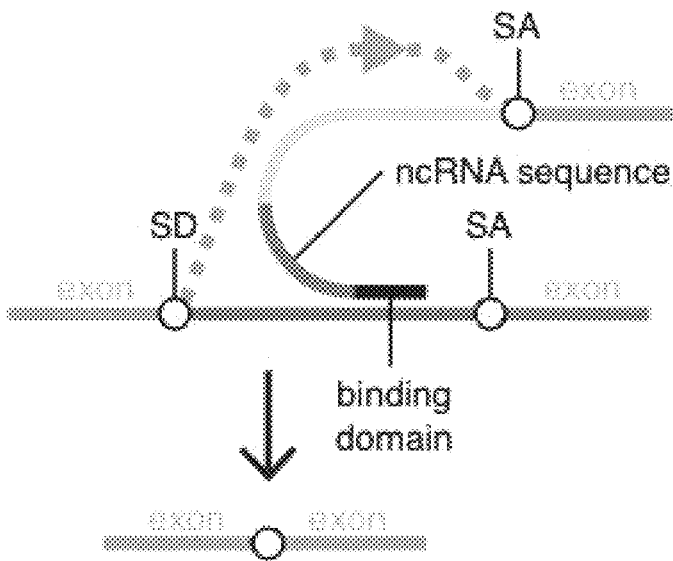
FIG. 1C provides a schematic, without wishing to be bound by theory, depicting an exemplary composition, system, and/or the one or more nucleic acids comprising one or more nucleotide sequences described herein for targeted trans-splicing of a pre-mRNA. Labeling of the composition, system, and/or the one or more nucleic acids comprising one or more nucleotide sequences described herein indicates the segments corresponding to an RNA binding domain, a non-coding RNA (ncRNA), SA, and exon. Labeling of the pre-mRNA indicates segments of the pre-mRNA corresponding to the 5' exon, SD, SA, and 3' exon.
Figure 1D:
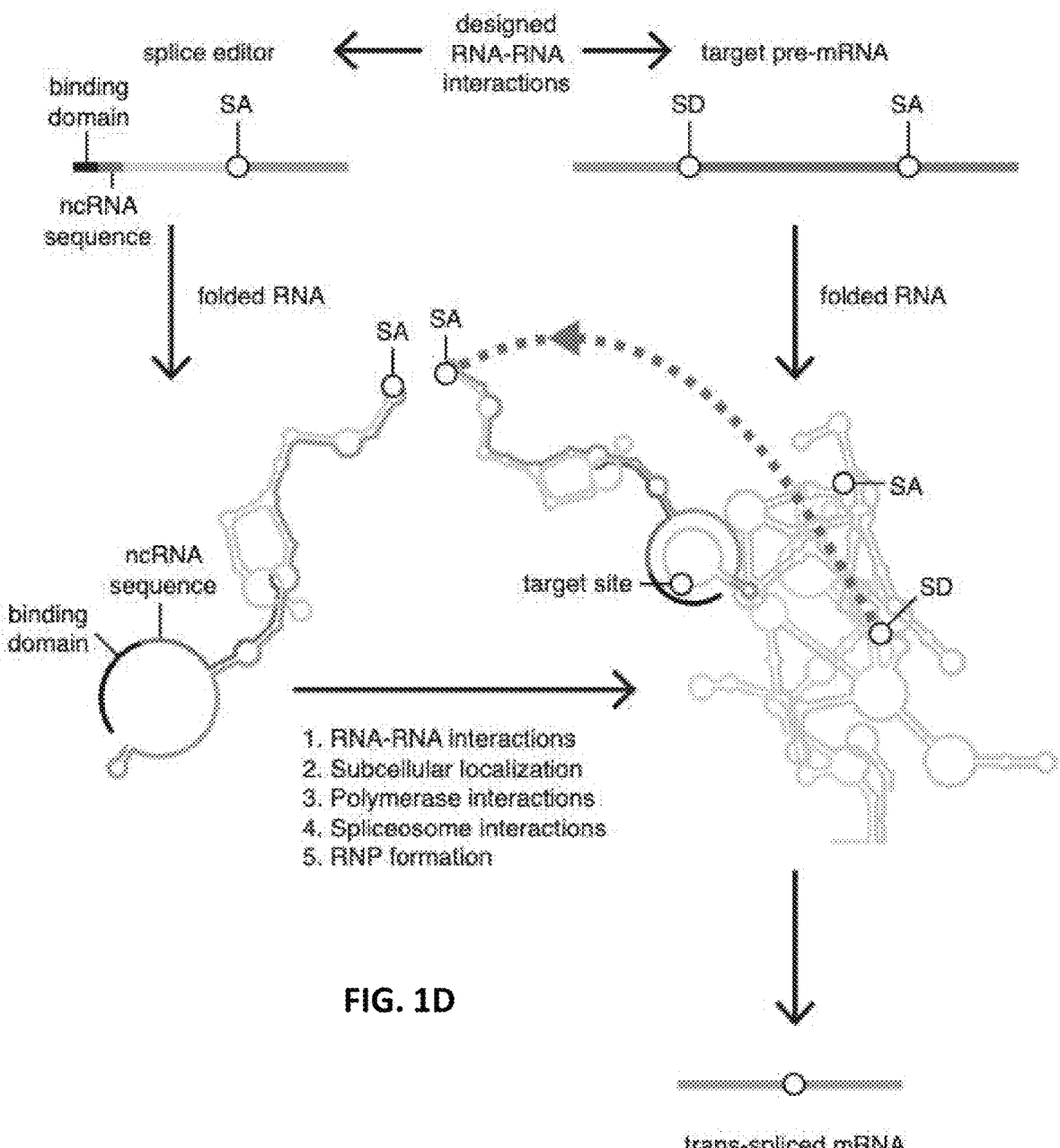
FIG. 1D provides a schematic, without wishing to be bound by theory, depicting a predicted secondary structure of an exemplary composition, system, and/or the one or more nucleic acids comprising one or more nucleotide sequences described herein and pre-mRNA and the interactions between the composition, system, and/or the one or more nucleic acids comprising one or more nucleotide sequences described herein and pre-mRNA that yield a trans-splicing mRNA product.

In contrast, splicing in trans ("trans-splicing") occurs between two different RNA molecules, wherein the 3' splice site (splice acceptor) of a second RNA is attacked by the 3' OH of the 5' exon of a first RNA, resulting in ligation of the 5' exon of the first RNA and the 3' exon of the second RNA, thereby forming a chimeric RNA (see, e.g., FIG. 1B).

The present disclosure provides composition or system suitable for targeting trans-splicing of a pre-mRNA in a cell comprising one or more nucleic acids comprising one or more nucleotide sequences comprising: (a) at least one intronic sequence comprising: (i) one or more binding domain sequences of about 4 to about 300 nucleotides each with complementarity to a pre-mRNA target sequence; and (ii) a small nuclear RNA (snRNA) or a small nucleolar RNA (snoRNA) sequence of about 7 to about 300 nucleotides in length which forms a secondary structure and/or comprises a sequence motif to direct the one or more binding domains to the pre-mRNA target sequence; (b) a splice acceptor and/or splice donor sequence; and (c) at least one exonic sequence. In some embodiments, the composition, system, and/or the one or more nucleic acids comprising one or more nucleotide sequences is designed to bind to a specific region of a target RNA (e.g., pre-mRNA), thereby enabling splicing between the one or more splice sites of the composition, system, and/or the one or more nucleic acids comprising one or more nucleotide sequences and one or more splice sites of the target RNA (e.g., pre-mRNA). In some embodiments, the trans-splicing results in a chimeric mRNA comprising the at least one exonic sequence of the composition, system, and/or the one or more nucleic acids comprising one or more nucleotide sequences and one or more exons of the target RNA (e.g., pre-mRNA).

In humans, exon definition is determined by splice sites paired across an exon (e.g., a splice acceptor (3' splice site) at the 5' end of the exon and a splice donor (5' splice site) at the 3'end of the exon). Other splicing signals (e.g., branch point sequences, polypyrimidine tracts, exonic (or intronic) splicing enhancers and silencers) contribute to proper splicing together of exons to form a mature mRNA. During pre-mRNA splicing, the spliceosome searches for a pair of closely spaced splice sites. Without being bound by theory, the composition, system, and/or the one or more nucleic acids comprising one or more nucleotide sequences described herein mediate efficient trans-splicing by bringing a splice site of the target RNA (e.g., pre-mRNA, e.g., a splice acceptor or splice donor of the target pre-mRNA) into close proximity with a splice site of the composition, system, and/or the one or more nucleic acids comprising one or more nucleotide sequences (e.g., a splice acceptor or splice donor of the composition, system, and/or the one or more nucleic acids comprising one or more nucleotide sequences), such that the spliceosome mediates splicing between the splice site of the target pre-mRNA and the splice site of the composition, system, and/or the one or more nucleic acids comprising one or more nucleotide sequences.

In some embodiments, the composition, system, and/or the one or more nucleic acids comprising one or more nucleotide sequences comprise a nucleotide sequence comprising from 5' to 3' (i) at least one intronic sequence comprising an RNA-guided domain; (ii) a splice acceptor; and (iii) at least one exonic sequence.

In some embodiments, the composition, system, and/or the one or more nucleic acids comprising one or more nucleotide sequences comprise a nucleotide sequence comprising from 5' to 3' (i) at least one exonic sequence; (ii) a splice donor; and (iii) at least one intronic sequence comprising an RNA-guided domain.

In some embodiments, the at least one intronic sequences comprises one or more splicing signals (e.g., a branch point sequence, a polypyrimidine tract, an ISE, and/or an ISS). In some embodiments, the at least one exonic sequences comprises one or more splicing signals (e.g., an ESE and/or an ESS).

In aspects, disclosed herein is a composition or system for targeting trans-splicing of a pre-mRNA in a cell, comprising one or more nucleic acids comprising one or more nucleotide sequences comprising from 5' to 3': (a) a splice donor and/or a splice acceptor; and (b) at least one intronic sequence comprising a snRNA or snoRNA sequence comprising an H/ACA box or a C/D box and one or more binding domain sequences of about 4 to about 300 nucleotides each with complementarity to a pre-mRNA target sequence.

In the embodiments, disclosed herein is a composition or system of any one of the embodiments disclosed herein, the viral vector of any one of the embodiments disclosed herein, or the lipid nanoparticle of any one of the embodiments disclosed herein, or the pharmaceutical composition of any one of the embodiments disclosed herein, or the method of any one of the embodiments disclosed herein, or the kit of any one of the embodiments disclosed herein, wherein the binding domain sequence is between about 1 nucleotide, or about 5 nucleotides, or about 10 nucleotides, or about 50 nucleotides, or about 100 nucleotides, or about 1000 nucleotides near a H/ACA box or C/D box sequence.

In the embodiments, disclosed herein is a composition or system of any one of the embodiments disclosed herein, the viral vector of any one of the embodiments disclosed herein, or the lipid nanoparticle of any one of the embodiments disclosed herein, or the pharmaceutical composition of any one of the embodiments disclosed herein, or the method of any one of the embodiments disclosed herein, or the kit of any one of the embodiments disclosed herein, wherein the snoRNA is a H/ACA snoRNA (SNORA), C/D snoRNA (SNORD), or a small cajal RNA (scaRNA).

In the embodiments, disclosed herein is a composition or system of any one of the embodiments disclosed herein, the viral vector of any one of the embodiments disclosed herein, or the lipid nanoparticle of any one of the embodiments disclosed herein, or the pharmaceutical composition of any one of the embodiments disclosed herein, or the method of any one of the embodiments disclosed herein, or the kit of any one of the embodiments disclosed herein, wherein the snoRNA is SNORA101B, SNORA48, SNORA54, SNORA66, SNORA73A, or SNORA8, or the snoRNA is SNORA101B, SNORA48, SNORA54, SNORA66, SNORA73A, or SNORA8 with at least one or more mutations.

In the embodiments, disclosed herein is a composition or system of any one of the embodiments disclosed herein, the viral vector of any one of the embodiments disclosed herein, or the lipid nanoparticle of any one of the embodiments disclosed herein, or the pharmaceutical composition of any one of the embodiments disclosed herein, or the method of any one of the embodiments disclosed herein, or the kit of any one of the embodiments disclosed herein, wherein the snoRNA is in cis with respect to the repRNA.

In the embodiments, disclosed herein is a composition or system of any one of the embodiments disclosed herein, the viral vector of any one of the embodiments disclosed herein, or the lipid nanoparticle of any one of the embodiments disclosed herein, or the pharmaceutical composition of any one of the embodiments disclosed herein, or the method of any one of the embodiments disclosed herein, or the kit of any one of the embodiments disclosed herein, wherein the snoRNA is in trans with respect to the repRNA.

In the embodiments, disclosed herein is a composition or system of any one of the embodiments disclosed herein, the viral vector of any one of the embodiments disclosed herein, or the lipid nanoparticle of any one of the embodiments disclosed herein, or the pharmaceutical composition of any one of the embodiments disclosed herein, or the method of any one of the embodiments disclosed herein, or the kit of any one of the embodiments disclosed herein, wherein the repRNA comprises a splice donor and/or a splice acceptor.

In the embodiments, disclosed herein is a composition or system of any one of the embodiments disclosed herein, the viral vector of any one of the embodiments disclosed herein, or the lipid nanoparticle of any one of the embodiments disclosed herein, or the pharmaceutical composition of any one of the embodiments disclosed herein, or the method of any one of the embodiments disclosed herein, or the kit of any one of the embodiments disclosed herein, wherein the repRNA comprises a splice donor and/or a splice acceptor, and wherein the snoRNA and snRNA are in trans with respect to the repRNA.

In the embodiments, disclosed herein is a composition or system of any one of the embodiments disclosed herein, the viral vector of any one of the embodiments disclosed herein, or the lipid nanoparticle of any one of the embodiments disclosed herein, or the pharmaceutical composition of any one of the embodiments disclosed herein, or the method of any one of the embodiments disclosed herein, or the kit of any one of the embodiments disclosed herein, wherein a mutation in H and/or ACA motifs substantially decreases the trans-splicing efficiency.

In the embodiments, disclosed herein is a composition or system of any one of the embodiments disclosed herein, the viral vector of any one of the embodiments disclosed herein, or the lipid nanoparticle of any one of the embodiments disclosed herein, or the pharmaceutical composition of any one of the embodiments disclosed herein, or the method of any one of the embodiments disclosed herein, or the kit of any one of the embodiments disclosed herein, wherein the snoRNA is added to the 3' end of a 5' repRNA.

In the embodiments, disclosed herein is a composition or system of any one of the embodiments disclosed herein, the viral vector of any one of the embodiments disclosed herein, or the lipid nanoparticle of any one of the embodiments disclosed herein, or the pharmaceutical composition of any one of the embodiments disclosed herein, or the method of any one of the embodiments disclosed herein, or the kit of any one of the embodiments disclosed herein, wherein the addition of a SNORA modification on a transcript stabilizes the 3' end of the transcript after ribozyme cleavage and polyA removal.

In the embodiments, disclosed herein is a composition or system of any one of the embodiments disclosed herein, the viral vector of any one of the embodiments disclosed herein, or the lipid nanoparticle of any one of the embodiments disclosed herein, or the pharmaceutical composition of any one of the embodiments disclosed herein, or the method of any one of the embodiments disclosed herein, or the kit of any one of the embodiments disclosed herein, wherein the snoRNA is added to the 5' end of a 3' repRNA.

In the embodiments, disclosed herein is a composition or system of any one of the embodiments disclosed herein, the viral vector of any one of the embodiments disclosed herein, or the lipid nanoparticle of any one of the embodiments disclosed herein, or the pharmaceutical composition of any one of the embodiments disclosed herein, or the method of any one of the embodiments disclosed herein, or the kit of any one of the embodiments disclosed herein, wherein the snoRNA is added to the 3' end of a 3' repRNA.

In the embodiments, disclosed herein is a composition or system of any one of the embodiments disclosed herein, the viral vector of any one of the embodiments disclosed herein, or the lipid nanoparticle of any one of the embodiments disclosed herein, or the pharmaceutical composition of any one of the embodiments disclosed herein, or the method of any one of the embodiments disclosed herein, or the kit of any one of the embodiments disclosed herein, wherein the snoRNA is added to the 5' end of a 5' repRNA.

In the embodiments, disclosed herein is a composition or system of any one of the embodiments disclosed herein, the viral vector of any one of the embodiments disclosed herein, or the lipid nanoparticle of any one of the embodiments disclosed herein, or the pharmaceutical composition of any one of the embodiments disclosed herein, or the method of any one of the embodiments disclosed herein, or the kit of any one of the embodiments disclosed herein, wherein the SNORA sequence has at least about 80%, or at least about 85%, or at least about 90%, or at least about 95%, or at least about 96%, or at least about 97%, or at least about 98%, or at least about 99% identity to any one of SEQ ID NOs: 590-628, 630-632, 634-635, 638, 640, 642, 644-645, 647-648, 650, 652-653, 655, 657, 732-737, 741-746, 748-749, 751-758, 760-761, 763-765, 767, 771-774, 776-778, and 780-789.

RNA Guided Domain

In some embodiments, the RNA guided domain comprises a nucleotide sequence comprising (i) one or more binding domains, each having complementarity to a target sequence in the target RNA (e.g., pre-mRNA); and (ii) a snRNA and/or snoRNA. In some embodiments, the one or more binding domains mediate binding of the trans-splicing nucleic acid molecules to a target RNA (e.g., pre-mRNA) in a cell. In some embodiments, the snRNA and/or snoRNA mediates assembly into an RNP.

In some embodiments, the RNA guided domain comprises a nucleotide sequence having from 5' to 3': (i) one or more binding domains, each having complementarity to a target sequence in the target RNA (e.g., pre-mRNA); and (ii) a snRNA and/or snoRNA.

In some embodiments, the RNA guided domain comprises a nucleotide sequence having from 5' to 3': (i) a snRNA and/or snoRNA; and (ii) one or more binding domains, each having complementarity to a target sequence in the target RNA (e.g., pre-mRNA).

In some embodiments, the RNA guided domain comprises a nucleotide sequence having a snRNA and/or snoRNA, wherein the one or more binding domains are inserted into the snRNA and/or snoRNA or exchanged for contiguous nucleotides of the snRNA and/or snoRNA.

Target Sequence

In some embodiments, the one or more binding domains of the RNA guided domain are each complementary to a target sequence in a target RNA (e.g., pre-mRNA) targeted for trans-splicing. As used herein, the term "target sequence" refers to a sequence of contiguous nucleotides present in a target RNA (e.g., pre-mRNA) targeted for trans-splicing. As used herein, the term "contiguous nucleotides" refers to a string of nucleotides that are covalently linked and immediately adjacent to one another. In some embodiments, the target sequence is at least about 4, 5, 6, 7, 8, 9, 10, 11, 12, 13, 14, 15, 16, 17, 18, 19, or 20 nucleotides in length. In some embodiments, the target sequence is less than about 300, 250, 200, 100, 150, or 50 nucleotides in length. In some embodiments, the target sequence is about 5-10, about 5-15, about 5-20, about 10-20, about 10-30, about 10-40, about 10-50, about 10-60, about 10-70, about 10-80, about 10-90, about 10-100, about 50-100, about 50-150, about 50-200, about 50-250, about 50-300, about 100-200, about 100-300, or about 200-300 nucleotides in length.

In some embodiments, the target sequence is in a region comprising a splice site in the target RNA (e.g., pre-mRNA) targeted for trans-splicing. As used herein, "a splice site in the target RNA (e.g., pre-mRNA) targeted for trans-splicing" refers to a splice site in the target RNA (e.g., pre-mRNA) selected for trans-splicing, wherein upon introducing a composition, system, and/or the one or more nucleic acids comprising one or more nucleotide sequences described herein to a cell comprising the target RNA (e.g., pre-mRNA), a trans-splicing event mediates ligation between the splice site of the target RNA (e.g., pre-mRNA) and a splice site of the composition, system, and/or the one or more nucleic acids comprising one or more nucleotide sequences described herein. In some embodiments, the target sequence is upstream the splice site in the target RNA (e.g., pre-mRNA) targeted for trans-splicing. In some embodiments, the target sequence is downstream the splice site in the target RNA (e.g., pre-mRNA) targeted for trans-splicing. In some embodiments, the target sequence is in a region comprising the splice site in the target RNA (e.g., pre-mRNA) targeted for trans-splicing, wherein the region spans at least about 50, about 100, about 150, about 200, about 300, about 400, about 500, about 1,000, about 2,000, about 3,000, about 4,000, about 5,000 nucleotides.

In some embodiments, the target sequence is proximal to the splice site in the target RNA (e.g., pre-mRNA) targeted for trans-splicing. As used herein, the term "proximal to the splice site" refers to a region of less than about 500 nucleotides extending upstream and/or downstream of the splice site in the target RNA (e.g., pre-mRNA) targeted for trans-splicing.

In some embodiments, the target sequence is proximal to a splice acceptor targeted for trans-splicing. In some embodiments, the target sequence is upstream a splice acceptor targeted for trans-splicing. In some embodiments, the target sequence is downstream of a splice acceptor targeted for trans-splicing. In some embodiments, the target sequence overlaps a splice acceptor targeted for trans-splicing.

In some embodiments, the target sequence is proximal to a splice donor targeted for trans-splicing.

In some embodiments, the target sequence is upstream a splice donor targeted for trans-splicing.

In some embodiments, the target sequence is downstream of a splice donor targeted for trans-splicing. In some embodiments, the target sequence overlaps a splice donor targeted for trans-splicing.

In some embodiments, the target sequence is in a region of the target RNA (e.g., pre-mRNA) comprising an exon targeted for trans-splicing. As used herein, an "exon targeted for trans-splicing" refers to an exon in the target RNA that is selected for removal following trans-splicing between the target RNA and a composition, system, and/or the one or more nucleic acids comprising one or more nucleotide sequences described herein, wherein the trans-splicing results in ligation between one or more exons of the target RNA (e.g., pre-mRNA) and the at least one exonic sequence of the composition, system, and/or the one or more nucleic acids comprising one or more nucleotide sequences described herein to form a chimeric RNA molecule, and wherein the exon targeted for trans-splicing is present in the target RNA, but absent in the chimeric RNA molecule formed by the trans-splicing event.

In some embodiments, the target sequence is upstream the exon targeted for trans-splicing. In some embodiments, the target sequence is downstream the exon targeted for trans-splicing. In some embodiments, the target sequence is within the exon targeted for trans-splicing.

In some embodiments, the target sequence is proximal to a splice acceptor of the exon targeted for trans-splicing. In some embodiments, the target sequence is upstream the splice acceptor of the exon targeted for trans-splicing. In some embodiments, the target sequence is downstream the splice acceptor of the exon targeted for trans-splicing. In some embodiments, the target sequence overlaps the splice acceptor of the exon targeted for trans-splicing.

In some embodiments, the target sequence is proximal to a splice donor of the exon targeted for trans-splicing. In some embodiments, the target sequence is upstream the splice donor of the exon targeted for trans-splicing. In some embodiments, the target sequence is downstream the splice donor of the exon targeted for trans-splicing. In some embodiments, the target sequence overlaps the splice donor of the exon targeted for trans-splicing.

RNA Binding Domain

In some embodiments, the binding domain complementary to a target sequence in the target RNA (e.g., pre-mRNA) is at least 4 nucleotides in length. In some embodiments, the binding domain is less than about 300 nucleotides in length. In some embodiments, the binding domain is at least about 5, about 6, about 7, about 8, about 9, about 10, about 11, about 12, about 13, about 14, about 15, about 16, about 17, about 18, about 19 or about 20 nucleotides in length. In some embodiments, the binding domain about 250 to about 300, about 200 to about 300, about 150 to about 300, about 100 to about 300, about 50 to about 300, about 100 to about 250, about 100 to about 200, about 100 to about 150, about 50 to about 250, about 50 to about 200, about 50 to about 150, about 50 to about 100, or about 300, 250, 200, 150, 100, or 50 nucleotides in length.

In some embodiments, the binding domain is about 5 to about 20, about 5 to about 30, about 5 to about 40, about 5 to about 50, about 10 to about 50, about 10 to about 100, about 20 to about 100, about 30 to about 100, about 40 to about 100, about 50 to about 100, about 50 to about 150, about 50 to about 200, about 50 to about 250, about 100 to about 150, about 100 to about 200, about 100 to about 250, or about 100 to about 300 nucleotides in length.

In some embodiments, the binding domain is 10-50 nucleotides in length, e.g., 10-45, 10-40, 10-35, 10-30, 10-20, 11-45, 11-40, 11-35, 11-30, 11-20, 12-45, 12-40, 12-35, 12-30, 12-25, 12-20, 13-45, 13-40, 13-35, 13-30, 13-25, 13-20, 14-45, 14-40, 14-35, 14-30, 14-25, 14-20, 15-45, 15-40, 15-35, 15-30, 15-25, 15-20, 16-45, 16-40, 16-35, 16-30, 16-25, 16-20, 17-45, 17-40, 17-35, 17-30, 17-25, 17-20, 18-45, 18-40, 18-35, 18-30, 18-25, 18-20, 19-45, 19-40, 19-35, 19-30, 19-25, 19-20, e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length.

In some embodiments, the RNA-guided domain comprises one binding domain. In some embodiments, the RNA-guided domain comprises more than one binding domain. In some embodiments, the RNA-guided domain comprises 2, 3, 4, 5, 6, 7, 8, 9, or 10 binding domains. In some embodiments, the more than one binding domains are immediately adjacent to one another. In some embodiments, the more than one binding domains are linked by an intervening nucleotide spacer sequence.

In some embodiments, the one or more binding domains each comprise a sequence that is sufficiently complementary to its target sequence. In embodiments, the one or more binding domains comprising a sequence that is sufficiently complementary to its target sequence enables the composition, system, and/or the one or more nucleic acids comprising one or more nucleotide sequences described herein to specifically bind to the target sequence by forming base pairs. As used herein, the term "base pair" refers to two nucleobases on opposite complementary nucleic acid strands that interact by formation of specific hydrogen bonding (e.g., Watson-Crick, Hoogsteen, or reversed Hoogsteen hydrogen bonding). In some embodiments, the base pair is formed by Watson-Crick base pairing. As understood by the skilled artisan, Watson-Crick base pairing refers to the set of base pairing rules wherein a purine nucleobase binds to a pyrimidine nucleobase to form a complementary base pair. The nature of the hydrogen bonding depends upon the particular base pair. For example, a guanosine-cytosine base pair is formed by three hydrogen bonds and the adenine-thymine or adenine-uracil base pair is formed by two hydrogen bonds. It is understood that analogs or derivatives of canonical nucleobases will form base pair interactions via Watson Crick base pairing or non-canonical base pairing.

A binding domain that "specifically binds to" a target sequence in a target RNA (e.g., pre-mRNA) refers to one that will not appreciably bind to a reference sequence, e.g., a nucleic acid lacking the target sequence. For example, a composition, system, and/or the one or more nucleic acids comprising one or more nucleotide sequences described herein comprising a binding domain that specifically binds a target sequence will exhibit substantially higher binding affinity for a target RNA (e.g., pre-mRNA) comprising a nucleotide sequence comprising the target sequence compared to a target RNA (e.g., pre-mRNA) lacking the target sequence. As is understood by the skilled artisan, the binding affinity between a first nucleic acid strand and a second nucleic acid strand is measured as the melting Temperature©), which is the temperature at which half the first nucleic acid strand is duplexed to the second nucleic acid strand.

In some embodiments, a binding domain is complementary to a target sequence in the target RNA (e.g., pre-mRNA) if it base-pairs to the target sequence under conditions suitable for modulating trans-splicing. Such conditions can be stringent conditions, e.g., combination of the target RNA (e.g., pre-mRNA) and composition, system, and/or the one or more nucleic acids comprising one or more nucleotide sequences described herein in buffer comprising 400 mM NaCl, 40 mM PIPES pH 6.4, 1 mM EDTA at a temperature of 50° C.-70° C. for 12-16 hours, followed by washing (see, e.g., "Molecular Cloning: A Laboratory Manual, Sambrook, et al. (1989) Cold Spring Harbor Laboratory Press). Other conditions include physiologically relevant conditions as can be encountered inside an organism. The skilled person will be able to determine the set of conditions most appropriate for a test of complementarity of two sequences in accordance with the ultimate application of the hybridized nucleotides.

snRNAs and/or snoRNAs

As used herein, a "snRNA" refers to a class of small RNA molecules that are found within the splicing speckles and Cajal bodies of the cell nucleus in eukaryotic cells. The length of an average snRNA is about 150 nucleotides. They are transcribed by either RNA polymerase II or RNA polymerase III. Their primary function is in the processing of pre-messenger RNA (hnRNA) in the nucleus. They have also been shown to aid in the regulation of transcription factors (7SK RNA) or RNA polymerase II (B2 RNA), and maintaining the telomeres. snRNA are typically associated with a set of specific proteins, and the complexes are referred to as small nuclear ribonucleoproteins (snRNP, often pronou"ced "s"urps"). Each snRNP particle is composed of a snRNA component and several snRNP-specific proteins (including Sm proteins, a family of nuclear proteins). Prior to the present disclosure, the most common human snRNA components of these complexes are known, respectively, as: U1 spliceosomal RNA, U2 spliceosomal RNA, U4 spliceosomal RNA, U5 spliceosomal RNA, and U6 spliceosomal RNA. Their nomenclature derives from their high uridine content.

In various embodiments, the present disclosure provides identifying a snRNA and/or snoRNA sequence from a database. Databases listing snRNA and/or snoRNA sequences are known in the art. For example, in some embodiments, the database is RNAcentral (see, e.g., Nucleic Acids Res 45: D128 (2017). RNAcentral is a searchable database that provides snRNA and/or snoRNA sequences annotated with unique identifiers and information regarding the one or more species in which the RNA sequence has been observed.

In some embodiments the present disclosure provides identifying a snRNA and/or snoRNA expressed by a cell or organism. Methods to identify snRNA and/or snoRNAs are known in the art. In some embodiments, cellular RNA is extracted from a cell or organism, separated by PAGE and elution from the gel, and snRNAs and/or snoRNAs are identified by sequence analysis (e.g., via 2D RNA fingerprinting or enzymatic or chemical RNA sequencing). In some embodiments, a cDNA library is generated by reverse transcription of snRNAs and/or snoRNAs obtained from a cell or organism through a selection process based on size or antibody-binding that is then subjected to sequence analysis. In some embodiments, total RNA is harvested from a cell or organism and microarray hybridization is used to detect snRNAs and/or snoRNAs. In some embodiments, genomic SELEX is used to identify snRNAs and/or snoRNAs obtained from a cell or organism. In some embodiments, the snRNA and/or snoRNA sequence is identified from any known organism. In some embodiments, the organism is a bacteria. In some embodiments, the organism is a archaebacteria. In some embodiments, the organism is a metazoan. In some embodiments, the organism is a vertebrate. In some embodiments, the organism is a mammal, amphibian, reptile, fish, or bird. In some embodiments, the organism is a human.

In some embodiments, snRNA and/or snoRNA functions to modify, alter, inhibit, or promote RNP formation and/or canonical processing. In some embodiments, the snRNA and/or snoRNA assembles into an RNP. In some embodiments, the RNP interacts with an RNA secondary structure of the composition, system, and/or the one or more nucleic acids comprising one or more nucleotide sequences described herein. In embodiments, the RNP stabilizes the RNA secondary structure of the composition, system, and/or the one or more nucleic acids comprising one or more nucleotide sequences described herein. In embodiments, the one or more RNA secondary structures comprises a single-stranded RNA sequence, a double-stranded RNA sequence, or a combination thereof. In some embodiments, the one or more RNA secondary structure comprises a duplex structure, a stem-loop, a pseudoknot, an internal loop, a multi-branch loop, a bulge loop, an external loop, or a combination thereof. In some embodiments, the RNP functions stabilize RNA-RNA interactions within the composition, system, and/or the one or more nucleic acids comprising one or more nucleotide sequences described herein and/or with a target RNA (e.g., pre-mRNA). In some embodiments, the RNP functions in to protect the composition, system, and/or the one or more nucleic acids comprising one or more nucleotide sequences described herein from degradation. In some embodiments, the RNP functions in to localize the composition, system, and/or the one or more nucleic acids comprising one or more nucleotide sequences described herein to a subcellular compartment comprising a target pre-mRNA. Methods to measure assembly of one or more nucleic acids (e.g., RNA or DNA) and one or more proteins to form an RNP are known in the art. Such methods include, but are not limited to, electrophoretic mobility shift assay (EMSA), DNA or RNA pull-down assays, oligonucleotide-targeted RNase H protection assays, fluorescent in situ hybridization co-localization, co-immunoprecipitation assays, and RNA sequencing and cross-linking methods such as high throughput sequencing crosslinking immunoprecipitation (HITS-CLIP).

In embodiments, the repRNA comprises at least one or more snRNA or snoRNA sequences. In embodiments, the at least one or more snRNA or snoRNA sequences stabilize the repRNA. In embodiments, the repRNA comprises an artificial smU7 system. In embodiments, the artificial smU7 system stabilizes the repRNA. In embodiments, the least one or more snRNA or snoRNA sequences comprise a pseudoknot at the 5' end of the snRNA or snoRNA. In embodiments, the pseudoknot at the 5' end of the snRNA or snoRNA stabilizes the repRNA. In embodiments, the least one or more snRNA or snoRNA sequences comprise a pseudoknot at the 3' end of the snRNA or snoRNA. In embodiments, the pseudoknot at the 3' end of the snRNA or snoRNA stabilizes the repRNA.

In some embodiments, a snRNA and/or snoRNA sequence identified according to a method described herein is incorporated into a composition, system, and/or the one or more nucleic acids comprising one or more nucleotide sequences described herein. In some embodiments, the entire snRNA and/or snoRNA sequence is incorporated into the composition, system, and/or the one or more nucleic acids comprising one or more nucleotide sequences described herein. In some embodiments, a portion of the snRNA and/or snoRNA sequence is incorporated into the composition, system, and/or the one or more nucleic acids comprising one or more nucleotide sequences described herein.

In some embodiments, a composition, system, and/or the one or more nucleic acids comprising one or more nucleotide sequences described herein comprises an snRNA and/or snoRNA sequence or portion thereof.

In some embodiments, the snRNA and/or snoRNA sequence or portion thereof is less than about 500 nucleotides in length. In some embodiments, the snRNA and/or snoRNA sequence or portion thereof is less than about 400 nucleotides in length. In some embodiments, the snRNA and/or snoRNA sequence or portion thereof is less than about 300 nucleotides in length. In some embodiments, the snRNA and/or snoRNA sequence or portion thereof is about 250 to about 300, about 200 to about 300, about 150 to about 300, about 100 to about 300, about 50 to about 300, about 100 to about 250, about 100 to about 200, about 100 to about 150, about 50 to about 250, about 50 to about 200, about 50 to about 150, about 50 to about 100, or about 300, 250, 200, 150, 100, or 50 nucleotides in length.

In some embodiments, the snRNA and/or snoRNA sequence or portion thereof is at least about 5, about 6, about 7, about 8, about 9, about 10, about 11, about 12, about 13, about 14, about 15, about 16, about 17, about 18, about 19 or about 20 nucleotides in length.

In some embodiments, the snRNA and/or snoRNA sequence or portion thereof is about 5 to about 20, about 5 to about 30, about 5 to about 40, about 5 to about 50, about 10 to about 50, about 10 to about 100, about 20 to about 100, about 30 to about 100, about 40 to about 100, about 50 to about 100, about 50 to about 150, about 50 to about 200, about 50 to about 250, about 100 to about 150, about 100 to about 200, about 100 to about 250, or about 100 to about 300 nucleotides in length.

In some embodiments, the snRNA and/or snoRNA sequence or portion thereof comprises one or more RNA secondary structures that assembles into an RNP. In some embodiments, the one or more RNA secondary structures comprises a single-stranded RNA sequence, a double-stranded RNA sequence, or a combination thereof. In some embodiments, the one or more RNA secondary structure comprises a duplex structure, a stem-loop, a pseudoknot, an internal loop, a multi-branch loop, a bulge loop, an external loop, or a combination thereof. Methods to determine the secondary structure formed by an RNA sequence are known in the art. In some embodiments, the method comprises an experimental assay, e.g., nuclear magnetic resonance, cryo-electron microscopy, or X-ray crystal structure analysis. In some embodiments, the method comprises a computational prediction, e.g., based on a thermodynamic model such as Turner's nearest-neighbor model (Schroeder, et al, Methods Enzymol. 468, 371-387 (2009); Turner, et al Nucleic Acids Res. 38, D280-2 (2010)) or the Zuker algorithm (Zuker, et al Nucleic Acids Res. 9, 133-148 (1981); Zuker, et al Nucleic Acids Res. 31, 3406-3415 (2003); Markham, et al Methods Mol. Biol. 453, 3-31 (2008); Hofacker, et al Nucleic Acids Res. 31, 3429-3431 (2003); Lorenz, Algorithms Mol. Biol. 6, 26 (2011); Matthews, et al Molecular Modeling of Nucleic Acids. Vol. 682 of ACS Symposium Series. 246-257; Reuther, et al BMC Bioinform. 11, 129 (2010)); a machine learning technique such as CONTRAfold (Do, et al Bioinformatics 22, e90-8 (2006); Foo, et al Advances in Neural Information Processing Systems 20, 377-384), ContextFold (Zakov, et al J. Comput. Biol. 18, 1525-1542 (2011)); a probabilistic generative model such as stochastic context-free grammars (Rivas, et al RNA 18, 193-212 (2012)); a hybrid model such as SimFold (Andronescu, et al Bioinformatics 23, i19-28 (2007); Andronescu et al RNA 16, 2304-2318 (2010)) or MXfold (Akiyama, et al J. Bioinform. Comput. Biol. 16, 1840025 (2018)); a deep learning approach such as SPOT-RNA (Singh, et al Nat. Commun. 10, 5407 (2019)) or E2Efold (Chen et al Proceedings of the 8th International Conference on Learning Representations; arXiv:2002.05810 (2020)).

In some embodiments, the one or more RNA secondary structures comprises a single-stranded RNA sequence, a double-stranded RNA sequence, or a combination thereof. In some embodiments, the one or more RNA secondary structure comprises a duplex structure, a stem-loop, a pseudoknot, an internal loop, a multi-branch loop, a bulge loop, an external loop, or a combination thereof. In some embodiments, the snRNA and/or snoRNA sequence or portion thereof comprises a sequence motif that assembles into an RNP. In some embodiments, the sequence motif comprises a single-stranded RNA sequence that assembles into an RNP. In some embodiments, the snRNA and/or snoRNA sequence or portion thereof comprises a sequence motif and one or more RNA secondary structures that assemble into an RNP. In some embodiments, the secondary structure and/or a sequence motif assembles with one or more proteins in a human cell to form an RNP.

In embodiments, the composition or system further comprises In embodiments, the composition or system further comprises a protein that forms an RNP or is within an RNP, with the snRNA or snoRNA, or a nucleic acid encoding the protein that forms, or is within, the RNP. In embodiments, the snRNA, snoRNA, protein that forms an RNP, a protein within the RNP, and/or a nucleic acid encoding the protein that forms or is within the RNP comprises a modification or mutation that attenuates, weakens, reduces, decreases, or ablates RNP activity, and/or leads to attenuation of RNA modifying activity as compared to an unmodified form, the RNP activity optionally being selected from cleavage, nucleic acid processing, pseudouridylation, and/or methylation. In embodiments, the snRNA, snoRNA, protein that forms an RNP, and/or a nucleic acid encoding the protein that forms the RNP or is within RNP comprises a modification or mutation that increases, stimulates, or enhances RNP activity, or enhances RNA modifying activity, the RNP activity optionally being selected from cleavage, nucleic acid processing, pseudouridylation, and/or methylation as compared to an unmodified form. In embodiments, the repRNA comprises at least one or more pseudouridylation sites. In embodiments, the repRNA comprises no pseudouridylation sites. In embodiments, the repRNA is modified to comprise at least 1, 2, 3 4, 5, 6, 7, 8, 9, 10, 11, 12, 13, 14, 15, 16, 17, 18, 19, 20, 21, 22, 23, 24, 25, 26, 27, 28, 29, 30 or more pseudouridylation sites than the number of pseudouridylation sites in (i) an unmodified state of the snRNA or snoRNA or (ii) an exonic sequence.

In some embodiments, the snRNA and/or snoRNA sequence or portion thereof comprises one or more RNA secondary structures. In some embodiments, the snRNA and/or snoRNA sequence or portion thereof comprises one or more sequence motifs. In some embodiments, the snRNA and/or snoRNA sequence or portion thereof comprises one or more RNA secondary structures and one or more sequence motifs. In some embodiments, the sequence motif comprises a sequence selected from Table 1. In some embodiments, the sequence motif comprises an H consensus sequence comprising or consisting of a sequence set forth in Table 1. In some embodiments, the H consensus sequence comprises or consists of ANANNA, where N=A, C, G, or U. In some embodiments, the sequence motif comprises an ACA consensus sequence comprising or consisting of a sequence set forth in Table 1. In some embodiments, the ACA consensus sequence comprises or consists of ACA. In some embodiments, the sequence motif comprises an H/ACA box, wherein the H/ACA box comprises a sequence comprising an H consensus sequence and an ACA consensus sequence, each comprising a sequence set forth in Table 1. In some embodiments, the H/ACA box comprises a sequence comprising ANANNA, where N=A, C, G, or U and ACA. In some embodiments, the sequence motif comprises a C consensus sequence comprising or consisting of a sequence set forth in Table 1. In some embodiments, the C consensus sequence comprises or consists of RUGAUGA, where R=A or G. In some embodiments, the sequence motif comprises a D consensus sequence comprising or consisting of a sequence set forth in Table 1. In some embodiments, the D consensus sequence comprises or consists of SEQ ID NO: 6. In some embodiments, the sequence motif comprises a C/D box, wherein the C/D box comprises a C consensus sequence and a D consensus sequence, each comprising a sequence set forth in Table 1. In some embodiments, the C/D box comprises RUGAUGA, where R=A or G and SEQ ID NO: 6. In some embodiments, the sequence motif comprises an Sm motif comprising a sequence set forth in Table 1. In some embodiments, the Sm motif comprises AAUUUUUGG. In some embodiments, the Sm motif comprises AAUUUGUCU.

TABLE 1

| snRNA and/or snoRNA sequence Motifs | |
| --- | --- |
| Name/Identifier | RNA Sequence |
| H box | ANANNA<br>N = A, C, G, or U |
| ACA box | ACA |
| Sm motif | AAUUUUUGG |
| Sm U7 motif | AAUUUGUCU |
| C box | RUGAUGA<br>R = A or G |
| D box | CUGA |
| C' box | RUGAUGA |
| D' box | CUGA |

In some embodiments, a composition, system, and/or the one or more nucleic acids comprising one or more nucleotide sequences described herein comprises a snRNA and/or snoRNA sequence having at least about 60%, about 65%, about 70%, about 75%, about 80%, about 85%, about 90%, about 91%, about 92%, about 93%, about 94%, about 95%, about 96%, about 97%, about 98%, about 99% identity to a sequence selected from SEQ ID NOs: 9-209, 211-628, 630-632, 634-635, 638, 640, 642, 644-645, 647-648, 650, 652-653, 655, 657, 732-737, 741-746, 748-749, 751-758, 760-761, 763-765, 767, 771-774, 776-778, and 780-789, or portion thereof. In some embodiments, a composition, system, and/or the one or more nucleic acids comprising one or more nucleotide sequences described herein comprises a snRNA and/or snoRNA sequence selected from SEQ ID NOs: 9-209, 211-628, 630-632, 634-635, 638, 640, 642, 644-645, 647-648, 650, 652-653, 655, 657, 732-737, 741-746, 748-749, 751-758, 760-761, 763-765, 767, 771-774, 776-778, and 780-789, or a portion thereof.

In some embodiments, the snRNA and/or snoRNA sequence or portion thereof comprises a contiguous nucleotide sequence of at least about 5, about 6, about 7, about 8, about 9, about 10, about 11, about 12, about 13, about 14, about 15, about 16, about 17, about 18, about 19 or about 20 nucleotides in length, wherein the contiguous nucleotide sequence comprises a Sm sequence motif (e.g., an Sm sequence motif set forth in Table 1).

In some embodiments, the snRNA and/or snoRNA sequence or portion thereof comprises a contiguous nucleotide sequence of about 5 to about 20, about 5 to about 30, about 5 to about 40, about 5 to about 50, about 10 to about 50, about 20 to about 50, about 30 to about 50, or about 40 to about 50 nucleotides in length, wherein the contiguous nucleotide sequence comprises a Sm sequence motif (e.g., an Sm sequence motif set forth in Table 1).

In some embodiments, the snRNA and/or snoRNA sequence or portion thereof comprises a contiguous nucleotide sequence of about 30 to about 100, about 40 to about 100, about 50 to about 100, about 50 to about 150, about 50 to about 200, about 50 to about 250, about 100 to about 150, about 100 to about 200, about 100 to about 250, or about 100 to about 300 nucleotides in length, wherein the contiguous nucleotide sequence comprises a Sm sequence motif (e.g., an Sm sequence motif set forth in Table 1).

In some embodiments, the snRNA and/or snoRNA sequence or portion thereof comprises a contiguous nucleotide sequence of about 30 to about 100, about 40 to about 100, about 50 to about 100, about 50 to about 150, about 50 to about 200, about 50 to about 250, about 100 to about 150, about 100 to about 200, about 100 to about 250, or about 100 to about 300 nucleotides in length, wherein the contiguous nucleotide sequence comprises a (i) H consensus sequence (e.g., a H consensus sequence set forth in Table 1); (ii) ACA consensus sequence (e.g., an ACA consensus sequence set forth in Table 1); or (iii) combination of (i)-(ii).

In some embodiments, the snRNA and/or snoRNA sequence or portion thereof comprises a contiguous nucleotide sequence of about 30 to about 100, about 40 to about 100, about 50 to about 100, about 50 to about 150, about 50 to about 200, about 50 to about 250, about 100 to about 150, about 100 to about 200, about 100 to about 250, or about 100 to about 300 nucleotides in length, wherein the contiguous nucleotide sequence comprises a (i) C-box motif described herein (e.g., a C-box motif set forth in Table 1), (ii) C'-box motif described herein (e.g., a C'-box motif set forth in Table 1), (iii) D-box motif described herein (e.g., a D-box motif set forth in Table 1), (iv) a D'-box motif described herein (e.g., a D'-box motif set forth in Table 1), or (v) a combination of (i)-(iv).

In some embodiments, the snRNA and/or snoRNA sequence or portion thereof comprises a nucleotide sequence having at least about 60%, about 65%, about 70%, about 75%, about 80%, about 85%, about 90%, about 91%, about 92%, about 93%, about 94%, about 95%, about 96%, about 97%, about 98%, about 99% identity to a sequence selected from SEQ ID NOs: 9-209, 211-628, 630-632, 634-635, 638, 640, 642, 644-645, 647-648, 650, 652-653, 655, 657, 732-737, 741-746, 748-749, 751-758, 760-761, 763-765, 767, 771-774, 776-778, and 780-789, wherein the nucleotide sequence comprises a region of at least about 5, about 6, about 7, about 8, about 9, about 10, about 11, about 12, about 13, about 14, about 15, about 16, about 17, about 18, about 19 or about 20 nucleotides in length, wherein the region comprises one or more Sm sequence motifs (e.g., one or more Sm sequence motifs set forth in Table 1).

In some embodiments, the snRNA and/or snoRNA sequence or portion thereof comprises a nucleotide sequence having at least about 60%, about 65%, about 70%, about 75%, about 80%, about 85%, about 90%, about 91%, about 92%, about 93%, about 94%, about 95%, about 96%, about 97%, about 98%, about 99% identity to a sequence selected from SEQ ID NOs: 9-209, 211-628, 630-632, 634-635, 638, 640, 642, 644-645, 647-648, 650, 652-653, 655, 657, 732-737, 741-746, 748-749, 751-758, 760-761, 763-765, 767, 771-774, 776-778, and 780-789, wherein the nucleotide sequence comprises a region of at least about 5 to about 20, about 5 to about 30, about 5 to about 40, about 5 to about 50, about 10 to about 50, about 20 to about 50, about 30 to about 50, or about 40 to about 50 nucleotides in length, wherein the region comprises one or more Sm sequence motifs (e.g., one or more Sm sequence motifs set forth in Table 1).

In some embodiments, the snRNA and/or snoRNA sequence or portion thereof comprises a nucleotide sequence having at least about 60%, about 65%, about 70%, about 75%, about 80%, about 85%, about 90%, about 91%, about 92%, about 93%, about 94%, about 95%, about 96%, about 97%, about 98%, about 99% identity to a sequence selected from SEQ ID NOs: 9-209, 211-628, 630-632, 634-635, 638, 640, 642, 644-645, 647-648, 650, 652-653, 655, 657, 732-737, 741-746, 748-749, 751-758, 760-761, 763-765, 767, 771-774, 776-778, and 780-789, wherein the nucleotide sequence comprises a region of at least about 30 to about 100, about 40 to about 100, about 50 to about 100, about 50 to about 150, about 50 to about 200, about 50 to about 250, about 100 to about 150, about 100 to about 200, about 100 to about 250, or about 100 to about 300 nucleotides in length, wherein the region comprises one or more Sm sequence motifs (e.g., one or more Sm sequence motifs set forth in Table 1).

In some embodiments, the snRNA and/or snoRNA sequence or portion thereof comprises a nucleotide sequence having at least about 60%, about 65%, about 70%, about 75%, about 80%, about 85%, about 90%, about 91%, about 92%, about 93%, about 94%, about 95%, about 96%, about 97%, about 98%, about 99% identity to a sequence selected from SEQ ID NOs: 9-209, 211-628, 630-632, 634-635, 638, 640, 642, 644-645, 647-648, 650, 652-653, 655, 657, 732-737, 741-746, 748-749, 751-758, 760-761, 763-765, 767, 771-774, 776-778, and 780-789, wherein the nucleotide sequence comprises a region of at least about 30 to about 100, about 40 to about 100, about 50 to about 100, about 50 to about 150, about 50 to about 200, about 50 to about 250, about 100 to about 150, about 100 to about 200, about 100 to about 250, or about 100 to about 300 nucleotides in length, wherein the region comprises (i) an H consensus sequence (e.g., an H consensus sequence set forth in Table 1); (ii) an ACA consensus sequence (e.g., an ACA consensus sequence set forth in Table 1); or (iii) a combination of (i)-(ii).

In some embodiments, the snRNA and/or snoRNA sequence or portion thereof comprises a nucleotide sequence having at least about 60%, about 65%, about 70%, about 75%, about 80%, about 85%, about 90%, about 91%, about 92%, about 93%, about 94%, about 95%, about 96%, about 97%, about 98%, about 99% identity to a sequence selected from SEQ ID NOs: 9-209, 211-628, 630-632, 634-635, 638, 640, 642, 644-645, 647-648, 650, 652-653, 655, 657, 732-737, 741-746, 748-749, 751-758, 760-761, 763-765, 767, 771-774, 776-778, and 780-789, wherein the nucleotide sequence comprises a region of at least about 30 to about 100, about 40 to about 100, about 50 to about 100, about 50 to about 150, about 50 to about 200, about 50 to about 250, about 100 to about 150, about 100 to about 200, about 100 to about 300 nucleotides in length, (i) a C-box motif described herein (e.g., a C-box motif set forth in Table 1), (ii) a C'-box motif described herein (e.g., a C'-box motif set forth in Table 1), (iii) a D-box motif described herein (e.g., a D-box motif set forth in Table 1), (iv) a D'-box motif described herein (e.g., a D'-box motif set forth in Table 1), or (v) a combination of (i)-(iv).

In some embodiments, a composition, system, and/or the one or more nucleic acids comprising one or more nucleotide sequences described herein comprises a full-length snRNA or portion thereof comprising a nucleotide sequence comprising one or more sequence motifs described herein (e.g., one or more sequence motifs set forth in Table 1). In some embodiments, an snRNA sequence described herein or identified according to a method described herein is incorporated into a composition, system, and/or the one or more nucleic acids comprising one or more nucleotide sequences described herein. In some embodiments, a full-length snRNA sequence described herein or identified according to a method described herein is incorporated into a composition, system, and/or the one or more nucleic acids comprising one or more nucleotide sequences described herein. In some embodiments, a portion of a snRNA sequence described herein or identified according to a method described herein (e.g., a region of contiguous nucleotides in the snRNA) is incorporated into a composition, system, and/or the one or more nucleic acids comprising one or more nucleotide sequences described herein. In some embodiments, the full-length snRNA or portion of the snRNA assembles into a small nuclear RNP (snRNP). In some embodiments, the full-length snRNA or the portion of the snRNA comprises one or more secondary RNA structures that assembles to form an snRNP. In some embodiments, the full-length snRNA or the portion of the snRNA comprises one or more sequence motifs that assembles to form an snRNP. In some embodiments, the full-length snRNA or the portion of the snRNA comprises (i) one or more one or more secondary RNA structures, and (ii) one or more sequence motifs, wherein (i), (ii), or both assemble to form an snRNP.

Exemplary metazoan snRNA systems include U1 and U11 snRNAs, which are snRNAs that guide spliceosome RNPs to splice sites (Black, et al (1985) Cell 42:737-750; Kolossova, et al (1997) RNA 3:227). Other snRNAs include U2, U4, U4atac, U5, U6, U6atac, and U12, which also form RNPs in the major and minor spliceosome (Turunen, et al (2013) RNA 4:61-76; Nguyen, et al (2015), Nature 523:47-52; Charenton, et al (2019) Science 364:362-367). U7 RNAs are responsible for histone pre-mRNA cleavage and poly-adenylation (Strub, et al (1984) EMBO journal 3:2801-2807; Soldati, et al (1988), Molecular and Cellular Biology 8:1518-1524; Cotton, et al (1988) The EMBO Journal 7:801-808).

In some embodiments, a composition, system, and/or the one or more nucleic acids comprising one or more nucleotide sequences described herein comprises a full-length snRNA or portion thereof comprising a nucleotide sequence comprising one or more sequence motifs described herein (e.g., one or more sequence motifs set forth in Table 1), and wherein the snRNA is selected from RNU1-1, RNU1-100P, RNU1-101P, RNU1-103P, RNU1-104P, RNU1-105P, RNU1-107P, RNU1-108P, RNU1-109P, RNU1-112P, RNU1-114P, RNU1-115P, RNU1-116P, RNU1-117P, RNU1-119P, RNU1-11P, RNU1-123P, RNU1-124P, RNU1-125P, RNU1-128P, RNU1-129P, RNU1-130P, RNU1-131P, RNU1-132P, RNU1-133P, RNU1-134P, RNU1-136P, RNU1-138P, RNU1-139P, RNU1-140P, RNU1-141P, RNU1-142P, RNU1-143P, RNU1-146P, RNU1-148P, RNU1-149P, RNU1-14P, RNU1-150P, RNU1-151P, RNU1-153P, RNU1-154P, RNU1-155P, RNU1-15P, RNU1-16P, RNU1-17P, RNU1-18P, RNU1-19P, RNU1-2, RNU1-20P, RNU1-21P, RNU1-22P, RNU1-23P, RNU1-24P, RNU1-27P, RNU1-28P, RNU1-29P, RNU1-3, RNU1-30P, RNU1-31P, RNU1-32P, RNU1-33P, RNU1-34P, RNU1-35P, RNU1-36P, RNU1-38P, RNU1-39P, RNU1-4, RNU1-40P, RNU1-41P, RNU1-42P, RNU1-43P, RNU1-44P, RNU1-45P, RNU1-46P, RNU1-47P, RNU1-48P, RNU1-49P, RNU1-51P, RNU1-52P, RNU1-54P, RNU1-55P, RNU1-56P, RNU1-57P, RNU1-58P, RNU1-5P, RNU1-61P, RNU1-62P, RNU1-63P, RNU1-64P, RNU1-65P, RNU1-67P, RNU1-68P, RNU1-6P, RNU1-70P, RNU1-72P, RNU1-73P, RNU1-74P, RNU1-75P, RNU1-76P, RNU1-77P, RNU1-78P, RNU1-79P, RNU1-7P, RNU1-80P, RNU1-82P, RNU1-83P, RNU1-84P, RNU1-86P, RNU1-88P, RNU1-89P, RNU1-8P, RNU1-91P, RNU1-93P, RNU1-94P, RNU1-95P, RNU1-96P, RNU1-97P, RNU1-98P, RNU11, RNU11-2P, RNU11-3P, RNU11-4P, RNU11-5P, RNU11-6P, RNU12, RNU12-2P, RNU2-12P, RNU2-13P, RNU2-16P, RNU2-18P, RNU2-19P, RNU2-24P, RNU2-27P, RNU2-30P, RNU2-31P, RNU2-34P, RNU2-35P, RNU2-37P, RNU2-38P, RNU2-41P, RNU2-42P, RNU2-46P, RNU2-50P, RNU2-53P, RNU2-55P, RNU2-60P, RNU2-66P, RNU2-69P, RNU2-70P, RNU2-72P, RNU2-7P, RNU2-9P, RNU4-1, RNU4-10P, RNU4-11P, RNU4-12P, RNU4-13P, RNU4-14P, RNU4-15P, RNU4-16P, RNU4-17P, RNU4-18P, RNU4-2, RNU4-20P, RNU4-21P, RNU4-22P, RNU4-23P, RNU4-24P, RNU4-26P, RNU4-27P, RNU4-28P, RNU4-29P, RNU4-30P, RNU4-31P, RNU4-32P, RNU4-33P, RNU4-34P, RNU4-35P, RNU4-36P, RNU4-37P, RNU4-38P, RNU4-39P, RNU4-40P, RNU4-41P, RNU4-42P, RNU4-43P, RNU4-44P, RNU4-45P, RNU4-46P, RNU4-47P, RNU4-49P, RNU4-4P, RNU4-50P, RNU4-51P, RNU4-52P, RNU4-53P, RNU4-54P, RNU4-55P, RNU4-56P, RNU4-57P, RNU4-58P, RNU4-59P, RNU4-5P, RNU4-60P, RNU4-61P, RNU4-62P, RNU4-63P, RNU4-64P, RNU4-65P, RNU4-66P, RNU4-67P, RNU4-68P, RNU4-69P, RNU4-6P, RNU4-70P, RNU4-71P, RNU4-72P, RNU4-73P, RNU4-74P, RNU4-75P, RNU4-76P, RNU4-77P, RNU4-78P, RNU4-79P, RNU4-7P, RNU4-80P, RNU4-81P, RNU4-82P, RNU4-83P, RNU4-84P, RNU4-85P, RNU4-87P, RNU4-88P, RNU4-89P, RNU4-8P, RNU4-90P, RNU4-91P, RNU4-92P, RNU4-9P, RNU4ATAC, RNU4ATAC10P, RNU4ATAC11P, RNU4ATAC12P, RNU4ATAC13P, RNU4ATAC14P, RNU4ATAC15P, RNU4ATAC16P, RNU4ATAC17P, RNU4ATAC18P, RNU4ATAC2P, RNU4ATAC3P, RNU4ATAC4P, RNU4ATAC5P, RNU4ATAC6P, RNU4ATAC7P, RNU4ATAC8P, RNU4ATAC9P, RNU5A-1, RNU5A-2P, RNU5A-3P, RNU5A-4P, RNU5A-5P, RNU5A-6P, RNU5A-7P, RNU5A-8P, RNU5B-1, RNU5B-2P, RNU5B-3P, RNU5B-4P, RNU5B-6P, RNU5D-1, RNU5D-2P, RNU5E-1, RNU5E-10P, RNU5E-3P, RNU5E-4P, RNU5E-5P, RNU5E-6P, RNU5E-7P, RNU5E-8P, RNU5E-9P, RNU5F-1, RNU5F-2P, RNU5F-3P, RNU5F-4P, RNU5F-6P, RNU5F-7P, RNU5F-8P, RNU6-1, RNU6-1000P, RNU6-1001P, RNU6-1003P, RNU6-1004P, RNU6-1005P, RNU6-1006P, RNU6-1007P, RNU6-1008P, RNU6-1009P, RNU6-100P, RNU6-1010P, RNU6-1011P, RNU6-1012P, RNU6-1013P, RNU6-1014P, RNU6-1015P, RNU6-1016P, RNU6-1017P, RNU6-1018P, RNU6-1019P, RNU6-101P, RNU6-1020P, RNU6-1021P, RNU6-1022P, RNU6-1023P, RNU6-1024P, RNU6-1025P, RNU6-1026P, RNU6-1027P, RNU6-1028P, RNU6-1029P, RNU6-102P, RNU6-1031P, RNU6-1032P, RNU6-1034P, RNU6-1035P, RNU6-1036P, RNU6-1037P, RNU6-1038P, RNU6-1039P, RNU6-103P, RNU6-1040P, RNU6-1041P, RNU6-1042P, RNU6-1043P, RNU6-1044P, RNU6-1045P, RNU6-1046P, RNU6-1047P, RNU6-1048P, RNU6-1049P, RNU6-104P, RNU6-1050P, RNU6-1051P, RNU6-1052P, RNU6-1053P, RNU6-1054P, RNU6-1055P, RNU6-1056P, RNU6-1057P, RNU6-1059P, RNU6-105P, RNU6-1060P, RNU6-1061P, RNU6-1062P, RNU6-1064P, RNU6-1065P, RNU6-1066P, RNU6-1067P, RNU6-1068P, RNU6-1069P, RNU6-106P, RNU6-1071P, RNU6-1072P, RNU6-1073P, RNU6-1074P, RNU6-1075P, RNU6-1076P, RNU6-1077P, RNU6-1078P, RNU6-

1079P, RNU6-107P, RNU6-1080P, RNU6-1081P, RNU6-1082P, RNU6-1083P, RNU6-1084P, RNU6-1085P, RNU6-1086P, RNU6-1087P, RNU6-1088P, RNU6-1089P, RNU6-108P, RNU6-1090P, RNU6-1091P, RNU6-1092P, RNU6-1093P, RNU6-1094P, RNU6-1095P, RNU6-1096P, RNU6-1097P, RNU6-1098P, RNU6-1099P, RNU6-109P, RNU6-10P, RNU6-1100P, RNU6-1101P, RNU6-1102P, RNU6-1103P, RNU6-1104P, RNU6-1105P, RNU6-1106P, RNU6-1107P, RNU6-1108P, RNU6-1109P, RNU6-110P, RNU6-1110P, RNU6-1111P, RNU6-1112P, RNU6-1113P, RNU6-1114P, RNU6-1115P, RNU6-1116P, RNU6-1117P, RNU6-1118P, RNU6-1119P, RNU6-111P, RNU6-1120P, RNU6-1121P, RNU6-1122P, RNU6-1123P, RNU6-1124P, RNU6-1125P, RNU6-1126P, RNU6-1127P, RNU6-1128P, RNU6-1129P, RNU6-112P, RNU6-1130P, RNU6-1131P, RNU6-1132P, RNU6-1133P, RNU6-1134P, RNU6-1135P, RNU6-1136P, RNU6-1137P, RNU6-1138P, RNU6-113P, RNU6-1140P, RNU6-1141P, RNU6-1143P, RNU6-1144P, RNU6-1145P, RNU6-1146P, RNU6-1147P, RNU6-1148P, RNU6-1149P, RNU6-114P, RNU6-1150P, RNU6-1151P, RNU6-1152P, RNU6-1153P, RNU6-1154P, RNU6-1155P, RNU6-1156P, RNU6-1157P, RNU6-1158P, RNU6-1159P, RNU6-115P, RNU6-1160P, RNU6-1161P, RNU6-1162P, RNU6-1163P, RNU6-1164P, RNU6-1165P, RNU6-1167P, RNU6-1168P, RNU6-1169P, RNU6-116P, RNU6-1170P, RNU6-1171P, RNU6-1172P, RNU6-1174P, RNU6-1175P, RNU6-1176P, RNU6-1177P, RNU6-1178P, RNU6-1179P, RNU6-117P, RNU6-1180P, RNU6-1181P, RNU6-1183P, RNU6-1184P, RNU6-1186P, RNU6-1187P, RNU6-1188P, RNU6-1189P, RNU6-118P, RNU6-1190P, RNU6-1191P, RNU6-1192P, RNU6-1193P, RNU6-1194P, RNU6-1195P, RNU6-1196P, RNU6-1197P, RNU6-1198P, RNU6-1199P, RNU6-119P, RNU6-11P, RNU6-1200P, RNU6-1201P, RNU6-1203P, RNU6-1204P, RNU6-1205P, RNU6-1206P, RNU6-1207P, RNU6-1208P, RNU6-1209P, RNU6-120P, RNU6-1210P, RNU6-1211P, RNU6-1212P, RNU6-1213P, RNU6-1214P, RNU6-1215P, RNU6-1216P, RNU6-1217P, RNU6-1218P, RNU6-1219P, RNU6-121P, RNU6-1220P, RNU6-1222P, RNU6-1223P, RNU6-1224P, RNU6-1225P, RNU6-1226P, RNU6-1227P, RNU6-1228P, RNU6-1229P, RNU6-122P, RNU6-1230P, RNU6-1231P, RNU6-1232P, RNU6-1233P, RNU6-1234P, RNU6-1235P, RNU6-1236P, RNU6-1237P, RNU6-1238P, RNU6-1239P, RNU6-123P, RNU6-1240P, RNU6-1241P, RNU6-1242P, RNU6-1243P, RNU6-1244P, RNU6-1245P, RNU6-1246P, RNU6-1247P, RNU6-1248P, RNU6-1249P, RNU6-1250P, RNU6-1251P, RNU6-1252P, RNU6-1254P, RNU6-1255P, RNU6-1256P, RNU6-1257P, RNU6-1258P, RNU6-125P, RNU6-1260P, RNU6-1261P, RNU6-1262P, RNU6-1263P, RNU6-1264P, RNU6-1265P, RNU6-1266P, RNU6-1267P, RNU6-1268P, RNU6-1269P, RNU6-126P, RNU6-1270P, RNU6-1271P, RNU6-1272P, RNU6-1273P, RNU6-1274P, RNU6-1275P, RNU6-1276P, RNU6-1277P, RNU6-1278P, RNU6-1279P, RNU6-127P, RNU6-1280P, RNU6-1281P, RNU6-1282P, RNU6-1283P, RNU6-1284P, RNU6-1285P, RNU6-1286P, RNU6-1287P, RNU6-1288P, RNU6-1289P, RNU6-128P, RNU6-1290P, RNU6-1291P, RNU6-1292P, RNU6-1293P, RNU6-1294P, RNU6-1296P, RNU6-1297P, RNU6-1298P, RNU6-1299P, RNU6-129P, RNU6-12P, RNU6-1300P, RNU6-1301P, RNU6-1303P, RNU6-1304P, RNU6-1305P, RNU6-1306P, RNU6-1307P, RNU6-1308P, RNU6-1309P, RNU6-130P, RNU6-1310P, RNU6-1311P, RNU6-1312P, RNU6-1313P, RNU6-1314P, RNU6-1315P, RNU6-1316P, RNU6-1317P, RNU6-1318P, RNU6-1319P, RNU6-131P, RNU6-1320P, RNU6-1321P, RNU6-1322P, RNU6-1323P, RNU6-1324P, RNU6-1325P, RNU6-1326P, RNU6-1327P, RNU6-1328P, RNU6-1329P, RNU6-132P, RNU6-1330P, RNU6-

1331P, RNU6-1332P, RNU6-1333P, RNU6-1334P, RNU6-1335P, RNU6-1336P, RNU6-1337P, RNU6-1338P, RNU6-1339P, RNU6-133P, RNU6-1340P, RNU6-135P, RNU6-136P, RNU6-137P, RNU6-138P, RNU6-139P, RNU6-13P, RNU6-140P, RNU6-141P, RNU6-142P, RNU6-143P, RNU6-144P, RNU6-145P, RNU6-146P, RNU6-147P, RNU6-148P, RNU6-14P, RNU6-150P, RNU6-151P, RNU6-152P, RNU6-153P, RNU6-154P, RNU6-155P, RNU6-156P, RNU6-157P, RNU6-158P, RNU6-159P, RNU6-15P, RNU6-160P, RNU6-161P, RNU6-162P, RNU6-163P, RNU6-164P, RNU6-165P, RNU6-166P, RNU6-167P, RNU6-168P, RNU6-169P, RNU6-16P, RNU6-170P, RNU6-171P, RNU6-172P, RNU6-173P, RNU6-174P, RNU6-175P, RNU6-176P, RNU6-177P, RNU6-178P, RNU6-179P, RNU6-17P, RNU6-180P, RNU6-181P, RNU6-182P, RNU6-183P, RNU6-184P, RNU6-185P, RNU6-187P, RNU6-188P, RNU6-189P, RNU6-18P, RNU6-190P, RNU6-191P, RNU6-192P, RNU6-193P, RNU6-194P, RNU6-195P, RNU6-196P, RNU6-197P, RNU6-198P, RNU6-199P, RNU6-19P, RNU6-2, RNU6-200P, RNU6-201P, RNU6-202P, RNU6-203P, RNU6-204P, RNU6-205P, RNU6-206P, RNU6-207P, RNU6-208P, RNU6-209P, RNU6-20P, RNU6-210P, RNU6-211P, RNU6-212P, RNU6-213P, RNU6-214P, RNU6-215P, RNU6-216P, RNU6-217P, RNU6-218P, RNU6-219P, RNU6-21P, RNU6-220P, RNU6-221P, RNU6-222P, RNU6-223P, RNU6-224P, RNU6-225P, RNU6-226P, RNU6-227P, RNU6-228P, RNU6-229P, RNU6-22P, RNU6-230P, RNU6-231P, RNU6-232P, RNU6-233P, RNU6-234P, RNU6-235P, RNU6-236P, RNU6-237P, RNU6-238P, RNU6-239P, RNU6-23P, RNU6-240P, RNU6-241P, RNU6-242P, RNU6-243P, RNU6-244P, RNU6-245P, RNU6-246P, RNU6-247P, RNU6-248P, RNU6-249P, RNU6-24P, RNU6-250P, RNU6-251P, RNU6-252P, RNU6-253P, RNU6-254P, RNU6-255P, RNU6-256P, RNU6-257P, RNU6-258P, RNU6-259P, RNU6-25P, RNU6-260P, RNU6-261P, RNU6-262P, RNU6-263P, RNU6-264P, RNU6-266P, RNU6-267P, RNU6-268P, RNU6-269P, RNU6-26P, RNU6-270P, RNU6-271P, RNU6-272P, RNU6-273P, RNU6-274P, RNU6-275P, RNU6-276P, RNU6-277P, RNU6-278P, RNU6-279P, RNU6-27P, RNU6-280P, RNU6-281P, RNU6-282P, RNU6-283P, RNU6-284P, RNU6-285P, RNU6-286P, RNU6-287P, RNU6-288P, RNU6-289P, RNU6-28P, RNU6-290P, RNU6-291P, RNU6-293P, RNU6-294P, RNU6-295P, RNU6-296P, RNU6-297P, RNU6-298P, RNU6-299P, RNU6-29P, RNU6-300P, RNU6-301P, RNU6-302P, RNU6-303P, RNU6-304P, RNU6-306P, RNU6-307P, RNU6-308P, RNU6-309P, RNU6-30P, RNU6-310P, RNU6-311P, RNU6-312P, RNU6-313P, RNU6-314P, RNU6-315P, RNU6-316P, RNU6-317P, RNU6-318P, RNU6-319P, RNU6-31P, RNU6-320P, RNU6-321P, RNU6-322P, RNU6-323P, RNU6-324P, RNU6-325P, RNU6-326P, RNU6-327P, RNU6-328P, RNU6-329P, RNU6-32P, RNU6-330P, RNU6-331P, RNU6-332P, RNU6-333P, RNU6-334P, RNU6-335P, RNU6-336P, RNU6-337P, RNU6-338P, RNU6-339P, RNU6-33P, RNU6-340P, RNU6-341P, RNU6-342P, RNU6-343P, RNU6-344P, RNU6-345P, RNU6-346P, RNU6-347P, RNU6-348P, RNU6-349P, RNU6-34P, RNU6-351P, RNU6-352P, RNU6-353P, RNU6-354P, RNU6-355P, RNU6-356P, RNU6-358P, RNU6-359P, RNU6-35P, RNU6-360P, RNU6-361P, RNU6-362P, RNU6-363P, RNU6-364P, RNU6-365P, RNU6-366P, RNU6-367P, RNU6-368P, RNU6-369P, RNU6-36P, RNU6-370P, RNU6-371P, RNU6-373P, RNU6-374P, RNU6-375P, RNU6-376P, RNU6-377P, RNU6-378P, RNU6-379P, RNU6-37P, RNU6-380P, RNU6-381P, RNU6-382P, RNU6-383P, RNU6-384P, RNU6-386P, RNU6-387P, RNU6-388P, RNU6-389P, RNU6-38P, RNU6-390P, RNU6-391P, RNU6-392P, RNU6-393P, RNU6-394P, RNU6-395P, RNU6-396P, RNU6-397P, RNU6-398P, RNU6-399P, RNU6-39P, RNU6-3P, RNU6-400P, RNU6-401P, RNU6-402P, RNU6-403P, RNU6-405P, RNU6-406P, RNU6-407P, RNU6-408P, RNU6-409P, RNU6-40P, RNU6-410P, RNU6-411P, RNU6-412P, RNU6-413P, RNU6-414P, RNU6-415P, RNU6-416P, RNU6-417P, RNU6-418P, RNU6-419P, RNU6-41P, RNU6-420P, RNU6-421P, RNU6-422P, RNU6-424P, RNU6-425P, RNU6-426P, RNU6-428P, RNU6-429P, RNU6-42P, RNU6-430P, RNU6-431P, RNU6-432P, RNU6-433P, RNU6-434P, RNU6-435P, RNU6-436P, RNU6-437P, RNU6-438P, RNU6-439P, RNU6-43P, RNU6-440P, RNU6-441P, RNU6-442P, RNU6-444P, RNU6-445P, RNU6-446P, RNU6-447P, RNU6-448P, RNU6-449P, RNU6-44P, RNU6-450P, RNU6-451P, RNU6-452P, RNU6-453P, RNU6-454P, RNU6-455P, RNU6-456P, RNU6-457P, RNU6-458P, RNU6-45P, RNU6-460P, RNU6-461P, RNU6-462P, RNU6-463P, RNU6-464P, RNU6-465P, RNU6-466P, RNU6-467P, RNU6-468P, RNU6-469P, RNU6-46P, RNU6-470P, RNU6-471P, RNU6-472P, RNU6-473P, RNU6-474P, RNU6-475P, RNU6-476P, RNU6-477P, RNU6-478P, RNU6-479P, RNU6-47P, RNU6-480P, RNU6-481P, RNU6-482P, RNU6-483P, RNU6-484P, RNU6-485P, RNU6-486P, RNU6-487P, RNU6-488P, RNU6-489P, RNU6-48P, RNU6-490P, RNU6-491P, RNU6-492P, RNU6-493P, RNU6-494P, RNU6-495P, RNU6-496P, RNU6-497P, RNU6-498P, RNU6-499P, RNU6-49P, RNU6-4P, RNU6-500P, RNU6-501P, RNU6-502P, RNU6-503P, RNU6-504P, RNU6-505P, RNU6-506P, RNU6-507P, RNU6-508P, RNU6-509P, RNU6-50P, RNU6-510P, RNU6-511P, RNU6-512P, RNU6-513P, RNU6-514P, RNU6-516P, RNU6-517P, RNU6-518P, RNU6-519P, RNU6-520P, RNU6-521P, RNU6-522P, RNU6-523P, RNU6-524P, RNU6-525P, RNU6-526P, RNU6-527P, RNU6-528P, RNU6-529P, RNU6-530P, RNU6-531P, RNU6-532P, RNU6-533P, RNU6-534P, RNU6-535P, RNU6-536P, RNU6-537P, RNU6-538P, RNU6-539P, RNU6-53P, RNU6-540P, RNU6-541P, RNU6-542P, RNU6-543P, RNU6-544P, RNU6-545P, RNU6-546P, RNU6-547P, RNU6-548P, RNU6-549P, RNU6-54P, RNU6-550P, RNU6-551P, RNU6-552P, RNU6-553P, RNU6-554P, RNU6-555P, RNU6-556P, RNU6-557P, RNU6-558P, RNU6-559P, RNU6-55P, RNU6-560P, RNU6-561P, RNU6-562P, RNU6-563P, RNU6-564P, RNU6-565P, RNU6-566P, RNU6-567P, RNU6-56P, RNU6-570P, RNU6-571P, RNU6-572P, RNU6-573P, RNU6-574P, RNU6-575P, RNU6-576P, RNU6-577P, RNU6-578P, RNU6-579P, RNU6-57P, RNU6-580P, RNU6-581P, RNU6-582P, RNU6-583P, RNU6-584P, RNU6-586P, RNU6-587P, RNU6-588P, RNU6-589P, RNU6-58P, RNU6-590P, RNU6-591P, RNU6-592P, RNU6-593P, RNU6-595P, RNU6-596P, RNU6-597P, RNU6-598P, RNU6-599P, RNU6-59P, RNU6-5P, RNU6-600P, RNU6-601P, RNU6-602P, RNU6-603P, RNU6-604P, RNU6-605P, RNU6-606P, RNU6-607P, RNU6-608P, RNU6-609P, RNU6-60P, RNU6-610P, RNU6-611P, RNU6-612P, RNU6-613P, RNU6-614P, RNU6-615P, RNU6-616P, RNU6-617P, RNU6-618P, RNU6-619P, RNU6-61P, RNU6-620P, RNU6-621P, RNU6-622P, RNU6-623P, RNU6-624P, RNU6-625P, RNU6-626P, RNU6-627P, RNU6-628P, RNU6-629P, RNU6-62P, RNU6-630P, RNU6-631P, RNU6-632P, RNU6-633P, RNU6-634P, RNU6-635P, RNU6-636P, RNU6-637P, RNU6-638P, RNU6-639P, RNU6-63P, RNU6-640P, RNU6-641P, RNU6-642P, RNU6-643P, RNU6-644P, RNU6-645P, RNU6-646P, RNU6-647P, RNU6-648P, RNU6-649P, RNU6-64P, RNU6-650P, RNU6-651P, RNU6-652P, RNU6-653P, RNU6-654P, RNU6-655P, RNU6-656P, RNU6-657P, RNU6-658P, RNU6-659P, RNU6-65P, RNU6-660P, RNU6-661P, RNU6-662P, RNU6-663P, RNU6-664P, RNU6-665P, RNU6-666P, RNU6-667P, RNU6-668P, RNU6-669P, RNU6-66P, RNU6-670P, RNU6-672P, RNU6-673P, RNU6-674P, RNU6-675P,

RNU6-677P, RNU6-678P, RNU6-679P, RNU6-67P, RNU6-680P, RNU6-681P, RNU6-682P, RNU6-684P, RNU6-685P, RNU6-686P, RNU6-687P, RNU6-689P, RNU6-68P, RNU6-690P, RNU6-692P, RNU6-693P, RNU6-694P, RNU6-695P, RNU6-696P, RNU6-697P, RNU6-698P, RNU6-699P, RNU6-6P, RNU6-7, RNU6-700P, RNU6-701P, RNU6-702P, RNU6-703P, RNU6-704P, RNU6-705P, RNU6-706P, RNU6-707P, RNU6-708P, RNU6-709P, RNU6-70P, RNU6-710P, RNU6-711P, RNU6-712P, RNU6-713P, RNU6-714P, RNU6-715P, RNU6-716P, RNU6-717P, RNU6-718P, RNU6-719P, RNU6-71P, RNU6-720P, RNU6-721P, RNU6-722P, RNU6-723P, RNU6-724P, RNU6-725P, RNU6-726P, RNU6-727P, RNU6-728P, RNU6-729P, RNU6-72P, RNU6-730P, RNU6-731P, RNU6-732P, RNU6-733P, RNU6-735P, RNU6-737P, RNU6-738P, RNU6-739P, RNU6-73P, RNU6-740P, RNU6-741P, RNU6-742P, RNU6-743P, RNU6-744P, RNU6-745P, RNU6-746P, RNU6-747P, RNU6-748P, RNU6-749P, RNU6-74P, RNU6-750P, RNU6-751P, RNU6-752P, RNU6-753P, RNU6-754P, RNU6-755P, RNU6-756P, RNU6-757P, RNU6-758P, RNU6-759P, RNU6-75P, RNU6-760P, RNU6-761P, RNU6-762P, RNU6-763P, RNU6-764P, RNU6-765P, RNU6-766P, RNU6-767P, RNU6-768P, RNU6-769P, RNU6-76P, RNU6-770P, RNU6-771P, RNU6-772P, RNU6-774P, RNU6-775P, RNU6-776P, RNU6-777P, RNU6-778P, RNU6-77P, RNU6-780P, RNU6-781P, RNU6-782P, RNU6-783P, RNU6-784P, RNU6-785P, RNU6-786P, RNU6-787P, RNU6-788P, RNU6-789P, RNU6-78P, RNU6-790P, RNU6-791P, RNU6-792P, RNU6-793P, RNU6-794P, RNU6-795P, RNU6-796P, RNU6-797P, RNU6-798P, RNU6-799P, RNU6-79P, RNU6-8, RNU6-800P, RNU6-801P, RNU6-803P, RNU6-804P, RNU6-805P, RNU6-806P, RNU6-807P, RNU6-808P, RNU6-809P, RNU6-80P, RNU6-810P, RNU6-811P, RNU6-812P, RNU6-813P, RNU6-815P, RNU6-816P, RNU6-817P, RNU6-818P, RNU6-819P, RNU6-81P, RNU6-820P, RNU6-821P, RNU6-822P, RNU6-823P, RNU6-824P, RNU6-826P, RNU6-827P, RNU6-828P, RNU6-829P, RNU6-82P, RNU6-830P, RNU6-831P, RNU6-832P, RNU6-833P, RNU6-834P, RNU6-835P, RNU6-836P, RNU6-837P, RNU6-838P, RNU6-839P, RNU6-83P, RNU6-840P, RNU6-841P, RNU6-842P, RNU6-843P, RNU6-844P, RNU6-845P, RNU6-847P, RNU6-848P, RNU6-849P, RNU6-84P, RNU6-850P, RNU6-851P, RNU6-853P, RNU6-854P, RNU6-855P, RNU6-856P, RNU6-857P, RNU6-858P, RNU6-859P, RNU6-85P, RNU6-860P, RNU6-861P, RNU6-862P, RNU6-863P, RNU6-864P, RNU6-865P, RNU6-866P, RNU6-867P, RNU6-869P, RNU6-86P, RNU6-871P, RNU6-873P, RNU6-874P, RNU6-875P, RNU6-876P, RNU6-877P, RNU6-878P, RNU6-879P, RNU6-87P, RNU6-880P, RNU6-881P, RNU6-882P, RNU6-883P, RNU6-884P, RNU6-885P, RNU6-886P, RNU6-887P, RNU6-888P, RNU6-889P, RNU6-88P, RNU6-890P, RNU6-891P, RNU6-892P, RNU6-893P, RNU6-894P, RNU6-895P, RNU6-896P, RNU6-897P, RNU6-898P, RNU6-899P, RNU6-89P, RNU6-9, RNU6-900P, RNU6-901P, RNU6-902P, RNU6-903P, RNU6-904P, RNU6-905P, RNU6-906P, RNU6-907P, RNU6-908P, RNU6-909P, RNU6-90P, RNU6-910P, RNU6-911P, RNU6-912P, RNU6-913P, RNU6-914P, RNU6-915P, RNU6-916P, RNU6-917P, RNU6-918P, RNU6-919P, RNU6-91P, RNU6-920P, RNU6-921P, RNU6-922P, RNU6-923P, RNU6-924P, RNU6-925P, RNU6-926P, RNU6-927P, RNU6-928P, RNU6-929P, RNU6-92P, RNU6-930P, RNU6-931P, RNU6-932P, RNU6-933P, RNU6-934P, RNU6-935P, RNU6-936P, RNU6-937P, RNU6-938P, RNU6-939P, RNU6-940P, RNU6-941P, RNU6-942P, RNU6-943P, RNU6-944P, RNU6-945P, RNU6-946P, RNU6-947P, RNU6-948P, RNU6-949P, RNU6-94P, RNU6-950P, RNU6-951P, RNU6-952P, RNU6-953P, RNU6-954P, RNU6-955P, RNU6-956P,

RNU6-957P, RNU6-958P, RNU6-959P, RNU6-95P, RNU6-960P, RNU6-961P, RNU6-964P, RNU6-965P, RNU6-966P, RNU6-967P, RNU6-968P, RNU6-969P, RNU6-970P, RNU6-971P, RNU6-972P, RNU6-973P, RNU6-974P, RNU6-975P, RNU6-976P, RNU6-977P, RNU6-978P, RNU6-979P, RNU6-97P, RNU6-980P, RNU6-982P, RNU6-983P, RNU6-984P, RNU6-985P, RNU6-986P, RNU6-987P, RNU6-988P, RNU6-989P, RNU6-98P, RNU6-990P, RNU6-991P, RNU6-992P, RNU6-993P, RNU6-994P, RNU6-995P, RNU6-996P, RNU6-997P, RNU6-998P, RNU6-999P, RNU6-99P, RNU6ATAC, RNU6ATAC10P, RNU6ATAC11P, RNU6ATAC12P, RNU6ATAC13P, RNU6ATAC14P, RNU6ATAC15P, RNU6ATAC16P, RNU6ATAC17P, RNU6ATAC18P, RNU6ATAC19P, RNU6ATAC20P, RNU6ATAC21P, RNU6ATAC22P, RNU6ATAC23P, RNU6ATAC24P, RNU6ATAC25P, RNU6ATAC26P, RNU6ATAC27P, RNU6ATAC28P, RNU6ATAC29P, RNU6ATAC2P, RNU6ATAC30P, RNU6ATAC31P, RNU6ATAC32P, RNU6ATAC33P, RNU6ATAC34P, RNU6ATAC36P, RNU6ATAC37P, RNU6ATAC38P, RNU6ATAC39P, RNU6ATAC3P, RNU6ATAC40P, RNU6ATAC41P, RNU6ATAC42P, RNU6ATAC4P, RNU6ATAC5P, RNU6ATAC6P, RNU6ATAC7P, RNU6ATAC8P, RNU6ATAC9P, RNU6V, RNU7-1, RNU7-102P, RNU7-103P, RNU7-104P, RNU7-105P, RNU7-106P, RNU7-107P, RNU7-10P, RNU7-110P, RNU7-111P, RNU7-113P, RNU7-115P, RNU7-116P, RNU7-119P, RNU7-11P, RNU7-120P, RNU7-121P, RNU7-123P, RNU7-124P, RNU7-125P, RNU7-126P, RNU7-127P, RNU7-128P, RNU7-129P, RNU7-12P, RNU7-130P, RNU7-133P, RNU7-134P, RNU7-136P, RNU7-137P, RNU7-138P, RNU7-13P, RNU7-140P, RNU7-141P, RNU7-143P, RNU7-144P, RNU7-147P, RNU7-148P, RNU7-149P, RNU7-14P, RNU7-151P, RNU7-152P, RNU7-153P, RNU7-154P, RNU7-155P, RNU7-156P, RNU7-157P, RNU7-159P, RNU7-160P, RNU7-161P, RNU7-164P, RNU7-165P, RNU7-167P, RNU7-169P, RNU7-170P, RNU7-171P, RNU7-172P, RNU7-173P, RNU7-174P, RNU7-175P, RNU7-176P, RNU7-179P, RNU7-180P, RNU7-181P, RNU7-182P, RNU7-183P, RNU7-185P, RNU7-186P, RNU7-187P, RNU7-188P, RNU7-18P, RNU7-190P, RNU7-192P, RNU7-193P, RNU7-194P, RNU7-195P, RNU7-196P, RNU7-197P, RNU7-19P, RNU7-200P, RNU7-20P, RNU7-21P, RNU7-22P, RNU7-23P, RNU7-24P, RNU7-25P, RNU7-26P, RNU7-27P, RNU7-28P, RNU7-29P, RNU7-2P, RNU7-30P, RNU7-34P, RNU7-35P, RNU7-37P, RNU7-38P, RNU7-3P, RNU7-40P, RNU7-41P, RNU7-43P, RNU7-45P, RNU7-46P, RNU7-47P, RNU7-48P, RNU7-49P, RNU7-4P, RNU7-50P, RNU7-51P, RNU7-52P, RNU7-53P, RNU7-54P, RNU7-55P, RNU7-56P, RNU7-57P, RNU7-59P, RNU7-60P, RNU7-61P, RNU7-62P, RNU7-63P, RNU7-65P, RNU7-66P, RNU7-67P, RNU7-69P, RNU7-6P, RNU7-70P, RNU7-71P, RNU7-73P, RNU7-74P, RNU7-75P, RNU7-77P, RNU7-79P, RNU7-7P, RNU7-80P, RNU7-81P, RNU7-82P, RNU7-84P, RNU7-85P, RNU7-87P, RNU7-88P, RNU7-8P, RNU7-90P, RNU7-92P, RNU7-93P, RNU7-94P, RNU7-95P, RNU7-96P, RNU7-97P, RNU7-99P, RNU7-9P, RNVU1-1, RNVU1-14, RNVU1-15, RNVU1-17, RNVU1-18, RNVU1-19, RNVU1-2, RNVU1-21, RNVU1-22, RNVU1-23, RNVU1-24, RNVU1-25, RNVU1-26, RNVU1-27, RNVU1-28, RNVU1-29, RNVU1-2A, RNVU1-3, RNVU1-30, RNVU1-31, RNVU1-32, RNVU1-33, RNVU1-34, RNVU1-4, RNVU1-6, RNVU1-7, RNVU1-8, U1, U2, U4, U6, U7.

In some embodiments, a composition, system, and/or the one or more nucleic acids comprising one or more nucleotide sequences described herein comprises a full-length snRNA or portion thereof comprising a nucleotide sequence comprising one or more sequence motifs described herein (e.g., one or more sequence motifs set forth in Table 1), and wherein the snRNA is selected from a U1 snRNA, a U2 snRNA, a U4 snRNA, a U4atac snRNA, a U5 snRNA, a U6 snRNA, a U6atac snRNA, a U11 snRNA, a U12 snRNA, and a U7 snRNA.

In embodiments, the snRNA comprises a M6A modification. In embodiments, the snRNA comprises a M6A modification when the present methods are undertaken in cis or trans, as described herein. In embodiments, the snRNA or snoRNA is modified to comprise at least one or more M6A sites. In embodiments, the snRNA or snoRNA is modified to comprise at least 1, 2, 3 4, 5, 6, 7, 8, 9, 10, 11, 12, 13, 14, 15, 16, 17, 18, 19, 20, 21, 22, 23, 24, 25, 26, 27, 28, 29, 30 or more M6A sites than the number of M6A modifications in (i) an unmodified state of the snRNA or snoRNA or (ii) an exonic sequence. In embodiments, the snRNA or snoRNA is modified to not comprise M6A sites. In embodiments, the repRNA comprises at least one or more M6A sites. In embodiments, the repRNA is modified to comprise at least 1, 2, 3 4, 5, 6, 7, 8, 9, 10, 11, 12, 13, 14, 15, 16, 17, 18, 19, 20, 21, 22, 23, 24, 25, 26, 27, 28, 29, 30 or more M6A sites than the number of M6A sites in (i) an unmodified state of the repRNA or (ii) an exonic sequence. In embodiments, the repRNA comprises no M6A sites.

In embodiments, the repRNA further comprises a ribozyme site. In embodiments, the ribozyme site is a hairpin, hammerhead, hepatitis delta virus (HDV), Varkud satellite (VS), or glmS ribozyme site, or a variant thereof. In embodiments, the ribozyme site is a HDV ribozyme site. In embodiments, the ribozyme site is a twister ribozyme site. In embodiments, the ribozyme site is upstream of the one or more exons and/or introns of the repRNA. In embodiments, the ribozyme cleaves the target. In embodiments, the ribozyme is a trans-cleaving ribozyme.

In embodiments, the repRNA comprises at least one intronic spacer sequence comprising at least one ISE and ESS sequences. In embodiments, the at least one intronic spacer sequence comprising at least one ISE and ESS sequences increases trans-splicing efficiency of a target RNA as compared to an unmodified form. In embodiments, the repRNA comprises at least one intronic spacer sequence comprising at least one ISE and ESS sequences. In embodiments, the at least one intronic spacer sequence comprising at least one ISE and ESS sequences decreases trans-splicing efficiency of a target RNA as compared to an unmodified form. In embodiments, the repRNA comprises at least one intronic spacer sequence comprising at least one ISE and ESS sequences. In embodiments, the at least one intronic spacer sequence comprising at least one ISE and ESS sequences increases trans-splicing efficiency of a off-target RNA as compared to an unmodified form. In embodiments, the repRNA comprises at least one intronic spacer sequence comprising at least one ISE and ESS sequences. In embodiments, the at least one intronic spacer sequence comprising at least one ISE and ESS sequences decreases trans-splicing efficiency of a off-target RNA as compared to an unmodified form.

In embodiments, the repRNA comprises a ESS, ESE, ISS, and/or ISE sequence. In embodiments, the repRNA targets one or more of ESS, ESE, ISS, and/or ISE. In embodiments, an interaction, modulation and/or binding to one or more of ESS, ESE, ISS, and/or ISE reduces or ablates interaction, modulation and/or binding of the one or more of the ESS, ESE, ISS, and/or ISE with a target. In embodiments, the repRNA comprises exon sequences with ESE and ESS sequences. In embodiments, the exon sequences with ESE and ESS sequences increase or decrease trans-splicing efficiency to an RNA target as compared to an unmodified form. In embodiments, the repRNA comprises exon sequences with ESE and ESS sequences. In embodiments, the repRNA comprises exon sequences with ESE and ESS sequences increase or decrease trans-splicing efficiency to an RNA off-target as compared to an unmodified form. In embodiments, the repRNA comprises at least one or more G4 structures. In embodiments, the repRNA comprises at least one or more G4 structures sequester SD/SA motifs. In embodiments, the G4 structure is unwound, such as by DHX36 or CNBP, and remains trapped in the unwound state in the presence of a complementary sequence (e.g., endogenous target or exogenously delivered trigger RNA). In embodiments, the G4 structure decreases off-targets as compared to an unmodified form.

In embodiments, the repRNA comprises a modification comprising at least one or more scaffolding sequences. In embodiments, the at least one or more scaffolding sequences mediates (e.g., recruits) phase condensate-like formation and/or improves local concentrations of repRNAs and other targeted proteins and/or RNA as compared to an unmodified form. In embodiments, the repRNA comprises a modification comprising at least one or more sequences to target the repRNA to the promoter of the target gene of interest, or to proximal condensates that may contain the promoter. In embodiments, the one or more sequences comprises an enhancer RNA, snRNA and/or snoRNA sequences.

In embodiments, the repRNA comprises a modification. In embodiments, the repRNA modification improves interaction and localization to a DNA sequence of the non-template strand of the target gene as compared to an unmodified form. In embodiments, the DNA sequence of the non-template strand of the target gene is the promoter, intron, exon, or enhancer. In embodiments, the modification improves interaction and localization to the DNA sequence of the non-template strand of the target gene through protein-directed (e.g. transcription factor, dCas, ZNF, or other RBP) or nucleotide-directed (e.g., R-loop) methods as compared to an unmodified form.

In embodiments, the repRNA comprises a modification comprising additional RNA elements. In embodiments, the modification comprising additional RNA elements improves subnuclear localization to nuclear speckles for enhanced trans-splicing efficiency as compared to an unmodified form. In embodiments, the additional RNA element comprise NEAT1 and/or MALAT1, or a fragment thereof. In embodiments, the additional RNA element comprises a nucleotide sequence of SEQ ID NO: 712, or a fragment or variant thereof, optionally having at least about 90%, or at least about 95%, or at least about 97%, or at least about 98%, or at least about 99% identity thereto and/or or having about 1 to about 20 (e.g. about 1, or about 2, or about 3, or about 4, or about 5) nucleic acid modifications, optionally selected from substitutions, additions, or deletions. In embodiments, the repRNA comprises a modification. In embodiments, the repRNA modification enables targeting to site of transcription of target RNAs. In embodiments, the repRNA comprises a modification comprising 5' UTR or 3' UTR modifications.

In embodiments, the modification alters intracellular or intranuclear localization based on interactions with endogenous or exogenously supplied molecules (e.g., RNA G4 interactions with transcription factors or other proteins that are localized to specific cellular compartments).

In embodiments, the repRNA comprises a modification in the 5' UTR of the repRNA. In embodiments, the modification in the 5' UTR of the repRNA increases stability as compared to an unmodified form. In embodiments, the modification in the 5' UTR of the repRNA decreases stability as compared to an unmodified form. In embodiments, the modification in the 5' UTR of the repRNA increases or decreases translation efficiency as compared to an unmodified form. In embodiments, the repRNA comprises a modification in the 3' UTR of the repRNA. In embodiments, the modification in the 3' UTR of the repRNA increases stability as compared to an unmodified form. In embodiments, the modification in the 3' UTR of the repRNA decreases stability as compared to an unmodified form. In embodiments, the modification in the 3' UTR of the repRNA increases or decreases translation efficiency as compared to an unmodified form.

In embodiments, the repRNA comprises a modification comprising modifying the repRNA to comprise a G4 structure that mediates recruitment of splicing-associated RBPs.

In embodiments, the repRNA comprises a modification comprising at least one or more toehold switches in the repRNA. In embodiments, the at least one or more toehold switches in the repRNA conditionally activate or deactivate (e.g., SD/SA occlusion, binding motif occlusion, or RBP occlusion) upon detection of an endogenous or exogenously supplied target RNA.

In embodiments, the repRNA comprises a modification comprising at least one or more complementary riboregulators in repRNAs (in cis). In embodiments, the at least one or more complementary riboregulators in repRNAs (in cis) occlude splice donor (SD) site and reduce off-target trans-splicing.

In embodiments, the repRNA comprises a modification comprising at least one or more self-complementary riboregulators in repRNAs (in cis). In embodiments, the at least one or more self-complementary riboregulators in repRNAs (in cis) occlude splice acceptor (SA) site and reduce off-target trans-splicing.

In embodiments, the repRNA comprises a modification comprising at least one or more self-complementary riboregulators in repRNAs (in trans). In embodiments, the at least one or more self-complementary riboregulators in repRNAs (in trans) occlude splice donor (SD) site and reduce off-target trans-splicing.

In embodiments, the repRNA comprises a modification comprising at least one or more self-complementary riboregulators in repRNAs (in trans). In embodiments, the at least one or more self-complementary riboregulators in repRNAs (in trans) occlude splice acceptor (SA) site and reduce off-target trans-splicing.

In embodiments, the repRNA comprises a modification comprising at least one or more binding motifs. In embodiments, the at least one or more binding motifs increase trans-splicing efficiency, target specificity, and target site occlusion (SA, SD, ISS, ISE, ESE, and ESS) as compared to an unmodified form.

In embodiments, the repRNA comprises a modification. In embodiments, the repRNA modification enables induction of trans-splicing in response to a stimulus as compared to an unmodified form. In embodiments, the repRNA comprises a modification to turn off or decrease trans-splicing in response to a stimulus as compared to an unmodified form.

In embodiments, the repRNA comprises a modification. In embodiments, the repRNA modification enables small molecule induction of trans-splicing as compared to an unmodified form. In embodiments, the repRNA comprises a modification. In embodiments, the repRNA modification represses small molecule induction of trans-splicing as compared to an unmodified form.

In embodiments, the repRNA comprises a modification. In embodiments, the repRNA modification enables light induction of trans-splicing.

In embodiments, the repRNA comprises a modification comprising at least one or more motifs that are bound and regulated by light-sensitive proteins.

In embodiments, the repRNA comprises a ribozyme site that cleaves at the 5' end of the repRNA.

In embodiments, the repRNA comprises a ribozyme site that cleaves at the 3' end of the repRNA.

In embodiments, the repRNA comprises a ribozyme site that cleaves the snRNA or snoRNA at the 5' end of the repRNA. In embodiments, the repRNA comprises a ribozyme site that cleaves the snRNA or snoRNA at the 3' end of the repRNA.

In embodiments, the composition or system further comprises at least one pre-rRNA stemloop to remove either the 5'cap or 3' polyA tail.

In some embodiments, the snRNA is a U1 snRNA. In some embodiments, the U1 snRNA assembles into a U1 RNP. In some embodiments, the snRNA is a U2 snRNA. In some embodiments, the U2 snRNA assembles into a U2 RNP. In some embodiments, the snRNA is a U4 snRNA. In some embodiments, the U1 snRNA assembles into a U4 RNP. In some embodiments, the snRNA is a U4atac snRNA. In some embodiments, the U1 snRNA assembles into a U4atac RNP. In some embodiments, the snRNA is a U5 snRNA. In some embodiments, the U1 snRNA assembles into a U5 RNP. In some embodiments, the snRNA is a U6 snRNA. In some embodiments, the U1 snRNA assembles into a U6 RNP. In some embodiments, the snRNA is a U6atac snRNA. In some embodiments, the U1 snRNA assembles into a U6atac RNP. In some embodiments, the snRNA is a U7 snRNA. In some embodiments, the U1 snRNA assembles into a U7 RNP. In some embodiments, the snRNA is a U11 snRNA. On some embodiments, the U1 snRNA assembles into a U11 RNP. In some embodiments, the snRNA is a U12 snRNA. In some embodiments, the U1 snRNA assembles into a U12 RNP.

In some embodiments, the snRNA and/or snoRNA comprises a Sm sequence motif. In some embodiments, the Sm sequence motif assembles with an Sm protein to form an RNP. In some embodiments, the Sm protein is B/B', D3, D2, D1, E, F, and G Sm proteins.

In some embodiments, a composition, system, and/or the one or more nucleic acids comprising one or more nucleotide sequences described herein comprises a full-length snoRNA or portion thereof comprising a nucleotide sequence comprising one or more sequence motifs described herein (e.g., one or more sequence motifs set forth in Table 1). In some embodiments, a snoRNA sequence described herein or identified according to a method described herein is incorporated into a composition, system, and/or the one or more nucleic acids comprising one or more nucleotide sequences described herein. In some embodiments, a full-length snoRNA sequence described herein or identified according to a method described herein is incorporated into a composition, system, and/or the one or more nucleic acids comprising one or more nucleotide sequences described herein. In some embodiments, a portion of a snoRNA sequence described herein or identified according to a method described herein (e.g., a region of contiguous nucleotides in the snRNA) is incorporated into a composition, system, and/or the one or more nucleic acids comprising one or more nucleotide sequences described herein.

In some embodiments, the full-length snoRNA or portion thereof assembles into a small nucleolar RNP (snoRNP). snoRNAs are responsible for RNA methylation and RNA pseudouridylation (Bachellerie 2002, Kiss 2004). There are two classes of snoRNAs, namely (i) H/ACA box snoRNAs which are responsible for pseudouridylation and (ii) C/D box snoRNAs which are responsible 'or "—O-ribose methylation (Jorjani 2016, Kufel 2019). snoRNAs can also form RNPs termed snoRNPs (Khanna 2006) and hybridize to their RNA targets via Watson-Crick base pairing (Jin 2007).

In some embodiments, the full-length snoRNA or portion thereof comprises an H/ACA box. In some embodiments, the H/ACA box comprises a nucleotide sequence comprising from 5' to 3' an H consensus sequence (e.g., an H consensus sequence comprising the sequence set forth in Table 1) and an ACA consensus sequence (e.g., an ACA consensus sequence comprising the sequence set forth in Table 1). In some embodiments, the H/ACA box snoRNA assembles to form an H/ACA snoRNP. In some embodiments, the full-length snoRNA or portion thereof comprises a C/D box. In some embodiment, the C/D box comprises a nucleotide sequence comprising from 5' to 3' a C consensus sequence (e.g., a C consensus sequence comprising the sequence set forth in Table 1), a D' consensus sequence (e.g., a D' consensus sequence comprising the sequence set forth in Table 1), a C' consensus sequence (e.g., a C' consensus sequence comprising the sequence set forth in Table 1), and a D consensus sequence (e.g., a D consensus sequence comprising the sequence set forth in SEQ ID NO: 6). In some embodiments, the C/D box snoRNP assembles to form a C/D snoRNP.

In some embodiments, a composition, system, and/or the one or more nucleic acids comprising one or more nucleotide sequences described herein comprises a full-length snoRNA or portion thereof comprising a nucleotide sequence comprising one or more sequence motifs described herein (e.g., one or more sequence motifs set forth in Table 1), and wherein the snoRNA is selected from SCARNA18, SCARNA18B, SNORA1, SNORA10, SNORA108, SNORA10B, SNORA11, SNORA11B, SNORA11C, SNORA11D, SNORA11E, SNORA11F, SNORA11G, SNORA12, SNORA13, SNORA14A, SNORA14B, SNORA15, SNORA15B-1, SNORA15B-2, SNORA16A, SNORA16B, SNORA17A, SNORA17B, SNORA18, SNORA19, SNORA1B, SNORA20, SNORA20B, SNORA21, SNORA21B, SNORA22, SNORA22B, SNORA22C, SNORA24, SNORA24B, SNORA25, SNORA25B, SNORA26, SNORA27, SNORA28, SNORA29, SNORA2A, SNORA2B, SNORA2C, SNORA30, SNORA30B, SNORA31, SNORA31B, SNORA32, SNORA33, SNORA35, SNORA35B, SNORA36A, SNORA36B, SNORA36C, SNORA37, SNORA38, SNORA38B, SNORA3A, SNORA3B, SNORA3C, SNORA4, SNORA40, SNORA40B, SNORA40C, SNORA41, SNORA41B, SNORA44, SNORA46, SNORA47, SNORA48, SNORA48B, SNORA49, SNORA50A, SNORA50B, SNORA50C, SNORA50D, SNORA51, SNORA52, SNORA54, SNORA55, SNORA56, SNORA57, SNORA58, SNORA58B, SNORA59A, SNORA5A, SNORA5B, SNORA5C, SNORA6, SNORA60, SNORA61, SNORA62, SNORA63, SNORA63B, SNORA63C, SNORA63D, SNORA63E, SNORA64, SNORA65, SNORA66, SNORA67, SNORA68, SNORA68B, SNORA69, SNORA70, SNORA70B, SNORA70C, SNORA70D, SNORA70E, SNORA70F, SNORA70G, SNORA70H, SNORA70I, SNORA70J, SNORA71, SNORA71A, SNORA71C, SNORA71D, SNORA71E, SNORA72, SNORA73, SNORA74, SNORA74D, SNORA75, SNORA75B, SNORA77, SNORA77B, SNORA78, SNORA79, SNORA79B, SNORA7A, SNORA7B, SNORA8, SNORA80A, SNORA80B, SNORA80C, SNORA80D, SNORA80E, SNORA81, SNORA84, SNORA9, SNORA9B, SNORD10, SNORD100, SNORD101, SNORD102, SNORD104, SNORD105, SNORD105B, SNORD107, SNORD108, SNORD109A, SNORD109B, SNORD11, SNORD110, SNORD111, SNORD111B, SNORD112, SNORD113-1, SNORD113-2, SNORD113-3, SNORD113-4, SNORD113-5, SNORD113-6, SNORD113-7, SNORD113-8, SNORD113-9, SNORD114-1, SNORD114-10, SNORD114-11, SNORD114-12, SNORD114-13, SNORD114-14, SNORD114-15, SNORD114-16, SNORD114-17, SNORD114-18, SNORD114-19, SNORD114-2, SNORD114-20, SNORD114-21, SNORD114-22, SNORD114-23, SNORD114-24, SNORD114-25, SNORD114-26, SNORD114-27, SNORD114-28, SNORD114-29, SNORD114-3, SNORD114-30, SNORD114-31, SNORD114-4, SNORD114-5, SNORD114-6, SNORD114-7, SNORD114-9, SNORD115, SNORD115-1, SNORD115-10, SNORD115-11, SNORD115-12, SNORD115-13, SNORD115-14, SNORD115-15, SNORD115-16, SNORD115-17, SNORD115-18, SNORD115-19, SNORD115-2, SNORD115-20, SNORD115-21, SNORD115-22, SNORD115-23, SNORD115-24, SNORD115-25, SNORD115-26, SNORD115-27, SNORD115-28, SNORD115-29, SNORD115-3, SNORD115-30, SNORD115-31, SNORD115-32, SNORD115-33, SNORD115-34, SNORD115-35, SNORD115-36, SNORD115-37, SNORD115-38, SNORD115-39, SNORD115-4, SNORD115-40, SNORD115-41, SNORD115-42, SNORD115-43, SNORD115-44, SNORD115-45, SNORD115-46, SNORD115-47, SNORD115-48, SNORD115-5, SNORD115-6, SNORD115-7, SNORD115-8, SNORD115-9, SNORD116, SNORD116-1, SNORD116-10, SNORD116-11, SNORD116-12, SNORD116-13, SNORD116-14, SNORD116-15, SNORD116-16, SNORD116-17, SNORD116-18, SNORD116-19, SNORD116-2, SNORD116-20, SNORD116-21, SNORD116-22, SNORD116-23, SNORD116-24, SNORD116-25, SNORD116-26, SNORD116-27, SNORD116-28, SNORD116-29, SNORD116-3, SNORD116-30, SNORD116-4, SNORD116-5, SNORD116-6, SNORD116-7, SNORD116-8, SNORD116-9, SNORD117, SNORD118, SNORD11B, SNORD12, SNORD121A, SNORD121B, SNORD123, SNORD124, SNORD125, SNORD126, SNORD127, SNORD12B, SNORD12C, SNORD13, SNORD13D, SNORD13E, SNORD13P1, SNORD13P3, SNORD14, SNORD14A, SNORD14B, SNORD14C, SNORD14D, SNORD14E, SNORD15A, SNORD15B, SNORD16, SNORD18, SNORD18A, SNORD18B, SNORD18C, SNORD19, SNORD19B, SNORD19C, SNORD1A, SNORD1B, SNORD1C, SNORD2, SNORD20, SNORD21, SNORD22, SNORD23, SNORD24, SNORD25, SNORD26, SNORD27, SNORD28, SNORD28B, SNORD29, SNORD30, SNORD31B, SNORD32A, SNORD32B, SNORD33, SNORD34, SNORD35A, SNORD35B, SNORD36, SNORD36A, SNORD36B, SNORD36C, SNORD37, SNORD38A, SNORD38B, SNORD38C, SNORD38D, SNORD39, SNORD41, SNORD42, SNORD42A, SNORD42B, SNORD43, SNORD45A, SNORD45B, SNORD45C, SNORD46, SNORD48, SNORD49A, SNORD49B, SNORD4A, SNORD4B, SNORD5, SNORD50B, SNORD51, SNORD52, SNORD53, SNORD53B, SNORD54, SNORD55, SNORD56, SNORD56B, SNORD57, SNORD58, SNORD58A, SNORD58B, SNORD58C, SNORD59A, SNORD6, SNORD60, SNORD61, SNORD62, SNORD62A, SNORD62B, SNORD63, SNORD63B, SNORD64, SNORD65, SNORD65B, SNORD65C, SNORD66, SNORD67, SNORD68, SNORD69, SNORD7, SNORD70, SNORD70B, SNORD71, SNORD72, SNORD73A, SNORD73B, SNORD74B, SNORD77B, SNORD79, SNORD8, SNORD81, SNORD82, SNORD83, SNORD83A, SNORD83B, SNORD84, SNORD86, SNORD87, SNORD88A, SNORD88B, SNORD88C, SNORD89, SNORD9, SNORD90, SNORD92, SNORD93, SNORD94, SNORD95, SNORD96A, SNORD96B, SNORD97, SNORD98, SNORD99, U8, snoZ196.

Methods to Engineer a Composition, System, or Nucleic Acid of the Disclosure

The present disclosure provides methods to engineer a composition, system, and/or the one or more nucleic acids comprising one or more nucleotide sequences described herein. In some embodiments, the method comprises (A) identifying one or more candidate snRNAs and/or snoR-NAs; (B) obtaining a snRNA and/or snoRNA sequence f; and (C) producing a composition, system, and/or the one or more nucleic acids comprising one or more nucleotide sequences described herein comprising a nucleotide sequence comprising (i) an intronic sequence comprising (a) the snRNA and/or snoRNA sequence, and (b) one or more binding domains described herein; (ii) a splice acceptor and/or splice donor; and (iii) one or more exonic sequences, thereby providing a composition, system, and/or the one or more nucleic acids comprising one or more nucleotide sequences described herein for targeting trans-splicing of the target RNA (e.g., target pre-mRNA). In some embodiments, the method comprises introducing the composition, system, and/or the one or more nucleic acids comprising one or more nucleotide sequences described herein to a cell or population of cells and determining the efficiency of trans-splicing of the target RNA (e.g., target pre-mRNA) according to a method described herein. In some embodiments, the efficiency of trans-splicing of the composition, system, and/or the one or more nucleic acids comprising one or more nucleotide sequences described herein is compared to that of a control nucleic acid. In some embodiments, the control nucleic acid comprises (i), (ii), and (iii) and lacks the snRNA and/or snoRNA sequence.

Methods of Identifying Candidate snRNA and/or snoRNA Sequences

In some embodiments, identifying one or more candidate snRNA and/or snoRNA sequences comprises (i) obtaining one or more snRNA and/or snoRNA sequences from a database and/or by experimental analysis of RNA expressed by a cell or organism as described herein; (ii) predicting the secondary structure formed by the one or more snRNA and/or snoRNA sequences according to a method described herein; (iii) comparing the predicted secondary structure of (ii) to a reference secondary structure (e.g., a secondary structure present in a snRNA and/or snoRNA known in the art); and (iv) selecting one or more candidate snRNA and/or snoRNA sequences with a predicted secondary structure having substantial similarity to the reference secondary structure.

Computational methods for predicting the secondary structures formed by a snRNA and/or snoRNA sequence are known in the art (see, e.g., Lorenz, et al. ViennaRNA Package 2.0 Algorithms for Molecular Biology, 6:1 26, 2011). Methods for performing RNA sequence analysis by comparing predicted secondary structures to a reference secondary structure are also known in the art (see, e.g., Eddy, et al (1994) Nucleic Acids Res 22:2079).

In some embodiments, identifying one or more candidate snRNA and/or snoRNA sequences comprises (i) obtaining one or more snRNA and/or snoRNA sequences from a database and/or by experimental analysis of RNA expressed by a cell or organism as described herein; (ii) predicting the secondary structure formed by the one or more snRNA and/or snoRNA sequences according to a method described herein; (iii) comparing the predicted secondary structure of (ii) to a reference secondary structure (e.g., a secondary structure present in a snRNA and/or snoRNA known in the art); and (iv) selecting one or more candidate snRNA and/or snoRNA sequences with a predicted secondary structure having substantial similarity to the reference secondary structure and comprising a sequence motif described herein (e.g., a sequence motif comprises one or more sequences set forth in Table 1).

In some embodiments, the one or more candidate snRNA and/or snoRNA sequences are selected from any one or any combination of sequences set forth in SEQ ID NOs: 9-209, 211-628, 630-632, 634-635, 638, 640, 642, 644-645, 647-648, 650, 652-653, 655, 657, 732-737, 741-746, 748-749, 751-758, 760-761, 763-765, 767, 771-774, 776-778, and 780-789.

Method of Obtaining a snRNA and/or snoRNA Sequence

In some embodiments, obtaining a snRNA and/or snoRNA sequence for inclusion in a composition, system, and/or the one or more nucleic acids comprising one or more nucleotide sequences described herein comprises (i) identifying one or more candidate snRNA and/or snoRNA sequences as described herein; and (ii) selecting a snRNA and/or snoRNA sequence from the one or more candidate snRNA and/or snoRNA sequences.

In some embodiments, obtaining the snRNA and/or snoRNA sequence comprises selecting a snRNA and/or snoRNA sequence from the one or more candidate snRNA and/or snoRNA sequences (e.g., one or more candidate snRNA and/or snoRNA sequences selected from any one or any combination of sequences set forth in SEQ ID NOs: 9-209, 211-628, 630-632, 634-635, 638, 640, 642, 644-645, 647-648, 650, 652-653, 655, 657, 732-737, 741-746, 748-749, 751-758, 760-761, 763-765, 767, 771-774, 776-778, and 780-789), wherein the snRNA and/or snoRNA sequence is at least about 7, about 8, about 9, about 10, about 11, about 12, about 13, about 14, or about 15 nucleotides in length and comprises a Sm motif described herein (e.g., a Sm motif set forth in Table 1). In some embodiments, the snRNA and/or snoRNA sequence is about 7 nucleotides in length and comprises a Sm motif described herein (e.g., a Sm motif set forth in Table 1). In some embodiments, the snRNA and/or snoRNA sequence is about 8 nucleotides in length and comprises a Sm motif described herein (e.g., a Sm motif set forth in Table 1). In some embodiments, the snRNA and/or snoRNA sequence is about 9 nucleotides in length and comprises a Sm motif described herein (e.g., a Sm motif set f©rth in Table 1). In some embodiments, the snRNA and/or snoRNA sequence is about 10 nucleo©ides in length and comprises a Sm motif described herein (e.g., a Sm motif set forth in Table 1). In some embodiments, the snRNA and/or snoRNA sequence is about 11 nucleotides in length and comprises a Sm motif described herein (e.g., a Sm motif set forth in Table 1). In some embodiments, the snRNA and/or snoRNA sequence is about 12 nucleotides in length and comprises a Sm motif described herein (e.g., a Sm motif set forth in Table 1).

In some embodiments, obtaining the snRNA and/or snoRNA sequence comprises selecting a snRNA and/or snoRNA sequence from the one or more candidate snRNA and/or snoRNA sequences (e.g., one or more candidate snRNA and/or snoRNA sequences selected from any one or any combination of sequences set forth in SEQ ID NOs: 9-209, 211-628, 630-632, 634-635, 638, 640, 642, 644-645, 647-648, 650, 652-653, 655, 657, 732-737, 741-746, 748-749, 751-758, 760-761, 763-765, 767, 771-774, 776-778, and 780-789), wherein the snRNA and/or snoRNA sequence is at least about 40, about 45, about 50, about 55, about 60, about 65, about 70, about 75, about 80, about 85, about 90, about 95, or about 100 nucleotides in length and comprises a Sm motif described herein (e.g., a Sm motif set forth in Table 1).

In some embodiments, obtaining the snRNA and/or snoRNA sequence comprises selecting a snRNA and/or snoRNA sequence having at least about 60%, about 65%, about 70%, about 75%, about 80%, about 85%, about 90%, about 91%, about 92%, about 93%, about 94%, about 95%, about 96%, about 97%, about 98%, about 99% to one or more candidate snRNA and/or snoRNA sequences or a portion thereof (e.g., one or more candidate snRNA and/or snoRNA sequences selected from any one or any combination of sequences set forth in SEQ ID NOs: 9-209, 211-628, 630-632, 634-635, 638, 640, 642, 644-645, 647-648, 650, 652-653, 655, 657, 732-737, 741-746, 748-749, 751-758, 760-761, 763-765, 767, 771-774, 776-778, and 780-789), wherein the snRNA and/or snoRNA se©uence is at least about 40, about 45, about 50, about 55, about 60, about 65, about 70, about 75, about 80, about 85, about 90, about 95, or about 100 nucleotides in length and comprises a Sm motif described herein (e.g., a Sm motif set forth in Table 1).

In some embodiments, obtaining the snRNA and/or snoRNA sequence comprises selecting a snRNA and/or snoRNA sequence from the one or more candidate snRNA and/or snoRNA sequences (e.g., one or more candidate snRNA and/or snoRNA sequences selected from any one or any combination of sequences set forth in SEQ ID NOs: 9-209, 211-628, 630-632, 634-635, 638, 640, 642, 644-645, 647-648, 650, 652-653, 655, 657, 732-737, 741-746, 748-749, 751-758, 760-761, 763-765, 767, 771-774, 776-778, and 780-789), wherein the snRNA and/or snoRNA sequence is at least about 40, about 45, about 50, about 55, about 60, about 65, about 70, about 75, about 80, about 85, about 90, about 95, or about 100 nucleotides in length and comprises a H-box motif described herein (e.g., a H-box motif set forth in Table 1).

In some embodiments, obtaining the snRNA and/or snoRNA sequence comprises selecting a snRNA and/or snoRNA sequence having at least about 60%, about 65%, about 70%, about 75%, about 80%, about 85%, about 90%, about 91%, about 92%, about 93%, about 94%, about 95%, about 96%, about 97%, about 98%, about 99% to one or more candidate snRNA and/or snoRNA sequences or a portion thereof (e.g., one or more candidate snRNA and/or snoRNA sequences selected from any one or any combination of sequences set forth in SEQ ID NOs: 9-209, 211-628, 630-632, 634-635, 638, 640, 642, 644-645, 647-648, 650, 652-653, 655, 657, 732-737, 741-746, 748-749, 751-758, 760-761, 763-765, 767, 771-774, 776-778, or a portion thereof), wherein the snRNA and/or snoRNA sequence is at least about 40, about 45, about 50, about 55, about 60, about 65, about 70, about 75, about 80, about 85, about 90, about 95, or about 100 nucleotides in length and comprises a H-box motif described herein (e.g., a H-box motif set forth in Table 1).

In some embodiments, obtaining the snRNA and/or snoRNA sequence comprises selecting a snRNA and/or snoRNA sequence from the one or more candidate snRNA and/or snoRNA sequences (e.g., one or more candidate snRNA and/or snoRNA sequences selected from any one or any combination of sequences set forth in SEQ ID NOs: 9-209, 211-628, 630-632, 634-635, 638, 640, 642, 644-645, 647-648, 650, 652-653, 655, 657, 732-737, 741-746, 748-749, 751-758, 760-761, 763-765, 767, 771-774, 776-778, and 780-789), wherein the snRNA and/or snoRNA sequence is at least about 40, about 45, about 50, about 55, about 60, about 65, about 70, about 75, about 80, about 85, about 90, about 95, or about 100 nucleotides in length and comprises an ACA-box motif described herein (e.g., an ACA-box motif set forth in Table 1).

In some embodiments, obtaining the snRNA and/or snoRNA sequence comprises selecting a snRNA and/or snoRNA sequence having at least about 60%, about 65%, about 70%, about 75%, about 80%, about 85%, about 90%, about 91%, about 92%, about 93%, about 94%, about 95%, about 96%, about 97%, about 98%, about 99% to one or more candidate snRNA and/or snoRNA sequences or a portion thereof (e.g., one or more candidate snRNA and/or snoRNA sequences selected from any one or any combination of sequences set forth in SEQ ID NOs: 9-209, 211-628, 630-632, 634-635, 638, 640, 642, 644-645, 647-648, 650, 652-653, 655, 657, 732-737, 741-746, 748-749, 751-758, 760-761, 763-765, 767, 771-774, 776-778, and 780-789, or a portion thereof), wherein the snRNA and/or snoRNA sequence is at least about 40, about 45, about 50, about 55, about 60, about 65, about 70, about 75, about 80, about 85, about 90, about 95, or about 100 nucleotides in length and comprises a ACA-box motif described herein (e.g., a ACA-box motif set forth in Table 1).

In some embodiments, obtaining the snRNA and/or snoRNA sequence comprises selecting a snRNA and/or snoRNA sequence from the one or more candidate snRNA and/or snoRNA sequences (e.g., one or more candidate snRNA and/or snoRNA sequences selected from any one or any combination of sequences set forth in SEQ ID NOs: 9-209, 211-628, 630-632, 634-635, 638, 640, 642, 644-645, 647-648, 650, 652-653, 655, 657, 732-737, 741-746, 748-749, 751-758, 760-761, 763-765, 767, 771-774, 776-778, and 780-789), wherein the snRNA and/or snoRNA sequence is at least about 40, about 45, about 50, about 55, about 60, about 65, about 70, about 75, about 80, about 85, about 90, about 95, or about 100 nucleotides in length and comprises an H-box and an ACA-box motif described herein (e.g., a H-box and a ACA-box motif set forth in Table 1).

In some embodiments, obtaining the snRNA and/or snoRNA sequence comprises selecting a snRNA and/or snoRNA sequence having at least about 60%, about 65%, about 70%, about 75%, about 80%, about 85%, about 90%, about 91%, about 92%, about 93%, about 94%, about 95%, about 96%, about 97%, about 98%, about 99% to one or more candidate snRNA and/or snoRNA sequences or a portion thereof (e.g., one or more candidate snRNA and/or snoRNA sequences selected from any one or any combination of sequences set forth in SEQ ID NOs: 9-209, 211-628, 630-632, 634-635, 638, 640, 642, 644-645, 647-648, 650, 652-653, 655, 657, 732-737, 741-746, 748-749, 751-758, 760-761, 763-765, 767, 771-774, 776-778, and 780-789 or a portion thereof), wherein the snRNA and/or snoRNA sequence is at least about 40, about 45, about 50, about 55, about 60, about 65, about 70, about 75, about 80, about 85, about 90, about 95, or about 100 nucleotides in length and comprises an H-box and an ACA-box motif described herein (e.g., a H-box and a ACA-box motif set forth in Table 1).

In some embodiments, obtaining the snRNA and/or snoRNA sequence comprises selecting a snRNA and/or snoRNA sequence from the one or more candidate snRNA and/or snoRNA sequences (e.g., one or more candidate snRNA and/or snoRNA sequences selected from any one or any combination of sequences set forth in SEQ ID NOs: 9-209, 211-628, 630-632, 634-635, 638, 640, 642, 644-645, 647-648, 650, 652-653, 655, 657, 732-737, 741-746, 748-749, 751-758, 760-761, 763-765, 767, 771-774, 776-778, and 780-789), wherein the snRNA and/or snoRNA sequence is at least about 40, about 45, about 50, about 55, about 60, about 65, about 70, about 75, about 80, about 85, about 90, about 95, or about 100 nucleotides in length and comprises a (i) C-box motif described herein (e.g., a C-box motif set forth in Table 1), (ii) C'-box motif described herein (e.g., a C'-box motif set forth in Table 1), (iii) D-box motif described herein (e.g., a D-box motif set forth in Table 1), (iv) a D'-box motif described herein (e.g., a D'-box motif set forth in Table 1), or (v) a combination of (i)-(iv).

In some embodiments, obtaining the snRNA and/or snoRNA sequence comprises selecting a snRNA and/or snoRNA sequence having at least about 60%, about 65%, about 70%, about 75%, about 80%, about 85%, about 90%, about 91%, about 92%, about 93%, about 94%, about 95%, about 96%, about 97%, about 98%, about 99% to one or more candidate snRNA and/or snoRNA sequences or a portion thereof (e.g., one or more candidate snRNA and/or snoRNA sequences selected from any one or any combination of sequences set forth in SEQ ID NOs: 9-209, 211-628, 630-632, 634-635, 638, 640, 642, 644-645, 647-648, 650, 652-653, 655, 657, 732-737, 741-746, 748-749, 751-758, 760-761, 763-765, 767, 771-774, 776-778, and 780-789, or a portion thereof), wherein the sequence is at least about 40, about 45, about 50, about 55, about 60, about 65, about 70, about 75, about 80, about 85, about 90, about 95, or about 100 nucleotides in length and comprises a (i) C-box motif described herein (e.g., a C-box motif set forth in Table 1), (ii) C'-box motif described herein (e.g., a C'-box motif set forth in Table 1), (iii) D-box motif described herein (e.g., a D-box motif set forth in Table 1), (iv) a D'-box motif described herein (e.g., a D'-box motif set forth in Table 1), or (v) a combination of (i)-(iv).

Methods of Producing the Composition, System, and/or the Nucleotide Sequences

The composition, system, and/or the one or more nucleic acids comprising one or more nucleotide sequences described herein are produced by suitable nucleic acid synthesis method or means known in the art. In some embodiments, the composition, system, and/or the one or more nucleic acids comprising one or more nucleotide sequences described herein is produced as an RNA. In some embodiments, the composition, system, and/or the one or more nucleic acids comprising one or more nucleotide sequences described herein is produced as a DNA. The present disclosure further provides delivery systems comprising the composition, system, and/or the one or more nucleic acids comprising one or more nucleotide sequences described herein, e.g., a vector comprising the composition, system, and/or the one or more nucleic acids comprising one or more nucleotide sequences described herein, a lipid particle comprising the composition, system, and/or the one or more nucleic acids comprising one or more nucleotide sequences described herein.

Methods of producing the composition, system, and/or the one or more nucleic acids comprising one or more nucleotide sequences described herein include, but are not limited to, in vitro transcription (IVT), synthetic and/or chemical synthesis methods, or a combination thereof. In some embodiments, enzymatic (e.g., IVT), solid-phase, liquid-phase, combined synthetic methods, small region synthesis, and ligation methods are utilized.

In embodiments, the disclosure provides compositions, systems, and/or the one or more nucleic acids comprising one or more nucleotide sequences described herein are produced using IVT enzymatic synthesis methods. Methods of making polynucleotides by IVT are known in the art and are described in International Application PCT/US2013/30062.

In embodiments, the disclosure provides composition, system, and/or the one or more nucleic acids comprising one or more nucleotide sequences described herein chemically synthesized by any means described in the art. In some embodiments, the composition, system, and/or the one or more nucleic acids comprising one or more nucleotide sequences described herein are produced by oligonucleotide synthesis. Oligonucleotide synthesis is the chemical synthesis of relatively short fragments or strands of single-stranded nucleic acids with a defined chemical structure (sequence). Methods of oligonucleotide synthesis are known in the art (see e.g., Reese (2005) Organic & Biomolecular Chemistry 3 (21): 3851). While chemical synthetic procedures are continually expanding, purifications of such nucleic acids by procedures such as high performance liquid chromatography (HPLC, which avoids the use of gels such as PAGE) tends to become more challenging as polynucleotide lengths increase significantly beyond a hundred or so nucleotides. One approach used for generating nucleic acids of greater length is to produce two or more molecules that are ligated together.

Methods of Determining Tran Splicing Efficiency

In embodiments, the disclosure provides methods to determine the efficiency of trans-splicing of a target RNA (e.g., pre-mRNA) using a composition, system, and/or the one or more nucleic acids comprising one or more nucleotide sequences described herein.

In embodiments, the method comprises use of a fluorescence-based splicing reporter assay. In embodiments, the assay comprises contacting a reporter cell or population of cells with the composition, system, and/or the one or more nucleic acids comprising one or more nucleotide sequences described herein according to a method described herein (e.g., via transfection with a viral vector encoding the composition, system, and/or the one or more nucleic acids comprising one or more nucleotide sequences described herein), wherein the composition, system, and/or the one or more nucleic acids comprising one or more nucleotide sequences described herein comprises at least one exon encoding a reporter molecule, wherein a trans-splicing event is indicated by the presence of a fluorescent signal from the reporter molecule that is detected using a method known in the art. For example, in some embodiments, the reporter molecule is a fluorescent protein detected using fluorescence-activated cell sorting (FACS). For example, in some embodiments, the composition, system, and/or the one or more nucleic acids comprising one or more nucleotide sequences described herein comprises a nucleotide sequence encoding a first portion of a fluorescent protein and the target RNA comprises a nucleotide sequence encoding a second portion of a fluorescent protein, wherein the trans-splicing generates an RNA comprising a nucleotide sequence encoding the full-length fluorescent protein, and wherein the trans-splicing event is detected using a method of fluorescent measurement (e.g., FACS).

In embodiments, the composition, system, and/or the one or more nucleic acids comprising one or more nucleotide sequences described herein is introduced to a cell using a method described herein (e.g., via a viral or non-viral vector) for a duration, whereupon RNA from the cell is extracted and trans-splicing products are detected. For example, an mRNA spliced from a target RNA (e.g., a target pre-mRNA) is analyzed by a suitable method known in the art (e.g., end-point or quantitative RT-PCR or RNA sequencing). In some embodiments, a cell or population of cells is contacted with the composition, system, and/or the one or more nucleic acids comprising one or more nucleotide sequences described herein, wherein next-generating sequencing (NGS) techniques are used to determine the extent of trans-splicing. For example, in some embodiments, mRNA extracted from cells treated or contacted with a composition, system, and/or the one or more nucleic acids comprising one or more nucleotide sequences described herein is enzymatically converted into cDNA, which is further by analyzed by NGS analysis to determine the extent of mRNA molecule comprising exonic sequence incorporated from the composition, system, and/or the one or more nucleic acids comprising one or more nucleotide sequences described herein.

In embodiments, trans-splicing is determined by protein sequence analysis of a polypeptide translated from an mRNA spliced from the pre-mRNA. In some embodiments, an RNA-guided molecule corrects a mutation by the incorporation of a corrected exon, wherein translation of the mRNA resulting from trans-splicing of the pre-mRNA and the composition, system, and/or the one or more nucleic acids comprising one or more nucleotide sequences described herein generates a polypeptide comprising an amino acid sequence encoded by the corrected exon. The protein sequence analysis is performed using techniques including, but not limited to, Sanger sequencing, mass spectrometry, functional assays that measure an enzymatic activity of the polypeptide, or immunoblotting using an antibody reactive to the corrected amino acid sequence.

In embodiments, trans-splicing is determined by measuring the activity of a protein translated from an mRNA spliced from the pre-mRNA. For example, in some embodiments, the protein is an enzyme and the method of measuring trans-splicing comprises measuring enzymatic activity using a functional ELISA.

In embodiments, a method for measuring the efficiency of trans-splicing using a composition, system, and/or the one or more nucleic acids comprising one or more nucleotide sequences described herein is described in U.S. application Ser. No. 16/994,230, incorporated herein by reference.

In embodiments, a method for measuring the efficiency of trans-splicing using a composition, system, and/or the one or more nucleic acids comprising one or more nucleotide sequences described herein is any one described in Chen, et al (2009) *Gene Ther* 16:211; Rindt, et al (2012) *Cell Mol Life Sci* 69:4191; Monjaret, et al (2014) *Mol Ther* 22: 1176; Berger, et al (2015) *Mol Ther* 23: 918.

In embodiments, a method described herein is used to measure the efficiency of trans-splicing of a pre-mRNA using a composition, system, and/or the one or more nucleic acids comprising one or more nucleotide sequences described herein.

In embodiments, the introduction of the composition or system to the cell results in an efficiency of trans-splicing that is greater than a composition or system lacking the snRNA or snoRNA sequence.

In embodiments, the efficiency of trans-splicing is greater than about 10%, about 20%, about 30%, about 40%, about 50%, about 60%, about 70%, about 80%, about 90%, or about 99%.

In embodiments, a composition, system, and/or the one or more nucleic acids comprising one or more nucleotide sequences described herein comprising a nucleotide sequence comprising (i) at least one intronic sequence comprising one or more binding domains each having complementarity to a target sequence in the pre-mRNA and a snRNA and/or snoRNA; (ii) one or more splice sites (e.g., a splice acceptor and/or splice donor); and (iii) at least one exonic sequence results in an efficiency of trans-splicing that is greater than the composition, system, and/or the one or more nucleic acids comprising one or more nucleotide sequences described herein without the snRNA and/or snoRNA, as measured using a method described herein. In some embodiments, the composition, system, and/or the one or more nucleic acids comprising one or more nucleotide sequences described herein results in an efficiency of trans-splicing that is increased by at least about 1.5-fold, about 2-fold, about 3-fold, about 4-fold, about 5-fold, about 10-fold, or about 20-fold compared to the efficiency of trans-splicing of a composition, system, and/or the one or more nucleic acids comprising one or more nucleotide sequences described herein without the snRNA and/or snoRNA.

Vectors

In embodiments, the disclosure provides a vector comprising the composition, system, and/or the one or more nucleic acids comprising one or more nucleotide sequences described herein. As used herein, t"e term" "vecto"" refers to a nucleic acid molecule capable of transporting another nucleic acid to which it has been linked. In some embodiments, the vector is a DNA vector. In some embodiments, the vector is circular. In some embodiments, the vector is linear. Non-limiting exemplary vectors include plasmids, phagemids, cosmids, artificial chromosomes, minichromosomes, transposons, viral vectors, and expression vectors.

In embodiments, the vector is an expression vector, wherein the expression vector is capable of directing the expression of nucleic acids to which it is operably linked. As used herein, an "expression vector" or "recombinant expression vector" refers to a replicon, such as plasmid, phage, virus, or cosmid, to which another DNA segment, ".e. an" "inser"", is attached so as to bring about the replication of the attached segment in a cell.

In embodiments, the vector or expression vector is a plasmid. As used he"ein, a" "plasmi"" refers to a circular double-stranded DNA loop into which additional nucleic acid segments are ligated.

In embodiments, the vector or expression vector is a viral vector, wherein additional nucleic acid segments are ligated into the viral genome. Non-limiting exemplary viral vectors include viral vectors based on vaccinia virus; poliovirus; adenovirus; adeno-associated virus; SV40; herpes simplex virus; human immunodeficiency virus; picornaviruses. Non-limiting exemplary viral vectors also include viral vectors based on a retrovirus such as a Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus. In some embodiments, the vectors is for use in eukaryotic target cells and includes, but is not limited to, pXT1, pSG5, pSVK3, pBPV, pMSG, and pSVLSV40 (Pharmacia).

In embodiments, the vector comprises one or more transcription and/or translation control elements. In embodiments, the more transcription and/or translation control elements used depends on the target cell population and the vector system. In embodiments, any number of suitable transcription and translation control elements, including constitutive and inducible promoters, transcription enhancer elements, transcription terminators, etc. are used in the expression vector, such as those further described below.

In embodiments, a vector comprising a composition, system, and/or the one or more nucleic acids comprising one or more nucleotide sequences described herein is operably linked to a control element, e.g., a transcriptional control element, such as a promoter. In embodiments, the transcriptional control element is functional in a eukaryotic cell, e.g., a mammalian cell, e.g., a human cell. In embodiments, the composition, system, and/or the one or more nucleic acids comprising one or more nucleotide sequences described herein is operably linked to one or more control elements that enable expression in eukaryotic cells, e.g., mammalian cells, e.g., human cells.

In embodiments, the expression vector comprises a promoter that is an inducible promoter (e.g., a heat shock promoter, tetracycline-regulated promoter, steroid-regulated promoter, metal-regulated promoter, estrogen receptor-regulated promoter, etc.). Examples of inducible promoters include, but are not limited to, T7 RNA polymerase promoter, T3 RNA polymerase promoter, Isopropyl-beta-D-thiogalactopyranoside (IPTG)-regulated promoter, lactose induced promoter, heat shock promoter, Tetracycline-regulated promoter (e.g., Tet-ON, Tet-OFF, etc.), steroid-regulated promoter, metal-regulated promoter, estrogen receptor-regulated promoter, etc. In some embodiments, an inducible promoters is regulated by molecules including, but not limited to, doxycycline; RNA polymerase, e.g., T7 RNA polymerase; an estrogen receptor; an estrogen receptor fusion; etc.

In embodiments, the promoter is a constitutive promoter (e.g., CMV promoter, UBC promoter).

In embodiments, the promoter is a spatially restricted and/or temporally restricted promoter (e.g., a tissue specific promoter, a cell type specific promoter, etc.). Spatially restricted promoters can also be referred to as enhancers, transcriptional control elements, control sequences, etc. Any convenient spatially restricted promoter is suitable for use in the present disclosure, and the choice of a suitable promoter (e.g., a liver-specific promoter, a brain specific promoter, a promoter that drives expression in a subset of neurons, a promoter that drives expression in the germline, a promoter that drives expression in the lungs, a promoter that drives expression in muscles, a promoter that drives expression in islet cells of the pancreas, etc.) will depend on the organism. For example, various spatially restricted promoters are known for plants, flies, worms, mammals, mice, etc. Thus, a spatially restricted promoter can be used to regulate the expression of a composition, system, and/or the one or more nucleic acids comprising one or more nucleotide sequences described herein in a wide variety of different tissues and cell types, depending on the organism. Some spatially restricted promoters are also temporally restricted such that the promoter is in the "ON" state or "OFF" state during specific stages of embryonic development or during specific stages of a biological process. For illustration purposes, examples of spatially restricted promoters include, but are not limited to, liver-specific promoters, neuron-specific promoters, adipocyte-specific promoters, cardiomyocyte-specific promoters, smooth muscle-specific promoters, photoreceptor-specific promoters, etc.

Suitable promoters for use in the present disclosure include those derived from viruses and are referred to herein as viral promoters, or they include those derived from an organism, including prokaryotic or eukaryotic organisms. In embodiments, a suitable promoter for use in the present disclosure include any promoter that drives expression by an RNA polymerase (e.g., pol I, pol II, pol III).

Exemplary promoters include, but are not limited to, the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6) (Miyagishi et al., Nature Biotechnology 20, 497-500 (2002)), an enhanced U6 promoter (e.g., Xia et al., Nucleic Acids Res. 2003 Sep. 1; 31(17)), a human H1 promoter (H1), and the like.

Exemplary eukaryotic promoters (i.e., promoters functional in a eukaryotic cell) include, but are not limited to, those from cytomegalovirus (CMV) immediate early, herpes simplex virus (HSV) thymidine kinase, early and late SV40, long terminal repeats (LTRs) from retrovirus, human elongation factor-1 promoter (EF1), a hybrid construct comprising the cytomegalovirus (CMV) enhancer fused to the chicken beta-actin promoter (CAG), murine stem cell virus promoter (MSCV), phosphoglycerate kinase-1 locus promoter (PGK), and mouse metallothionein-I.

In embodiments, the disclosure provides a vector comprising a composition, system, and/or the one or more nucleic acids comprising one or more nucleotide sequences described herein and an RNA polymerase III promoter (e.g., U6 and H1). Descriptions of and parameters for enhancing the use of such promoters are known in art, and additional information and approaches are regularly being described; see, e.g., Ma, H. et al., Molecular Therapy—Nucleic Acids 3, e161 (2014).

In embodiments, the expression vector comprises a ribosome binding site for translation initiation and a transcription terminator. In some embodiments, the expression vector comprises appropriate sequences for amplifying expression. In some embodiments, the expression vector comprises nucleotide sequences encoding non-native tags (e.g., histidine tag, hemagglutinin tag, green fluorescent protein, etc.), for example, that are operably-linked to the composition, system, and/or the one or more nucleic acids comprising one or more nucleotide sequences described herein.

Methods of introducing a nucleic acid to a host cell or a population of host cells are known in the art, and any known method can be used to introduce a nucleic acid (e.g., an expression construct) into a cell. In some embodiments, a composition, system, and/or the one or more nucleic acids comprising one or more nucleotide sequences described herein or vector comprising the composition, system, and/or the one or more nucleic acids comprising one or more nucleotide sequences described herein are provided to a population of cells using well-developed transfection techniques; see, e.g. Angel and Yanik (2010) pLOS ONE 5 (7): e 11756, and the commercially available TransMessenger® reagents from Qiagen, Stemfect™ RNA Transfection Kit from Stemgent, and TransIT®-mRNA Transfection Kit from Mims Bio LLC (See, also Beumer et al. (2008). PNAS 105 (50): 19821-19826).

In embodiments, the composition, system, and/or the one or more nucleic acids comprising one or more nucleotide sequences described herein is introduced to the cell or a population of cells as an RNA. In some embodiments, the RNA has chemistries suitable for delivery, tolerability, and stability within cells, e.g., following in vivo or in vitro administration. In some embodiments, the RNA is modified, e.g., comprises a modified sugar moiety, a modified internucleoside linkage, a modified nucleoside, a modified nucleotide and/or combinations thereof. In some embodiments, the modified RNA exhibits one or more of the following properties: is not immune stimu©atory; is nuclease resistant; has improved cell uptake; has increased half-life; has increased translation efficiency; and/or is not toxic to cells or mammals, e.g., following contact with cells in vivo or ex vivo or in vitro.

Delivery Agents

In embodiments, delivery of a composition, system, and/or the one or more nucleic acids comprising one or more nucleotide sequences described herein is performed by one or more methods described herein. In embodiments, the composition, system, and/or the one or more nucleic acids comprising one or more nucleotide sequences described herein is delivered by viral vectors, lipid nonaparticles (LNPs), synthetic polymers, or a combination thereof. In some embodiments, the methods of delivery described herein are suitable for administering a composition, system, and/or the one or more nucleic acids comprising one or more nucleotide sequences described herein nucleic acid of the disclosure to a target cell population or target tissue for the purpose of cellular, ex vivo, or in vivo targeting of a pre-mRNA in the target cell or target tissue for trans-splicing.

In embodiments, the delivery comprises administering the composition, system, and/or the one or more nucleic acids comprising one or more nucleotide sequences described herein as RNA or DNA. In embodiments, the delivery comprises administering the composition, system, and/or the one or more nucleic acids comprising one or more nucleotide sequences described herein as a DNA formulated as an LNP or a polymeric nanoparticle. In some embodiments, the delivery comprises administering composition, system, and/or the one or more nucleic acids comprising one or more nucleotide sequences described herein as an RNA formulated as an LNP or a polymeric nanoparticle.

In embodiments, the delivery comprises administering a recombinant expression vector comprising the composition, system, and/or the one or more nucleic acids comprising one or more nucleotide sequences described herein (e.g., plasmid, viral vector). In some embodiments, the recombinant expression vector is a non-viral vector (e.g., a plasmid). In some embodiments, the recombinant expression vector is a viral vector (e.g., an AAV). In some embodiments, the recombinant expression vector is a circular RNA (cirRNA). In some embodiments, the delivery comprises formulation of the one or more recombinant expression vectors using LNPs or polymeric nanoparticles. In some embodiments, a combination of a viral vector and a non-viral delivery vehicle are used.

In embodiments, the composition, system, and/or the one or more nucleic acids comprising one or more nucleotide sequences described herein are delivered by non-viral delivery vehicles including, but not limited to, nanoparticles, liposomes, ribonucleoproteins, positively charged peptides, small molecule-RNA conjugates, aptamer-RNA chimeras, and RNA-fusion protein complexes. Non-limiting exemplary non-viral delivery vehicles include those described in Peer and Lieberman, Gene Therapy, 18:1127-1133 (2011) (which focuses on non-viral delivery vehicles for siRNA that are also useful for delivery of other polynucleotides).

In embodiments, e.g., for trans-delivery, multiple delivery agents are used to deliver the elements. For example, in embodiments, multiple AAVs are used to deliver the elements. In embodiments, e.g., for trans-delivery, multiple different delivery agents are used to deliver the elements. In embodiments, e.g., for trans-delivery, multiple different delivery agents are used to deliver the elements, e.g., an AAV and a different delivery agent, e.g., an LNP.

Viral Delivery

In some embodiments, the composition or system is introduced to the cell by a single viral vector, such as AAV. In some embodiments, the viral vector (e.g., AAV vector) comprises one or more composition, system, and/or the one or more nucleic acids comprising one or more nucleotide sequences described herein. In some embodiments, the cloning capacity of the viral vector is sufficient to deliver the composition, system, and/or the one or more nucleic acids comprising one or more nucleotide sequences described herein.

In some embodiments, a recombinant adeno-associated virus (rAAV) vector is used for delivery. Techniques to produce rAAV particles, in which an AAV genome to be packaged that includes the polynucleotide to be delivered (e.g., nucleic acid encoding one or more gRNAs and/or a site-directed endonuclease), rep and cap genes, and helper virus functions are provided to a cell are standard in the art. Production of rAAV typically requires that the following components are present within a single cell (denoted herein as a packaging cell): a rAAV genome, AAV rep and cap genes separate from (i.e., not in) the rAAV genome, and helper virus functions. The AAV rep and cap genes can be from any AAV serotype for which recombinant virus can be derived, and can be from a different AAV serotype than the rAAV genome ITRs, including, but not limited to, AAV serotypes AAV-1, AAV-2, AAV-3, AAV-4, AAV-5, AAV-6, AAV-7, AAV-8, AAV-9, AAV-10, AAV-11, AAV-12, AAV-13 AAV rh.74 and tropism modified AAV vectors. Production of pseudotyped rAAV is disclosed in, for example, U.S. Pat. No. 7,056,602.

In some embodiments, a method of generating a packaging cell involves creating a cell line that stably expresses all of the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing (Samulski et al., 1982, Proc. Natl. Acad. S6. USA, 79:2077-2081), addition of synthetic linkers containing restriction endonuclease cleavage sites (Laughlin et al., 1983, Gene, 23:65-73) or by direct, blunt-end ligation (Senapathy & Carter, 1984, J. Biol. Chem., 259:4661-4666). The packaging cell line can then be infected with a helper virus, such as adenovirus. The advantages of this method are that the cells are selectable and are suitable for large-scale production of rAAV. Other examples of suitable methods employ adenovirus or baculovirus, rather than plasmids, to introduce rAAV genomes and/or rep and cap genes into packaging cells.

General principles of rAAV production are reviewed in, for example, Carter, 1992, Current Opinions in Biotechnology, 1533-539; and Muzyczka, 1992, Curr. Topics in Microbial. And Immunol., 158:97-129). Various approaches are described in Ratschin et al., Mol. Cell. Biol. 4:2072 (1984); Hermonat et al., Proc. Natl. Acad. Sci. USA, 81:6466 (1984); Tratschin et al., Mol. Cell. Biol. 5:3251 (1985); Mclaughlin et al., J. Virol., 62:1963 (1988); and Lebkowski et al., 1988 Mol. Cell. Biol., 7:349 (1988). Samulski et al. (1989, J. Virol., 63:3822-3828); U.S. Pat. No. 5,173,414; WO 95/13365 and corresponding U.S. Pat. No. 5,658,776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al. (1995) Vaccine 13:1244-1250; Paul et al. (1993) Human Gene Therapy 4:609-615; Clark et al. (1996) Gene Therapy 3:1124-1132; U.S. Pat. Nos. 5,786,211; 5,871,982; and 6,258,595.

In addition to adeno-associated viral vectors, other viral vectors can be used. Such viral vectors include, but are not limited to, adenovirus, lentivirus, alphavirus, enterovirus, pestivirus, baculovirus, herpesvirus, Epstein Barr virus, papovavirus, poxvirus, vaccinia virus, and herpes simplex virus.

Nanoparticle Compositions

In some embodiments, the composition or system for targeting trans-splicing of a pre-mRNA in a cell comprising one or more nucleic acids comprising one or more nucleotide sequences is delivered to a host cell (e.g., ex vivo) or a subject by a nanoparticle (e.g., a lipid nanoparticle). In some embodiments, the nucleic acid or expression vector is formulated in nanoparticles or other delivery vehicles, (e.g., polymeric nanoparticles) to facilitate cellular uptake and/or to protect them from degradation when delivered to a subject.

In embodiments, the composition or system is formulated as a lipid nanoparticle. Lipid nanoparticles include, but are not limited to, liposomes and micelles. Any number of lipids may be present, including cationic and/or ionizable lipids, anionic lipids, neutral lipids, amphipathic lipids, conjugated lipids (e.g., PEGylated lipids), and/or structural lipids. Such lipids can be used alone or in combination.

Nanoparticles are ultrafine particles typically ranging between 1 and 100 to 500 nanometers (nm) in size with a surrounding interfacial layer and often exhibiting a size-related or size-dependent property. Nanoparticle compositions are myriad and encompass lipid nanoparticles (LNPs), liposomes (e.g., lipid vesicles), and lipoplexes. For example, a nanoparticle composition can be a liposome having a lipid bilayer with a diameter of 500 nm or less. In some embodiments, nanoparticle compositions are vesicles including one or more lipid bilayers. In certain embodiments, a nanoparticle composition includes two or more concentric bilayers separated by aqueous compartments. Lipid bilayers can be functionalized and/or crosslinked to one another. Lipid bilayers can include one or more ligands, proteins, or channels.

In embodiments, the nanoparticle composition comprises a composition, system, and/or the one or more nucleic acids comprising one or more nucleotide sequences described herein and/or a recombinant expression vector comprising the composition, system, and/or the one or more nucleic acids comprising one or more nucleotide sequences described herein.

In embodiments, the disclosure provides LNP compositions comprising: (a) a composition, system, and/or the one or more nucleic acids comprising one or more nucleotide sequences described herein or an expression vector comprising the composition, system, and/or the one or more nucleic acids comprising one or more nucleotide sequences described herein; and (b) one or more lipid moieties selected from the group consisting of amino lipids, helper lipids, structural lipids, phospholipids, ionizable lipids, PEG lipids, lipoid, and cholesterol or cholesterol derivatives. In some embodiments, the disclosure provides LNP compositions comprising: (a) a composition, system, and/or the one or more nucleic acids comprising one or more nucleotide sequences described herein or an expression vector comprising the composition, system, and/or the one or more nucleic acids comprising one or more nucleotide sequences described herein; and (b) one or more lipid moieties selected from the group consisting of ionizable lipids, amino lipids, anionic lipids, neutral lipids, amphipathic lipids, helper lipids, structural lipids, PEG lipids, and lipoids, and optionally (c) targeting moieties.

In some embodiments, the LNP composition comprise one or more lipid moieties promote or enhances cellular uptake by the apolipoprotein E (apoE)-low density lipoprotein receptor (LDLR) pathway. For example, certain ionizable lipids are known in the art for increasing cellular uptake of LNPs by the apoE-LDLR pathway (see, e.g., Semple, et al (2010) NAT BIOTECH 28:172). In some embodiments, the LNP composition comprises one or more lipid moieties that promote or enhances cellular uptake by an apoE-LDLR independent pathway.

In some embodiments, the LNPs of the present disclosure are formed by any method known in the art including, but not limited to, a continuous mixing method, a direct dilution process, and an in-line dilution process. Additional techniques and methods suitable for the preparation of the LNPs described herein include coacervation, microemulsions, supercritical fluid technologies, phase-inversion temperature (PIT) techniques.

Pharmaceutical Compositions

In embodiments, the disclosure provides pharmaceutical compositions comprising the composition or system of any one of the embodiments described herein, the viral vector of any one of the embodiments described herein, or the lipid nanoparticle of any one of the embodiments described herein, and a pharmaceutically acceptable carrier.

In embodiments, the pharmaceutical composition comprises (1) an expression vector comprising one or more nucleic acids comprising one or more nucleotide sequences described herein, and (2) a pharmaceutically acceptable carrier or diluent. In some embodiments, the pharmaceutical composition comprises one or more nucleic acids comprising one or more nucleotide sequences or recombinant expression vector (e.g., AAV) comprising the one or more nucleic acids comprising one or more nucleotide sequences formulated as a lipid composition (e.g., LNP), and (2) a pharmaceutically acceptable carrier or diluent. In some embodiments, the pharmaceutical composition comprises a therapeutically effective amount of the one or more nucleic acids comprising one or more nucleotide sequences or recombinant expression vectors.

Exemplary pharmaceutically acceptable excipients such as carriers, solvents, stabilizers, adjuvants, diluents, etc., depending upon the particular mode of administration and dosage form. Contemplated pharmaceutical compositions can be generally formulated to achieve a physiologically compatible pH, depending on the formulation and route of administration. In some embodiments, the compositions comprise a therapeutically effective amount of one or more nucleic acids comprising one or more nucleotide sequences or recombinant expression vectors, together with one or more pharmaceutically acceptable excipients.

Suitable excipients can include, for example, carrier molecules that include large, slowly metabolized macromolecules. Other exemplary excipients can include antioxidants, chelating agents, carbohydrates, stearic acid, liquids such as oils, water, saline, glycerol and ethanol, wetting or emulsifying agents, pH buffering substances, and the like.

Pharmaceutical compositions can be formulated into preparations in solutions, suppositories, injections. In some embodiments, the pharmaceutical composition is formulated to result in systemic administration of the composition, system, and/or the one or more nucleic acids comprising one or more nucleotide sequences described herein or recombinant expression vectors, for example, following enteral or parenteral administration. In some embodiments, the pharmaceutical composition is formulated to result in localized administration of the composition, system, and/or the one or more nucleic acids comprising one or more nucleotide sequences described herein, and/or the viral vectors, for example, following regional administration or implantation. In some embodiments, the pharmaceutical composition is formulated for immediate activity or for sustained release of the composition, system, and/or the one or more nucleic acids comprising one or more nucleotide sequences described herein, and/or the viral vectors or recombinant expression vectors.

Typically, an effective amount the composition, system, and/or the one or more nucleic acids comprising one or more nucleotide sequences described herein, and/or viral vector described herein, can be provided, for example, for use in a method of treating a subject having a disease or disorder. Methods of calculating the effective amount or effective dose are within the skill of one of ordinary skill in the art. The final amount to be administered is dependent upon the route of administration and upon the nature of the disorder that is to be treated. A competent clinician will be able to determine an effective amount of the composition, system, and/or the one or more nucleic acids comprising one or more nucleotide sequences described herein, recombinant expression vectors, or delivery system described herein to administer to the patient to halt or reverse the progression of the disorder.

In some embodiments, based on animal data, and other information available for the trans-splicing system, a clinician can determine the maximum safe dose for an individual, depending on the route of administration. For instance, an intravenously administered dose can be more than an intrathecally administered dose, given the greater body of fluid into which the therapeutic composition is being administered. Similarly, compositions which are rapidly cleared from the body can be administered at higher doses, or in repeated doses, in order to maintain a therapeutic concentration. Utilizing ordinary skill, the competent clinician will be able to optimize the dosage of a particular therapeutic in the course of routine clinical trials.

For inclusion in a medicament, the composition, system, and/or the one or more nucleic acids comprising one or more nucleotide sequences described herein, including the viral vector described herein, can be obtained from a suitable commercial source. In some embodiments, therapies based on the composition, system, and/or the one or more nucleic acids comprising one or more nucleotide sequences described herein, and/or the viral vector, recombinant expression vectors, or delivery system described herein to be used for therapeutic administration, must be sterile. Therapeutic compositions can be generally placed into a container having a sterile access port, for example, an intravenous solution bag or vial having a stopper pierceable by a hypodermic injection needle. In some embodiments, the therapeutic components are stored in unit or multi-dose containers, for example, sealed ampules or vials, as an aqueous solution or as a lyophilized formulation for reconstitution.

Methods and Use

In embodiments, the disclosure provides cellular, ex vivo, in vitro, and/or in vivo methods comprising use of the compositions, systems, and/or the one or more nucleic acids comprising one or more nucleotide sequences described herein to target trans-splicing of a target RNA (e.g., pre-mRNA) in a cell. In some embodiments, the methods comprise use of the composition, system, and/or the one or more nucleic acids comprising one or more nucleotide sequences described herein to correct a mutation in a target RNA (e.g., pre-mRNA). In some embodiments, the disclosure provides methods of treating a patient with a disease or disorder, comprising administering a composition, system, and/or the one or more nucleic acids comprising one or more nucleotide sequences described herein, the viral vector, or pharmaceutical composition described herein to target trans-splicing of a target RNA (e.g., pre-mRNA) in a target cell population and/or target tissue, thereby treating the disease or disorder.

Figure 17:
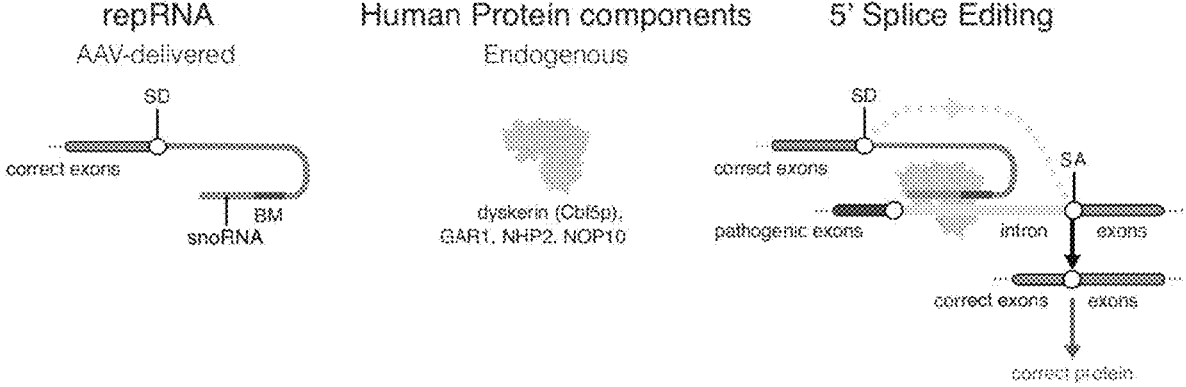
FIG. 17 is a non-limiting pictorial representation of an AAV-deliverable snoRNA-based trans-splicing molecule.

Without wishing to be bound by theory, in embodiments, trans-splicing methods with snoRNA exhibit higher activity and/or efficiency than methods of trans-splicing using snRNA, or other RNA-based methods. Traditionally, without wishing to be bound by theory, snoRNAs have not been incorporated into long ncRNA for splicing because they form secondary and tertiary structures (e.g., lariat) that are generally processed into smaller RNAs, which limits their use. In embodiments, the snoRNA sequence binds a ribonucleoprotein (RNP), such as dyskerin (Cbf5p), GAR1, NHP2, NOP10, etc., to direct trans-splicing of the pre-mRNA target sequence (e.g., as shown in FIG. 17).

In embodiments, the method for trans-splicing of a pre-mRNA target sequence comprises introducing into a cell one or more trans-splicing RNA molecules comprising one or more small nucleolar RNA (snoRNA) sequence of about 7 to about 300 nucleotides in length, at least one splice acceptor site or splice donor site (e.g., at a boundary of one or more intron/exon), one or more binding domains comprising a nucleic acid sequence that binds to one or more pre-mRNA target sequences, and replacing at least a portion of the pre-mRNA target sequence. In embodiments, at least a portion of the one or more trans-splicing RNA molecules recognizes one or more pre-mRNA target sequences. In embodiments, the method comprises splicing at least one exonic sequence into the pre-mRNA target sequence.

In embodiments, the RNA trans-splicing molecule of methods herein is oriented 3' to 5' or 5' to 3', e.g., with a snoRNA sequence at the 5' end or 3' end of the molecule. In embodiments, the RNA trans-splicing molecule is snoRNA-based and uses a H/ACA for 5' editing, which is placed on 3' end of one or more intronic sequence. In embodiments, the RNA trans-splicing molecule is snoRNA-based and uses a C/D box for 3' editing, which is placed on 5' end of one or more intronic sequence.

In embodiments, the RNA trans-splicing molecule is snoRNA-based and comprises one or more target binding domain (e.g., anti-sense region (ASR)), located within the snoRNA region and/or outside the snoRNA region.

In embodiments, the snoRNA comprises H/ACA box consensus sequences, where the H consensus sequence is oriented 5' (upstream) of an ACA consensus sequence. In embodiments, the snoRNA sequence comprises at least one binding domain sequence positioned: (i) upstream the H consensus sequence; (ii) downstream the ACA consensus sequence; (iii) between the H consensus sequence and the ACA consensus sequence; or (iv) a combination of (i)-(iii).

In embodiments, the snoRNA comprises C/D box consensus sequences. In embodiments, the C/D box consensus sequence, oriented 5' to 3', comprises a C consensus sequence, a D' consensus sequence, a C' consensus sequence, and a D consensus sequence. In embodiments, the snoRNA sequence comprises the snoRNA sequence comprises at least one binding domain positioned (i) upstream the C consensus sequence; (ii) between the C consensus sequence and the D' consensus sequence; (iii) between the D' consensus sequence and the C' consensus sequence; (iv) between the C' consensus sequence and the D consensus sequence; (v) downstream the D consensus sequence; or (vi) a combination of (i)-(v).

In embodiments, the snoRNA sequence binds a ribonucleoprotein (RNP) to direct trans-splicing of the pre-mRNA target sequence.

In embodiments, the RNA trans-splicing comprises a snoRNA and one or more additional intronic RNA sequences. In embodiments, the one or more additional intronic RNA sequences comprises one or more snRNA. In embodiments, the snRNA is selected from a U7 snRNA, a U1 snRNA, a U2 snRNA, a U4 snRNA, a U4atac snRNA, a U5 snRNA, a U6 snRNA, a U6atac snRNA, a U11 snRNA, and a U12 snRNA. In embodiments, the snRNA is a U7 snRNA. In embodiments, the snRNA and/or snoRNA sequence assembles into an RNP. In embodiments, the snRNA and/or snoRNA sequence comprises a sequence motif that assembles into an RNP.

Persons skilled in the art, with the benefit of this disclosure in its entirety, will be aware of the methods to identify various sequence motifs (snoRNA, snRNA, or otherwise) which may bind RNPs and/or act as splice signals (e.g., splice acceptor, splice donor, etc.), for example using tools such as SPLICEAI, as described in Jaganathan, et al. "Predicting Splicing from Primary Sequence with Deep Learning," (2019) Cell, Vol. 176: pp. 535-548, the entire contents of which are incorporated by reference, and/or using PANGOLIN, as described in Zeng & Li, "Predicting RNA splicing from DNA sequence using Pangolin," (2022), *Genome Biology*, Vol. 23, Article 103, the entire contents of which are incorporated by reference.

In embodiments, the RNA trans-splicing methods, compositions, and/or systems further comprises one or more proteins that forms, is associated with, or is within, an RNP. In embodiments, the RNA trans-splicing methods, compositions, and/or systems further comprises one or more nucleic acid sequences encoding one or more proteins that are associated with, or are within, the RNP. In embodiments, the RNP is associated with an snRNA and/or snoRNA. In embodiments, the methods comprise introduction into the cell a plasmid, viral vector, non-viral vector, or circular RNA (cirRNA) which encodes one or more proteins for RNP formation.

In embodiments, the trans-splicing RNA comprises one or more binding domains, each comprising about 4 nucleotides to about 300 nucleotides. In embodiments, the one or more binding domains are located outside the snoRNA sequence. In embodiments, the one or more binding domains are located within the snoRNA sequence (e.g., between one or more H/ACA box consensus sequences, or between one or more C/D box consensus sequences). In embodiments, the one or more binding domains are located both within and outside of the snoRNA sequence. In embodiments, the snoRNA comprises 2 binding domain sequences, or comprises more than 2 binding domains (e.g., comprises 3 binding domains, 4 binding domains, 5 binding domains, etc.). In embodiments, the one or more binding domain sequences is about 5 to about 20, about 5 to about 30, about 5 to about 40, about 5 to about 50, about 10 to about 50, about 10 to about 100, about 20 to about 100, about 30 to about 100, about 40 to about 100, about 50 to about 100, about 50 to about 150, about 50 to about 200, about 50 to about 250, about 100 to about 150, about 100 to about 200, about 100 to about 250, or about 100 to about 300 nucleotides in length, including size ranges therebetween, each binding domain having at least 80% complementarity to a pre-mRNA target sequence.

In embodiments, the one or more binding domain sequences is a reverse complementary sequence (e.g., relative to the pre-mRNA target sequence) that comprises about or at least about 80% complementarity to one or more pre-mRNA target sequence, about or at least about 85% complementarity to one or more pre-mRNA target sequence, about or at least about 90% complementarity to one or more pre-mRNA target sequence, about or at least about 95% complementarity to one or more pre-mRNA target sequence, about or at least about 96% complementarity to one or more pre-mRNA target sequence, about or at least about 97% complementarity to one or more pre-mRNA target sequence, about or at least about 98% complementarity to one or more pre-mRNA target sequence, or about or at least about 99% complementarity to one or more pre-mRNA target sequence, including percent identity therebetween.

In embodiments, the one or more reverse complimentary sequences between the one or more binding domains and one or more pre-mRNA target sequences is about 4 nucleotides to about 20,000 nucleotides or more in length (e.g., about or at least about 100 nucleotides, 500 nucleotides, 1000 nucleotides, 2000 nucleotides, 3000 nucleotides, 4000 nucleotides, 5000 nucleotides, 6000 nucleotides, 7000 nucleotides, 8000 nucleotides, 9000 nucleotides, 10000 nucleotides, 15000 nucleotides, 20000 nucleotides, etc., including size ranges therebetween).

In embodiments, the pre-mRNA target sequence comprises an USH2A pre-mRNA sequence, or wherein the target comprises intron 12 and/or exon 13 of the USH2A pre-mRNA.

In embodiments, the snoRNA comprises one or more M6A sites. In embodiments, the snoRNA comprises at least 1, 2, 3 4, 5, 6, 7, 8, 9, 10, 11, 12, 13, 14, 15, 16, 17, 18, 19, 20, 21, 22, 23, 24, 25, 26, 27, 28, 29, 30, 40, or 50 or more M6A sites.

In embodiments, the snoRNA comprises a nucleic acid sequence of SNORA101B, SNORA48, SNORA54, SNORA66, SNORA73A, or SNORA8; or one of SNORA101B, SNORA48, SNORA54, SNORA66, SNORA73A, or SNORA8 comprising one or more nucleic acid substitutions, deletions, or extensions relative to a wild-type sequence.

In embodiments, the snoRNA nucleic acid sequence has at least about 90%, about 95%, about 98%, or about 99% identity to a nucleic acid selected from any one of SEQ ID NOs: 590-628, 630-632, 634-635, 638, 640, 642, 644-645, 647-648, 650, 652-653, 655, 657, 732-737, 741-746, 748-749, 751-758, 760-761, 763-765, 767, 771-774, 776-778, and 780-789 (e.g., Table 6). In embodiments, the snoRNA nucleic acid sequence comprises a nucleic acid sequence selected from any one of SEQ ID NOs: 590-628, 630-632, 634-635, 638, 640, 642, 644-645, 647-648, 650, 652-653, 655, 657, 732-737, 741-746, 748-749, 751-758, 760-761, 763-765, 767, 771-774, 776-778, and 780-789.

In embodiments, the at least one intronic sequence comprises one or more splicing signals, e.g., as described herein. In embodiments, the one or more splicing signals comprise one or more of an exonic splicing enhancer (ESE), an intronic splicing enhancer (ISE), an exonic splicing silencer (ESS), intronic splicing silencer (ISS), a polypyrimidine tract, a branch point, and a combination thereof. In embodiments, the one or more splicing signals includes splice acceptors and/or splice donors. In embodiments, the one or more splicing signals includes cryptic splice sites (css). In embodiments, the one or more splicing signals includes a boundary sequence between an intron and an exon. In embodiments, the one or more splicing signals includes one or more splice sites, including sequence regions where splicing factors (e.g., like U1, etc.) and/or complex formation with splicing factors, and/or splicing factor recruitment occurs, whether or not splicing takes place at such sites. Persons skilled in the art, with the benefit of this disclosure in its entirety, will be aware of the methods to identify various splicing signals (ESE, ISE, ESS, ISS, polypyrimidine tract, branch point, css, SA, SD, etc.) and various sequences thereof, including sequences which may recruit or form RNPs and/or act as splice signals, for example using tools such as SPLICEAI (as described in Jaganathan, et al. 2019) and/or PANGOLIN (as described in Zeng & Li, 2022). In embodiments, the trans-splicing RNA molecule comprises one or more polypyrimidine tracts (PPT), branch points (BP), and splice acceptors (SA), optionally comprising one or more splice donor (SD), and is suitable for 3' editing of the pre-mRNA target sequence.

In embodiments, the trans-splicing RNA molecule comprises one or more splice donors (SD), and optionally comprises one or more polypyrimidine tracts, branch points, and splice acceptors (SA), and is suitable for 5' editing of the pre-mRNA target sequence.

In embodiments, the trans-splicing RNA molecule further comprises one or more ribozyme sites, e.g., as described herein. In embodiments, the one or more ribozyme sites comprises a hairpin, hammerhead, hepatitis delta virus (HDV), twister ribozyme site, Varkud satellite (VS), or glmS ribozyme site, or a variant thereof. In embodiments, the ribozyme removes the 3' UTR of the trans-splicing molecule.

In embodiments, the trans-splicing molecule comprises a sequence of MALAT1 and/or NEAT1 (e.g., SEQ ID NO: 712).

In embodiments, the trans-splicing RNA molecule further comprises one or more of a 5' cap, 5' UTR, 3' untranslated region (UTR), and 3' polyA signal/tail.

In embodiments, the method comprises introducing the one or more trans-splicing RNA molecules into one or more cells. In embodiments, the introduction further comprises contacting the cell with a plasmid, viral vector, non-viral vector, or circular RNA (cirRNA) encoding the one or more trans-splicing RNA molecules. In embodiments, the introduction further comprises contacting the cell with multiple plasmids, viral vectors, non-viral vectors, or circular RNAs (cirRNAs), each encoding distinct trans-splicing RNA molecules. In embodiments, the contacting the cell comprises using a delivery vehicle comprising a lipid nanoparticle (LNP) or polymeric nanoparticles (e.g., wherein the nucleic acid payload is encapsulated in the delivery vehicle components). In embodiments, the viral vector is an adenoviral vector (AAV).

In aspects, described herein are AAV-based vectors for use in performing methods herein as a delivery vehicle to target cells for trans-splicing. In embodiments, the AAV is a cell-specific trans-serotypes for cell-specific delivery. In embodiments, method herein comprise using AAVs encoding one or more trans-splicing nucleic acids, e.g., as described herein.

Cellular RNA Editing

In embodiments, the method comprises introducing a composition, system, and/or the one or more nucleic acids comprising one or more nucleotide sequences described herein, the viral vector, or pharmaceutical composition described herein to a cell or cell population. In some embodiments, the method comprises contacting the cell with a composition, system, and/or the one or more nucleic acids comprising one or more nucleotide sequences described herein, the viral vector, or pharmaceutical composition described herein. In some embodiments, the cell is a eukaryotic cell. In some embodiments, the eukaryotic cell is a mammalian cell. In some embodiments, the eukaryotic cell is a rodent cell. In some embodiments, the eukaryotic cell is a human cell. In some embodiments, the cell is a patient-derived cell.

The composition, system, and/or the one or more nucleic acids comprising one or more nucleotide sequences described herein, the viral vector, or pharmaceutical composition described herein may be introduced into the cell via any methods known in the art, such as, e.g., viral or bacteriophage infection, transfection, conjugation, protoplast fusion, lipofection, electroporation, calcium phosphate precipitation, polyethyleneimine (PEI)-mediated transfection, DEAE-dextran-mediated transfection, liposome-mediated transfection, particle gun technology, calcium phosphate precipitation, shear-driven cell permeation, fusion to a cell-penetrating peptide followed by cell contact, microinjection, and nanoparticle-mediated delivery. In some embodiments, the vector system may be introduced into the cell via viral infection.

In embodiments, the disclosure provides a method for targeting trans-splicing of a target RNA (e.g., pre-mRNA) in a cell, the method comprising contacting the cell with a composition, system, and/or the one or more nucleic acids comprising one or more nucleotide sequences described herein, the viral vector, or pharmaceutical composition described herein, wherein when the cell is contacted with the composition, system, and/or the one or more nucleic acids comprising one or more nucleotide sequences described herein, the viral vector, or pharmaceutical composition described herein, the one or more binding domains of the one or more nucleic acids comprising one or more nucleotide sequences described herein binds to the target RNA (e.g., pre-mRNA) and trans-splicing results in ligation of one or more exons of the target RNA (e.g., pre-mRNA) to one or more exons of the one or more nucleic acids comprising one or more nucleotide sequences described herein.

In embodiments, the disclosure provides a method for targeting trans-splicing of a pre-mRNA in a cell or a population of cells comprising a disease-causing mutation, the method comprising contacting the cell or population of cells with a composition, system, and/or the one or more nucleic acids comprising one or more nucleotide sequences described herein, the viral vector, or pharmaceutical composition described herein, wherein when the cell is contacted with the one or more nucleic acids comprising one or more nucleotide sequences described herein, the one or more binding domains of the one or more nucleic acids comprising one or more nucleotide sequences described herein binds to the pre-mRNA and trans-splicing results in ligation of one or more exons of the pre-mRNA to one or more exons of the one or more nucleic acids comprising one or more nucleotide sequences described herein, thereby resulting in a mRNA lacking the disease-causing mutation.

In embodiments, the disclosure provides a method for targeting trans-splicing of a pre-mRNA in a cell or a population of cells derived from a patient having a disease or disorder, the method comprising contacting the cell or population of cells with a one or more nucleic acids comprising one or more nucleotide sequences described herein, the viral vector, or pharmaceutical composition described herein, wherein when the cell or population of cells is contacted with the composition, system, and/or the one or more nucleic acids comprising one or more nucleotide sequences described herein, the viral vector, or pharmaceutical composition described herein, the one or more binding domains of the one or more nucleic acids comprising one or more nucleotide sequences described herein binds to the target RNA (e.g., pre-mRNA) and trans-splicing results in ligation of one or more exons of the target RNA (e.g., pre-mRNA) to one or more exons of the one or more nucleic acids comprising one or more nucleotide sequences described herein, wherein the cell or population of cells is reintroduced to the patient, thereby treating or ameliorating the disease or disorder.

In Vivo RNA Editing

The present disclosure provides methods for treating a patient having a disease or disorder using the composition, system, and/or the one or more nucleic acids comprising one or more nucleotide sequences described herein, the viral vector, or pharmaceutical composition described herein. In some embodiments, the disease or disorder is associated with one or more mutations in a target RNA, wherein the method targets trans-splicing of the target RNA to remove the one or more mutations.

In embodiments, the disclosure provides a method of treating a patient having a disease or disorder, comprising administering to the patient a composition, system, and/or the one or more nucleic acids comprising one or more nucleotide sequences described herein, the viral vector, or pharmaceutical composition described herein.

In embodiments, the disclosure provides a method of treating a patient having a disease or disorder by targeting trans-splicing of a target RNA (e.g. pre-mRNA) in a target tissue or cell population, the method comprising administering to the patient a composition, system, and/or the one or more nucleic acids comprising one or more nucleotide sequences described herein, the viral vector, or pharmaceutical composition described herein, wherein when the composition, system, and/or the one or more nucleic acids comprising one or more nucleotide sequences described herein, the viral vector, or pharmaceutical composition described herein is administered the one or more nucleic acids comprising one or more nucleotide sequences described herein binds to a target RNA (e.g., pre-mRNA) and trans-splicing results in ligation of one or more exons of the target RNA (e.g., pre-mRNA) to one or more exons of the composition, system, and/or the one or more nucleic acids comprising one or more nucleotide sequences described herein, thereby treating or ameliorating the disease or disorder.

In embodiments, the disclosure provides a method of treating a patient having a disease or disorder associated with one or more mutations in a pre-mRNA in a target tissue or cell population, the method comprising administering to the patient a composition, system, and/or the one or more nucleic acids comprising one or more nucleotide sequences described herein, the viral vector, or pharmaceutical composition described herein, wherein when the composition, system, and/or the one or more nucleic acids comprising one or more nucleotide sequences described herein is administered, the one or more nucleic acids comprising one or more nucleotide sequences described herein binds to a pre-mRNA and trans-splicing results in ligation of one or more exons of the pre-mRNA to one or more exons of the one or more nucleic acids comprising one or more nucleotide sequences described herein, wherein the trans-splicing results in an mRNA lacking the disease-causing mutation, thereby treating or ameliorating the disease or disorder.

In embodiments, the route of administration is any sufficient for delivery of the composition, system, and/or the one or more nucleic acids comprising one or more nucleotide sequences described herein, the viral vector, or pharmaceutical composition described herein to the target tissue or cell population ascertained by one of skill in the art.

In embodiments, administration of the composition, system, and/or the one or more nucleic acids comprising one or more nucleotide sequences described herein, the viral vector, or pharmaceutical composition described herein results in correction of a mutation in a pre-mRNA in a target tissue or cell population in the patient.

The term "treatment" refers to the application of one or more methods described herein for the amelioration of a disease. In some embodiments, the specific procedure is the administration of a composition, system, and/or the one or more nucleic acids comprising one or more nucleotide sequences described herein, the viral vector, or pharmaceutical composition described herein. "Treatment" of an individual (e.g. a mammal, such as a human) or a cell is any type of intervention used in an attempt to alter the natural course of the individual or cell. Treatment includes, but is not limited to, administration of a composition, system, and/or the one or more nucleic acids comprising one or more nucleotide sequences described herein, the viral vector, or pharmaceutical composition described herein, and may be performed either prophylactically or subsequent to the initiation of a pathologic event or contact with an etiologic agent. Treatment includes any desirable effect on the symptoms or pathology of a disease or condition, and may include, for example, minimal changes or improvements in one or more measurable markers of the disease or condition, and may include, for example, minimal changes or improvements in one or more measurable markers of the disease or condition being treated.

The terms "patient," "subject," "individual," and the like are used interchangeably herein, and refer to any animal amenable to the methods described herein. In some embodiments, the patient, subject, or individual is a human.

Kits

The present disclosure provides kits for carrying out the methods described herein. In some embodiments, the kit comprises a composition, system, and/or the one or more nucleic acids comprising one or more nucleotide sequences described herein, the viral vector, or pharmaceutical composition described herein.

In some embodiments, the kit comprises a composition, system, and/or the one or more nucleic acids comprising one or more nucleotide sequences described herein, the viral vector, or pharmaceutical composition described herein and a reagent for reconstitution and/or dilution of the composition, system, and/or the one or more nucleic acids comprising one or more nucleotide sequences described herein, the viral vector, or pharmaceutical composition described herein.

In some embodiments, the kit comprise one or more additional reagents, where such additional reagents are selected from a buffer, a buffer for introducing the composition, system, and/or the one or more nucleic acids comprising one or more nucleotide sequences described herein, recombinant expression vector, delivery system into a cell, a wash buffer, a control reagent, a control vector, a control polynucleotide, a reagent for in vitro production of the recombinant expression vector or delivery system, adaptors for sequencing and the like. A buffer can be a stabilization buffer, a reconstituting buffer, a diluting buffer, or the like. A kit can also comprise one or more components that can be used to facilitate or enhance the on-target binding or the trans-splicing of the composition, system, and/or the one or more nucleic acids comprising one or more nucleotide sequences described herein.

In addition to the above-mentioned components, a kit can further comprise instructions for using the components of the kit to practice the methods. The instructions for practicing the methods can be recorded on a suitable recording medium. For example, the instructions can be printed on a substrate, such as paper or plastic, etc. The instructions can be present in the kits as a package insert, in the labeling of the container of the kit or components thereof (i.e., associated with the packaging or subpackaging), etc. The instructions can be present as an electronic storage data file present on a suitable computer readable storage medium, e.g. CD-ROM, diskette, flash drive, etc. In some instances, the actual instructions are not present in the kit, but means for obtaining the instructions from a remote source (e.g. via the Internet), can be provided. An example of this case is a kit that comprises a web address where the instructions can be viewed and/or from which the instructions can be downloaded. As with the instructions, this means for obtaining the instructions can be recorded on a suitable substrate.

In some embodiments, the kit comprises a container comprising the composition, system, and/or the one or more nucleic acids comprising one or more nucleotide sequences described herein, the viral vector, or pharmaceutical composition described herein described herein, and instructions for use targeting trans-splicing of a target RNA (e.g., pre-mRNA) in a cell or a population of cells.

In some embodiments, the kit comprises a container comprising the composition, system, and/or the one or more nucleic acids comprising one or more nucleotide sequences described herein, the viral vector, or pharmaceutical composition described herein, and instructions for administering the one or more nucleic acids comprising one or more nucleotide sequences, the recombinant expression vector, the delivery system, or the pharmaceutical composition to a patient in need thereof to target trans-splicing of a target RNA (e.g., pre-mRNA) in a cell or a population of cells of the patient.

In various embodiments, the "subject" refers to any animal (e.g., a mammal), including, but not limited to, humans, and non-human animals (including, but not limited to, non-human primates, dogs, cats, rodents, horses, cows, pigs, mice, rats, hamsters, rabbits, and the like (e.g., which is to be the recipient of a particular treatment, or from whom cells are harvested)). In embodiments, the subject is a human.

It will also be understood that, although the terms first, second, etc., may be used herein to describe various elements, these elements should not be limited by these terms.

These terms are only used to distinguish one element from another. For example, a first subject could be termed a second subject, and, similarly, a second subject could be termed a first subject, without departing from the scope of the present disclosure. The first subject and the second subject are both subjects, but they are not the same subject. Furthermore, the terms "subject," "user," and "patient" are used interchangeably herein.

As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features. Although the open-ended term "comprising," as a synonym of terms such as including, containing, or having, is used herein to describe and claim the disclosure, the present technology, or embodiments thereof, may alternatively be described using more limiting terms such as "consisting of" or "consisting essentially of" the recited ingredients.

Unless defined otherwise, all technical and scientific terms herein have the same meaning as commonly understood by one of ordinary skill in the art to which this disclosure belongs. Although any methods and materials, similar or equivalent to those described herein, can be used in the practice or testing of the present disclosure, the preferred methods and materials are described herein. All publications, patents, and patent publications cited are incorporated by reference herein in their entirety for all purposes.

This disclosure is further illustrated by the following non-limiting examples.

EXAMPLES

Example 1: Selection of ncRNAs

Figure 1E:
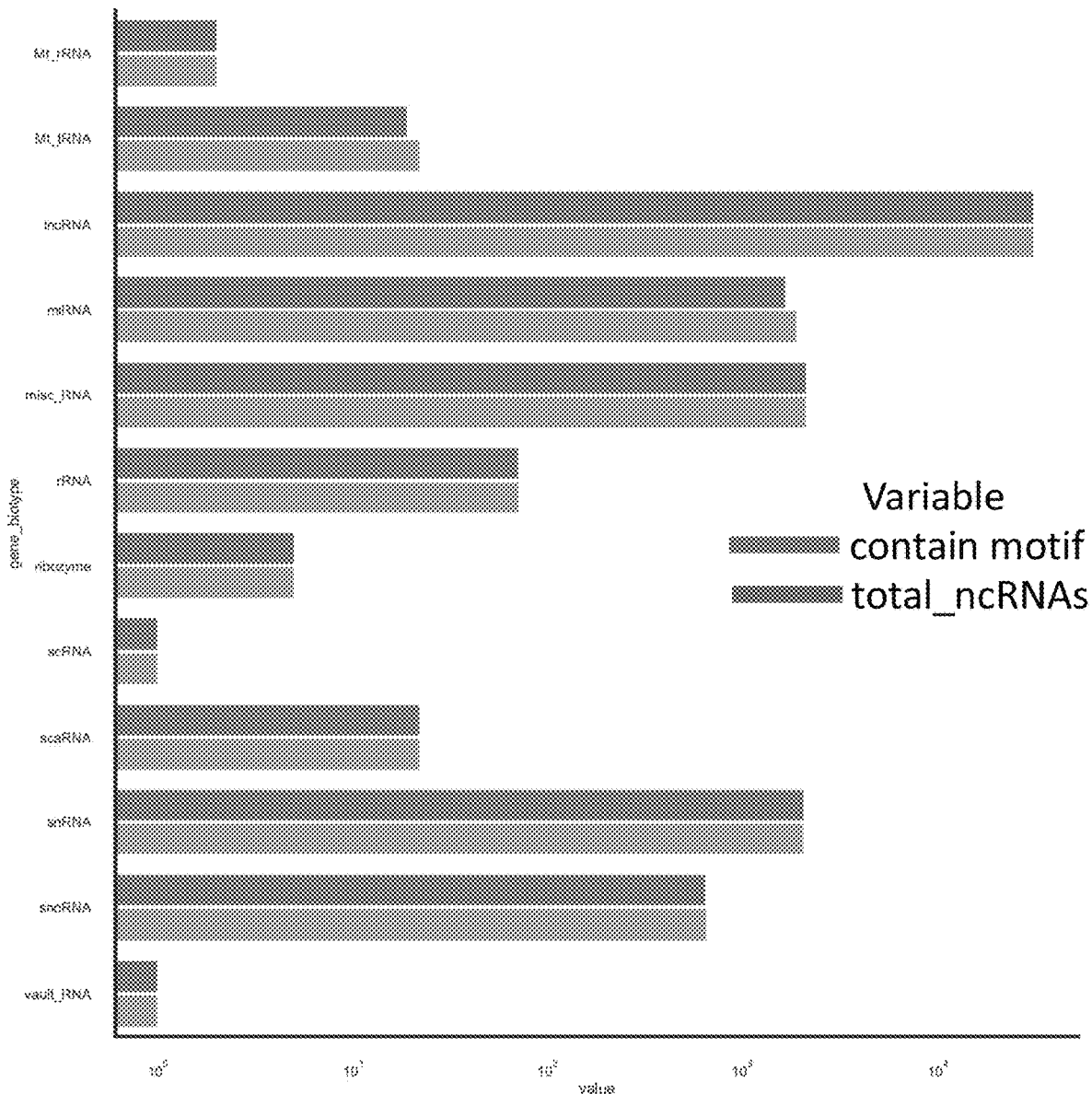
FIG. 1E provides a graph showing the proportion of ncRNAs identified as containing a sequence motif (Sm sequence motif, H/ACA box, and/or C/D box).
Figure 1F:
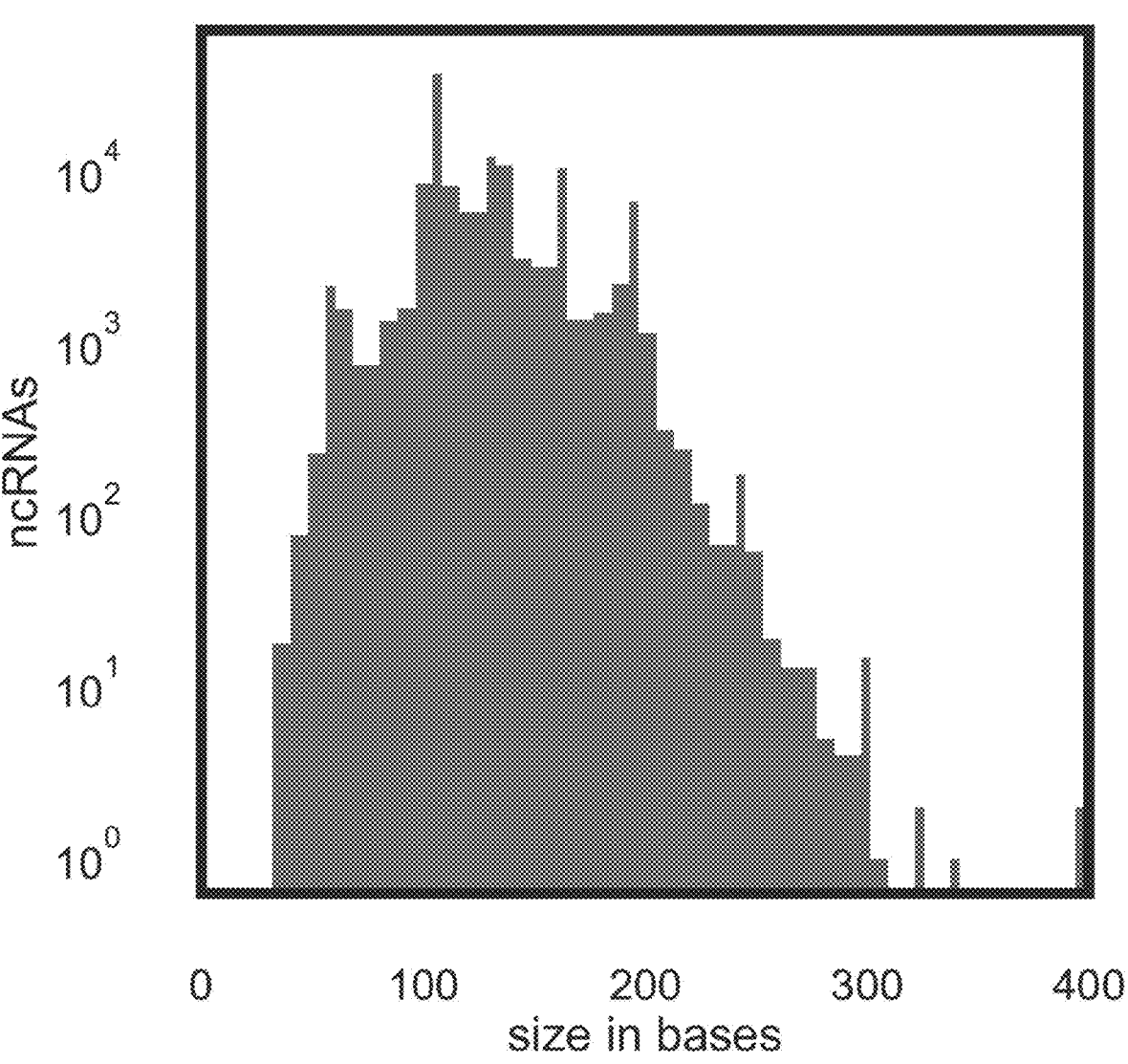
FIG. 1F provides a graph showing the length in number of nucleotides for exemplary ncRNAs of the disclosure.

The experiments of this example describe the methods used to identify ncRNAs for inclusion in composition, system, and/or the one or more nucleic acids comprising one or more nucleotide sequences described herein capable of targeting a pre-mRNA and producing a trans-splicing event. As shown in FIG. 1E, it was determined that nearly all ncRNA sequences mined from public databases contain a sequence motif identified in Table 1. RNAlib-2.5.1 software was used to predict the secondary structure of the ncRNA sequences identified in the public domain, including metazoan U1 snRNA sequences, U11 snRNA sequences, U7 snRNA sequences, Sm sequences, and H/ACA snoRNA sequences. The predicted secondary structures were compared to known secondary structures using an RNA covariance model (see, e.g., Eddy, et al (1994) *Nucleic Acids Research* 22:2079-2088). ncRNA sequences having a predicted secondary structure with similarity to known secondary structures were selected for further evaluation. This approach provided more than 120,000 candidate ncRNA sequences. As shown in FIG. 1F, the candidate ncRNA sequences ranged from approximately 7 nucleotides to more than 300 nucleotides in length. Exemplary candidate ncRNA sequences that were identified by this computational analysis are set forth in SEQ ID NOs: 9-209, 211-628, 630-632, 634-635, 638, 640, 642, 644-645, 647-648, 650, 652-653, 655, 657.

Example 2: Design and Testing of Compositions, Systems and Nucleic Acids for Trans-Splicing The experiments of this example show the design and testing of composition, system, and/or the one or more nucleic acids comprising one or more nucleotide sequences described herein for targeted trans-splicing. The nucleic acid molecules comprise a nucleotide sequence with (a) an intronic sequence having (i) at least one binding domain sequence complementary to a target sequence in a pre-mRNA, and (ii) a ncRNA sequence; (b) a splice site; and (c) at least one exonic sequence. The ncRNA sequences were selected from the candidate ncRNAs identified as described in Example 1. The composition, system, and/or the one or more nucleic acids comprising one or more nucleotide sequences described herein were engineered to incorporate the entire candidate ncRNA sequence or a portion thereof comprising a secondary structure and/or sequence motif identified in Table 1.

Figure 2A:
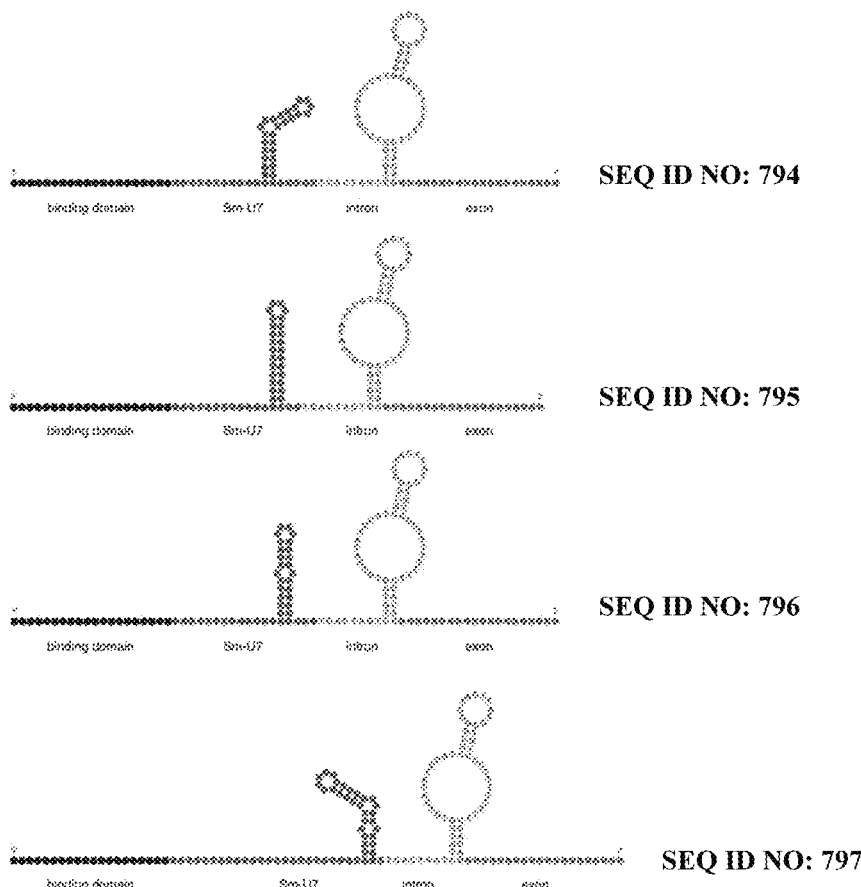
FIG. 2A, FIG. 2B, and FIG. 2C provide a schematic, without wishing to be bound by theory, depicting the extended and folded secondary structure of an exemplary composition, system, and/or the one or more nucleic acids comprising one or more nucleotide sequences described herein having 5' to 3' an RNA binding domain, an ncRNA having an Sm sequence motif and a U7 snRNA, intron, SA, and exon (SEQ ID NO: 794, SEQ ID NO: 795, SEQ ID NO: 796, and SEQ ID NO: 797) (FIG. 2A) and the interaction of the exemplary composition, system, and/or the one or more nucleic acids comprising one or more nucleotide sequences described herein with a target pre-mRNA that initiates a trans-splicing event between the SD of the pre-mRNA and the SA of the exemplary composition, system, and/or the one or more nucleic acids comprising one or more nucleotide sequences described herein (FIG. 2A, FIG. 2B, and FIG. 2C).
Figure 2A:
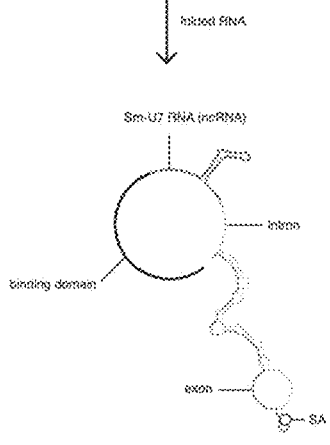
Figure 2B:
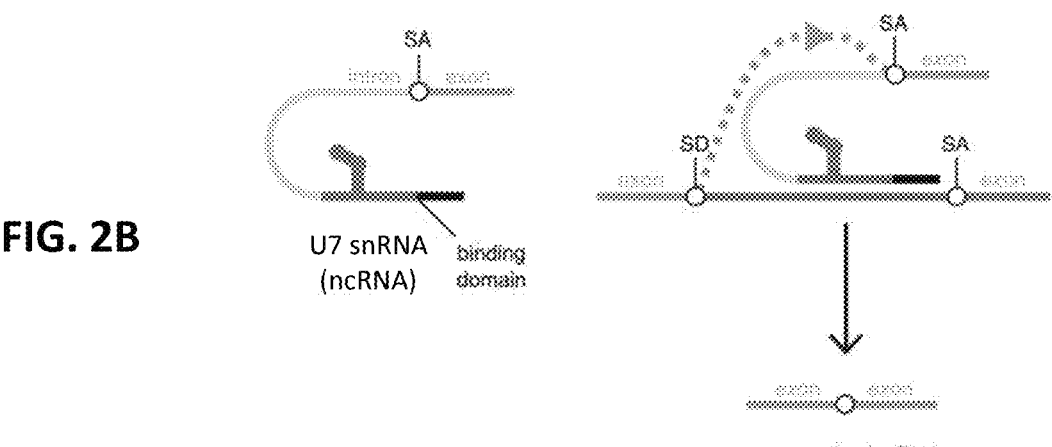
Figure 2C:
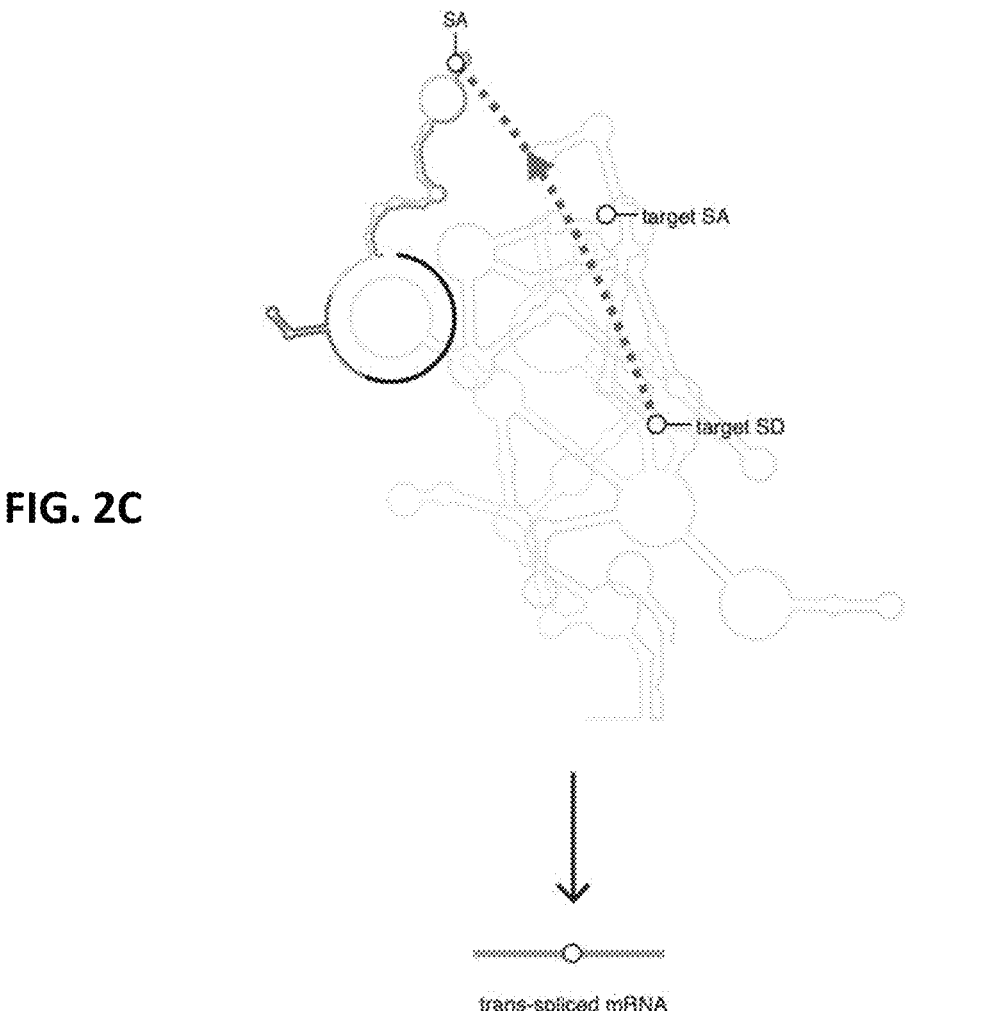
Figure 3A:
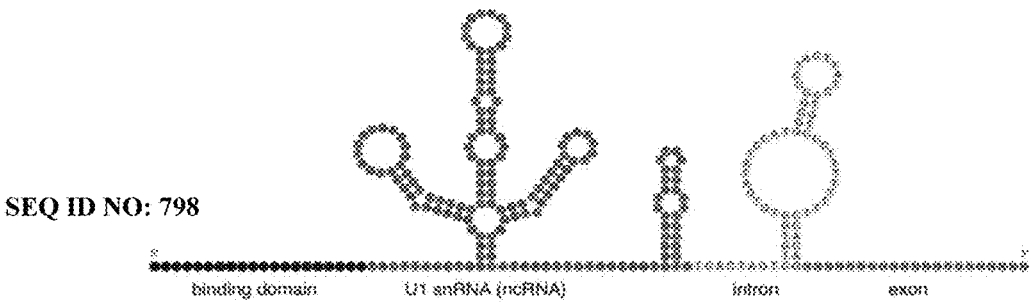
FIG. 3A, FIG. 3B, and FIG. 3C provide a schematic, without wishing to be bound by theory, depicting the extended and folded secondary structure of an exemplary composition, system, and/or the one or more nucleic acids comprising one or more nucleotide sequences described herein having 5' to 3' an RNA binding domain, U1 snRNA, intron, SA, and exon (SEQ ID NO: 798, SEQ ID NO: 799, and SEQ ID NO: 800) (FIG. 3A) and the interaction of the exemplary composition, system, and/or the one or more nucleic acids comprising one or more nucleotide sequences described herein with a target pre-mRNA that initiates a trans-splicing event between the SD of the pre-mRNA and the SA of the exemplary composition, system, and/or the one or more nucleic acids comprising one or more nucleotide sequences described herein (FIG. 3A, FIG. 3B, and FIG. 3C).
Figure 3A:
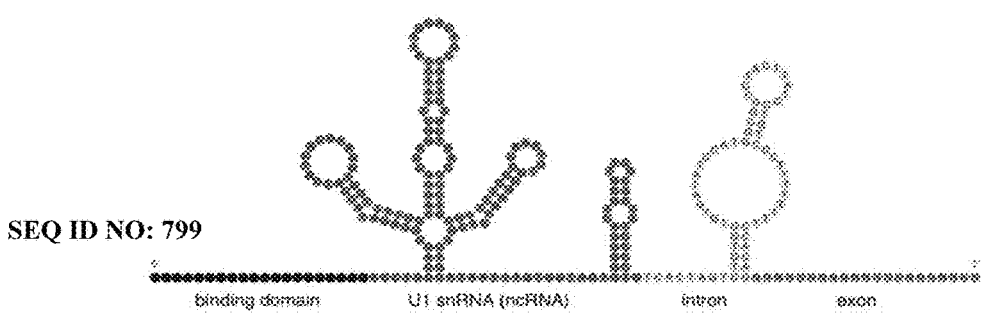
Figure 3A:
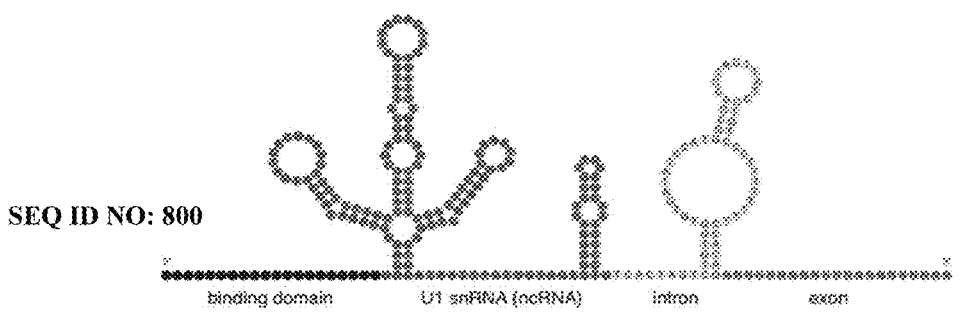
Figure 3A:
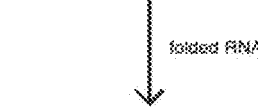
Figure 3A:
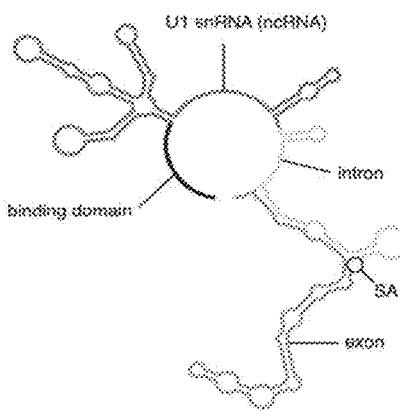
Figure 3B:
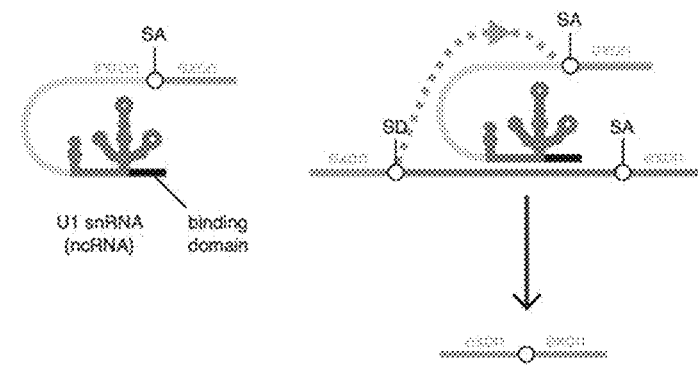
Figure 3C:
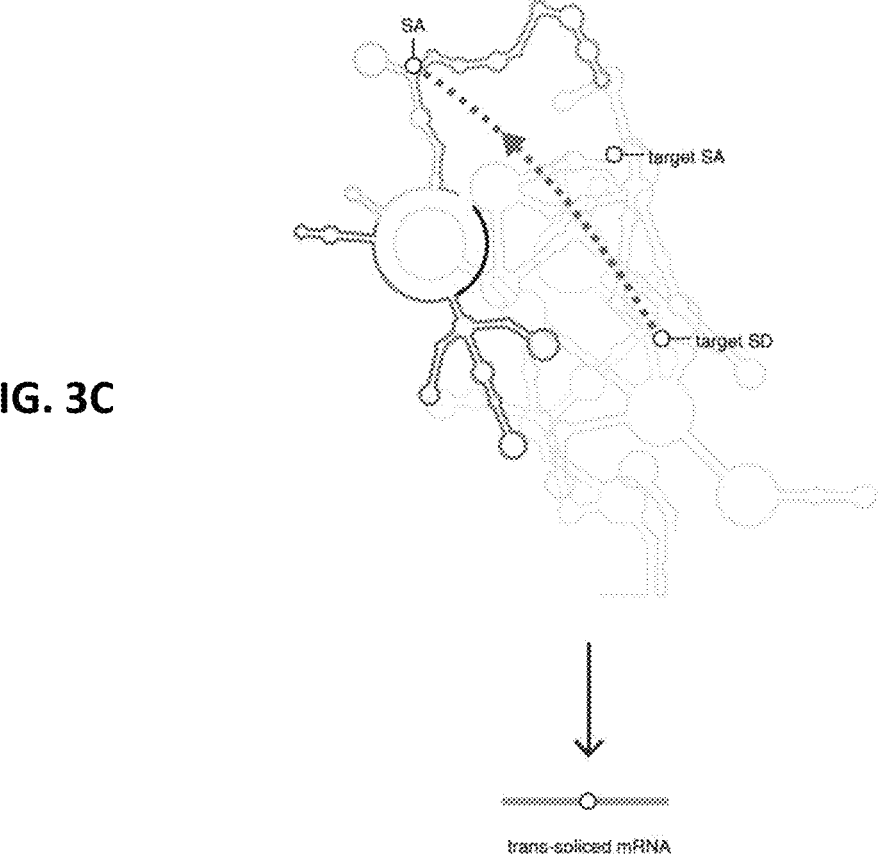
Figure 4A:
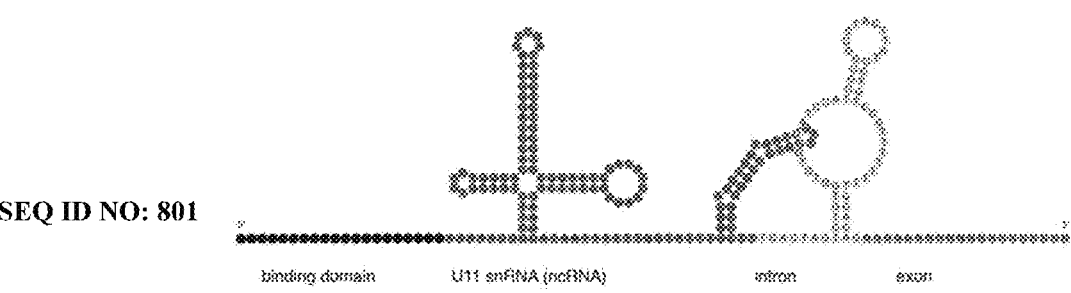
FIG. 4A, FIG. 4B, and FIG. 4C provide a schematic, without wishing to be bound by theory, depicting the extended and folded secondary structure of a composition, system, and/or the one or more nucleic acids comprising one or more nucleotide sequences described herein having 5' to 3' an RNA binding domain, U11 snRNA, intron, SA, and exon (SEQ ID NO: 800, SEQ ID NO: 801, SEQ ID NO: 802, and SEQ ID NO: 803) (FIG. 4A) and the interaction of the exemplary composition, system, and/or the one or more nucleic acids comprising one or more nucleotide sequences described herein with a target pre-mRNA that initiates a trans-splicing event between the SD of the pre-mRNA and the SA of the exemplary composition, system, and/or the one or more nucleic acids comprising one or more nucleotide sequences described herein (FIG. 4A, FIG. 4B, and FIG. 4C).
Figure 4A:
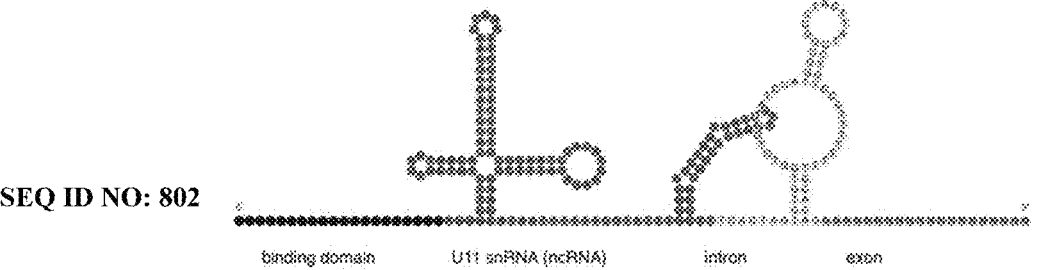
Figure 4A:
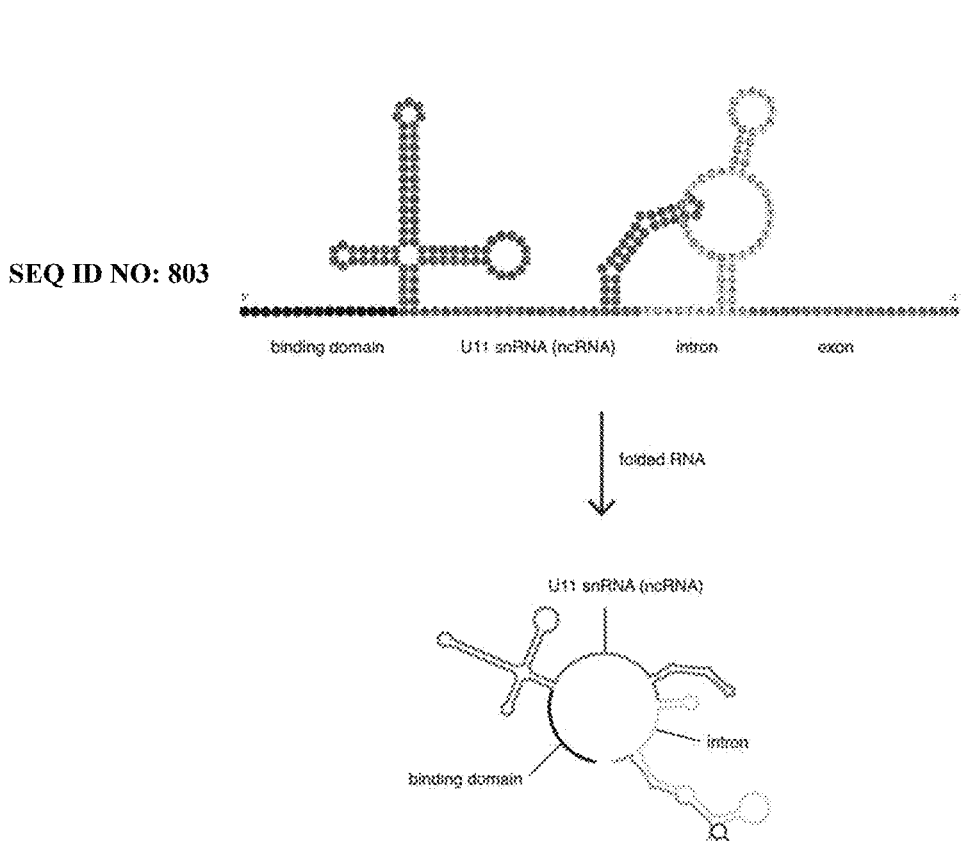
Figure 4B:
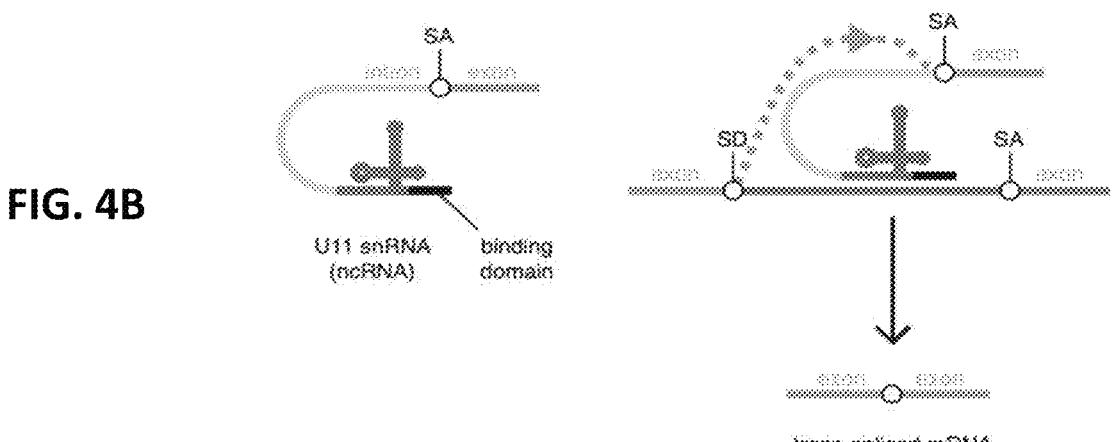
Figure 4C:
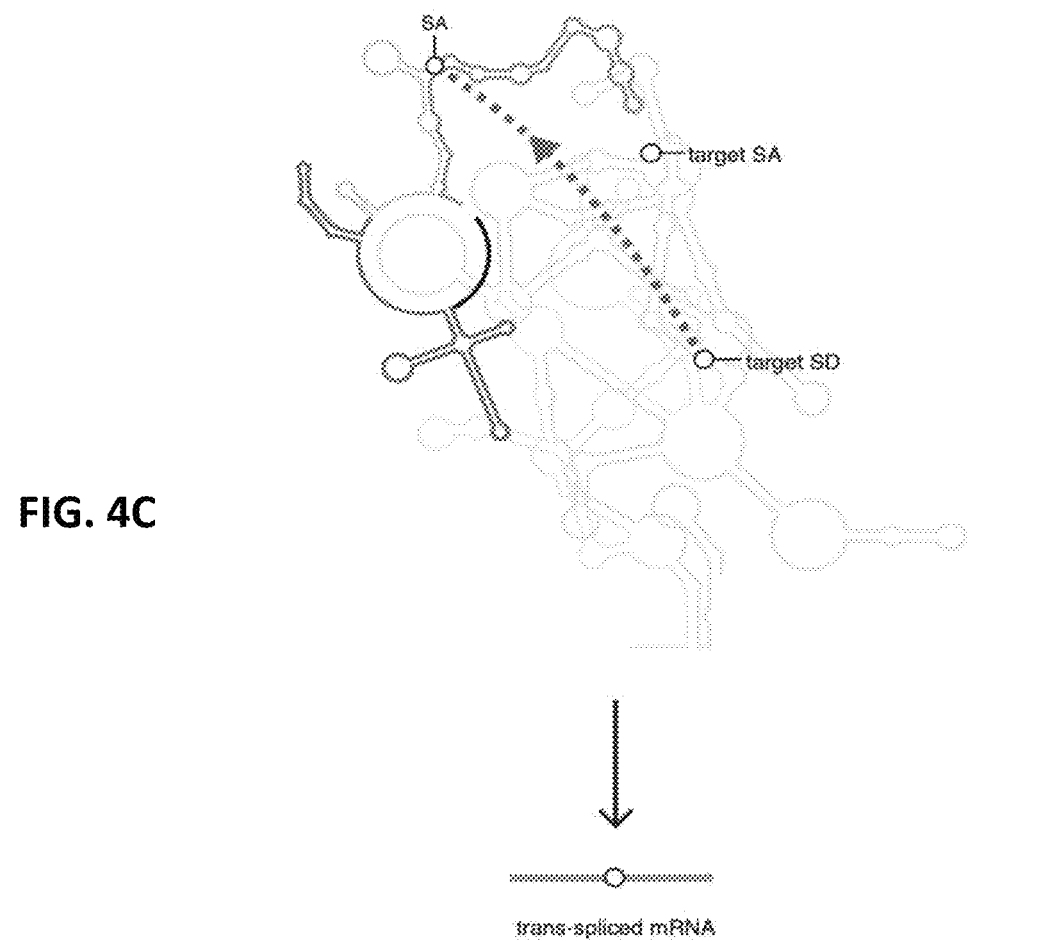

A first set of nucleic acid molecules were designed to have a ncRNA sequence derived from a snRNA and to undergo trans-splicing at a splice donor in a pre-mRNA (for correction of a mutation at the 5'end of an exon). The nucleic acid molecules had a nucleotide sequence arranged 5' to 3' (a) an intron having (i) a binding domain sequence, (ii) a snRNA sequence (a U1 snRNA; U11 snRNA; a Sm sequence motif and U7 snRNA; or a Sm sequence motif), (iii) a branch point, and (iv) a polypyrimidine tract; (b) a splice acceptor; and (c) an exon. Schematics of exemplary U1-based composition, system, and/or the one or more nucleic acids comprising one or more nucleotide sequences described herein composition, system, and/or the one or more nucleic acids comprising one or more nucleotide sequences described herein are shown in FIG. 2A, FIG. 2B, and FIG. 2C and sequences are provided in the table of Table 6 (in rows of Table 6 in which the column titled "Region 2" is assigned a label of "U1_X_Y" in which X and Y are integers). Schematics of exemplary U11-based composition, system, and/or the one or more nucleic acids comprising one or more nucleotide sequences described herein are shown in FIG. 3A, FIG. 3B, and FIG. 3C and sequences are provided in the table of Table 6 (in rows of Table 6 in which the column titled "Region 2" is assigned a label of "U11_X_Y" in which X and Y are integers). Schematics of exemplary U7-based composition, system, and/or the one or more nucleic acids comprising one or more nucleotide sequences described herein are shown in FIG. 4A, FIG. 4B, and FIG. 4C and sequences are provided in Table 6 (in rows of Table 6 in which the column titled "Region 2" is assigned a label beginning with "Sm_Z" in which Z is an integer and the column titled "Region 3" is assigned a label beginning with "U7_X" in which X is an integer). Schematics of exemplary Sm-based composition, system, and/or the one or more nucleic acids comprising one or more nucleotide sequences described herein are shown in FIG. 5A, FIG. 5B, and FIG. 5C and sequences are provided in Table 6 (in rows of Table 6 in which the column titled "Region 2" is assigned a label beginning with "Sm_Z" in which Z is an integer and the column titled "Region 3" is assigned a label "adeno_intron").

Figure 6A:
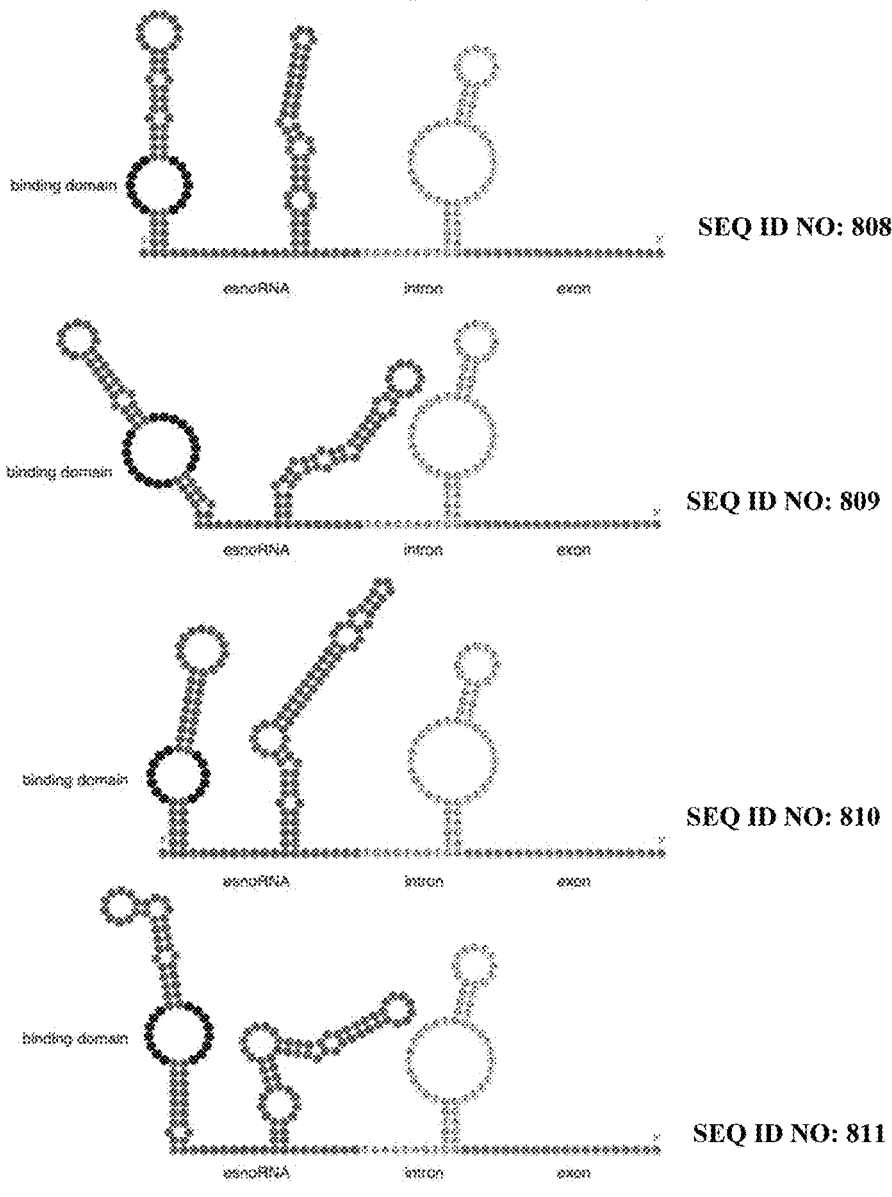
Figure 6B:
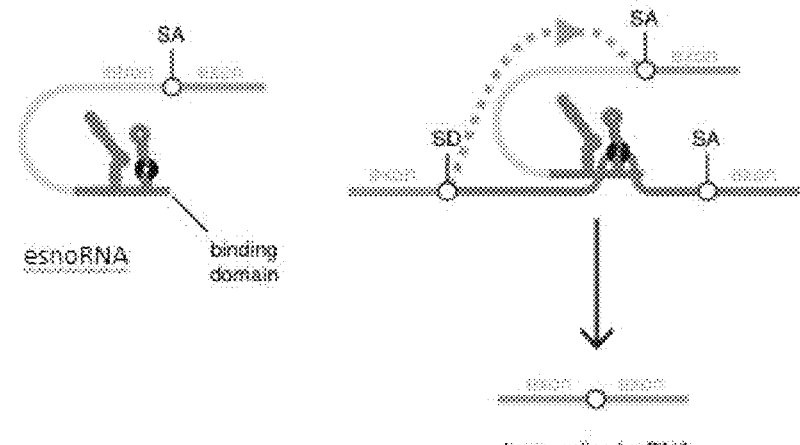
Figure 6B:
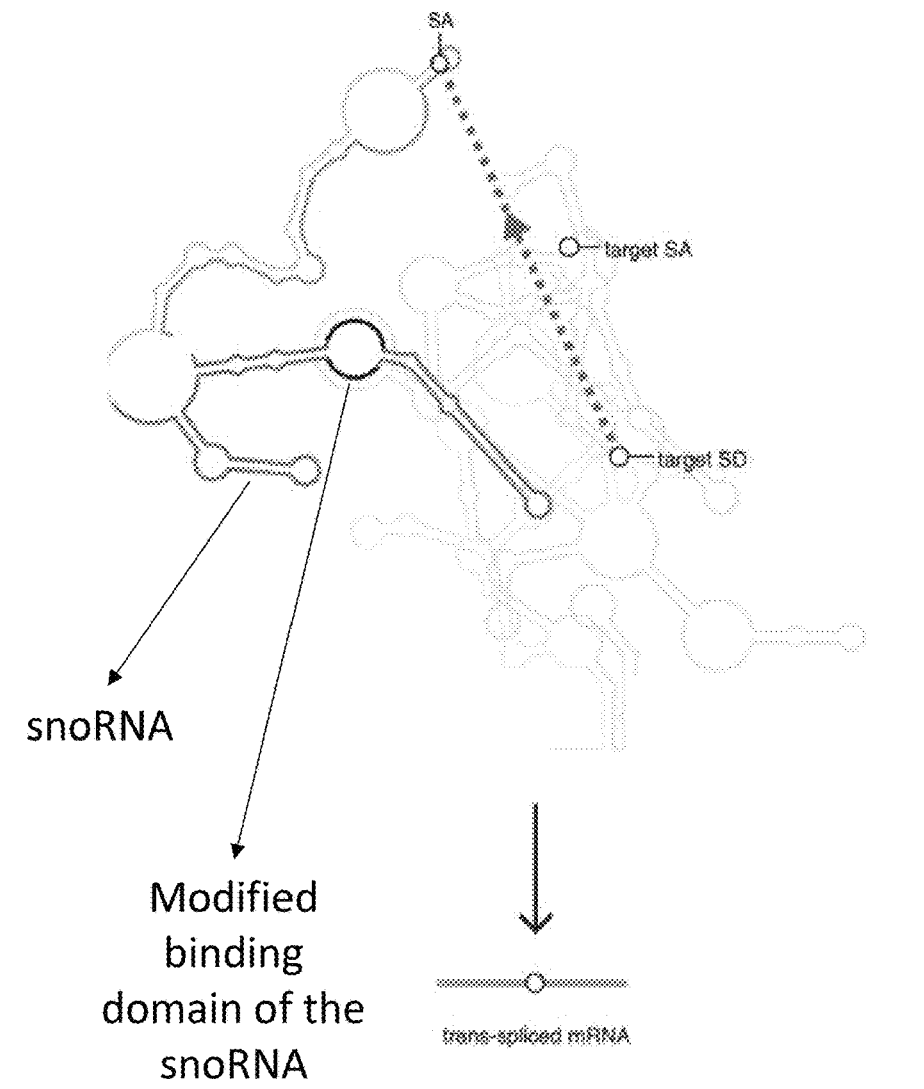

A second set of nucleic acid molecule were designed to have a ncRNA sequence derived from a H/ACA snoRNA and to undergo trans-splicing at a splice donor in a pre-mRNA (for correction of a mutation at the 5'end of an exon). The nucleic acid molecules had a nucleotide sequence arranged 5' to 3' (a) an intron having (i) a first and second binding domain inserted into an H/ACA box snoRNA sequence, (ii) a branch point, and (iii) a polypyrimidine tract; (b) a splice acceptor; and (c) an exon. Schematics of exemplary snoRNA-based composition, system, and/or the one or more nucleic acids comprising one or more nucleotide sequences described herein are shown in FIG. 6A, FIG. 6B, and FIG. 6C and sequences are provide in Table 6 (in rows of Table 6 in which the column titled "Region 1" is assigned a label beginning with "sno" "SNO" or "SCARNA").

The nucleic acid molecules are evaluated for trans-splicing by using reporter cells, where correct RNA edits generate a mRNA that produces a fluorescent protein. The composition, system, and/or the one or more nucleic acids comprising one or more nucleotide sequences described herein are be introduced to the reporter cells via viral or non-viral methods. Viral methods include but are not limited to lentivirus, AAV, and adenovirus. Non-viral methods include but are not limited to transfection or electroporation. The cells are first transfected with a splice donor reporter construct encoding a pre-mRNA under control of a CMV promoter, the pre-mRNA comprising a blue fluorescent protein (BFP), a self-cleaving p2A linker, a truncated GFP (5'GFP), and a splice donor. The BFP is used to confirm stable expression of the reporter construct. The reporter construct has a matrix metallopeptidase 9 (MMP9) intron 1 and exon 2 downstream the splice donor to ensure splicing an event can occur, followed by a bovine growth hormone polyadenylation signal (bGHpA) to allow for stable expression of the construct. The composition, system, and/or the one or more nucleic acids comprising one or more nucleotide sequences described herein have an exon that is the second half of the truncated GFP (3'GFP) and trans-splicing results in expression of full-length GFP. Reporter cells with correct edits generate signal via a fluorescent reporter and are sorted via FACS. Sorted cells are sequenced to identify active compositions, systems, and/or the one or more nucleic acids comprising one or more nucleotide sequences described herein.

Example 3: U7 gRNAs Enable and Enhance Trans-Splicing

Figure 7A:
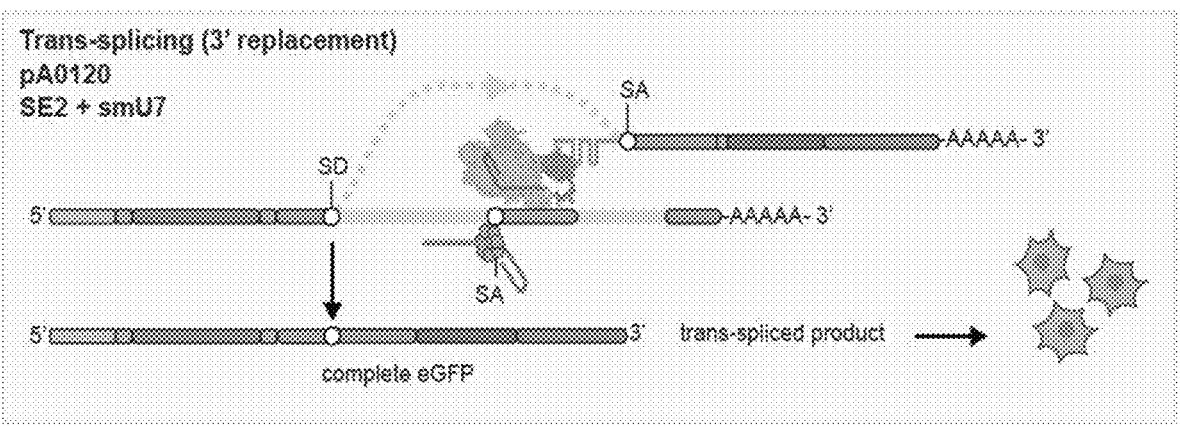
FIG. 7A and FIG. 7B show a schematic (FIG. 7A) and experimental data (FIG. 7B) demonstrating U7 guide RNAs ("gRNAs") enhance Cas13-based trans-splicing.
Figure 7B:

The experiments of this example show how U7 gRNAs enable and enhance trans-splicing in a variety of experimental conditions. In FIG. 7A and FIG. 7B, WT HEK293FT cells or cells with a PiggyBac integrated reporter were seeded 16 hours prior to transfection. At a confluence of 60-80%, cells were transfected with 25 ng reporter plasmid, 25 ng smU7 guide plasmid, 25 ng dCas13F3-MCP plasmid, 25 ng Cas13 gRNA plasmid, and 25 ng repRNA plasmid. For various conditions lacking one or more of these elements, pUC19 plasmid was substituted at equivalent inputs to normalize transfection efficiency. All cells were transfected using Lipofectamine 2000. Approximately 48 hours after transfection, cells were trypsinized using TrypLE and assayed via flow cytometry. Editing efficiency was determined as the percentage of all GFP+ cells after gating for BFP+ singlets. FIG. 7A provides a schematic, without wishing to be bound by theory, depicting a U7 gRNA enhancing Cas13-based trans-splicing. FIG. 7B is a graph showing data of the USH2A trans-splicing system and the combination U7 gRNAs with an RNA-targeting CRISPR-Cas (protein and CRISPR gRNA) and a repair RNA enables, compared to conditions where the U7 gRNA are not provided (RNA-targeting CRISPR-Cas system and repair RNA alone), or conditions where the U7 gRNA sequence is mutated, or conditions where the U7 gRNA is targeting a different sequence (non-targeting guide). These experiments in FIG. 7A and FIG. 7B demonstrate how U7 gRNAs enable and enhance Cas13-based trans-splicing.

Figure 8A:
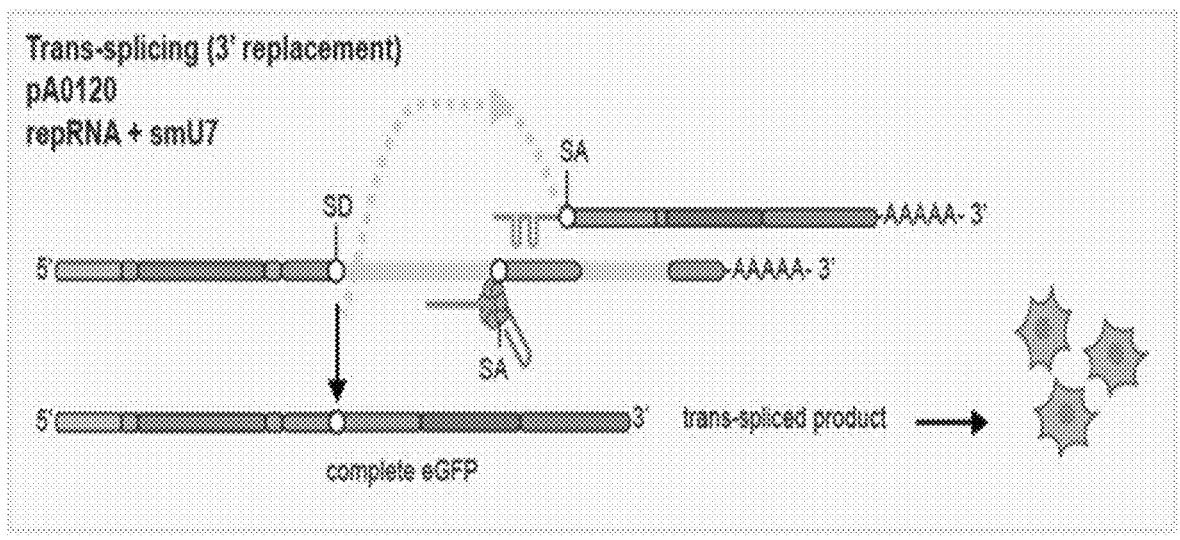
FIG. 8A and FIG. 8B show a schematic (FIG. 8A) and experimental data (FIG. 8B) demonstrating the combination of U7 gRNAs with a repRNA in trans, which enables exon replacement.
Figure 8B:
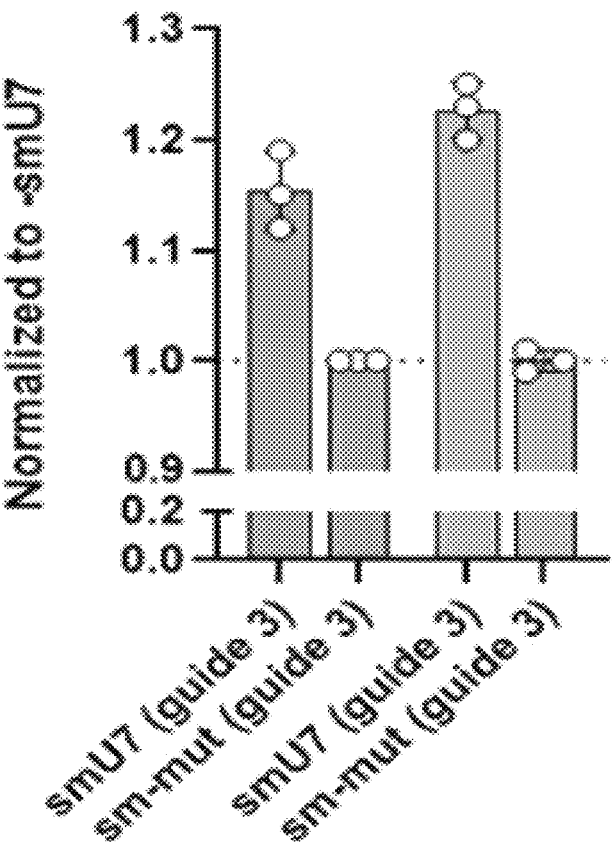

The experiment in FIG. 8A and FIG. 8B show experimental data demonstrating the combination of U7 gRNAs with a repRNA in trans, which enables exon replacement. In these experiments, WT HEK293FT cells or cells with a PiggyBac integrated reporter were seeded 16 hours prior to transfection. At a confluence of 60-80%, cells were transfected with 25 ng reporter plasmid, 25 ng smU7 guide plasmid, and 25 ng repRNA plasmid. For various conditions lacking one or more of these elements, pUC19 plasmid was substituted at equivalent inputs to normalize transfection efficiency. Antisense region (ASR) sequences used in these experiments are shown in Table 3 and Table 4. All cells were transfected using Lipofectamine 2000. Approximately 48 hours after transfection cells, were trypsinized using TrypLE and assayed via flow cytometry. Editing efficiency was determined as the percentage of all GFP+ cells after gating for BFP+singlets. FIG. 8A provides a schematic, without wishing to be bound by theory, depicting a U7 gRNA enhancing Cas13-based trans-splicing. The experiments in FIG. 8B show data of the USH2A trans-splicing system and the combination U7 gRNAs with a repair RNA in trans, which enables exon replacement, compared to conditions where the U7 gRNA is not provided (repRNA alone), or conditions where the gRNA sequence is mutated, or conditions where the U7 gRNA is targeting a different sequence (non-targeting guide).

Figure 9:
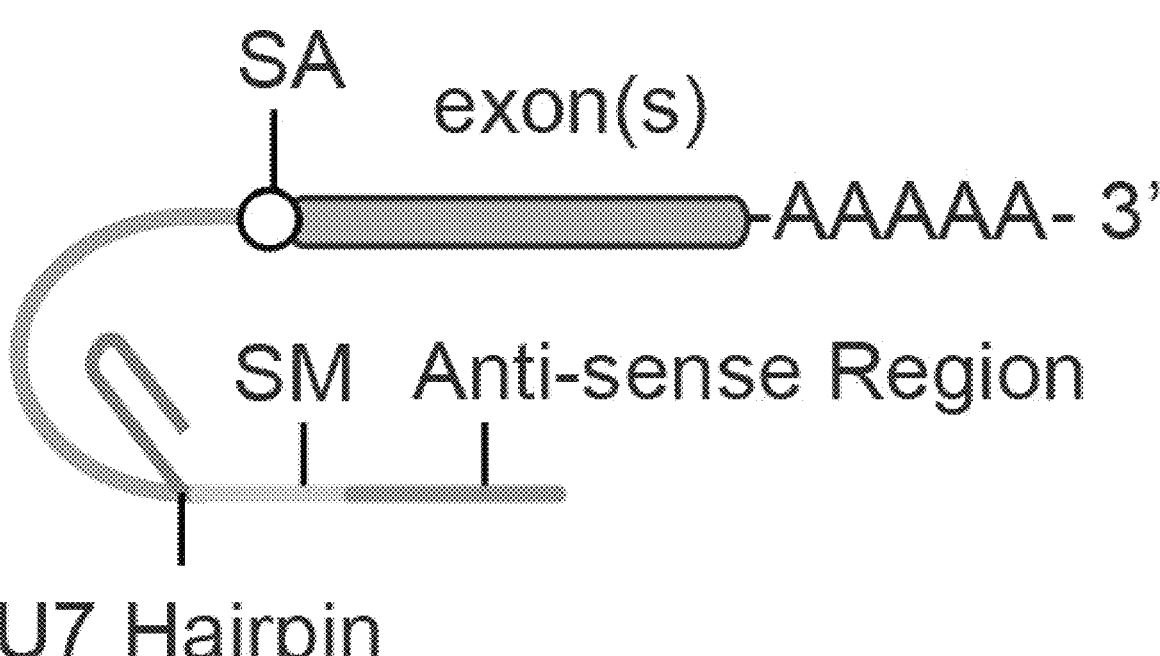
FIG. 9 provides a schematic, without wishing to be bound by theory, depicting U7 grepRNA design for 3' replacement.

FIG. 9 provides a schematic, without wishing to be bound by theory, depicting U7 grepRNA design for 3' replacement. The U7 grepRNA design shown in FIG. 9 can include an additional anti-sense binding motif elsewhere in the grepRNA to increase hybridization to the target RNA. In these experiments, the length of the U7 ASR sequence can be variable and maintain function, such as at least or about 10 nucleotides to at least or about 80 nucleotides.

Figure 10A:
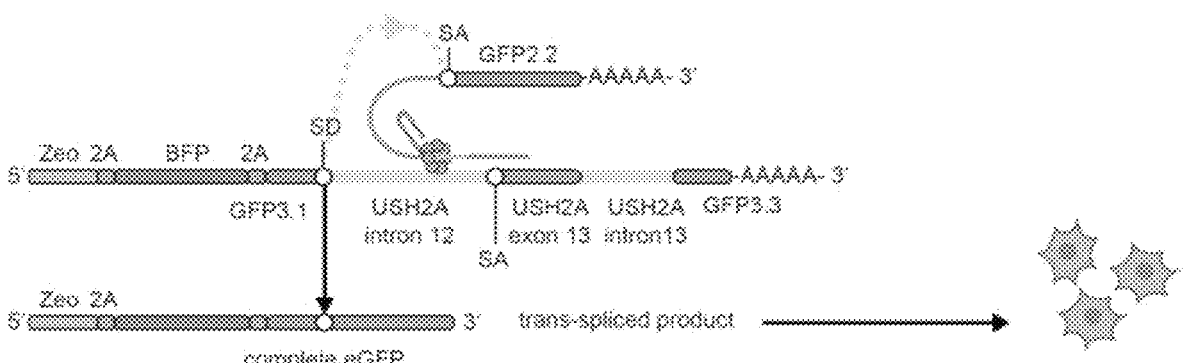
FIG. 10A and FIG. 10B show experimental data demonstrating 3' trans-splicing using a U7 grepRNA.
Figure 10B:
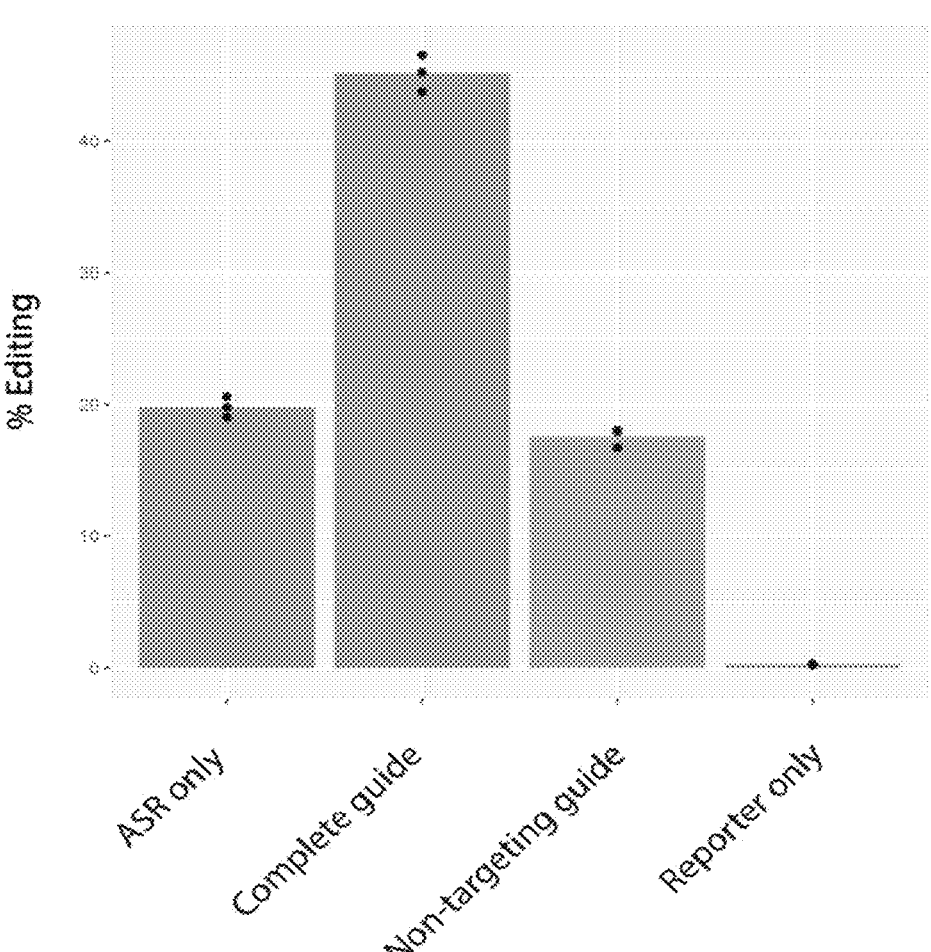

The experiments in FIG. 10A and FIG. 10B show experimental data demonstrating 3' trans-splicing using a U7 grepRNA. In these experiments, WT HEK293 cells were transfected with 25 ng pA0120 reporter, 50 ng (g) repRNA and 25 ng pUC19 using Lipofectamine 3000. The cells were incubated for 48 hours before being trypsinized and analyzed on flow cytometry. FIG. 10A shows the design of an experiment of 3' trans-splicing and exon replacement using a U7 grepRNA, compared to a non-targeting ASR sequence, or a grepRNA lacking the U7 hairpin. (Table 4) FIG. 10B is a graph showing U7-guided trans-splicing on an USH2A target (3' RNA replacement) with transient transfection leading to 45% trans-splicing efficiency.

Accordingly, the results of the experiments of this example demonstrate U7 gRNAs enable and enhance trans-splicing.

Example 4: snoRNAs Enable and Enhance Trans-Splicing

The experiments in this example demonstrate how snoR-NAs enable and enhance trans-splicing activity and efficiency in a variety of conditions.

Figure 11:
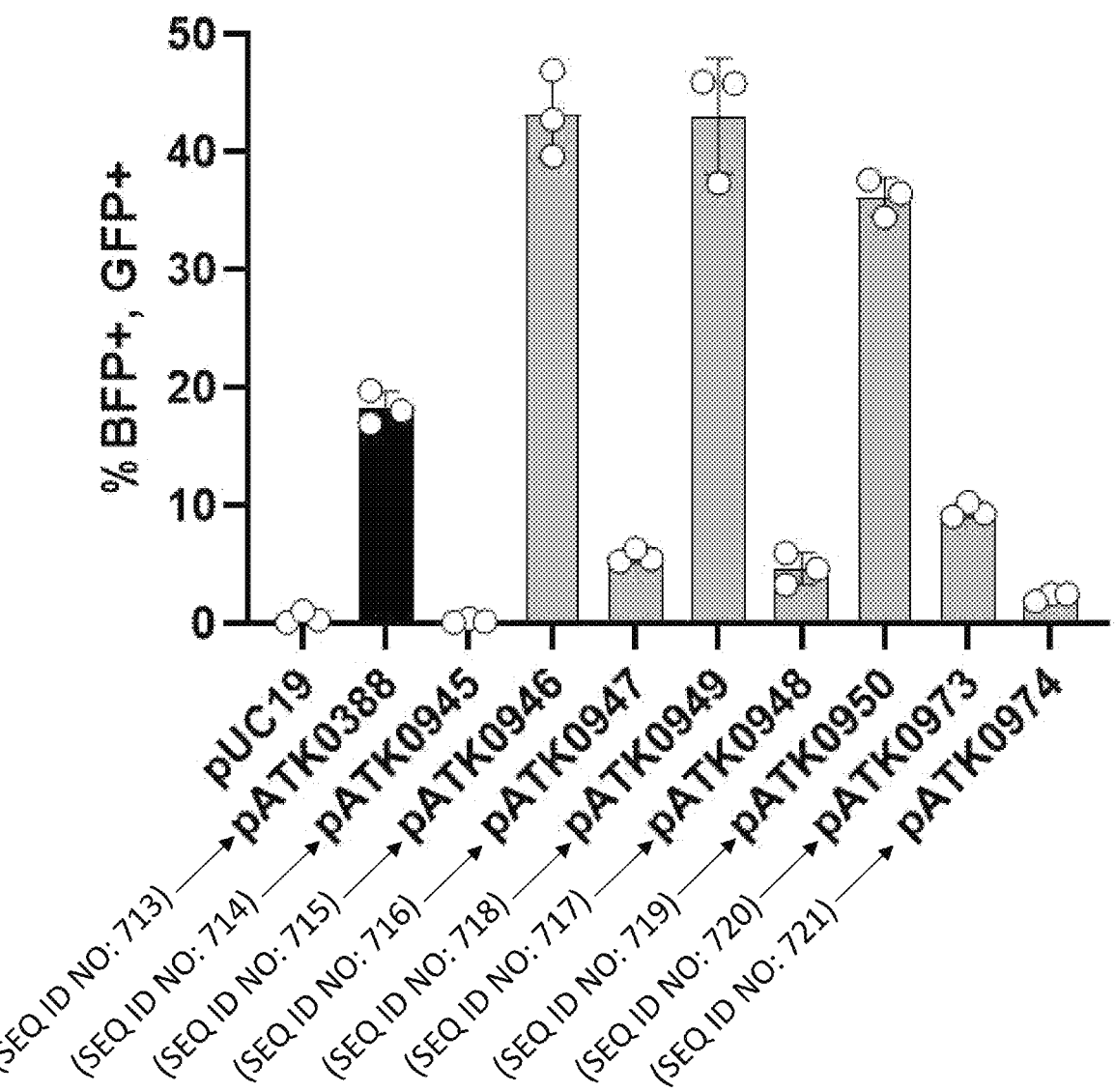
FIG. 11 is a graph showing how the addition of SNORA48-like sequences to the 3'end of 5' repRNAs significantly increased trans-splicing efficiency.

The experiments in FIG. 11 show how the addition of SNORA48-like sequences to the 3' end of repRNAs designed to edit the 5' end of the target significantly increased trans-splicing efficiency. FIG. 11 shows pATK0388 (SEQ ID NO: 713), pATK0945 ((SEQ ID NO: 714), pATK0946 (SEQ ID NO: 715), pATK0947 (SEQ ID NO: 716), pATK0948 (SEQ ID NO: 717), pATK0949 (SEQ ID NO: 718), pATK0950 (SEQ ID NO: 719), pATK0973 (SEQ ID NO: 720), and pATK0974 (SEQ ID NO: 721). The experiments in FIG. 11 show how mutations in the H and ACA motifs substantially decrease the trans-splicing efficiency because they cannot form RNPs (ribonuclear proteins), which confirms, without wishing to be bound by theory, the role of H and ACA motifs in the formation of RNPs, and also without wishing to be bound by theory, how the RNP is important for the observed increase in activity. In these experiments, repRNAs were designed with or without (pATK388 control) SNORA modifications. pATK388 lacks a snoRNA. 50 ng of each repRNA plasmid was co-transfected with pUC19 (filler DNA) into a reporter cell line (HEK293FT cells) using Lipofectamine 3000. Cells were collected and analyzed by flow cytometry 48-hrs post-transfection. The y-axis shows the percentage of GFP positive cells of BFP+/GFP+singlets. These experiments demonstrate the addition of SNORA48 significantly improved trans-splicing with repRNAs.

Figure 12A:
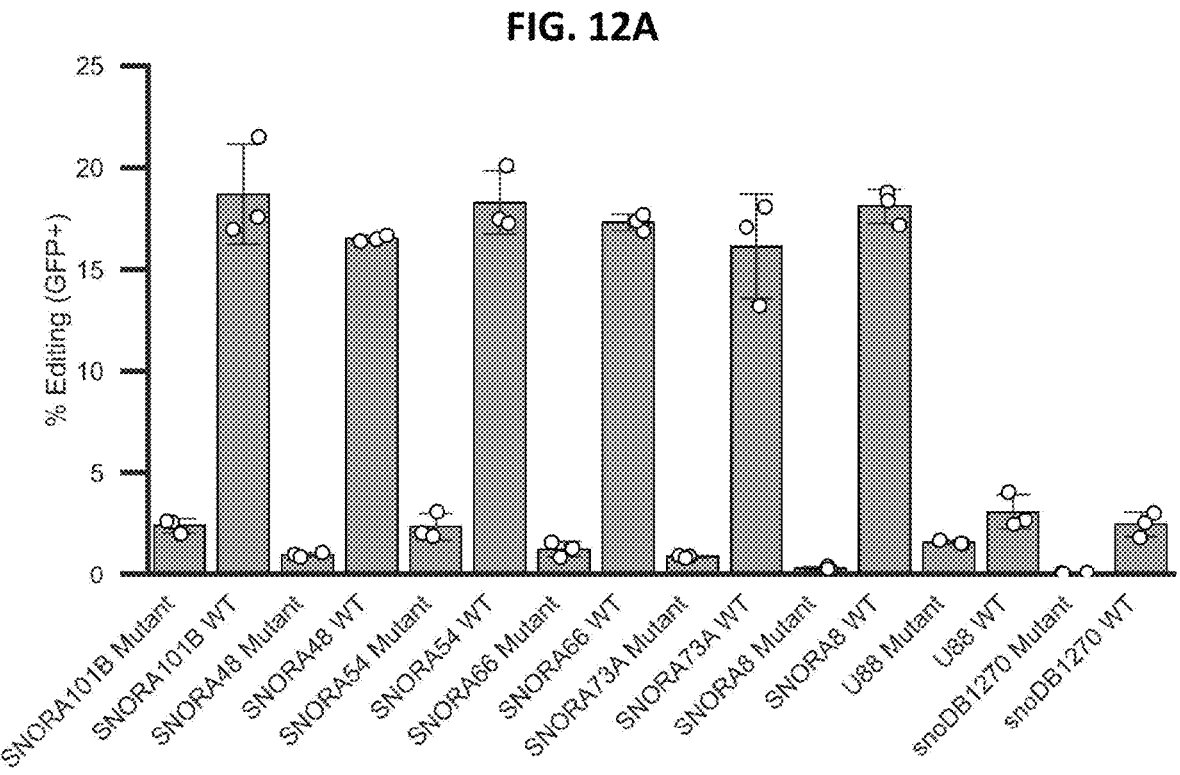
FIG. 12A and FIG. 12B show experimental data showing snoRNAs broadly increase trans-splicing efficiency.
Figure 12B:
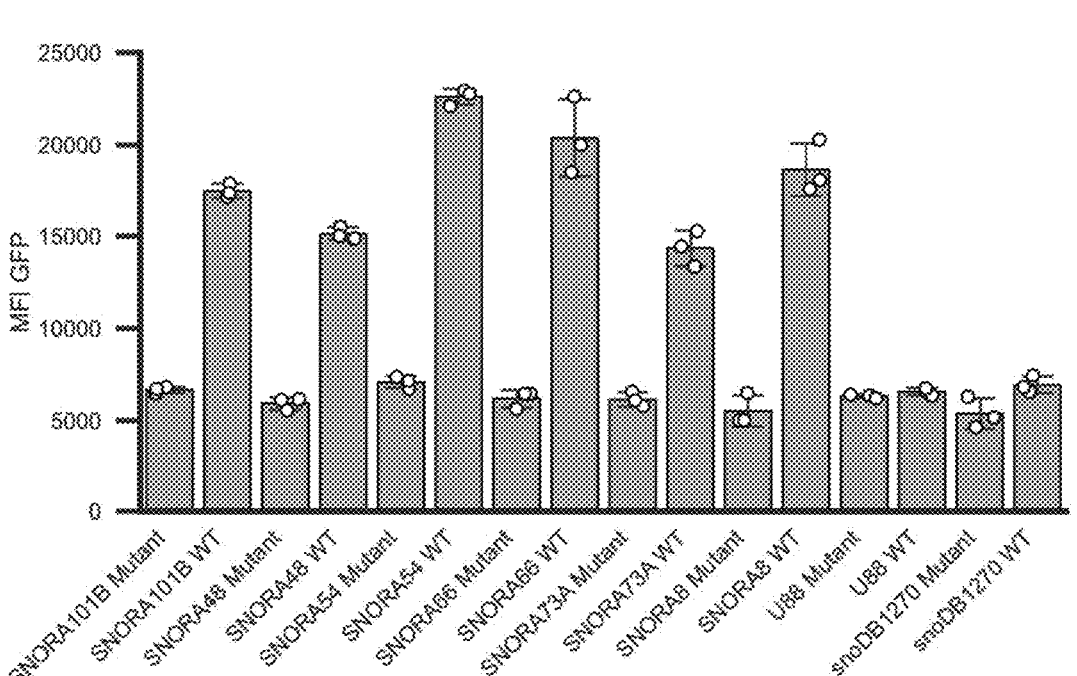

The experiments in FIGS. 12A-12B show how snoRNAs broadly increase trans-splicing efficiency. In these experiments, repRNAs were designed with wildtype or mutant SNORA modifications. 50 ng of each repRNA plasmid was co-transfected with pUC19 (filler DNA) into a reporter cell line (HEK293FT cells) using Lipofectamine 3000. Cells were collected and analyzed by flow cytometry 48-hrs post-transfection. The y-axis shows the percentage of GFP positive cells of BFP+/GFP+singlets. Mutant conditions impair RNP formation, thus resulting in lower trans-splicing. Overall, the experiments of this example demonstrate the RNA can be stabilized with RNP formation, and the experiments show that snoRNA sequences led to increased trans-splicing efficiency.

Figures 13A, 13B, 13C:
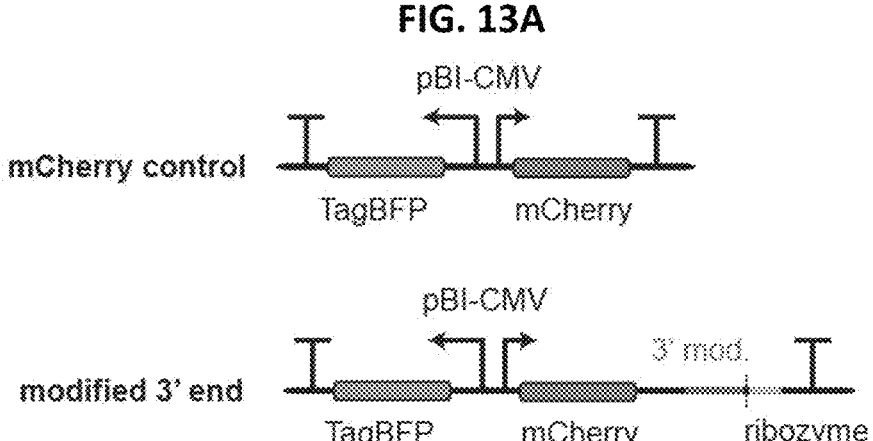
FIG. 13A is an image.
FIG. 13B and FIG. 13C are graphs showing experimental data illustrating how SNORA modifications on transcripts stabilize the 3' ends of transcripts after ribozyme cleavage and polyA removal.

The experiments in FIG. 13A, FIG. 13B, and FIG. 13C show how SNORA modifications on transcripts stabilize the 3' ends of transcripts after ribozyme cleavage and poly A removal. In these experiments, plasmids were designed with bidirectional promoters constitutively expressing TagBFP (reference control) and mCherry, with or without a 3' end modification followed by a self-cleaving ribozyme. Transcripts for mCherry were hypothesized to fail to produce mCherry protein after ribozyme cleavage and polyA removal unless stabilized by a 3' end modification. The WT MALAT1 3' UTR (contains RNase P cleavage site) has previously been shown to enable "leaky" translation. Cells were collected and analyzed by flow cytometry 48-hrs post-transfection. The y-axis shows ratio of mCherry and BFP fluorescent medians (MFI).

Figure 14A:
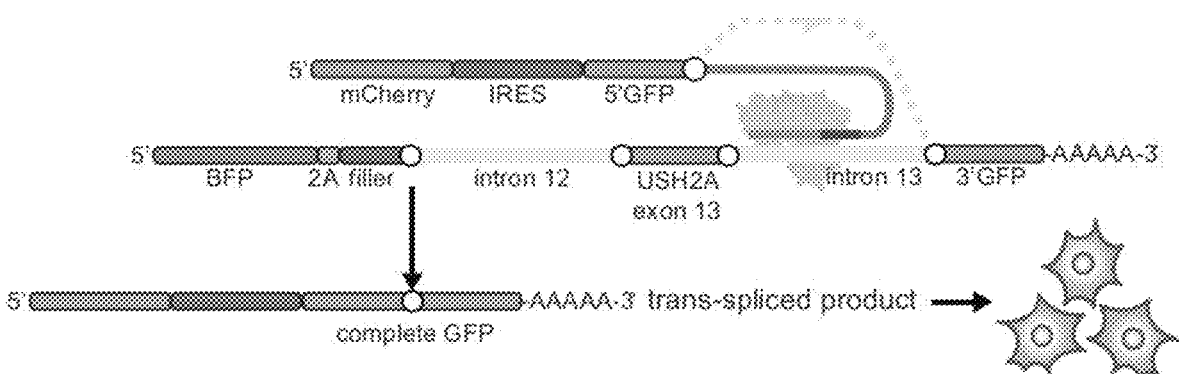
FIG. 14A is a graphical representation of a snoRNA-based trans-splice molecule.
Figure 14B:
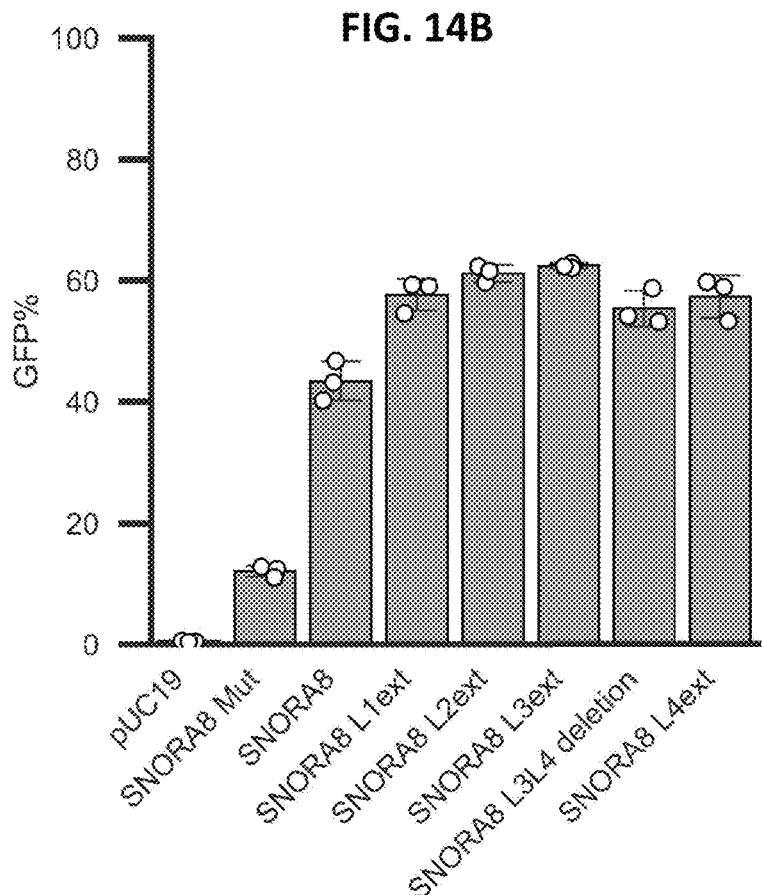
FIG. 14B is a graph showing how SNORA8 is permissive of extensions and deletions in the targeting regions.

The experiments in FIGS. 14A-14B show how SNORA8 is permissive of extensions and deletions in the targeting regions. In these experiments, repRNAs were designed with wildtype or mutant SNORA modifications. In these experiments, the pATK388 repRNA lacks any SNORA modification and serves as a reference control for trans-splicing. 50 ng of each repRNA plasmid was co-transfected with pUC19 (filler DNA) into a reporter cell line (HEK293FT cells) using Lipofectamine 3000. Cells were collected and analyzed by flow cytometry 48-hrs post-transfection. The y-axis shows the percentage of GFP positive cells of BFP+/GFP+ singlets. This data demonstrates the snoRNA is permissive to modifications that can modulate and/or increase trans-splicing efficiency and activity.

Figures 15A, 15B:
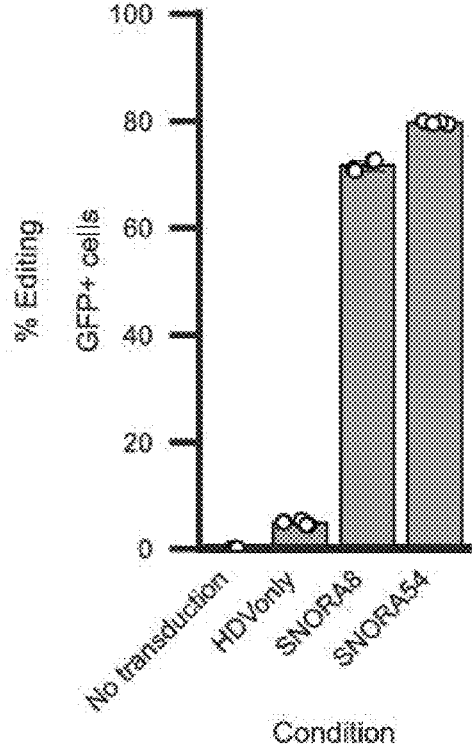
FIG. 15A is an image.
FIG. 15B is a graph showing how repRNAs with SNORA modifications are delivered to cells via AAV to edit endogenous reporter RNAs.

The experiments in FIG. 15A and FIG. 15B show how repRNAs with SNORA modifications are delivered to cells via AAV to edit endogenous reporter RNAs. The experiments tested whether or not SNORA modifications stabilize the 3' end of a repRNA. In these experiments, AAV2 virus with repRNA cargos were transduced into a reporter cell line (HEK293FT cells) at an MOI of 1E5. Cells were collected and analyzed by flow cytometry 48-hours post-transduction. The y-axis shows the percentage of GFP positive cells of BFP+/GFP+ singlets. SE3 vector is the repRNA without any 3' end modification. These experiments show how cells transduced with repRNAs containing SNORA modifications showed greatly improved trans-splicing efficiency relative to the SE3 control, which does not include snoRNA sequences.

Figure 16A:
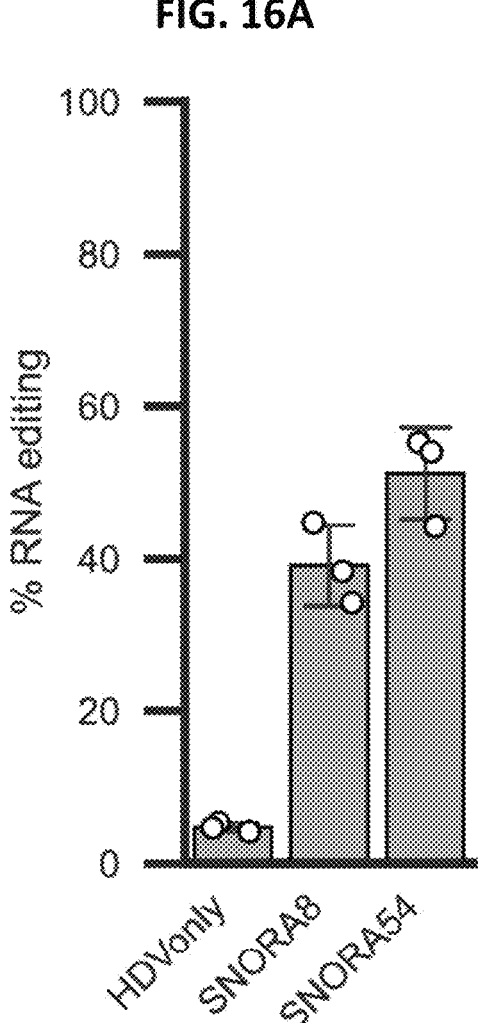
FIG. 16A and FIG. 16B are graphs showing how repRNAs with SNORA modifications are delivered to cells via AAV to edit endogenous reporter RNAs.
Figure 16B:
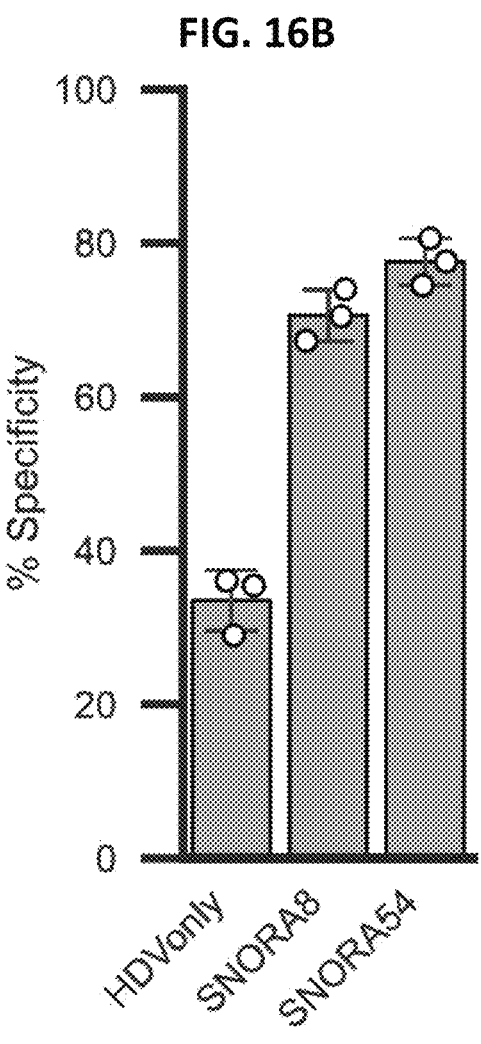

The experiments in FIG. 16A and FIG. 16B are show how repRNAs with SNORA modifications are delivered to cells via AAV to edit endogenous reporter RNAs. In these experiments, an AAV2 virus with repRNA cargos was transduced into a reporter cell line (HEK293FT cells) at an MOI of 1E5. Cells were collected and RNA was analyzed by nanopore sequencing. SE3 vector is a repRNA without any 3' end modification. These experiments demonstrate that cells transduced with repRNAs containing SNORA modifications showed a significant improvement in trans-splicing efficiency relative to the SE3 control (HDV only), which does not include snoRNA sequences. SNORA-based repRNAs led to a higher activity for trans-splicing, as well as increased specificity.

Accordingly, the results of the experiments of this example demonstrate how snoRNAs enable and enhance trans-splicing activity and efficiency in a variety of conditions.

Example 5: Mutability and Functional Screening of snoRNAs for Trans-Splicing The experiments in this example demonstrates modification of snoRNAs to modulate trans-splicing activity in vitro.

Figure 18:
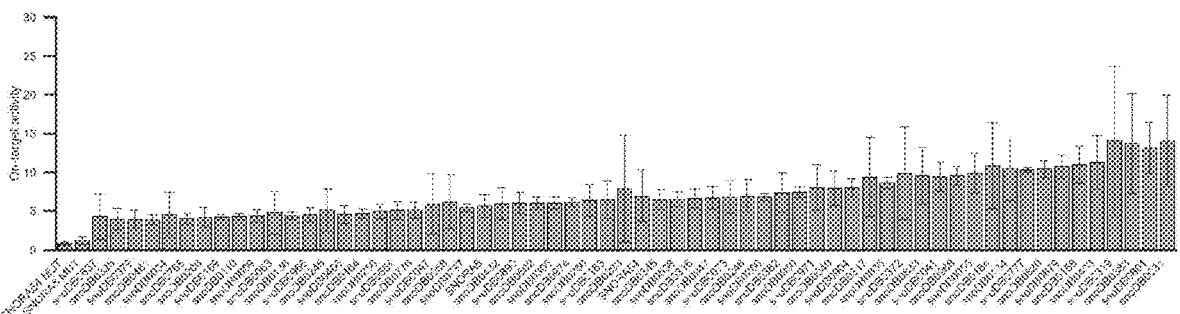
FIG. 18 is a non-limiting graphical representation of various trans-splicing molecules that were modified to include snoRNA sequences (e.g., SEQ ID NOs: 732-793, Table 6). All snoRNA sequences containing trans-splicing repair RNAs demonstrated higher trans-splicing activity than trans-splicing repair RNAs which did not form human RNPs.
Figure 19A:
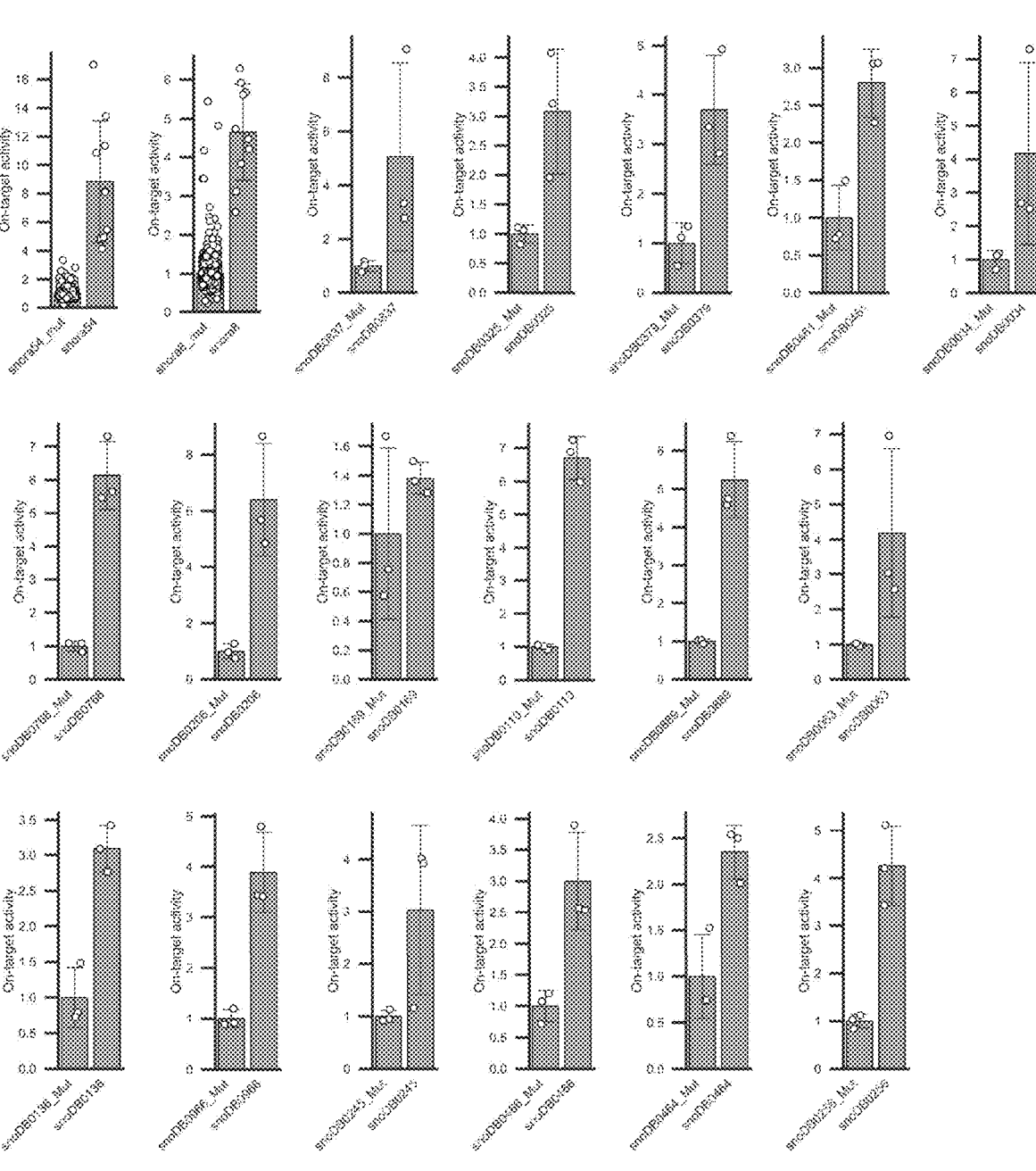
FIGS. 19A-19D are non-limiting graphical representations of a repair RNA (repRNA) modified with snoRNAs (e.g., SEQ ID NOs: 732-793, Table 6). snoRNA trans-splicing molecules showed significantly higher trans-splicing activity compared to repRNA with a mutated snoRNA sequence that does not form human RNPs.
Figure 19B:
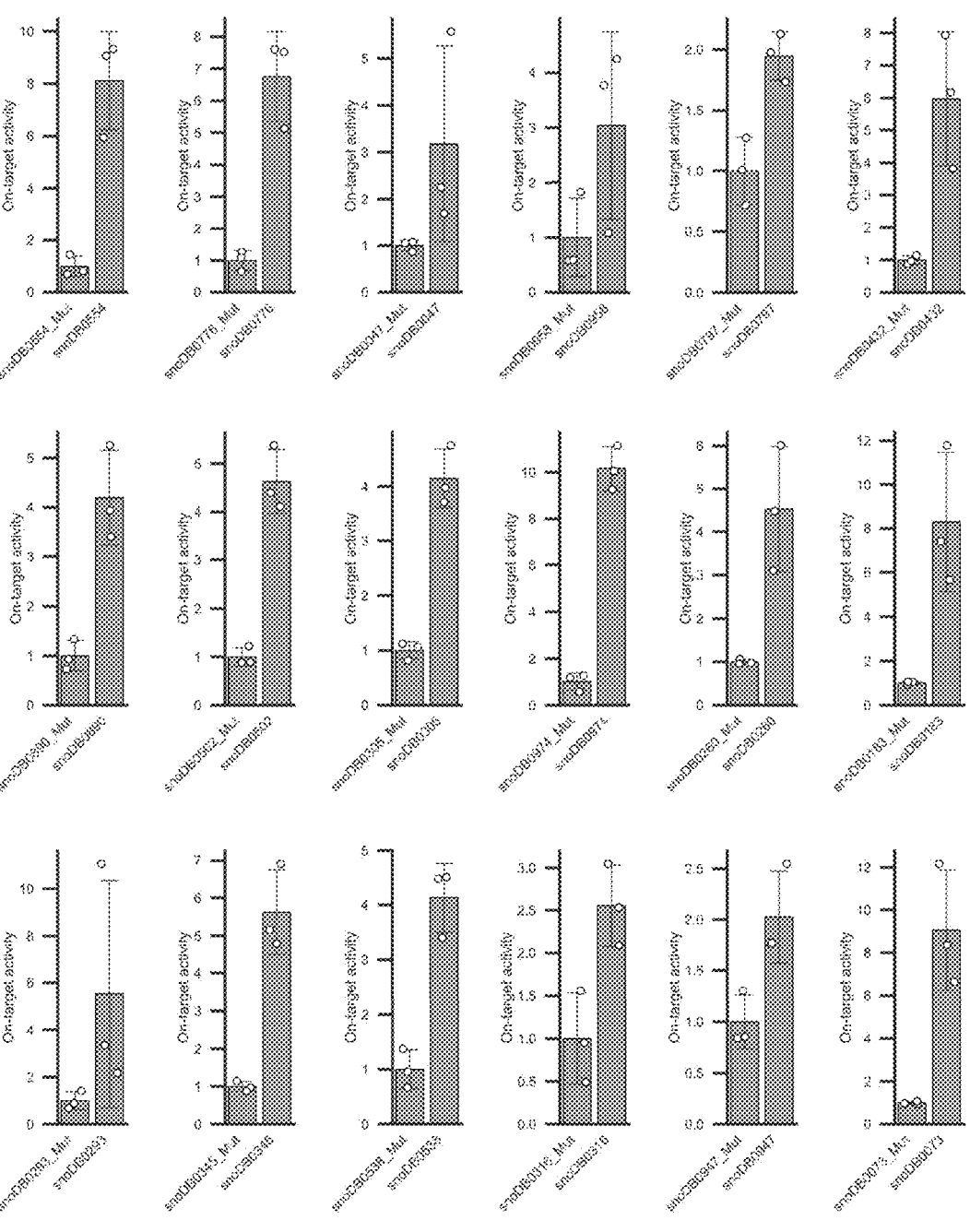
Figure 19C:
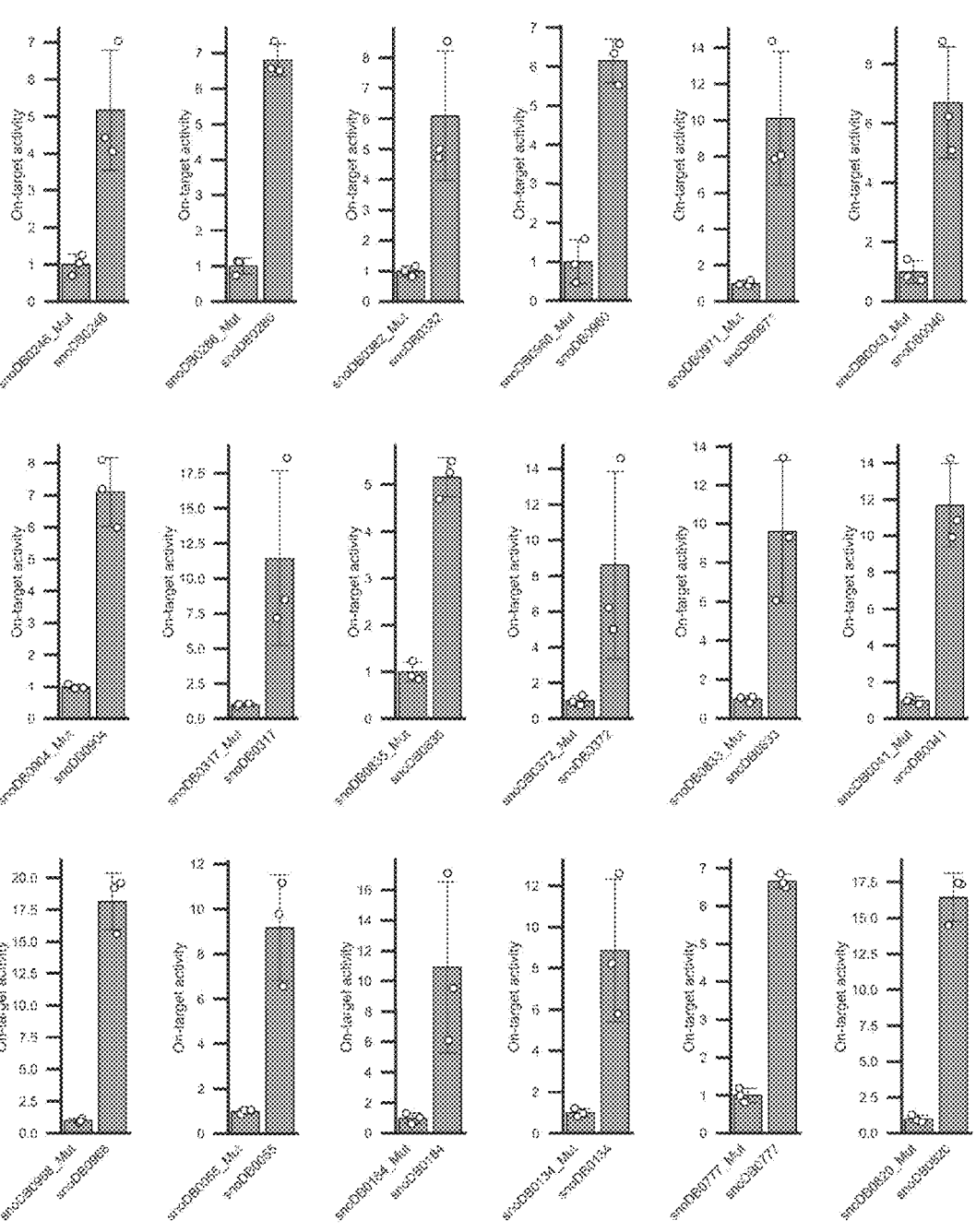
Figure 19D:
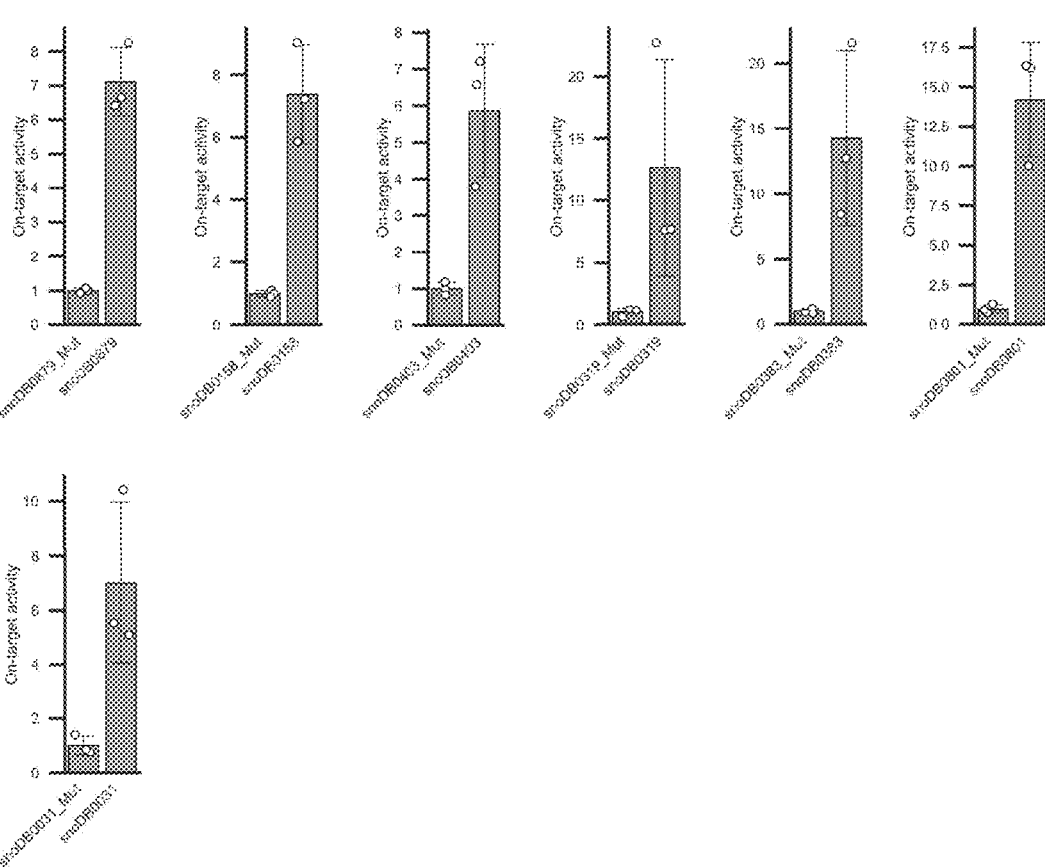

As shown in FIG. 18, various trans-splicing molecules were modified to include snoRNA sequences. All snoRNA sequences containing trans-splicing repair RNAs demonstrated higher trans-splicing activity than trans-splicing repair RNAs which did not form human RNPs (e.g., SNORA54 MUT, SNORA8 MUT). HEK293FT cells were transfected with trans-splicing molecules using LIPO-FECTAMINE 2000, per the manufacturer's instructions. RNA was extracted from cells using QIAGEN RNEASY mini extraction kit, per the manufacturer's protocol. RNA-seq libraries were constructed and sequenced on an ILLU- MINA platform to determine the trans-splicing rates. Various snoRNA sequences had a >10-fold effect on trans-splicing efficiency. All snoRNA sequences had a >4-fold effect on trans-splicing efficiency.

As shown in FIGS. 19A-19D, a repair RNA (repRNA) modified with snoRNAs depicted in Table 6 (SEQ ID NOs: 732-793) shows significantly higher trans-splicing activity than compared to a repRNA that has a mutated snoRNA sequence that does not form a human RNP ("_Mut" versions of each as shown in FIGS. 19A-19D). snoRNA sequences which were mutated to no longer form human RNP complexes still showed some degree of trans-splicing, albeit several fold lower in efficiency. HEK293FT cells were transfected with trans-splicing repRNA molecules using LIPOFECTAMINE 2000, per the manufacturer's instructions. RNA was extracted from cells using QIAGEN RNEASY mini extraction kit, per the manufacturer's protocol. RNA-seq libraries were constructed and sequenced on an ILLUMINA platform to determine trans-splicing rates.

Figure 20:
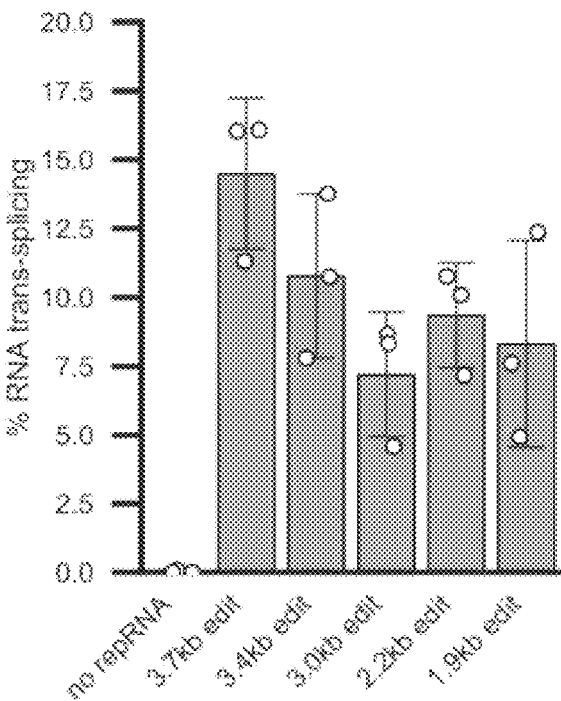
FIG. 20 is a non-limiting graphical representation of repRNAs with SNORA54 (as an illustrative example) being able to efficiently trans-splice independent of the size of the edit. Larger edits did not result in lower efficiency.

As shown in FIG. 20, repRNAs with SNORA54 (as an illustrative example) were able to efficiently trans-splice independent of the size of the edit. Larger edits did not result in lower efficiency. HEK293FT cells were transfected with trans-splicing repRNA molecules using LIPOFECTAMINE 2000, per the manufacturer's instructions. RNA was extracted from cells using QIAGEN RNEASY mini extraction kit, per the manufacturer's protocol. RNA was sequenced with NANOPORE sequencing to determine trans-splicing efficiency.

Figure 21:
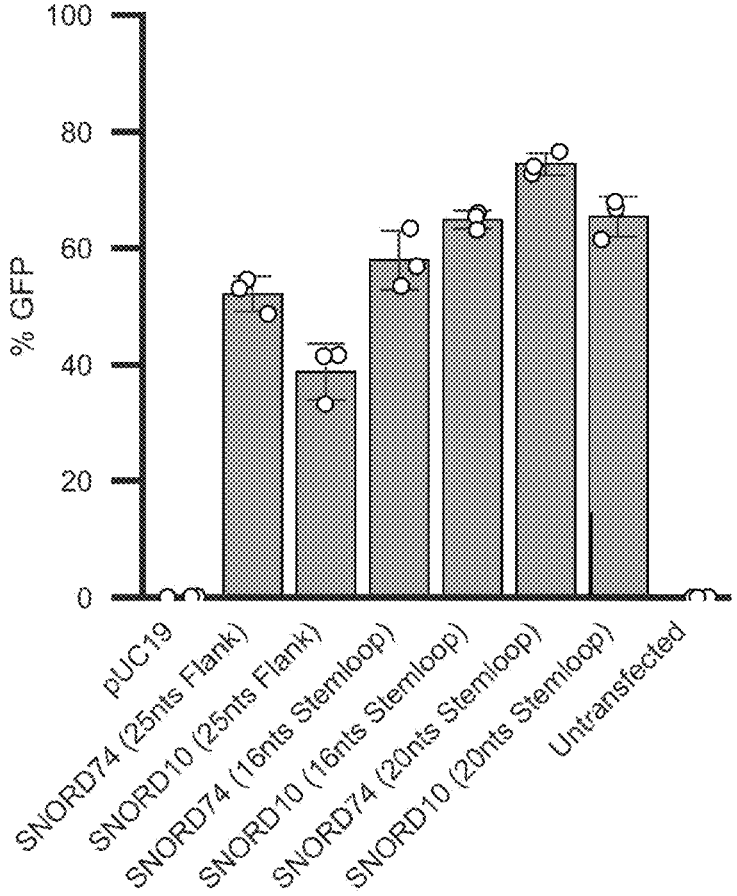
FIG. 21 is a non-limiting graphical representation of GFP correction using repRNAs with C/D-box snoRNA sequences enabling high trans-splicing rates.

As shown in FIG. 21, repRNAs with C/D-box snoRNA sequences enabled high trans-splicing rates. HEK293FT cells were transfected with trans-splicing repRNA molecules using LIPOFECTAMINE 2000, per the manufacturer's instructions. Cells were analyzed for GFP correction using a BECKMAN COULTER CYTOFLEX system.

Figure 22:
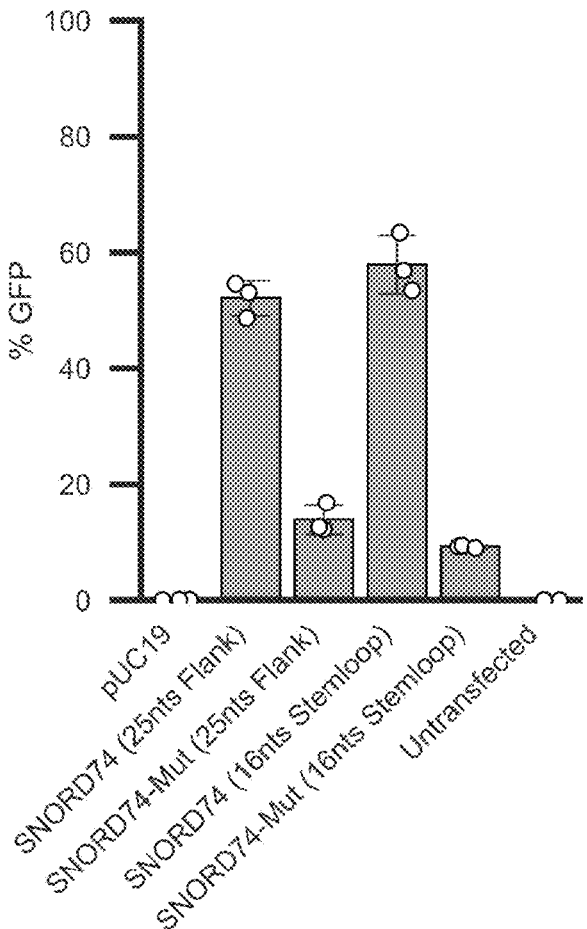
FIG. 22 is a non-limiting graphical representation of GFP correction using repRNAs with C/D-box snoRNA sequences enabling high trans-splicing rates, showing RNP formation increases efficiency.

As shown in FIG. 22, repRNAs with C/D-box snoRNA sequences enabled high trans-splicing rates. Mutants that prevented snoRNP formation edit at baseline trans-splicing rates (e.g., "-Mut" forms as shown in FIG. 22) demonstrated that RNP formation dramatically improves trans-splicing rates. HEK293FT cells were transfected with trans-splicing repRNA molecules using lipofectamine 2000, per the manufacturer's instructions. Cells were analyzed for GFP correction using a BECKMAN COULTER CYTOFLEX system.

TABLE 2

| Category | description | element_seq |
|---|---|---|
| SD targeting | Sm_consensus-U7-hg_USH2A_int13_SD_20 bp_1-filler | (SEQ ID NO: 658) ACACAGGCACTGGCCACTGA-AATTTTTGGAG-(SEQ ID NO: 659) taggctttctggcttttcaccggaaagcccct_AAATGATTAAATTAA |
| SD targeting | Sm_consensus-U7-hg_USH2A_int13_SD_20 bp_3-filler | (SEQ ID NO: 660) GATTAGGCACACACAGGCAC-AATTTTTGGAG-(SEQ ID NO: 659) taggctttctggcttttcaccggaaagcccct_AAATGATTAAATTAA |
| SD targeting | Sm_consensus-U7-hg_USH2A_int13_SD_20 bp_5-filler | (SEQ ID NO: 662) CTTCCTTGACGATTAGGCAC-AATTTTTGGAG-(SEQ ID NO: 659) taggctttctggcttttcaccggaaagcccct_AAATGATTAAATTAA |
| SD targeting | Sm_consensus-U7-hg_USH2A_int13_SD_20 bp_6-filler | (SEQ ID NO: 664) ACCTTCTTCCTTGACGATTA-AATTTTTGGAG-(SEQ ID NO: 659) taggctttctggcttttcaccggaaagcccct_AAATGATTAAATTAA |
| Random U7 control | Sm.rand-U7-hg_USH2A_int13_SD_20 bp_1-filler | (SEQ ID NO: 666) ACACAGGCACTGGCCACTGA-TGCGTGTCATT-(SEQ ID NO: 659) taggctttctggcttttcaccggaaagcccct_AAATGATTAAATTAA |

TABLE 2-continued

| Category | description | element_seq |
|---|---|---|
| Random U7 control | Sm.rand-U7-hg_USH2A_int13_SD_20 bp_2-filler | (SEQ ID NO: 668) GGCACACACAGGCACTGGCC-TGCGTGTCATT-<br>(SEQ ID NO: 659) taggctttctggcttttcaccggaaagcccct_<br>AAATGATTAAATTAA |
| Random Sm control | Sm_consensus-U7-NT_BM_2-filler | (SEQ ID NO: 670) ACGAGCTCAGCCTATGCGAG-AATTTTTGGAG-<br>(SEQ ID NO: 659) taggctttctggcttttcaccggaaagcccct_<br>AAATGATTAAATTAA |
| Random Sm control | Sm_consensus-U7-NT_BM_3-filler | (SEQ ID NO: 672) CCACCTACCCTATCGTGCGG-AATTTTTGGAG-<br>(SEQ ID NO: 659) taggctttctggcttttcaccggaaagcccct_<br>AAATGATTAAATTAA |
| | | Format for the above sequences:<br>{Binding Motif}-{Sm consensus/Sm rand}-{U7/U7<br>rand}_{filler} |

TABLE 3

| ASR ID | ASR se'ue'ce ("-")<br>(SEQ ID NO.) | Length<br>(nt) | Sm sequence<br>(SEQ ID NO.) |
|---|---|---|---|
| smU7 guide 3 | TAAAATATATTTAAAAGGTG<br>(SEQ ID NO: 702) | 20 | AATTTTTGGAG<br>SEQ ID NO: 701) |
| sm-mut | TAAAATATATTTAAAAGGTG<br>(SEQ ID NO: 702) | 20 | AACGCGTCATG<br>(SEQ ID NO: 703) |
| NT | GTTCCGCGTTACATAACTTA<br>(SEQ ID NO: 707) | 20 | AATTTTTGGAG<br>(SEQ ID NO: 701) |

TABLE 4

| ASR ID | ASR se'ue'ce ("-")<br>(SEQ ID NO.) | Length (nt) |
|---|---|---|
| 7 | TCACACCTAAGCCCTAAAGA<br>(SEQ ID NO: 706) | 20 |
| NT | GTTCCGCGTTACATAACTTA<br>(SEQ ID NO: 707) | 20 |

TABLE 5 grepRNA sequences:
GGCTTTCTGGCTTTTTACCGGAAAGCC U7 hairpin
*AATTTTTGGAG* smOPT (SEQ ID NO: 701)
AACGCGTCATG sm-mut (SEQ ID NO: 703)
TCACACCTAAGCCCTAAAGA Anti-sense Region (SEQ ID NO: 706)

pATK1014    TCACACCTAAGCCCTAAAGAGAGCCTGTACTTGTTAACACCGAATGTGATGCCCTGTAGGCCTTCCTGA     g7 ASR only<br>
                  CTATGGCGGCCTACTTATCCTGTCCCTTTTTTTTCCACAGGAGCGCACCATCTTCTTCAAGGACGACG<br>
                  GCAACTACAAGACCCGCGCCGAGGTGAAGTTCGAGGGCGACACCCTGGTGAACCGCATCGAGCTG<br>
                  AAGGGCATCGACTTCAAGGAGGACGGCAACATCCTGGGGCACAAGCTGGAGTACAACTACAACAG<br>
                  CCACAACGTCTATATCATGGCCGACAAGCAGAAGAACGGCATCAAGGTGAACTTCAAGATCCGCCA<br>
                  CAACATCGAGGACGGCAGCGTGCAGCTCGCCGACCACTACCAGCAGAACACCCCCATCGGCGACG<br>
                  GCCCCGTGCTGCTGCCCGACAACCACTACCTGAGCACCCAGTCCGCCCTGAGCAAAGACCCCAACG<br>
                  AGAAGCGCGATCACATGGTCCTGCTGGAGTTCGTGACCGCCGCCGGGATCACTCTCGGCATGGACG<br>
                  AGCTGTACAAGTAATGGCTTGTTTATTGCAGCTTATAATGGTTACAAATAA (SEQ ID NO: 708)

pATK1016    TCACACCTAAGCCCTAAAGAAAATTTTTGGATAGGCTTTCTGGCTTTTTACCGGAAAGCCCTGCC     g7 full U7<br>
                  TGTACTTGTTAACACCGAATGTGATGCCCTGTAGGCCTTCCTGACTATGGCGGCCTACTTATCCTGTC     gRNA<br>
                  CCTTTTTTTTCCACAGGAGCGCACCATCTTCTTCAAGGACGACGGCAACTACAAGACCCGCGCCGAG<br>
                  GTGAAGTTCGAGGGCGACACCCTGGTGAACCGCATCGAGCTGAAGGGCATCGACTTCAAGGAGGA<br>
                  CGGCAACATCCTGGGGCACAAGCTGGAGTACAACTACAACAGCCACAACGTCTATATCATGGCCGA<br>
                  CAAGCAGAAGAACGGCATCAAGGTGAACTTCAAGATCCGCCACAACATCGAGGACGGCAGCGTGC<br>
                  AGCTCGCCGACCACTACCAGCAGAACACCCCCATCGGCGACGGCCCCGTGCTGCTGCCCGACAACC<br>
                  ACTACCTGAGCACCCAGTCCGCCCTGAGCAAAGACCCCAACGAGAAGCGCGATCACATGGTCCTGC<br>
                  TGGAGTTCGTGACCGCCGCCGGGATCACTCTCGGCATGGACGAGCTGTACAAGTAATGGCTTGTTT<br>
                  ATTGCAGCTTATAATGGTTACAAATAA (SEQ ID NO: 709)

pATK1019    GTTCCGCGTTACATAACTTAAAATTTTTGGATAGGCTTTCTGGCTTTTTACCGGAAAGCCCTGCCT     NT full U7<br>
                  GTACTTGTTAACACCGAATGTGATGCCCTGTAGGCCTTCCTGACTATGGCGGCCTACTTATCCTGTC     gRNA<br>
                  CTTTTTTTTCCACAGGAGCGCACCATCTTCTTCAAGGACGACGGCAACTACAAGACCCGCGCCGAGG<br>
                  TGAAGTTCGAGGGCGACACCCTGGTGAACCGCATCGAGCTGAAGGGCATCGACTTCAAGGAGGAC<br>
                  GGCAACATCCTGGGGCACAAGCTGGAGTACAACTACAACAGCCACAACGTCTATATCATGGCCGAC<br>
                  AAGCAGAAGAACGGCATCAAGGTGAACTTCAAGATCCGCCACAACATCGAGGACGGCAGCGTGCA<br>
                  GCTCGCCGACCACTACCAGCAGAACACCCCCATCGGCGACGGCCCCGTGCTGCTGCCCGACAACCA<br>
                  CTACCTGAGCACCCAGTCCGCCCTGAGCAAAGACCCCAACGAGAAGCGCGATCACATGGTCCTGCT<br>
                  GGAGTTCGTGACCGCCGCCGGGATCACTCTCGGCATGGACGAGCTGTACAAGTAATGGCTTGTTTA<br>
                  TTGCAGCTTATAATGGTTACAAATAA (SEQ ID NO: 710)

TABLE 5-continued

| | | |
|---|---|---|
| b_g7_<br>smMut_<br>3repRNA | GTCGGTCTCGGATCTCACACCTAAGCCCTAAAGAAACGCGTCATGTAGGCTTTCTGGCTTTTTACCG<br>GAAAGCCCCTGCCTGTACTTGTTAACACCGAATGTGATGCCCTGTAGGCCTTCCTGACTATGGCGGC<br>CTACTTATCCTGTCCCTTTTTTTTTCCACAGGAGCGCACCATCTTCTTCAAGGACGACGGCAACTACAA<br>GACCCGCGCCGAGGTGAAGTTCGAGGGCGACACCCTGGTGAACCGCATCGAGCTGAAGGGCATCG<br>ACTTCAAGGAGGACGGCAACATCCTGGGGCACAAGCTGGAGTACAACTACAACAGCCACAACGTCT<br>ATATCATGGCCGACAAGCAGAAGAACGGCATCAAGGTGAACTTCAAGATCCGCCACAACATCGAG<br>GACGGCAGCGTGCAGCTCGCCGACCACTACCAGCAGAACACCCCCATCGGCGACGGCCCCGTGCTG<br>CTGCCCGACAACCACTACCTGAGCACCCAGTCCGCCCTGAGCAAAGACCCCAACGAGAAGCGCGAT<br>CACATGGTCCTGCTGGAGTTCGTGACCGCCGCCGGGATCACTCTCGGCATGGACGAGCTGTACAAG<br>TAATGGCCGAGACC (SEQ ID NO: 711) | guide 7 BM<br>smU7 Mut-<br>intronic<br>spacer<br>(50 nts)-<br>Splice<br>acceptor-<br>GFP 2.2 |

TABLE 6

SEQUENCE LISTING

| SEQ<br>ID<br>NO | Name/<br>ID | Sequence |
|---|---|---|
| 1 | H box | ANANNA N = A, C, G, OR U |
| 2 | ACA box | ACA |
| 3 | Sm<br>consensus<br>motf | AAUUUUUGG |
| 4 | Sm U7<br>motif | AAUUUGUCU |
| 5 | C box | RUGAUGA R = A OR G |
| 6 | D box | 'UGA |
| 7 | '' box | RUG'UGA |
| 8 | '' box | CUGA |
| 9 | U1_1_0 | AUACUUACGUAACAGGAGAAAAUACGGCCAUGAAGUUGGUGUUUCUCGGGGGCGAUUUCUCCAUUGUACUCAGUAUG<br>UGCUGACUGACUCCUGUUACUUCCACAUGUGGGGAAACUGGACUGUAAUUUGUGGUGGUGGGGAAUUGCGUUCGCGC |
| 10 | U1_1_1 | UACUUACGUAACAGGAGAAAAUACGGCCAUGAAGUUGGUGUUUCUCGGGGGCGAUUUCUCCAUUGUACUCAGUAUGU<br>GCUGACUGACUCCUGUUACUUCCACAUGUGGGGAAACUGGACUGUAAUUUGUGGUGGUGGGGAAUUGCGUUCGCGCU |
| 11 | U1_1_2 | ACUUACGUAACAGGAGAAAAUACGGCCAUGAAGUUGGUGUUUCUCGGGGGCGAUUUCUCCAUUGUACUCAGUAUGUG<br>CUGACUGACUCCUGUUACUUCCACAUGUGGGGAAACUGGACUGUAAUUUGUGGUGGUGGGGAAUUGCGUUCGCGCUU |
| 12 | U1_1_3 | CUUACGUAACAGGAGAAAAUACGGCCAUGAAGUUGGUGUUUCUCGGGGGCGAUUUCUCCAUUGUACUCAGUAUGUGC<br>UGACUGACUCCUGUUACUUCCACAUGUGGGGAAACUGGACUGUAAUUUGUGGUGGUGGGGAAUUGCGUUCGCGCUUU |
| 13 | U1_1_4 | UUACGUAACAGGAGAAAAUACGGCCAUGAAGUUGGUGUUUCUCGGGGGCGAUUUCUCCAUUGUACUCAGUAUGUGCU<br>GACUGACUCCUGUUACUUCCACAUGUGGGGAAACUGGACUGUAAUUUGUGGUGGUGGGGAAUUGCGUUCGCGCUUUC |
| 14 | U1_1_5 | UACGUAACAGGAGAAAAUACGGCCAUGAAGUUGGUGUUUCUCGGGGGCGAUUUCUCCAUUGUACUCAGUAUGUGCUG<br>ACUGACUCCUGUUACUUCCACAUGUGGGGAAACUGGACUGUAAUUUGUGGUGGUGGGGAAUUGCGUUCGCGCUUUCU |
| 15 | U1_1_6 | ACGUAACAGGAGAAAAUACGGCCAUGAAGUUGGUGUUUCUCGGGGGCGAUUUCUCCAUUGUACUCAGUAUGUGCUGA<br>CUGACUCCUGUUACUUCCACAUGUGGGGAAACUGGACUGUAAUUUGUGGUGGUGGGGAAUUGCGUUCGCGCUUUCUU |
| 16 | U1_1_7 | CGUAACAGGAGAAAAUACGGCCAUGAAGUUGGUGUUUCUCGGGGGCGAUUUCUCCAUUGUACUCAGUAUGUGCUGAC<br>UGACUCCUGUUACUUCCACAUGUGGGGAAACUGGACUGUAAUUUGUGGUGGUGGGGAAUUGCGUUCGCGCUUUCUUC |
| 17 | U1_1_8 | GUAACAGGAGAAAAUACGGCCAUGAAGUUGGUGUUUCUCGGGGGCGAUUUCUCCAUUGUACUCAGUAUGUGCUGACU<br>GACUCCUGUUACUUCCACAUGUGGGGAAACUGGACUGUAAUUUGUGGUGGUGGGGAAUUGCGUUCGCGCUUUCUUCU |
| 18 | U1_1_9 | UAACAGGAGAAAAUACGGCCAUGAAGUUGGUGUUUCUCGGGGGCGAUUUCUCCAUUGUACUCAGUAUGUGCUGACUG<br>ACUCCUGUUACUUCCACAUGUGGGGAAACUGGACUGUAAUUUGUGGUGGUGGGGAAUUGCGUUCGCGCUUUCUUCU |
| 19 | U1_2_0 | AUAUUUACUUGGCAGGGGAGAUAACGUGACCACGAAGGUGGUUUUCCCAGGGCUGAGGCUUAUUCAUUGUACUCCGG<br>AUGUGCUGACCCCUGCGAUUUCCCCAAAUGUGGGAAACUCGACUGCAUAAUUUGUGGUAGUGGGGGGCUGUGUCCGU |
| 20 | U1_2_1 | UAUUUACUUGGCAGGGGAGAUAACGUGACCACGAAGGUGGUUUUCCCAGGGCUGAGGCUUAUUCAUUGUACUCCGGA<br>UGUGCUGACCCCUGCGAUUUCCCCAAAUGUGGGAAACUCGACUGCAUAAUUUGUGGUAGUGGGGGGCUGUGUCCGUG |
| 21 | U1_2_2 | AUUUACUUGGCAGGGGAGAUAACGUGACCACGAAGGUGGUUUUCCCAGGGCUGAGGCUUAUUCAUUGUACUCCGGAU<br>GUGCUGACCCCUGCGAUUUCCCCAAAUGUGGGAAACUCGACUGCAUAAUUUGUGGUAGUGGGGGGCUGUGUCCGUGC |

TABLE 6-continued

| | | |
|---|---|---|
| | | SEQUENCE LISTING |

| SEQ ID NO | Name/ ID | Sequence |
|---|---|---|
| 22 | U1_2_3 | UUUACUUGGCAGGGGAGAUAACGUGACCACGAAGGUGGUUUUCCCAGGGCUGAGGCUUAUUCAUUGUACUCCGGAUG UGCUGACCCCUGCGAUUUCCCCAAAUGUGGGAAACUCGACUGCAUAAUUUGUGGUAGUGGGGGGCUGUGUCCGUGCU |
| 23 | U1_2_4 | UUACUUGGCAGGGGAGAUAACGUGACCACGAAGGUGGUUUUCCCAGGGCUGAGGCUUAUUCAUUGUACUCCGGAUGU GCUGACCCCUGCGAUUUCCCCAAAUGUGGGAAACUCGACUGCAUAAUUUGUGGUAGUGGGGGGCUGUGUCCGUGCUU |
| 24 | U1_2_5 | UACUUGGCAGGGGAGAUAACGUGACCACGAAGGUGGUUUUCCCAGGGCUGAGGCUUAUUCAUUGUACUCCGGAUGUG CUGACCCCUGCGAUUUCCCCAAAUGUGGGAAACUCGACUGCAUAAUUUGUGGUAGUGGGGGGCUGUGUCCGUGCUUU |
| 25 | U1_2_6 | ACUUGGCAGGGGAGAUAACGUGACCACGAAGGUGGUUUUCCCAGGGCUGAGGCUUAUUCAUUGUACUCCGGAUGUGC UGACCCCUGCGAUUUCCCCAAAUGUGGGAAACUCGACUGCAUAAUUUGUGGUAGUGGGGGGCUGUGUCCGUGCUUUU |
| 26 | U1_2_7 | CUUGGCAGGGGAGAUAACGUGACCACGAAGGUGGUUUUCCCAGGGCUGAGGCUUAUUCAUUGUACUCCGGAUGUGCU GACCCCUGCGAUUUCCCCAAAUGUGGGAAACUCGACUGCAUAAUUUGUGGUAGUGGGGGGCUGUGUCCGUGCUUUUC |
| 27 | U1_2_8 | UUGGCAGGGGAGAUAACGUGACCACGAAGGUGGUUUUCCCAGGGCUGAGGCUUAUUCAUUGUACUCCGGAUGUGCUG ACCCCUGCGAUUUCCCCAAAUGUGGGAAACUCGACUGCAUAAUUUGUGGUAGUGGGGGGCUGUGUCCGUGCUUUUCC |
| 28 | U1_2_9 | UGGCAGGGGAGAUAACGUGACCACGAAGGUGGUUUUCCCAGGGCUGAGGCUUAUUCAUUGUACUCCGGAUGUGCUGA CCCCUGCGAUUUCCCCAAAUGUGGGAAACUCGACUGCAUAAUUUGUGGUAGUGGGGGGCUGUGUCCGUGCUUUUCCC |
| 29 | U1_3_0 | AUACUUACCUGGCAGGGCAGAUACCAUGAUCUUAAAGGCAGUUUUCCCAGGGCAAGGCUUAUCCAUUCCACUCUGGA UCCAUUAUAGGGGCAUGCUGAUCCCUGGAAUUGCCCCAAAUGUGGGAAGCUCUACUGCAAAAUUUUUGGUAGUGAGC |
| 30 | U1_3_1 | UACUUACCUGGCAGGGCAGAUACCAUGAUCUUAAAGGCAGUUUUCCCAGGGCAAGGCUUAUCCAUUCCACUCUGGAU CCAUUAUAGGGGCAUGCUGAUCCCUGGAAUUGCCCCAAAUGUGGGAAGCUCUACUGCAAAAUUUUUGGUAGUGAGCG |
| 31 | U1_3_2 | ACUUACCUGGCAGGGCAGAUACCAUGAUCUUAAAGGCAGUUUUCCCAGGGCAAGGCUUAUCCAUUCCACUCUGGAUC CAUUAUAGGGGCAUGCUGAUCCCUGGAAUUGCCCCAAAUGUGGGAAGCUCUACUGCAAAAUUUUUGGUAGUGAGCGA |
| 32 | U1_3_3 | CUUACCUGGCAGGGCAGAUACCAUGAUCUUAAAGGCAGUUUUCCCAGGGCAAGGCUUAUCCAUUCCACUCUGGAUCC AUUAUAGGGGCAUGCUGAUCCCUGGAAUUGCCCCAAAUGUGGGAAGCUCUACUGCAAAAUUUUUGGUAGUGAGCGAU |
| 33 | U1_3_4 | UUACCUGGCAGGGCAGAUACCAUGAUCUUAAAGGCAGUUUUCCCAGGGCAAGGCUUAUCCAUUCCACUCUGGAUCCA UUAUAGGGGCAUGCUGAUCCCUGGAAUUGCCCCAAAUGUGGGAAGCUCUACUGCAAAAUUUUUGGUAGUGAGCGAUG |
| 34 | U1_3_5 | UACCUGGCAGGGCAGAUACCAUGAUCUUAAAGGCAGUUUUCCCAGGGCAAGGCUUAUCCAUUCCACUCUGGAUCCAU UAUAGGGGCAUGCUGAUCCCUGGAAUUGCCCCAAAUGUGGGAAGCUCUACUGCAAAAUUUUUGGUAGUGAGCGAUGG |
| 35 | U1_3_6 | ACCUGGCAGGGCAGAUACCAUGAUCUUAAAGGCAGUUUUCCCAGGGCAAGGCUUAUCCAUUCCACUCUGGAUCCAUU AUAGGGGCAUGCUGAUCCCUGGAAUUGCCCCAAAUGUGGGAAGCUCUACUGCAAAAUUUUUGGUAGUGAGCGAUGGC |
| 36 | U1_3_7 | CCUGGCAGGGCAGAUACCAUGAUCUUAAAGGCAGUUUUCCCAGGGCAAGGCUUAUCCAUUCCACUCUGGAUCCAUUA UAGGGGCAUGCUGAUCCCUGGAAUUGCCCCAAAUGUGGGAAGCUCUACUGCAAAAUUUUUGGUAGUGAGCGAUGGCA |
| 37 | U1_3_8 | CUGGCAGGGCAGAUACCAUGAUCUUAAAGGCAGUUUUCCCAGGGCAAGGCUUAUCCAUUCCACUCUGGAUCCAUUAU AGGGGCAUGCUGAUCCCUGGAAUUGCCCCAAAUGUGGGAAGCUCUACUGCAAAAUUUUUGGUAGUGAGCGAUGGCAU |
| 38 | U1_3_9 | UGGCAGGGCAGAUACCAUGAUCUUAAAGGCAGUUUUCCCAGGGCAAGGCUUAUCCAUUCCACUCUGGAUCCAUUAUA GGGGCAUGCUGAUCCCUGGAAUUGCCCCAAAUGUGGGAAGCUCUACUGCAAAAUUUUUGGUAGUGAGCGAUGGCAUU |
| 39 | U1_4_0 | AUACUUACCUGGCAGGGGAGAUACCAUGAUCACGAAGGUGGUUUUCCCAGGGCGAGGCUUAUCCAUUGCACUCCGGA UGUGCUGACCCCUGCGAUUUCCCCAAAUGUGGGAAACUCGACUGCAUAAUUUGUGGUAGUGGGGGACUGCGUUCGCG |
| 40 | U1_4_1 | UACUUACCUGGCAGGGGAGAUACCAUGAUCACGAAGGUGGUUUUCCCAGGGCGAGGCUUAUCCAUUGCACUCCGGAU GUGCUGACCCCUGCGAUUUCCCCAAAUGUGGGAAACUCGACUGCAUAAUUUGUGGUAGUGGGGGACUGCGUUCGCGC |
| 41 | U1_4_2 | ACUUACCUGGCAGGGGAGAUACCAUGAUCACGAAGGUGGUUUUCCCAGGGCGAGGCUUAUCCAUUGCACUCCGGAUG UGCUGACCCCUGCGAUUUCCCCAAAUGUGGGAAACUCGACUGCAUAAUUUGUGGUAGUGGGGGACUGCGUUCGCGCU |
| 42 | U1_4_3 | CUUACCUGGCAGGGGAGAUACCAUGAUCACGAAGGUGGUUUUCCCAGGGCGAGGCUUAUCCAUUGCACUCCGGAUGU GCUGACCCCUGCGAUUUCCCCAAAUGUGGGAAACUCGACUGCAUAAUUUGUGGUAGUGGGGGACUGCGUUCGCGCUU |
| 43 | U1_4_4 | UUACCUGGCAGGGGAGAUACCAUGAUCACGAAGGUGGUUUUCCCAGGGCGAGGCUUAUCCAUUGCACUCCGGAUGUG CUGACCCCUGCGAUUUCCCCAAAUGUGGGAAACUCGACUGCAUAAUUUGUGGUAGUGGGGGACUGCGUUCGCGCUUU |
| 44 | U1_4_5 | UACCUGGCAGGGGAGAUACCAUGAUCACGAAGGUGGUUUUCCCAGGGCGAGGCUUAUCCAUUGCACUCCGGAUGUGC UGACCCCUGCGAUUUCCCCAAAUGUGGGAAACUCGACUGCAUAAUUUGUGGUAGUGGGGGACUGCGUUCGCGCUUUC |
| 45 | U1_4_6 | ACCUGGCAGGGGAGAUACCAUGAUCACGAAGGUGGUUUUCCCAGGGCGAGGCUUAUCCAUUGCACUCCGGAUGUGCU GACCCCUGCGAUUUCCCCAAAUGUGGGAAACUCGACUGCAUAAUUUGUGGUAGUGGGGGACUGCGUUCGCGCUUUCC |
| 46 | U1_4_7 | CCUGGCAGGGGAGAUACCAUGAUCACGAAGGUGGUUUUCCCAGGGCGAGGCUUAUCCAUUGCACUCCGGAUGUGCUG ACCCCUGCGAUUUCCCCAAAUGUGGGAAACUCGACUGCAUAAUUUGUGGUAGUGGGGGACUGCGUUCGCGCUUUCCC |

TABLE 6-continued

|  | | |
|---|---|---|

SEQUENCE LISTING

| SEQ ID NO | Name/ ID | Sequence |
|---|---|---|
| 47 | U1_4_8 | CUGGCAGGGGAGAUACCAUGAUCACGAAGGUGGUUUUCCCAGGGCGAGGCUUAUCCAUUGCACUCCGGAUGUGCUGA<br>CCCCUGCGAUUUCCCCAAAUGUGGGAAACUCGACUGCAUAAUUUGUGGUAGUGGGGGACUGCGUUCGCGCUUUCCCC |
| 48 | U1_4_9 | UGGCAGGGGAGAUACCAUGAUCACGAAGGUGGUUUUCCCAGGGCGAGGCUUAUCCAUUGCACUCCGGAUGUGCUGAC<br>CCCUGCGAUUUCCCCAAAUGUGGGAAACUCGACUGCAUAAUUUGUGGUAGUGGGGGACUGCGUUCGCGCUUUCCCCU |
| 49 | U1_5_0 | AUACUUCCCUGACAGGGGAGAUACCUAGGAAUCCAACUUCCCAGGGCAAGACUGAUCUAUUGCACUAUGGAUGUGCC<br>GACCCCUGAGAUUUACAAAAUUGUGGGAAACUCAACUGCAUAAUUUAUGGAAAUGAAGGACUGUGUUUGCGCUUUCA |
| 50 | U1_5_1 | UACUUCCCUGACAGGGGAGAUACCUAGGAAUCCAACUUCCCAGGGCAAGACUGAUCUAUUGCACUAUGGAUGUGCCG<br>ACCCCUGAGAUUUACAAAAUUGUGGGAAACUCAACUGCAUAAUUUAUGGAAAUGAAGGACUGUGUUUGCGCUUUCA |
| 51 | U1_5_2 | ACUUCCCUGACAGGGGAGAUACCUAGGAAUCCAACUUCCCAGGGCAAGACUGAUCUAUUGCACUAUGGAUGUGCCGA<br>CCCCUGAGAUUUACAAAAUUGUGGGAAACUCAACUGCAUAAUUUAUGGAAAUGAAGGACUGUGUUUGCGCUUUCA |
| 52 | U1_5_3 | CUUCCCUGACAGGGGAGAUACCUAGGAAUCCAACUUCCCAGGGCAAGACUGAUCUAUUGCACUAUGGAUGUGCCGAC<br>CCCUGAGAUUUACAAAAUUGUGGGAAACUCAACUGCAUAAUUUAUGGAAAUGAAGGACUGUGUUUGCGCUUUCA |
| 53 | U1_5_4 | UUCCCUGACAGGGGAGAUACCUAGGAAUCCAACUUCCCAGGGCAAGACUGAUCUAUUGCACUAUGGAUGUGCCGACC<br>CCUGAGAUUUACAAAAUUGUGGGAAACUCAACUGCAUAAUUUAUGGAAAUGAAGGACUGUGUUUGCGCUUUCA |
| 54 | U1_5_5 | UCCCUGACAGGGGAGAUACCUAGGAAUCCAACUUCCCAGGGCAAGACUGAUCUAUUGCACUAUGGAUGUGCCGACCC<br>CUGAGAUUUACAAAAUUGUGGGAAACUCAACUGCAUAAUUUAUGGAAAUGAAGGACUGUGUUUGCGCUUUCA |
| 55 | U1_5_6 | CCCUGACAGGGGAGAUACCUAGGAAUCCAACUUCCCAGGGCAAGACUGAUCUAUUGCACUAUGGAUGUGCCGACCCC<br>UGAGAUUUACAAAAUUGUGGGAAACUCAACUGCAUAAUUUAUGGAAAUGAAGGACUGUGUUUGCGCUUUCA |
| 56 | U1_5_7 | CCUGACAGGGGAGAUACCUAGGAAUCCAACUUCCCAGGGCAAGACUGAUCUAUUGCACUAUGGAUGUGCCGACCCCU<br>GAGAUUUACAAAAUUGUGGGAAACUCAACUGCAUAAUUUAUGGAAAUGAAGGACUGUGUUUGCGCUUUCA |
| 57 | U1_5_8 | CUGACAGGGGAGAUACCUAGGAAUCCAACUUCCCAGGGCAAGACUGAUCUAUUGCACUAUGGAUGUGCCGACCCCUG<br>AGAUUUACAAAAUUGUGGGAAACUCAACUGCAUAAUUUAUGGAAAUGAAGGACUGUGUUUGCGCUUUCA |
| 58 | U1_5_9 | UGACAGGGGAGAUACCUAGGAAUCCAACUUCCCAGGGCAAGACUGAUCUAUUGCACUAUGGAUGUGCCGACCCCUGA<br>GAUUUACAAAAUUGUGGGAAACUCAACUGCAUAAUUUAUGGAAAUGAAGGACUGUGUUUGCGCUUUCA |
| 59 | U1_6_0 | AAACUUCUCUGCCAGGGGAGAUACCAUGAUCACAAAGGUGGCUUUCUCAGGGAAAGGCUGAUUUAUUGCACUCCAGA<br>UGUGCUGACCCCUGAGAUUUCUCCAAAUGUGGGAAACUCAGCUGCAUAAUUUGUGGAAGCGAAGGACUGUGUUUGUG |
| 60 | U1_6_1 | AACUUCUCUGCCAGGGGAGAUACCAUGAUCACAAAGGUGGCUUUCUCAGGGAAAGGCUGAUUUAUUGCACUCCAGAU<br>GUGCUGACCCCUGAGAUUUCUCCAAAUGUGGGAAACUCAGCUGCAUAAUUUGUGGAAGCGAAGGACUGUGUUUGUGC |
| 61 | U1_6_2 | ACUUCUCUGCCAGGGGAGAUACCAUGAUCACAAAGGUGGCUUUCUCAGGGAAAGGCUGAUUUAUUGCACUCCAGAUG<br>UGCUGACCCCUGAGAUUUCUCCAAAUGUGGGAAACUCAGCUGCAUAAUUUGUGGAAGCGAAGGACUGUGUUUGUGCU |
| 62 | U1_6_3 | CUUCUCUGCCAGGGGAGAUACCAUGAUCACAAAGGUGGCUUUCUCAGGGAAAGGCUGAUUUAUUGCACUCCAGAUGU<br>GCUGACCCCUGAGAUUUCUCCAAAUGUGGGAAACUCAGCUGCAUAAUUUGUGGAAGCGAAGGACUGUGUUUGUGCUU |
| 63 | U1_6_4 | UUCUCUGCCAGGGGAGAUACCAUGAUCACAAAGGUGGCUUUCUCAGGGAAAGGCUGAUUUAUUGCACUCCAGAUGUG<br>CUGACCCCUGAGAUUUCUCCAAAUGUGGGAAACUCAGCUGCAUAAUUUGUGGAAGCGAAGGACUGUGUUUGUGCUUU |
| 64 | U1_6_5 | UUCUCUGCCAGGGGAGAUACCAUGAUCACAAAGGUGGCUUUCUCAGGGAAAGGCUGAUUUAUUGCACUCCAGAUGUGC<br>UGACCCCUGAGAUUUCUCCAAAUGUGGGAAACUCAGCUGCAUAAUUUGUGGAAGCGAAGGACUGUGUUUGUGCUUUC |
| 65 | U1_6_6 | CUCUGCCAGGGGAGAUACCAUGAUCACAAAGGUGGCUUUCUCAGGGAAAGGCUGAUUUAUUGCACUCCAGAUGUGCU<br>GACCCCUGAGAUUUCUCCAAAUGUGGGAAACUCAGCUGCAUAAUUUGUGGAAGCGAAGGACUGUGUUUGUGCUUUCA |
| 66 | U1_6_7 | UCUGCCAGGGGAGAUACCAUGAUCACAAAGGUGGCUUUCUCAGGGAAAGGCUGAUUUAUUGCACUCCAGAUGUGCUG<br>ACCCCUGAGAUUUCUCCAAAUGUGGGAAACUCAGCUGCAUAAUUUGUGGAAGCGAAGGACUGUGUUUGUGCUUUCAU |
| 67 | U1_6_8 | CUGCCAGGGGAGAUACCAUGAUCACAAAGGUGGCUUUCUCAGGGAAAGGCUGAUUUAUUGCACUCCAGAUGUGCUGA<br>CCCCUGAGAUUUCUCCAAAUGUGGGAAACUCAGCUGCAUAAUUUGUGGAAGCGAAGGACUGUGUUUGUGCUUUCAUG |
| 68 | U1_6_9 | UGCCAGGGGAGAUACCAUGAUCACAAAGGUGGCUUUCUCAGGGAAAGGCUGAUUUAUUGCACUCCAGAUGUGCUGAC<br>CCCUGAGAUUUCUCCAAAUGUGGGAAACUCAGCUGCAUAAUUUGUGGAAGCGAAGGACUGUGUUUGUGCUUUCAUGU |
| 69 | U1_7_0 | AUACUUCUCUGCCAGGGGAGAUACUGUGAUCAUGAAGGUGGCUUUCCCAGGGCAAGGCUGAUCUAUUGCAUUCUGGA<br>UGUGCUGACUCCUACGAUUUCCCCAAGUGUGGGAAACUCAACUGCAUAAUUUGUGGAAGUAAUGACUGUGUUUGCAC |
| 70 | U1_7_1 | UACUUCUCUGCCAGGGGAGAUACUGUGAUCAUGAAGGUGGCUUUCCCAGGGCAAGGCUGAUCUAUUGCAUUCUGGAU<br>GUGCUGACUCCUACGAUUUCCCCAAGUGUGGGAAACUCAACUGCAUAAUUUGUGGAAGUAAUGACUGUGUUUGCACU |

TABLE 6-continued

SEQUENCE LISTING

| SEQ ID NO | Name/ ID | Sequence |
|---|---|---|
| 71 | U1_7_2 | ACUUCUCUGCCAGGGGAGAUACUGUGAUCAUGAAGGUGGCUUUCCCAGGGCAAGGCUGAUCUAUUGCAUUCUGGAUG<br>UGCUGACUCCUACGAUUUCCCCAAGUGUGGGAAACUCAACUGCAUAAUUUGUGGAAGUAAUGACUGUGUUUGCACUU |
| 72 | U1_7_3 | CUUCUCUGCCAGGGGAGAUACUGUGAUCAUGAAGGUGGCUUUCCCAGGGCAAGGCUGAUCUAUUGCAUUCUGGAUGU<br>GCUGACUCCUACGAUUUCCCCAAGUGUGGGAAACUCAACUGCAUAAUUUGUGGAAGUAAUGACUGUGUUUGCACUUU |
| 73 | U1_7_4 | UUCUCUGCCAGGGGAGAUACUGUGAUCAUGAAGGUGGCUUUCCCAGGGCAAGGCUGAUCUAUUGCAUUCUGGAUGUG<br>CUGACUCCUACGAUUUCCCCAAGUGUGGGAAACUCAACUGCAUAAUUUGUGGAAGUAAUGACUGUGUUUGCACUUUC |
| 74 | U1_7_5 | UCUCUGCCAGGGGAGAUACUGUGAUCAUGAAGGUGGCUUUCCCAGGGCAAGGCUGAUCUAUUGCAUUCUGGAUGUGC<br>UGACUCCUACGAUUUCCCCAAGUGUGGGAAACUCAACUGCAUAAUUUGUGGAAGUAAUGACUGUGUUUGCACUUUCA |
| 75 | U1_7_6 | CUCUGCCAGGGGAGAUACUGUGAUCAUGAAGGUGGCUUUCCCAGGGCAAGGCUGAUCUAUUGCAUUCUGGAUGUGCU<br>GACUCCUACGAUUUCCCCAAGUGUGGGAAACUCAACUGCAUAAUUUGUGGAAGUAAUGACUGUGUUUGCACUUUCAC |
| 76 | U1_7_7 | UCUGCCAGGGGAGAUACUGUGAUCAUGAAGGUGGCUUUCCCAGGGCAAGGCUGAUCUAUUGCAUUCUGGAUGUGCUG<br>ACUCCUACGAUUUCCCCAAGUGUGGGAAACUCAACUGCAUAAUUUGUGGAAGUAAUGACUGUGUUUGCACUUUCACG |
| 77 | U1_7_8 | CUGCCAGGGGAGAUACUGUGAUCAUGAAGGUGGCUUUCCCAGGGCAAGGCUGAUCUAUUGCAUUCUGGAUGUGCUGA<br>CUCCUACGAUUUCCCCAAGUGUGGGAAACUCAACUGCAUAAUUUGUGGAAGUAAUGACUGUGUUUGCACUUUCACGU |
| 78 | U1_7_9 | UGCCAGGGGAGAUACUGUGAUCAUGAAGGUGGCUUUCCCAGGGCAAGGCUGAUCUAUUGCAUUCUGGAUGUGCUGAC<br>UCCUACGAUUUCCCCAAGUGUGGGAAACUCAACUGCAUAAUUUGUGGAAGUAAUGACUGUGUUUGCACUUUCACGU |
| 79 | U1_8_0 | AUACUUCCCUGCCAGGGGAGAUACCGUGAUCAUGAAGGUGGCUUUCCCAGGGAAAGGCCGAUAUGUUGCACUCUAGA<br>UGUGCUGACCCGUGAGAUUUCCCCAAAUGUGGGACACUCAAAUGCAUAAUUGGUGGAAGUGAAGGACUGUGUUUGUG |
| 80 | U1_8_1 | UACUUCCCUGCCAGGGGAGAUACCGUGAUCAUGAAGGUGGCUUUCCCAGGGAAAGGCCGAUAUGUUGCACUCUAGAU<br>GUGCUGACCCGUGAGAUUUCCCCAAAUGUGGGACACUCAAAUGCAUAAUUGGUGGAAGUGAAGGACUGUGUUUGUGC |
| 81 | U1_8_2 | ACUUCCCUGCCAGGGGAGAUACCGUGAUCAUGAAGGUGGCUUUCCCAGGGAAAGGCCGAUAUGUUGCACUCUAGAUG<br>UGCUGACCCGUGAGAUUUCCCCAAAUGUGGGACACUCAAAUGCAUAAUUGGUGGAAGUGAAGGACUGUGUUUGUGCU |
| 82 | U1_8_3 | CUUCCCUGCCAGGGGAGAUACCGUGAUCAUGAAGGUGGCUUUCCCAGGGAAAGGCCGAUAUGUUGCACUCUAGAUGU<br>GCUGACCCGUGAGAUUUCCCCAAAUGUGGGACACUCAAAUGCAUAAUUGGUGGAAGUGAAGGACUGUGUUUGUGCUU |
| 83 | U1_8_4 | UUCCCUGCCAGGGGAGAUACCGUGAUCAUGAAGGUGGCUUUCCCAGGGAAAGGCCGAUAUGUUGCACUCUAGAUGUG<br>CUGACCCGUGAGAUUUCCCCAAAUGUGGGACACUCAAAUGCAUAAUUGGUGGAAGUGAAGGACUGUGUUUGUGCUUU |
| 84 | U1_8_5 | UCCCUGCCAGGGGAGAUACCGUGAUCAUGAAGGUGGCUUUCCCAGGGAAAGGCCGAUAUGUUGCACUCUAGAUGUGC<br>UGACCCGUGAGAUUUCCCCAAAUGUGGGACACUCAAAUGCAUAAUUGGUGGAAGUGAAGGACUGUGUUUGUGCUUUC |
| 85 | U1_8_6 | CCCUGCCAGGGGAGAUACCGUGAUCAUGAAGGUGGCUUUCCCAGGGAAAGGCCGAUAUGUUGCACUCUAGAUGUGCU<br>GACCCGUGAGAUUUCCCCAAAUGUGGGACACUCAAAUGCAUAAUUGGUGGAAGUGAAGGACUGUGUUUGUGCUUUCA |
| 86 | U1_8_7 | CCUGCCAGGGGAGAUACCGUGAUCAUGAAGGUGGCUUUCCCAGGGAAAGGCCGAUAUGUUGCACUCUAGAUGUGCUG<br>ACCCGUGAGAUUUCCCCAAAUGUGGGACACUCAAAUGCAUAAUUGGUGGAAGUGAAGGACUGUGUUUGUGCUUUCA |
| 87 | U1_8_8 | CUGCCAGGGGAGAUACCGUGAUCAUGAAGGUGGCUUUCCCAGGGAAAGGCCGAUAUGUUGCACUCUAGAUGUGCUGA<br>CCCGUGAGAUUUCCCCAAAUGUGGGACACUCAAAUGCAUAAUUGGUGGAAGUGAAGGACUGUGUUUGUGCUUUCA |
| 88 | U1_8_9 | UGCCAGGGGAGAUACCGUGAUCAUGAAGGUGGCUUUCCCAGGGAAAGGCCGAUAUGUUGCACUCUAGAUGUGCUGAC<br>CCGUGAGAUUUCCCCAAAUGUGGGACACUCAAAUGCAUAAUUGGUGGAAGUGAAGGACUGUGUUUGUGCUUUCA |
| 89 | U1_9_0 | UUAACUACCUGACAGAGGAGAUACUGUGAUCAUGAAAGUGGUUUUCCUAGGGCAAGACUUAUCCGUUGCACUCCAGA<br>UGUGCUGACUCAUGCAAUUUCCCCAAAUGUGGGAAACUCGACUACAUAAUUUCUGGUGGUAGGGGACUGCGUUCAUG |
| 90 | U1_9_1 | UAACUACCUGACAGAGGAGAUACUGUGAUCAUGAAAGUGGUUUUCCUAGGGCAAGACUUAUCCGUUGCACUCCAGAU<br>GUGCUGACUCAUGCAAUUUCCCCAAAUGUGGGAAACUCGACUACAUAAUUUCUGGUGGUAGGGGACUGCGUUCAUGU |
| 91 | U1_9_2 | AACUACCUGACAGAGGAGAUACUGUGAUCAUGAAAGUGGUUUUCCUAGGGCAAGACUUAUCCGUUGCACUCCAGAUG<br>UGCUGACUCAUGCAAUUUCCCCAAAUGUGGGAAACUCGACUACAUAAUUUCUGGUGGUAGGGGACUGCGUUCAUGUU |
| 92 | U1_9_3 | ACUACCUGACAGAGGAGAUACUGUGAUCAUGAAAGUGGUUUUCCUAGGGCAAGACUUAUCCGUUGCACUCCAGAUGU<br>GCUGACUCAUGCAAUUUCCCCAAAUGUGGGAAACUCGACUACAUAAUUUCUGGUGGUAGGGGACUGCGUUCAUGUUC |
| 93 | U1_9_4 | CUACCUGACAGAGGAGAUACUGUGAUCAUGAAAGUGGUUUUCCUAGGGCAAGACUUAUCCGUUGCACUCCAGAUGUG<br>CUGACUCAUGCAAUUUCCCCAAAUGUGGGAAACUCGACUACAUAAUUUCUGGUGGUAGGGGACUGCGUUCAUGUUCU |
| 94 | U1_9_5 | UACCUGACAGAGGAGAUACUGUGAUCAUGAAAGUGGUUUUCCUAGGGCAAGACUUAUCCGUUGCACUCCAGAUGUGC<br>UGACUCAUGCAAUUUCCCCAAAUGUGGGAAACUCGACUACAUAAUUUCUGGUGGUAGGGGACUGCGUUCAUGUUCUC |
| 95 | U1_9_6 | ACCUGACAGAGGAGAUACUGUGAUCAUGAAAGUGGUUUUCCUAGGGCAAGACUUAUCCGUUGCACUCCAGAUGUGCU<br>GACUCAUGCAAUUUCCCCAAAUGUGGGAAACUCGACUACAUAAUUUCUGGUGGUAGGGGACUGCGUUCAUGUUCUCC |

TABLE 6-continued

| SEQ ID NO | Name/ ID | Sequence |
|---|---|---|
| 96 | U1_9_7 | CCUGACAGAGGAGAUACUGUGAUCAUGAAAGUGGUUUUCCUAGGGCAAGACUUAUCCGUUGCACUCCAGAUGUGCUG ACUCAUGCAAUUUCCCCAAAUGUGGGAAACUCGACUACAUAAUUUCUGGUGGUAGGGGACUGCGUUCAUGUUCUCCC |
| 97 | U1_9_8 | CUGACAGAGGAGAUACUGUGAUCAUGAAAGUGGUUUUCCUAGGGCAAGACUUAUCCGUUGCACUCCAGAUGUGCUGA CUCAUGCAAUUUCCCCAAAUGUGGGAAACUCGACUACAUAAUUUCUGGUGGUAGGGGACUGCGUUCAUGUUCUCCCC |
| 98 | U1_9_9 | UGACAGAGGAGAUACUGUGAUCAUGAAAGUGGUUUUCCUAGGGCAAGACUUAUCCGUUGCACUCCAGAUGUGCUGAC UCAUGCAAUUUCCCCAAAUGUGGGAAACUCGACUACAUAAUUUCUGGUGGUAGGGGACUGCGUUCAUGUUCUCCCCU |
| 99 | U1_10_0 | AGACUUAUCUGGCAGGGGAGACACCAUGAACAUGAGGAUAGUUUCCCAAGGCAAGUUUCAACCCUUGCACUCUAGA UGAUGAGAUUACUUAAUGGGUACAAUGCAUGUGAUUUGGGUAAUGGAUACUGUAGAAACACUGACGUCAC |
| 100 | U1_10_1 | GACUUAUCUGGCAGGGGAGACACCAUGAACAUGAGGAUAGUUUUCCCAAGGCAAGUUUCAACCCUUGCACUCUAGAU GAUGAGAUUACUUAAUGGGUACAAUGCAUGUGAUUUGGGUAAUGGAUACUGUAGAAACACUGACGUCAC |
| 101 | U1_10_2 | ACUUAUCUGGCAGGGGAGACACCAUGAACAUGAGGAUAGUUUUCCCAAGGCAAGUUUCAACCCUUGCACUCUAGAUG AUGAGAUUACUUAAUGGGUACAAUGCAUGUGAUUUGGGUAAUGGAUACUGUAGAAACACUGACGUCAC |
| 102 | U1_10_3 | CUUAUCUGGCAGGGGAGACACCAUGAACAUGAGGAUAGUUUUCCCAAGGCAAGUUUCAACCCUUGCACUCUAGAUGA UGAGAUUACUUAAUGGGUACAAUGCAUGUGAUUUGGGUAAUGGAUACUGUAGAAACACUGACGUCAC |
| 103 | U1_10_4 | UUAUCUGGCAGGGGAGACACCAUGAACAUGAGGAUAGUUUUCCCAAGGCAAGUUUCAACCCUUGCACUCUAGAUGAU GAGAUUACUUAAUGGGUACAAUGCAUGUGAUUUGGGUAAUGGAUACUGUAGAAACACUGACGUCAC |
| 104 | U1_10_5 | UAUCUGGCAGGGGAGACACCAUGAACAUGAGGAUAGUUUUCCCAAGGCAAGUUUCAACCCUUGCACUCUAGAUGAUG AGAUUACUUAAUGGGUACAAUGCAUGUGAUUUGGGUAAUGGAUACUGUAGAAACACUGACGUCAC |
| 105 | U1_10_6 | AUCUGGCAGGGGAGACACCAUGAACAUGAGGAUAGUUUUCCCAAGGCAAGUUUCAACCCUUGCACUCUAGAUGAUGA GAUUACUUAAUGGGUACAAUGCAUGUGAUUUGGGUAAUGGAUACUGUAGAAACACUGACGUCAC |
| 106 | U1_10_7 | UCUGGCAGGGGAGACACCAUGAACAUGAGGAUAGUUUUCCCAAGGCAAGUUUCAACCCUUGCACUCUAGAUGAUGAG AUUACUUAAUGGGUACAAUGCAUGUGAUUUGGGUAAUGGAUACUGUAGAAACACUGACGUCAC |
| 107 | U1_10_8 | CUGGCAGGGGAGACACCAUGAACAUGAGGAUAGUUUUCCCAAGGCAAGUUUCAACCCUUGCACUCUAGAUGAUGAGA UUACUUAAUGGGUACAAUGCAUGUGAUUUGGGUAAUGGAUACUGUAGAAACACUGACGUCAC |
| 108 | U1_10_9 | UGGCAGGGGAGACACCAUGAACAUGAGGAUAGUUUUCCCAAGGCAAGUUUCAACCCUUGCACUCUAGAUGAUGAGAU UACUUAAUGGGUACAAUGCAUGUGAUUUGGGUAAUGGAUACUGUAGAAACACUGACGUCAC |
| 109 | U1_11_0 | AGACUCAUCUGGCAGCGGAGAUACCAUGAACAUCACGGUAGUUUUCCCAAAGCAAGUUUCCACCCUUGCACUCCGGA UGAUGAGACAUUACUUAAUGGAUACAAUGCAUGUGAUUUGAGUGAUGGAUACUGUGGAAACACCGACUUCAC |
| 110 | U1_11_1 | GACUCAUCUGGCAGCGGAGAUACCAUGAACAUCACGGUAGUUUUCCCAAAGCAAGUUUCCACCCUUGCACUCCGGAU GAUGAGACAUUACUUAAUGGAUACAAUGCAUGUGAUUUGAGUGAUGGAUACUGUGGAAACACCGACUUCAC |
| 111 | U1_11_2 | ACUCAUCUGGCAGCGGAGAUACCAUGAACAUCACGGUAGUUUUCCCAAAGCAAGUUUCCACCCUUGCACUCCGGAUG AUGAGACAUUACUUAAUGGAUACAAUGCAUGUGAUUUGAGUGAUGGAUACUGUGGAAACACCGACUUCAC |
| 112 | U1_11_3 | CUCAUCUGGCAGCGGAGAUACCAUGAACAUCACGGUAGUUUUCCCAAAGCAAGUUUCCACCCUUGCACUCCGGAUGA UGAGACAUUACUUAAUGGAUACAAUGCAUGUGAUUUGAGUGAUGGAUACUGUGGAAACACCGACUUCAC |
| 113 | U1_11_4 | UCAUCUGGCAGCGGAGAUACCAUGAACAUCACGGUAGUUUUCCCAAAGCAAGUUUCCACCCUUGCACUCCGGAUGAU GAGACAUUACUUAAUGGAUACAAUGCAUGUGAUUUGAGUGAUGGAUACUGUGGAAACACCGACUUCAC |
| 114 | U1_11_5 | CAUCUGGCAGCGGAGAUACCAUGAACAUCACGGUAGUUUUCCCAAAGCAAGUUUCCACCCUUGCACUCCGGAUGAUG AGACAUUACUUAAUGGAUACAAUGCAUGUGAUUUGAGUGAUGGAUACUGUGGAAACACCGACUUCAC |
| 115 | U1_11_6 | AUCUGGCAGCGGAGAUACCAUGAACAUCACGGUAGUUUUCCCAAAGCAAGUUUCCACCCUUGCACUCCGGAUGAUGA GACAUUACUUAAUGGAUACAAUGCAUGUGAUUUGAGUGAUGGAUACUGUGGAAACACCGACUUCAC |
| 116 | U1_11_7 | UCUGGCAGCGGAGAUACCAUGAACAUCACGGUAGUUUUCCCAAAGCAAGUUUCCACCCUUGCACUCCGGAUGAUGAG ACAUUACUUAAUGGAUACAAUGCAUGUGAUUUGAGUGAUGGAUACUGUGGAAACACCGACUUCAC |
| 117 | U1_11_8 | CUGGCAGCGGAGAUACCAUGAACAUCACGGUAGUUUUCCCAAAGCAAGUUUCCACCCUUGCACUCCGGAUGAUGAGA CAUUACUUAAUGGAUACAAUGCAUGUGAUUUGAGUGAUGGAUACUGUGGAAACACCGACUUCAC |
| 118 | U1_11_9 | UGGCAGCGGAGAUACCAUGAACAUCACGGUAGUUUUCCCAAAGCAAGUUUCCACCCUUGCACUCCGGAUGAUGAGAC AUUACUUAAUGGAUACAAUGCAUGUGAUUUGAGUGAUGGAUACUGUGGAAACACCGACUUCAC |
| 119 | U1_12_0 | AGACUUGGCAGGGGAGAUAGCAUGAUCACGAAGGUGGUUUUUCCCAAGGCAAGAUUUAUUCACUGCACUCUGGAUGUG CUGACCCCUACGAUUUCCGCCCAAUGGGGAAGCUUGACUGCUUAGUUUGUUGUGGCAGGGGACUGUGUUCACACUUU |

TABLE 6-continued

SEQUENCE LISTING

| SEQ ID NO | Name/ID | Sequence |
|---|---|---|
| 120 | U1_12_1 | GACUUGGCAGGGGAGAUAGCAUGAUCACGAAGGUGGUUUUCCCAAGGCAAGAUUUAUUCACUGCACUCUGGAUGUGC UGACCCCUACGAUUUCCGCCCAAUGGGGAAGCUUGACUGCUUAGUUUGUUGUGGCAGGGGACUGUGUUCACACUUUU |
| 121 | U1_12_2 | ACUUGGCAGGGGAGAUAGCAUGAUCACGAAGGUGGUUUUCCCAAGGCAAGAUUUAUUCACUGCACUCUGGAUGUGCU GACCCCUACGAUUUCCGCCCAAUGGGGAAGCUUGACUGCUUAGUUUGUUGUGGCAGGGGACUGUGUUCACACUUUUC |
| 122 | U1_12_3 | CUUGGCAGGGGAGAUAGCAUGAUCACGAAGGUGGUUUUCCCAAGGCAAGAUUUAUUCACUGCACUCUGGAUGUGCUG ACCCCUACGAUUUCCGCCCAAUGGGGAAGCUUGACUGCUUAGUUUGUUGUGGCAGGGGACUGUGUUCACACUUUUCC |
| 123 | U1_12_4 | UUGGCAGGGGAGAUAGCAUGAUCACGAAGGUGGUUUUCCCAAGGCAAGAUUUAUUCACUGCACUCUGGAUGUGCUGA CCCCUACGAUUUCCGCCCAAUGGGGAAGCUUGACUGCUUAGUUUGUUGUGGCAGGGGACUGUGUUCACACUUUUCCC |
| 124 | U1_12_5 | UGGCAGGGGAGAUAGCAUGAUCACGAAGGUGGUUUUCCCAAGGCAAGAUUUAUUCACUGCACUCUGGAUGUGCUGAC CCCUACGAUUUCCGCCCAAUGGGGAAGCUUGACUGCUUAGUUUGUUGUGGCAGGGGACUGUGUUCACACUUUUCCCG |
| 125 | U1_12_6 | GGCAGGGGAGAUAGCAUGAUCACGAAGGUGGUUUUCCCAAGGCAAGAUUUAUUCACUGCACUCUGGAUGUGCUGACC CCUACGAUUUCCGCCCAAUGGGGAAGCUUGACUGCUUAGUUUGUUGUGGCAGGGGACUGUGUUCACACUUUUCCCGG |
| 126 | U1_12_7 | GCAGGGGAGAUAGCAUGAUCACGAAGGUGGUUUUCCCAAGGCAAGAUUUAUUCACUGCACUCUGGAUGUGCUGACCC CUACGAUUUCCGCCCAAUGGGGAAGCUUGACUGCUUAGUUUGUUGUGGCAGGGGACUGUGUUCACACUUUUCCCGG |
| 127 | U1_12_8 | CAGGGGAGAUAGCAUGAUCACGAAGGUGGUUUUCCCAAGGCAAGAUUUAUUCACUGCACUCUGGAUGUGCUGACCCC UACGAUUUCCGCCCAAUGGGGAAGCUUGACUGCUUAGUUUGUUGUGGCAGGGGACUGUGUUCACACUUUUCCCGG |
| 128 | U1_12_9 | AGGGGAGAUAGCAUGAUCACGAAGGUGGUUUUCCCAAGGCAAGAUUUAUUCACUGCACUCUGGAUGUGCUGACCCCU ACGAUUUCCGCCCAAUGGGGAAGCUUGACUGCUUAGUUUGUUGUGGCAGGGGACUGUGUUCACACUUUUCCCGG |
| 129 | U1_13_0 | AUACUUAACAUGGCAGAGGAGAUAUCAUAAUCACAAAGGUAGUUUUCCCAGGGCAAGCCUUAUCCACUGCAUUCCAG AUGUGCUCACCUCUGUGGUUUCCCCAAAUGUGGAAAACUGGACUGCAUAAUUUGUGGUAGCGGGGGACUGCAUUAAU |
| 130 | U1_13_1 | UACUUAACAUGGCAGAGGAGAUAUCAUAAUCACAAAGGUAGUUUUCCCAGGGCAAGCCUUAUCCACUGCAUUCCAGA UGUGCUCACCUCUGUGGUUUCCCCAAAUGUGGAAAACUGGACUGCAUAAUUUGUGGUAGCGGGGGACUGCAUUAAUA |
| 131 | U1_13_2 | ACUUAACAUGGCAGAGGAGAUAUCAUAAUCACAAAGGUAGUUUUCCCAGGGCAAGCCUUAUCCACUGCAUUCCAGAU GUGCUCACCUCUGUGGUUUCCCCAAAUGUGGAAAACUGGACUGCAUAAUUUGUGGUAGCGGGGGACUGCAUUAAUAC |
| 132 | U1_13_3 | CUUAACAUGGCAGAGGAGAUAUCAUAAUCACAAAGGUAGUUUUCCCAGGGCAAGCCUUAUCCACUGCAUUCCAGAUG UGCUCACCUCUGUGGUUUCCCCAAAUGUGGAAAACUGGACUGCAUAAUUUGUGGUAGCGGGGGACUGCAUUAAUACC |
| 133 | U1_13_4 | UUAACAUGGCAGAGGAGAUAUCAUAAUCACAAAGGUAGUUUUCCCAGGGCAAGCCUUAUCCACUGCAUUCCAGAUGU GCUCACCUCUGUGGUUUCCCCAAAUGUGGAAAACUGGACUGCAUAAUUUGUGGUAGCGGGGGACUGCAUUAAUACCU |
| 134 | U1_13_5 | UAACAUGGCAGAGGAGAUAUCAUAAUCACAAAGGUAGUUUUCCCAGGGCAAGCCUUAUCCACUGCAUUCCAGAUGUG CUCACCUCUGUGGUUUCCCCAAAUGUGGAAAACUGGACUGCAUAAUUUGUGGUAGCGGGGGACUGCAUUAAUACCUU |
| 135 | U1_13_6 | AACAUGGCAGAGGAGAUAUCAUAAUCACAAAGGUAGUUUUCCCAGGGCAAGCCUUAUCCACUGCAUUCCAGAUGUGC UCACCUCUGUGGUUUCCCCAAAUGUGGAAAACUGGACUGCAUAAUUUGUGGUAGCGGGGGACUGCAUUAAUACCUUC |
| 136 | U1_13_7 | ACAUGGCAGAGGAGAUAUCAUAAUCACAAAGGUAGUUUUCCCAGGGCAAGCCUUAUCCACUGCAUUCCAGAUGUGCU CACCUCUGUGGUUUCCCCAAAUGUGGAAAACUGGACUGCAUAAUUUGUGGUAGCGGGGGACUGCAUUAAUACCUUCC |
| 137 | U1_13_8 | CAUGGCAGAGGAGAUAUCAUAAUCACAAAGGUAGUUUUCCCAGGGCAAGCCUUAUCCACUGCAUUCCAGAUGUGCUC ACCUCUGUGGUUUCCCCAAAUGUGGAAAACUGGACUGCAUAAUUUGUGGUAGCGGGGGACUGCAUUAAUACCUUCCU |
| 138 | U1_13_9 | AUGGCAGAGGAGAUAUCAUAAUCACAAAGGUAGUUUUCCCAGGGCAAGCCUUAUCCACUGCAUUCCAGAUGUGCUCA CCUCUGUGGUUUCCCCAAAUGUGGAAAACUGGACUGCAUAAUUUGUGGUAGCGGGGGACUGCAUUAAUACCUUCCUC |
| 139 | U11_1_0 | AAAAAGGGCUUCUGCUGUGAGUGGCACACAUAGGGCAUCGUUUGCUCUUGGUGCCAGAAUCAACAUCAAGAGAUUUC AGAAGCAUAAUUUUUUGGUACUUGGGCAGCUGGUGAUCAUUGGUCCUGUAGCCCUU |
| 140 | U11_1_1 | AAAAGGGCUUCUGCUGUGAGUGGCACACAUAGGGCAUCGUUUGCUCUUGGUGCCAGAAUCAACAUCAAGAGAUUUCA GAAGCAUAAUUUUUUGGUACUUGGGCAGCUGGUGAUCAUUGGUCCUGUAGCCCUU |
| 141 | U11_1_2 | AAAGGGCUUCUGCUGUGAGUGGCACACAUAGGGCAUCGUUUGCUCUUGGUGCCAGAAUCAACAUCAAGAGAUUUCAG AAGCAUAAUUUUUUGGUACUUGGGCAGCUGGUGAUCAUUGGUCCUGUAGCCCUU |
| 142 | U11_1_3 | AAGGGCUUCUGCUGUGAGUGGCACACAUAGGGCAUCGUUUGCUCUUGGUGCCAGAAUCAACAUCAAGAGAUUUCAGA AGCAUAAUUUUUUGGUACUUGGGCAGCUGGUGAUCAUUGGUCCUGUAGCCCUU |
| 143 | U11_1_4 | AGGGCUUCUGCUGUGAGUGGCACACAUAGGGCAUCGUUUGCUCUUGGUGCCAGAAUCAACAUCAAGAGAUUUCAGAA GCAUAAUUUUUUGGUACUUGGGCAGCUGGUGAUCAUUGGUCCUGUAGCCCUU |
| 144 | U11_1_5 | GGGCUUCUGCUGUGAGUGGCACACAUAGGGCAUCGUUUGCUCUUGGUGCCAGAAUCAACAUCAAGAGAUUUCAGAAG CAUAAUUUUUUGGUACUUGGGCAGCUGGUGAUCAUUGGUCCUGUAGCCCUU |

TABLE 6-continued

SEQUENCE LISTING

| SEQ ID NO | Name/ID | Sequence |
|-----------|---------|----------|
| 145 | U11_1_6 | GGCUUCUGCUGUGAGUGGCACACAUAGGGCAUCGUUUGCUCUUGGUGCCAGAAUCAACAUCAAGAGAUUUCAGAAGC<br>AUAAUUUUUUGGUACUUGGGCAGCUGGUGAUCAUUGGUCCUGUAGCCCUU |
| 146 | U11_1_7 | GCUUCUGCUGUGAGUGGCACACAUAGGGCAUCGUUUGCUCUUGGUGCCAGAAUCAACAUCAAGAGAUUUCAGAAGCA<br>UAAUUUUUUGGUACUUGGGCAGCUGGUGAUCAUUGGUCCUGUAGCCCUU |
| 147 | U11_1_8 | CUUCUGCUGUGAGUGGCACACAUAGGGCAUCGUUUGCUCUUGGUGCCAGAAUCAACAUCAAGAGAUUUCAGAAGCAU<br>AAUUUUUUGGUACUUGGGCAGCUGGUGAUCAUUGGUCCUGUAGCCCUU |
| 148 | U11_1_9 | UUCUGCUGUGAGUGGCACACAUAGGGCAUCGUUUGCUCUUGGUGCCAGAAUCAACAUCAAGAGAUUUCAGAAGCAUA<br>AUUUUUUGGUACUUGGGCAGCUGGUGAUCAUUGGUCCUGUAGCCCUU |
| 149 | U11_2_0 | AAAAAAGCUGCUGUUGUGAGUGAUACAUGCAGGGCAACUUGAUUGCUCUUAGUGCAGAAUUGACAUCAAGGAAUUUU<br>UGGAAGUAUAAUUUUUUGGCAGGUGGAUAGCUGGUUGUAUUAGUCCAUUCUC |
| 150 | U11_2_1 | AAAAAAGCUGCUGUUGUGAGUGAUACAUGCAGGGCAACUUGAUUGCUCUUAGUGCAGAAUUGACAUCAAGGAAUUUU<br>GGAAGUAUAAUUUUUUGGCAGGUGGAUAGCUGGUUGUAUUAGUCCAUUCUC |
| 151 | U11_2_2 | AAAAAGCUGCUGUUGUGAGUGAUACAUGCAGGGCAACUUGAUUGCUCUUAGUGCAGAAUUGACAUCAAGGAAUUUUG<br>GAAGUAUAAUUUUUUGGCAGGUGGAUAGCUGGUUGUAUUAGUCCAUUCUC |
| 152 | U11_2_3 | AAAAGCUGCUGUUGUGAGUGAUACAUGCAGGGCAACUUGAUUGCUCUUAGUGCAGAAUUGACAUCAAGGAAUUUUGG<br>AAGUAUAAUUUUUUGGCAGGUGGAUAGCUGGUUGUAUUAGUCCAUUCUC |
| 153 | U11_2_4 | AAAGCUGCUGUUGUGAGUGAUACAUGCAGGGCAACUUGAUUGCUCUUAGUGCAGAAUUGACAUCAAGGAAUUUUGGA<br>AGUAUAAUUUUUUGGCAGGUGGAUAGCUGGUUGUAUUAGUCCAUUCUC |
| 154 | U11_2_5 | AAGCUGCUGUUGUGAGUGAUACAUGCAGGGCAACUUGAUUGCUCUUAGUGCAGAAUUGACAUCAAGGAAUUUUGGAA<br>GUAUAAUUUUUUGGCAGGUGGAUAGCUGGUUGUAUUAGUCCAUUCUC |
| 155 | U11_2_6 | AGCUGCUGUUGUGAGUGAUACAUGCAGGGCAACUUGAUUGCUCUUAGUGCAGAAUUGACAUCAAGGAAUUUUGGAAG<br>UAUAAUUUUUUGGCAGGUGGAUAGCUGGUUGUAUUAGUCCAUUCUC |
| 156 | U11_2_7 | GCUGCUGUUGUGAGUGAUACAUGCAGGGCAACUUGAUUGCUCUUAGUGCAGAAUUGACAUCAAGGAAUUUUGGAAGU<br>AUAAUUUUUUGGCAGGUGGAUAGCUGGUUGUAUUAGUCCAUUCUC |
| 157 | U11_2_8 | CUGCUGUUGUGAGUGAUACAUGCAGGGCAACUUGAUUGCUCUUAGUGCAGAAUUGACAUCAAGGAAUUUUGGAAGUA<br>UAAUUUUUUGGCAGGUGGAUAGCUGGUUGUAUUAGUCCAUUCUC |
| 158 | U11_2_9 | UGCUGUUGUGAGUGAUACAUGCAGGGCAACUUGAUUGCUCUUAGUGCAGAAUUGACAUCAAGGAAUUUUGGAAGUAU<br>AAUUUUUUGGCAGGUGGAUAGCUGGUUGUAUUAGUCCAUUCUC |
| 159 | U11_3_0 | AAAAAGGGCUUCUGUCAUGAGUGGCACACAUAGGACAACUCAAUUUCUCUUCAUGCAGAAUAAACAUCAAGAGAUUU<br>UGGAAGCGUAAUUUUUGGUAGUUGGGCAGCUGGUGAUCACUGGUGCCAGCACCCUU |
| 160 | U11_3_1 | AAAAGGGCUUCUGUCAUGAGUGGCACACAUAGGACAACUCAAUUUCUCUUCAUGCAGAAUAAACAUCAAGAGAUUUU<br>GGAAGCGUAAUUUUUGGUAGUUGGGCAGCUGGUGAUCACUGGUGCCAGCACCCUU |
| 161 | U11_3_2 | AAAGGGCUUCUGUCAUGAGUGGCACACAUAGGACAACUCAAUUUCUCUUCAUGCAGAAUAAACAUCAAGAGAUUUUG<br>GAAGCGUAAUUUUUGGUAGUUGGGCAGCUGGUGAUCACUGGUGCCAGCACCCUU |
| 162 | U11_3_3 | AAGGGCUUCUGUCAUGAGUGGCACACAUAGGACAACUCAAUUUCUCUUCAUGCAGAAUAAACAUCAAGAGAUUUUGG<br>AAGCGUAAUUUUUGGUAGUUGGGCAGCUGGUGAUCACUGGUGCCAGCACCCUU |
| 163 | U11_3_4 | AGGGCUUCUGUCAUGAGUGGCACACAUAGGACAACUCAAUUUCUCUUCAUGCAGAAUAAACAUCAAGAGAUUUUGGA<br>AGCGUAAUUUUUGGUAGUUGGGCAGCUGGUGAUCACUGGUGCCAGCACCCUU |
| 164 | U11_3_5 | GGGCUUCUGUCAUGAGUGGCACACAUAGGACAACUCAAUUUCUCUUCAUGCAGAAUAAACAUCAAGAGAUUUUGGAA<br>GCGUAAUUUUUGGUAGUUGGGCAGCUGGUGAUCACUGGUGCCAGCACCCUU |
| 165 | U11_3_6 | GGCUUCUGUCAUGAGUGGCACACAUAGGACAACUCAAUUUCUCUUCAUGCAGAAUAAACAUCAAGAGAUUUUGGAAG<br>CGUAAUUUUUGGUAGUUGGGCAGCUGGUGAUCACUGGUGCCAGCACCCUU |
| 166 | U11_3_7 | GCUUCUGUCAUGAGUGGCACACAUAGGACAACUCAAUUUCUCUUCAUGCAGAAUAAACAUCAAGAGAUUUUGGAAGC<br>GUAAUUUUUGGUAGUUGGGCAGCUGGUGAUCACUGGUGCCAGCACCCUU |
| 167 | U11_3_8 | CUUCUGUCAUGAGUGGCACACAUAGGACAACUCAAUUUCUCUUCAUGCAGAAUAAACAUCAAGAGAUUUUGGAAGCG<br>UAAUUUUUGGUAGUUGGGCAGCUGGUGAUCACUGGUGCCAGCACCCUU |
| 168 | U11_3_9 | UUCUGUCAUGAGUGGCACACAUAGGACAACUCAAUUUCUCUUCAUGCAGAAUAAACAUCAAGAGAUUUUGGAAGCGU<br>AAUUUUUGGUAGUUGGGCAGCUGGUGAUCACUGGUGCCAGCACCCUU |

TABLE 6-continued

| | | SEQUENCE LISTING |
|---|---|---|

| SEQ ID NO | Name/ ID | Sequence |
|---|---|---|
| 169 | U11_4_0 | AAAAAGGGCUUCUGUCAUGAGUGGCCUAUGUAGGGCAACCAGAUUGCUCUUCAUGUGGAAUUGACAUCAAGAGCUUU CAGAAGUGUAUUUUUUGGAAGUUGGGCAGCUGGUAAUCAUUGGUCUUGGCAUCCUU |
| 170 | U11_4_1 | AAAAGGGCUUCUGUCAUGAGUGGCCUAUGUAGGGCAACCAGAUUGCUCUUCAUGUGGAAUUGACAUCAAGAGCUUUC AGAAGUGUAUUUUUUGGAAGUUGGGCAGCUGGUAAUCAUUGGUCUUGGCAUCCUU |
| 171 | U11_4_2 | AAAGGGCUUCUGUCAUGAGUGGCCUAUGUAGGGCAACCAGAUUGCUCUUCAUGUGGAAUUGACAUCAAGAGCUUUCA GAAGUGUAUUUUUUGGAAGUUGGGCAGCUGGUAAUCAUUGGUCUUGGCAUCCUU |
| 172 | U11_4_3 | AAGGGCUUCUGUCAUGAGUGGCCUAUGUAGGGCAACCAGAUUGCUCUUCAUGUGGAAUUGACAUCAAGAGCUUUCAG AAGUGUAUUUUUUGGAAGUUGGGCAGCUGGUAAUCAUUGGUCUUGGCAUCCUU |
| 173 | U11_4_4 | AGGGCUUCUGUCAUGAGUGGCCUAUGUAGGGCAACCAGAUUGCUCUUCAUGUGGAAUUGACAUCAAGAGCUUUCAGA AGUGUAUUUUUUGGAAGUUGGGCAGCUGGUAAUCAUUGGUCUUGGCAUCCUU |
| 174 | U11_4_5 | GGGCUUCUGUCAUGAGUGGCCUAUGUAGGGCAACCAGAUUGCUCUUCAUGUGGAAUUGACAUCAAGAGCUUUCAGAA GUGUAUUUUUUGGAAGUUGGGCAGCUGGUAAUCAUUGGUCUUGGCAUCCUU |
| 175 | U11_4_6 | GGCUUCUGUCAUGAGUGGCCUAUGUAGGGCAACCAGAUUGCUCUUCAUGUGGAAUUGACAUCAAGAGCUUUCAGAAG UGUAUUUUUUGGAAGUUGGGCAGCUGGUAAUCAUUGGUCUUGGCAUCCUU |
| 176 | U11_4_7 | GCUUCUGUCAUGAGUGGCCUAUGUAGGGCAACCAGAUUGCUCUUCAUGUGGAAUUGACAUCAAGAGCUUUCAGAAGU GUAUUUUUUGGAAGUUGGGCAGCUGGUAAUCAUUGGUCUUGGCAUCCUU |
| 177 | U11_4_8 | CUUCUGUCAUGAGUGGCCUAUGUAGGGCAACCAGAUUGCUCUUCAUGUGGAAUUGACAUCAAGAGCUUUCAGAAGUG UAUUUUUUGGAAGUUGGGCAGCUGGUAAUCAUUGGUCUUGGCAUCCUU |
| 178 | U11_4_9 | UUCUGUCAUGAGUGGCCUAUGUAGGGCAACCAGAUUGCUCUUCAUGUGGAAUUGACAUCAAGAGCUUUCAGAAGUGU AUUUUUUGGAAGUUGGGCAGCUGGUAAUCAUUGGUCUUGGCAUCCUU |
| 179 | U11_5_0 | AAAGGGGGCUUCUGUCAUGAGUGGCACACAUUGGGCAACUCAACUGCUCUUCAUGAGGAAUCAACAUCAGGAGGUUU UGGAAGAAUGAUUUUUUUGGUAGUUGGGCAGCUUGUGAGAAAAAAAUGUUUUCAGGCAAAUCCUC |
| 180 | U11_5_1 | AAGGGGGCUUCUGUCAUGAGUGGCACACAUUGGGCAACUCAACUGCUCUUCAUGAGGAAUCAACAUCAGGAGGUUUU GGAAGAAUGAUUUUUUUGGUAGUUGGGCAGCUUGUGAGAAAAAAAUGUUUUCAGGCAAAUCCUC |
| 181 | U11_5_2 | AGGGGGCUUCUGUCAUGAGUGGCACACAUUGGGCAACUCAACUGCUCUUCAUGAGGAAUCAACAUCAGGAGGUUUUG GAAGAAUGAUUUUUUUGGUAGUUGGGCAGCUUGUGAGAAAAAAAUGUUUUCAGGCAAAUCCUC |
| 182 | U11_5_3 | GGGGGCUUCUGUCAUGAGUGGCACACAUUGGGCAACUCAACUGCUCUUCAUGAGGAAUCAACAUCAGGAGGUUUUGG AAGAAUGAUUUUUUUGGUAGUUGGGCAGCUUGUGAGAAAAAAAUGUUUUCAGGCAAAUCCUC |
| 183 | U11_5_4 | GGGGCUUCUGUCAUGAGUGGCACACAUUGGGCAACUCAACUGCUCUUCAUGAGGAAUCAACAUCAGGAGGUUUUGGA AGAAUGAUUUUUUUGGUAGUUGGGCAGCUUGUGAGAAAAAAAUGUUUUCAGGCAAAUCCUC |
| 184 | U11_5_5 | GGGCUUCUGUCAUGAGUGGCACACAUUGGGCAACUCAACUGCUCUUCAUGAGGAAUCAACAUCAGGAGGUUUUGGAA GAAUGAUUUUUUUGGUAGUUGGGCAGCUUGUGAGAAAAAAAUGUUUUCAGGCAAAUCCUC |
| 185 | U11_5_6 | GGCUUCUGUCAUGAGUGGCACACAUUGGGCAACUCAACUGCUCUUCAUGAGGAAUCAACAUCAGGAGGUUUUGGAAG AAUGAUUUUUUUGGUAGUUGGGCAGCUUGUGAGAAAAAAAUGUUUUCAGGCAAAUCCUC |
| 186 | U11_5_7 | GCUUCUGUCAUGAGUGGCACACAUUGGGCAACUCAACUGCUCUUCAUGAGGAAUCAACAUCAGGAGGUUUUGGAAGA AUGAUUUUUUUGGUAGUUGGGCAGCUUGUGAGAAAAAAAUGUUUUCAGGCAAAUCCUC |
| 187 | U11_5_8 | CUUCUGUCAUGAGUGGCACACAUUGGGCAACUCAACUGCUCUUCAUGAGGAAUCAACAUCAGGAGGUUUUGGAAGAA UGAUUUUUUUGGUAGUUGGGCAGCUUGUGAGAAAAAAAUGUUUUCAGGCAAAUCCUC |
| 188 | U11_5_9 | UUCUGUCAUGAGUGGCACACAUUGGGCAACUCAACUGCUCUUCAUGAGGAAUCAACAUCAGGAGGUUUUGGAAGAAU GAUUUUUUUGGUAGUUGGGCAGCUUGUGAGAAAAAAAUGUUUUCAGGCAAAUCCUC |
| 189 | U11_6_0 | AAAAAGGGCUUCUGUCGUGAGUGGCACACGUAGGGCAACUCGAUUGCUCUGCGUGCGGAAUCGACAUCAAGAGAUUU CGGAAGCAUAAUUUUUUGGUAUUUGGGCAGCUGGUGAUCGUUGGUCCCGGCGCCCUU |
| 190 | U11_6_1 | AAAAGGGCUUCUGUCGUGAGUGGCACACGUAGGGCAACUCGAUUGCUCUGCGUGCGGAAUCGACAUCAAGAGAUUUC GGAAGCAUAAUUUUUUGGUAUUUGGGCAGCUGGUGAUCGUUGGUCCCGGCGCCCUU |
| 191 | U11_6_2 | AAAGGGCUUCUGUCGUGAGUGGCACACGUAGGGCAACUCGAUUGCUCUGCGUGCGGAAUCGACAUCAAGAGAUUUCG GAAGCAUAAUUUUUUGGUAUUUGGGCAGCUGGUGAUCGUUGGUCCCGGCGCCCUU |
| 192 | U11_6_3 | AAGGGCUUCUGUCGUGAGUGGCACACGUAGGGCAACUCGAUUGCUCUGCGUGCGGAAUCGACAUCAAGAGAUUUCGG AAGCAUAAUUUUUUGGUAUUUGGGCAGCUGGUGAUCGUUGGUCCCGGCGCCCUU |
| 193 | U11_6_4 | AGGGCUUCUGUCGUGAGUGGCACACGUAGGGCAACUCGAUUGCUCUGCGUGCGGAAUCGACAUCAAGAGAUUUCGGA AGCAUAAUUUUUUGGUAUUUGGGCAGCUGGUGAUCGUUGGUCCCGGCGCCCUU |

TABLE 6-continued

| SEQ ID NO | Name/ ID | Sequence |
|---|---|---|
| | | SEQUENCE LISTING |
| 194 | U11_6_5 | GGGCUUCUGUCGUGAGUGGCACACGUAGGGCAACUCGAUUGCUCUGCGUGCGGAAUCGACAUCAAGAGAUUUCGGAA GCAUAAUUUUUUGGUAUUUGGGCAGCUGGUGAUCGUUGGUCCCGGCGCCCUU |
| 195 | U11_6_6 | GGCUUCUGUCGUGAGUGGCACACGUAGGGCAACUCGAUUGCUCUGCGUGCGGAAUCGACAUCAAGAGAUUUCGGAAG CAUAAUUUUUUGGUAUUUGGGCAGCUGGUGAUCGUUGGUCCCGGCGCCCUU |
| 196 | U11_6_7 | GCUUCUGUCGUGAGUGGCACACGUAGGGCAACUCGAUUGCUCUGCGUGCGGAAUCGACAUCAAGAGAUUUCGGAAGC AUAAUUUUUUGGUAUUUGGGCAGCUGGUGAUCGUUGGUCCCGGCGCCCUU |
| 197 | U11_6_8 | CUUCUGUCGUGAGUGGCACACGUAGGGCAACUCGAUUGCUCUGCGUGCGGAAUCGACAUCAAGAGAUUUCGGAAGCA UAAUUUUUUGGUAUUUGGGCAGCUGGUGAUCGUUGGUCCCGGCGCCCUU |
| 198 | U11_6_9 | UUCUGUCGUGAGUGGCACACGUAGGGCAACUCGAUUGCUCUGCGUGCGGAAUCGACAUCAAGAGAUUUCGGAAGCAU AAUUUUUUGGUAUUUGGGCAGCUGGUGAUCGUUGGUCCCGGCGCCCUU |
| 199 | U11_7_0 | AAAAAGGGCUUCUGUCGUGAGUGGCACACGUAGGGCAACUCGAUUGCUCUGCGUGCGGAAUCGACAUCAAGAGAUUU CGGAAGCAUAAUUUUUUGGUAUUUGGGCAGCUGGUGAUCGUUGGUCCCGGCGCC |
| 200 | U11_7_1 | AAAAGGGCUUCUGUCGUGAGUGGCACACGUAGGGCAACUCGAUUGCUCUGCGUGCGGAAUCGACAUCAAGAGAUUUC GGAAGCAUAAUUUUUUGGUAUUUGGGCAGCUGGUGAUCGUUGGUCCCGGCGCC |
| 201 | U11_7_2 | AAAGGGCUUCUGUCGUGAGUGGCACACGUAGGGCAACUCGAUUGCUCUGCGUGCGGAAUCGACAUCAAGAGAUUUCG GAAGCAUAAUUUUUUGGUAUUUGGGCAGCUGGUGAUCGUUGGUCCCGGCGCC |
| 202 | U11_7_3 | AAGGGCUUCUGUCGUGAGUGGCACACGUAGGGCAACUCGAUUGCUCUGCGUGCGGAAUCGACAUCAAGAGAUUUCGG AAGCAUAAUUUUUUGGUAUUUGGGCAGCUGGUGAUCGUUGGUCCCGGCGCC |
| 203 | U11_7_4 | AGGGCUUCUGUCGUGAGUGGCACACGUAGGGCAACUCGAUUGCUCUGCGUGCGGAAUCGACAUCAAGAGAUUUCGGA AGCAUAAUUUUUUGGUAUUUGGGCAGCUGGUGAUCGUUGGUCCCGGCGCC |
| 204 | U11_7_5 | GGGCUUCUGUCGUGAGUGGCACACGUAGGGCAACUCGAUUGCUCUGCGUGCGGAAUCGACAUCAAGAGAUUUCGGAA GCAUAAUUUUUUGGUAUUUGGGCAGCUGGUGAUCGUUGGUCCCGGCGCC |
| 205 | U11_7_6 | GGCUUCUGUCGUGAGUGGCACACGUAGGGCAACUCGAUUGCUCUGCGUGCGGAAUCGACAUCAAGAGAUUUCGGAAG CAUAAUUUUUUGGUAUUUGGGCAGCUGGUGAUCGUUGGUCCCGGCGCC |
| 206 | U11_7_7 | GCUUCUGUCGUGAGUGGCACACGUAGGGCAACUCGAUUGCUCUGCGUGCGGAAUCGACAUCAAGAGAUUUCGGAAGC AUAAUUUUUUGGUAUUUGGGCAGCUGGUGAUCGUUGGUCCCGGCGCC |
| 207 | U11_7_8 | CUUCUGUCGUGAGUGGCACACGUAGGGCAACUCGAUUGCUCUGCGUGCGGAAUCGACAUCAAGAGAUUUCGGAAGCA UAAUUUUUUGGUAUUUGGGCAGCUGGUGAUCGUUGGUCCCGGCGCC |
| 208 | U11_7_9 | UUCUGUCGUGAGUGGCACACGUAGGGCAACUCGAUUGCUCUGCGUGCGGAAUCGACAUCAAGAGAUUUCGGAAGCAU AAUUUUUUGGUAUUUGGGCAGCUGGUGAUCGUUGGUCCCGGCGCC |
| 209 | Sm consensus | AAUUUUUGGAG |
| 210 | Sm_1 | AAUUUUUGGAG |
| 211 | Sm_2 | UAUUUUUGGAG |
| 212 | Sm_ | GAUUUUUGGAG |
| 213 | Sm_4 | CAUUUUUGGAG |
| 214 | Sm_5 | AUUUUUUGGAG |
| 215 | Sm_6 | AGUUUUUGGAG |
| 216 | Sm_7 | ACUUUUUGGAG |
| 217 | Sm_8 | AAAUUUUGGAG |
| 218 | Sm_9 | AAGUUUUGGAG |
| 219 | Sm_10 | AACUUUUGGAG |
| 220 | Sm_11 | AAUAUUUGGAG |
| 221 | Sm_12 | AAUGUUUGGAG |
| 222 | Sm_13 | AAUCUUUGGAG |

TABLE 6-continued

| SEQ ID NO | Name/ ID | Sequence |
|---|---|---|
| | | SEQUENCE LISTING |
| 223 | Sm_14 | AAUUAUUGGAG |
| 224 | Sm_15 | AAUUGUUGGAG |
| 225 | Sm_16 | AAUUCUUGGAG |
| 226 | Sm_17 | AAUUUAUGGAG |
| 227 | Sm_18 | AAUUUGUGGAG |
| 228 | Sm_19 | AAUUUCUGGAG |
| 229 | Sm_20 | AAUUUUAGGAG |
| 230 | Sm_21 | AAUUUUGGGAG |
| 231 | Sm_22 | AAUUUUCGGAG |
| 232 | Sm_23 | AAUUUUUAGAG |
| 233 | Sm_24 | AAUUUUUUGAG |
| 234 | Sm_25 | AAUUUUUCGAG |
| 235 | Sm_26 | AAUUUUUGAAG |
| 236 | Sm_27 | AAUUUUUGUAG |
| 237 | Sm_28 | AAUUUUUGCAG |
| 238 | Sm_29 | AAUUUUUGGUG |
| 239 | Sm_30 | AAUUUUUGGGG |
| 240 | Sm_31 | AAUUUUUGGCG |
| 241 | Sm_32 | AAUUUUUGGAA |
| 242 | Sm_33 | AAUUUUUGGAU |
| 243 | Sm_34 | AAUUUUUGGAC |
| 244 | Sm_35 | AAUGUUUUGAG |
| 245 | Sm_36 | AAUUUGUGUAG |
| 246 | Sm_37 | AGUUUUUGGAA |
| 247 | Sm_38 | AUUUUGUGGAG |
| 248 | Sm_39 | AAUGUUUGCAG |
| 249 | Sm_40 | AAUGUUGGGAG |
| 250 | Sm_41 | AAUUGCUGGAG |
| 251 | Sm_42 | AAUUUUAGCAG |
| 252 | Sm_43 | AAGGUUUGGAG |
| 253 | Sm_44 | GAUUUGUGGAG |
| 254 | Sm_45 | ACUUUUUGGAA |
| 255 | Sm_46 | AAAUUAUGGAG |
| 256 | Sm_47 | AAUUUUGCGAG |
| 257 | Sm_48 | AAUUUCUGGAA |
| 258 | Sm_49 | UAUUUUUGGUG |
| 259 | Sm_50 | GAUUUUAGGAG |

TABLE 6-continued

| SEQ ID NO | Name/ID | Sequence |
|---|---|---|
| SEQUENCE LISTING | | |
| 260 | Sm_51 | AAUCUGUGGAG |
| 261 | Sm_52 | AAAUUUUAGAG |
| 262 | Sm_53 | AAUUUUUCGAC |
| 263 | Sm_54 | AAUUUUUGGGU |
| 264 | Sm_55 | AAUCUUUGGAA |
| 265 | Sm_56 | AAUUAUUGGUG |
| 266 | Sm_57 | AAUUUUAAGAG |
| 267 | Sm_58 | AAUGUUAGGAG |
| 268 | Sm_59 | AAUUUUAGAAG |
| 269 | Sm_60 | AUUUUUUGGCG |
| 270 | Sm_61 | AACUUUUGGUG |
| 271 | Sm_62 | AAUGUUUGGAU |
| 272 | Sm_63 | AAUUUUAGGAU |
| 273 | Sm_64 | AAUUUUUGAUG |
| 274 | Sm_65 | AAUUCUUGGUG |
| 275 | Sm_66 | AAUCCUUGGAG |
| 276 | Sm_67 | AAUUUUUCAAG |
| 277 | Sm_68 | CAUUUUUGCAG |
| 278 | Sm_69 | CAUUUUUCGAG |
| 279 | Sm_70 | AAUUUUGGGCG |
| 280 | Sm_71 | AGUUUUUGCAG |
| 281 | Sm_72 | AAAAUUUGGAG |
| 282 | Sm_73 | AACUCUUGGAG |
| 283 | Sm_74 | AAUUUGUGGAC |
| 284 | Sm_75 | ACUUUUUGGUG |
| 285 | Sm_76 | AUUUUUUGAAG |
| 286 | Sm_77 | AUUUUUUGGAA |
| 287 | Sm_78 | AAGUUAUGGAG |
| 288 | Sm_79 | CAUUUCUGGAG |
| 289 | Sm_80 | AGUUCUUGGAG |
| 290 | Sm_81 | AAUUUUGGAAG |
| 291 | Sm_82 | AGUAUUUGGAG |
| 292 | Sm_83 | AAUUUUUGGGC |
| 293 | Sm_84 | AAUUCUUGUAG |
| 294 | Sm_85 | AAUUUUGGGAA |
| 295 | Sm_86 | UAUUUUUUGAG |
| 296 | Sm_87 | AACUUUUGUAG |

TABLE 6-continued

| SEQ ID NO | Name/ ID | Sequence |
|---|---|---|
| 297 | Sm_88 | AAUUAUUGCAG |
| 298 | Sm_89 | AAUUUUUGGUA |
| 299 | Sm_90 | AAUUUUCGAAG |
| 300 | Sm_91 | UAUCUUUGGAG |
| 301 | Sm_92 | AAUUUUUCGUG |
| 302 | Sm_93 | AAUCUUUGGCG |
| 303 | Sm_94 | GAUUUAUGGAG |
| 304 | Sm_95 | AAUUUUUCGAA |
| 305 | Sm_96 | CCUUUUUGGAG |
| 306 | Sm_97 | UAUUUUUGAAG |
| 307 | Sm_98 | AAUUUUUGUAA |
| 308 | Sm_99 | AAUUUUGAGAG |
| 309 | Sm_100 | AAGUAUUGGAG |
| 310 | Sm_101 | AAUUUUAGGAC |
| 311 | Sm_102 | AAUUUUUAAAG |
| 312 | Sm_103 | AAUUCUUGGAU |
| 313 | Sm_104 | AAUUUGUGGUG |
| 314 | Sm_105 | AAUUUUCGGGG |
| 315 | Sm_106 | ACUUUUUUGAG |
| 316 | Sm_107 | AAGUUUCGGAG |
| 317 | Sm_108 | ACUUUUGGGAG |
| 318 | Sm_109 | GACUUUUGGAG |
| 319 | Sm_110 | CUUUUUUGGAG |
| 320 | Sm_111 | CAUUGUUGGAG |
| 321 | Sm_112 | AAUAUUUUGAG |
| 322 | Sm_113 | AAGUUUUGGCG |
| 323 | Sm_114 | AAUUUUAGGAA |
| 324 | Sm_115 | AACUUGUGGAG |
| 325 | Sm_116 | AUUUUUUGGGG |
| 326 | Sm_117 | AAUUUUUAGAU |
| 327 | Sm_118 | UAUUUUGGGAG |
| 328 | Sm_119 | AAUUUGUGGGG |
| 329 | Sm_120 | AAUUUUUAGGG |
| 330 | Sm_121 | AAUUUUCGUAG |
| 331 | Sm_122 | AAUUUUCUGAG |
| 332 | Sm_123 | GAUUCUUGGAG |
| 333 | Sm_124 | AAUCUUUGGAU |

TABLE 6-continued

SEQUENCE LISTING

| SEQ ID NO | Name/ ID | Sequence |
|---|---|---|
| 334 | Sm_125 | AAAUUUUGGCG |
| 335 | Sm_126 | AAUCAUUGGAG |
| 336 | Sm_127 | AACUUUUGGCG |
| 337 | Sm_128 | AAUUUUUGGGA |
| 338 | Sm_129 | AAUGUUUGGUG |
| 339 | Sm_130 | AAUUUAUGCAG |
| 340 | Sm_131 | AAUCUCUGGAG |
| 341 | Sm_132 | AGUUUGUGGAG |
| 342 | Sm_133 | AAGUUUUGGAU |
| 343 | Sm_134 | UAUUUUUGGCG |
| 344 | Sm_135 | AAUUUCUGAAG |
| 345 | Sm_136 | UAUUUCUGGAG |
| 346 | Sm_137 | AAUUUUUGCUG |
| 347 | Sm_138 | AAAUCUUGGAG |
| 348 | Sm_139 | AAAUUUUUGAG |
| 349 | Sm_140 | UAUUUUUGUAG |
| 350 | Sm_141 | GAUUAUUGGAG |
| 351 | Sm_142 | AAGUUCUGGAG |
| 352 | Sm_143 | AAUCUUUGAAG |
| 353 | Sm_144 | AAAUAUUGGAG |
| 354 | Sm_145 | AACUAUUGGAG |
| 355 | Sm_146 | AAUAUAUGGAG |
| 356 | Sm_147 | AUUCUUUGGAG |
| 357 | Sm_148 | GAUUUUUGAAG |
| 358 | Sm_149 | AAGUUUUGGUG |
| 359 | Sm_150 | AAUCUUUGCAG |
| 360 | Sm_151 | ACUUUUUGGCG |
| 361 | Sm_152 | GAUUUUGGGAG |
| 362 | Sm_153 | CAUUUUUGGAA |
| 363 | Sm_154 | AAUUUUUUGAC |
| 364 | Sm_155 | AAAUUUUGCAG |
| 365 | Sm_156 | ACUUUUUGAAG |
| 366 | Sm_157 | AGUCUUUGGAG |
| 367 | Sm_158 | AGUUUAUGGAG |
| 368 | Sm_159 | ACUUCUUGGAG |
| 369 | Sm_160 | AAUUUUUUCAG |
| 370 | Sm_161 | AAUUUUCGGAU |

TABLE 6-continued

| SEQ ID NO | Name/ ID | Sequence |
|---|---|---|
| 371 | Sm_162 | AAUUUUUGUAU |
| 372 | Sm_163 | AAUGUCUGGAG |
| 373 | Sm_164 | AAUUGUUGGGG |
| 374 | Sm_165 | AAUUUAUGGAC |
| 375 | Sm_166 | AAUUUAUGAAG |
| 376 | Sm_167 | AAUUUAUGGGG |
| 377 | Sm_168 | AAUUUGUCGAG |
| 378 | Sm_169 | AAUUGUUGGAA |
| 379 | Sm_170 | UGUUUUUGGAG |
| 380 | Sm_171 | AAAUUUAGGAG |
| 381 | Sm_172 | AAUUUUUUGUG |
| 382 | Sm_173 | CAUUCUUGGAG |
| 383 | Sm_174 | AAUUCUCGGAG |
| 384 | Sm_175 | AAUUUUUAUAG |
| 385 | Sm_176 | ACUUUUUAGAG |
| 386 | Sm_177 | AAUUGUUAGAG |
| 387 | Sm_178 | CGUUUUUGGAG |
| 388 | Sm_179 | AAUUUUUGCGG |
| 389 | Sm_180 | AAGUUUUGAAG |
| 390 | Sm_181 | AAUUUUCGGAA |
| 391 | Sm_182 | AAUUUUUCCAG |
| 392 | Sm_183 | AUUUUUUGUAG |
| 393 | Sm_184 | AAUCUUUAGAG |
| 394 | Sm_185 | AAUUUUACGAG |
| 395 | Sm_186 | CAUUUUUGGCG |
| 396 | Sm_187 | AAUUUGCGGAG |
| 397 | Sm_188 | CAUCUUUGGAG |
| 398 | Sm_189 | AACUUUUGAAG |
| 399 | Sm_190 | AAUUUUUCUAG |
| 400 | U7_1 | CAGGUUUUCCAGUGUUCACUGAAAUUUGUCUCU |
| 401 | U7_2 | AAGGUUUUCUGGUCUUUAUCAGAAAGCCUCC |
| 402 | U7_3 | CAGGUUUUCUGGUUUUCACUGCAAAACCCCA |
| 403 | U7_4 | CAGACUUUACGGUGCUUACCAGAAAGCUCCC |
| 404 | U7_5 | CACGUUUUCCGGUUGUCACUCCCAGGUAGGCUGGGGAAGAGGCAU |
| 405 | U7_6 | CAGUCUUUCCAGUUUUUGCCGGAAAGCCCCU |
| 406 | U7_7 | CAGGCUUUCUGGUUUUUGCCAGAAAGCCCCC |
| 407 | U7_8 | CAGGUUUUUCAGUUUUCACCAGAAUGCCCAC |

TABLE 6-continued

| SEQ ID NO | Name/ID | Sequence |
|---|---|---|
| 408 | U7_9 | CAGGUUUUCUGGUCUUUACUGGAAAGCCCAA |
| 409 | U7_10 | CAGGCUUUCCGGUUUUUACCAGAAAGCCCCC |
| 410 | U7_11 | CAGGUUUUUCGGUUUUUACUGGAAAGCCCCA |
| 411 | U7_12 | CAGGCUUUCCAGUAAAUACAGGAAAGCCCUC |
| 412 | U7_13 | CAGGCUUUCCGGUUUUUGCUGGAAAGACUCC |
| 413 | U7_14 | AAGGUUUUCUGGUCUUUACUGAAAAGCCCCA |
| 414 | U7_15 | UGGGCUUUCUGUUUUUUACGAGAAAGUCCUC |
| 415 | U7_16 | CAGAUUUCUCAGUUUUCACUGGAAACCCUU |
| 416 | U7_17 | CAGGUUUUCCUGUCUUCACCGGAACUCCCCA |
| 417 | U7_18 | CAGGUUUUCUGGUUUGCACUAGAAAAACCAUA |
| 418 | U7_19 | CAGAUUUUCUGGUUUUUACCAGAAAAUUUAA |
| 419 | U7_20 | CAGGUCUUCUUGUUUUUACUGGAAAAUCCUC |
| 420 | U7_21 | CAGGUUUUCCGGUCUUCACCAGAAACCCCU |
| 421 | U7_22 | CAGGUUUUCCGAUUUUUACUGGAAAGCCCUU |
| 422 | U7_23 | CAGGUUUUCUGGUUUUCCAGAAAACCUCC |
| 423 | U7_24 | CAGGUUUUCCAGUUUUCACUGGAACCUCU |
| 424 | U7_25 | CCGGCUUUCCAGUUUUGCCGGAAAGCCCCC |
| 425 | U7_26 | CAGGUUUUCUGGUUUUUACCAGAACUUAA |
| 426 | U7_27 | CACGUUUUCCGGUUGUCACUCCCAGGUGGGCUCGGGAAGAGGCAU |
| 427 | U7_28 | CAGGCUUUCCGGUCUUUACCGGAAAGCCUAU |
| 428 | U7_29 | CAGGCUUUCUGGUUUUUGCCGGAAAGCCCUC |
| 429 | U7_30 | CAGGCUUUCAGGUCUUUGCCAGAAAGCCCCA |
| 430 | U7_31 | CAGGCUUUCUUGUUUUCACUGGAAGCCUCC |
| 431 | U7_32 | CAGGUUUUUCAGUCUUCACCGGAAAGCUCCC |
| 432 | U7_33 | CAGAUUUUCUGGUUUUCACCACGAAAGAAAUGUCAUU |
| 433 | U7_34 | CAGUUCUCCUGGAUUUUACAGGAAAACCCC |
| 434 | U7_35 | CAGGCUUUCUGGCAUUUGCCAGAAAGCCCUG |
| 435 | U7_36 | CAGACUUUCCUGUUUUUAACAGAAAGCCCCC |
| 436 | U7_37 | CAGGCUUUCCGGUUUUUGCUGGAAAGCUCCC |
| 437 | U7_38 | CAGCUUUUCCAGUUUUCACUGAGGUAAA |
| 438 | U7_39 | UAGGUUUUCUGGUUUUUAUUGGGAAAUCACA |
| 439 | U7_40 | CAGGGUUUCUGGUGGUACCAGCAGACUCCACA |
| 440 | U7_41 | CAAGUUUCCCAGUUUUCACUGGAACCUCCG |
| 441 | U7_42 | CAGAUUUUCCAGUUUUUACUAGAAACCCCCC |
| 442 | U7_43 | CAGGGUUUCCAGUUUUCACUGUAUACCAUCC |
| 443 | U7_44 | CAAGUUCUCUGGUCUUCACUGGAAAACCCAU |
| 444 | U7_45 | UAGAUUUUCUGGUCUUUACCAGAAAGACUCC |

TABLE 6-continued

| SEQ ID NO | Name/ ID | Sequence |
|---|---|---|
| 445 | U7_46 | GCAGGUUUUCUGGUUUUUAUUGGAAAACCUUC |
| 446 | U7_47 | CAGGUUUUCCACUUUUCACCAGAAACUGCCUCU |
| 447 | U7_48 | UAGGCUUUCCGGUUUUUUGCAGGAAAGCCCCC |
| 448 | U7_49 | CAGGUUUUCCAGUCUUUACCAGAAAGCCACU |
| 449 | U7_50 | CAGGUUUUUUGGUCUUCACAGGAAACUUCCCCU |
| 450 | U7_51 | CAGGUUUUCUGCUUUUCACUGGAAGACUCCC |
| 451 | U7_52 | CAGACUUUCCAGUUUUUGCCAGAAAGCCCAC |
| 452 | U7_53 | CAGGCUUUCUGGUUUUUGCCCAAAAGCCUCU |
| 453 | U7_54 | CAGGUUUUCCAAUCUUCACUGAAAAGCUUUA |
| 454 | U7_55 | CUGGUUCCUAGUCUUCACUGGAAGCACCCUC |
| 455 | U7_56 | GGCUUUCCGCUCUUCAUUGGAAAGCCCAU |
| 456 | U7_57 | CAGGUUUUUCAGUUUUUAGCAGAAAACCUCC |
| 457 | U7_58 | CAGGUUCUCUGGUUUUUACUGAAACCAAA |
| 458 | U7_59 | CAGGUUUUCCAGUCUUCACUGGAAAGCCCUU |
| 459 | U7_60 | CAGGCUUUCUGGUUUUUGCCGGAAGGCCUCC |
| 460 | U7_61 | CAGGUUUUCUGUUUUUUAACUAGAAAACUCCC |
| 461 | U7_62 | UAGGCUUUCUGGUUUUUGCUGGAAAGCCCCC |
| 462 | U7_63 | CAGGUUUCCCGGUUUUUACCAGAAAAAUCUAA |
| 463 | U7_64 | CAGGUUUUCCAGUCUUUACCAGAAAUGCCCCC |
| 464 | U7_65 | GGUUUUCUGGUCAUCGCUGGAAACACCCUC |
| 465 | U7_66 | CAACCUUUCUGGUUUUUGCUAGAAAGUUCUC |
| 466 | U7_67 | CAGGCCUUUGGGUCUUUACUGGAAAACCCCU |
| 467 | U7_68 | UAUGUUUUCCGGUUUUCACUCCCAGGUAGGCUCGG |
| 468 | U7_69 | CAAAUUUUCUGGCUUUUCCAGGAAAAUCCCC |
| 469 | U7_70 | UAGGUUUUCCAGUGACCAGAAAAUCCUC |
| 470 | U7_71 | CAGGUCUUCGGGUUUUUAACUGGAAACCUUC |
| 471 | U7_72 | GCAGGCUUUCCAGUUUUUUCUGGAAAGCCUCA |
| 472 | U7_73 | GGCUUUCUGGUUUUUACUGGAAAGCCCCC |
| 473 | U7_74 | CAGGUUUCCCAGUAUUCACCGGAAAGCUCCA |
| 474 | U7_75 | CAGGCUUUCUAGUUUUCCCACACUAAGAAACAAAAAAACCUGU |
| 475 | U7_76 | GCAAGCUUUCUGGUUUUUGGCCAAAAAGCCACC |
| 476 | U7_77 | UUCUGGUUUUCACCAGAAACCACU |
| 477 | U7_78 | GCAAGUUUUCUAGCCUGUACCUGAAAGCCUCA |
| 478 | U7_79 | AAGUUUUCUUGUUUUUACCAGAAAACUCCU |
| 479 | U7_80 | GGCUUUCCAAUUUUUGCCAGAAAGCCCCC |
| 480 | U7_81 | AGCUGGUUUUCUGGUUUUCACCGGAAGACCCAU |
| 481 | U7_82 | CAGGCCUUCUGGUUUUUUGCUGGGAAGUCCCCA |

TABLE 6-continued

| SEQ ID NO | Name/ ID | Sequence |
|---|---|---|
| 482 | U7_83 | CAGGUUUUCCAGUUUGUACCAGAAAACCCCU |
| 483 | U7_84 | CAGGUUUCACCCAAAAACCCAC |
| 484 | U7_85 | UAGGCUUUCUGGCUUUUUACCGGAAAGCCCCU |
| 485 | U7_86 | CAGGGUUUCUGGUUUUCACCAGGAAACAAAA |
| 486 | U7_87 | CAGGUUUUCCUGUCUUUACUAGAAACCCCUC |
| 487 | U7_88 | CAGGUUUUAUAGGUUUUUACCAGAAAACUUCC |
| 488 | U7_89 | CAGGCUUCCCAAUUUUUGCUGGAAAGCCCCU |
| 489 | U7_90 | CAGGCUUUUUGGGUUAGGUCAGAAAGUCCCC |
| 490 | U7_91 | CAGGUUUUUGGUUUUUUAGCGAAACCCUC |
| 491 | U7_92 | CAGGCUUUCUGGUUUUCACCAUAAAAUGCCCCA |
| 492 | U7_93 | CAGGUCUUCGGGGUUUUACAAAAAGAAGAAGAAAUCCACCCCC |
| 493 | U7_94 | CAAGUUCUCUGGUCUCCCAACAAGAAACCCCC |
| 494 | U7_95 | CAGGAUUUCUGGUUUCUGGUGGAAAGCUCCCAU |
| 495 | U7_96 | AGGCUUUCCAGUUUUUGCUGGAAAGCCCCU |
| 496 | U7_97 | CAGGUUUUCCAGUCUUUGUCAAAUGCCUUC |
| 497 | U7_98 | CAGGCUUUCCAGUUUUUGCCAGUGUGAACCCAAA |
| 498 | U7_99 | CAGGCUUUCUGGUUUUUAUCAGAAAGCCUCC |
| 499 | U7_100 | GAGGUUUUCUGGUUUUCACCAGAACCAACCCUU |
| 500 | U7_101 | CAGAUUUUCCAGCUUUUACUGGAAGCCCCCU |
| 501 | U7_102 | CAGGUUUUCUGGUUUUUCACUGGAAAAUACCUCA |
| 502 | U7_103 | CAUGUUUUUUGGUGUUAAUAAAAACCCGCACAC |
| 503 | U7_104 | AAGGCUUUCCGGUUUUUGCAGGAAAGCAACC |
| 504 | U7_105 | AGUCUUUCCGGGUUUUGUCAGAAAGGCCCU |
| 505 | U7_106 | GCAGGUUUUCUGGUUUCUACUGGAAGCUUCU |
| 506 | U7_107 | CAGGCUUUCUGGUUUUUACUGGAAAGCCCCU |
| 507 | U7_108 | CAGGCUUUCCAAUUUUUGCCAGAAAGCUCCC |
| 508 | U7_109 | CAGGUUUUCUGGUUCUCACCAGAAAACGCCA |
| 509 | U7_110 | CAGGUUUUCUGGUCUUCACUGGAAGACCACU |
| 510 | U7_111 | CAGGUGGUUUUCCGGUCUUUACCAGUAAGCCCCC |
| 511 | U7_112 | CAGGUUUUCCAGUUUCUACCAGAAACCCCUA |
| 512 | U7_113 | CAGGUUUUCUGGUCUUUACCAGAAAAGUCUCC |
| 513 | U7_114 | CCAGGCUUUCUGGUUUUUACCGGAAAGCCCCG |
| 514 | U7_115 | CAGGUUUUUCACUUUUUACUAGAAAAACCAGU |
| 515 | U7_116 | UAGGCUUUCUGGGAGGUCUUUACCAGAAAGCCUCC |
| 516 | U7_117 | UACAUUUUCCAGUUUUUCACCAGGAAUCUGCCU |
| 517 | U7_118 | UAGGUUUUCCAGUUUUUCACCAGAAAAUCCCG |
| 518 | U7_119 | CAGGUUUUCUGGUUUUUUACGAGACUCCCCCA |

TABLE 6-continued

SEQUENCE LISTING

| SEQ ID NO | Name/ID | Sequence |
|---|---|---|
| 519 | U7_120 | CAGGCUUUCUGUUUUUUGCUAAAAUCCUCC |
| 520 | U7_121 | CUGGGCGUACUGGCUCACGCCUAUAAUCCCAA |
| 521 | U7_122 | GGCUCUCCGGUUUUUGCCAGAAUGCCCAC |
| 522 | U7_123 | UGGGUUUUCUGGUGAAAACUAGACUGCCCCC |
| 523 | U7_124 | CAGGCUUUCUGGUUUUUUACAGGAAGGCCCCU |
| 524 | U7_125 | GGUUUUCUGGUUCUCACUGGAAAACCCCC |
| 525 | U7_126 | CAGGCUUUCCGGUAAAGACUGGAAAGCCCCU |
| 526 | U7_127 | CAGGUUUUCCAGUUUUUACCAGAAAACUCUC |
| 527 | U7_110_C1A | AAGGUUUUCUGGUCUUCACUGGAAGACCACU |
| 528 | U7_110_C1G | GAGGUUUUCUGGUCUUCACUGGAAGACCACU |
| 529 | U7_110_C1T | UAGGUUUUCUGGUCUUCACUGGAAGACCACU |
| 530 | U7_110_A2C | CCGGUUUUCUGGUCUUCACUGGAAGACCACU |
| 531 | U7_110_A2G | CGGGUUUUCUGGUCUUCACUGGAAGACCACU |
| 532 | U7_110_A2T | CUGGUUUUCUGGUCUUCACUGGAAGACCACU |
| 533 | U7_110_G3T_C28A | CAUGUUUUCUGGUCUUCACUGGAAGACAACU |
| 534 | U7_110_G3C_C28G | CACGUUUUCUGGUCUUCACUGGAAGACGACU |
| 535 | U7_110_G3A_C28T | CAAGUUUUCUGGUCUUCACUGGAAGACUACU |
| 536 | U7_110_G4C_C27G | CAGCUUUUCUGGUCUUCACUGGAAGAGCACU |
| 537 | U7_110_G4A_C27T | CAGAUUUUCUGGUCUUCACUGGAAGAUCACU |
| 538 | U7_110_G4T_C27A | CAGUUUUUCUGGUCUUCACUGGAAGAACACU |
| 539 | U7_110_T5G_A26C | CAGGGUUUCUGGUCUUCACUGGAAGCCCACU |
| 540 | U7_110_T5A_A26T | CAGGAUUUCUGGUCUUCACUGGAAGUCCACU |
| 541 | U7_110_T5C_A26G | CAGGCUUUCUGGUCUUCACUGGAAGGCCACU |
| 542 | U7_110_T6G_G25C | CAGGUGUUCUGGUCUUCACUGGAACACCACU |
| 543 | U7_110_T6A_G25T | CAGGUAUUCUGGUCUUCACUGGAAUACCACU |
| 544 | U7_110_T6C_G25G | CAGGUCUUCUGGUCUUCACUGGAAGACCACU |
| 545 | U7_110_T6T_G25A | CAGGUUUUCUGGUCUUCACUGGAAAACCACU |

TABLE 6-continued

| SEQ ID NO | Name/ ID | Sequence |
|---|---|---|
| SEQUENCE LISTING | | |
| 546 | U7_110_ T7C_A24G | CAGGUUCUCUGGUCUUCACUGGAGGACCACU |
| 547 | U7_110_ T7G_A24C | CAGGUUGUCUGGUCUUCACUGGACGACCACU |
| 548 | U7_110_ T7A_A24T | CAGGUUAUCUGGUCUUCACUGGAUGACCACU |
| 549 | U7_110_ T8A_A23T | CAGGUUUACUGGUCUUCACUGGUAGACCACU |
| 550 | U7_110_ T8G_A23C | CAGGUUUGCUGGUCUUCACUGGCAGACCACU |
| 551 | U7_110_ T8C_A23G | CAGGUUUCCUGGUCUUCACUGGGAGACCACU |
| 552 | U7_110_ C9T_G22A | CAGGUUUUUUGGUCUUCACUGAAAGACCACU |
| 553 | U7_110_ C9G_G22C | CAGGUUUUGUGGUCUUCACUGCAAGACCACU |
| 554 | U7_110_ C9A_G22T | CAGGUUUUAUGGUCUUCACUGUAAGACCACU |
| 555 | U7_110_ T10C_G21G | CAGGUUUUCCGGUCUUCACUGGAAGACCACU |
| 556 | U7_110_ 1T0A_G21T | CAGGUUUUCAGGUCUUCACUUGAAGACCACU |
| 557 | U7_110_ T10T_G21A | CAGGUUUUCUGGUCUUCACUAGAAGACCACU |
| 558 | U7_110_ T10G_G21C | CAGGUUUUCGGGUCUUCACUCGAAGACCACU |
| 559 | U7_110_ G11T_T20A | CAGGUUUUCUUGUCUUCACAGGAAGACCACU |
| 560 | U7_110_ G11A_T20T | CAGGUUUUCUAGUCUUCACUGGAAGACCACU |
| 561 | U7_110_ G11G_T20C | CAGGUUUUCUGGUCUUCACCGGAAGACCACU |
| 562 | U7_110_ G11C_T20G | CAGGUUUUCUCGUCUUCACGGGAAGACCACU |
| 563 | U7_110_ G12T_C19A | CAGGUUUUCUGUUCUUCAAUGGAAGACCACU |
| 564 | U7_110_ G12A_C19T | CAGGUUUUCUGAUCUUCAUUGGAAGACCACU |
| 565 | U7_110_ G12C_C19G | CAGGUUUUCUGCUCUUCAGUGGAAGACCACU |
| 566 | U7_110_ T13C_A18G | CAGGUUUUCUGGCCUUCGCUGGAAGACCACU |
| 567 | U7_110_ T13G_A18C | CAGGUUUUCUGGGCUUCCCUGGAAGACCACU |
| 568 | U7_110_ T13A_A18T | CAGGUUUUCUGGACUUCUCUGGAAGACCACU |
| 569 | U7_110_ C14T | CAGGUUUUCUGGUUUUCACUGGAAGACCACU |
| 570 | U7_110_ C14A | CAGGUUUUCUGGUAUUCACUGGAAGACCACU |

TABLE 6-continued

| SEQ ID NO | Name/ID | Sequence |
|---|---|---|
| 571 | U7_110_C14G | CAGGUUUUCUGGUGUUCACUGGAAGACCACU |
| 572 | U7_110_T15A | CAGGUUUUCUGGUCAUCACUGGAAGACCACU |
| 573 | U7_110_T15G | CAGGUUUUCUGGUCGUCACUGGAAGACCACU |
| 574 | U7_110_T15C | CAGGUUUUCUGGUCCUCACUGGAAGACCACU |
| 575 | U7_110_T16A | CAGGUUUUCUGGUCUACACUGGAAGACCACU |
| 576 | U7_110_T16G | CAGGUUUUCUGGUCUGCACUGGAAGACCACU |
| 577 | U7_110_T16C | CAGGUUUUCUGGUCUCCACUGGAAGACCACU |
| 578 | U7_110_C17A | CAGGUUUUCUGGUCUUACUGGAAGACCACU |
| 579 | U7_110_C17G | CAGGUUUUCUGGUCUUGACUGGAAGACCACU |
| 580 | U7_110_C17T | CAGGUUUUCUGGUCUUUACUGGAAGACCACU |
| 581 | U7_110_A29G | CAGGUUUUCUGGUCUUCACUGGAAGACCGCU |
| 582 | U7_110_A29C | CAGGUUUUCUGGUCUUCACUGGAAGACCCCU |
| 583 | U7_110_A29T | CAGGUUUUCUGGUCUUCACUGGAAGACCUCU |
| 584 | U7_110_C30G | CAGGUUUUCUGGUCUUCACUGGAAGACCAGU |
| 585 | U7_110_C30T | CAGGUUUUCUGGUCUUCACUGGAAGACCAUU |
| 586 | U7_110_C30A | CAGGUUUUCUGGUCUUCACUGGAAGACCAAU |
| 587 | U7_110_T31A | CAGGUUUUCUGGUCUUCACUGGAAGACCACA |
| 588 | U7_110_T31G | CAGGUUUUCUGGUCUUCACUGGAAGACCACG |
| 589 | U7_110_T31C | CAGGUUUUCUGGUCUUCACUGGAAGACCACC |
| 590 | SNORA38 | UCCUCCUACAAAGGCGUGUCUGUGGUUCCCUGUCUUUGGACACGUAAGAAUUGGAGGAAAAUAAAUGUGGAUUUGGG AAACUUUGAGGCCAGCUUGCUUCUUGCAGGCUCAUGAUCAACCAAUCUCACAUAA |
| 591 | SNORA24 | CUCCAUGUAUCUUUGGGACCUGUCAGCCGUGGCAGUCUCCCUUCCUAGCCAUGGAAGAGCAUAUCCUUGUUUAUUGG CAAAGCUGUCACCAUUUAAUUGGUAUCAGAUUCUGACUUGCACAAGUAACAUUC |
| 592 | SNORA72 | CUGCGAAUAUUCUCGCUGUUCUGAUUUUGUAAUAGUCAGGACAGGCUAAACAUUCGCUAUAUUAAGACCAUGCAUGU GUCCCCAAACCUAGUUCUUUCCCUAGGUCUGGUUUCAUAAAUGCUGGUGAUAAAC |
| 593 | SNORA15 | GCAUGGCCGAAUACUGUGUUUUUAUCAGUAGUUUACACAGCCAGACACCAUGCAAAAGCAGUCUUCCCUUUAGAAUG ACUGAUGGUAUGCUAAGGUUUUUCAUAGCAUAUCAUUAUUAAAGGUGAAUACAAAU |
| 594 | SNORA8 | UGCACUGCAUGGUAUCUGCACUCAGCAGUUUACACCUGCUAGGGUGUUCAAAGGUCAGUGCUAUAGAAAUUCAGUAU CUGGCAUCGUUGGUUUUCUUGGCUUUGUGCUUGUUAAACCUGGUAUUUCUACUGAUACAGUA |

TABLE 6-continued

| SEQUENCE LISTING | | |
|---|---|---|
| SEQ ID NO | Name/ ID | Sequence |
| 595 | SNORA52 | UGGUCCAUCCUAAUCCCUGCCGGUCCAUCUGUGGCCUGCCAGGUUUCGCUUGUGGACCAGAGCACCCUAGAAGCCUC ACCCGAGGAGUGAGCAGGGCUCCAGUGGGCUCACGUCAUGGGCACUUCUAGACACUC |
| 596 | SNORA60 | CACCUGCAUUCAAAAAUGAUCACGGGCUGCCUGUGCUCUGGUCAUCAAUAACGCAGGGAGAGGAAUUGCUGAAAGCC GUUUCCCGUGUUUGGAGGGUUCACACCUGUCCCUUUCAAAUGCUGGCGCUUUCACACAC |
| 597 | SNORA14A | UGCAUUCUUAAACCCUCUUGGUGGCUUCCCUGUAAAUGCUUCCAAGAUAUGAGCGAAUGCUAUAGAAAUUGCAGGAA AGUCCAAAGGGCUGCGCGUCUCCUGUGGCUCAGUCUUAUUUCAUACCUGCAACAUCU |
| 598 | SNORA68 | AUUGCACCUAAACCCAAGAAUCACUGUUUCUUAUAGCGGUGGUUUAAACAGAGGUGCAAACAGCAAGCGGAUCUUGU CGCCUUUGGGGGGCUGUGGCCGUGCCCCUCAAAGUGAAUUUGGAGGUUCCACAACU |
| 599 | SNORA20 | CUUCCCAUUUAUUUGCUGCUUGUAGUCUCACAGUGAUACGAGCAGUUAUACGCAUGGGAUAAAAUAACAUUGGGCCA CUGUAAAUUGAGAUGAAGUAACCAUUUUCAUCUCUUCUGCAGGGACUAGACAUUG |
| 600 | SNORA14B | CUGCAUUCUUAAACCCUCUUGGUAGCUUCGUUCUAAGUGCUUCCAAGAUAUGAGUGAAUGCUAUAGAAAUUGCAGGG GAGUCCAAAGGGCUGCGCUUCUCCCGUGGCUCAGUCUUAUUUCAUACCUGCGACAUCU |
| 601 | SNORA63 | AGGCAGGAUCUAGUUACAUUGUAGCUGUGAAGUGCUGCAUUGUCUUUGCCCCCUGCUCAAAAUAAAACUGUUACCUU UCAAGCCCUGUCUGCCAUGGUGCUGUAGCAGCAGGGAUGUUUGGUCUCAUACAU |
| 602 | SCARNA4 | ACUGGAGGACUAAGGAGGCUGGGUCUGAUGAGGCAAGAUUUUGCUGAUACAUUGCUCCUAGAAAAAAGGGUUGGCAA GAGCAGCCCUGGAGACUCACACGGCUGACUGUUCUACCCAACACUC |
| 603 | SNORA63C | AAGCAGGAUUCAGACUACAAUAUAGCUGUUAAGUGCUGUAUUGUCAUUCCCCCUGCUCAAAUUAAAGUUGUUUCUUA ACUAUACCCAUCUGCUAUUCUGUAGCAGCCAGGGAUGCUUGGUCACAUACAU |
| 604 | SNORA51 | GGCUUCCUAGUACUUACCAUGGUCUGUGUUCUUACGCUGACUGUAUAGAAACAGGAGGCAGAGUAAACCGACCCCAC AUAUACCUCAGCCCAGGCCCUGUGCUGCGUCUGUAUUGUGAAUCAGGAGACAUGG |
| 605 | SCARNA21 | UGGCUCGAUUUCCUGGGGGGGUGGUCUCAGCCCACUCCACCUCCCCUCAGCCGAGCCUAGAGUAGAGGGGCCAGGCAU CCUCCCCAGGGGAGGGGCGUUGAAGCAAGGAGCCUCUCCUGGGCUGUCCUAGCCUCACAUUU |
| 606 | SNORA18 | GUUGAGGUCUAUCCCGAUAGGUCUUUUUCCUGUAGCCUGCACGUUGUUGGAAAUGCCUCAUAGAGUAACUCUGUGAUU UUACUUUACUUACAGGACUAUUGUUACAUCUGUGGGAAGGAACCACAAGACAGUU |
| 607 | SNORA68B | UUCUCACCUAAACCCAAGAAUCACUGUUUCUUAUAGCGGUGGUUUAAACAGAGGUGCAAACAGCAAGUGAAUCUCGU CGCCUUUGCGGGGCUGUGGCCAUGCCCCUCAAAGGAAAUUUGGAGGCUCUACAGCC |
| 608 | SNORA25 | AGGUCAUUUCAAAGAGGUCUUGUGAGGCUGUGAAACCAAGAGCUCUUAACACUGCGACCAAAGAUGGAAGUUCUCUA UAGGAUGCCAUGGCAUUUGAUGGUGCUAUGUUUUCUUGAGGAGAUAUAAGA |
| 609 | SNORA38B | CCCUCCUACAAAGGCAUGUCUAUAGUUCCUUGUCUUUGGACAUGUAAGAAUUGGAGGCAAAGAAAUGUGGACUUGGA GAAAUCUGGGGCCAGCUUGCUCUCCGCAGGCUCAAGAUCAACCAUCCCACAUAG |
| 610 | SNORA77 | GCAGACUCACUAUGCACCUGACUGUACUUCCAGGCAGGUGCUUUUUCUGUCUGCCAGAGAAACAUUCCAGGGUGCUG UGGCUGCCUCACCUAUCCAGGGCGAUGCAGCUCCCUGGGGACACAGGU |
| 611 | SNORA77B | GCAGACUCACUCUGCAUCUGACUAUACUUCCAGGCGGGUGCUUUUUCUGUCUGCCAGAUAAACAUUCCAGGGUGCUG UGGCCGCCUCACGUAUCCAGAGUGAUGCAGCUCCCUGGGGACACAGGU |
| 612 | SNORA79B | UGAUGGCUGUUCCUCUCACUGCUUGAAGCCUUAGGCAGUGGGAUUUUGAUCCAUCAUAUAUCAAAAAUGGCUUAUCU UCACUCAGGGCACCAUGAGGAUGGGCUGGCUGUCCGUUAGUGCCUUCUGAUUUUUGCGGAGUCAAACAAUU |
| 613 | SNORA70EL5 | CUGGGGAAUUCAAACUUGUGUUAAGAAAAUGUGUCCCAGUGUGCAAUGGCUGCAAACAGCAGCUUCCUUGGUAGUGU AUGCAGCCUGUUUGUUGUACGGGUUGCUCUAAAGGGCCUUGGAGACAGUC |
| 614 | SNORA25L6 | AGGUCACUUCAAAGAGGGCUUGUGGGGCUGUGAAACCAAGAGGUCUUAACAGUAUGACCAAAAACUGAAGUUCUCUA UAGGAUGCUGUAGCACUCAAUGGUGCUAUGUUUUCCUCAGGAGAUAUGA |
| 615 | SNORA104 | CUGUCCGUUGCUGGCUUCACAAGUACUAGUAUAAUUUUUAAAAUGUUUUAUUAUUUUGAAAAUAAUGUUGUAAUUCA UGCCAGGGACUGACAAAAGACUUGAGACAGGAUGGUUAUUCUUGUCAGCUAAGGUCACAUUG |
| 616 | SNORA98 | UCCAAACAGACACUGAUGGCACCUUCUGCCAUUUAGGAAUUUGUUUUAAAACAGACAUUUGUCUAGAUAUUUCCUUU GUGGCCUCCUCCCCAUCAAAAGUCAAUCAAACAUCG |
| 617 | ACA59 | GCCCUAUGUUAAAAUUUUAAUUCUGCACUUACUAACUAUCUUGGGAACCUUGGGCAAGUAACCAACCUCUUGUGCUU UGGUUUCCUCAUUGGUAAAAUGGGGAUAACAGUACUUACCUCACAGAGUUGUUGAGAGGAACAAAU |
| 618 | SNORA63B | AUGCAGGUACUGUUACAAUACAACUGAUGUGUUUUGUUGUCGUUCCCCCUGCUUAAAGCACUUGAUGCAUAACUCUG UCUACCUUCAUUCCGUAGUAAGACAGAGACGCUUGGCUUCAGACAUUU |
| 619 | SNORA120 | UCACUGCCCUGCUCACCCUUCCUGAGUCCGGCGGCAAGGGUAACUCUGGGAGCAUCGUAGAGGGCAGAGAAGAAGAA ACCCUGAGGUCCCAUUAUGUCAGCCCCUUCUAUCACACGGGAGGAGACUGAGGACAGAAAGGGAACAGAG |

TABLE 6-continued

SEQUENCE LISTING

| SEQ ID NO | Name/ ID | Sequence |
|---|---|---|
| 620 | SNORA116 | CUUUUCUCAGUGGGUGCAAGAAGAUUAAGCCACAUUCUGGCUUUAGAGAGGCAUUUCUGAGAGAGAUGAAGGACACUU<br>CGUUCCCCAGCCCCAACCUAAGCAUGUGACUGUACUCACCUUGUCAGAUGCUGUUGGAACCUGGCUGACA |
| 621 | SCARNA15 | CUGGAGGACUAAGGAGGCUGGGUCUGAUGAGGCAAGAUUUUGCUGAUACAUUGCUCCUAGAAAAAAGGGUUGGCAAG<br>AGCAGCCCUGGAGACUCACACGGCUGACUGUUCUACCCAACACUC |
| 622 | snoU109 | UAGUGUGGAACUGUCUACUCCUCAUUCCUGUGGAAGCAGGAAUACAUUCAUAACAUGCUCCAUUAAAAAAGGAGUUC<br>UAGGCCAGGCAGCGUGCCUCAUGCCUGGAAUCCCAGCACUU |
| 623 | SNORA68L2 | AUACCUAAACCCAAGAAUCACUUUCUUAUAGUGAUGAUUUAAACAGAUGCAAACAGCGAGCACAUCUUGUCACCUUU<br>GCGGGACUGUGGCUGUGCCCCUCGCAGUAAAUUUGGAGGUUCUACAUCC |
| 624 | SNORA63E | AGGCAGGAUCUAGUUACAUUGUAGCUGUGAAGUGCUGCAUUGUCUUUGCCCCCUGCUCAAAAUAAAACUGUUACCUU<br>UCAAGCCCUGUCUGCCAUGGUGCUGUAGCAGCAGGGAUGUUUGGUCUCAUACAUGU |
| 625 | SNORA75 | CACUAGAAGACAGAAUUCACAGAAGUAGCAUUUCACCUUUUGCCUUUACAGAAGUAUAUUUGGCUGUUUUGUGAGAC<br>AUUC |
| 626 | SNORA95 | ACUUUUACAGGUAGAAUAGUAAAGCACAGUGUUGAUUGCCCAAGAUUUAUUUUACUUUGAAAAAAUUAGAAAUUUAU<br>UACUAUAGCAAAUGUCUAGAACUUUGGAAACAAGU |
| 627 | SNORA31B | AUGCAUCUAUUUGACAGACCUGGAGCAGUUGCUAUCUGCUGCUAUGGUUUCCACCACAGAUGCAAGAAGAACAUGUC<br>CUUGCGCUUUCCGUCUGUCUAAUUGUGGCAGCUGAGAUUGAAUAGAGGAAUACAGGA |
| 628 | SNORA50_1 | AAGCACUGCCUUUGAACCUGAUGUGUCUUGUUUGUAGCUUCACGGGCCAAGCAACAGUGCUAGAGCAUAACGACUUG<br>UUAUAACUGGGGCUCUUCAGCUCUCAACUGAACUGCUCUUUUAAAAACAAGGUACAUUU |
| 628 | SNORA50_2 | AAGCACUGCCUUUGAACCUGAUGUGUCUUGUUUGUAGCUUCACGGGCCAAGCAACAGUGCUAGAGCAUAACGACUUG<br>UUAUAACUGGGGCUCUUCAGCUCUCAACUGAACUGCUCUUUUAAAAACAAGGUACAUUU |
| 630 | ACA13 | AGCCUUUGUGUUGCCCAUUCACUUUGGAAACUAGUGAAUGUGGUGUCAAAAAAGGCGUAAAUUAAACGCUUUGCAGC<br>CUUUUCCUGCCCUUAAAUUUGAUACCUUUGGUGUAGGAGCUGCAUAAGUAACAGUU |
| 631 | ACA36_2 | UUCCAAAGUGUUGAGUUCAGUCCAGGGCAGCUUCCCUGUUCUGUUAAUUAAACUUUGGGACAUUAAAAUGGGCUAAG<br>GGAGAUGAUUGGGUAGAAAGUAUUAUUCUAUUCAUUUGCCUCCCAGCCUACAAAA |
| 632 | ACA28_1 | AAGCAACACUCUGUGGCAGAUGAUCAAAACUGUCUGACACAAUUUGAGCUUGCUAUAGCAAGAAAGUCUAACCUAUU<br>CCGGUGUUCUCUCUCCCAUGAGACAAGCCGUUAUAUAGACUUAAACAGU |
| 632 | ACA28_2 | AAGCAACACUCUGUGGCAGAUGAUCAAAACUGUCUGACACAAUUUGAGCUUGCUAUAGCAAGAAAGUCUAACCUAUU<br>CCGGUGUUCUCUCUCCCAUGAGACAAGCCGUUAUAUAGACUUAAACAGU |
| 634 | ACA41 | UUCCACAGCUACUGGUCUGCAGCUGUUCUUAUGGUAGCAGUUGUGGCAUUCCUCUGUGGGAAAGAAACUGUUAACAC<br>AAACACCUCUUUCUUAGCAAAACAGAAAGUGGGUAUAUAUGUGUGACAGACACAA |
| 635 | ACA5_2 | UGCAGCCGUGUCAAAUUCAGUACCUGUCCUAUGCAUGGUAGGCACUGGCCCAGAAGGCUGCCACAGAAACACUGUGA<br>CUCAUGGGCCCUGUUCCUGUGUCCCAGGCUCAGGGAUAAAUUUGGUUACAGACAUCA |
| 594 | ACA8_1 | UGCACUGCAUGGUAUCUGCACUCAGCAGUUUACACCUGCUAGGGUGUUCAAAGGUCAGUGCUAUAGAAAUUCAGUAU<br>CUGGCAUCGUUGGUUUUCUUGGCUUUGUGCUUGUUAAACCUGGUAUUUCUACUGAUACAGUA |
| 594 | ACA8_2 | UGCACUGCAUGGUAUCUGCACUCAGCAGUUUACACCUGCUAGGGUGUUCAAAGGUCAGUGCUAUAGAAAUUCAGUAU<br>CUGGCAUCGUUGGUUUUCUUGGCUUUGUGCUUGUUAAACCUGGUAUUUCUACUGAUACAGUA |
| 638 | ACA5_1 | UGCAGCCGUGUCAAUUCAGUACCUGUCCUAUGCAUGGUAGGCACUGGCCCAGAAGGCUGCCACAGAAACACUGUGAC<br>UCAUGGGCCCUGUUCCUGUGUCCCAGGCUCAGGGAUAAAUUUGGUUACAGACAUCA |
| 631 | ACA36_1 | UUCCAAAGUGUUGAGUUCAGUCCAGGGCAGCUUCCCUGUUCUGUUAAUUAAACUUUGGGACAUUAAAAUGGGCUAAG<br>GGAGAUGAUUGGGUAGAAAGUAUUAUUCUAUUCAUUUGCCUCCCAGCCUACAAAA |
| 640 | ACA42_1 | UGGUAAUGGAUUUAUGGUGGGUCCUUCUCUGUGGGCCUCUCAUAGUGUACCCAUGCCAUAGCAAAUGGCAGCCUCGA<br>ACCAUUGCCCAGUCCCCUUACCUGUGGGCUGUGAGCACUGAAGGGGGUUGCACAGUG |
| 640 | ACA42_2 | UGGUAAUGGAUUUAUGGUGGGUCCUUCUCUGUGGGCCUCUCAUAGUGUACCCAUGCCAUAGCAAAUGGCAGCCUCGA<br>ACCAUUGCCCAGUCCCCUUACCUGUGGGCUGUGAGCACUGAAGGGGGUUGCACAGUG |
| 642 | ACA44_1 | CAGCAUGUUUCCAAGGGCUGUGGCUGGUCAUAGCCAUGGGAUCUCCAACUGCAUGCAAGAGCAACCUGGAAAGACUU<br>UGACAGCGCAGGUCAGUACAAUACCUGCAAGCUGCCACUCAGCUUUCCUAUAAUG |
| 642 | ACA44_2 | CAGCAUGUUUCCAAGGGCUGUGGCUGGUCAUAGCCAUGGGAUCUCCAACUGCAUGCAAGAGCAACCUGGAAAGACUU<br>UGACAGCGCAGGUCAGUACAAUACCUGCAAGCUGCCACUCAGCUUUCCUAUAAUG |

SEQUENCE LISTING

| SEQ ID NO | Name/ ID | Sequence |
|---|---|---|
| 644 | ACA10_2 | GGUCUCUCAGCUCCGCUUAACCACACGGGUCCAGUGUGUGCUUGGCGUGUUUUCAGGGGAGGCAGAGAAAGGCUCUCC UAAUGCACGACAGACCCGCCCAGAAUGGCCUCUCUGUUCCUAGGAGUGCGACAAUU |
| 645 | ACA46 | AGCACUAUAUUUAAACCUGUGGAUGGGAAUAUUCCCCAUUCUUGGUUACGCUGUAGUGCAAAAGAAUUCCUGGCUCU CUGUUGCACAGCUGACUUGUGCCAUUCUGCUGUUGCUGUAUAGAGUUAAGGAACAUGG |
| 644 | ACA10_1 | GGUCUCUCAGCUCCGCUUAACCACACGGGUCCAGUGUGUGCUUGGCGUGUUUUCAGGGGAGGCAGAGAAAGGCUCUCC UAAUGCACGACAGACCCGCCCAGAAUGGCCUCUCUGUUCCUAGGAGUGCGACAAUU |
| 647 | ACA1 | UGCCUCAUUCUAGAGAAUGGGCACUGUUGAUCAUGGUGUCCAAAAAUAGUUAAUGUGGCUAAAUUGAGACAGGUUAU GCUUCCAUCACAGUAUGCAUAUUGCAGUGGUGACAAUGAGACCUGUAACAUUU |
| 648 | ACA2A_1 | UAGGCCCUGAAUCAAGACCAAUGGUUUGCUGUAGCUGUUGGGUUUCAAACAGGAGCUAAGAGUGAUGUCUUCCUUGUG GUCUGUUGGCUAUUCAGUAUUCCAGUGCGAAUUGCCAAUUCAGUUGGAAGAAACAUAG |
| 648 | ACA2A_2 | UAGGCCCUGAAUCAAGACCAAUGGUUUGCUGUAGCUGUUGGGUUUCAAACAGGAGCUAAGAGUGAUGUCUUCCUUGUG GUCUGUUGGCUAUUCAGUAUUCCAGUGCGAAUUGCCAAUUCAGUUGGAAGAAACAUAG |
| 650 | ACA3_1 | AUCGAGGCUAGAGUCACGCUUGGGUAUCGGCUAUUGCCUGAGUGUGCUAGAGUCCUCGAAGAGUAACUGCUGACCUU AUUCACUGGCUGUGGGCCUUAUGGCACAGUCAGUCACCAGGUUAGAGACAUGC |
| 650 | ACA3_2 | AUCGAGGCUAGAGUCACGCUUGGGUAUCGGCUAUUGCCUGAGUGUGCUAGAGUCCUCGAAGAGUAACUGCUGACCUU AUUCACUGGCUGUGGGCCUUAUGGCACAGUCAGUCACCAGGUUAGAGACAUGC |
| 652 | ACA6 | UGCACACUAUUAAAGCUCAGGGUGGAGGCCAGUCUUGGCUCAUGAACUUCUGAGUGUCGGAAGUGUGCUAUAUCAAU GGCAGGAUUUUCGCUAACACCAGUAGAGCUUGCCUCUAUGACUGGAGUUUGGUAGUACUCGCUGCCACAUAG |
| 653 | ACA7_1 | GACCUCCUGGGAUCGCAUCUGGAGAGUGCCUAGUAUUCUGCCAGCUUCGGAAAGGGAGGGAAAGCAAGCCUGGCAGA GGCACCCAUUCCAUUCCCAGCUUGCUCCGUAGCUGGCGAUUGGAAGACACUCUGCGACAGUG |
| 653 | ACA7_2 | GACCUCCUGGGAUCGCAUCUGGAGAGUGCCUAGUAUUCUGCCAGCUUCGGAAAGGGAGGGAAAGCAAGCCUGGCAGA GGCACCCAUUCCAUUCCCACUUGCUCCGUAGCUGGCGAUUGGAAGACACUCUGCGACAGUG |
| 655 | ACA9_1 | UAGCAAGCCUCCAGCGUGCUUGGGUCUGCGGUGACCCUAUGCAUUCCUUCAGUGCUUGCUAGAACAGUUUUGAAACG GUUUGAGGCCUUGCCCUGCUCCAUCCAGAGCAAGGUUAUAGAAAUUUCAGACAAUG |
| 655 | ACA9_2 | UAGCAAGCCUCCAGCGUGCUUGGGUCUGCGGUGACCCUAUGCAUUCCUUCAGUGCUUGCUAGAACAGUUUUGAAACG GUUUGAGGCCUUGCCCUGCUCCAUCCAGAGCAAGGUUAUAGAAAUUUCAGACAAUG |
| 657 | ACA16 | UUGGCCCUUAUCGAAGCUGCAGCUGCUUCCGCAUAGCUGCUGUGGUCAAAAAGGAGCCCAGAGUGACAGUUUUCCUU GACGGUCGCCGUUCUGUUUGUUGUAACUGAUCUGCAACAUUUUGGGGAAAAUACAGUU |
| 732 | snoDB0837 | AUCCAAGGUGAUUCCCUCUCCAAGGGGACAUCAGUGCCUCUCAGGAAAGUAGCAGCUUGGAAUAGAAUCUGGCAUGC CUAAGGCCUUUGGGGAACUGGGAUGCUUAUUUCCUCUGCCUUCCUUGGCUGCCCACAUGG |
| 733 | snoDB0325 | UUGCACAGUGAACACCCAAGUGUGCUUUAUAGUUCCCUUGGCUUUGACCCUGUGCUAGAGCAUUGCCUGCUCUUCUC CUCUGCAUUAAAAGGAAUAUUUAUCCUUUUAAAUGUAUUCAGAAAGCCAGCACAUUA |
| 734 | snoDB0379 | UACCUCCCAGGAUGGCAUCUGGAAGUGGAUAGUAUUCUGCCAGCUUUGGAAACUGGAUGAAAAGCAAAUCUGGCAGA GGUACCCAUUUCAUUCCCAGCUUGCUCAGUAGCUGGUGAUUGGAAGAAACUCUGCAACAGUG |
| 735 | snoDB0461 | GGGUCAUUUCAAAGAGGGCUUAUGAGGCUGUGAAACCCAGAGCUCUUAACGCUGUGACCAAAGAUGGAAGUUCUCUA UAGGAAGCCAUAGCACUCCUAAUGUUUGGUGCUAUGUUUUCCUGAGGAGAUAUAAAA |
| 736 | snoDB0034 | CUGCAGCCAAUUAAGCCGACUGAGUUCCUUUCCUCAUGGGGGCCCAGUGUGCAAUGGCUGUAAAUAGCAGCUUCCUU GGUAGUGUAUGCAGCCUGUUUGUUGUAUGGGUUGCUCUAAGGGACCUUGGAGACAGUC |
| 737 | snoDB0768 | CUCCAUGUAUCUUUGGGACCUGUCAAGUGUGGCAGUCUCCCUUCCUUGCCAUGGAAGAGCAUAUUCUUGUUUACCAG CAAAGCUGUCACCAUUUAAUUGGUAUCAGAUUCUGACUUGCACAAGUAACAUUC |
| 591 | snoDB0206 | CUCCAUGUAUCUUUGGGACCUGUCAGCCGUGGCAGUCUCCCUUCCUAGCCAUGGAAGAGCAUAUCCUUGUUUAUUGG CAAAGCUGUCACCAUUUAAUUGGUAUCAGAUUCUGACUUGCACAAGUAACAUUC |
| 601 | snoDB0169 | AGGCAGGAUCUAGUUACAUUGUAGCUGUGAAGUGCUGCAUUGUCUUUGCCCCCUGCUCAAAAUAAAACUGUUACCUU UCAAGCCCUGUCUGCCAUGGUGCUGUAGCAGCAGGGAUGUUUGGUCUCAUCAU |
| 634 | snoDB0110 | UUCCACAGCUACUGGUCUGCAGCUGUUCUUAUGGUAGCAGUUGUGGCAUUCCUCUGUGGGAAAGAAACUGUUAACAC AAACACCUCUUUCUUAGCAAAACAGAAAGUGGGUAUAUAUGUGUGACAGACACAA |
| 741 | snoDB0889 | GCCUGCAUUCGUAAGUGAUCACGGGCUGCCCGUGUCCUGGUCAUUGGUAGUGCAGGCAGAGGAAAUGCGGGAAAGGU UGCUGUGUUUGGAGGGUCCACAUCUUCACCCUCCUGUCCCAGGAGCUUUCCUACA |
| 742 | snoDB0063 | GUGCAAACUCGAUCACUAGCUCUGCGUGAUGUGGCAGAAGCGAAGGGAACCAGGUUUGCAAAAGUAACUGUGGUGAU GGAAAUGUGUUAGCCUCAGACACUACUGAGGUGGUUCUUUCUAUCCUAGUACAGUC |

TABLE 6-continued

| SEQ ID NO | Name/ ID | Sequence |
|---|---|---|
| 743 | snoDB0136 | UUCCAAAGUGUUGAGUUCAGUCCAGGGCAGCUUCCCUGUUCUGUUAAUUAAACUUUGGGACAUUGAAAUGGGCUAGG GGAGAUGAUUGGGUAGAAAGCAUUAUUUUAUUCAUUUGCCUCCCAGCCUACAAAA |
| 744 | snoDB0966 | CCCUUGGCCCUUAUCGAAGCUGCAGCUGCUUCCGCAUAGCUGCUGUGGUCAAAAAGGAGCCCAGAGUGACAGUUUUC CUUGACGGUCGCCGUUCUGUUUGUUGUAACUGAUCUGCAACAUUUUGGGAAAAUACAGUU |
| 745 | snoDB0245 | UGGAGGACUGAGAAGGUGAGGCAGUUUUGCCCCGUGCUGCCUUCCACCGGUUAAGACCUCCAAAAUCGAAGGGCUGC CCAGGCAGAGGAUGUCCCCUUGCCACCCUUGGAGGGGCAGCGCUGUGCUGGCCGACAUUUG |
| 746 | snoDB0466 | GUUGAGGUCUAUCCCGAUGGGGCUUUUCCUGUAGCCUGCACAUCGUUGGAAACGCCUCAUAGAGUAACUCUGUGGUU UUACUUUACUCACAGGACUAUUGUUAGAUCUGUGGGAAGGAAUUACAAGACAGUU |
| 594 | snoDB0464 | UGCACUGCAUGGUAUCUGCACUCAGCAGUUUACACCUGCUAGGGGUGUUCAAAGGUCAGUGCUAUAGAAAUUCAGUAU CUGGCAUCGUUGGUUUUCUUGGCUUUGUGCUUGUUAAACCUGGUAUUUCUACUGAUACAGUA |
| 748 | snoDB0256 | UCCAGCUGUAGGCAGCUGCCUAGGUUGUCUUGUACCUAGGCAAGUGUUACACUGCUGGGAGAACAGCAGCCAAUAGC UGGUUGGCAUUCUGGCCCUGGUUCAUGCCAACUCUUGUGUUGACUACCCCAGGAUGCCAGCAUA |
| 749 | snoDB0554 | CUUCCUCAGCCUUACUCCCAGGGACUUUUUGUUGCCUGUAAAGUGCUCUCGGCAUUGCCUGAGGAUAGAUGAGAAAGCA CAUAUCCCUCCCCAGUAAGACGCUGUUUUCUUUUGGGGCCUACAAGUUGAGCUGACAGU |
| 644 | snoDB0776 | GGUCUCUCAGCUCCGCUUAACCACACGGGUCCAGUGUGUGCUUGGCGUGUUUUCAGGGAGGCAGAGAAAGGCUCUCC UAAUGCACGACAGACCCGCCCAGAAUGGCCUCUCUGUUCCUAGGAGUGCGACAAUU |
| 751 | snoDB0047 | GCAUGGUAAUGGAUUUAUGGUGGGGUCCUUCUCUGUGGGCCUCUCAUAGUGUACCCAUGCCAUAGCAAAUGGCAGCCU CGAACCAUUGCCCAGUCCCCUUACCUGUGGGCUGUGAGCACUGAAGGGGGUUGCACAGUG |
| 752 | snoDB0958 | GCGCUGUCUUUGAGCCCCCGCCGAGCUUCCUCGUGGCGCCGGGGGGUCAAUCUGCAGCGCUAGAGCAUGUGCUUGCGC AUAACUGGGGCCGCCUGGCCUCCCGCGGGGCGGCCUUUUUAACCGCGAGCGACAAGA |
| 753 | snoDB0797 | GCAUGGGUUUGGAUUUAUGAUGGGCUGGAUUCCCUAGGCCUCUCAUAGUACCCCAUGCCAGAGCAAACUGUAGCCCC AACCAUUGCCGGGCCUCUAUGCCUGUAGGCUGCUGGCACUGAAGUGGGUUGCACAGUA |
| 754 | snora8 | UGCACUGCAUGGUAUCUGCACUCAGCAGUUUAUACCUGCUAGGGGUGUUCAAAGGUCAGUGCUAUAGAAAUUCAGUAU CUGGCAUCGUUGGUUUUCUUGGCUUUGUGCUUGUUAAACCUGGUAUUUCUACUGAUACAGU |
| 755 | snoDB0432 | GCCCUGUGGGUUGCUGGAUGCUGUUGUGCAUGGACAGCUCUCCAGUGGAUUCGAUGGGCCAUAGCAAUCCUGUGAUUU AUGCAUGGAGGCUGCUUCUCCUCAGCAGCUGCCAUAGCCCGGUCGCUGGUACAUGA |
| 756 | snoDB0890 | ACCUGCAUUCAAAAAUGAUCACGGGCUGCCUGUGCUCUCGGUCAUCAAUAACGCAGGGAGAGGAAUUGCUGAAAGCCG UUUCCCGUGUUUGGAGGGUUCACACCUGUCCCUUUCAAAUGCUGGCGCUUUCACACA |
| 757 | snoDB0502 | GCCGAGACUAGAGUCACAUCCUGACACAACUCUUGUCCUGGUGUGCUAGAGUACUCGAAGAGAAUCUACUGGUCUUG AUUCACUGGUGGGGGCAGUCGGUGCCCCCGUUAGUGCCCAGAUCAGAAACAUAC |
| 758 | snoDB0305 | GCAUGGGUUUGGAUUAUGACAGGCCCAUCCCCCUGGACCUCUCAUAGUGCCCCAUGCCAGAGCAAACUGUGGCCCCG AACCAUUGCCUGGCUUCUGUACCCGUGGGCCACUGGCACUGAAGAGGGUUUACACAGUG |
| 628 | snoDB0974 | AAGCACUGCCUUUGAACCUGAUGUGUCUUGUUUGUAGCUUCACGGGCCAAGCAACAGUGCUAGAGCAUAACGACUUG UUAUAACUGGGGCUCUUCAGCUCUCAACUGAACUGCUCUUUUUAAAAACAAGGUACAUUU |
| 760 | snoDB0260 | CUGCAGCCAAUUAAGCCGACUGAGUUCCUUUCCUCAUGGGGGCCCAGUGUGCAAUCGCUGCAAACAGCAGCUUCCUU GGUAGUAUAUGCAGCCUGUUUAUUGUACGGGUUGCUCUACGGGACCUUGGAGACAGGC |
| 761 | snoDB0183 | AAGCAGGAUUCAGACUACAAUAUAGCUGCUAAGUGCUGUGUUGUCGUUCCCCCUGCUUAAAAUAAAGUUGUUUCUUA ACUAUACCUGUCUGCUAUUCUCCUGUAGCAGCCAGGGACGCUUGGUCUCAUACAU |
| 762 | snoDB0293 | UCCUCCUACAAAGGCGUGUCUGUGGGUUCCCUGUCUUUGGACACGUAAGAAUUGGAGGAAAAUAAAUGUGGAUUUGGG AAACUUUGAGGCCAGCUUGCUUCUUGCAGGCUCAUGAUCAACCAAUCUCACAUAA |
| 590 | snora54 | GAGCACUGUUCGUAACCCGUUAGCCUGGCUGUAGCUAAUGGGUUCCAUUCCGGUGCAAUAGCAUUUCCAGCGACACA UGACUGACUGACUGGUGGCUUUCAGUUUCAGGUCUUGGAGACAAAU |
| 764 | snoDB0345 | UUUCCCUGACCUGGGUAGAGUGGCAUCCAGUUGGUGGUGCCCAUCUCUAUAUCAGCCAGGGACAAAGCAACCCCUUGU UCCUCCCAGCUUGGCUUUUCAUCUGUGCCUAUGCCUGGUUCAUGCCUUGGACACAUUU |
| 765 | snoDB0538 | UUGGCCCUGAAUCAAGGCCAGCAGUUUGCUGAAGCUGUUGGGUUUCAAGCAGGAGCCUAAAGAAUUGUCUUUCUAUGG UCUGUUGGCCAUUUCAUAACUUUGGAAAUGUAAUGGUCAAUUCAUUAGAAAGAAACAUGA |
| 635 | snoDB0316 | UGCAGCCGUGUCAAAUUCAGUACCUGUCCUAUGCAUGGUAGGCACUGGCCCAGAAGGCUGCCACAGAAACACUGUGA CUCAUGGGCCCUGUUCCUGUGUCCCAGGCUCAGGGAUAAAUUUUGGUUACAGACAUCA |

TABLE 6-continued

SEQUENCE LISTING

| SEQ ID NO | Name/ ID | Sequence |
|---|---|---|
| 767 | snoDB0947 | GCAUGGGUUUGGAUUUAUGAUGGGCCCGUCCCCCUGGACCUCUCAUAGUACCCCAUGCCAGAGCAAACUGUAGCCCU GAACCAUUGCCUGGCCUCUGUUCCCGUAGGCUGCUGGCACUGAAGUGGGUUGCACAAUA |
| 642 | snoDB0073 | CAGCAUGUUUCCAAGGGCUGUGGCUGGUCAUAGCCAUGGGAUCUCCAACUGCAUGCAAGAGCAACCUGGAAAGACUU UGACAGCGCAGGUCAGUACAAUACCUGCAAGCUGCCACUCAGCUUUCCUAUAAUG |
| 630 | snoDB0246 | AGCCUUUGUGUUGCCCAUUCACUUUGGAAACUAGUGAAUGUGGGUGUCAAAAAAGGCGUAAAUUAAACGCUUUGCAGC CUUUUCCUGCCCUUAAAUUUGAUACCUUUGGUGUAGGAGCUGCAUAAGUAACAGUU |
| 599 | snoDB0286 | CUUCCCAUUUAUUUGCUGCUUGUAGUCUCACAGUGAUACGAGCAGUUAUACGCAUGGGAUAAAAUAACAUUGGGCCA CUGUAAAUUGAGAUGAAGUAACCAUUUUCAUCUCUUCUGCAGGGACUAGACAUUG |
| 771 | snoDB0382 | AAAGCAGGUUGCAAUUACAGUGCUUCAUUUUGUGGGAAGUACUGCCAUUAUCCUGCUGAAAGAAAAGCCGUGUUAAUC AUUUUUGAUUUUGCCUUUAUGAGGGUAAAAUCAUGACAGAUUGACAUGGACAAUU |
| 772 | snoDB0960 | GCACUGCUUUAGAGCCUCUGCGUGUCUGGCUGUGGCCUCAGGGGUCUAGCAGCAGUGCUAGAGCAGACCCAGCUUGU CAGAUCCGGGGCUGCUUAGAGGCCACCUAAGUGAUUCCUUUGGCAGCAAGCAACAUUC |
| 773 | snoDB0971 | GCUGUCCUGGACCUGUUGGCACCACAGACAGUUGCUCUGCCUGUGCCUGUGGCCUCGGGGCAAAGAGAAAGUGGCGAU UUCUACACUCAGUGCUCGGGAACCAGUGGGCACUGAGAAUGGUUUAUGGCCUGACAUUA |
| 774 | snoDB0040 | UUCCAAAGUGUUAAGUUCAGUUCAGGGUAGCUUCCCUGCUCUGUUAAUUAAACUUUGGAACAUUGAAACUGGCUAGG GAAAAUGAUUGGAUAGAAACUAUUAUUCUAUUCAUUUAUCCCCAGCCUACAAAA |
| 598 | snoDB0904 | AUUGCACCUAAACCCAAGAAUCACUGUUUCUUAUAGCGGUGGUUUAAACAGAGGUGCAAACAGCAAGCGGAUCUUGU CGCCUUUGGGGGGGCUGUGGCCGUGCCCCUCAAAGUGAAUUUGGAGGUUCCACAACU |
| 776 | snoDB0317 | UGCAGUCAAGUCAAAUUCAGUGCCCGUUUCUGUCAUAGCGGGGGCUGGCCCAGAUGGCUGCCACAGCAAGCUCCACA GCUCAUGGGCCCUGGGUCACCUACCCUGGGACCUGGGGAUAAGUUUGGCUGUGGACAGUG |
| 777 | snoDB0835 | UGUCCCUGACCUGGGUAGAGUGGCAUCUGGUUGGUGAUGCCCAUCUCAUAUCAGCCAGGGACAAAGCAACUCCUUGU UCAUCCCAGCUUGGCUUUUGAUCCGUGCCCAUGCCUGGUUCAUGCCUUGGACACAUAG |
| 778 | snoDB0372 | CCGCAGCCAAUUAAGCCGACUGAGUUCCUUUCCUCAUGGGGACCCAGUGUGCGAUGGCUGCACACAGCAGCUUCCUU GGUAGUGUACGCAGCCUGUUGGUUGUAUGGGGUUGCUCUAAGGGACCUUGGAGACAGGC |
| 609 | snoDB0833 | CCCUCCUACAAAGGCAUGUCUAUAGUUCCUUGUCUUUGGACAUGUAAGAAUUGGAGGCAAAGAAAUGUGGACUUGGA GAAAUCUGGGGCCAGCUUGCUCUCCGCAGGCUCAAGAUCAACCAUCCCACAUAG |
| 780 | snoDB0041 | GGGCAUACCCGUAGACCUUGUCUGACUGUGCUCAUGGCCAGGCAGGGGGGACAGUGUAUGCAAGAGUAAUGUGGAGU UUGUGCUAACUCUAGCCAGCUUAAUUAGUGACUGGAUAAAUUGCACAACUCUCACAUUC |
| 781 | snoDB0968 | ACUGCCCCUAGAGGCGUUGCAGCUGUGGCUGCCGUGUCACAUCUGUGUCAUUAGGUGGCAGAGAUUAGAGAGGCUAU GUCUACGCUCAGCGUUCUGCCCCGUGAACGUUUGAAUGUUUGAUAGUCUCACACUC |
| 782 | snoDB0055 | GCACCUGAAUCUUUCCCAUUCCUUGCUGCCUCGUGCCGGUGUGGGGACAGAUGGUGCUACAGAAUGAGCAGAGGAAA UCCAGACAGGUUGUUUUCCAUUUGUCUUUGGGGCCUGUCUCUACAGCUCUGCCACAUUU |
| 783 | snoDB0184 | CUACCAAAAGUUAGCUUUUUGGGGGGGCAGGGUUUUUAAGUAACCUUUGCCAACUUGGGCUAUUUGGAAGAGUAAAAGA CCACACUCCACAGUGGGCUAUACCACUUAGUAUAGUUCGCUACUAUUUUGUGGCCUACAUG |
| 784 | snoDB0134 | GCAUGGGUUUGGAUUUAUGACAGGCCCGUCACCCUGGGCCUGUCAUAGUACCCCAUGCCAGAGCAAACUGUGUCCCC GAACCAUUGCCUGGCCUCUGUGCCCGUAGGCUGCUGGCACUGAAGUGGGUUGCACAGUG |
| 785 | snoDB0777 | ACUCUCUCGGCUCUGCAUAGUUGCACUUGGCUUCACCCGUGUGACUUUCGUAACGGGGAGAGAGAGAAAAGAUCUCC UCAGGACCUCGGAUGGGCCUUACUGUGGCCUCUCUCUUUCCUUGAGGGGUGCAACAGGC |
| 786 | snoDB0820 | CCCCUUUUAAAAGCACUCAAUGGGCCUGUGGCUAAUGACCUAUUGAGCCGUCAAGAAAGGGGAGAGUGAAAACAUCG CUUUUGGGUGAAGUGGCAACAUGUGUUGUUUGCUUCAAUCGGUGGUGUGACAAGG |
| 787 | snoDB0879 | GGCCUCCUGGGUGCUUACCACAGGCUGUGUUCUUACACUGACUGUAUAGAAAGAGGAGGUAGAGUAAACCUACCCCAU AUACACCUCAGCUCAGGCCCUGUGCCUGGUCUGUAUUGUGAAUGGGGGAACAUAG |
| 788 | snoDB0158 | GGGCAUACUCGUAGACCUUGCCUGACUGUGCUCAUGUCCAGGCAGGGGGGACAGUGUAUGCAAGAAUAAUUUGGAGU UCCUGCCAGCUCUAACCAGCUUCAUCAGUGGCUGGAUAAAUUGCAGGACUCUAAACAUUU |
| 789 | snoDB0403 | CUGCGAAUAUUCUCGCUGUUCUGAUUUUGUAAUAGUCAGGACAGGCUAAACAUUCGCUAUAUUAAGACCAUGCAUGU GUCCCCAAACCUAGUUCUUUCCCUAGGUCUGGUUUUUAUAAAUGCUGGUGAUAAAC |
| 655 | snoDB0319 | UAGCAAGCCUCCAGCGUGCUUGGGGUCUGCGGUGACCCUAUGCAUUCCUUCAGUGCUUGCUAGAACAGUUUUGAAACG GUUUGAGGCCUUGCCCUGCUCCAUCCAGAGCAAGGUUAUAGAAAUUUCAGACAAUG |
| 631 | snoDB0383 | UUCCAAAGUGUUGAGUUCAGUCCAGGGCAGCUUCCCUGUUCUGUUAAUUAAACUUUGGGACAUUAAAAUGGGCUAAG GGAGAUGAUUGGGUAGAAAGUAUUAUUCUAUUCAUUUGCCUCCCAGCCUACAAAA |

TABLE 6-continued

SEQUENCE LISTING

| SEQ ID NO | Name/ ID | Sequence |
|---|---|---|
| 645 | snoDB0801 | AGCACUAUAUUUAAACCUGUGGAUGGGAAUAUUCCCCAUUCUUGGUUACGCUGUAGUGCAAAAGAAUUCCUGGCUCU CUGUUGCACAGCUGACUUGUGCCAUUCUGCUGUUGCUGUAUAGAGUUAAGGAACAUGG |
| 600 | snoDB0031 | CUGCAUUCUUAAACCCUCUUGGUAGCUUCGUUCUAAGUGCUUCCAAGAUAUGAGUGAAUGCUAUAGAAAUUGCAGGG GAGUCCAAAGGGCUGCGCUUCUCCCGUGGCUCAGUCUUAUUUCAUACCUGCGACAUCU |

What is claimed is:

1. A method for trans-splicing of one or more pre-mRNA target sequences in a eukaryotic cell comprising:

(a) introducing into the eukaryotic cell a trans-splicing RNA molecule comprising:

(i) a small nucleolar RNA (snoRNA) sequence, wherein the snoRNA sequence comprises:

an H box RNA sequence having the polynucleotide sequence of ANANNA, where N is A, C, G, or U, an ACA box RNA sequence having the polynucleotide sequence of ACA, and has at least 80% identity to a nucleic acid selected from any one of SEQ ID NOs: 590-628, 630-632, 634-635, 638, 640, 642, 644-645, 647-648, 650, 652-653, 655, and 657;

(ii) one or more exonic sequences to replace at least a portion of the one or more pre-mRNA target sequences;

(iii) at least one splice acceptor site or splice donor site located at a 3' boundary of the one or more exonic sequences, and wherein the at least one splice acceptor site or splice donor site and the one or more exonic sequences are located 5' of the snoRNA sequence; and (iv) one or more binding domains, each comprising a nucleic acid sequence of 5 to 300 nucleotides in length and having at least about 95% complementarity with the one or more pre-mRNA target sequences, and that binds to the one or more pre-mRNA target sequences via complementary base pairing, wherein the one or more binding domain sequences are positioned (i) upstream of the H box RNA sequence; (ii) downstream of the ACA box RNA sequence; (iii) between the H box RNA sequence and the ACA box RNA sequence; or (iv) a combination of (i)-(iii), (b) binding at least a portion of the one or more binding domains of the trans-splicing RNA molecule to the one or more pre-mRNA target sequences via complementary base pairing;

(c) recruiting a ribonucleoprotein (RNP) to direct splicing of the one or more exonic sequences into the one or more pre-mRNA target sequences; and (d) replacing at least a portion of the one or more pre-mRNA target sequences with the one or more exonic sequences.

2. The method of claim 1, wherein the one or more binding domains comprise 2 binding domains, or wherein the one or more binding domains comprise more than 2 binding domains.

3. The method of claim 1, wherein each of the one or more binding domains are 5 to 20, 5 to 30, 5 to 40, 5 to 50, 10 to 50, 10 to 100, 20 to 100, 30 to 100, 40 to about 100, 50 to 100, 50 to 150, 50 to 200, 50 to 250, 100 to 150, 100 to 200, 100 to 250, or 100 to 300 nucleotides in length, each having at least 95% complementarity to the one or more pre-mRNA target sequences.

4. The method of claim 1, wherein the one or more pre-mRNA target sequences comprises an USH2A pre-mRNA sequence, or wherein the one or more pre-mRNA target sequences comprises intron 12 and/or exon 13 of an USH2A pre-mRNA.

5. The method of claim 1, wherein the snoRNA sequence comprises one or more M6A sites.

6. The method of claim 5, wherein the snoRNA sequence comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 M6A sites.

7. The method of claim 1, wherein the snoRNA sequence has at least 90%, at least 95%, at least 98%, or at least 99% identity to a nucleic acid selected from any one of SEQ ID NOs: 590-628, 630-632, 634-635, 638, 640, 642, 644-645, 647-648, 650, 652-653, 655, and 657.

8. The method of claim 7, wherein the snoRNA sequence comprises a nucleic acid sequence selected from any one of SEQ ID NOs: 590-628, 630-632, 634-635, 638, 640, 642, 644-645, 647-648, 650, 652-653, 655, and 657.

9. The method of claim 1, wherein the trans-splicing RNA molecule comprises one or more splicing signals.

10. The method of claim 9, wherein the one or more splicing signals are selected from an exonic splicing enhancer (ESE), an intronic splicing enhancer (ISE), an exonic splicing silencer (ESS), intronic splicing silencer (ISS), a U1 binding motif, a polypyrimidine tract, a branch point, and a combination thereof.

11. The method of claim 1, wherein the trans-splicing RNA molecule comprises at least one splice donor site or splice acceptor site, and one or more polypyrimidine tracts, branch points, and is suitable for 5' editing of the one or more pre-mRNA target sequences.

12. The method of claim 1, wherein the trans-splicing RNA molecule further comprises a ribozyme site.

13. The method of claim 12, wherein the ribozyme site comprises a hairpin, hammerhead, hepatitis delta virus (HDV), twister ribozyme site, Varkud satellite (VS), or glmS ribozyme site, or a variant thereof.

14. The method of claim 1, wherein the trans-splicing RNA molecule further comprises one or more of a 5' cap, 5' UTR, 3' untranslated region (UTR), and 3' polyA signal/tail.

15. The method of claim 1, wherein the trans-splicing RNA molecule is introduced into the cell via a plasmid, viral vector, non-viral vector, or circular RNA (cirRNA), encoding the trans-splicing RNA molecule; and/or wherein the trans-splicing RNA molecule is introduced into the cell via a delivery vehicle comprising a lipid nanoparticle (LNP) or a polymeric nanoparticle.

16. The method of claim 1, wherein the method further comprises introducing multiple trans-splicing RNA molecules into the cell via multiple plasmids, viral vectors, non-viral vectors, or circular RNAs (cirRNAs), wherein each of the multiple plasmids, viral vectors, non-viral vectors, or cirRNAs encodes a distinct trans-splicing RNA molecule.

17. A method for trans-splicing of one or more pre-mRNA target sequences in a eukaryotic cell comprising:

(a) introducing into the eukaryotic cell a trans-splicing RNA molecule comprising:

(i) a small nucleolar RNA (snoRNA) sequence, wherein the snoRNA sequence comprises:

an H box RNA sequence having the polynucleotide sequence of ANANNA, where N is A, C, G, or U, an ACA box RNA sequence having the polynucleotide sequence of ACA, and has at least 80% identity to a nucleic acid selected from any one of SEQ ID NOs: 732-737, 741-746, 748-749, 751-758, 760-761, 763-765, 767, 771-774, 776-778, and 780-789;

(ii) one or more exonic sequences to replace at least a portion of the one or more pre-mRNA target sequences;

(iii) at least one splice acceptor site or splice donor site located at a 3' boundary of the one or more exonic sequences, and wherein the at least one splice acceptor site or splice donor site and the one or more exonic sequences are located 5' of the snoRNA sequence; and (iv) one or more binding domains, each comprising a nucleic acid sequence of 5 to 300 nucleotides in length and having at least 95% complementarity with the one or more pre-mRNA target sequences, and that binds to the one or more pre-mRNA target sequences via complementary base pairing, wherein the one or more binding domain sequences are positioned (i) upstream of the H box RNA sequence; (ii) downstream of the ACA box RNA sequence; (iii) between the H box RNA sequence and the ACA box RNA sequence; or (iv) a combination of (i)-(iii), (b) binding at least a portion of the one or more binding domains of the trans-splicing RNA molecule to the one or more pre-mRNA target sequences via complementary base pairing;

(c) recruiting a ribonucleoprotein (RNP) to direct splicing of the one or more exonic sequences into the one or more pre-mRNA target sequences; and (d) replacing at least a portion of the one or more pre-mRNA target sequences with the one or more exonic sequences.

18. The method of claim 17, wherein the one or more binding domains comprise 2 binding domains, or wherein the one or more binding domains comprise more than 2 binding domains.

19. The method of claim 17, wherein each of the one or more binding domains are 5 to 20, 5 to 30, 5 to 40, 5 to 50, 10 to 50, 10 to 100, 20 to 100, 30 to 100, 40 to 100, 50 to 100, 50 to 150, 50 to 200, 50 to 250, 100 to 150, 100 to 200, 100 to 250, or 100 to 300 nucleotides in length, each having at least 95% complementarity to the one or more pre-mRNA target sequences.

20. The method of claim 17, wherein the one or more pre-mRNA target sequences comprises an USH2A pre-mRNA sequence, or wherein the one or more pre-mRNA target sequences comprises intron 12 and/or exon 13 of an USH2A pre-mRNA.

21. The method of claim 17, wherein the snoRNA sequence comprises one or more M6A sites.

22. The method of claim 21, wherein the snoRNA sequence comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 M6A sites.

23. The method of claim 17, wherein the snoRNA sequence has at least 90%, at least 95%, at least 98%, or at least 99% identity to a nucleic acid selected from any one of SEQ ID NOs: 732-737, 741-746, 748-749, 751-758, 760-761, 763-765, 767, 771-774, 776-778, and 780-789.

24. The method of claim 23, wherein the snoRNA sequence comprises a nucleic acid sequence selected from any one of SEQ ID NOs: 732-737, 741-746, 748-749, 751-758, 760-761, 763-765, 767, 771-774, 776-778, and 780-789.

25. The method of claim 17, wherein the trans-splicing RNA molecule comprises one or more splicing signals.

26. The method of claim 25, wherein the one or more splicing signals are selected from an exonic splicing enhancer (ESE), an intronic splicing enhancer (ISE), an exonic splicing silencer (ESS), intronic splicing silencer (ISS), a U1 binding motif, a polypyrimidine tract, a branch point, and a combination thereof.

27. The method of claim 17, wherein the trans-splicing RNA molecule comprises at least one splice donor site or splice acceptor site, and one or more polypyrimidine tracts, branch points, and is suitable for 5' editing of the one or more pre-mRNA target sequences.

28. The method of claim 17, wherein the trans-splicing RNA molecule further comprises a ribozyme site.

29. The method of claim 28, wherein the ribozyme site comprises a hairpin, hammerhead, hepatitis delta virus (HDV), twister ribozyme site, Varkud satellite (VS), or glmS ribozyme site, or a variant thereof.

30. The method of claim 17, wherein the trans-splicing RNA molecule further comprises one or more of a 5' cap, 5' UTR, 3' untranslated region (UTR), and 3' polyA signal/tail.

31. The method of claim 17, wherein the trans-splicing RNA molecule is introduced into the cell via a plasmid, viral vector, non-viral vector, or circular RNA (cirRNA), encoding the trans-splicing RNA molecule; and/or wherein the trans-splicing RNA molecule is introduced into the cell via a delivery vehicle comprising a lipid nanoparticle (LNP) or a polymeric nanoparticle.

32. The method of claim 17, wherein the method further comprises introducing multiple trans-splicing RNA molecules into the cell via multiple plasmids, viral vectors, non-viral vectors, or circular RNAs (cirRNAs), wherein each of the multiple plasmids, viral vectors, non-viral vectors, or cirRNAs encodes a distinct trans-splicing RNA molecule.

* * * * *